(12) United States Patent
Loew et al.

(10) Patent No.: US 12,421,323 B2
(45) Date of Patent: *Sep. 23, 2025

(54) MULTISPECIFIC ANTIBODY MOLECULES COMPRISING LAMBDA AND KAPPA LIGHT CHAINS

(71) Applicant: Marengo Therapeutics, Inc., Cambridge, MA (US)

(72) Inventors: Andreas Loew, Boston, MA (US); Brian Edward Vash, Cambridge, MA (US); Stephanie J. Maiocco, Arlington, MA (US)

(73) Assignee: MARENGO THERAPEUTICS, INC., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/316,804

(22) Filed: May 12, 2023

(65) Prior Publication Data

US 2023/0272119 A1 Aug. 31, 2023

Related U.S. Application Data

(62) Division of application No. 16/335,822, filed as application No. PCT/US2017/053053 on Sep. 22, 2017, now Pat. No. 11,673,971.

(Continued)

(51) Int. Cl.
*C07K 16/46* (2006.01)
*A61P 35/00* (2006.01)
(Continued)

(52) U.S. Cl.
CPC ............ *C07K 16/468* (2013.01); *A61P 35/00* (2018.01); *C07K 16/00* (2013.01); *C07K 16/246* (2013.01); *C07K 16/2818* (2013.01); *C07K 16/2878* (2013.01); *C07K 16/40* (2013.01); *C07K 16/44* (2013.01); *C07K 2317/31* (2013.01); *C07K 2317/515* (2013.01); *C07K 2317/567* (2013.01)

(58) Field of Classification Search
None
See application file for complete search history.

(56) References Cited

U.S. PATENT DOCUMENTS

| 4,816,567 A | 3/1989 | Cabilly et al. |
| 5,223,409 A | 6/1993 | Ladner et al. |

(Continued)

FOREIGN PATENT DOCUMENTS

| CN | 102858800 A | 1/2013 |
| CN | 103261220 A | 8/2013 |

(Continued)

OTHER PUBLICATIONS

Lund et al., The Journal of Immunology 157:4963-4969 (Year: 1996).*

(Continued)

*Primary Examiner* — Phuong Huynh
(74) *Attorney, Agent, or Firm* — Wilson Sonsini Goodrich & Rosati

(57) ABSTRACT

Multispecific, e.g., bispecific, antibody molecules that include a kappa light chain polypeptide and one lambda light chain polypeptide, and methods of making and using the multispecific antibody molecules, are disclosed.

13 Claims, 35 Drawing Sheets

Specification includes a Sequence Listing.

Gel of reduced samples of multispecific molecule 2 following kappa/lambda select analysis

Related U.S. Application Data

(60) Provisional application No. 62/399,319, filed on Sep. 23, 2016, provisional application No. 62/474,569, filed on Mar. 21, 2017.

(51) Int. Cl.

| | |
|---|---|
| *C07K 16/00* | (2006.01) |
| *C07K 16/24* | (2006.01) |
| *C07K 16/28* | (2006.01) |
| *C07K 16/40* | (2006.01) |
| *C07K 16/44* | (2006.01) |

(56) References Cited

U.S. PATENT DOCUMENTS

| | | |
|---|---|---|
| 5,225,539 A | 7/1993 | Winter |
| 5,585,089 A | 12/1996 | Queen et al. |
| 5,624,821 A | 4/1997 | Winter et al. |
| 5,648,260 A | 7/1997 | Winter et al. |
| 5,693,761 A | 12/1997 | Queen et al. |
| 5,693,762 A | 12/1997 | Queen et al. |
| 5,731,116 A | 3/1998 | Matsuo et al. |
| 5,811,097 A | 9/1998 | Allison et al. |
| 5,849,500 A | 12/1998 | Breitling et al. |
| 7,476,724 B2 | 1/2009 | Dennis et al. |
| 7,501,121 B2 | 3/2009 | Tchistiakova et al. |
| 7,943,743 B2 | 5/2011 | Korman et al. |
| 7,943,873 B2 | 5/2011 | Gopikrishnan et al. |
| 8,008,449 B2 | 8/2011 | Korman et al. |
| 8,354,509 B2 | 1/2013 | Carven et al. |
| 8,552,156 B2 | 10/2013 | Takayanagi et al. |
| 8,609,089 B2 | 12/2013 | Langermann et al. |
| 11,291,721 B2 * | 4/2022 | Loew .................. A61K 38/177 |
| 11,673,971 B2 * | 6/2023 | Loew .................. C07K 16/44 |
| | | 530/387.3 |
| 2004/0009530 A1 | 1/2004 | Wilson et al. |
| 2010/0028330 A1 | 2/2010 | Collins et al. |
| 2011/0150892 A1 | 6/2011 | Thudium et al. |
| 2012/0039906 A1 | 2/2012 | Olive |
| 2012/0114649 A1 | 5/2012 | Langermann et al. |
| 2013/0317200 A1 | 11/2013 | Elson et al. |
| 2014/0044728 A1 | 2/2014 | Takayanagi et al. |
| 2019/0338048 A1 | 11/2019 | Urosev et al. |

FOREIGN PATENT DOCUMENTS

| | | |
|---|---|---|
| CN | 104011221 A | 8/2014 |
| CN | 105612182 A | 5/2016 |
| EP | 0125023 A1 | 11/1984 |
| EP | 0171496 A2 | 2/1986 |
| EP | 0173494 A2 | 3/1986 |
| EP | 0184187 A2 | 6/1986 |
| EP | 0388151 A1 | 9/1990 |
| EP | 0519596 A1 | 12/1992 |
| EP | 2581113 A1 | 4/2013 |
| GB | 2188638 A | 10/1987 |
| JP | 2013545738 A | 12/2013 |
| JP | 2015502409 A | 1/2015 |
| WO | WO-8601533 A1 | 3/1986 |
| WO | WO-8605133 A1 | 9/1986 |
| WO | WO-8702671 A1 | 5/1987 |
| WO | WO-9002809 A1 | 3/1990 |
| WO | WO-9100906 A1 | 1/1991 |
| WO | WO-9110741 A1 | 7/1991 |
| WO | WO-9117271 A1 | 11/1991 |
| WO | WO-9201047 A1 | 1/1992 |
| WO | WO-9203917 A1 | 3/1992 |
| WO | WO-9203918 A1 | 3/1992 |
| WO | WO-9209690 A2 | 6/1992 |
| WO | WO-9215679 A1 | 9/1992 |
| WO | WO-9218619 A1 | 10/1992 |
| WO | WO-9220791 A1 | 11/1992 |
| WO | WO-9301288 A1 | 1/1993 |
| WO | WO-9404678 A1 | 3/1994 |
| WO | WO-9856915 A2 | 12/1998 |
| WO | WO-9945110 A1 | 9/1999 |
| WO | WO-0034784 A1 | 6/2000 |
| WO | WO-0056772 A1 | 9/2000 |
| WO | WO-0060070 A1 | 10/2000 |
| WO | WO-0164942 A1 | 9/2001 |
| WO | WO-03074679 A2 * | 9/2003 ............ C07K 16/00 |
| WO | WO-2006105338 A2 | 10/2006 |
| WO | WO-2006121168 A1 | 11/2006 |
| WO | WO-2007005874 A2 | 1/2007 |
| WO | WO-2009101611 A1 | 8/2009 |
| WO | WO-2009114335 A2 | 9/2009 |
| WO | WO-2010019570 A2 | 2/2010 |
| WO | WO-2010027827 A2 | 3/2010 |
| WO | WO-2010077634 A1 | 7/2010 |
| WO | WO-2011066342 A2 | 6/2011 |
| WO | WO-2011080350 A1 | 7/2011 |
| WO | WO-2011155607 A1 | 12/2011 |
| WO | WO-2012023053 A2 | 2/2012 |
| WO | WO-2013079174 A1 | 6/2013 |
| WO | WO-2013096291 A2 | 6/2013 |
| WO | WO-2014008218 A1 | 1/2014 |
| WO | WO-2015052230 A1 | 4/2015 |
| WO | WO-2017059551 A1 | 4/2017 |
| WO | WO-2018057955 A1 | 3/2018 |

OTHER PUBLICATIONS

Piche-Nicholas et al., MABS 10(1): 81-94 (Year: 2018).*
Adachi, Osamu et al. Targeted Disruption of the MyD88 Gene Results in Loss of IL-1-and IL-8-Mediated Function. Immunity 9(1):143-150 (1998).
Co-pending U.S. Appl. No. 18/301,052, inventors Loew; Andreas et al., filed Apr. 13, 2023.
Dixon, Andrew S. et al. NanoLuc complementation reporter optimized for accurate measurement of protein interactions in cells. ACS Chemical Biology 11(2):400-408 (2015).
Dorfman, Albert, and Melvin L Ott. A turbidimetric method for the assay of hyaluronidase. The Journal of biological chemistry 172(2):367-375 (1948).
Doyle, Sean et al. IRF3 Mediates a TLR3/TLR4-Specific Antiviral Gene Program. Immunity 17(3):251-263 (2002).
Ipilimumab. CAS 477202-00-9. chemicalbook.com [Website] Retrieved Oct. 8, 2024 at: https://www.chemicalbook.com/CASEN_477202-00-9.htm. 3 pages.
Kabat, Elvin A. et al. Sequences of Proteins of Immunological Interest. Fifth Edition, NIH Pub. No. 91-3242. Public Health Service, U.S. Department of Health and Human Services, National Institutes of Health: 647-669 (1991).
Seidel, Ursula J E. et al. Natural Killer Cell Mediated Antibody-dependent Cellular Cytotoxicity in Tumor Immunotherapy With Therapeutic Antibodies. Frontiers in Immunology 4:76, 1-8 (2013).
U.S. Appl. No. 16/335,822 Notice of Allowance dated Jan. 10, 2023.
Mar. 24, 2022 Final Office Action U.S. Appl. No. 16/335,822.
Aug. 10, 2021 Non-Final Office Action U.S. Appl. No. 16/335,822.
Agostinis, P. et al, "Photodynamic Therapy of Cancer: An Update", CA Cancer J. Clin, 2011, vol. 61, No. 4, pp. 250-281.
Al-Lazikani, B. et al, "Standard Conformations for Canonical Structures of Immunoglobulins", J. Mol. Biol., 1997, vol. 273 , pp. 927-948.
Altschul et al., Gapped Blast and Psi-Blast: A New Generation Of Protein Database Search Programs. Nucleic Acids Research 25(17):3389-3402 (1997).
Altschul, S F, et al., Basic Local Alignment Search Tool. Journal of Molecular Biology 215(3):403-410 (1990).
Arnon, T.I. et al, "Recognition of viral hemagglutinins by NKp44 but not by NKp30", Eur J. Immunol., 2001, vol. 31, No. 9, pp. 2680-2689.
Barbas, C.F. et al, "Assembly of combinatorial antibody libraries on phage surfaces: The gene III site", PNAS, 1991, vol. 88, pp. 7978-7982.
Barrios, Y. et al, "Length of antibody heavy chain complementarity determining region 3 as a specificity-determining factor", Journal of Molecular Recognition, 2004, vol. 17, pp. 332-338.

(56) References Cited

OTHER PUBLICATIONS

Beidler, C.B. et al., "Cloning and high level expression of a chimeric antibody with specificity for human carcinoembryonic antigen", J. Immuno, 1988, vol. 141, pp. 4053-4060.
Better, M. et al., "*Escherichia coli* Secretion of an Active Chimeric Antibody Fragment", Science, 1988, vol. 240, No. 4855, pp. 1041-1043.
Bird et al., Single-Chain Antigen-binding Proteins. Science 242(4877):423-426 (1988).
Bruggemann, M. et al., Designer Mice: The Production of Human Antibody Repertoires in Transgenic Animals, Terhorst C. Malavasi F, Albertini A (eds): Generation of Antibodies by Cell and Gene Immortalization, Year Immunol, 1993, vol. 7, pp. 33-40.
Bruggemann, M. et al., "Human antibody production in transgenic mice: expression from 100kb of the human IgH locus", Eur J. Immunol, 1991, vol. 21, pp. 1323-1326.
Chothia, C. et al., "Canonical Structures for the Hypervariable Regions of Immunoglobulins", J. Mol. Biol, 1987, vol. 196, pp. 901-917.
Clackson, T. et al., Making antibody fragments using phage display libraries, Nature, 1991, vol. 352, pp. 624-628.
Colcher, D. et al, "Single-Chain Antibodies in Pancreatic Cancer", Ann Ny Acad Sci, 1999, vol. 880, pp. 263-280.
Coloma, J. et al, "Design and production of novel tetravalent bispecific antibodies", Nature Biotech, 1997, vol. 15, pp. 159-163.
Costa-Mattioli, M. et al., "RAPping production of type I interferon in pDCs through mTOR", 2008, Nature Immunol, vol. 9, No. 10, pp. 1097-1099.
Dhimolea et al., "World Bispecific Antibody Summit, Sep. 27-28, 2011, Boston, MA", mAbs, 2012, vol. 4, Issue 1, pp. 4-13.
Edwards, B.M. et al., "The Remarkable Flexibility of the Human Antibody Repertoire; Isolation of Over One Thousand Different Antibodies to a Single Protein, BLyS", J. Mol. Biol., 2003, vol. 334, pp. 103-118.
Fischer, N. et al., "Exploiting light chains for the scalable generation and platform purification of native human bispecific IgG", Nature Communications, 2015, 6:6113, pp. 1-12.
Fuchs, P. et al., "Targeting Recombinant Antibodies to the surface of *Escherichia coli*: Fusion to the Peptidoglycan associated Lipoprotein", Nature Publishing Group, 1991, vol. 9, No. 12, pp. 1369-1372.
Garrard, L. et al., "FAB Assembly and Enrichment in a Monovalent Phage Display System", Nature Publishing Group, 1991, vol. 9, pp. 1373-1377.
Garrity, D. et al, "The activating NKG2D receptor assembles in the membrane with two signaling dimers into a hexameric structure", Proc Natl Acad Sci USA, 2005, vol. 102, No. 21, pp. 7641-7646.
Gram, H. et al, In vitro selection and affinity maturation of antibodies from a naïve combinatorial immunoglobulin library, PNAS, 1992, vol. 89, pp. 3576-3580.
Green, L.L. et al, "Antigen-specific human monoclonal antibodies from mice engineered with human Ig heavy and light chain YACS", Nature Genet, 1994, vol. 7, pp. 13-21.
Griffiths, A.D. et al, "Human anti-self antibodies with high specificity from phage display libraries", The EMBO Journal, 1993, vol. 12, No. 2, pp. 725-734.
Hamid, O. et al., "Safety and Tumor Responses with Lambrolizumab (Anti-PD-1) in Melanoma", The New England Journal of Medicine, 2013, vol. 369, No. 2, pp. 134-144.
Hawkins, R. et al., "Selection of phage antibodies by binding affinity. Mimicking affinity maturation", J. Mol. Biol., 1992, vol. 226, No. 3, pp. 889-896.
Hay, B. et al., "Bacteriophage cloning and *Escherichia coli* expression of a human IgM Fab" Hum Antibodies Hybridomas, 1992, vol. 3, No. 2, pp. 81-85.
Hoogenboom, H.R. et al, "Multi-subunit proteins on the surface of filamentous phage: methodologies for displaying antibody (Fab) heavy and light chains", Nuc Acid Res, 1991, vol. 19, No. 15, pp. 4133-4137.

Huse, W. et al., "Generation of a large combinatorial library of the immunoglobulin repertoire in phage lambda" Science, 1989, vol. 246, No. 4935, pp. 1275-1281.
Huston et al., Protein Engineering Of Antibody Binding Sites: Recovery Of Specific Activity In An Anti-digoxin Single-chain Fv Analogue Produced In *Escherichia coli*. PNAS USA 85(16):5879-5883 (1988).
International Search Report and Written Opinion issued in PCT/US2017/053053, mailed Feb. 27, 2018.
Jayaram et al., "Germline VH/VL pairing in antibodies", Protein Engineering, Design & Selection, 2012, vol. 25, No. 10, pp. 523-529.
Jones et al., Replacing The Complementarity-determining Regions In A Human Antibody With Those From A Mouse. Nature 321(6069):522-525 (1986).
Lefranc, M.P.., "IMGT, the international ImMunoGene Tics database", Nucleic Acids Research, 2001, vol. 29, No. 1, pp. 207-209.
Li P. et al., "Design and synthesis of paclitaxel conjugated with an ErbB2-recognizing peptide," EC-1, 2007, Biopolymers, vol. 87, No. 4, pp. 225-230.
Liu, A. et al., "Production of a mouse-human chimeric monoclonal antibody to CD20 with potent Fc-dependent biologic activity", J Immunol, 1987, vol. 139, No. 10, pp. 3521-3526.
Liu, A.Y. et al., "Chimeric mouse-human IgG1 antibody that can mediate lysis of cancer cells", PNAS, 1987, vol. 84, pp. 3439-3443.
Liu, D.Z. et al, "Synthesis of 2'-paclitaxel 2-glucopyranosyl succinate for specific targeted delivery to cancer cells", Bioorganic & Medicinal Chemistry Letters, 2007, vol. 17, pp. 617-620.
Lloyd et al., Modelling the Human Immune Response: Performance of a 10" Human Antibody Repertoire Against a Broad Panel of Therapeutically Relevant Antigens. Protein Engineering Design & Selection. 22(3):159-168 (2009).
Lobuglio, A. et al., "Phase I Clinical Trial of CO17-1A Monoclonal Antibody", Hybridomia, 1986, vol. 5, No. 1, pp. S117-S123.
Lonberg et al., Antigen-specific human antibodies from mice comprising four distinct genetic modifications. Nature 368:856-859 (1994).
Maccallum, R M, et al., Antibody-Antigen Interactions: Contact Analysis And Binding Site Topography. Journal of Molecular Biology 262(5):732-745 (1996).
Malinge, presentation entitled "Maximizing Assembly and Yield of Unmodified Bispecific Antibodies," World Bispecific Summit 2015, retrieved from the internet at bispecific.com/wp-content/uploads/sites/90/2015/07/Day-1-1600-Pauline-Malinge-YES.pdf, 25 pages.
Mandelboim, O. et al., "Recognition of hemagglutinins on virus-infected cells by NKp46 activates lysis by human NK cells", Nature, 2001, vol. 409, No. 6823, pp. 1055-1060.
Martin, A. et al., "Chapter 3: Protein Sequence and Structure Analysis of Antibody Variable Domains", In: Antibody Engineering Lab Manual (Ed: Duebel, S. and Kontermann, R., Springer-Verlag, Heidelberg), 2010, vol. 2, pp. 33-51.
Martin, F. et al., "The affinity-selection of a minibody polypeptide inhibitor of human interleukin-6", EMBO J., 1994, vol. 13, No. 22, pp. 5303-5309.
Mcconnell, S.J. et al., "Tendamistat as a scaffold for conformationally constrained phage peptide libraries", J Mol Biol, 1995, vol. 250, No. 4, pp. 460-470.
Meyers, E. et al., "Optimal alignments in linear space", Cabios, 1988, vol. 4, No. 1, pp. 11-17.
Morrison, Sherie L., "Transfectomas provide novel chimeric antibodies", Science, 1985, vol. 229, No. 4719, pp. 1202-1207.
Morrison, S.L. et al, "Chimeric human antibody molecules: Mouse antigen-binding domains with human constant region domains", Proc Natl Acad Sci, 1984, vol. 81, pp. 6851-6855.
Needleman et al., A General Method Applicable to the Search for Similarities in the Amino Acid Sequence of Two Proteins. Journal of Molecular Biology 48:444-453 (1970).
Nishimura, Y. et al., "Recombinant Human-Mouse Chimeric Monoclonal Antibody Specific for Common Acute Lymphocytic Leukemia Antigen", Canc. Res, 1987, vol. 47, pp. 999-1005.
Oi, V. et al., "Chimeric Antibodies", BioTechniques, 1986, vol. 4, No. 3, pp. 214-221.

(56) References Cited

OTHER PUBLICATIONS

Pardoll, D.M., "The blockade of immune checkpoints in cancer immunotherapy", Nat Rev Cancer, 2012, Vo. 12, pp. 252-264.
Park, Y.P. et al., "Complex Regulation of human NKG2D-DAP10 cell surface expression: opposing roles of the γc cytokines and TGF-β1", Blood, 2011, vol. 118, No. 11, pp. 3019-3027.
Rakoff-Nahoum, S. et al., "Toll-like receptors and cancer", Nat Revs Cancer, 2009, vol. 9, pp. 57-63.
Reiter, Y et al., "Antibody Engineering of Recombinant Fv Immunotoxins for Improved Targeting of Cancer: Disulfide-stabilized Fv Immunotoxins", Clin Cancer Res, 1996, vol. 2, pp. 245-252.
Ridgway, J. et al, Knobs-into holes engineering of antibody CH3 domains for heavy chain heterodimerization, Protein Engineering, 1996, vol. 9, No. 7. pp. 617-621.
Rosenberg, S. et al., "Use of Tumor-Infiltrating Lymphocytes and Interleukin-2 in the Immunotherapy of Patients with Metastatic Melanoma", New Eng J of Med, 1988, vol. 319, pp. 1676-1680.
Rudikoff et al., Single Amino Acid Substitution Altering Antigen-binding Specificity. PNAS USA 79(6):1979-1983 (1982).
Saleh, M.N. et al, "A phase II trial of murine monoclonal antibody 17-1A and interferon-γ: clinical and immunological data", Cancer Immunol Immunother, 1990, vol. 32, pp. 185-190.
Scaviner, D. et al., "Protein displays of the human immunoglobulin heavy, kappa and lambda variable and joining regions", Exp. Clin. Immunogenet., 1999, vol. 16, pp. 234-240.
Shaw, D. et al., "Mouse/human chimeric antibodies to a tumor-associated antigen: biologic activity of the four human IgG sub-classes", Journal of the National Cancer Institute, 1988, vol. 80, No. 19. pp. 1553-1559.
Spiess, C. et al, "Alternative molecular formats and therapeutic applications for bispecific antibodies", Molecular Immunology, 2015, vol. 67, pp. 95-106.
Sun, L.K. et al., "Chimeric antibody with human constant regions and mouse variable regions directed against carcinoma-associated antigen 17-1A", PNAS, 1987, vol. 84, pp. 214-218.
Thorpe, P. E., "Vascular Targeting Agents as Cancer Therapeutics", Clinc Cancer Res, 2004, vol. 10, pp. 415-427.
Toughiri et al., "Comparing domain interactions within antibody Fabs with kappa and lambda light chains," mAbs, 2016, vol. 8, No. 7, pp. 1276-1285.
Tramontano et al.: The making of the minibody: an engineered beta-protein for the display of conformationally constrained peptides. J. Mol. Recognition. 7:9-24 (1994).
Tuaillon, N. et al., "Human immunoglobulin heavy-chain minilocus recombination in transgenic mice: Gene-segment use in μ and γ transcripts," PNAS, 1993, vol. 90, pp. 3720-3724.
Verhoeyen, M. et al., "Reshaping Human Antibodies: Grafting an Antilysozyme Activity", Science, 1988, vol. 239, pp. 1534-1536.
Weidle, U. et al, "The Intriguing Options of Multispecific Antibody Formats for Treatment of Cancer", Cancer Genomics & Proteomics, 2013, vol. 1, pp. 1-18.
Wood, C. R. et al., "The synthesis and in vivo assembly of functional antibodies in yeast", Nature Publishing Group, 1985, vol. 314, No. 4, pp. 446-449.
Wu et al., Humanization Of A Murine Monoclonal Antibody By Simultaneous Optimization Of Framework And CDR residues. J Mol Biol 294(1):151-162 (Nov. 19, 1999).
Xu, Y. et al., "Production of bispecific antibodies in "knobs-into-holes" using a cell-free expression system", mAbs, 2015,. vol. 7. MP/ 1, pp. 231-242.

* cited by examiner

Gel of multispecific molecule 1

Gel of multispecific molecule 3

Gel of multispecific molecule 4

Gel of multispecific molecule 5

Gel of multispecific molecule 6

Gel of multispecific molecule 7

Gel of multispecific molecule 8

Gel of multispecific molecule 9

Intact mass spectrometry analysis of papain-cleaved multispecific molecule 4

SEQUENCE LISTING

```
Sequence total quantity: 418
SEQ ID NO: 1            moltype = DNA   length = 1269
FEATURE                 Location/Qualifiers
source                  1..1269
                        mol_type = other DNA
                        organism = synthetic construct
SEQUENCE: 1
atggaaaccg acacactgct gctgtgggtg ctgttgttgt gggtgccagg atctacagga  60
caggtgcagc tggttgaatc tggtggcgga gtggtgcagc tggcagatc tctgagactg  120
tcttgtgccg cctctggctt cgccttctct tcttacggca tgcactgggt ccgacaggcc  180
cctggaaaag gactggaatg ggtcgccgtg atttggttcg acggcaccaa gaagtactac  240
accgactccg tgaagggcag attcaccatc agccgggaca actccaagaa caccctgtac  300
ctgcagatga taccctgag agccgaggac accgccgtgt actactgtgc cagagataga  360
ggcatcggcg ctcggagagg cccttactat atggatgtgt ggggcaaggg caccaccgtg  420
acagtgtcct ctgcttctac caagggaccc agctttttcc ctctggctcc atcctctaag  480
tccacctctg gtggaaccgc tgctctgggc tgtctggtca aggattactt ccctgagcct  540
gtgaccgtgt cctggaactc tggtgctctg acatccggcg tgcacacctt ccagctgtg  600
ctgcagtcct ctggcctgta ctctctgtcc tctgtcgtga ccgtgccttc tagctctctg  660
ggcacccaga cctacatctg caacgtgaac cacaagcctt ccaacaccaa agtggacaag  720
agagtggaac ccaagtcctg cggatcttct ggcggcggag aagcggagg cggaggatct  780
agcggcggag tgttcaccct ggaagatttc gtcggcgatt gggagcagac cgccgcctat  840
aatctggacc aggttctgga acaaggcggc gtgtcctctc tgctgcagaa tctggctgtg  900
tctgtgaccc ctatccagag aatcgtgcgc tctggcgagc agcccctgaa gatcgacatc  960
cacgtgatca tcccttacga gggcctgtct gccgatcaga tggctcagat cgaagggtg  1020
ttcaaggtgg tgtaccccgt ggacgaccac cacttcaaag tgatcctgcc ttacggcacc  1080
ctggtcatcg atggcgtgac cccaaacatg ctgaactact cggcagacc ctacgaggga  1140
atcgccgtgt cgatggcaa gaaaatcacc gtgaccggca cactgtggaa cggcaacaag  1200
atcatcgacg agcggctgat cacccctgac ggctctatgc tgttcagagt gaccatcaac  1260
tcctaatga                                                          1269

SEQ ID NO: 2            moltype = DNA   length = 789
FEATURE                 Location/Qualifiers
source                  1..789
                        mol_type = other DNA
                        organism = synthetic construct
SEQUENCE: 2
atggaaaccg acacactgct gctgtgggtg ctgttgttgt gggtgccagg ctctaccggc  60
gacatccaga tgacccagtc tccatcctct ctgtctgcct ctgtgggcga cagagtgacc  120
atcacctgta gagccagcca gtccatctcc tcctacctga actggtatca gcagaagcct  180
ggcaaggctc ccaagctgct gatctacgct gctagctctc tgcagtctgg cgtgccctct  240
agattttccg gctctggctc tggcaccgac ttcaccctga caatcagttc cctgcagcct  300
gaggacttcg ccacctacta ctgccagcag tcctacagca cacccttgac ctttggcgga  360
ggcaccaagg tggaaatcaa gagaaccgtg gccgctcctt ccgtgttcat cttcccacca  420
tccgacgaac agctgaagtc cggacacgct tctgtcgtg gcctgctgaa caacttctac  480
cctcgggaag ccaaggtgca gtggaaggtg gacaatgccc tgcagtccgg caactcccaa  540
gagtctgtga ccgagcagga ctccaaggac tctacctaca gcctgtcctc cacactgacc  600
ctgtctaagg ccgactacga aaagcacaag gtgtacgcct gtgaagtgac ccaccaggga  660
ctgtctagcc ccgtgaccaa gtcttttcaac agaggcgagt gcggatcttc tggtggcgga  720
ggaagcggag gcggaggatc atctggcgga gtgaccggct acagactgtt cgaagagatc  780
ctgtaatga                                                           789

SEQ ID NO: 3            moltype = DNA   length = 708
FEATURE                 Location/Qualifiers
source                  1..708
                        mol_type = other DNA
                        organism = synthetic construct
SEQUENCE: 3
atggaaaccg acacactgct gctgtgggtg ctgttgttgt gggtgccagg ctctaccggc  60
gacatccaga tgacccagtc tccatcctct ctgtctgcct ctgtgggcga cagagtgacc  120
atcacctgta gagccagcca gtccatctcc tcctacctga actggtatca gcagaagcct  180
ggcaaggctc ccaagctgct gatctacgct gctagctctc tgcagtctgg cgtgccctct  240
agattttccg gctctggctc tggcaccgac ttcaccctga caatcagttc cctgcagcct  300
gaggacttcg ccacctacta ctgccagcag tcctacagca cacccttgac ctttggcgga  360
ggcaccaagg tggaaatcaa gagaaccgtg gccgctcctt ccgtgttcat cttcccacca  420
tccgacgaac agctgaagtc cggacacgct tctgtcgtg gcctgctgaa caacttctac  480
cctcgggaag ccaaggtgca gtggaaggtg gacaatgccc tgcagtccgg caactcccaa  540
gagtctgtga ccgagcagga ctccaaggac tctacctaca gcctgtcctc cacactgacc  600
ctgtctaagg ccgactacga aaagcacaag gtgtacgcct gtgaagtgac ccaccaggga  660
ctgtctagcc ccgtgaccaa gtcttttcaac agaggcgagt gctaatga              708

SEQ ID NO: 4            moltype = DNA   length = 1254
FEATURE                 Location/Qualifiers
source                  1..1254
                        mol_type = other DNA
                        organism = synthetic construct
SEQUENCE: 4
atggaaaccg acacactgct gctgtgggtg ctgttgttgt gggtgccagg atctacaggc  60
gaagtgcagt tggtgcagtc tggcgccgaa gtgaagaagt ccggcgagtc cctgaagatc  120
```

```
tcctgcaaag gctccggcta ctccttcacc tcttactgga tcggctgggt ccgacagatg   180
cctggcaaag gactggaatg gatgggcatc ttctacccg gcgactcctc taccagatac   240
tcccctagct ttcagggcca agtgaccatc tccgccgaca agtctgtgaa caccgcctac   300
ctgcagtggt cctctctgaa ggcctctgac accgccatgt actactgcgc cagaagaaga   360
aactggggca acgccttcga tatctggggc cagggaacaa tggtcaccgt gtcctctgct   420
tccaccaagg gaccttccgt gtttcctctg gctccttcca gcaagtctac ctctggtgga   480
accgctgctc tgggctgcct ggtcaaggat tactttcctg agcctgtgac cgtgtcttgg   540
aactctggtg ctctgacctc cggcgtgcac acatttccag ctgtgctgca gtcctccggc   600
ctgtactctc tgtcctctgt cgtgaccgtg ccttctagct ctctgggcac ccagacctac   660
atctgcaacg tgaaccacaa gccttccaac accaaggtgg acaagagagt ggaacccaag   720
tcttgcggat cttccggtgg cggaggatct ggcggaggtg gaagtagtgg cggagtgttc   780
accctggaag atttcgtcgg cgattgggag cagaccgccg cctataatct ggaccaggtt   840
ctggaacaag gcggcgtcag ctctctgctg cagaatctgg ctgtgtctgt gaccccatc   900
cagagaatcg tgcgctctgg cgagaacgct ctgaagatcg acatccacgt gatcatccct   960
tacgagggcc tgtctgccga tcagatggct cagatcgaag aggtgttcaa ggtggtgtac   1020
cccgtggacg accaccactt caaagtgatc ctgccttacg gcaccctggt catcgatggc   1080
gtgaccccaa acatgctgaa ctacttcggc agacccacg agggaatcgc cgtgttcgac   1140
ggcaagaaaa tcaccgtgac cggcacactg tggaacggca acaagatcat cgacgagcgg   1200
ctgatcaccc ctgacggctc tatgctgttc cgcgtgacca tcaactccta atga         1254

SEQ ID NO: 5           moltype = DNA   length = 792
FEATURE                Location/Qualifiers
source                 1..792
                       mol_type = other DNA
                       organism = synthetic construct
SEQUENCE: 5
atggaaaccg acacactgct gctgtgggtg ctgttgttgt gggtgccagg atctacaggc    60
gagatcgtgc tgacccagtc tcctggcaca ttgtctctga gtcctggcga gagagctacc   120
ctgtcttgca gagcttccca gtccgtgtcc tcttcctacc tggcctggta tcagcagaag   180
cctggacagg ctcccagact gctgatctac ggcgcctctt ctagagccac aggcatccct   240
gacagattct ccggctctgg ctctggcacc gacttcaccc tgaccatctc tagactggaa   300
cccgaggact tcgccgtgta ctactgccag cagtatggct cctctacctg gacctttgga   360
cagggcacca aggtggaaat caagagaacc gtggccgctc cttccgtgtt catcttccca   420
ccatctgacg agcagctgaa gtccggcaca gcttctgtcg tgtgcctgct gaacaacttc   480
taccctcggg aagccaaggt gcagtggaag gtggacaatg ccctgcagtc cggcaactcc   540
caagagtctg tgaccgagca ggactccaag gactctacct acagcctgtc ctccacactg   600
accctgtcta aggccgacta cgagaagcac aaggtgtacg cctgtgaagt gacccaccag   660
ggactgtcta gccccgtgac caagtctttc aacagaggcg agtgcggatc ttctggtggc   720
ggaggatctg gcggaggcgg atctagtggc ggagtgaccg gctacagact gttcgaagag   780
atcctgtaat ga                                                       792

SEQ ID NO: 6           moltype = DNA   length = 711
FEATURE                Location/Qualifiers
source                 1..711
                       mol_type = other DNA
                       organism = synthetic construct
SEQUENCE: 6
atggaaaccg acacactgct gctgtgggtg ctgttgttgt gggtgccagg atctacaggc    60
gagatcgtgc tgacccagtc tcctggcaca ttgtctctga gtcctggcga gagagctacc   120
ctgtcttgca gagcttccca gtccgtgtcc tcttcctacc tggcctggta tcagcagaag   180
cctggacagg ctcccagact gctgatctac ggcgcctctt ctagagccac aggcatccct   240
gacagattct ccggctctgg ctctggcacc gacttcaccc tgaccatctc tagactggaa   300
cccgaggact tcgccgtgta ctactgccag cagtatggct cctctacctg gacctttgga   360
cagggcacca aggtggaaat caagagaacc gtggccgctc cttccgtgtt catcttccca   420
ccatctgacg agcagctgaa gtccggcaca gcttctgtcg tgtgcctgct gaacaacttc   480
taccctcggg aagccaaggt gcagtggaag gtggacaatg ccctgcagtc cggcaactcc   540
caagagtctg tgaccgagca ggactccaag gactctacct acagcctgtc ctccacactg   600
accctgtcta aggccgacta cgagaagcac aaggtgtacg cctgtgaagt gacccaccag   660
ggactgtcta gccccgtgac caagtctttc aacagaggcg agtgctaatg a             711

SEQ ID NO: 7           moltype = DNA   length = 1257
FEATURE                Location/Qualifiers
source                 1..1257
                       mol_type = other DNA
                       organism = synthetic construct
SEQUENCE: 7
atggaaaccg acacactgct gctgtgggtg ctgttgttgt gggtgccagg atctacaggc    60
gaaggccagt tggttcagtc tggcggagga cttgttcacc ctggcggatc tctgagactg   120
tcttgtgctg gtctggctt cacctttctcc agctacggca tgcactgggt tcgacaggcc   180
cctggaaaag gactggaatg ggtgtccgga atcggcaccg gcggaggcac ctattctacc   240
gattctgtga agggcagatt caccatcagc cgggacaacg ccaagaactc cctgtacctg   300
cagatgaaca gcctgagagc cgaggacatg gccgtgtact actgtgccag aggcgattac   360
tacggctccg gctctttctt cgactgttgg ggacagggca cactggtcac cgtgtcctct   420
gcttccacca agggaccctc tgtgttccct ctggctccag caagtctacc tacctctggt   480
ggaaccgctg ctctgggctg cctggtcaag gattactttc ctgagcctgt gaccgtgtct   540
tggaactctg gtgctctgac ctccggcgtg cacacatttc cagctgtgct gcagtcctcc   600
ggcctgtact ctctgtcctc tgtcgtgacc gtgccttcta gctctctggg cacccagacc   660
tacatctgca acgtgaacca caagccttcc aacaccaagg tggacaagag agtggaaccc   720
aagtcttgcg atcttctgg cggcggagga agcggaggcg gaggatctag tggcggagtg   780
```

-continued

```
tttaccctgg aagatttcgt cggcgattgg gagcagaccg ccgcctataa tctggaccag   840
gttctggaac aaggcggcgt cagctctctg ctgcagaatc tggctgtgtc tgtgaccect   900
atccagagaa tcgtgcgctc tggcgagaac gccctgaaga tcgacatcca cgtgatcatc   960
ccttacgagg gcctgtctgc cgatcagatg gctcagatcg aagaggtgtt caaggtggta  1020
taccccgtgg acgaccacca cttcaaagtg atcctgactt acggcaccct ggtcatcgat  1080
ggcgtgaccc caaacatgct gaactacttc ggcagaccct acgagggaat cgccgtgttc  1140
gacggcaaga aaatcaccgt gaccggcaca ctgtggaacg gcaacaagat catcgacgag  1200
cggctgatca cccctgacgg ctccatgctg tttagagtga ccatcaactc ctaatga     1257

SEQ ID NO: 8             moltype = DNA   length = 789
FEATURE                  Location/Qualifiers
source                   1..789
                         mol_type = other DNA
                         organism = synthetic construct
SEQUENCE: 8
atggaaaccg acacactgct gctgtgggtg ctgttgttgt gggtgccagg ctctaccggc    60
gacatccaga tgacccagtc tccatcctct ctgtctgcct ctgtgggcga cagagtgacc   120
atcacctgta gagcctctca gggcatctct agctggctgg cctggtatca gcagaagcct   180
gagaaggccc ctaagagcct gatctacgct gccagttctc tgcagtctgg cgtgccctct   240
agattctctg gctctggatc tggcaccgac ttcaccctga caatctctag cctgcagcct   300
gaggacttcg ccacctacta ctgccagcag tacaacagct accctcctac cttggccag   360
ggcaccaagc tggaaatcaa gagaaccgtg gccgctcctc ccgtgttcat cttcccacca   420
tctgacgagc agctgaagtc cggcacagct tctgtcgtgt gcctgctgaa caacttctac   480
cctcgggaag ccaaggtgca gtggaaggtg gacaatgccc tgcagtccgg caactcccaa   540
gagtctgtga ccgagcagga ctccaaggac tctacctaca gcctgtcctc cacactgacc   600
ctgtctaagg ccgactacga aagcacaag gtgtacgcct gtgaagtgac ccaccaggga   660
ctgtctagcc ccgtgaccaa gtctttcaac agaggcgagt gcggatcttc tggtggcgga   720
ggatctggcg gaggtggaag tagtggcggc gtgaccggct acagactgtt cgaagagatc   780
ctgtaatga                                                           789

SEQ ID NO: 9             moltype = DNA   length = 708
FEATURE                  Location/Qualifiers
source                   1..708
                         mol_type = other DNA
                         organism = synthetic construct
SEQUENCE: 9
atggaaaccg acacactgct gctgtgggtg ctgttgttgt gggtgccagg ctctaccggc    60
gacatccaga tgacccagtc tccatcctct ctgtctgcct ctgtgggcga cagagtgacc   120
atcacctgta gagcctctca gggcatctct agctggctgg cctggtatca gcagaagcct   180
gagaaggccc ctaagagcct gatctacgct gccagttctc tgcagtctgg cgtgccctct   240
agattctctg gctctggatc tggcaccgac ttcaccctga caatctctag cctgcagcct   300
gaggacttcg ccacctacta ctgccagcag tacaacagct accctcctac cttggccag   360
ggcaccaagc tggaaatcaa gagaaccgtg gccgctcctc ccgtgttcat cttcccacca   420
tctgacgagc agctgaagtc cggcacagct tctgtcgtgt gcctgctgaa caacttctac   480
cctcgggaag ccaaggtgca gtggaaggtg gacaatgccc tgcagtccgg caactcccaa   540
gagtctgtga ccgagcagga ctccaaggac tctacctaca gcctgtcctc cacactgacc   600
ctgtctaagg ccgactacga aagcacaag gtgtacgcct gtgaagtgac ccaccaggga   660
ctgtctagcc ccgtgaccaa gtctttcaac agaggcgagt gctaatga                708

SEQ ID NO: 10            moltype = DNA   length = 1254
FEATURE                  Location/Qualifiers
source                   1..1254
                         mol_type = other DNA
                         organism = synthetic construct
SEQUENCE: 10
atggaaaccg acacactgct gctgtgggtg ctgttgttgt gggtgccagg atctacagga    60
caggtgcagt tggtgcagtc tggcgccgaa gtgaagaaac tggcgcttc tgtgaaggtg   120
tcctgcaagg cctctggcta ctccttcacc aactactaca tccactgggt ccgacaggcc   180
cctggacaga gattggagtg gatgggctgg atcaacgccg gaacggcaa caccaagtac   240
tcccagaaat tccagggcag agtgaccatc accagagaca cctctgcctc caccgcctac   300
atggaactgt ccagcctgag atctgaggac accgccgtgt actactgcgt gcggagacag   360
cggttcccct actactttga ttattgggc cagggcaccc tggtcaccgt gtcctctgct   420
tctacaaagg gcccctctgt gttccctctg gctccttcct ctaaatccac ctctggcgga   480
acagctgctc tgggctgtct ggtcaaggac tactttccg agctcggtgt cgtgtcttgg   540
aactctggtg ctctgacatc cggcgtgcac accttccag ctgtgctgca gtcctctggc   600
ctgtactctc tgtcctctgt cgtgaccgtg ccttctagct ctctgggcac ccagacctac   660
atctgcaacg tgaaccacaa gccttctaac accaaggtgg acaagagagt ggaacccaag   720
tcttgcggat cttctggtgg cggaggatct ggcgagggc gatctagtgg cggagtgttc   780
accctggaag atttcgtcgg cgattggag cagaccgcc cctataatct ggaccaggtt   840
ctggaacaag gcggggtgtc ctctctgctg cagaatctgg ctgtgtctgt gaccccatc   900
cagagaatcg tgcgctctgg cgagaacgcc ctgaagatcg acatccacgt gatcatccct   960
tacgagggcc tgtctgccga tcagatggct cagatcgaag aggtgttcaa ggtggtgtac  1020
cccgtggacg accaccactt caaagtgatc ctgccttacg gcaccctcgt gatcgatggc  1080
gtgaccccaa acatgctgaa ctacttcggc agaccctacg aggaatgc cgtgttcgac   1140
ggcaagaaaa tcaccgtgac cggcacactg tggaacggaa acaagatcat cgacgagcgg  1200
ctgatcaccc ctgacggctc tatgctgttt agagtgacaa tcaactccta atga          1254

SEQ ID NO: 11            moltype = DNA   length = 789
FEATURE                  Location/Qualifiers
```

```
source                    1..789
                          mol_type = other DNA
                          organism = synthetic construct
SEQUENCE: 11
atggaaaccg acacactgct gctgtgggtg ctgttgttgt gggtgccagg atctacaggc   60
gagatcgtgc tgacccagtc tcctgccaca ttgtctgtgt ctcccggcga gagagctacc  120
ctgtcttgta gagcttctca gtccgtgggc accaacgtgg cctggtatca gcagaaacct  180
ggacaggccc ctcgggtgct gatctactct acctcttcta gagccaccgg catcaccgac  240
agattctctg gctctggatc tggcaccgac ttcaccctga ccatctccag actggaacct  300
gaggacttcg ccgtgtacta ctgccagcag ttcaacaagt cccctctgac ctttggcgga  360
ggcaccaagg tggaaatcaa gagaaccgtg gccgctcctt ccgtgttcat cttcccacca  420
tctgacgagc agctgaagtc cggcacagct tctgtcgtgt gcctgctgaa caacttctac  480
cctcgggaag ccaaggtgca gtggaaggtg gacaatgccc tgcagtccgg caactcccaa  540
gagtctgtga ccgagcagga ctccaaggac tctacctaca gcctgtcctc cacactgacc  600
ctgtctaagg ccgactacga gaagcacaag gtgtacgcct gtgaagtgac ccaccaggga  660
ctgtctagcc ccgtgaccaa gtctttcaac agaggcgagt gcggatcttc tggtggcgga  720
ggaagcggag gcggaggatc atctggcgga gtgaccggct acagactgtt cgaagagatc  780
ctgtaatga                                                          789

SEQ ID NO: 12              moltype = DNA   length = 708
FEATURE                    Location/Qualifiers
source                     1..708
                           mol_type = other DNA
                           organism = synthetic construct
SEQUENCE: 12
atggaaaccg acacactgct gctgtgggtg ctgttgttgt gggtgccagg atctacaggc   60
gagatcgtgc tgacccagtc tcctgccaca ttgtctgtgt ctcccggcga gagagctacc  120
ctgtcttgta gagcttctca gtccgtgggc accaacgtgg cctggtatca gcagaaacct  180
ggacaggccc ctcgggtgct gatctactct acctcttcta gagccaccgg catcaccgac  240
agattctctg gctctggatc tggcaccgac ttcaccctga ccatctccag actggaacct  300
gaggacttcg ccgtgtacta ctgccagcag ttcaacaagt cccctctgac ctttggcgga  360
ggcaccaagg tggaaatcaa gagaaccgtg gccgctcctt ccgtgttcat cttcccacca  420
tctgacgagc agctgaagtc cggcacagct tctgtcgtgt gcctgctgaa caacttctac  480
cctcgggaag ccaaggtgca gtggaaggtg gacaatgccc tgcagtccgg caactcccaa  540
gagtctgtga ccgagcagga ctccaaggac tctacctaca gcctgtcctc cacactgacc  600
ctgtctaagg ccgactacga gaagcacaag gtgtacgcct gtgaagtgac ccaccaggga  660
ctgtctagcc ccgtgaccaa gtctttcaac agaggcgagt gctaatga              708

SEQ ID NO: 13              moltype = DNA   length = 1251
FEATURE                    Location/Qualifiers
source                     1..1251
                           mol_type = other DNA
                           organism = synthetic construct
SEQUENCE: 13
atggaaaccg acacactgct gctgtgggtg ctgctcttgt gggtgccagg atctacagga   60
caggtgcagc tggtggaatc tggtggcgga gttgtgcagc ctggcagatc cctgagactg  120
tcttgtgccg cctccggctt cacctttctcc agctacacca tgcactgggt ccgacaggcc  180
cctggcaaag gattggagtg ggtcaccttc atctcttacg acggcaacaa caagtactac  240
gccgactccg tgaagggcag attcaccatc tctcgggaca actccaagaa caccctgtac  300
ctgcagatga actccctgag agccgaggac accgccatct actactgtgc tagaaccggc  360
tggctgggcc cctttgatta ttggggacag ggcaccctgg tcaccgtgtc ctctgcttct  420
accaagggac ccagcgtgtt ccctctggct ccttccagca gtctacctc tggcggaaca  480
gctgctctgg gctgcctggt caaggactac tttcctgagc ctgtgaccgt gtcttggaac  540
tctggcgctc tgacatccgg cgtgcacaca tttccagctg tgctgcagtc ctccggcctg  600
tactctctgt cctctgtcgt gaccgtgcct tccagctctc tgggaaccca gacctacatc  660
tgcaatgtga accacaagcc ttccaacacc aaggtggaca agagagtgga acccaagtcc  720
tgcggatctt ctgcggcgg aggatctggg ggaggtggta gttcaggcgg agtgttcacc  780
ctggaagatt tctcggcga ctgggagcag accgccgcct ataatctgga ccaggtgctg  840
gaacaaggcg gcgttagttc cctgctgcag aacctggtgt ctgtgacccc tatccag     900
agaatcgtgc ggagcggcga gaacgccctg aagatcgata tccacgtgat catccccttac  960
gagggcctga cgccgatca gatggctcag atcgaagagg tgttcaaggt ggtgtacccc 1020
gtggacgacc accacttcaa agtgatcctg ccttacggca cccctcgtgat cgatggcgtg 1080
accccaaaca tgctgaacta cttcggcaga ccctacgagg aatcgccgt gttcgacggc 1140
aagaaaatca ccgtgaccgg cacactgtgg aatggcaaca agatcatcga cgagcggctg 1200
atcaccctg acggctccat gctgttcaga gtgaccatca cagctgatg a            1251

SEQ ID NO: 14              moltype = DNA   length = 792
FEATURE                    Location/Qualifiers
source                     1..792
                           mol_type = other DNA
                           organism = synthetic construct
SEQUENCE: 14
atggaaaccg acacactgct gctgtgggtg ctgttgttgt gggtgccagg atctacaggc   60
gagatcgtgc tgacccagtc tcctggcaca ttgtctgtgt ctcccggcga gagagctacc  120
ctgtcttgca gagcttccca gtccgtggga tcttcctacc tggcctggta tcagcagaag  180
cctggacagg ctcccagact gctgatctac ggcgcctttt ctagagccac aggcatccct  240
gacagattct ccggctctgg ctctggcacc gacttcaccc tgaccatctc tagactggaa  300
cccgaggact tcgccgtgta ctactgccag cagtatggc ctctcttg gaccttgga  360
cagggcacca aggtggaaat caagagaacc gtggccgctc cttccgtgtt catcttccca  420
```

```
ccatctgacg agcagctgaa gtccggcaca gcttctgtcg tgtgcctgct gaacaacttc    480
taccctcggg aagccaaggt gcagtggaag gtggacaatg ccctgcagtc cggcaactcc    540
caagagtctg tgaccgagca ggactccaag gactctacct acagcctgtc ctccacactg    600
accctgtcta aggccgacta cgagaagcac aaggtgtacg cctgtgaagt gacccaccag    660
ggactgtcta gccccgtgac caagtctttc aacagaggcg agtgcggatc ttctggtggc    720
ggaggatctg gcggaggcgg atctagtggc ggagtgaccg gctacagact gttcgaagag    780
atcctgtaat ga                                                        792

SEQ ID NO: 15              moltype = DNA    length = 711
FEATURE                    Location/Qualifiers
source                     1..711
                           mol_type = other DNA
                           organism = synthetic construct
SEQUENCE: 15
atggaaaccg acacactgct gctgtgggtg ctgctcttgt gggtgccagg atctacaggc     60
gagatcgtgc tgacccagtc tcctggcaca ctgtcactgt ctccaggcga gagagctacc    120
ctgtcctgta gagcctctca gtccgtgggc tcctcttacc tggcttggta tcagcagaag    180
cccggccagg ctcctagact gttgatctac ggcgccttct ccagagccac aggcatccct    240
gatagattct ccggctctgg ctctggcacc gacttcaccc tgaccatctc cagactggaa    300
cccgaggact tcgccgtgta ctactgtcag cagtacggct cctctccttg gacctttggc    360
cagggcacca aggtggaaat caagcggaca gtggccgctc cttccgtgtt catcttccca    420
ccttccgacg agcagctgaa gtccggcaca gcttctgtcg tgtgcctgct gaacaacttc    480
taccctcggg aagccaaggt gcagtggaag gtggacaatg ccctgcagtc cggcaactcc    540
caagagtctg tgaccgagca ggactccaag gacagcacct acagcctgtc ctccacactg    600
accctgtcca aggccgacta cgagaagcac aaggtgtacg cctgcgaagt gacccatcag    660
ggcctgtcta gccctgtgac caagtctttc aaccggggcg agtgctgatg a             711

SEQ ID NO: 16              moltype = DNA    length = 1248
FEATURE                    Location/Qualifiers
source                     1..1248
                           mol_type = other DNA
                           organism = synthetic construct
SEQUENCE: 16
atggaaaccg acacactgct gctgtgggtg ctgttgttgt gggtgccagg atctacaggc     60
gaagtgcagt tggtgcagtc tggcgccgaa gtgaagaagc ctggcgagtc cctgaagatc    120
tcctgcaaag gctccggcta catcttcacc aactactgga tcgcctgggt ccgacagatg    180
cctggcaaag gcctggaatc catgggcatc atctaccccg gcgactccga catcagatac    240
agcccatctt tccagggcca agtgaccatc tccgccgaca gtatctcac  accgcctac     300
ctgcagtggt cctctctgaa ggcctctgac accgccatgt actactgcgc cagacagac    360
atcgagggct tcgattattg gggcagaggc accctggtca ccgtgtcctc tgcttctaca    420
aagggccccc tgtgttccc  tctggctcct tcctctaaat ccacctctgg cggaaccgct    480
gctctgggct gtctggtcaa ggattacttc cctgagcctg tgaccgtgtc ttggaactct    540
ggtgctctga catccggcgt gcacaccttt ccagctgtcc tgcagtcctc tggcctgtac    600
tctctgtcct ctgtcgtgac cgtgccttct agctctctgg gcacccagac ctacatctgc    660
aacgtgaacc acaagccttc caacaccaag gtggacaaga gagtgaaacc caagtcttgc    720
ggatcttctg gtgcggagg atctggcgga ggcggatcta gtggcggagt gttcaccctg    780
gaagatttcg tcggcgcatt ggagcagacc gccgcctata atctggacca ggttctggaa    840
caaggcggcg tcagctctct gctgcagaat ctggctgtgt ctgtgacccc tatccagaga    900
atcgtgcgct ctggcgagaa cgctctgaag atcgacatcc acgtgatcat cccttacgag    960
ggcctgtctg ccgatcagat ggctcagatc gaagaggtgt tcaaggtggt gtaccccgtg   1020
gacgaccacc acttcaaagt gatcctgcct tacgacgtgt cctgtgatca tggcgtgaag   1080
ccaaacatgc tgaactactt cggcagacc  tacgagggaa tcgccgtgtt cgacggcaag   1140
aaaatcaccg tgaccggcac actgtggaac ggcaacaaga tcatcgacga gcggctgatc   1200
accctgacg  gctctatgct gttccgcgtg accatcaact cctaatga               1248

SEQ ID NO: 17              moltype = DNA    length = 792
FEATURE                    Location/Qualifiers
source                     1..792
                           mol_type = other DNA
                           organism = synthetic construct
SEQUENCE: 17
atggaaaccg acacactgct gctgtgggtg ctgttgttgt gggtgccagg atctacaggc     60
gagatcgtgc tgacccagtc tcctggcaca ttgtctctga gtcctggcga gagagctacc    120
ctgtcttgca gagcttccca gtccgtgtcc tctagctct ggcctggta tcagcagaag     180
cccggacagg ctcctagact gctgatctac ggcgcctctt ctagagccac aggcatccct    240
gatagactgt ccggctctgg ctctggcacc gactttaccc tgaccatcac cagactggaa    300
cccgaggact tcgccgtgta ctactgccag cagtacgact cctctgccat cacctttggc    360
cagggcacaa gactggaaat caagagaacc gtggccgctc cttccgtgtt catcttccca    420
ccatctgacg agcagctgaa gtccggcaca gcttctgtcg tgtgcctgct gaacaacttc    480
taccctcggg aagccaaggt gcagtggaag gtggacaatg ccctgcagtc cggcaactcc    540
caagagtctg tgaccgagca ggactccaag gactctacct acagcctgtc ctccacactg    600
accctgtcta aggccgacta cgagaagcac aaggtgtacg cctgtgaagt gacccaccag    660
ggactgtcta gccccgtgac caagtctttc aacagaggcg agtgcggatc ttctggtggc    720
ggaggatctg gcggaggcgg atctagtggc ggagtgaccg gctacagact gttcgaagag    780
atcctgtaat ga                                                        792

SEQ ID NO: 18              moltype = DNA    length = 711
FEATURE                    Location/Qualifiers
source                     1..711
```

```
                        mol_type = other DNA
                        organism = synthetic construct
SEQUENCE: 18
atggaaaccg acacactgct gctgtgggtg ctgttgttgt gggtgccagg atctacaggc  60
gagatcgtgc tgacccagtc tcctggcaca ttgtctctga gtcctggcga gagagctacc 120
ctgtcttgca gagcttccca gtccgtgtcc tctagcttct tcgcctggta tcagcagaag 180
cccggacagg ctcctagact gctgatctac ggcgcctctt ctagagccac aggcatccct 240
gatagactgt ccggctctgg ctctggcacc gactttaccc tgaccatcac cagactggaa 300
cccgaggact cgccgtgta ctactgccag cagtacgact cctctgccat cacctttggc 360
cagggcacaa gactggaaat caagagaacc gtgccgctc cttccgtgtt catcttccca 420
ccatctgacg agcagctgaa gtccggcaca gcttctgtcg tgtgcctgct gaacaacttc 480
taccctcggg aagccaaggt gcagtggaag gtggacaatg ccctgcagtc cggcaactcc 540
caagagtctg tgaccgagca ggactccaag gactctacct acagcctgtc ctccacactg 600
accctgtcta aggccgacta cgagaagcac aaggtgtacg cctgtgaagt gacccaccag 660
ggactgtcta gccccgtgac caagtctttc aacagaggcg agtgctaatg a           711

SEQ ID NO: 19           moltype = DNA  length = 1245
FEATURE                 Location/Qualifiers
source                  1..1245
                        mol_type = other DNA
                        organism = synthetic construct
SEQUENCE: 19
atggaaaccg acacactgct gctgtgggtg ctgttgttgt gggtgccagg atctacagga  60
caggtgcagt tggtgcagtc tggcgccgaa gtgaagaaac ctggcgcttc tgtgaaggtg 120
tcctgcaagg cctctggcta cacctttacc agctactcca tctcctgggt ccgacaggct 180
cctggacaag gattggagtg gatgggctgg atctccgtct acaacggcaa caccaactac 240
gcccagaaat tccagggcag agtgaccatg accaccgaca cctctacctc caccgcctac 300
ctggaactga tccctgag atctgacgac accgccgtgt actactgcgc cagagatcct 360
atcgctgctg gctattgggg acagggcaca ctggttaccg tgtcctctgc ttctaccaag 420
ggaccctctg tgttccctct ggctccttcc agcaagtcta cctctggtgg aaccgctgct 480
ctggctgtc tggtcaagga ttacttccct gagcctgtga ccgtgtcttg gaactctggt 540
gctctgacct ccggcgtgca cacatttcca gctgtgctgc agtcctccgg cctgtactct 600
ctgtcctctg tcgtgaccgt gccttctagc tctctgggca cccagaccta catctgcaac 660
gtgaaccaca agcttccaa caccaaggtg gacaagagag tggaacccaa gtctgcggga 720
tcttctggtg gcggaggatc tggcggaggt ggaagtagtg gcggagtgtt caccctggta 780
gatttcgtcg gcgattggga gcagaccgcc gcctataatc tggaccaggt tctggaacaa 840
ggcggcgtca gctctctgct gcagaatctg gctgtgtctg tgaccccat ccagagaatt 900
gtgcgctctg gcgagaacgc cctgaagatc gacatccacg tgatcatccc ttacgagggc 960
ctgtctgccg atcagatggc tcagatcgaa gaggtgttca aggtggtcta cccgtggac 1020
gaccaccact tcaaagtgat cctgccttac ggcaccctgg tcatcgatgg cgtgacccca 1080
aacatgctga actacttcgg cagaccctac gagggaatcg ccgtgttcga cggcaagaaa 1140
atcaccgtga ccggcacact gtggaacgga aacaagatca tcgacgagcg gctgatcacc 1200
cctgacggct ctatgctgtt ccgcgtgacc atcaactcct aatga                 1245

SEQ ID NO: 20           moltype = DNA  length = 792
FEATURE                 Location/Qualifiers
source                  1..792
                        mol_type = other DNA
                        organism = synthetic construct
SEQUENCE: 20
atggaaaccg acacactgct gctgtgggtg ctgttgttgt gggtgccagg atctacaggc  60
gagatcgtgc tgacccagtc tcctggcaca ttgtctctga gtcctggcga gagagctacc 120
ctgtcttgca gagcttccca gtccgtgtcc tctacctacc tggcctggta tcagcagaag 180
cctggacagg ctcccagact gctgatctac ggcgcctctt ctagagccac aggcatccct 240
gacagattct ccggctctgg ctctggcacc gacttcaccc tgaccatctc tagactggaa 300
cccgaggact cgccgtgta ctactgccag cagtatggc cctctcctcg gacctttgga 360
cagggcacca aggtggaaat caagagaacc gtgccgctc cttccgtgtt catcttccca 420
ccatctgacg agcagctgaa gtccggcaca gcttctgtcg tgtgcctgct gaacaacttc 480
taccctcggg aagccaaggt gcagtggaag gtggacaatg ccctgcagtc cggcaactcc 540
caagagtctg tgaccgagca ggactccaag gactctacct acagcctgtc ctccacactg 600
accctgtcta aggccgacta cgagaagcac aaggtgtacg cctgtgaagt gacccaccag 660
ggactgtcta gccccgtgac caagtctttc aacagaggcg agtgcggatc ttctggtggc 720
ggaggatctg gcggaggcgg atctagtggc ggagtgaccg ctacagact gttcgaagag 780
atcctgtaat ga                                                      792

SEQ ID NO: 21           moltype = DNA  length = 711
FEATURE                 Location/Qualifiers
source                  1..711
                        mol_type = other DNA
                        organism = synthetic construct
SEQUENCE: 21
atggaaaccg acacactgct gctgtgggtg ctgttgttgt gggtgccagg atctacaggc  60
gagatcgtgc tgacccagtc tcctggcaca ttgtctctga gtcctggcga gagagctacc 120
ctgtcttgca gagcttccca gtccgtgtcc tctacctacc tggcctggta tcagcagaag 180
cctggacagg ctcccagact gctgatctac ggcgcctctt ctagagccac aggcatccct 240
gacagattct ccggctctgg ctctggcacc gacttcaccc tgaccatctc tagactggaa 300
cccgaggact cgccgtgta ctactgccag cagtatggc cctctcctcg gacctttgga 360
cagggcacca aggtggaaat caagagaacc gtgccgctc cttccgtgtt catcttccca 420
ccatctgacg agcagctgaa gtccggcaca gcttctgtcg tgtgcctgct gaacaacttc 480
```

```
taccctcggg aagccaaggt gcagtggaag gtggacaatg ccctgcagtc cggcaactcc    540
caagagtctg tgaccgagca ggactccaag gactctacct acagcctgtc ctccacactg    600
accctgtcta aggccgacta cgagaagcac aaggtgtacg cctgtgaagt gacccaccag    660
ggactgtcta gccccgtgac caagtctttc aacagaggcg agtgctaatg a             711

SEQ ID NO: 22           moltype = DNA   length = 1254
FEATURE                 Location/Qualifiers
source                  1..1254
                        mol_type = other DNA
                        organism = synthetic construct
SEQUENCE: 22
atggaaaccg acacactgct gctgtgggtg ctgttgttgt gggtgccagg atctacaggc     60
caggtccagc tgcaagaatc tggccctgga ctggtcaagc cttctggcac cctgtctctg    120
acatgtgctg tgtccggcgg ctccatctcc tcctctaatt ggtggtcttg ggtccgacag    180
cctcctggca aaggactgga atggatcggc gagatctacc actccggctc caccaactac    240
aaccccagcc tgaagtccag agtgaccatc tccgtggaca gtccaagaa ccagttctcc     300
ctgaagctgt cctctgtgac cgctgccgat accgccgtgt actactgtgc tagatggacc    360
ggcagaaccg acgcctttga tatctggggc cagggcacaa tggtcaccgt gtcctctgct    420
tctaccaagg gaccctctgt gttccctctg gctccttcca gcaagtctac ctctggtgga    480
accgctgctc tgggctgcct ggtcaaggat tactttcctg agcctgtgac cgtgtcttgg    540
aactctggtg ctctgacctc cggcgtgcac acatttccag ctgtgctgca gtctagcggc    600
ctgtactctc tgtctagcgt cgtgaccgtg ccttctgctt ctgggcactc cagacctac    660
atctgcaacg tgaaccacaa gccttccaac accaaggtgg acaagagagt ggaacccaag    720
tcttgcggat cttctggtgg cggaggatct ggcggaggtg aagtagtgg cggagtgttc     780
accctggaag atttcgtcgg cgattgggag cagaccgccg cctataatct ggaccaggtt    840
ctggaacaag gcgcgtcag ctctctgctg cagaatcctg ctgtgtctgt gaccctatc     900
cagagaatcg tgcgctctgg cgagaacgcc ctgaagatcg acatccacgt gatcatccct    960
tacgagggcc tgtctgccga tcagatggct cagatcgaag aggtgttcaa ggtggtgtac    1020
cccgtggacg accaccactt caaagtgatc ctgcccttacg gcaccctggt catcgatggc    1080
gtgaccccaa acatgctgaa ctacttcggc agacccctacg agggaatcgc cgtgttcgac    1140
ggcaagaaaa tcaccgtgac cggcacactg tggaacggca acaagatcat cgacgagcgg    1200
ctgatcaccc ctgacggctc tatgctgttc cgcgtgacca tcaactccta atga           1254

SEQ ID NO: 23           moltype = DNA   length = 804
FEATURE                 Location/Qualifiers
source                  1..804
                        mol_type = other DNA
                        organism = synthetic construct
SEQUENCE: 23
atggaaaccg acacactgct gctgtgggtg ctgttgttgt gggtgccagg atctacaggc     60
gacgtcgtga tgacccagtc tcctctgtct ctgcctgtga cacctggcga gcctgcctcc    120
atctcttgca gatcttctca gtccctgctg cactccaacg gctacaacta cctggactgg    180
tatctgcaga agcccggcca gtctccacag ctgctgatct acctgggctc taacagagcc    240
tctggcgtgc ccgatagatt ctctggctct ggatctggca ccgacttcac cctgaagatc    300
tccagagtgg aagccgagga cgtgggcgtg tactactgta tgcagggcac ccactggcct    360
ctgaccttg acagggcac caaggtgaa atcaagagaa ccgtggccgc tccttccgtg      420
ttcatcttcc caccatctga cgagcagctg aagtccggca cagcttctgt cgtgtgcctg    480
ctgaacaact tctacccteg ggaagccaag gtgcagtgga aggtggacaa tgccctgcag    540
tccggcaact cccaagagtc tgtgaccgag caggactcca aggactctac ctacagcctg    600
tcctccacac tgaccctgtc taaggccgac tacgagaagc acaaggtgta cgcctgtgaa    660
gtgacccacc agggactgtc tagccccgtg accaagtctt tcaacagagg cgagtgcgga    720
tcttctggtg gcggaggatc tggcggaggt ggaagtagtg gcggcgtgac cggctacaga    780
ctgttcgaag agatcctgta atga                                           804

SEQ ID NO: 24           moltype = DNA   length = 723
FEATURE                 Location/Qualifiers
source                  1..723
                        mol_type = other DNA
                        organism = synthetic construct
SEQUENCE: 24
atggaaaccg acacactgct gctgtgggtg ctgttgttgt gggtgccagg atctacaggc     60
gacgtcgtga tgacccagtc tcctctgtct ctgcctgtga cacctggcga gcctgcctcc    120
atctcttgca gatcttctca gtccctgctg cactccaacg gctacaacta cctggactgg    180
tatctgcaga agcccggcca gtctccacag ctgctgatct acctgggctc taacagagcc    240
tctggcgtgc ccgatagatt ctctggctct ggatctggca ccgacttcac cctgaagatc    300
tccagagtgg aagccgagga cgtgggcgtg tactactgta tgcagggcac ccactggcct    360
ctgaccttg acagggcac caaggtgaa atcaagagaa ccgtggccgc tccttccgtg      420
ttcatcttcc caccatctga cgagcagctg aagtccggca cagcttctgt cgtgtgcctg    480
ctgaacaact tctacccteg ggaagccaag gtgcagtgga aggtggacaa tgccctgcag    540
tccggcaact cccaagagtc tgtgaccgag caggactcca aggactctac ctacagcctg    600
tcctccacac tgaccctgtc taaggccgac tacgagaagc acaaggtgta cgcctgtgaa    660
gtgacccacc agggactgtc tagccccgtg accaagtctt tcaacagagg cgagtgctaa    720
tga                                                                  723

SEQ ID NO: 25           moltype = DNA   length = 1263
FEATURE                 Location/Qualifiers
source                  1..1263
                        mol_type = other DNA
                        organism = synthetic construct
```

SEQUENCE: 25
```
atggaaaccg acacactgct gctgtgggtg ctgttgttgt gggtgccagg atctacaggc  60
gaagtgcagt tgttgcagtc tggcggagga ttggttcagc ctggcggatc tctgagactg  120
tcttgtgccg cctccggctt catgttcagc agatacccta tgcactgggt ccgacaggcc  180
cctggaaaag gactggaatg ggtcggatct atctctgcga gtgccggcgc taccccttac  240
gctgattctg tgaagggcag attcaccatc agccgggaca actccaagaa cacccctgtac 300
ctgcagatga actccctgag agccgaggac accgccgtgt actactgcgc caaggacttc  360
tatcagatcc tgaccggcaa cgccttcgat tattgggggcc agggcacaac cgtgaccgtg  420
tcctctgctt ctaccaaggg accctctgtg ttccctctgg ctccttccag caagtctacc  480
tctggtggaa ccgctgctct gggctgcctg gtcaaggatt actttcctga gcctgtgaca  540
gtgtcctgga actctggtgc tctgacctcc ggcgtgcaca catttccagc tgtgctgcag  600
tcctccggcc tgtactctct gtcctctgtc gtgacagtgc cttccagctc tctgggcacc  660
cagacctaca tctgcaacgt gaaccacaag ccttccaaca ccaaggtgga caagagagtg  720
gaaccaaagt cttgcgatc ttctggtggc ggtggaagtg gcggaggtgg aagttcaggc  780
ggagtgttca ccctcgaaga tttcgtcggc gattgggagc agaccgccgc ctataatctg  840
gaccaggttc tggaacaagg cggcgttagc tctctgctgc agaatctggc tgtgtctgtg  900
accccctatcc agagaatcgt gcgctctggc gagaacgccc tgaagatcga catccacgtg  960
atcatccctt acgaggcct gtctgccgat cagatgctc agatcgaaga ggtgttcaag 1020
gtggtgtacc ccgtgacga ccaccacttc aaagtgatcc tgccttacgg caccctggtc 1080
atcgatggcg tgaccccaaa catgctgaac tacttcggca gaccctacga ggaatcgcc  1140
gtgttcgacg gcaagaaaat caccgtgaca ggcaccctgt ggaacggcaa cagatcatc  1200
gacgagcggc tgatcacccc tgacggctct atgctgttca gagtgaccat caactcctaa 1260
tga                                                              1263
```

SEQ ID NO: 26    moltype = DNA   length = 789
FEATURE         Location/Qualifiers
source          1..789
                mol_type = other DNA
                organism = synthetic construct
SEQUENCE: 26
```
atggaaaccg acacactgct gctgtgggtg ctgttgttgt gggtgccagg ctctaccggc  60
gacatccaga tgacccagtc tccaagctct gtgtctgcct ctctgggcga cagagtgacc  120
atcacctgta gagcctctca gggcatctcc tcctacctgg cctggtatca gcagaagcct  180
ggcaaggctc ccaagctgct gatctacgct aagtctaccc tgcagtccgg cgtgccctcc  240
agatttctg gctctggatc tggcaccgac ttcaccctga ccatcagttc tctgcagcct  300
gaggactccg ccacctacta ctgtcagcag tactggacct ttcctctgac cttcggcgga  360
ggcaccaagg tggaaatcaa agaaccgtg ccgctcctt ccgtgttcat cttcccacca  420
tctgacgagc agctgaagtc cggcacagct tctgtcgtgt gcctgctgaa caacttctac  480
cctcgggaag ccaaggtgca gtggaaggtg gacaatgcc tgcagcgcaa caactcccaa  540
gagtctgtga ccgagcagga ctccaaggac tctacctaca gcctgtcctc cacactgacc  600
ctgtctaagg ccgactacga aagcacaag gtgtacgcct gtgaagtgac ccaccaggga  660
ctgtctagcc ccgtgaccaa gtctttcaac agaggcgagt gcggatcttc tggcggcgga  720
ggaagcggag gcgaggatc tagcggcgga gttaccggct acagactgtt cgaagagatc  780
ctgtaatga                                                        789
```

SEQ ID NO: 27    moltype = DNA   length = 708
FEATURE         Location/Qualifiers
source          1..708
                mol_type = other DNA
                organism = synthetic construct
SEQUENCE: 27
```
atggaaaccg acacactgct gctgtgggtg ctgctcttgt gggtgccagg atctaccggc  60
gacatccaga tgacccagtc tccatcctct ctgtctgcca gctgggcga cagagtgacc  120
atcacctgta gagcctctca gggcatctcc tcctacctgg cctggtatca gcagaagcct  180
ggcaaggctc ccaagctgct gatctacgcc aagagcacac tgcagtctgg cgtgccctcc  240
agattctccg gctctggctc tggcaccgac tttaccctga caatctccag cctgcagcct  300
gaggactccg ccacctacta ctgtcagcag tactggacct ttccactgac cttcggcgga  360
ggcaccaagg tggaaatcaa agaaccgtg ccgctcctt ccgtgttcat cttccccacct  420
tccgacgagc agctgaagtc cggcacagct tctgtcgtgt gcctgctgaa caacttctac  480
cctcgggaag ccaaagtgca gtggaaggtg gacaacgctc tgcagtccgg caactcccaa  540
gagtctgtga ccgagcagga ctccaaggac agcacctaca gcctgtcctc cacactgacc  600
ctgtccaagg ccgactacga aagcacaag gtgtacgcct cgaagtgac ccatcaggc  660
ctgtctagcc ctgtgaccaa gtctttcaac cggggcgagt gctgatga              708
```

SEQ ID NO: 28    moltype = DNA   length = 1251
FEATURE         Location/Qualifiers
source          1..1251
                mol_type = other DNA
                organism = synthetic construct
SEQUENCE: 28
```
atggaaaccg acacactgct gctgtgggtg ctgttgttgt gggtgccagg atctacaggc  60
gaagtgcagt tggttcagtc tggcggagga ctggttaagc ctggcggatc tctgagactg  120
tcttgtgccg cctctggctt caccttctct agctttgcca tgcactgggt ccgacaggcc  180
cctggaaaag gcctggaatg gatctccgtg atcgataca ccggcactac gaccactcag  240
gactctgtga aggcagatt caccatctct cgggacaacg ccaagaactc cctgtacctg  300
cagatgaaca gcctgagagc cgaggacacc gccgtgtact attgtgccag actgggcaac  360
ttctactacg gcatggatgt gtggggccag ggcacaacag tgaccgtgtc ctctgcttct  420
accaaggac cctctgtgtt ccctctggct ccttccagca gtctacctc tggtggaacc  480
gctgctctgg gctgcctggt caaggattac tttcctgagc ctgtgacagt gtcctggaac  540
```

```
tctggtgctc tgacctccgg cgtgcacaca tttccagctg tgctgcagtc ctctggcctg    600
tactctctgt cctctgtcgt gaccgtgcct tctagctctc tgggcaccca gacctacatc    660
tgcaacgtga accacaagcc ttccaacacc aaggtggaca agagagtgga acccaagtct    720
tgcggatctt ctggtggcgg tggaagcgga ggcggaggat ctagtggcgg agtgttcacc    780
ctggaagatt tcgtcggcga ttgggagcag accgccgcc ataatctgga ccaggttctg    840
gaacaaggcg cgtcagctc tctgctgcag aatctggctg tgtctgtgac ccctatccag    900
agaatcgtgc gctctggcga gaacgccctg aagatcgaca tccacgtgat catcccttac    960
gagggcctgt ctgccgatca gatggctcag atcgaagagg tgttcaaggt ggtgtacccc   1020
gtggacgacc accacttcaa agtgatcctg ccttacggca ccctggtcat cgatggcgtg   1080
acccccaaaca tgctgaacta cttcggcaga ccctacgagg aatcgccgt gttcgacggc   1140
aagaaaatca ccgtgaccgg cacactgtgg aacggcaaca agatcatcga cgagcggctg   1200
atcacccctg acggctccat gctgtttaga gtgaccatca actcctaatg a            1251

SEQ ID NO: 29          moltype = DNA    length = 789
FEATURE                Location/Qualifiers
source                 1..789
                       mol_type = other DNA
                       organism = synthetic construct
SEQUENCE: 29
atggaaaccg acacactgct gctgtgggtg ctgttgttgt gggtgccagg atctacaggc     60
gagatcgtgc tgacccagtc tcctggcaca ttgtctgtgt ctcccggcga gagagctacc    120
ctgtcttgta gagcttccca gtccatcggc tccagcctgc actggtatca gcagaaacct    180
ggacaggccc ctcggctgct gattaagtac gcctctcagt ccctgtctgg catccctgac    240
agattctctg gctctggctc cggcaccgac ttcaccctga caatctctag actggaaccc    300
gaggacttcg ccgtgtacta ctgccaccag tctagcagac tgcctcacac cttggccag    360
ggcaccaagg tggaaatcaa gagaaccgtg gccgctcctt ccgtgttcat cttcccacca    420
tctgacgagc agctgaagtc tggcaccgct tctgtcgtgt gcctgctgaa caacttctac    480
cctcgggaag ccaaggtgca gtggaaggtg gacaatgccc tgcagtccgg caactcccaa    540
gagtctgtga ccgagcagga ctccaaggac tctacctaca gcctgtcctc cacactgacc    600
ctgtctaagg ccgactacga aagcacaag gtgtacgcct gtgaagtgac ccaccaggga    660
ctgtctagcc ccgtgaccaa gtcttcaac agaggcgagt gcggatcttc tggtggcgga    720
ggatctggcg gaggtggaag tagtggcggc gtgaccgct acagactgtt cgaagagatc    780
ctgtaatga                                                            789

SEQ ID NO: 30          moltype = DNA    length = 708
FEATURE                Location/Qualifiers
source                 1..708
                       mol_type = other DNA
                       organism = synthetic construct
SEQUENCE: 30
atggaaaccg acacactgct gctgtgggtg ctgttgttgt gggtgccagg atctacaggc     60
gagatcgtgc tgacccagtc tcctggcaca ttgtctgtgt ctcccggcga gagagctacc    120
ctgtcttgta gagcttccca gtccatcggc tccagcctgc actggtatca gcagaaacct    180
ggacaggccc ctcggctgct gattaagtac gcctctcagt ccctgtctgg catccctgac    240
agattctctg gctctggctc cggcaccgac ttcaccctga caatctctag actggaaccc    300
gaggacttcg ccgtgtacta ctgccaccag tctagcagac tgcctcacac cttggccag    360
ggcaccaagg tggaaatcaa gagaaccgtg gccgctcctt ccgtgttcat cttcccacca    420
tctgacgagc agctgaagtc tggcaccgct tctgtcgtgt gcctgctgaa caacttctac    480
cctcgggaag ccaaggtgca gtggaaggtg gacaatgccc tgcagtccgg caactcccaa    540
gagtctgtga ccgagcagga ctccaaggac tctacctaca gcctgtcctc cacactgacc    600
ctgtctaagg ccgactacga aagcacaag gtgtacgcct gtgaagtgac ccaccaggga    660
ctgtctagcc ccgtgaccaa gtctttcaac agaggcgagt gctaatga                708

SEQ ID NO: 31          moltype = DNA    length = 1251
FEATURE                Location/Qualifiers
source                 1..1251
                       mol_type = other DNA
                       organism = synthetic construct
SEQUENCE: 31
atggaaaccg acacactgct gctgtgggtg ctgttgttgt gggtgccagg atctaccgga     60
caggtggaac tggttgaatc tggtggcgga gtggtgcagc ctggcagatc tcagagactg    120
tcttgtgccg cctctggctt caccttctcc tcttacggca tgcactgggt ccgacaggcc    180
cctggaaaag actggaatgg gtcgccatc atttggttcg acggctcctc tacctactac    240
gccgattctg tgcggggcag attcaccatc tctcgggaca actccaagaa caccctgtac    300
ctgcagatga actccctgag agccgaggat accgccgtga cttctgtgc cagagagctg    360
gggagaagat acttcgatct gtggggcaga ggcaccctgg tgtctgtgtc ctctgcttct    420
accaagggac ccagcgttt ccctctggct ccatcctcta gtccacctc tggtggaacc    480
gctgctctgg gctgtctggt caaggattac ttccctgagc ctgtgaccgt gtcctggaac    540
tctggtgctc tgacatccgg cgtgcacacc tttccagctg tgctgcagtc ctctggcctg    600
tactctctgt cctctgtcgt gaccgtgcct tcttctagcc tgggcaccca gacctacatc    660
tgcaacgtga accacaagcc ttccaacacc aaagtggaca agagagtgga acccaagtct    720
tgcggatctt ctggcggcgg aggaagcgga ggcggaggat ctagcggcgg agtgttcacc    780
ctggaagatt tcgtcggcga ttgggagcag accgccgcct ataatctgga ccaggttctg    840
gaacaaggcg cgtcagctc tctgctgcag aatctggctg tgtctgtgac ccctatccag    900
agaatcgtgc gctctggcga gaacgccctg aagatcgaca tccacgtgat catcccttac    960
gagggcctgt ctgccgatca gatggcccag attgaagagg tgttcaaggt ggtgtacccc   1020
gtggacgacc accacttcaa agtgatcctg ccttacggca ccctcgtgat cgatggcgtg   1080
acccccaaaca tgctgaacta cttcggcaga ccctacgagg aatcgccgt gttcgatggc   1140
aagaaaatca ccgtgaccgg cacactgtgg aacggcaaca agatcatcga cgagcggctg   1200
```

```
atcacccctg acggctctat gctgttcaga gtgaccatca actcctaatg a           1251

SEQ ID NO: 32           moltype = DNA   length = 792
FEATURE                 Location/Qualifiers
source                  1..792
                        mol_type = other DNA
                        organism = synthetic construct
SEQUENCE: 32
atggaaaccg acacactgct gctgtgggtg ctgttgttgt gggtgccagg atctacaggc   60
gagatcgtgc tgacccagtc tcctgccaca ttgtctctga gtcctggcga gagagctacc  120
ctgtcttgca gagcttccca gtccgtgtcc tcctacctgg cctggtatca gcagaaacct  180
ggacaggccc ctcggctgct gatctacgat gcttctaaga gagccacagg catccccgcc  240
agattttctg gctctggatc tggcaccgac ttcaccctga ccatctctag cctggaacct  300
gaggacttcg ccgtgtacta ctgccagcag agatccaagt ggcctccttg gacctttgga  360
cagggcacca aggtggaatc taagagaacc gtggccgctc cttccgtgtt catcttccca  420
ccatctgacg agcagctgaa gtccggcaca gcttctgtcg tgtgcctgct gaacaacttc  480
taccctcggg aagccaaggt gcagtggaag gtggacaatg ccctgcagtc cggcaactcc  540
caagagtctg tgaccgagca ggactccaag gactctacct acagcctgtc ctccacactg  600
accctgtcta aggccgacta cgagaagcac aaggtgtacg cctgtgaagt gacccaccag  660
ggactgtcta gccccgtgac caagtctttc aacagaggcg agtgcggatc ttctggtggc  720
ggaggatctg gcggaggcgg atctagtggc ggagtgaccg gctacagact gttcgaagag  780
atcctgtaat ga                                                      792

SEQ ID NO: 33           moltype = DNA   length = 711
FEATURE                 Location/Qualifiers
source                  1..711
                        mol_type = other DNA
                        organism = synthetic construct
SEQUENCE: 33
atggaaaccg acacactgct gctgtgggtg ctgttgttgt gggtgccagg atctacaggc   60
gagatcgtgc tgacccagtc tcctgccaca ttgtctctga gtcctggcga gagagctacc  120
ctgtcttgca gagcttccca gtccgtgtcc tcctacctgg cctggtatca gcagaaacct  180
ggacaggccc ctcggctgct gatctacgat gcttctaaga gagccacagg catccccgcc  240
agattttctg gctctggatc tggcaccgac ttcaccctga ccatctctag cctggaacct  300
gaggacttcg ccgtgtacta ctgccagcag agatccaagt ggcctccttg gacctttgga  360
cagggcacca aggtggaatc taagagaacc gtggccgctc cttccgtgtt catcttccca  420
ccatctgacg agcagctgaa gtccggcaca gcttctgtcg tgtgcctgct gaacaacttc  480
taccctcggg aagccaaggt gcagtggaag gtggacaatg ccctgcagtc cggcaactcc  540
caagagtctg tgaccgagca ggactccaag gactctacct acagcctgtc ctccacactg  600
accctgtcta aggccgacta cgagaagcac aaggtgtacg cctgtgaagt gacccaccag  660
ggactgtcta gccccgtgac caagtctttc aacagaggcg agtgctaatg a           711

SEQ ID NO: 34           moltype = DNA   length = 1245
FEATURE                 Location/Qualifiers
source                  1..1245
                        mol_type = other DNA
                        organism = synthetic construct
SEQUENCE: 34
atggaaaccg acacactgct gctgtgggtg ctgttgttgt gggtgccagg atctacaggc   60
gaggtgcagt tggttgaatc tggcggagga ctggtgcagc ctggcagatc tctgagactg  120
tcttgcgccg cctccagatt caccttcgac gattacgcca tgcactgggt ccgacaggcc  180
cctggaaaag gattggagtg ggtgtccggc atctcctgga actctggcag aatcggctac  240
gccgactccg tgaagggcag attcacaatc tcccgggaca cgccgagaa ctccctgttc  300
ctgcagatga atggcctgag agccgaggac accgctctgt actattgcgc caagggcaga  360
gactccttcg atatctgggg ccagggcacc atggtcaccg tgtcctctgc ttctaccaag  420
ggaccctctg tgttccctct ggctccttcc agcaagtcta cctctggtgg aaccgctgct  480
ctgggctgcc tggtcaagga ttactttcct gagcctgtga ccgtgtcttg gaactccggt  540
gctctgacat ccggcgtgca cacatttcca gctgtgctgc agtcctctgg cctgtactct  600
ctgtcctctg tcgtgaccgt gccttctagc tctctgggca cccagaccta catctgcaac  660
gtgaaccaca agccttccaa caccaaggtg gacaagagag tggaaccaa gtcttgcgga  720
tcttctggtg gcggtggaag cggaggcgga ggatctagtg gcggagtgtt cacccctgga a  780
gatttcgtcg gcgattggga gcagaccgcc gcctataatc tggaccaggt tctgaacaa   840
ggcggcgtca gctctctgct gcagaatctg gctgtgtctg tgacccctat ccagagaatc  900
gtgcgctctg gcgagaacgc cctgaagatc gacatccacg tgatcatccc ttaccaggac  960
ctgtctgccg atcagatggc tcagatcgaa gaggtgttca aggtggtgta ccccgtggac  1020
gaccaccact tcaaagtgat cctgcctac ggcaccctgg tcatcgatgg cgtgaccccaa  1080
aacatgctga actacttcgg cagacccac gagggaatcg ccgtgttcga cggcaagaaa  1140
atcaccgtga ccggcacact gtggaacggc aacaagatca tcgacgagcg gctgatcacc  1200
cctgacggct ctatgctgtt cagagtgacc atcaactcct aatga                  1245

SEQ ID NO: 35           moltype = DNA   length = 789
FEATURE                 Location/Qualifiers
source                  1..789
                        mol_type = other DNA
                        organism = synthetic construct
SEQUENCE: 35
atggaaaccg acacactgct gctgtgggtg ctgttgttgt gggtgccagg ctctaccggc   60
gacatccaga tgacccagtc tccatcctct gtgtctgcct ctgtgggcga cagagtgacc  120
atcacctgta gagcctctca gggcatctct agctggctgg cctggtatca gcagaagcct  180
```

```
ggaaaggccc ctaagctgct gatctacggc gcctcttctc tggaatctgg cgtgccctct     240
agattctccg gctctggctc tggcaccgac tttaccctga caatcagctc cctgcagcct     300
gaggacttcg cctcttacta ctgccagcag gccaacagct tccccctatac ctttggccag    360
ggcaccaagc tggaaatcaa gagaaccgtg gccgctcctt ccgtgttcat cttcccacca     420
tctgacgagc agctgaagtc cggcacagct tctgtccgtg gcctgctgaa caacttctac     480
cctcgggaag ccaaggtgca gtggaaggtg gacaatgccc tgcagtccgg caactcccaa     540
gagtctgtga ccgagcagga ctccaaggac tctacctaca gcctgtcctc cacactgacc     600
ctgtctaagg ccgactacga gaagcacaag gtgtacgcct gtgaagtgac ccaccaggga    660
ctgtctagcc ccgtgaccaa gtctttcaac agaggcgagt gcggatcttc tggtggcgga    720
ggatctggcg gaggtggaag tagtggcggc gtgaccggct acagactgtt cgaagagatc    780
ctgtaatga                                                             789

SEQ ID NO: 36          moltype = DNA  length = 708
FEATURE                Location/Qualifiers
source                 1..708
                       mol_type = other DNA
                       organism = synthetic construct
SEQUENCE: 36
atggaaaccg acacactgct gctgtgggtg ctgttgttgt gggtgccagg ctctaccggc     60
gacatccaga tgacccagtc tccatcctct gtgtctgcct ctgtgggcga cagagtgacc    120
atcacctgta gagcctctca gggcatctct agctggctgg cctggtatca gcagaagcct    180
ggaaaggccc ctaagctgct gatctacggc gcctcttctc tggaatctgg cgtgccctct    240
agattctccg gctctggctc tggcaccgac tttaccctga caatcagctc cctgcagcct    300
gaggacttcg cctcttacta ctgccagcag gccaacagct tccccctata cctttggccag   360
ggcaccaagc tggaaatcaa gagaaccgtg gccgctcctt ccgtgttcat cttcccacca    420
tctgacgagc agctgaagtc cggcacagct tctgtccgtg gcctgctgaa caacttctac    480
cctcgggaag ccaaggtgca gtggaaggtg gacaatgccc tgcagtccgg caactcccaa    540
gagtctgtga ccgagcagga ctccaaggac tctacctaca gcctgtcctc cacactgacc    600
ctgtctaagg ccgactacga gaagcacaag gtgtacgcct gtgaagtgac ccaccaggga    660
ctgtctagcc ccgtgaccaa gtctttcaac agaggcgagt gctaatga                 708

SEQ ID NO: 37          moltype = DNA  length = 1251
FEATURE                Location/Qualifiers
source                 1..1251
                       mol_type = other DNA
                       organism = synthetic construct
SEQUENCE: 37
atggaaaccg acacactgct gctgtgggtg ctgttgttgt gggtgccagg atctacaggc     60
gaggtgcagt tgttggaatc tggcggagga ttggtgcagc ctggcggatc tctgagactg    120
tcttgtgccg cctctggctt caccttctcc gcctatgaga tgaagtgggt ccgacaggct    180
cctggcaaag gactggaatg ggtgtccgtg attggcccct ctgcggcttt tacctttac     240
gccgactccg tgaagggcag attcaccatc tctcgggaca actccaagaa caccctgtac    300
ctgcagatga actccctgag agccgaggac accgccgtgt actattgtgc caccgagggc    360
gacaacgacg cctttgatat ttggggccag ggcaccaccg tgaccgtgtc ctctgcttct    420
acaaagggcc cctctgtgtt ccctctggct ccttcctcta aatccacctc tggcggaacc    480
gctgctctgg gctgtctggt caaggattac ttccctgagc ctgtgacagt gtcctggaac    540
tctggtgctc tgacatccgg cgtgcacacc tttccagctg tgctgcagtc ctctggcctg    600
tactctctgt cctctgtcgt gacagtgcct tccagctctc tgggcaccca gacctacatc    660
tgcaacgtga accacaagcc ttccaacacc aaggtggaca gagagtggga acccaagtct    720
tgcggatctt ccggcggagg tggaagtggc ggaggcggat caagcggcgg agtgttcaca    780
ctggaagatt tcgtcggcga ttgggagcag accgccgtca ccaggttctg                840
gaacaaggcg gcgttagctc tctgctgcag aatctggctg tgtctgtgac ccctatccag    900
agaatcgtgc gctctggcga aacgccctg aagatcgaca tccacgtgat catccccttac    960
gagggcctgt ctgccgatca gatggctcag atcgaagagg tgttcaaggt ggtgtacccc   1020
gtggacgacc accacttcaa agtgatcctg cttacggca ccctggtcat cgatggcgtg    1080
accccaaaca tgctgaacta cttcggcaga ccctacgagg gaatcgccgt gttcgacggc   1140
aagaaaatca ccgtgacagg caccctgtgg aacggcaaca agatcatcga cgagcggctg   1200
atcaccctg acggctctat gctgttcaga gtgaccatca ctcctaatg a               1251

SEQ ID NO: 38          moltype = DNA  length = 792
FEATURE                Location/Qualifiers
source                 1..792
                       mol_type = other DNA
                       organism = synthetic construct
SEQUENCE: 38
atggaaaccg acacactgct gctgtgggtg ctgttgttgt gggtgccagg atctacaggc     60
gatatccaga tgacccagtc tcctgccaca ttgtctctga gtcctggcga gagagctacc    120
ctgtcttgca gagcttccca gtccgtgtcc tcctacctgg cctggtatca gcagaaacct    180
ggacaggccc ctcggctgct gatctacgat gcctctaata gagccacagg catccccgcc    240
agattctctg gctctggatc tggcaccgac ttcaccctga ccatctctag cctgaacct     300
gaggacttcg ccgtgtacta ctgccagcag agatccaact ggcctatgta caccttcggc    360
cagggcacca agctggaaat caagagaacc gtggccgctc cttccgtgtt catcttccca    420
ccatctgacg agcagctgaa gtccggcaca gcttctgtcc gtgcctgct gaacaacttc    480
taccctcggg aagccaaggt gcagtggaag gtggacaatg ccctgcagtc cggcaactcc    540
caagagtctg tgaccgagca ggactccaag gactctacct acagcctgtc ctccacactg    600
accctgtcta aggccgacta cgagaagcac aaggtgtacg cctgtgaagt gacccaccag    660
ggactgtcta gccccgtgac caagtctttc aacagaggcg agtgcggatc ttctggtggc    720
ggaggaagcg gaggcggagg atcatctggc ggagtgaccg gctacagact gttcgaagag    780
atcctgtaat ga                                                        792
```

```
SEQ ID NO: 39          moltype = DNA  length = 711
FEATURE                Location/Qualifiers
source                 1..711
                       mol_type = other DNA
                       organism = synthetic construct
SEQUENCE: 39
atggaaaccg acacactgct gctgtgggtg ctgttgttgt gggtgccagg atctacaggc   60
gatatccaga tgacccagtc tcctgccaca ttgtctctga gtcctggcga gagagctacc  120
ctgtcttgca gagcttccca gtccgtgtcc tcctacctgg cctggtatca gcagaaacct  180
ggacaggccc ctcggctgct gatctacgat gcctctaata gagccacagg catccccgcc  240
agattctctg gctctggatc tggcaccgac ttcaccctga ccatctctag cctggaacct  300
gaggacttcg ccgtgtacta ctgccagcag agatccaact ggcctatgta caccttcggc  360
cagggcacca agctggaaat caagagaacc gtggccgctc cttccgtgtt catcttccca  420
ccatctgacg agcagctgaa gtccggcaca gcttctgtcg tgtgcctgct gaacaacttc  480
tacccctcgg aagccaaggt gcagtggaag gtggacaatg ccctgcagtc cggcaactcc  540
caagagtctg tgaccgagca ggactccaag gactctacct acagcctgtc ctccacactg  600
accctgtcta aggccgacta cgagaagcac aaggtgtacg cctgtgaagt gacccaccag  660
ggactgtcta gccccgtgac caagtctttc aacagaggcg agtgctaatg a           711

SEQ ID NO: 40          moltype = DNA  length = 1266
FEATURE                Location/Qualifiers
source                 1..1266
                       mol_type = other DNA
                       organism = synthetic construct
SEQUENCE: 40
atggaaaccg acacactgct gctgtgggtg ctgttgttgt gggtgccagg atctacaggc   60
gaggtgcagt tggttgaatc tggcggagga ttggtgcagc ctggcggatc tctgagactg  120
tcttgtgccg cctccggctt caccttctcc tcttacgcta tgtcctgggt ccgacaggct  180
cctggcaaag gattggaagt ggtgtcccag atttctcctg ctggccggcta caccaactac  240
gccgattctg tgaagggcag attcaccatc tccgccgaca cctccaagaa caccgcctac  300
ctgcagatga actccctgag agctgaggac accgccgtgt actattgtgc tagaggcgag  360
ctgccctact accggatgtc caaagtgatg gatgtgtggg gccagggcac actggttacc  420
gtgtcctctg cttctaccaa gggacccctct gtgttccctc tggctccttc cagcaagtct  480
acctctggtg gaaccgctgc tctgggctgc ctggtcaagg attactttcc tgagcctgtg  540
accgtgtctt ggaactctgg tgctctgacc tccggcgtgc acacatttcc agctgtgctg  600
cagtcctccg gcctgtactc tctgtcctct gtcgtgaccg tgccttctag ctctctgggc  660
acccagacct acatctgcaa cgtgaaccac aagccttcca cacccaaggt ggacaagaga  720
gtggaaccca gtcttgcgg atcttctggt ggcggtggaa gtggcggagg tggaagttca  780
ggcgagtgt tcaccctgga agatttcgtc ggcgattggg agcagaccgc cgcctataat  840
ctggaccagg ttctggaaca aggcggcgtc agctctctgc tgcagaatct ggctgtgtct  900
gtgaccccta tccagagaat cgtgcgctct ggcgagaacg ccctgaagat cgacatccac  960
gtgatcatcc cttacgaggg cctgtctgcc gatcagatgg ctcagatcga agaggtgttc 1020
aaggtggtgt accccgtgga cgaccaccac ttcaaagtga tcctgccttt cggcacgctg 1080
gtcatcgatg gcgtgacccc aaacatgctg aactacttcg gcagccccta cgagggaatc 1140
gccgtgttca cggcaagaa aatcaccgtg accggcacac tgtggaacgg caacaagatc 1200
atcgacgagc ggctgatcac ccctgacggc tctatgctgt cagagtgac catcaactcc 1260
taatga                                                            1266

SEQ ID NO: 41          moltype = DNA  length = 789
FEATURE                Location/Qualifiers
source                 1..789
                       mol_type = other DNA
                       organism = synthetic construct
SEQUENCE: 41
atggaaaccg acacactgct gctgtgggtg ctgttgttgt gggtgccagg ctctaccggc   60
gacatccaga tgacccagtc tccatcctct ctgtctgcct ctgtgggcga cagagtgacc  120
atcacctgtc gggcctctca gtacttctcc tcctacctgg cctggtatca gcagaagcct  180
ggcaaggctc ccaagctgct gatctacggc gcctcttcta gagccctcgg cgtgccatct  240
agattctccg gctctggctc tggcaccgac tttaccctga caatcagctc cctgcagcct  300
gaggacttcg ccacctacta ctgtcagcag tacctgggct ctcctccaac ctttggccag  360
ggcaccaagg tggaaatcaa gagaaccgtg gccgctcctt ccgtgttcat cttcccacca  420
tctgacgagc agctgaagtc cggcacagct tctgtcgtgt gcctgctgaa caacttctac  480
cctcgggaag ccaaggtgca gtggaaggtg gacaatgccc tgcagtccgg caactccaa  540
gagtctgtga ccgagcagga ctccaaggac tctacctaca gcctgtcctc cacactgacc  600
ctgtctaagg ccgactacga agcacaag gtgtacgcct gtgaagtgac ccaccaggga  660
ctgtctagcc ccgtgaccaa gtctttcaac agaggcgagt gcgatcttc tggtggcgga  720
ggatctggcg gaggtggaag tagtggcggc gtgaccggct acagactgtt cgaagagatc  780
ctgtaatga                                                          789

SEQ ID NO: 42          moltype = DNA  length = 708
FEATURE                Location/Qualifiers
source                 1..708
                       mol_type = other DNA
                       organism = synthetic construct
SEQUENCE: 42
atggaaaccg acacactgct gctgtgggtg ctgttgttgt gggtgccagg ctctaccggc   60
gacatccaga tgacccagtc tccatcctct ctgtctgcct ctgtgggcga cagagtgacc  120
atcacctgtc gggcctctca gtacttctcc tcctacctgg cctggtatca gcagaagcct  180
```

```
ggcaaggctc ccaagctgct gatctacggc gcctcttcta gagcctctgg cgtgccatct    240
agattctccg gctctggctc tggcaccgac tttaccctga caatcagctc cctgcagcct    300
gaggacttcg ccacctacta ctgtcagcag tacctgggct ctcctccaac ctttggccag    360
ggcaccaagg tggaaatcaa gagaaccgtg gccgctcctt ccgtgttcat cttcccacca    420
tctgacgagc agctgaagtc cggcacagct tctgtcgtgt gcctgctgaa caacttctac    480
cctcgggaag ccaaggtgca gtggaaggtg acaatgccc tgcagtccgg caactcccaa    540
gagtctgtga ccgagcagga ctccaaggac tctacctaca gcctgtcctc cacactgacc    600
ctgtctaagg ccgactacga aagcacaag gtgtacgcct gtgaagtgac ccaccaggga    660
ctgtctagcc ccgtgaccaa gtctttcaac agaggcgagt gctaatga               708

SEQ ID NO: 43         moltype = DNA  length = 1287
FEATURE               Location/Qualifiers
source                1..1287
                      mol_type = other DNA
                      organism = synthetic construct
SEQUENCE: 43
atggaaaccg acacactgct gctgtgggtg ctgttgttgt gggtgccagg atctacaggc    60
gaagtgcagt tggtgcagtc tggcgccgaa gtgaagaaac ctggctcctc tgtgaaggtg    120
tcctgcaagg cttctggcgg caccttctcc tcttacgcca tctcttgggt ccgacaggct    180
cctggacaag gcttggagtg gatgggcggc atcatcccta tcttcggcac cgccaactac    240
gcccagaaat tccagggcag agtgaccatc accgccgaca gtctacctc caccgcctac    300
atggaactgt ccagcctgag atctgaggac accgccgtc actactgtgc tagagcccct    360
ctgcggttcc tggaatggtc tacccaggac cactactact attactacat ggacgtgtgg    420
ggcaagggca ccaccgtgac agtttcttcc gcttccacca agggaccag cgttttccct    480
ctggctccat cctccaagtc cacctctggt ggaacagctg ctctgggctg cctggtcaag    540
gattactttc ctgagcctgt gaccgtgtcc tggaactctg gtgctctgac atccggagtg    600
cacacctttc cagctgtgct gcagtcctct ggcctgtact ctctgtcctc tgtcgtgacc    660
gtgccttcta gctctctggg cacccagacc tacatctgca acgtgaacca caagccttcc    720
aacaccaaag tggacaagag agtggaaccc aagtcttgcg atcttccgg tggcggagga    780
tctggcggag gtggaagtag tggcggagtg ttcacccgg aagatttcgt cggcgattgg    840
gagcagaccg ccgcctataa tctggaccag gttctggaac aaggcggcgt gtcctctctg    900
ctgcagaatc tggctgtgtc tgtgaccct atccagagaa tcgtgcgctc tggcgagaac    960
gccctgaaga tcgacatcca cgtgatcatc ccttacgagg cctgtctgc cgatcagatg    1020
gctcagatcg aagaggtgtt caaggtggtg taccccgtgg acgaccacca cttcaaagtg    1080
atcctgcctt acggcaccct ggtcatcgat ggcgttcaca caaacatgct gaactactcc    1140
ggcagaccct acgagggaat cgccgtgttc gacggcaaga aaatcaccgt gaccggcaca    1200
ctgtggaacg caacaagat catcgacgag cggctgatca ccctgacgg ctctatgctg    1260
tttagagtga caatcaactc ctaatga                                        1287

SEQ ID NO: 44         moltype = DNA  length = 789
FEATURE               Location/Qualifiers
source                1..789
                      mol_type = other DNA
                      organism = synthetic construct
SEQUENCE: 44
atggaaaccg acacactgct gctgtgggtg ctgttgttgt gggtgccagg ctctaccgga    60
tcctctgagt tgcacagga ccctgctgtg tctgtggctc tgggacagac agtgcggatt    120
acctgtcagg gcgactccct gagatcttac tacgccacct ggtatcagca gaagcccgga    180
caggctccca tcctggttat ctacggcgag aacaagcggc cctctggcat ccctgataga    240
ttctctggcc cctcctccgg caataccgcc tctctgacaa ttactggcgc ccaggctgag    300
gacgaggccg actactattg caagtccaga gatggctctg gccagcactt ggtgttttgc    360
ggcggaacaa aactgaccgt gctgggccag cctaaggcca atcctacagt gaccctgttt    420
cctccatcct ccgaggaact gcaggccaac aaggctaccc tcgtgtgcct gatctctgac    480
ttttaccctg gcgctgtgac cgtggcttgg aaggctgatg gatctcctgt gaaggccggc    540
gtggaaacca ccaagcctag caagcagtcc aacaacaaat acgccgcctc ctcctacctg    600
tctctgaccc ctgaacagtg gaagtccac cggtcctact cttgccaagt gacccatgag    660
ggctccaccg tggaaaagac agtggccct accgagtgct ctggatctc tggtggcgga    720
ggatctggcg gaggtggaag tagtggcggc gtgaccggct acagactgtt cgaagagatc    780
ctgtaatga                                                            789

SEQ ID NO: 45         moltype = DNA  length = 708
FEATURE               Location/Qualifiers
source                1..708
                      mol_type = other DNA
                      organism = synthetic construct
SEQUENCE: 45
atggaaaccg acacactgct gctgtgggtg ctgctcttgt gggtgccagg ctctaccgga    60
tcctctgagc tgcacagga ccctgctgtg tctgtggctc tgggccagac agtgcggatt    120
acctgtcagg gcgactccct gagatcctac tacgccacct ggtatcagca gaagcctgga    180
caggctccca tcctggtcat ctacggcgag aacaagcggc cctctggcat ccctgataga    240
ttctccggct cctccagcgg caataccgcc tctctgacaa ttaccggcgc tcaggctgag    300
gacgaggccg actactactg caagtccaga gatggctccg ccagcacct ggttttggc    360
ggaggaacaa agctgaccgt gctgggccag cctaaggcca atcctaccgt gacactgttc    420
cctccatcct ccgaggaact gcaggccaac aaggctacct cgtgtccga gatctccgac    480
ttttaccctg gcgctgtgac cgtggcctgg aaggctgatg gatctcctgt gaaggctggc    540
gtggaaacca ccaagccttc caagcagtcc aacaacaaat acgccgcctc ctcctacctg    600
tctctgaccc ctgaacagtg gaagtccac cggtcctaca gctgccaagt gacccatgag    660
ggctccaccg tggaaaagac cgtggctcct accgagtgct cctgatga                708
```

SEQ ID NO: 46             moltype = DNA   length = 1260
FEATURE                   Location/Qualifiers
source                    1..1260
                          mol_type = other DNA
                          organism = synthetic construct
SEQUENCE: 46
atggaaaccg acacactgct gctgtgggtg ctgttgttgt gggtgccagg atctacaggc    60
gaagtgcagt tggttcagtc tggcggcgga gttgaaagac ctggcggatc tctgagactg   120
tcttgtgccg cctctggctt caccttcgac gactacgcta tgtcctgggt ccgacaggct   180
cctggcaaag gattggaatg ggtgtccggc atcaactggc aaggcggctc taccggctac   240
gccgattctg tgaagggcag agtgaccatc tctcggacac acgccaagaa ctccctgtac   300
ctgcagatga cagcctgag agccgaggac accgccgtgt actactgtgc taagatcctc   360
ggcgctggcg aggctggta cttcgattat tggggcaagg gcaccaccgt gaccgtgtcc   420
tctgcttcta caaagggccc ctctgtgttc cctctgcctc cttcctctaa atccacctct   480
ggcggaaccg ctgctctggg ctgtctggtc aaggattact tccctgagcc tgtgacagtg   540
tcctggaact ctggtgctct gacatccggc gtgcacacct tccagctgt gctgcagtcc   600
tctggcctgt actctctgtc ctctgtcgtg acagtgcctt ccagctctct gggcacccag   660
acctacatct gcaacgtgaa ccacaagcct tccaacacca aggtggacaa gagagtggaa   720
cccaagtctt gtgatcttc tggcggaggt ggaagcggag gcggaggatc aagtggcgga   780
gtgttcaccc tggaagattt cgtcggcgat tgggagcaga ccgccgccta taatctggac   840
caggttctgg aacaaggcgg cgttagctct ctgctgcaga atctggctgt gtctgtgacc   900
cctatccaga gaatcgtgcg ctctcgcgag aacgccctga agatcgacat ccacgtgatc   960
atcccttacg agggcctgtc tgccgatcag atggctcaga tcgaagaggt gttcaaggtg  1020
gtgtaccccg tggacgacca ccacttcaaa gtgatcctgc cttacggcac cctggtcatc  1080
gatggcgtga ccccaaacat gctgaactac ttcggcagac cctacgaggg aatcgccgtg  1140
ttcgacggca agaaaatcac cgtgacaggc accctgtgga acggcaacaa gatcatcgac  1200
gagcggctga tcaccctga cggctccatg ctgtttcgct gaccatcaa ctcctaatga   1260

SEQ ID NO: 47             moltype = DNA   length = 789
FEATURE                   Location/Qualifiers
source                    1..789
                          mol_type = other DNA
                          organism = synthetic construct
SEQUENCE: 47
atggaaaccg acacactgct gctgtgggtg ctgttgttgt gggtgccagg ctctaccgga    60
tcctctgagt tgacacagga ccctgctgtg tctgtggctc tgggacagac agtgcggatc   120
acctgttccg gcgactccct gagatcttac tacgcctcct ggtatcagca gaagcctgga   180
caggctcccg tgctggttat ctacggcgcc aacaacagac cttctggcat ccctgacaga   240
ttctccggct ccagctctgg caataccgcc tctctgacaa ttaccggcgc tcaggctgag   300
gacgaggccg actactactg caactctgcc gactcttccg gcaatcacgt tgtgtttggc   360
ggaggcacca agctgacagt gctgggccaa cctaaggcca atcctaccgt gacactgttc   420
cctccatcct ccgaggaact gcaggctaac aaggctaccc tcgtgtgcct gatctccgat   480
ttttaccctg gcgctgtgac cgtggcttgg aaggctgatc ttcctgt gaaggccggc    540
gtggaaacca ccaagcctag caagcagtcc aacaacaaat acgccgcctc ctcctacctg   600
tctctgaccc tgaacagtg gaagtcccac cggtcctact cttgccaagt gacccatgag   660
ggctccaccg tggaaaagac agtggcccct accgagtgct ctggatcttc tggtggcgga   720
ggaagcggag gcggaggatc atctggcgga gtgaccggct acagactgtt cgaagagatc   780
ctgtaatga                                                           789

SEQ ID NO: 48             moltype = DNA   length = 708
FEATURE                   Location/Qualifiers
source                    1..708
                          mol_type = other DNA
                          organism = synthetic construct
SEQUENCE: 48
atggaaaccg acacactgct gctgtgggtg ctgttgttgt gggtgccagg ctctaccgga    60
tcctctgagt tgacacagga ccctgctgtg tctgtggctc tgggacagac agtgcggatc   120
acctgttccg gcgactccct gagatcttac tacgcctcct ggtatcagca gaagcctgga   180
caggctcccg tgctggttat ctacggcgcc aacaacagac cttctggcat ccctgacaga   240
ttctccggct ccagctctgg caataccgcc tctctgacaa ttaccggcgc tcaggctgag   300
gacgaggccg actactactg caactctgcc gactcttccg gcaatcacgt tgtgtttggc   360
ggaggcacca agctgacagt gctgggccaa cctaaggcca atcctaccgt gacactgttc   420
cctccatcct ccgaggaact gcaggctaac aaggctaccc tcgtgtgcct gatctccgat   480
ttttaccctg gcgctgtgac cgtggcttgg aaggctgatc ttcctgt gaaggccggc    540
gtggaaacca ccaagcctag caagcagtcc aacaacaaat acgccgcctc ctcctacctg   600
tctctgaccc tgaacagtg gaagtcccac cggtcctact cttgccaagt gacccatgag   660
ggctccaccg tggaaaagac agtggcccct accgagtgct cttaatga                708

SEQ ID NO: 49             moltype = DNA   length = 1248
FEATURE                   Location/Qualifiers
source                    1..1248
                          mol_type = other DNA
                          organism = synthetic construct
SEQUENCE: 49
atggaaaccg acacactgct gctgtgggtg ctgttgttgt gggtgccagg atctacaggc    60
gaagtgcagt tggtgcagtc tggcgccgaa gtgaagaagc tggcgagtc cctgaagatc   120
tcctgcaaag gctccggcta ctccttctcc aactactgga tcggctgggt ccgacagatg   180
cctgcaaag gactggaatg gatgggcatc atcgaccccc caacagcta caccagatac   240
agccctagct ccaggggcca agtgaccatc tccgccgaca gtctatctc caccgcctac   300

```
ctgcagtggt cctctctgaa ggcctctgac accgccatgt actactgcgc cagatggtac    360
tacaagccct tcgatgtgtg gggcagggc acactggtta ccgtgtcctc tgcttctacc    420
aagggaccct ctgtgttccc tctggctcct ccagcaagt ctacctctgg tggaaccgct    480
gctctgggct gcctggtcaa ggattacttt cctgagcctg tgaccgtgtc ttggaactct    540
ggtgctctga cctccggcgt gcacacattt ccagctgtgc tgcagtcctc cggcctgtac    600
tctctgtcct ctgtcgtgac cgtgccttcc agctctctgg gcacccagac ctacatctgc    660
aacgtgaacc acaagccttc caacaccaag gtggacaaga gagtgaaacc caagtcttgc    720
ggatcttctg gtggcggagg atctggcgga ggtggaagta gtggcggagt gttcaccctg    780
gaagatttcg tcggcgattg ggagcagacc gccgccata atctggacca ggttctggaa    840
caaggcggcg tcagctctct gctgcagaat ctggctgtgt ctgtgacccc tatccagaga    900
atcgtgcgct ctggcgagaa cgctctgaag atcgacatcc acgtgatcat cccttacgag    960
ggcctgtctg ccgatcagat ggctcagatc gaagaggtgt tcaaggtggt gtaccccgtg   1020
gacgaccacc acttcaaagt gatcctgcct tacggcaccc tggtcatcga tggcgtgacc   1080
ccaaacatgc tgaactactt cggcagacct acgagggaa tcgacgtgtt cgacggcaag   1140
aaaatcaccg tgaccggcac actgtggaac ggcaacaaga tcatcgacga gcggctgatc   1200
accccttgacg gctctatgct gttccgcgtg accatcaact cctaatga                1248

SEQ ID NO: 50        moltype = DNA   length = 798
FEATURE              Location/Qualifiers
source               1..798
                     mol_type = other DNA
                     organism = synthetic construct
SEQUENCE: 50
atggaaaccg acacactgct gctgtgggtg ctgttgttgt gggtgccagg ctctacaggc      60
cagtctgttc tgactcagcc tccttctgtt tctggcgctc ctggcagag agtgaccatc     120
tcctgtaccg gctcctcctc taacatcggc tctggctacg tgcactg gtatcagcag       180
ctgcctggca cagcccctaa actgctgatc tacggcaact ccaagaggcc ttctggcgtg     240
cccgatagat ctctccggctc taagtctggc acctctgctt ctctggctat caccggcctg    300
cagtctgagg acgaggccga ttactactgc gcttcttgga ccgatggcct gagcctggtt    360
gtgtttggcg gcggaaacaaa gctgacagtg ctgggccagc ctaaggccaa tcctaccgtg    420
acactgttcc ctccatcctc cgaggaactg caggctaaca aggctaccct cgtgtgcctg    480
atctccgatt tttaccctgg cgctgtgacc gtggcttgga aggctgatgg atctcctgtg    540
aaggccggct ggaaaccac caagcctagc aagcagtcca acaacaaata cgccgcctcc    600
tcctacctgt ctctgaccce tgaacagtgg aagtccacc ggtcctactc ttgccaagtg    660
acccatgagg gctccaccgt ggaaaagaca gtgcccccta ccgagtgctc tggatcttct    720
ggtggcggag gatctggcgg aggtggaagt agtggcggcg tgaccggcta cagactgttc    780
gaagagatcc tgtaatga                                                    798

SEQ ID NO: 51        moltype = DNA   length = 717
FEATURE              Location/Qualifiers
source               1..717
                     mol_type = other DNA
                     organism = synthetic construct
SEQUENCE: 51
atggaaaccg acacactgct gctgtgggtg ctgttgttgt gggtgccagg ctctacaggc      60
cagtctgttc tgactcagcc tccttctgtt tctggcgctc ctggcagag agtgaccatc     120
tcctgtaccg gctcctcctc taacatcggc tctggctacg tgcactg gtatcagcag       180
ctgcctggca cagcccctaa actgctgatc tacggcaact ccaagaggcc ttctggcgtg     240
cccgatagat ctctccggctc taagtctggc acctctgctt ctctggctat caccggcctg    300
cagtctgagg acgaggccga ttactactgc gcttcttgga ccgatggcct gagcctggtt    360
gtgtttggcg gcggaaacaaa gctgacagtg ctgggccagc ctaaggccaa tcctaccgtg    420
acactgttcc ctccatcctc cgaggaactg caggctaaca aggctaccct cgtgtgcctg    480
atctccgatt tttaccctgg cgctgtgacc gtggcttgga aggctgatgg atctcctgtg    540
aaggccggct ggaaaccac caagcctagc aagcagtcca acaacaaata cgccgcctcc    600
tcctacctgt ctctgaccce tgaacagtgg aagtccacc ggtcctactc ttgccaagtg    660
acccatgagg gctccaccgt ggaaaagaca gtgccccta ccgagtgctc ttaatga        717

SEQ ID NO: 52        moltype = DNA   length = 1263
FEATURE              Location/Qualifiers
source               1..1263
                     mol_type = other DNA
                     organism = synthetic construct
SEQUENCE: 52
atggaaaccg acacactgct gctgtgggtg ctgttgttgt gggtgccagg atctacagga      60
caggtgcagt tggttcagtc tggcggagga cttgttcagc caggcggatc tctgagactg     120
tcttgtgccg cctctggctt caccttcgac gattacgcta tgcactggt ccgacaggcc     180
cctggaaaag gattggaatg ggtggccggc atctcctggg attctggctc taccggctac    240
gccgattccg tgaagggcag attcaccatc tctcgggaca acgccaagaa ctccctgtac    300
ctgcagatga acagcctgag agccgaggac accgccgtgt actactgtgc tagagatctg    360
ggcgcctacc agtgggtgga aggctttgat tattgggcc agggcaccct ggtcaccgtg    420
tcctctgctt ctacaaaggg ccccctctgtg ttccctctgg ctccttcctc taaatccacc    480
tctgcggaa ccgctgctct gggctgtctg gtcaaggatt acttccctga gcctgtgacc    540
gtgtcttgga actctggtgc tctgacatcc ggcgtgcaca cctttccagc tgtgctgcag    600
tcctctggac tgtactctct gtcctctgtc gtgaccgtgc cttctagctc tctgggcacc    660
cagacctaca tctgcaacgt gaaccacaag cctagcaaca ccaaggtgga caagagagtg    720
aaccccaagt cttgcggatc ttctggcggg gaggaagcg gaggcggagg atctagtggc    780
ggagtgttca ccctgaaaga tttcgtcggc gattgggagc agaccgccgc ctataatctg    840
gaccaggttc tggaacaagg cggcgtcagc tctctgctgc agaatctggc tgtgtctgtg    900
acccctatcc agagaatcgt gcgctctggc gagaacgccc tgaagatcga catccacgtg    960
```

```
atcatcccctt acgagggcct gtctgccgat cagatggctc agatcgaaga ggtgttcaag    1020
gtggtgtacc ccgtggacga ccaccacttc aaagtgatcc tgccttacgg cacccctcgtg   1080
atcgatggcg tgaccccaaa catgctgaac tacttcggca gacccctacga gggaatcgcc   1140
gtgttcgacg caagaaaat caccgtgacc ggcacactgt ggaacggcaa caagatcatc     1200
gacgagcggc tgatcacccc tgacggctcc atgctgttta gagtgaccat caactcctaa    1260
tga                                                                  1263

SEQ ID NO: 53         moltype = DNA   length = 792
FEATURE               Location/Qualifiers
source                1..792
                      mol_type = other DNA
                      organism = synthetic construct
SEQUENCE: 53
atggaaaccg acacactgct gctgtgggtg ctgttgttgt gggtgccagg ctctaccggc     60
tcttacgagt tgacacagga ccctgctgtg tctgtggctc tgggacagac agtgcggatt    120
acctgtcagg gcgactccct gagatcctac tacgcctcct ggtatcagca gaagcctgga    180
caggctcccg tgctggtcat ctacggcaag aacaacagac cctctggcat ccctgaccgg    240
ttctctcggct ctacctctgg caattccgcc agcctgacaa ttactggcgc tcaggctgag   300
gacgaggccg actactactg caactctaga gactcccctg caaccagtg ggtgttcggc     360
ggaggaacaa aagtgacagt gctcggcggc cagcctaagg ccaatcctac agtgaccctg    420
tttcctccat cctccgagga actgcaggcc aacaaggcta cccctcgtgtg cctgatctct   480
gacttttacc ctggcgctgt gaccgtggct tggaaggctg atggatctcc tgtgaaggct   540
ggcgtggaaa ccaccaagcc tagcaagcag tccaacaaca aatacgccgc ctcctcctac    600
ctgtctctga cccctgaaca gtggaagtcc caccggtcct actcttgcca agtgacccat   660
gagggctcca ccgtggaaaa gacagtggcc ctaccgagt gctctggatc ttctggtggc    720
ggaggatctg gcggaggtgg aagtagtggc ggcgtgaccg gctacagact gttcgaagag   780
atcctgtaat ga                                                         792

SEQ ID NO: 54         moltype = DNA   length = 711
FEATURE               Location/Qualifiers
source                1..711
                      mol_type = other DNA
                      organism = synthetic construct
SEQUENCE: 54
atggaaaccg acacactgct gctgtgggtg ctgctcttgt gggtgccagg ctctaccggc     60
tcttacgagc tgacacagga ccctgctgtg tctgtggctc tgggccagac agtgcggatt    120
acctgtcagg gcgactccct gagatcctac tacgcctcct ggtatcagca gaagcctgga    180
caggctcccg tgctggtcat ctacggcaag aacaaccggc ctagcggcat ccctgacaga    240
ttctctccggct ctacctccgg caactctgcc agcctgacaa ttactggcgc ccaggctgag  300
gacgaggccg actactactg caactccaga gactcccctg caaccagtg ggttttcggc     360
ggaggcacca aagtgacagt gctcggagga cagcccaagg ccaatcctac cgtgacactg    420
ttccctccat cctccgagga actgcaggcc aacaaggcta cccctcgtgtg cctgatctcc   480
gacttttacc ctggcgctgt gaccgtggcc tggaaggctg atggatctcc tgtgaaggct   540
ggcgtggaaa ccaccaagcc ttccaagcag tccaacaaca aatacgccgc ctcctcctac    600
ctgtctctga cccctgaaca gtggaagtcc caccggtcct acagctgcca agtgacccat   660
gagggctcca ccgtggaaaa gaccgtggct cctaccgagt gctcctgatg a              711

SEQ ID NO: 55         moltype = DNA   length = 1260
FEATURE               Location/Qualifiers
source                1..1260
                      mol_type = other DNA
                      organism = synthetic construct
SEQUENCE: 55
atggaaaccg acacactgct gctgtgggtg ctgttgttgt gggtgccagg ctctacaggc     60
gaagtgcagt tggttcagtc tggcggcgga gttgaaaagc ctggcggatc tctgagactg    120
tcttgtgccg cctctggctt caccttcgac gactatggca tgtcctgggt ccgacaggct    180
cctggcaaag gattgaatg ggtgtccgga atcaactgga atggcggctc taccggctac     240
gccgattctg tgaagggcag agtgaccatc tctcgggaca cgccaagaa ctccctgtac    300
ctgcagatga acagcctgag agccgacgac accgccgtgt actactgtgc taagatcctc    360
ggcgctggca gaggctggta tttcgatctg tggggcaagg gcaccaccgt gacagtgtcc    420
tctgcttcta ccaagggacc cagcgttttt cctctggctc catcctctaa gtccacctct    480
ggtgaaaccg ctgctctggg ctgtctggtc aaggattact ccctgagcc tgtgaccgtg    540
tcctggaact ctggtgctct gacatccggc gtgcacacct ttccagctgt gctgcagtcc    600
tctggcctgt actctctgtc ctctgtcgtg accgtgcctt ctagctctc gggcacccag    660
acctacatct gcaacgtgaa ccacaagcct tccaacacca aagtggacaa gagagtggaa    720
cccaagtcct gcgatcttc tgtggcgga ggatctggcg gaggtggaag tagtggcgga    780
gtgttccacc tggaagattt cgtcggcgat tgggagcaga ccgccgccta taatctggac    840
caggttctgg aacaaggcgg cgtgtcctct ctgctgcaga atctggctgt gtctgtgacc    900
cctatccaga gaatcgtgcg ctctggcgag aacgccctga gatgacat ccacgtgtcc    960
atcccttacg agggcctgtc tgccgatcag atggctcaga tcgaagaggt gttcaaggtg   1020
gtgtaccccg tggacgacca ccacttcaaa gtgatcctgc cttacggcac cctggtcatc   1080
gatggcgtga ccccaaacat gctgaactac ttcggcagac cctacgaggg aatcgccgtg   1140
ttcgacggca agaaaatcac cgtgaccggc acactgtgga cggcaacaa gatcatcgac   1200
gagcggctga tcacccctga cggctccatg ctgtttcgcg tgaccatcaa ctcctaatga   1260

SEQ ID NO: 56         moltype = DNA   length = 789
FEATURE               Location/Qualifiers
source                1..789
                      mol_type = other DNA
```

```
                      organism = synthetic construct
SEQUENCE: 56
atggaaaccg acacactgct gctgtgggtg ctgttgttgt gggtgccagg ctctaccgga    60
tcctctgagt tgacacagga ccctgctgtg tctgtggctc tgggacagac agtgcggatt   120
acctgtcagg gcgactccct gagatcctac tacgcctacc ggtatcagca gaagcctgga   180
caggctcccg tgctggtcat ctacggcaag aacaacagac cctctggcat ccctgaccgg   240
ttctccggat ctagctctgg caataccgcc agcctgacaa ttactggcgc tcaggctgag   300
gacgaggcca actactactg caactccaga gactcttccg caatcacgt ggtgtttggc    360
ggcggaacaa agctgacagt gctgggccag cctaaggcca atcctaccgt gacactgttc   420
cctccatcct ccgaggaact gcaggctaac aaggctaccc tcgtgtgcct gatctccgat   480
ttttaccctg gcgctgtgac cgtggcttgg aaggctgatg gatctcctgt gaaggccggc   540
gtggaaacca ccaagcctag caagcagtcc aacaacaaat acgccgcctc ctcctacctg   600
tctctgaccc tgaacagtg gaagtccac cggtcctact cttgccaagt gacccatgag    660
ggctccaccg tggaaaagac agtgcccct accgagtgct ctggatcttc tggtggcgga   720
ggatctggcg gaggtggaag tagtggcggc gtgaccggct acagactgtt cgaagagatc   780
ctgtaatga                                                           789

SEQ ID NO: 57          moltype = DNA    length = 708
FEATURE                Location/Qualifiers
source                 1..708
                       mol_type = other DNA
                       organism = synthetic construct
SEQUENCE: 57
atggaaaccg acacactgct gctgtgggtg ctgctcttgt gggtgccagg ctctaccgga    60
tcctctgagc tgacacagga ccctgctgtg tctgtggctc tgggcagac agtgcggatt    120
acctgtcagg gcgactccct gagatcctac tacgcctacc ggtatcagca gaagcctgga   180
caggctcccg tgctggtcat ctacggcaag aacaaccggc ctagcggcat ccctgacaga   240
ttctccggat cttccagcgg caataccgcc agcctgacaa ttactggcgc ccaggctgag   300
gacgaggcca actactactg caactccaga gactcctccg caatcacgt ggtgtttggc    360
ggcggaacaa agctgacagt gctgggccag cctaaggcca atcctaccgt gacactgttc   420
cctccatcct ccgaggaact gcaggccaac aaggctaccc tcgtgtgcct gatctccgac   480
ttttaccctg gcgctgtgac cgtggcctgg aaggctgatg gatctcctgt gaaggctggc   540
gtggaaacca ccaagcttc caagcagtcc aacaacaaat acgccgcctc ctcctacctg    600
tctctgaccc tgaacagtg gaagtccac cggtcctaca gctgccaagt gacccatgag    660
ggctccaccg tggaaaagac cgtggctcct accgagtgct cctgatga                708

SEQ ID NO: 58          moltype = DNA    length = 1242
FEATURE                Location/Qualifiers
source                 1..1242
                       mol_type = other DNA
                       organism = synthetic construct
SEQUENCE: 58
atggaaaccg acacactgct gctgtgggtg ctgttgttgt gggtgccagg atctacagga    60
caggtgcagt tggtgcagtc tggcgccgaa gtgaagaaac ctggcgcttc tgtgaaggtg   120
tcctgcaagg cctctggcta caccttacc tccagctaca tcaactgggt ccgacaggct    180
cctgacagg gacttgagtg gatgggcacc atcaatcctg tgtccggctc taccagctac   240
gcccagaaat tccagggcag agtgaccatg accagagaca cctccatctc caccgcctac   300
atggaactgt cccggctgag atctgacgac accgccgtgt actattgtgc cagaggcgga   360
tggttcgatt actggggaca gggcacactg gtcaccgtgt cctctgcttc taccaaggga   420
ccctctgtgt tccctctggc tccttccagc aagtctacct ctggtggaac cgctgctctg   480
ggctgcctgg tcaaggatta cttttcctgag cctgtgaccg tgtcttgaa ctctggtgct   540
ctgacctccg gcgtgcacac atttccagct gtgctgcagt cctccggcct gtactctctg   600
tcctctgtcg tgaccgtgcc ttcagctctct ctgggcaccc agacctacat ctgcaacgtg   660
aaccacaagc cttccaacac caaggtgac aagagagtgg aacccaagtc ttgcggatct    720
tctggtggcg gaggatctgg cggaggtgga agtagtgggc gagtgttcac cctggaagat   780
ttcgtcggcg attgggagca gaccgccgcc tataatctgg accaggttct ggaacaaggc   840
ggcgtcagct ctctgctgca gaatctggct gtgtctgtga cccctatcca gagaattgtg   900
cgctctggcg agaacgccct gaagatcgac atccacgtga tcatccctta cgagggcctg   960
tctgccgatc agatgctca gatcgaagag gtgttcaagg tggtgtaccc cgtggacgac  1020
caccacttca agtgatcct gccttacggc accctggtca tcgatggcgt gacccaaac   1080
atgctgaact acttcggcag accctacgag ggaatcgccg tgttcgacgg caagaaaatc  1140
accgtgaccg gcacactgtg gaacggcaac aagatcatcg acgagcggct gatcacccct  1200
gacggctcta tgctgttccg cgtgaccatc aactcctaat ga                    1242

SEQ ID NO: 59          moltype = DNA    length = 798
FEATURE                Location/Qualifiers
source                 1..798
                       mol_type = other DNA
                       organism = synthetic construct
SEQUENCE: 59
atggaaaccg acacactgct gctgtgggtg ctgttgttgt gggtgccagg ctctacaggc    60
cagtctgctt tgactcagcc tgcctctgtg tctggctccc ctggccagtc tatcaccatc   120
tcttgtaccg gcacctcctc cgacgtgggc tcctacaact acgtgaactg gtatcagcag   180
caccccggca aggcccctaa gctgatgatc tacggcgtgt ccaaacggcc cagcggagtg   240
tctaacagat tctccggctc caagtctggc aacaccgctt ctctgacaat cagcggactg   300
caggccgagg acgaggctga ttactactgt ggcaccttcg ctggcggctc ctactatggt   360
gttttggcg gcgaacaaa gctgaccgtg ctggccaac ctaaggccaa tcctaccgtg     420
acactgttcc tccatcctc cgaggaactg caggctaaca aggctaccct cgtgtgcctg   480
atctccgatt tttaccctgg cgctgtgacc gtggcttgga aggctgatgg atctcctgtg   540
```

```
aaggccggcg tggaaaccac caagcctagc aagcagtcca acaacaaata cgccgcctcc   600
tcctacctgt ctctgacccc tgaacagtgg aagtcccacc ggtcctactc ttgccaagtg   660
acccatgagg gctccaccgt ggaaaagaca gtgcccccta ccgagtgctc tggatcttct   720
ggtggcggag gatctggcgg aggtggaagt agtggcggcg tgaccggcta cagactgttc   780
gaagagatcc tgtaatga                                                 798

SEQ ID NO: 60           moltype = DNA  length = 717
FEATURE                 Location/Qualifiers
source                  1..717
                        mol_type = other DNA
                        organism = synthetic construct
SEQUENCE: 60
atggaaaccg acacactgct gctgtgggtg ctgttgttgt gggtgccagg ctctacaggc    60
cagtctctgc ttgactcagc ctgcctctgt gtctggctcc ctggccagtc tatccaccatc  120
tcttgtaccg gcacctcctc cgacgtgggg tcctacaact acgtgaactg gtatcagcag   180
cacccccggca aggcccctaa gctgatgatc tacggcgtgt ccaaacgggcc agcggagtg   240
tctaacagat tctccggctc caagtctggc aacaccgctt ctctgacaat cagcggactg   300
caggccgagg acgaggctga ttactactgt ggcaccttcg ctgccggctc ctactatggt   360
gttttttggcg gcggaacaaa gctgaccgtg ctgggccaac taaggccaaa tcctaccgtg   420
acactgttcc ctccatcctc cgaggaactg caggctaaca aggctaccct cgtgtgcctg   480
atctccgatt tttaccctgg cgctgtgacc gtggcttgga aggctgatgg atctcctgtg   540
aaggccggcg tggaaaccac caagcctagc aagcagtcca acaacaaata cgccgcctcc   600
tcctacctgt ctctgacccc tgaacagtgg aagtcccacc ggtcctactc ttgccaagtg   660
acccatgagg gctccaccgt ggaaaagaca gtgcccccta ccgagtgctc ttaatga      717

SEQ ID NO: 61           moltype = DNA  length = 1245
FEATURE                 Location/Qualifiers
source                  1..1245
                        mol_type = other DNA
                        organism = synthetic construct
SEQUENCE: 61
atggaaaccg acacactgct gctgtgggtg ctgttgttgt gggtgccagg ctctacaggc    60
gaagtgcagt tggtgcagtc tggcgccgaa gtgaagaaac ctggctcctc tgtgaaggtg   120
tcctgcaagg cttctggcgg caccttctcc tcttacgcca tctcttgggt ccgacaggct   180
cctggacaag gcttggagtg gatgggcggc atcggcccttt ttttcggcac cgccaactac   240
gcccagaaat tccagggcag agtgaccatc accgccgacg agtctacctc caccgcttac   300
atggaactgt ccagcctgag atctgaggac accgccgtgt actactgcgc cagagacacc   360
ccttacttcg attattgggg ccagggcacc ctggtcaccg tgtcctctgc ttctacaaag   420
ggcccctctg tgttccctct ggctcctagc tctaagtcta catctggcgg aaccgctgct   480
ctgggctgcc tggtcaagga ttactttcct gagcctgtga ccgtgtcttg gaactctggt   540
gctctgacct ccggcgtgca cacatttcca gctgtgctgc agtcctccgg cctgtactct   600
ctgtcctctg tcgtgaccgt gccttctagc tctctgggca cccagaccta catctgcaac   660
gtgaaccaca agccttccaa caccaaggtg gacaagagag tggaacccaa gtcttgcgga   720
tcttccggtg gcggaggaag cggaggcgga ggatctagtg gcggagtgtt cacccctggaa  780
gatttcgtcg gcgattggga gcagaccgcc gcctataatc tggaccaggt tctgaacaa    840
ggcggggtgt cctctctgct gcagaatctg gctgtgtctg tgacccccta t ccagagaatc  900
gtgcgctctg gcgagaacgc cctgaagatc gacatccacg tgatcatccc ttacgagggc  960
ctgtctgccg atcagatggc tcagatcgaa gaggtgttca aggtggtgta ccccgtggac  1020
gaccaccact tcaaagtgat cctgccttac ggcaccctcg tgatcgatgg cgtgacccca  1080
aacatgctga actacttcgg cagacccttac gagggaatcg ccgtgttcga cggcaagaaa  1140
atcaccgtga ccggcacact gtggaacggc aacaagatca tcgacgagcg gctgatcacc  1200
cctgacggct ctatgctgtt tagagtgaca atcaactcct aatga                   1245

SEQ ID NO: 62           moltype = DNA  length = 789
FEATURE                 Location/Qualifiers
source                  1..789
                        mol_type = other DNA
                        organism = synthetic construct
SEQUENCE: 62
atggaaaccg acacactgct gctgtgggtg ctgttgttgt gggtgccagg ctctaccggc    60
tcttatgagc tgacacagcc tctgtctgtg tctgtggctc tgggccagac cgccagaatc   120
acctgtctg gcgacagcat ccccaactac tacgtgtact ggtatcagca gaagcccggc   180
caggctcctg tgctggtcat ctacgacgac tccaacagac ccagcggcat ccctgagaga   240
ttctctccggct ctaactctgg caacaccgcc acactgacca tctctagac acaggcccgac  300
gacgaggccg actactactg ccagtctttc gacagctctc tgaacgccga agtgttcggc   360
ggaggcacaa aactgacagt gctgggccag cctaaggcca atcctaccgt gacactgttc   420
cctccatcct ccgaggaact gcaggctaac aaggctaccc tcgtgtgcct gatctccgat   480
ttttaccctg gcgctgtgac cgtggcttgg aaggctgatg gatctcctgt gaaggccggc   540
gtggaaacca ccaagcctag caagcagtcc aacaacaaat acgccgcctc ctcctacctg   600
tctctgaccc ctgaacagtg gaagtcccac cggtcctact cttgccaagt gacccatgag   660
ggctccaccg tggaaaagac agtgccccct accgagtgct ctggatcttc tggtggcgga   720
ggatctggcg gaggtggaag tagtggcggc gtgaccggct acagactgtt cgaagagatc   780
ctgtaatga                                                           789

SEQ ID NO: 63           moltype = DNA  length = 708
FEATURE                 Location/Qualifiers
source                  1..708
                        mol_type = other DNA
                        organism = synthetic construct
```

```
SEQUENCE: 63
atggaaaccg acacactgct gctgtgggtg ctgttgttgt gggtgccagg ctctaccggc   60
tcttatgagc tgacacagcc tctgtctgtg tctgtggctc tgggccagac cgccagaatc  120
acctgttctg cgacagcat  ccccaactac tacgtgtact ggtatcagca gaagcccggc  180
caggcctctg tgctggtcat ctacgacgac tccaacagac ccagcggcat ccctgagaga  240
ttctccggct ctaactctgg caacaccgcc acactgacca tctctagagc acaggctggc  300
gacgaggccg actactactg ccagtctttc gacagctctc tgaacgccga agtgttcggc  360
ggaggcacaa aactgacagt gctgggccag cctaaggcca tcctaccgt  gacactgttc  420
cctccatcct ccgaggaact gcaggctacc tcgtgtgcct gatctccgat             480
ttttaccctg gcgctgtgac cgtggctgg aaggctgatg gatctcctgt gaaggccggc   540
gtggaaacca ccaagcctag caagcagtcc aacaacaaat acgccgcctc ctcctacctg  600
tctctgaccc tgaacagtg  gaagtcccac cggtcctact cttgccaagt gacccatgag  660
ggctccaccg tggaaaagac agtggcccct accgagtgct cttaatga               708

SEQ ID NO: 64           moltype = DNA  length = 1239
FEATURE                 Location/Qualifiers
source                  1..1239
                        mol_type = other DNA
                        organism = synthetic construct
SEQUENCE: 64
atggaaaccg acacactgct gctgtgggtg ctgttgttgt gggtgccagg atctacaggc   60
gaagtgcagt tggtgcagtc tggcgccgaa gtgaagaaac ctggcgcttc tgtgaaggtg  120
tcctgcaagg cctctggcta cacctttacc ggctaccaca tgcactgggt ccgacaggct  180
ccaggacaag gattgagtg  gatgggctgg atcaacccca actccggcgt gaccaaatac  240
gcccagaaat tccagggcag agtgaccatg accagagaca cctccatcaa caccgcctac  300
atggaactgt cccggctgag attcgacgac accgacgtgt actattgtgc caccggcggc  360
tttggctatt ggggagaggg aacactggtc accgtgtcct ctgcttctac caagggaccc  420
tccgtgtttc ctctggctcc ttccagcaag tctacctctg gtgaaccgc  tgctctgggc  480
tgcctggtca aggattactt tcctgagcct gtgaccgtgt cttggaactc tggtgctctg  540
accagcggcg tgcacacatt tccagctgtg ctgcagtcct ccggcctgta ctctctgctc  600
tctgtcgtga ccgtgccttc tagctctctg gcacccagga cctacatctg caacgtgaac  660
cacaagcctt ccaacaccaa ggtggacaag agagtggaac ccaagtcttg cggatcttct  720
ggtggcggag gatctggcgg aggtggaagt agtggcggag tgttcaccct ggaagatttc  780
gtcggcgatt gggagcagac cgccgcctat aatctgacc  aggtctggga acaaggcggc  840
gtcagctctc tgctgcagaa tctggctgtg tctgtgaccc tcatccagag aatcgtgcgg  900
tctggcagaa acgccctgaa gatcgacatc cacgtgatca tccctacga  gggcctgtct  960
gccgatcaga tggctcagat cgaagaggtg ttcaaggtgg tgtaccccgt ggacgaccac 1020
cacttcaaag tgatcctgcc ttacggcacc ctggtcatcg atggcgtgac cccaaacatg 1080
ctgaactact tcggcagacc ctacgaggga atccgtgct  tcgacggcaa gaaaatcacc 1140
gtgaccggca cactgtggaa cggcaacaag atcatcgacg agcggctgat caccctgac  1200
ggctctatgc tgttccgcgt gaccatcaac tcctaatga                        1239

SEQ ID NO: 65           moltype = DNA  length = 795
FEATURE                 Location/Qualifiers
source                  1..795
                        mol_type = other DNA
                        organism = synthetic construct
SEQUENCE: 65
atggaaaccg acacactgct gctgtgggtg ctgttgttgt gggtgccagg atctacaggc   60
ctgcctgttc tgacacagcc tcctagcgtg tccaagggcc tgagacagac cgctacactg  120
acctgcaccg gcaactctaa caacgtggga aatcagggcg ctgcctggtt gcagcagcat  180
cagggacaac ctccaaagct gctgtcctac cggaaccaca atagaccttc cggcgtgtcc  240
gagcggttca gcccttctag atctggcgac acctctagcc tgaccatcac tggactgcag  300
cctgaggacg aggccgatta ctactgtctg gcctgggatt cttctctgcg ggcctttgtg  360
tttggcaccg gcacaaaact gaccgtgctg ggccagccta aggccaatcc tacagtgacc  420
ctgtttcctc catcctccga ggaactgcag gccaacaagg ctaccctcgt gtgcctgatc  480
tctgactttt accctggcgc tgtgaccgtg gcttggaagg ctgatggatc tcctgtgaag  540
gccggcgtgg aaaccaccaa gcctagcaag cagtccaaca caaatacgc  cgcctcctcc  600
tacctgtctc tgacccctga acagtggaag tccaccggt  cctactcttg ccaagtgacc  660
catgagggct ccaccgtgga aaagacagtg gcccctaccg agtgctctgg atcttctggt  720
ggcggaggat ctggcggagg tggaagtagt ggcggcgtga ccggctacag actgttcgaa  780
gagatcctgt aatga                                                   795

SEQ ID NO: 66           moltype = DNA  length = 714
FEATURE                 Location/Qualifiers
source                  1..714
                        mol_type = other DNA
                        organism = synthetic construct
SEQUENCE: 66
atggaaaccg acacactgct gctgtgggtg ctgctcttgt gggtgccagg atctacagga   60
ctgcccgtgt tgacccagcc tcctagcgtt tccaagggcc tgagacagac cgccacactg  120
acctgtaccg caactctaa  caacgtgggc aatcagggcg ctgcctggtt gcagcagcat  180
cagggacagc ctccaaagct gctgtcctac cggaaccaca acagacctag cggcgtgtcc  240
gagcggttca gcccttctag atctggcgac acctccagca tggactgcag            300
cctgaggacg aggccgacta ctattgtctg gcctgggaca gctccctgcg ggcctttgtt  360
tttggcaccg gcaccaagct gaccgtgctg ggacaaccta aggccaatcc tacgtgaca   420
ctgttccctc catcctccga ggaactgcag gccaacaagg ctaccctcgt gtgcctgatc  480
tccgactttt accctggcgc tgtgaccgtg gcctggaagg ctgatggatc tcctgtgaag  540
gctggcgtgg aaaccaccaa gccttccaag cagtccaaca caaatacgc  cgcctcctcc  600
```

```
tacctgtctc tgacccctga acagtggaag tcccaccggt cctacagctg ccaagtgacc    660
catgagggct ccaccgtgga aaagaccgtg gctcctaccg agtgctcctg atga          714

SEQ ID NO: 67           moltype = DNA   length = 1233
FEATURE                 Location/Qualifiers
source                  1..1233
                        mol_type = other DNA
                        organism = synthetic construct
SEQUENCE: 67
atggaaaccg acacactgct gctgtgggtg ctgttgttgt gggtgccagg atctacaggc    60
gaggtgcagt tggttgaatc tggcggagga ttggtgcagc ctggcggatc tctgagactg   120
tcttgtgtgg cctccggctt caccttctcc gactactgga tgtcctgggt ccgacaggct   180
cctggcaaag gactggaatg ggtcgccaac atcaagaaag acggctccgt gaactactac   240
gtggactccg tgaagggcag attcaccatc tctcgggaca acgccaagaa ctccctgtac   300
ctgcagatga acagcctgag agccgaggac accgccgtgt actactgcac cagattcgat   360
tattggggcc agggcaccct ggtcaccgtg tcctctgctt ctacaaaggg ccctctgtg    420
ttccctctgg ctccttcctc taaatccacc tctggcggaa ccgctgctct gggctgtctg   480
gtcaaggatt acttccctga gcctgtgacc gtgtcttgga actctggtgc tctgacatcc   540
ggcgtgcaca cctttccagc tgtgctgcag tcctctggcc tgtactctct gtcctctgtc   600
gtgaccgtgc cttctagctc tctgggcacc cagacctaca tctgcaacgt gaaccacaag   660
ccttccaaca ccaaggtgga caagagagtg gaacccaagt cttgcggatc ttctggtggt   720
ggtggaagtg gcggaggcgg ttcttcaggc ggagtgttca ccctggaaga tttcgtcgga   780
gattgggagc agaccgccgc ctataatctg gaccaggttc tggaacaagg cggcgtcagc   840
tctctgctgc agaatctggc tgtgtctgtg acccctatcc agagaatcgt gcgctctggc   900
gagaacgccc tgaagatcga catccacgtg atcatccctt acgagggcct gtctgccgat   960
cagatggctc agatcgaaga ggtgttcaag gtggtgatcc ccgtggacga ccaccacttc   1020
aaagtgatcc tgcctacgg caccctcgtg atcgatggcg tgaccccaaa catgctgaac   1080
tacttcggca gacctacga gggaatcgcc gtgttcgacg gcaagaaaat caccgtgacc   1140
ggcacactgt ggaacggcaa caagatcatc gacgagcggc tgatcacccc tgacggctcc   1200
atgctgttta gagtgaccat caactcctaa tga                                1233

SEQ ID NO: 68           moltype = DNA   length = 795
FEATURE                 Location/Qualifiers
source                  1..795
                        mol_type = other DNA
                        organism = synthetic construct
SEQUENCE: 68
atggaaaccg acacactgct gctgtgggtg ctgttgttgt gggtgccagg atctacaggc    60
caggctggat tgacacagcc tcctagcgtg tccaagggcc tgagacagac cgctcacactg   120
acctgcaccg gcaactctaa caacgtggga aatcagggcg ctgcctggtt gcagcagcat   180
cagggacatc ctccaaagct gctgttctac cggaacaaca atagagcctc cggcatctcc   240
gagcggctgt ctgcttctag atctggcaat accgccagcc tgaccatcac tggactgcag   300
cctgaggacg aggccgacta ctattgcctg acctgggact cctctctgtc cgtggttggtt   360
tttggcggcg gaacaaagct gacagtgctg ggcagccta aggccaatcc taccgtgaca   420
ctgttccctc catcctccga ggaactgcag gctaacaagg ctaccctcgt gtgcctgatc   480
tccgattttt accctggcgc tgtgaccgtg gcttggaagg ctgatggatc tcctgtgaag   540
gccggcgtgg aaaccaccaa gccttagcaag cagtccaaca acaaatacgc cgcctcctcc   600
tacctgtctc tgacccctga acagtggaag tcccaccggt cctactcttg ccaagtgacc   660
catgagggct ccaccgtgga aaagacagtg gccctaccg agtgctctgg atcttctggt   720
ggcggaggat ctggcggagg tggaagtagt ggcggcgtga ccggctacag actgttcgaa   780
gagatcctgt aatga                                                   795

SEQ ID NO: 69           moltype = DNA   length = 714
FEATURE                 Location/Qualifiers
source                  1..714
                        mol_type = other DNA
                        organism = synthetic construct
SEQUENCE: 69
atggaaaccg acacactgct gctgtgggtg ctgctcttgt gggtgccagg atctacagga    60
caggctggct tgacccagcc tcctagcgtt tccaagggcc tgagacagac cgccacactg   120
acctgtaccg gcaactctaa caacgtgggc aatcagggcg ctgcctggtt gcagcagcat   180
cagggacatc ctccaaagct gctgttctac cggaacaaca acagagcctc cggcatctcc   240
gagcggctgt ctgcttctag atccggcaat accgccagcc tgaccatcac tggactgcag   300
cctgaggacg aggccgacta ctattgcctg acctgggact cctctctgtc cgtggttgtt   360
tttggcggag gcaccaagct gacagtgctg ggacagccta aggccaatcc taccgtgaca   420
ctgttccctc catcctccga ggaactgcag gccaacaagg ctaccctcgt gtgcctgatc   480
tccgactttt accctggcgc tgtgaccgtg gcctggaagg ctgatggatc tcctgtgaag   540
gctggcgtgg aaaccaccaa gccttccaag cagtccaaca acaaatacgc cgcctcctcc   600
tacctgtctc tgacccctga acagtggaag tcccaccggt cctacagctg ccaagtgacc   660
catgagggct ccaccgtgga aaagaccgtg gctcctaccg agtgctcctg atga          714

SEQ ID NO: 70           moltype = DNA   length = 1242
FEATURE                 Location/Qualifiers
source                  1..1242
                        mol_type = other DNA
                        organism = synthetic construct
SEQUENCE: 70
atggaaaccg acacactgct gctgtgggtg ctgctcttgt gggtgccagg atctacagga    60
caggtgcagc tggtggaatc tggtggcgga gttgtgcagc ctggcagatc cctgagactg   120
```

```
tcttgtgccg cctccggctt caccttctcc tcttacggaa tgcactgggt ccgacaggcc    180
cctggcaaag gattggagtg ggtcgccttc atcagatacg acggctccaa caagtactac    240
gccgactccg tgaagggcag attcaccatc tctcgggaca actccaagaa cacccctgta    300
ctgcagatga actccctgag agccgaggac accgccgtgt actactgcaa gacccacggc    360
tctcacgaca attggggcca gggcacaatg gtcaccgtgt cctctgcttc caccaaggga    420
ccctctgtgt tccctctggc tccttccagc aagtctacct ctgcggaac agctgctctg    480
ggctgcctgg tcaaggacta cttttcctgag cctgtgaccg tgtcttggaa ctctggcgct    540
ctgacatccg gcgtgcacac cttttccagct gtgctgcaat cctccggcct gtactctctg    600
tcctccgtcg tgaccgtgcc ttctagctct ctgggcaccc agacctacat ctgcaatgtg    660
aaccacaagc cttccaacac caaggtggac aagagagtgg aacccaagtc ctgcggatcc    720
tctggcggcg gaggatctgg cggaggtggt agttcaggcg gagtgttcac cctgaagat     780
ttcgtcggcg actgggagca gaccgccgcc tataatctgg accaggtgct ggaacaaggc    840
ggcgtcagtt ctctgctgca gaacctggct gtgtctgtga ccctatcca gagaatcgtg    900
cggagcgcg agaacgccct gaagatcgat atccacgtga tcatccctta cgaggtgcta    960
agcgccgatc agatgctcca gatcgaagag gtgttcaagg tggtgtaccc cgtggacgac   1020
caccacttca aagtgatcct gccttacggc acccctggtca tcgatggcgt gacccccaaac  1080
atgctgaact acttcggcag accctacgag ggaatcgccg tgttcgacgg caagaaaatc   1140
accgtgaccg gcacactgtg aacggcaac aagatcatcg acgagcggct gatcacccct   1200
gacggctcta tgctgttcag agtgaccatc aacagctgat ga                     1242

SEQ ID NO: 71          moltype = DNA  length = 798
FEATURE                Location/Qualifiers
source                 1..798
                       mol_type = other DNA
                       organism = synthetic construct
SEQUENCE: 71
atggaaaccg acacactgct gctgtgggtg ctgctcttgt gggtgccagg atctaccgga     60
cagtccgtgt tgacccagcc tccttctgtt tctggcgctc ctggccagag agtgaccatc    120
tcttgctccg gctctcggtc caacatcggc tccaatacc gtgaagtggta tcagcagctg    180
cccggcacag ctcccaaact gctgatctac tacaacgacc agcggccttc tggcgtgccc    240
gatagattct ctggctccaa gtctggcacc tctgccagcc tggctattac cggactgcag    300
gctgaggacg aggccgacta ctactgccag tcttacgacc ggtacaccca tcctgctctg    360
ctgtttggca ccggcaccaa agtgacagtg ctgggccagc ctaaggccaa tcctaccgtg    420
acactgttcc ctccatcctc cgaagaactg caggccaaca aggctacct cgtgtgcctg    480
atctccgact tttaccctgg cgctgtgacc gtgcctggtga aggctgatgg atctcctgtg    540
aaggctggcg tggaaaccac caagccttcc aagcagtcca acaacaaata cgccgcctcc    600
tcctacctgt ctctgacccc tgaacagtgg aagtcccacc ggtcctacag ctgccaagtg    660
acccatgagg gctccaccgt ggaaaagacc gtggctccta ccgagtgctc cggatcttct    720
ggtggcggag gatctggccg gaggcggttct tcaggcggag tgaccggcta cagactgttc    780
gaagagatcc tgtgatga                                                  798

SEQ ID NO: 72          moltype = DNA  length = 717
FEATURE                Location/Qualifiers
source                 1..717
                       mol_type = other DNA
                       organism = synthetic construct
SEQUENCE: 72
atggaaaccg acacactgct gctgtgggtg ctgctcttgt gggtgccagg atctaccgga     60
cagtccgtgt tgacccagcc tccttctgtt tctggcgctc ctggccagag agtgaccatc    120
tcttgctccg gctctcggtc caacatcggc tccaatacc gtgaagtggta tcagcagctg    180
cccggcacag ctcccaaact gctgatctac tacaacgacc agcggccttc tggcgtgccc    240
gatagattct ctggctccaa gtctggcacc tctgccagcc tggctattac cggactgcag    300
gctgaggacg aggccgacta ctactgccag tcttacgacc ggtacaccca tcctgctctg    360
ctgtttggca ccggcaccaa agtgacagtg ctgggccagc ctaaggccaa tcctaccgtg    420
acactgttcc ctccatcctc cgaagaactg caggccaaca aggctacct cgtgtgcctg    480
atctccgact tttaccctgg cgctgtgacc gtgcctggtga aggctgatgg atctcctgtg    540
aaggctggcg tggaaaccac caagccttcc aagcagtcca acaacaaata cgccgcctcc    600
tcctacctgt ctctgacccc tgaacagtgg aagtcccacc ggtcctacag ctgccaagtg    660
acccatgagg gctccaccgt ggaaaagacc gtggctccta ccgagtgctc ctgatga       717

SEQ ID NO: 73          moltype = DNA  length = 1410
FEATURE                Location/Qualifiers
source                 1..1410
                       mol_type = other DNA
                       organism = synthetic construct
SEQUENCE: 73
atggaaaccg acacactgct gctgtgggtg ctgctcttgt gggtgccagg atctacagga     60
caggtgcagc tggtggaatc tggtggcgga gttgtgcagc ctggcagatc cctgagactg    120
tcttgtgccg cctccggctt caccttctcc agctacacca tgcactgggt ccgacaggcc    180
cctggcaaag gattggagtg ggtcaccttc atcttacg acggcaacaa caagtactac     240
gccgactccg tgaagggcag attcaccatc tctcgggaca actccaagaa cacccctgta    300
ctgcagatga actccctgag agccgaggac accgccatct actactgtgc tagaaccggc    360
tggctgggcc ccttttgatta ttggggacag ggcaccctgg tcaccgtgtc ctctgcttct    420
accaagggac cacagcgtt ccctctggct cttccagca agtctacctc tggcggaaca    480
gctgctctgg gctgcctggt caaggactac tttcctgagc ctgtgaccgt gtcttggaac    540
tctggcgctc tgacatccgg cgtgcacaca tttccagctg tgctgcagtc ctccggcctg    600
tactctctgt cctctgtcgt gaccgtgcct tccagctctc tgggaaccca gacctacatc    660
tgcaatgtga accacaagcc ttccaacacc aaggtgacca gagagtgga acccaagtcc    720
tgcgacaaga cccacacctg tccaccatgt cctgctccag aactgctcgg cggacctcc    780
```

```
gtgttcctgt ttcctccaaa gcctaaggac accctgatga tctctcggac ccctgaagtg    840
acctgcgtgg tggtggatgt gtctcacgag gatcccgaag tgaagttcaa ttggtacgtg    900
gacggcgtgg aagtgcacaa cgccaagacc aagcctagag aggaacagta caactccacc    960
tacagagtgg tgtccgtgct gaccgtgctg caccaggatt ggctgaacgg caaagagtac    1020
aagtgcaaag tgtccaacaa ggccctgcct gctcctatcg aaaagaccat ctccaaggcc    1080
aagggccagc ctagggaacc ccaggtttac accctgcctc caagccggga agagatgacc    1140
aagaaccagg tgtccctgac ctgcctcgtg aagggattct acccctccga tatcgccgtg    1200
gaatgggagt ctaatggcca gcctgagaac aactacaaga acccctcc tgtgctggac     1260
tccgacggct cattcttcct gtactccaag ctgacagtgg acaagtccag atggcagcag    1320
ggcaacgtgt tctcctgctc cgtgatgcac gaggccctgc acaatcacta cacccagaag    1380
tccctgtctc tgagccccgg caagtgatga                                      1410

SEQ ID NO: 74           moltype = DNA  length = 1401
FEATURE                 Location/Qualifiers
source                  1..1401
                        mol_type = other DNA
                        organism = synthetic construct
SEQUENCE: 74
atggaaaccg acacactgct gctgtgggtg ctgctcttgt gggtgccagg atctacagga    60
caggtgcagc tggtggaatc tggtggcgga gttgtgcagc ctggcagatc cctgagactg    120
tcttgtgccg cctccggctt caccttctcc tcttacggaa tgcactgggt ccgacaggcc    180
cctggcaaag gattggagtg ggtcgccttc atcagatacg aaggctccaa caagtactac    240
gccgactccg tgaagggcag attcaccatc tctcggaca actccaagaa caccctgtac     300
ctgcagatga actccctgag agccgaggac accgccgtgt actactgcaa gacccacggc    360
tctcacgaca attgggcca gggcacaatg gtcaccgtgt cctctgcttc caccaaggga     420
cccctctgtgt tccctctggc tccttccagc aagtctacct gcggcaac agctgctctg     480
ggctgcctgg tcaaggacta cttccctgag cctgtgaccg tgtcttggaa ctctggcgct    540
ctgacatccg gcgtgcacac cttccagct gtgctgcaat cctccggcct gtactctctg     600
tcctccgtcg tgaccgtgcc ttctagctct ctgggcaccc agacctacat ctgcaatgtg    660
aaccacaagc cttccaacac caaggtggac aagagagtga acccaagtc ctgcgataag     720
acccacacct gtccaccatg tcctgctcca gaactgctcg gcggaccttc cgtgttcctg    780
tttcctccaa agcctaagga caccctgatg atctctcgga ccctgaagt gacctgcgtg     840
gtggtggatg tgtctcacga ggatcccgaa gtgaagttca attggtacgt ggacggcgtg    900
gaagtgcaca acgccaagac caagcctaga gaggaacagt acaactccac ctacagagtg    960
gtgtccgtgc tgaccgtgct gcaccaggat tggctgaacg gcaaagagta caagtgcaag    1020
gtgtccaaca aggccctgcc tgctcctatc gaaaagacca ctccaaggc caagggccag     1080
cctagggaac cccaggttta caccctgcct ccaagccggg aagagatgac caagaaccag    1140
gtgtccctga cctgcctcgt gaagggattc taccctccg atatcgccgt ggaatgggag     1200
tctaatggcc agcctgagaa caactacaag accacaccc tgtgctgga gggcaacgtg      1260
tcattcttcc tgtactccaa gctgacagtg gacaagtcca gatggcagca gggcaacgtg    1320
ttctcctgct ccgtgatgca cgaggccctg cacaatcact acacccagaa gtccctgtct    1380
ctgagccccg gcaagtgatg a                                               1401

SEQ ID NO: 75           moltype = DNA  length = 1161
FEATURE                 Location/Qualifiers
source                  1..1161
                        mol_type = other DNA
                        organism = synthetic construct
SEQUENCE: 75
atggaaaccg acacactgct gctgtgggtg ctgctcttgt gggtgccagg atctaccgga    60
cagtccgtgt tgacccagcc tccttctgtt tctggcgctc ctggccagag agtgaccatc    120
tcttgctccg gctctcggtc caacatcggc tccaatacgg tgaagtggta tcagcagctg    180
cccggcacag ctcccaaact gctgatctac tacaacgacc agcggccttc tggcgtgccc    240
gatagattct ctggctccaa gtctggcacc tctgccagcc tggctattac cggactgcag    300
gctgaggacg aggccgacta ctactgccag tcttacgacc ggtacaccca tcctgctctg    360
ctgtttggca ccggcaccaa agtgacagtg ctgggccagc ctaaggccaa tcctaccgtg    420
acactgttcc ctccatcctc cgaagaactg caggccaaca aggctaccct cgtgtgcctg    480
atctccgact tttaccctgg cgctgtgacc gtggcctgga aggctgatgg atctcctgtg    540
aaggctggcg tggaaaccac caagccttcc aagcagtcca acaacaaata cgccgcctcc    600
tcctacctgt ctctgacccc tgaacagtgg aagtcccacc ggtcctacag ctgccaagtg    660
acccatgagg gctccaccgt ggaaaagacc gtggctccta cagtgttc tggcggcgga     720
ggatctggcg gaggtggaag cggaggcggt ggatctgctc ctacctcctc cagcaccaag    780
aaaacccagc tgcagttgga gcatctgctg ctggacctgc agatgatcct gaacggcatc    840
aacaactaca agaacccaa gctgacccgg atgctgacgt tcaagtttgc catgcctaag    900
aaggccaccg agctgaaaca tctgcagtgc ctggaagagg aactgaagcc cctgaaggaa    960
gtgctgaatc tggcccagtc caagaacttc cacctgaggc ctcgggacct gatcagcaac    1020
atcaacgtga tcgtgctcga gctgaagggc tccgagacaa ccttcatgtg cgagtacgcc    1080
gacgagacag ctaccatcgt ggaatttctg aaccggtgga tcaccttctg ccagtccatc    1140
atcagcaccc tgacctgatg a                                               1161

SEQ ID NO: 76           moltype = DNA  length = 1845
FEATURE                 Location/Qualifiers
source                  1..1845
                        mol_type = other DNA
                        organism = synthetic construct
SEQUENCE: 76
atggaaaccg acacactgct gctgtgggtg ctgctcttgt gggtgccagg atctacagga    60
caggtgcagc tggtggaatc tggtggcgga gttgtgcagc ctggcagatc cctgagactg    120
tcttgtgccg cctccggctt caccttctcc tcttacggaa tgcactgggt ccgacaggcc    180
```

```
cctggcaaag gattggagtg ggtcgccttc atcagatacg acggctccaa caagtactac    240
gccgactccg tgaagggcag attcaccatc tctcgggaca actccaagaa caccctgtac    300
ctgcagatga actccctgag agccgaggac accgccgtgt actactgcaa gacccacggc    360
tctcacgaca attggggcca gggcacaatg gtcaccgtgt cctctgcttc caccaaggga    420
ccctctgtgt tccctctggc tccttccagc aagtctacct ctggcggaac agctgctctg    480
ggctgcctgg tcaaggacta cttcctgag cctgtgaccg tgtcttggaa ctctggcgct    540
ctgacatccg gcgtgcacac cttccagct gtgctgcaat cctccggcct gtactctctg    600
tcctccgtcg tgaccgtgcc ttctagctct ctgggcaccc agacctacat ctgcaatgtg    660
aaccacaagc cttccaacac caaggtggac aagagagtgg aacccaagtc ctgcgataag    720
acccacacct gtccaccatg tcctgctcca gaactgctcg gcggaccttc cgtgttcctg    780
tttcctccaa agcctaagga caccctgatg atctctcgga ccctgaagt gacctgcgtg    840
gtggtggatg tgtctcacga ggatcccgaa gtgaagttca attggtacgt ggacggcgtg    900
gaagtgcaca acgccaagac caagcctaga gaggaacagt acaactccac ctacagagtg    960
gtgtccgtgc tgaccgtgct gcaccaggat tggctgaacg gcaaagata caagtgcaag   1020
gtgtccaaca aggccctgcc tgctccatc gaaaagacca tctccaaggc caagggccag   1080
cctcgggaac ctcaagtctg taccctgcct cctagccggg aagagatgac caagaaccag   1140
gtgtccctgt cctgcgctgt gaagggcttc taccccttccg atatcgccgt ggaatgggag   1200
agcaatggcc agcctgagaa caactacaag accacacctc ctgtgctgga ctccgacggc   1260
tcattcttcc tggtgtccaa gctgacagtg gacaagtcca gatggcagca gggcaacgtg   1320
ttctcctgct ccgtgatgca cgaggccctg cacaatcact acacccagaa gtccctgtct   1380
ctgtctcccg gaaaggcgg cggaggatct ggcggaggtg gtagcggagg cggtggatct   1440
gctcctacct cctccagcac caagaaaacc cagctgcact tggagcatct gctgctggac   1500
ctccagatga tcctgaatgg catcaacaat tacaagaacc ccaagctcac ccggatgctg   1560
accgccaagt ttgccatgcc taagaaggcc accgagctga acatctgca gtgcctggaa   1620
gaggaactga agccctgga agaagtgctg aatctggccc agtccaagaa cttccacctg   1680
aggcctcggg acctgatctc caacatcaac gtgatcgtgc tcgagctgaa gggctccgag   1740
acaaccttca tgtgcgagta cgccgacgag acagctacca tcgtggaatt tctgaaccgg   1800
tggatcacct tctgccagtc catcatcagc accctgacct gatga             1845

SEQ ID NO: 77          moltype = DNA  length = 1845
FEATURE                Location/Qualifiers
source                 1..1845
                       mol_type = other DNA
                       organism = synthetic construct
SEQUENCE: 77
atggaaaccg acacactgct gctgtgggtg ctgctcttgt gggtgccagg atctacagga     60
caggtgcagc tggtggaatc tggtggcgga gttgtgcagc ctggcagatc cctgagactg    120
tcttgtgccg cctccggctt caccttctcc tcttacggaa tgcactgggt ccgacaggcc    180
cctggcaaag gattggagtg ggtcgccttc atcagatacg acggctccaa caagtactac    240
gccgactccg tgaagggcag attcaccatc tctcgggaca actccaagaa caccctgtac    300
ctgcagatga actccctgag agccgaggac accgccgtgt actactgcaa gacccacggc    360
tctcacgaca attggggcca gggcacaatg gtcaccgtgt cctctgcttc caccaaggga    420
ccctctgtgt tccctctggc tccttccagc aagtctacct ctggcggaac agctgctctg    480
ggctgcctgg tcaaggacta cttcctgag cctgtgaccg tgtcttggaa ctctggcgct    540
ctgacatccg gcgtgcacac cttccagct gtgctgcaat cctccggcct gtactctctg    600
tcctccgtcg tgaccgtgcc ttctagctct ctgggcaccc agacctacat ctgcaatgtg    660
aaccacaagc cttccaacac caaggtggac aagagagtgg aacccaagtc ctgcgataag    720
acccacacct gtccaccatg tcctgctcca gaactgctcg gcggaccttc cgtgttcctg    780
tttcctccaa agcctaagga caccctgatg atctctcgga ccctgaagt gacctgcgtg    840
gtggtggatg tgtctcacga ggatcccgaa gtgaagttca attggtacgt ggacggcgtg    900
gaagtgcaca acgccaagac caagcctaga gaggaacagt acaactccac ctacagagtg    960
gtgtccgtgc tgaccgtgct gcaccaggat tggctgaacg gcaaagata caagtgcaag   1020
gtgtccaaca aggccctgcc tgctccatc gaaaagacca tctccaaggc caagggccag   1080
cctagggaac cccaggttta caccctgcct ccagccgggg aagagatgac caagaaccag   1140
gtgtccctga cctgcctcgt gaagggattc taccccctccg atatcgccgt ggaatgggag   1200
tctaatggcc agcctgagaa caactacaag accacacctc ctgtgctgga ctccgacggc   1260
tcattcttcc tgtactccaa gctgacagtg gacaagtcca gatggcagca gggcaacgtg   1320
ttctcctgct ccgtgatgca cgaggccctg cacaatcact acacccagaa gtccctgtct   1380
ctgtctcccg gaaaggcgg cggaggatct ggcggaggtg gtagcggagg cggtggatct   1440
gctcctacct cctccagcac caagaaaacc cagctgcact tggagcatct gctgctggac   1500
ctccagatga tcctgaatgg catcaacaat tacaagaacc ccaagctcac ccggatgctg   1560
accgccaagt ttgccatgcc taagaaggcc accgagctga acatctgca gtgcctggaa   1620
gaggaactga agccctgga agaagtgctg aatctggccc agtccaagaa cttccacctg   1680
aggcctcggg acctgatctc caacatcaac gtgatcgtgc tcgagctgaa gggctccgag   1740
acaaccttca tgtgcgagta cgccgacgag acagctacca tcgtggaatt tctgaaccgg   1800
tggatcacct tctgccagtc catcatctcc acactgacct gatga             1845

SEQ ID NO: 78          moltype = DNA  length = 1410
FEATURE                Location/Qualifiers
source                 1..1410
                       mol_type = other DNA
                       organism = synthetic construct
SEQUENCE: 78
atggaaaccg acacactgct gctgtgggtg ctgctcttgt gggtgccagg atctacagga     60
caggtgcagc tggtggaatc tggtggcgga gttgtgcagc ctggcagatc cctgagactg    120
tcttgtgccg cctccggctt caccttctcc agctacacca tgcactgggt ccgacaggcc    180
cctggcaaag gattggagtg ggtcaccttc atctcttacg acggcaacaa caagtactac    240
gccgactccg tgaagggcag attcaccatc tctcgggaca actccaagaa caccctgtac    300
ctgcagatga actccctgag agccgaggac accgccatct actactgtgc tagaaccggc    360
```

```
tggctgggcc cctttgatta ttggggacag ggcaccctgg tcaccgtgtc ctctgcttct    420
accaagggac ccagcgtgtt ccctctggct ccttccagca agtctacctc tggcggaaca    480
gctgctctgg gctgcctggt caaggactac tttcctgagc ctgtgaccgt gtcttggaac    540
tctggcgctc tgacatccgg cgtgcacaca tttccagctg tgctgcagtc ctccggcctg    600
tactctctgt cctctgtcgt gaccgtgcct tccagctctc tgggaaccca gacctacatc    660
tgcaatgtga accacaagcc ttccaacacc aaggtggaca agagagtgga acccaagtcc    720
tgcgacaaga cccacacctg tccaccatgt cctgctccag aactgctcgg cggaccttcc    780
gtgttcctgt ttcctccaaa gcctaaggac accctgatga tctctcggac ccctgaagtg    840
acctgcgtgg tggtggatgt gtctcacgag gatcccgaag tgaagttcaa ttggtacgtg    900
gacggcgtgg aagtgcacaa cgccaagacc aagcctagag aggaacagta caactccacc    960
tacagagtgg tgtccgtgct gaccgtgctg caccaggatt ggctgaacgg caaagagtac   1020
aagtgcaagg tgtccaacaa ggccctgcct gtcctatcg aaaagaccat ctccaaggcc    1080
aagggccagc ctagggaacc ccaggtttac accctgcctc catgccggga agagatgacc   1140
aagaaccagg tgtccctgtg gtgcctggtt aagggcttct accctcga tatcgccgtg    1200
gaatgggagt ctaatggcca gcctgagaac aactacaaga caacccctcc tgtgctggac   1260
tccgacggct cattcttcct gtactccaag ctgacagtgg acaagtccag atggcagcag   1320
ggcaacgtgt tctcctgctc cgtgatgcac gaggccctgc acaatcacta cacccagaag   1380
tccctgtctc tgagccccgg caagtgatga                                    1410

SEQ ID NO: 79           moltype = DNA  length = 2241
FEATURE                 Location/Qualifiers
source                  1..2241
                        mol_type = other DNA
                        organism = synthetic construct
SEQUENCE: 79
atggaaaccg acacactgct gctgtgggtg ctgctcttgt gggtgccagg atctacagga     60
caggtgcagc tggtggaatc tggtggcgga gttgtgcagc ctggcagatc cctgagactg    120
tcttgtgccg cctccggctt caccttctcc agctacacca tgcactgggt ccgacaggcc    180
cctggcaaag gattggagtg ggtcaccttc atctcttacg acggcaacaa caagtactac    240
gccgactccg tgaagggcag attcaccatc tctcgggaca actccaagaa cacccctgcc    300
ctgcagatga actccctgag agccgaggac accgccatct actactgtgc tagaaccggc    360
tggctgggcc cctttgatta ttggggacag ggcaccctgg tcaccgtgtc ctctgcttct    420
accaagggac ccagcgtgtt ccctctggct ccttccagca agtctacctc tggcggaaca    480
gctgctctgg gctgcctggt caaggactac tttcctgagc ctgtgaccgt gtcttggaac    540
tctggcgctc tgacatccgg cgtgcacaca tttccagctg tgctgcagtc ctccggcctg    600
tactctctgt cctctgtcgt gaccgtgcct tccagctctc tgggaaccca gacctacatc    660
tgcaatgtga accacaagcc ttccaacacc aaggtggaca agagagtgga acccaagtcc    720
tgcgacaaga cccacacctg tccaccatgt cctgctccag aactgctcgg cggaccttcc    780
gtgttcctgt ttcctccaaa gcctaaggac accctgatga tctctcggac ccctgaagtg    840
acctgcgtgg tggtggatgt gtctcacgag gatcccgaag tgaagttcaa ttggtacgtg    900
gacggcgtgg aagtgcacaa cgccaagacc aagcctagag aggaacagta caactccacc    960
tacagagtgg tgtccgtgct gaccgtgctg caccaggatt ggctgaacgg caaagagtac   1020
aagtgcaagg tgtccaacaa ggccctgcct gtcctatcg aaaagaccat ctccaaggcc    1080
aagggccagc ctagggaacc ccaggtttac accctgcctc catgccggga agagatgacc   1140
aagaaccagg tgtccctgtg gtgcctggtt aagggcttct accctcga tatcgccgtg    1200
gaatgggagt ctaatggcca gcctgagaac aactacaaga caacccctcc tgtgctggac   1260
tccgacggct cattcttcct gtactccaag ctgacagtgg acaagtccag atggcagcag   1320
ggcaacgtgt tctcctgctc cgtgatgcac gaggccctgc acaatcacta cacccagaag   1380
tccctgtctc tgtctcccgg aaaaggcggg ggaggatctg gcggaggtgg tagcggaggc   1440
ggtggatctg aagttcagct ggttgagagt ggcggcggac tggttaagcc tggtggttct   1500
ctgagactga gctcgcgc ttctggcttc acattcagcc cctactccgt gttctgggtt   1560
cgacaagctc caggcaaggg cctcgaatgg gtgtcctcta tcaacaccga cagcacctac   1620
aagtattacg ctgacagcgt gaaaggccgg tttaccatca gcagagacaa cgccgagaac   1680
tccatcttcc tccagatgaa ttctctgcgc gctgaggata ccgctgtgta ctactgcgcc   1740
agagacagat cctactacgc ctttctcctcc ggctctctgt ctgactacta ctacggcctg   1800
gatgtgtggg gccagggaac acttgtgaca gtgtcaagtg gcggtggcgg tagtggcgga   1860
ggcggttctg gtggtggtgg ttcaggcggg ggtggcagcg atatcgtgat gacccagtct   1920
ccactgagcc tgagcgtgac acctggcgag cctgcctcta tctcctgcag atcctctcag   1980
tccctgctgc acaccaacct gtacaactac ctggattggt atgtgcagaa gcccggccag   2040
tctcctcagc tgctgatcta cctggcctcc aacagagctt ctggcgtgcc cgatagattc   2100
tccggttctg gctctggcac cgacttcacc ctgaagattt ccagagtgga aacagaggac   2160
gtgggcgtgt actattgcat gcaggctctg cagattcccc ggaccttcgg ccagggcacc   2220
aaaactggaa tcaagtgatg a                                              2241

SEQ ID NO: 80           moltype = DNA  length = 1155
FEATURE                 Location/Qualifiers
source                  1..1155
                        mol_type = other DNA
                        organism = synthetic construct
SEQUENCE: 80
atggaaaccg acacactgct gctgtgggtg ctgctcttgt gggtgccagg atctacaggc     60
gagatcgtgc tgacccagtc tcctggcaca ctgtcactgt ctccaggcga gagagctacc    120
ctgtcctgta gagcctctca gtccgtgggc tcctcttacc tggcttggta tcagcagaag    180
cccggccagg ctccctagact gttgatctac ggcgccttct ccagagccac aggcatccct    240
gatagattct ccggctctgg ctctggcacc gacttcaccc tgaccatctc cagactggaa    300
cccgaggact tcgccgtgta ctactgtcag cagtacggct cctctcccttg gacctttggc    360
cagggcacca aggtggaaat caagcggaca gtggccgctc cttccgtgtt catcttccca    420
ccttccgacg agcagctgaa gtccggcaca gcttctgtcg tgtgcctgct gaacaacttc    480
taccctcggg aagccaaggt gcagtggaag gtggacaatg ccctgcagtc cggcaactcc    540
```

```
caagagtctg tgaccgagca ggactccaag gacagcacct acagcctgtc ctccacactg   600
accctgtcca aggccgacta cgagaagcac aaggtgtacg cctgcgaagt gacccatcag   660
ggcctgtcta gccctgtgac caagtctttc aacagaggcg agtgtggcgg cggaggatct   720
ggcggaggtg gaagcggagg cggtggatct gctcctacct cctccagcac caagaaaacc   780
cagctgcagt tggagcatct gctgctggac ctgcagatga tcctgaacgg catcaacaac   840
tacaagaacc ccaagctgac ccggatgctg accgccaagt ttgccatgcc taagaaggcc   900
accgagctga acatctgcag gtgcctggaa gaggaactga agcccctgga agaagtgctg   960
aatctggccc agtccaagaa cttccacctg aggcctcggg acctgatctc caacatcaac  1020
gtgatcgtgc tcgagctgaa gggctccgag acaaccttca tgtgcgagta cgccgacgag  1080
actgctacca tcgtggaatt tctgaaccgg tggatcacct tctgccagtc catcatctct  1140
accctgacct gatga                                                   1155

SEQ ID NO: 81            moltype = DNA  length = 1419
FEATURE                  Location/Qualifiers
source                   1..1419
                         mol_type = other DNA
                         organism = synthetic construct
SEQUENCE: 81
atggaaaccg acacactgct gctgtgggtg ctgctcttgt gggtgccagg atctacaggc    60
gaagtgcagc tggttcaatc tggcggcgga gtggaaagac ctggcggatc tctgagactg   120
tcttgtgccg cctctggctt caccttcgac gactacggaa tgtcctgggt ccgacaggct   180
cctggcaaag gactggaatg ggtgtccggc atcaattgga acggggctc taccggctac   240
gccgactctg tgaagggcag agtgaccatc tccagagaca cgccaagaa ctccctgtac   300
ctgcagatga cagcctgag agccgaggac ccgccgtgt actactgtgc taagatcctc   360
ggcgctggca gaggctggta cttgatctg tggggcaagg caccaccgt gaccgttct   420
tccgcttcca ccaagggacc cagcgtgttc cctctgctc cttccagcaa gtctacctct   480
ggcgaacag ctgctctggg ctgcctggtc aaggactact ttcctgagcc tgtgaccgtg   540
tcctggaact ctggcgctct gacatctggc gtgcacacct ttccagctgt gctgcagtcc   600
tccggcctgt actctctgtc ctctgtcgtg accgtgcctt ccagctctct gggaacccag   660
acctacatct gcaatgtgaa ccacaagcct tccaacacca aggtggacaa gagagtgaa   720
cccaagtcct gcgacaagac ccacacctgt cctccatgtc ctgctccaga actgctcggc   780
ggaccttccg tgttcctgtt tcctccaaag cctaaggaca ccctgatgat ctctcggacc   840
cctgaagtga cctgcgtggt ggtggatgtg tctcacgagg atcccgaagt gaagttcaat   900
tggtacgtgg acggcgtgga agtgcacaat gccaagacca agcctagaga ggaacagtac   960
aactccacct acagagtggt gtccgtgctg accgtgctgc accaggattg gctgaacggc  1020
aaagagtaca agtgcaaggt gtccaacaag gccctgcctg ctcctatcga aaagaccatc  1080
agcaaggcca agggccagcc tcgggaacct caagtctgta ccctgcctcc tagccggaa  1140
gagatgacca agaaccaggt gtccctgtcc tgtgccgtga agggcttcta cccttccgat  1200
atcgccgtgg aatgggagag caatggccag ccagagaaca actacaagac aaccccct  1260
gtgctggact ccgacggctc attcttcctg gtgtccaagc tgacagtgga caagtccaga  1320
tggcagcagg gcaacgtgtt ctcctgctcc gtgatgcacg aggccctgca caatcactac  1380
acccagaagt ccctgtctct gagccccggc aagtgatga                         1419

SEQ ID NO: 82            moltype = DNA  length = 1413
FEATURE                  Location/Qualifiers
source                   1..1413
                         mol_type = other DNA
                         organism = synthetic construct
SEQUENCE: 82
atggaaaccg atacactgct gctgtgggtg ctgctcctct gggtgccagg atctacaggc    60
caggtccagc tgcaggaaag cggccctgga ctggtcaagc ctagccagac cctgagcctg   120
acctgtaccg tgtccggcgg cagcatcaac aacaacaatt actactggac atggatccgg   180
cagcaccccg gcaagggcct ggaatggatg ggctacatct actacagcgg ctccaccttc   240
tacaacccca gcctgaagtc cagagtgacc atcagcgtgg acaccagcaa gacccagttc   300
tccctgaagc tgagcagcgt gacagccgcc gacacagccg tgtactactg cgccagagaa   360
gataccatga ccggcctgga tgtgtgggc cagggcacca cagtgacagt gtctagcgcc   420
agcaccaagg gcccttagcgt gttccctctg cccctagct ctaagagcac atctggcgga   480
acagccgccc tgggctgcct ggtcaaggat tactttcctg agcccgtgac cgtgtcctgg   540
aactctggtg ctctgaccag cggcgtgcac acctttccag ctgtgctgca gagcagcggc   600
ctgtacagcc tgtctagcgt ggtcacagtg cctagcagca gcctgggcac acagacctac   660
atctgcaacg tgaaccacaa gcccagcaac accaaggtgg acaagcgggt ggaaccccaag   720
agctgcgaca gacccacac ctgtcctccc tgtcctgccc ctgaactgct gggcggacct   780
tccgtgttcc tgttccctcc aaagcccaag gacaccctga tgatcagccg gacccctgaa   840
gtgacctgcg tggtggtgga tgtgtccac gaggatccg aagtgaagtt caattgtac   900
gtggacggcg tggaagtgca caacgccaag accaagccca gagaggaaca gtacaacagc   960
acctaccggg tggtgtccgt gctgaccgtg ctgcaccagg actggctgaa cggcaaagag  1020
tacaagtgca aggtgtccaa caaggccctg ccagccccta tcgagaaaac catcagcaag  1080
gccaagggc agccccgcga acctcaggtg tacacactgc ctccctgccg ggaagagatg  1140
accaagaacc aggtgtccct gtggtgtctc tgaaggcct tctacccctc cgatatcgcc  1200
gtggaatggg agagcaacgg ccagcccgag aacaactaca agaccacccc tcccgtgctg  1260
gacagcgacg gcagcttctt cctgtactcc aaactgaccg tggacaagag ccggtggcag  1320
cagggcaatg tgttcagctg tagcgtgatg cacgaggccc tgcacaacca ctacacccag  1380
aagtccctgt ccctgagccc tggcaagtaa tga                               1413

SEQ ID NO: 83            moltype = DNA  length = 705
FEATURE                  Location/Qualifiers
source                   1..705
                         mol_type = other DNA
                         organism = synthetic construct
```

```
SEQUENCE: 83
atggaaaccg atacactgct gctgtgggtg ctgctcctct gggtgccagg cagcaccggc   60
gatatccaga tgacacagag ccctagcagc ctgagcgcca gcgtgggcga tagagtgacc  120
atcacctgtc gggccagcca gagcatcaac aactacctga actggtatca gcagaagccc  180
ggcaaggccc ctaccctgct gatctatgcc gcttctagcc tgcagagcgg cgtgcccagc  240
agattttctg gcagcagatc cggcaccgac ttcaccctga caatcagcag cctgcagccc  300
gaggacttcg ccgcctactt ctgccagcag acctacagca atcccacctt cggcagggcc  360
accaaggtgg aagtgaagag aacagtggcc gctcccagcg tgttcatctt cccacccagc  420
gacgagcagc tgaagtctgg cacagccagc gtcgtgtgcc tgctgaacaa cttctaccc  480
agagaagcca aggtgcagtg gaaggtggac aacgccctgc agtccggcaa cagccaggaa  540
agcgtcaccg agcaggacag caaggactcc acctacagcc tgtccagcac cctgaccctg  600
agcaaggccg actacgagaa gcacaaagtg tacgcctgcg aagtgaccca ccagggcctg  660
agcagccccg tgaccaagag cttcaataga ggcgagtgct aatga               705

SEQ ID NO: 84           moltype = DNA  length = 1416
FEATURE                 Location/Qualifiers
source                  1..1416
                        mol_type = other DNA
                        organism = synthetic construct
SEQUENCE: 84
atggaaaccg atacctgct gctgtgggtg ctgctcctct gggtgccagg atctacaggc    60
gaggtgcagc tgctggaatc tggcggagga ctggtgcagc ctggcggctc tctgagactg  120
tcttgtgccg cctccggctt caccttctct agctatatca tgatgtgggt ccgacaggcc  180
cctggcaagg gcctggaatg ggtgtcctct atctacccct ccggcggcat caccttttac  240
gccgacaccg tgaagggccg gttcaccatc tcccgggaca actccaagaa caccctgtac  300
ctgcagatga actccctgcg ggccgaggac accgccgtgt actactgcgc tagaatcaag  360
ctgggcaccg tgaccaccgt ggactattgg ggccagggca ccctggtcac cgtgtcctct  420
gcttctacca agggccccct cgtgttccct ctggcccctt ccagcaagtc cacctctggc  480
ggaaccgctg ctctgggctg cctggtcaag gactacttcc ccgagcccgt gaccgtgtct  540
tggaactctg gcgccctgac cagcggcgtg cacacatttc cagccgtgct gcagtccagc  600
ggcctgtact ctctgtcctc cgtcgtgaca gtgccctcca gctctctggg cacacagacc  660
tacatctgca acgtgaacca caagccctcc aacaccaagg tggacaagcg ggtggaaccc  720
aagtcctgcg acaagaccca cacctgtcct ccctgtcctg ccctgaact gctgggcgga  780
cccagcgtgt tcctgttccc tccaaagcct aaggacaccc tgatgatctc ccggacccct  840
gaagtgacct gcgtggtggt ggacgtgtcc cacgaggatc ccgaagtgaa gttcaattgg  900
tacgtggacg gcgtggaagt gcacaacgcc aagaccaagc ctagagagga cagtacaac  960
tccacctacc gggtggtgtc cgtgctgaca gtgctgcatc aggactggct gaacggcaaa 1020
gagtacaagt gcaaggtgtc caacaaggcc ctgccagccc ctatcgaaaa gaccatctcc 1080
aaggccaagg gccagcccaa gagagcctcaa gtctgcacac tgcctcccag ccgggaagag 1140
atgaccaaga accaggtgtc cctgagctgc gctgtgaagg gcttctaccc ttccgatatc 1200
gccgtggaat gggagagcaa cggccagccc gagaacaatt acaagaccac ccctcccgtg 1260
ctggactccg acggctcatt cttcctggtg tccaagctga ccgtggacaa gtcccggtgg 1320
cagcagggca acgtgttctc ctgctctgtg atgcacgagg ccctgcacaa ccactacacc 1380
cagaagtccc tgtccctgtc tcccggcaag taatga                            1416

SEQ ID NO: 85           moltype = DNA  length = 714
FEATURE                 Location/Qualifiers
source                  1..714
                        mol_type = other DNA
                        organism = synthetic construct
SEQUENCE: 85
atggaaaccg atacctgct gctgtgggtg ctgctcctct gggtgccagg ctctaccggc    60
cagtctgctc tgacccagcc tgcctctgtg tctggctccc ctggccagtc catcaccatc  120
agctgtaccg gcacctcctc cgacgtgggc ggctacaact acgtgtcctg gtatcagcag  180
catcccggca aggcccctaa gctgatgatc tacgacgtgt ccaaccggcc ctccggcgtg  240
tccaatcggt tctctggctc caagtccggc aacaccgcct ccctgacaat cagcggactg  300
caggccgagg acgaggccga ctactactgc tcctcctaca cctccagctc taccggggtg  360
ttcggcaccg gcaccaaagt gacagtgctg ggccagccca aggccaaccc caccgtgacc  420
ctgttccctc catcctccga ggaactgcag gctaacaagg ccaccctcgt gtgcctgatc  480
tccgacttct accctggcgc cgtgaccgtg gcttggaagg ctgatggctc tcctgtgaag  540
gccggcgtgg aaaccaccaa gccctccaag cagtccaaca acaaatacgc cgcctccagc  600
tacctgtccc tgacccctga gcagtggaag tccaccggt cctacagctg ccaggtcaca  660
catgagggct ccaccgtgga aaagaccgtg gcccctaccg agtgctccta atga         714

SEQ ID NO: 86           moltype = DNA  length = 1425
FEATURE                 Location/Qualifiers
source                  1..1425
                        mol_type = other DNA
                        organism = synthetic construct
SEQUENCE: 86
atggaaaccg acacactgct gctgtgggtg ctgctcttgt gggtgccagg atctacagga    60
caggtgcagc tggttcagtc tggcggagga ttggttcagc aggcggatc cctgagactg  120
tcttgtgccg cttctggctt caccttcgac gactacgcta tgcactgggt ccgacaggcc  180
cctggcaaag gattggaatg ggtggccggc atctcttggg actcggctc taccgctac  240
gccgactctg tgaagggcag attcaccatc tctcgggaca cgccaagaa ctccctgtac  300
ctgcagatga acagcctgag agccgaggac accgctctgt actactgcgc tagagatctg  360
ggcgcctacc agtgggtgga aggctttgat tattggggcc agggcaccct ggtcaccgtg  420
tcctctgctt ctaccaaggg cccagcgtg ttccctctgg ctccttccag caagtctacc  480
tctggcggaa cagctgctct gggctgcctg gtcaaggact actttcctga gcctgtgacc  540
```

```
gtgtcttgga actccggcgc tctgacatct ggcgtgcaca cctttccagc tgtgctgcag   600
tcctccggcc tgtactctct gtcctctgtc gtgaccgtgc cttccagctc tctgggaacc   660
cagacctaca tctgcaatgt gaaccacaag cctagcaaca ccaaggtgga caagagagtg   720
gaacccaagt cctgcaccat caagccctgt cctccatgca gtgcccccgc tcctaatctg   780
ctcggaggcc cttccgtgtt catcttccca cctaagatca aggacgtgct gatgatctcc   840
ctgtctccta tcgtgacctg cgtggtggtg gacgtgtccg aggatgatcc tgacgtgcag   900
atcagttggt tcgtgaacaa cgtggaagtg cacaccgctc agacccagac acacagagag   960
gactacaaca gcaccctgag agtggtgtct gccctgccta ccagcacca ggattggatg    1020
tccggcaaag aattcaagtg caaagtcaac aacaaggacc tgcctgctcc aatcgagcgg   1080
accatctcta agcctaaggg ctctgtcagg gcccctcagg tgtacgttct gcctccttgc   1140
gaggaagaga tgaccaagaa acaagtgacc ctgtggtgca tggtcaccga cttcatgccc   1200
gaggacatct acgtggaatg gaccaacaac ggcaagaccg agctgaacta caagaacacc   1260
gagcctgtgc tggactccga cggctcctac ttcatgtact ccaagctgcg cgtcgagaag   1320
aagaactggg tcgagagaaa ctcctactcc tgctccgtgg tgcacgaggg cctgcacaat   1380
caccacacca ccaagtcctt ctctcggacc cctggaaagt gatga                   1425

SEQ ID NO: 87         moltype = DNA   length = 1425
FEATURE               Location/Qualifiers
source                1..1425
                      mol_type = other DNA
                      organism = synthetic construct
SEQUENCE: 87
atggaaaccg acacactgct gctgtgggtg ctgctcttgt gggtgccagg atctacaggc    60
gaagtgcagc tgttgcagtc tggcggagga ttggttcagc ctggcggatc cctgagactg   120
tcttgtgccg cctctggctt catgttcagc agataccccc tgcactgggt ccgacaggcc   180
cctggaaaag gactggaatg ggtggagtcc atctccggac gtgccggctac taccccttac   240
gccgattctg tgaagggcag attcaccatc agccgggaca actccaagaa caccctgtac   300
ctgcagatga actccctgag agccgaggac accgccgtgt actactgcgc caaggacttc   360
taccagatcc tgaccggcaa cgccttcgac tattggggcc agggcacaac cgtgaccgtg   420
tcctctgctt ctaccaaggg acccagcgtg ttccctctgg ctccttccag caagtctcca   480
tctggcggaa cagctgctct gggctgcctg gtcaaggact actttcctga gcctgtgaca   540
gtgtcctgga actctggcgc tctgacatcc ggcgtgcaca cctttccagc tgtgctgcaa   600
tccagcggcc tgtactctct gtcctccgtc gtgacagtgc cttccagctc tctgggaacc   660
cagacctaca tctgcaatgt gaaccacaag ccttccaaca ccaaggtgga caagagagtg   720
gaacccaagt cctgcaccat caagccctgt cctccatgca gtgcccccgc tcctaatctg   780
ctcggaggcc cttccgtgtt catcttccca cctaagatca aggacgtgct gatgatctcc   840
ctgtctccta tcgtgacctg cgtggtggtg gacgtgtccg aggatgatcc tgacgtgcag   900
atcagttggt tcgtgaacaa cgtggaagtg cacaccgctc agacccagac acacagagag   960
gactacaaca gcaccctgag agtggtgtct gccctgccta ccagcacca ggattggatg    1020
tccggcaaag aattcaagtg caaagtcaac aacaaggacc tgcctgctcc aatcgagcgg   1080
accatctcta agcctaaggg ctctgtcgg gctcccaag tttgtgttct gcctccacct     1140
gaggaagaga tgaccaagaa acaagtgacc ctgtcctgcg ccgtgaccga cttcatgcct   1200
gaggacatct acgtggaatg gaccaacaac ggcaagaccg agctgaatta caagaacacc   1260
gagcctgtgc tggactccga cggctcctac ttcatggtgt ctaagctgcg cgtcgagaag   1320
aagaactggg tcgagagaaa ctcctactcc tgctccgtgg tgcacgaggg cctgcacaat   1380
caccacacca ccaagtcctt ctctcggacc cctggcaagt gatga                   1425

SEQ ID NO: 88         moltype = DNA   length = 1446
FEATURE               Location/Qualifiers
source                1..1446
                      mol_type = other DNA
                      organism = synthetic construct
SEQUENCE: 88
atggaaaccg acacactgct gctgtgggtg ctgctcttgt gggtgccagg atctacaggc    60
gaagtgcagc tggttcagtc tggcgccgaa gtgaagaaac ctggctcctc cgtgaaggtg   120
tcctgcaagg cttctggcgg caccttctcc tcttacgcca tctcctgggt ccgacaggct   180
cctggacaag gcttggaatg gatgggcggc atcatcccca tcttcggcac cgccaattac   240
gcccagaaat ccagggcag agtgaccatc accgccgaca gtctacctc caccgcctac   300
atggaactgt ccagcctgag atctgaggac accgccgtgt actactgcgc tagagccctg   360
ctgagattcc tggaatggtc tacccggac cactactact attactacat ggacgtgtgg   420
ggcaagggca ccaccgtgac agtttcttcc gcctccacca agggaccag cgtttttccc t  480
ctggctccat cctccaagtc cacctctggt ggaacagctg ctctgggctg cctggtcaag   540
gactactttc ctgagcctgt gaccgtgtcc tggaactctg gcgctctgac atctggcgtg   600
cacacctttc cagctgtgct gcagtcctcc ggcctgtact ctctgtccgt cgtgcctcca   660
gtgccttcca gctctctggg aacccagacc tacatctgca atgtgaacca caagccttcc   720
aacaccaagg tcgacaagag agtggaaccc aagtcctgcg acaagaccca cacctgtcct   780
ccatgtcctg ctccagaact gctcggcgga ccttccgtgt tcctgtttcc tccaaagcct   840
aaggacaccc tgatgatctc tcggacccct gaagtgacct gcgtggtggt ggatgtgtct   900
cacgaggacc cagaagtgaa gttcaattgg tacgtggacg gcgtggaagt gcacaacgtg   960
aagaccaagc ctagagagga acagtacaac tccacctaca gagtggtgtc cgtgctgacc   1020
gtgctgcacc aggattggct gaacggcaaa gagtacaagt gcaaggtctc caacaaggcc   1080
ctgcctgctc ctatcgaaaa gaccatctcc aaggccaagg gccagcctcg ggaacctcaa   1140
gtctgtaccc tgcctcctag ccgggaagag atgaccaaga accaggtgtc cctgtcctgt   1200
gccgtgaagg gcttctaccc ttccgatatc gccgtggaat gggagagcaa tggccagccg    1260
gagaacaact acaagacaac ccctcctgtg ctggactccg acggctcatt cttcctggtg   1320
tccaagctga gtgtggacaa gtccagatgg cagcagggca acgtgttctc ctgctccgtg   1380
atgcacgagg ccctgcacaa tcactacaca cagaagtccc tgtctctgag ccccggcaag   1440
tgatga                                                              1446
```

| SEQ ID NO: 89 | moltype = DNA length = 1395 |
|---|---|
| FEATURE | Location/Qualifiers |
| source | 1..1395 |
| | mol_type = other DNA |
| | organism = synthetic construct |

SEQUENCE: 89

```
atggaaaccg acacactgct gctgtgggtg ctgctcttgt gggtgccagg atctacagga   60
caggtgcagc tggtggaatc tggtggcgga gttgtgcagc ctggcagatc tctgagactg  120
gactgcaagg cctccggcat caccttctcc aactctggca tgcactgggt ccgacaggcc  180
cctggaaaag gactggaatg ggtcgccgtg atttggtacg acggctccaa gaggtactac  240
gccgactccg tgaagggcag attcaccatc tctcggaca actccaagaa caccctgttt  300
ctgcagatga actccctgag agccgaggac accgccgtgt actactgtgc caccaacgac  360
gattattggg gccagggcac actggtcacc gtgtcctctg cttctaccaa gggacccagc  420
gtgttccctc tggctccttc cagcaagtct acctctgggg gaacagctgc tctgggctgc  480
ctggtcaagg actactttcc tgagcctgtg accgtgtctt ggaactctgg cgctctgaca  540
tccggcgtgc acacctttcc agctgtgctg caatcctccg gcctgtactc tctgtcctcc  600
gtcgtgaccg tgccttctag ctctctgggc acccagacct acatctgcaa tgtgaaccac  660
aagccttcca acaccaaggt ggacaagaga gtggaaccca gtctgcga caagacccac  720
acctgtccac catgtcctgc tccagaactg ctcggcggac cttccgtgtt cctgtttcct  780
ccaaagccta aggacaccct gatgatctct cggacccctg aagtgacctg cgtggtggtg  840
gatgtgtctc acgaggatcc cgaagtgaag ttcaattggt acgtggacgg cgtggaagtg  900
cacaacgcca agacccaagcc tagagaggaa cagtacaacc ccacctacag agtggtgtcc  960
gtgctgaccg tgctgcacca ggattggctg aacggcaaag agtacaagtg caaggtgtcc 1020
aacaaggccc tgcctgctcc tatcgaaaag accatctcca aggccaaggg ccagcctagg 1080
gaacccagg tttacaccct gcctccatgc cgggaagaga tgaccaagaa ccaggtgtcc 1140
ctgtggtgcc tggttaaggg cttctacccc tccgatatcg ccgtggaatg ggagtctaat 1200
ggccagcctg agaacaacta caagacaacc cctcctgtgc tggactccga cggctcattc 1260
ttcctgtact ccaagctgac agtggacaag tccagatggc agcagggcaa cgtgttctcc 1320
tgctccgtga tgcacgaggc cctgcacaat cactacaccc agaagtccct gtctctgtcc 1380
cctggcaagt gatga                                                 1395
```

| SEQ ID NO: 90 | moltype = DNA length = 708 |
|---|---|
| FEATURE | Location/Qualifiers |
| source | 1..708 |
| | mol_type = other DNA |
| | organism = synthetic construct |

SEQUENCE: 90

```
atggaaaccg acacactgct gctgtgggtg ctgctcttgt gggtgccagg atctacaggc   60
gagatcgtgc tgacccagtc tcctgccaca ctgtcactgt ctccaggcga gagagctacc  120
ctgtcctgta gagcctctca gtccgtgtc tcttacctgg cctggtatca gcagaagcct  180
ggacaggctc cccggctgct gatctacgat gcctctaata gagccacagg catcccccgcc  240
agattctccg gatctggctc tggcacagac tttaccctga ccatctccag cctggaacct  300
gaggacttcg ccgtgtacta ctgccagcag cctctaact ggcctcggac cttttggccag  360
ggcaccaagg tggaaatcaa gcggacagtg gccgctcctt ccgtgttcat cttcccacct  420
tccgacgagc agctgaagtc tggcaccgct tctgtcgtgt gcctgctgaa caacttctac  480
cctcgggaag ccaaggtgca gtggaaggtg gacaatgccc tgcagtccgg caactcccaa  540
gagtcgtga ccgagcagga ctccaaggac agcacctaca gcctgtcctc cacactgacc  600
ctgtccaagg ccgactacga aagcacaag gtgtacgcct gcgaagtgac ccatcagggc  660
ctgtctagcc ctgtgaccaa gtctttcaac cggggcgagt gctgatga                 708
```

| SEQ ID NO: 91 | moltype = DNA length = 1401 |
|---|---|
| FEATURE | Location/Qualifiers |
| source | 1..1401 |
| | mol_type = other DNA |
| | organism = synthetic construct |

SEQUENCE: 91

```
atggaaaccg acacactgct gctgtgggtg ctgctcttgt gggtgccagg atctacagga   60
caggtgcagc tggtggaatc tggtggcgga gttgtgcagc ctggcagatc cctgagactg  120
tcttgtgccg cctccggctt caccttctcc tcttacggaa tgcactgggt ccgacaggcc  180
cctggcaaag gattggagtg ggtcgccttc atcagatacg acggctccaa caagtactac  240
gccgactccg tgaagggcag attcaccatc tctcggaca actccaagaa caccctgtac  300
ctgcagatga actccctgag agccgaggac accgccgtgt actactgcaa gacccacggc  360
tctcacgaca attggggcca gggcacaatg gtcaccgtgt cctctgcttc caccaaggga  420
ccctctgtgt tccctctggc tccttccagc aagtctacct ctgggggaac agctgctctg  480
ggctgcctgg tcaaggacta cttcctgag cctgtgaccg tgtcttggaa ctctggcgct  540
ctgacatccg gcgtgcacac cttttccagct gtgctgcaat cctccggcct gtactctctg  600
tcctccgtcg tgaccgtgcc ttctagctct ctgggcaccc agacctacat ctgcaatgtg  660
aaccacaagc cttccaacac caaggtggac aagagagtgg aacccaagtc ctgcgataag  720
acccacacct gtccaccatg tcctgctcca gaactgctcg gcggaccttc cgtgttcctg  780
tttcctccaa agcctaagga caccctgatg atctctcgga cccctgaagt gacctgcgtg  840
gtggtggatg tgtctcacga ggatcccgaa gtgaagttca attggtacgt ggacggcgtg  900
gaagtgcaca acgccaagac ccagcctaga ggaacagt acaactccac ctacagagtg  960
gtgtccgtgc tgaccgtgct gcaccaggat tggctgaacg gcaaagagta caagtgcaag 1020
gtgtccaaca aggccctgcc tgctcctatc gaaaagacca tctccaaggc caagggccag 1080
cctcggaac tcaagtctg taccctgcct cctagccggg aagagatgac caagaaccag 1140
gtgtccctgt cctgcgctgt gaagggcttc taccttccg atatcgccgt ggaatgggag 1200
agcaatggcc agcctgagaa caactacaag accacctc ctgtgctgga ctccgacggc 1260
tcattcttct tggtgtccaa gctgacagtg gacaagtcca gatggcagca gggcaacgtg 1320
ttctcctgct ccgtgatgca cgaggccctg cacaatcact acacccagaa gtccctgtct 1380
```

```
ctgagccccg gcaagtgatg a                                                      1401

SEQ ID NO: 92           moltype = AA  length = 401
FEATURE                 Location/Qualifiers
source                  1..401
                        mol_type = protein
                        organism = synthetic construct
SEQUENCE: 92
QVQLVESGGG VVQPGRSLRL SCAASGFAFS SYGMHWVRQA PGKGLEWVAV IWFDGTKKYY             60
TDSVKGRFTI SRDNSKNTLY LQMNTLRAED TAVYYCARDR GIGARRGPYY MDVWGKGTTV            120
TVSSASTKGP SVFPLAPSSK STSGGTAALG CLVKDYFPEP VTVSWNSGAL TSGVHTFPAV            180
LQSSGLYSLS SVVTVPSSSL GTQTYICNVN HKPSNTKVDK RVEPKSCGSS GGGGSGGGGS            240
SGGVFTLEDF VGDWEQTAAY NLDQVLEQGG VSSLLQNLAV SVTPIQRIVR SGENALKIDI            300
HVIIPYEGLS ADQMAQIEEV FKVVYPVDDH HFKVILPYGT LVIDGVTPNM LNYFGRPYEG            360
IAVFDGKKIT VTGTLWNGNK IIDERLITPD GSMLFRVTIN S                                401

SEQ ID NO: 93           moltype = AA  length = 241
FEATURE                 Location/Qualifiers
source                  1..241
                        mol_type = protein
                        organism = synthetic construct
SEQUENCE: 93
DIQMTQSPSS LSASVGDRVT ITCRASQSIS SYLNWYQQKP GKAPKLLIYA ASSLQSGVPS             60
RFSGSGSGTD FTLTISSLQP EDFATYYCQQ SYSTPLTFGG GTKVEIKRTV AAPSVFIFPP            120
SDEQLKSGTA SVVCLLNNFY PREAKVQWKV DNALQSGNSQ ESVTEQDSKD STYSLSSTLT            180
LSKADYEKHK VYACEVTHQG LSSPVTKSFN RGECGSSGGG GSGGGGSSGG VTGYRLFEEI            240
L                                                                           241

SEQ ID NO: 94           moltype = AA  length = 214
FEATURE                 Location/Qualifiers
source                  1..214
                        mol_type = protein
                        organism = synthetic construct
SEQUENCE: 94
DIQMTQSPSS LSASVGDRVT ITCRASQSIS SYLNWYQQKP GKAPKLLIYA ASSLQSGVPS             60
RFSGSGSGTD FTLTISSLQP EDFATYYCQQ SYSTPLTFGG GTKVEIKRTV AAPSVFIFPP            120
SDEQLKSGTA SVVCLLNNFY PREAKVQWKV DNALQSGNSQ ESVTEQDSKD STYSLSSTLT            180
LSKADYEKHK VYACEVTHQG LSSPVTKSFN RGEC                                        214

SEQ ID NO: 95           moltype = AA  length = 396
FEATURE                 Location/Qualifiers
source                  1..396
                        mol_type = protein
                        organism = synthetic construct
SEQUENCE: 95
EVQLVQSGAE VKKSGESLKI SCKGSGYSFT SYWIGWVRQM PGKGLEWMGI FYPGDSSTRY             60
SPSFQGQVTI SADKSVNTAY LQWSSLKASD TAMYYCARRR NWGNAFDIWG QGTMVTVSSA            120
STKGPSVFPL APSSKSTSGG TAALGCLVKD YFPEPVTVSW NSGALTSGVH TFPAVLQSSG            180
LYSLSSVVTV PSSSLGTQTY ICNVNHKPSN TKVDKRVEPK SCGSSGGGGS GGGGSSGGVF            240
TLEDFVGDWE QTAAYNLDQV LEQGGVSSLL QNLAVSVTPI QRIVRSGENA LKIDIHVIIP            300
YEGLSADQMA QIEEVFKVVY PVDDHHFKVI LPYGTLVIDG VTPNMLNYFG RPYEGIAVFD            360
GKKITVTGTL WNGNKIIDER LITPDGSMLF RVTINS                                     396

SEQ ID NO: 96           moltype = AA  length = 242
FEATURE                 Location/Qualifiers
source                  1..242
                        mol_type = protein
                        organism = synthetic construct
SEQUENCE: 96
EIVLTQSPGT LSLSPGERAT LSCRASQSVS SSYLAWYQQK PGQAPRLLIY GASSRATGIP             60
DRFSGSGSGT DFTLTISRLE PEDFAVYYCQ QYGSSTWTFG QGTKVEIKRT VAAPSVFIFP            120
PSDEQLKSGT ASVVCLLNNF YPREAKVQWK VDNALQSGNS QESVTEQDSK DSTYSLSSTL            180
TLSKADYEKH KVYACEVTHQ GLSSPVTKSF NRGECGSSGG GSGGGGSSGG GVTGYRLFEE            240
IL                                                                          242

SEQ ID NO: 97           moltype = AA  length = 215
FEATURE                 Location/Qualifiers
source                  1..215
                        mol_type = protein
                        organism = synthetic construct
SEQUENCE: 97
EIVLTQSPGT LSLSPGERAT LSCRASQSVS SSYLAWYQQK PGQAPRLLIY GASSRATGIP             60
DRFSGSGSGT DFTLTISRLE PEDFAVYYCQ QYGSSTWTFG QGTKVEIKRT VAAPSVFIFP            120
PSDEQLKSGT ASVVCLLNNF YPREAKVQWK VDNALQSGNS QESVTEQDSK DSTYSLSSTL            180
TLSKADYEKH KVYACEVTHQ GLSSPVTKSF NRGEC                                       215

SEQ ID NO: 98           moltype = AA  length = 397
FEATURE                 Location/Qualifiers
source                  1..397
```

```
                            mol_type = protein
                            organism = synthetic construct
SEQUENCE: 98
EGQLVQSGGG LVHPGGSLRL SCAGSGFTFS SYGMHWVRQA PGKGLEWVSG IGTGGGTYST      60
DSVKGRFTIS RDNAKNSLYL QMNSLRAEDM AVYYCARGDY YGSGSFFDCW GQGTLVTVSS     120
ASTKGPSVFP LAPSSKSTSG GTAALGCLVK DYFPEPVTVS WNSGALTSGV HTFPAVLQSS     180
GLYSLSSVVT VPSSSLGTQT YICNVNHKPS NTKVDKRVEP KSCGSSGGGG SGGGGSSGGV     240
FTLEDFVGDW EQTAAYNLDQ VLEQGGVSSL QNLAVSVTP  IQRIVRSGEN ALKIDIHVII     300
PYEGLSADQM AQIEEVFKVV YPVDDHHFKV ILPYGTLVID GVTPNMLNYF GRPYEGIAVF     360
DGKKITVTGT LWNGNKIIDE RLITPDGSML FRVTINS                             397

SEQ ID NO: 99           moltype = AA  length = 241
FEATURE                 Location/Qualifiers
source                  1..241
                        mol_type = protein
                        organism = synthetic construct
SEQUENCE: 99
DIQMTQSPSS LSASVGDRVT ITCRASQGIS SWLAWYQQKP EKAPKSLIYA ASSLQSGVPS      60
RFSGSGSGTD FTLTISSLQP EDFATYYCQQ YNSYPPTFGQ GTKLEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGECGSSGGG GSGGGGSSGG VTGYRLFEEI     240
L                                                                    241

SEQ ID NO: 100          moltype = AA  length = 214
FEATURE                 Location/Qualifiers
source                  1..214
                        mol_type = protein
                        organism = synthetic construct
SEQUENCE: 100
DIQMTQSPSS LSASVGDRVT ITCRASQGIS SWLAWYQQKP EKAPKSLIYA ASSLQSGVPS      60
RFSGSGSGTD FTLTISSLQP EDFATYYCQQ YNSYPPTFGQ GTKLEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                214

SEQ ID NO: 101          moltype = AA  length = 396
FEATURE                 Location/Qualifiers
source                  1..396
                        mol_type = protein
                        organism = synthetic construct
SEQUENCE: 101
QVQLVQSGAE VKKPGASVKV SCKASGYSFT NYYIHWVRQA PGQRLEWMGW INAGNGNTKY      60
SQKFQGRVTI TRDTSASTAY MELSSLRSED TAVYYCVRRQ RFPYYFDYWG QGTLVTVSSA     120
STKGPSVFPL APSSKSTSGG TAALGCLVKD YFPEPVTVSW NSGALTSGVH TFPAVLQSSG     180
LYSLSSVVTV PSSSLGTQTY ICNVNHKPSN TKVDKRVEPK SCGSSGGGGS GGGGSSGGVF     240
TLEDFVGDWE QTAAYNLDQV LEQGGVSSLL QNLAVSVTPI QRIVRSGENA LKIDIHVIIP     300
YEGLSADQMA QIEEVFKVVY PVDDHHFKVI LPYGTLVIDG VTPNMLNYFG RPYEGIAVFD     360
GKKITVTGTL WNGNKIIDER LITPDGSMLF RVTINS                              396

SEQ ID NO: 102          moltype = AA  length = 241
FEATURE                 Location/Qualifiers
source                  1..241
                        mol_type = protein
                        organism = synthetic construct
SEQUENCE: 102
EIVLTQSPAT LSVSPGERAT LSCRASQSVG TNVAWYQQKP GQAPRVLIYS TSSRATGITD      60
RFSGSGSGTD FTLTISRLEP EDFAVYYCQQ FNKSPLTFGG GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGECGSSGGG GSGGGGSSGG VTGYRLFEEI     240
L                                                                    241

SEQ ID NO: 103          moltype = AA  length = 214
FEATURE                 Location/Qualifiers
source                  1..214
                        mol_type = protein
                        organism = synthetic construct
SEQUENCE: 103
EIVLTQSPAT LSVSPGERAT LSCRASQSVG TNVAWYQQKP GQAPRVLIYS TSSRATGITD      60
RFSGSGSGTD FTLTISRLEP EDFAVYYCQQ FNKSPLTFGG GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                214

SEQ ID NO: 104          moltype = AA  length = 395
FEATURE                 Location/Qualifiers
source                  1..395
                        mol_type = protein
                        organism = synthetic construct
SEQUENCE: 104
QVQLVESGGG VVQPGRSLRL SCAASGFTFS SYTMHWVRQA PGKGLEWVTF ISYDGNNKYY      60
ADSVKGRFTI SRDNSKNTLY LQMNSLRAED TAIYYCARTG WLGPFDYWGQ GTLVTVSSAS     120
```

```
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKRVEPKS CGSSGGGGSG GGSSGGVFT    240
LEDFVGDWEQ TAAYNLDQVL EQGGVSSLLQ NLAVSVTPIQ RIVRSGENAL KIDIHVIIPY   300
EGLSADQMAQ IEEVFKVVYP VDDHHFKVIL PYGTLVIDGV TPNMLNYFGR PYEGIAVFDG   360
KKITVTGTLW NGNKIIDERL ITPDGSMLFR VTINS                             395

SEQ ID NO: 105           moltype = AA  length = 242
FEATURE                  Location/Qualifiers
source                   1..242
                         mol_type = protein
                         organism = synthetic construct
SEQUENCE: 105
EIVLTQSPGT LSLSPGERAT LSCRASQSVG SSYLAWYQQK PGQAPRLLIY GAFSRATGIP    60
DRFSGSGSGT DFTLTISRLE PEDFAVYYCQ QYGSSPWTFG QGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGECGSSGG GGSGGGGSSG GVTGYRLFEE   240
IL                                                                 242

SEQ ID NO: 106           moltype = AA  length = 215
FEATURE                  Location/Qualifiers
source                   1..215
                         mol_type = protein
                         organism = synthetic construct
SEQUENCE: 106
EIVLTQSPGT LSLSPGERAT LSCRASQSVG SSYLAWYQQK PGQAPRLLIY GAFSRATGIP    60
DRFSGSGSGT DFTLTISRLE PEDFAVYYCQ QYGSSPWTFG QGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                             215

SEQ ID NO: 107           moltype = AA  length = 394
FEATURE                  Location/Qualifiers
source                   1..394
                         mol_type = protein
                         organism = synthetic construct
SEQUENCE: 107
EVQLVQSGAE VKKPGESLKI SCKGSGYIFT NYWIAWVRQM PGKGLESMGI IYPGDSDIRY    60
SPSFQGQVTI SADKSITTAY LQWSSLKASD TAMYYCARHD IEGFDYWGRG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKRVEPKSC GSSGGGGSGG GGSSGGVFTL   240
EDFVGDWEQT AAYNLDQVLE QGGVSSLLQN LAVSVTPIQR IVRSGENALK IDIHVIIPYE   300
GLSADQMAQI EEVFKVVYPV DDHHFKVILP YGTLVIDGVT PNMLNYFGRP YEGIAVFDGK   360
KITVTGTLWN GNKIIDERLI TPDGSMLFRV TINS                              394

SEQ ID NO: 108           moltype = AA  length = 242
FEATURE                  Location/Qualifiers
source                   1..242
                         mol_type = protein
                         organism = synthetic construct
SEQUENCE: 108
EIVLTQSPGT LSLSPGERAT LSCRASQSVS SSFFAWYQQK PGQAPRLLIY GASSRATGIP    60
DRLSGSGSGT DFTLTITRLE PEDFAVYYCQ QYDSSAITFG QGTRLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGECGSSGG GGSGGGGSSG GVTGYRLFEE   240
IL                                                                 242

SEQ ID NO: 109           moltype = AA  length = 215
FEATURE                  Location/Qualifiers
source                   1..215
                         mol_type = protein
                         organism = synthetic construct
SEQUENCE: 109
EIVLTQSPGT LSLSPGERAT LSCRASQSVS SSFFAWYQQK PGQAPRLLIY GASSRATGIP    60
DRLSGSGSGT DFTLTITRLE PEDFAVYYCQ QYDSSAITFG QGTRLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                             215

SEQ ID NO: 110           moltype = AA  length = 393
FEATURE                  Location/Qualifiers
source                   1..393
                         mol_type = protein
                         organism = synthetic construct
SEQUENCE: 110
QVQLVQSGAE VKKPGASVKV SCKASGYTFT SYSISWVRQA PGQGLEWMGW ISVYNGNTNY    60
AQKFQGRVTM TTDTSTSTAY LELRSLRSDD TAVYYCARDP IAAGYWQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCG SSGGGGSGGG GSSGGVFTLE   240
DFVGDWEQTA AYNLDQVLEQ GGVSSLLQNL AVSVTPIQRI VRSGENALKI DIHVIIPYEG   300
LSADQMAQIE EVFKVVYPVD DHHFKVILPY GTLVIDGVTP NMLNYFGRPY EGIAVFDGKK   360
ITVTGTLWNG NKIIDERLIT PDGSMLFRVT INS                               393
```

```
SEQ ID NO: 111              moltype = AA  length = 242
FEATURE                     Location/Qualifiers
source                      1..242
                            mol_type = protein
                            organism = synthetic construct
SEQUENCE: 111
EIVLTQSPGT LSLSPGERAT LSCRASQSVS STYLAWYQQK PGQAPRLLIY GASSRATGIP    60
DRFSGSGSGT DFTLTISRLE PEDFAVYYCQ QYGSSPRTFG QGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGECGSSGG GGSGGGGSSG GVTGYRLFEE   240
IL                                                                 242

SEQ ID NO: 112              moltype = AA  length = 215
FEATURE                     Location/Qualifiers
source                      1..215
                            mol_type = protein
                            organism = synthetic construct
SEQUENCE: 112
EIVLTQSPGT LSLSPGERAT LSCRASQSVS STYLAWYQQK PGQAPRLLIY GASSRATGIP    60
DRFSGSGSGT DFTLTISRLE PEDFAVYYCQ QYGSSPRTFG QGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 113              moltype = AA  length = 396
FEATURE                     Location/Qualifiers
source                      1..396
                            mol_type = protein
                            organism = synthetic construct
SEQUENCE: 113
QVQLQESGPG LVKPSGTLSL TCAVSGGSIS SSNWWSWVRQ PPGKGLEWIG EIYHSGSTNY    60
NPSLKSRVTI SVDKSKNQFS LKLSSVTAAD TAVYYCARWT GRTDAFDIWG QGTMVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCGSSGGGGS GGGGSSGGVF   240
TLEDFVGDWE QTAAYNLDQV LEQGGVSSLL QNLAVSVTPI QRIVRSGENA LKIDIHVIIP   300
YEGLSADQMA QIEEVFKVVY PVDDHHFKVI LPYGTLVIDG VTPNMLNYFG RPYEGIAVFD   360
GKKITVTGTL WNGNKIIDER LITPDGSMLF RVTINS                             396

SEQ ID NO: 114              moltype = AA  length = 246
FEATURE                     Location/Qualifiers
source                      1..246
                            mol_type = protein
                            organism = synthetic construct
SEQUENCE: 114
DVVMTQSPLS LPVTPGEPAS ISCRSSQSLL HSNGYNYLDW YLQKPGQSPQ LLIYLGSNRA    60
SGVPDRFSGS GSGTDFTLKI SRVEAEDVGV YYCMQGTHWP LTFGQGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGECG SSGGGGSGGG GSSGGVTGYR   240
LFEEIL                                                              246

SEQ ID NO: 115              moltype = AA  length = 219
FEATURE                     Location/Qualifiers
source                      1..219
                            mol_type = protein
                            organism = synthetic construct
SEQUENCE: 115
DVVMTQSPLS LPVTPGEPAS ISCRSSQSLL HSNGYNYLDW YLQKPGQSPQ LLIYLGSNRA    60
SGVPDRFSGS GSGTDFTLKI SRVEAEDVGV YYCMQGTHWP LTFGQGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 116              moltype = AA  length = 399
FEATURE                     Location/Qualifiers
source                      1..399
                            mol_type = protein
                            organism = synthetic construct
SEQUENCE: 116
EVQLLQSGGG LVQPGGSLRL SCAASGFMFS RYPMHWVRQA PGKGLEWVGS ISGSGGATPY    60
ADSVKGRFTI SRDNSKNTLY LQMNSLRAED TAVYYCAKDF YQILTGNAFD YWGQGTTVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCGSSGG GGSGGGGSSG   240
GVFTLEDFVG DWEQTAAYNL DQVLEQGGVS SLLQNLAVSV TPIQRIVRSG ENALKIDIHV   300
IIPYEGLSAD QMAQIEEVFK VVYPVDDHHF KVILPYGTLV IDGVTPNMLN YFGRPYEGIA   360
VFDGKKITVT GTLWNGNKII DERLITPDGS MLFRVTINS                          399

SEQ ID NO: 117              moltype = AA  length = 241
FEATURE                     Location/Qualifiers
source                      1..241
                            mol_type = protein
```

```
SEQUENCE: 117
DIQMTQSPSS LSASLGDRVT ITCRASQGIS SYLAWYQQKP GKAPKLLIYA KSTLQSGVPS    60
RFSGSGSGTD FTLTISSLQP EDSATYYCQQ YWTFPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGECGSSGGG GSGGGGSSGG VTGYRLFEEI   240
L                                                                   241

SEQ ID NO: 118        moltype = AA  length = 214
FEATURE               Location/Qualifiers
source                1..214
                      mol_type = protein
                      organism = synthetic construct
SEQUENCE: 118
DIQMTQSPSS LSASLGDRVT ITCRASQGIS SYLAWYQQKP GKAPKLLIYA KSTLQSGVPS    60
RFSGSGSGTD FTLTISSLQP EDSATYYCQQ YWTFPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 119        moltype = AA  length = 395
FEATURE               Location/Qualifiers
source                1..395
                      mol_type = protein
                      organism = synthetic construct
SEQUENCE: 119
EVQLVQSGGG LVKPGGSLRL SCAASGFTFS SFAMHWVRQA PGKGLEWISV IDTRGATYYA    60
DSVKGRFTIS RDNAKNSLYL QMNSLRAEDT AVYYCARLGN FYYGMDVWGQ GTTVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CGSSGGGGSG GGGSSGGVFT   240
LEDFVGDWEQ TAAYNLDQVL EQGGVSSLLQ NLAVSVTPIQ RIVRSGENAL KIDIHVIIPY   300
EGLSADQMAQ IEEVFKVVYP VDDHHFKVIL PYGTLVIDGV TPNMLNYFGR PYEGIAVFDG   360
KKITVTGTLW NGNKIIDERL ITPDGSMLFR VTINS                              395

SEQ ID NO: 120        moltype = AA  length = 241
FEATURE               Location/Qualifiers
source                1..241
                      mol_type = protein
                      organism = synthetic construct
SEQUENCE: 120
EIVLTQSPGT LSVSPGERAT LSCRASQSIG SSLHWYQQKP GQAPRLLIKY ASQSLSGIPD    60
RFSGSGSGTD FTLTISRLEP EDFAVYYCHQ SSRLPHTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGECGSSGGG GSGGGGSSGG VTGYRLFEEI   240
L                                                                   241

SEQ ID NO: 121        moltype = AA  length = 214
FEATURE               Location/Qualifiers
source                1..214
                      mol_type = protein
                      organism = synthetic construct
SEQUENCE: 121
EIVLTQSPGT LSVSPGERAT LSCRASQSIG SSLHWYQQKP GQAPRLLIKY ASQSLSGIPD    60
RFSGSGSGTD FTLTISRLEP EDFAVYYCHQ SSRLPHTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 122        moltype = AA  length = 395
FEATURE               Location/Qualifiers
source                1..395
                      mol_type = protein
                      organism = synthetic construct
SEQUENCE: 122
QVELVESGGG VVQPGRSQRL SCAASGFTFS SYGMHWVRQA PGKGLEWVAI IWFDGSTYY     60
ADSVRGRFTI SRDNSKNTLY LQMNSLRAED TAVYFCAREL GRRYFDLWGR GTLVSVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CGSSGGGGSG GGGSSGGVFT   240
LEDFVGDWEQ TAAYNLDQVL EQGGVSSLLQ NLAVSVTPIQ RIVRSGENAL KIDIHVIIPY   300
EGLSADQMAQ IEEVFKVVYP VDDHHFKVIL PYGTLVIDGV TPNMLNYFGR PYEGIAVFDG   360
KKITVTGTLW NGNKIIDERL ITPDGSMLFR VTINS                              395

SEQ ID NO: 123        moltype = AA  length = 242
FEATURE               Location/Qualifiers
source                1..242
                      mol_type = protein
                      organism = synthetic construct
SEQUENCE: 123
EIVLTQSPAT LSLSPGERAT LSCRASQSVS SYLAWYQQKP GQAPRLLIYD ASKRATGIPA    60
RFSGSGSGTD FTLTISSLEP EDFAVYYCQQ RSKWPPWTFG QGTKVESKRT VAAPSVFIFP   120
PSDEQLKSGT ASVVCLLNNF YPREAKVQWK VDNALQSGNS QESVTEQDSK DSTYSLSSTL   180
```

```
TLSKADYEKH KVYACEVTHQ GLSSPVTKSF NRGECGSSGG GGSGGGGSSG GVTGYRLFEE    240
IL                                                                  242

SEQ ID NO: 124          moltype = AA  length = 215
FEATURE                 Location/Qualifiers
source                  1..215
                        mol_type = protein
                        organism = synthetic construct
SEQUENCE: 124
EIVLTQSPAT LSLSPGERAT LSCRASQSVS SYLAWYQQKP GQAPRLLIYD ASKRATGIPA    60
RFSGSGSGTD FTLTISSLEP EDFAVYYCQQ RSKWPPWTFG QGTKVESKRT VAAPSVFIFP    120
PSDEQLKSGT ASVVCLLNNF YPREAKVQWK VDNALQSGNS QESVTEQDSK DSTYSLSSTL    180
TLSKADYEKH KVYACEVTHQ GLSSPVTKSF NRGEC                               215

SEQ ID NO: 125          moltype = AA  length = 393
FEATURE                 Location/Qualifiers
source                  1..393
                        mol_type = protein
                        organism = synthetic construct
SEQUENCE: 125
EVQLVESGGG LVQPGRSLRL SCAASRFTFD DYAMHWVRQA PGKGLEWVSG ISWNSGRIGY    60
ADSVKGRFTI SRDNAENSLF LQMNGLRAED TALYYCAKGR DSFDIWGQGT MVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSCG SSGGGGSGGG GSSGGVFTLE    240
DFVGDWEQTA AYNLDQVLEQ GGVSSLLQNL AVSVTPIQRI VRSGENALKI DIHVIIPYEG    300
LSADQMAQIE EVFKVVYPVD DHHFKVILPY GTLVIDGVTP NMLNYFGRPY EGIAVFDGKK    360
ITVTGTLWNG NKIIDERLIT PDGSMLFRVT INS                                 393

SEQ ID NO: 126          moltype = AA  length = 241
FEATURE                 Location/Qualifiers
source                  1..241
                        mol_type = protein
                        organism = synthetic construct
SEQUENCE: 126
DIQMTQSPSS VSASVGDRVT ITCRASQGIS SWLAWYQQKP GKAPKLLIYG ASSLESGVPS    60
RFSGSGSGTD FTLTISSLQP EDFASYYCQQ ANSFPYTFGQ GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGECGSSGGG GSGGGGSSGG VTGYRLFEEI    240
L                                                                   241

SEQ ID NO: 127          moltype = AA  length = 214
FEATURE                 Location/Qualifiers
source                  1..214
                        mol_type = protein
                        organism = synthetic construct
SEQUENCE: 127
DIQMTQSPSS VSASVGDRVT ITCRASQGIS SWLAWYQQKP GKAPKLLIYG ASSLESGVPS    60
RFSGSGSGTD FTLTISSLQP EDFASYYCQQ ANSFPYTFGQ GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 128          moltype = AA  length = 395
FEATURE                 Location/Qualifiers
source                  1..395
                        mol_type = protein
                        organism = synthetic construct
SEQUENCE: 128
EVQLLESGGG LVQPGGSLRL SCAASGFTFS AYEMKWVRQA PGKGLEWVSV IGPSGGFTFY    60
ADSVKGRFTI SRDNSKNTLY LQMNSLRAED TAVYYCATEG DNDAFDIWGQ GTTVTVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKRVEPKS CGSSGGGGSG GGGSSGGVFT    240
LEDFVGDWEQ TAAYNLDQVL EQGGVSSLLQ NLAVSVTPIQ RIVRSGENAL KIDIHVIIPY    300
EGLSADQMAQ IEEVFKVVYP VDDHHFKVIL PYGTLVIDGV TPNMLNYFGR PYEGIAVFDG    360
KKITVTGTLW NGNKIIDERL ITPDGSMLFR VTINS                               395

SEQ ID NO: 129          moltype = AA  length = 242
FEATURE                 Location/Qualifiers
source                  1..242
                        mol_type = protein
                        organism = synthetic construct
SEQUENCE: 129
DIQMTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPMYTFG QGTKLEIKRT VAAPSVFIFP    120
PSDEQLKSGT ASVVCLLNNF YPREAKVQWK VDNALQSGNS QESVTEQDSK DSTYSLSSTL    180
TLSKADYEKH KVYACEVTHQ GLSSPVTKSF NRGECGSSGG GGSGGGGSSG GVTGYRLFEE    240
IL                                                                  242

SEQ ID NO: 130          moltype = AA  length = 215
FEATURE                 Location/Qualifiers
```

```
source                     1..215
                           mol_type = protein
                           organism = synthetic construct
SEQUENCE: 130
DIQMTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPMYTFG QGTKLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 131             moltype = AA   length = 400
FEATURE                    Location/Qualifiers
source                     1..400
                           mol_type = protein
                           organism = synthetic construct
SEQUENCE: 131
EVQLVESGGG LVQPGGSLRL SCAASGFTFS SYAMSWVRQA PGKGLEWVSQ ISPAGGYTNY    60
ADSVKGRFTI SADTSKNTAY LQMNSLRAED TAVYYCARGE LPYYRMSKVM DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKR VEPKSCGSSS GGGSGGGGSS   240
GGVFTLEDFV GDWEQTAAYN LDQVLEQGGV SSLLQNLAVS VTPIQRIVRS GENALKIDIH   300
VIIPYEGLSA DQMAQIEEVF KVVYPVDDHH FKVILPYGTL VIDGVTPNML NYFGRPYEGI   360
AVFDGKKITV TGTLWNGNKI IDERLITPDG SMLFRVTINS                         400

SEQ ID NO: 132             moltype = AA   length = 241
FEATURE                    Location/Qualifiers
source                     1..241
                           mol_type = protein
                           organism = synthetic construct
SEQUENCE: 132
DIQMTQSPSS LSASVGDRVT ITCRASQYFS SYLAWYQQKP GKAPKLLIYG ASSRASGVPS    60
RFSGSGSGTD FTLTISSLQP EDFATYYCQQ YLGSPPTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGECGSSGGG GSGGGGSSGG VTGYRLFEEI   240
L                                                                   241

SEQ ID NO: 133             moltype = AA   length = 214
FEATURE                    Location/Qualifiers
source                     1..214
                           mol_type = protein
                           organism = synthetic construct
SEQUENCE: 133
DIQMTQSPSS LSASVGDRVT ITCRASQYFS SYLAWYQQKP GKAPKLLIYG ASSRASGVPS    60
RFSGSGSGTD FTLTISSLQP EDFATYYCQQ YLGSPPTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 134             moltype = AA   length = 407
FEATURE                    Location/Qualifiers
source                     1..407
                           mol_type = protein
                           organism = synthetic construct
SEQUENCE: 134
EVQLVQSGAE VKKPGSSVKV SCKASGGTFS SYAISWVRQA PGQGLEWMGG IIPIFGTANY    60
AQKFQGRVTI TADKSTSTAY MELSSLRSED TAVYYCARAP LRFLEWSTQD HYYYYMDVW   120
GKGTTVTVSS ASTKGPSVFP LAPSSKSTSG GTAALGCLVK DYFPEPVTVS WNSGALTSGV   180
HTFPAVLQSS GLYSLSSVVT VPSSSLGTQT YICNVNHKPS NTKVDKRVEP KSCGSSGGGG   240
SGGGGSSGGV FTLEDFVGDW EQTAAYNLDQ VLEQGGVSSL LQNLAVSVTP IQRIVRSGEN   300
ALKIDIHVII PYEGLSADQM AQIEEVFKVV YPVDDHHFKV ILPYGTLVID GVTPNMLNYF   360
GRPYEGIAVF DGKKITVTGT LWNGNKIIDE RLITPDGSML FRVTINS                 407

SEQ ID NO: 135             moltype = AA   length = 241
FEATURE                    Location/Qualifiers
source                     1..241
                           mol_type = protein
                           organism = synthetic construct
SEQUENCE: 135
SSELTQDPAV SVALGQTVRI TCQGDSLRSY YATWYQQKPG QAPILVIYGE NKRPSGIPDR    60
FSGSSSGNTA SLTITGAQAE DEADYYCKSR DGSGQHLVFG GGTKLTVLGQ PKANPTVTLF   120
PPSSEELQAN KATLVCLISD FYPGAVTVAW KADGSPVKAG VETTKPSKQS NNKYAASSYL   180
SLTPEQWKSH RSYSCQVTHE GSTVEKTVAP TECSGSSGGG GSGGGGSSGG VTGYRLFEEI   240
L                                                                   241

SEQ ID NO: 136             moltype = AA   length = 214
FEATURE                    Location/Qualifiers
source                     1..214
                           mol_type = protein
                           organism = synthetic construct
SEQUENCE: 136
SSELTQDPAV SVALGQTVRI TCQGDSLRSY YATWYQQKPG QAPILVIYGE NKRPSGIPDR    60
```

```
FSGSSSGNTA SLTITGAQAE DEADYYCKSR DGSGQHLVFG GGTKLTVLGQ PKANPTVTLF  120
PPSSEELQAN KATLVCLISD FYPGAVTVAW KADGSPVKAG VETTKPSKQS NNKYAASSYL  180
SLTPEQWKSH RSYSCQVTHE GSTVEKTVAP TECS                              214

SEQ ID NO: 137          moltype = AA   length = 398
FEATURE                 Location/Qualifiers
source                  1..398
                        mol_type = protein
                        organism = synthetic construct
SEQUENCE: 137
EVQLVQSGGG VERPGGSLRL SCAASGFTFD DYAMSWVRQA PGKGLEWVSG INWQGGSTGY   60
ADSVKGRVTI SRDNAKNSLY LQMNSLRAED TAVYYCAKIL GAGRGWYFDY WGKGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCGSSGGG GSGGGGSSGG  240
VFTLEDFVGD WEQTAAYNLD QVLEQGGVSS LLQNLAVSVT PIQRIVRSGE NALKIDIHVI  300
IPYEGLSADQ MAQIEEVFKV VYPVDDHHFK VILPYGTLVI DGVTPNMLNY FGRPYEGIAV  360
FDGKKITVTG TLWNGNKIID ERLITPDGSM LFRVTINS                          398

SEQ ID NO: 138          moltype = AA   length = 241
FEATURE                 Location/Qualifiers
source                  1..241
                        mol_type = protein
                        organism = synthetic construct
SEQUENCE: 138
SSELTQDPAV SVALGQTVRI TCSGDSLRSY YASWYQQKPG QAPVLVIYGA NNRPSGIPDR   60
FSGSSSGNTA SLTITGAQAE DEADYYCNSA DSSGNHVVFG GGTKLTVLGQ PKANPTVTLF  120
PPSSEELQAN KATLVCLISD FYPGAVTVAW KADGSPVKAG VETTKPSKQS NNKYAASSYL  180
SLTPEQWKSH RSYSCQVTHE GSTVEKTVAP TECSGSSGGG GSGGGGSSGG VTGYRLFEEI  240
L                                                                  241

SEQ ID NO: 139          moltype = AA   length = 214
FEATURE                 Location/Qualifiers
source                  1..214
                        mol_type = protein
                        organism = synthetic construct
SEQUENCE: 139
SSELTQDPAV SVALGQTVRI TCSGDSLRSY YASWYQQKPG QAPVLVIYGA NNRPSGIPDR   60
FSGSSSGNTA SLTITGAQAE DEADYYCNSA DSSGNHVVFG GGTKLTVLGQ PKANPTVTLF  120
PPSSEELQAN KATLVCLISD FYPGAVTVAW KADGSPVKAG VETTKPSKQS NNKYAASSYL  180
SLTPEQWKSH RSYSCQVTHE GSTVEKTVAP TECS                              214

SEQ ID NO: 140          moltype = AA   length = 394
FEATURE                 Location/Qualifiers
source                  1..394
                        mol_type = protein
                        organism = synthetic construct
SEQUENCE: 140
EVQLVQSGAE VKKPGESLKI SCKGSGYSFS NYWIGWVRQM PGKGLEWMGI IDPSNSYTRY   60
SPSFQGQVTI SADKSISTAY LQWSSLKASD TAMYYCARWY YKPFDVWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKRVEPKSC GSSGGGGSGG GGSSGGVFTL  240
EDFVGDWEQT AAYNLDQVLE QGGVSSLLQN LAVSVTPIQR IVRSGENALK IDIHVIIPYE  300
GLSADQMAQI EEVFKVVYPV DDHHFKVILP YGTLVIDGVT PNMLNYFGRP YEGIAVFDGK  360
KITVTGTLWN GNKIIDERLI TPDGSMLFRV TINS                              394

SEQ ID NO: 141          moltype = AA   length = 244
FEATURE                 Location/Qualifiers
source                  1..244
                        mol_type = protein
                        organism = synthetic construct
SEQUENCE: 141
QSVLTQPPSV SGAPGQRVTI SCTGSSSNIG SGYDVHWYQQ LPGTAPKLLI YGNSKRPSGV   60
PDRFSGSKSG TSASLAITGL QSEDEADYYC ASWTDGLSLV VFGGGTKLTV LGQPKANPTV  120
TLFPPSSEEL QANKATLVCL ISDFYPGAVT VAWKADGSPV KAGVETTKPS KQSNNKYAAS  180
SYLSLTPEQW KSHRSYSCQV THEGSTVEKT VAPTECSGSS GGGGSGGGGS SGGVTGYRLF  240
EEIL                                                               244

SEQ ID NO: 142          moltype = AA   length = 217
FEATURE                 Location/Qualifiers
source                  1..217
                        mol_type = protein
                        organism = synthetic construct
SEQUENCE: 142
QSVLTQPPSV SGAPGQRVTI SCTGSSSNIG SGYDVHWYQQ LPGTAPKLLI YGNSKRPSGV   60
PDRFSGSKSG TSASLAITGL QSEDEADYYC ASWTDGLSLV VFGGGTKLTV LGQPKANPTV  120
TLFPPSSEEL QANKATLVCL ISDFYPGAVT VAWKADGSPV KAGVETTKPS KQSNNKYAAS  180
SYLSLTPEQW KSHRSYSCQV THEGSTVEKT VAPTECS                           217

SEQ ID NO: 143          moltype = AA   length = 399
```

```
FEATURE                 Location/Qualifiers
source                  1..399
                        mol_type = protein
                        organism = synthetic construct
SEQUENCE: 143
QVQLVQSGGG LVQPGGSLRL SCAASGFTFD DYAMHWVRQA PGKGLEWVAG ISWDSGSTGY    60
ADSVKGRFTI SRDNAKNSLY LQMNSLRAED TALYYCARDL GAYQWVEGFD YWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCGSSGG GGSGGGGSSG   240
GVFTLEDFVG DWEQTAAYNL DQVLEQGGVS SLLQNLAVSV TPIQRIVRSG ENALKIDIHV   300
IIPYEGLSAD QMAQIEEVFK VVYPVDDHHF KVILPYGTLV IDGVTPNMLN YFGRPYEGIA   360
VFDGKKITVT GTLWNGNKII DERLITPDGS MLFRVTINS                          399

SEQ ID NO: 144          moltype = AA  length = 242
FEATURE                 Location/Qualifiers
source                  1..242
                        mol_type = protein
                        organism = synthetic construct
SEQUENCE: 144
SYELTQDPAV SVALGQTVRI TCQGDSLRSY YASWYQQKPG QAPVLVIYGK NNRPSGIPDR    60
FSGSTSGNSA SLTITGAQAE DEADYYCNSR DSPGNQWVFG GGTKVTVLGG QPKANPTVTL   120
FPPSSEELQA NKATLVCLIS DFYPGAVTVA WKADGSPVKA GVETTKPSKQ SNNKYAASSY   180
LSLTPEQWKS HRSYSCQVTH EGSTVEKTVA PTECSGSSGG GGSGGGGSSG GVTGYRLFEE   240
IL                                                                  242

SEQ ID NO: 145          moltype = AA  length = 215
FEATURE                 Location/Qualifiers
source                  1..215
                        mol_type = protein
                        organism = synthetic construct
SEQUENCE: 145
SYELTQDPAV SVALGQTVRI TCQGDSLRSY YASWYQQKPG QAPVLVIYGK NNRPSGIPDR    60
FSGSTSGNSA SLTITGAQAE DEADYYCNSR DSPGNQWVFG GGTKVTVLGG QPKANPTVTL   120
FPPSSEELQA NKATLVCLIS DFYPGAVTVA WKADGSPVKA GVETTKPSKQ SNNKYAASSY   180
LSLTPEQWKS HRSYSCQVTH EGSTVEKTVA PTECS                              215

SEQ ID NO: 146          moltype = AA  length = 398
FEATURE                 Location/Qualifiers
source                  1..398
                        mol_type = protein
                        organism = synthetic construct
SEQUENCE: 146
EVQLVQSGGG VERPGGSLRL SCAASGFTFD DYGMSWVRQA PGKGLEWVSG INWNGGSTGY    60
ADSVKGRVTI SRDNAKNSLY LQMNSLRAED TAVYYCAKIL GAGRGWYFDL WGKGTTVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCGSSGGG GSGGGGSSGG   240
VFTLEDFVGD WEQTAAYNLD QVLEQGGVSS LLQNLAVSVT PIQRIVRSGE NALKIDIHVI   300
IPYEGLSADQ MAQIEEVFKV VYPVDDHHFK VILPYGTLVI DGVTPNMLNY FGRPYEGIAV   360
FDGKKITVTG TLWNGNKIID ERLITPDGSM LFRVTINS                           398

SEQ ID NO: 147          moltype = AA  length = 241
FEATURE                 Location/Qualifiers
source                  1..241
                        mol_type = protein
                        organism = synthetic construct
SEQUENCE: 147
SSELTQDPAV SVALGQTVRI TCQGDSLRSY YASWYQQKPG QAPVLVIYGK NNRPSGIPDR    60
FSGSSSGNTA SLTITGAQAE DEADYYCNSR DSSGNHVVFG GGTKLTVLGQ PKANPTVTLF   120
PPSSEELQAN KATLVCLISD FYPGAVTVAW KADGSPVKAG VETTKPSKQS NNKYAASSYL   180
SLTPEQWKSH RSYSCQVTHE GSTVEKTVAP TECSGSSGGG GSGGGGSSGG VTGYRLFEEI   240
L                                                                   241

SEQ ID NO: 148          moltype = AA  length = 214
FEATURE                 Location/Qualifiers
source                  1..214
                        mol_type = protein
                        organism = synthetic construct
SEQUENCE: 148
SSELTQDPAV SVALGQTVRI TCQGDSLRSY YASWYQQKPG QAPVLVIYGK NNRPSGIPDR    60
FSGSSSGNTA SLTITGAQAE DEADYYCNSR DSSGNHVVFG GGTKLTVLGQ PKANPTVTLF   120
PPSSEELQAN KATLVCLISD FYPGAVTVAW KADGSPVKAG VETTKPSKQS NNKYAASSYL   180
SLTPEQWKSH RSYSCQVTHE GSTVEKTVAP TECS                               214

SEQ ID NO: 149          moltype = AA  length = 392
FEATURE                 Location/Qualifiers
source                  1..392
                        mol_type = protein
                        organism = synthetic construct
SEQUENCE: 149
```

```
QVQLVQSGAE VKKPGASVKV SCKASGYTFT SSYINWVRQA PGQGLEWMGT INPVSGSTSY    60
AQKFQGRVTM TRDTSISTAY MELSRLRSDD TAVYYCARGG WFDYWGQGTL VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCGS SGGGGSGGGG SSGGVFTLED   240
FVGDWEQTAA YNLDQVLEQG GVSSLLQNLA VSVTPIQRIV RSGENALKID IHVIIPYEGL   300
SADQMAQIEE VFKVVYPVDD HHFKVILPYG TLVIDGVTPN MLNYFGRPYE GIAVFDGKKI   360
TVTGTLWNGN KIIDERLITP DGSMLFRVTI NS                                 392

SEQ ID NO: 150          moltype = AA  length = 244
FEATURE                 Location/Qualifiers
source                  1..244
                        mol_type = protein
                        organism = synthetic construct
SEQUENCE: 150
QSALTQPASV SGSPGQSITI SCTGTSSDVG SYNYVNWYQQ HPGKAPKLMI YGVSKRPSGV    60
SNRFSGSKSG NTASLTISGL QAEDEADYYC GTFAGGSYYG VFGGGTKLTV LGQPKANPTV   120
TLFPPSSEEL QANKATLVCL ISDFYPGAVT VAWKADGSPV KAGVETTKPS KQSNNKYAAS   180
SYLSLTPEQW KSHRSYSCQV THEGSTVEKT VAPTECSGSS GGGGSGGGGS SGGVTGYRLF   240
EEIL                                                                244

SEQ ID NO: 151          moltype = AA  length = 217
FEATURE                 Location/Qualifiers
source                  1..217
                        mol_type = protein
                        organism = synthetic construct
SEQUENCE: 151
QSALTQPASV SGSPGQSITI SCTGTSSDVG SYNYVNWYQQ HPGKAPKLMI YGVSKRPSGV    60
SNRFSGSKSG NTASLTISGL QAEDEADYYC GTFAGGSYYG VFGGGTKLTV LGQPKANPTV   120
TLFPPSSEEL QANKATLVCL ISDFYPGAVT VAWKADGSPV KAGVETTKPS KQSNNKYAAS   180
SYLSLTPEQW KSHRSYSCQV THEGSTVEKT VAPTECS                            217

SEQ ID NO: 152          moltype = AA  length = 393
FEATURE                 Location/Qualifiers
source                  1..393
                        mol_type = protein
                        organism = synthetic construct
SEQUENCE: 152
EVQLVQSGAE VKKPGSSVKV SCKASGGTFS SYAISWVRQA PGQGLEWMGG IGPFFGTANY    60
AQKFQGRVTI TADESTSTAY MELSSLRSED TAVYYCARDT PYFDYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCG SSGGGGSGGG GSSGGVFTLE   240
DFVGDWEQTA AYNLDQVLEQ GGVSSLLQNL AVSVTPIQRI VRSGENALKI DIHVIIPYEG   300
LSADQMAQIE EVFKVVYPVD DHHFKVILPY GTLVIDGVTP NMLNYFGRPY EGIAVFDGKK   360
ITVTGTLWNG NKIIDERLIT PDGSMLFRVT INS                                393

SEQ ID NO: 153          moltype = AA  length = 241
FEATURE                 Location/Qualifiers
source                  1..241
                        mol_type = protein
                        organism = synthetic construct
SEQUENCE: 153
SYELTQPLSV SVALGQTARI TCSGDSIPNY YVWYQQKPG QAPVLVIYDD SNRPSGIPER    60
FSGSNSGNTA TLTISRAQAG DEADYYCQSF DSSLNAEVFG GGTKLTVLGQ PKANPTVTLF   120
PPSSEELQAN KATLVCLISD FYPGAVTVAW KADGSPVKAG VETTKPSKQS NNKYAASSYL   180
SLTPEQWKSH RSYSCQVTHE GSTVEKTVAP TECSGSSGGG GSGGGGSSGG VTGYRLFEEI   240
L                                                                    241

SEQ ID NO: 154          moltype = AA  length = 214
FEATURE                 Location/Qualifiers
source                  1..214
                        mol_type = protein
                        organism = synthetic construct
SEQUENCE: 154
SYELTQPLSV SVALGQTARI TCSGDSIPNY YVWYQQKPG QAPVLVIYDD SNRPSGIPER    60
FSGSNSGNTA TLTISRAQAG DEADYYCQSF DSSLNAEVFG GGTKLTVLGQ PKANPTVTLF   120
PPSSEELQAN KATLVCLISD FYPGAVTVAW KADGSPVKAG VETTKPSKQS NNKYAASSYL   180
SLTPEQWKSH RSYSCQVTHE GSTVEKTVAP TECS                                214

SEQ ID NO: 155          moltype = AA  length = 391
FEATURE                 Location/Qualifiers
source                  1..391
                        mol_type = protein
                        organism = synthetic construct
SEQUENCE: 155
EVQLVQSGAE VKKPGASVKV SCKASGYTFT GYHMHWVRQA PGQGLEWMGW INPNSGVTKY    60
AQKFQGRVTM TRDTSINTAY MELSRLRFDD TDVYYCATGG FGYWGEGTLV TVSSASTKGP   120
SVFPLAPSSK STSGGTAALG CLVKDYFPEP VTVSWNSGAL TSGVHTFPAV LQSSGLYSLS   180
SVVTVPSSSL GTQTYICNVN HKPSNTKVDK RVEPKSCGSS GGGGSGGGGS SGGVFTLEDF   240
VGDWEQTAAY NLDQVLEQGG VSSLLQNLAV SVTPIQRIVR SGENALKIDI HVIIPYEGLS   300
```

```
ADQMAQIEEV FKVVYPVDDH HFKVILPYGT LVIDGVTPNM LNYFGRPYEG IAVFDGKKIT    360
VTGTLWNGNK IIDERLITPD GSMLFRVTIN S                                  391

SEQ ID NO: 156          moltype = AA  length = 243
FEATURE                 Location/Qualifiers
source                  1..243
                        mol_type = protein
                        organism = synthetic construct
SEQUENCE: 156
LPVLTQPPSV SKGLRQTATL TCTGNSNNVG NQGAAWLQQH QGQPPKLLSY RNHNRPSGVS    60
ERFSPSRSGD TSSLTITGLQ PEDEADYYCL AWDSSLRAFV FGTGTKLTVL GQPKANPTVT   120
LFPPSSEELQ ANKATLVCLI SDFYPGAVTV AWKADGSPVK AGVETTKPSK QSNNKYAASS   180
YLSLTPEQWK SHRSYSCQVT HEGSTVEKTV APTECSGSSG GGGSGGGGSS GGVTGYRLFE   240
EIL                                                                 243

SEQ ID NO: 157          moltype = AA  length = 216
FEATURE                 Location/Qualifiers
source                  1..216
                        mol_type = protein
                        organism = synthetic construct
SEQUENCE: 157
LPVLTQPPSV SKGLRQTATL TCTGNSNNVG NQGAAWLQQH QGQPPKLLSY RNHNRPSGVS    60
ERFSPSRSGD TSSLTITGLQ PEDEADYYCL AWDSSLRAFV FGTGTKLTVL GQPKANPTVT   120
LFPPSSEELQ ANKATLVCLI SDFYPGAVTV AWKADGSPVK AGVETTKPSK QSNNKYAASS   180
YLSLTPEQWK SHRSYSCQVT HEGSTVEKTV APTECS                             216

SEQ ID NO: 158          moltype = AA  length = 389
FEATURE                 Location/Qualifiers
source                  1..389
                        mol_type = protein
                        organism = synthetic construct
SEQUENCE: 158
EVQLVESGGG LVQPGGSLRL SCVASGFTFS DYWMSWVRQA PGKGLEWVAN IKKDGSVNYY    60
VDSVKGRFTI SRDNAKNSLY LQMNSLRAED TAVYYCTRFD YWGQGTLVTV SSASTKGPSV   120
FPLAPSSKST SGGTAALGCL VKDYFPEPVT VSWNSGALTS GVHTFPAVLQ SSGLYSLSSV   180
VTVPSSSLGT QTYICNVNHK PSNTKVDKRV EPKSCGSSGG GGSGGGGSSG GVFTLEDFVG   240
DWEQTAAYNL DQVLEQGGVS SLLQNLAVSV TPIQRIVRSG ENALKIDIHV IIPYEGLSAD   300
QMAQIEEVFK VVYPVDDHHF KVILPYGTLV IDGVTPNMLN YFGRPYEGIA VFDGKKITVT   360
GTLWNGNKII DERLITPDGS MLFRVTINS                                     389

SEQ ID NO: 159          moltype = AA  length = 243
FEATURE                 Location/Qualifiers
source                  1..243
                        mol_type = protein
                        organism = synthetic construct
SEQUENCE: 159
QAGLTQPPSV SKGLRQTATL TCTGNSNNVG NQGAAWLQQH QGHPPKLLFY RNNNRASGIS    60
ERLSASRSGN TASLTITGLQ PEDEADYYCL TWDSSLSVVV FGGGTKLTVL GQPKANPTVT   120
LFPPSSEELQ ANKATLVCLI SDFYPGAVTV AWKADGSPVK AGVETTKPSK QSNNKYAASS   180
YLSLTPEQWK SHRSYSCQVT HEGSTVEKTV APTECSGSSG GGGSGGGGSS GGVTGYRLFE   240
EIL                                                                 243

SEQ ID NO: 160          moltype = AA  length = 216
FEATURE                 Location/Qualifiers
source                  1..216
                        mol_type = protein
                        organism = synthetic construct
SEQUENCE: 160
QAGLTQPPSV SKGLRQTATL TCTGNSNNVG NQGAAWLQQH QGHPPKLLFY RNNNRASGIS    60
ERLSASRSGN TASLTITGLQ PEDEADYYCL TWDSSLSVVV FGGGTKLTVL GQPKANPTVT   120
LFPPSSEELQ ANKATLVCLI SDFYPGAVTV AWKADGSPVK AGVETTKPSK QSNNKYAASS   180
YLSLTPEQWK SHRSYSCQVT HEGSTVEKTV APTECS                             216

SEQ ID NO: 161          moltype = AA  length = 392
FEATURE                 Location/Qualifiers
source                  1..392
                        mol_type = protein
                        organism = synthetic construct
SEQUENCE: 161
QVQLVESGGG VVQPGRSLRL SCAASGFTFS SYGMHWVRQA PGKGLEWVAF IRYDGSNKYY    60
ADSVKGRFTI SRDNSKNTLY LQMNSLRAED TAVYYCKTHG SHDNWGQGTM VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCGS SGGGGSGGGG SSGGVFTLED   240
FVGDWEQTAA YNLDQVLEQG GVSSLLQNLA VSVTPIQRIV RSGENALKID IHVIIPYEGL   300
SADQMAQIEE VFKVVYPVDD HHFKVILPYG TLVIDGVTPN MLNYFGRPYE GIAVFDGKKI   360
TVTGTLWNGN KIIDERLITP DGSMLFRVTI NS                                 392

SEQ ID NO: 162          moltype = AA  length = 244
FEATURE                 Location/Qualifiers
```

```
source                    1..244
                          mol_type = protein
                          organism = synthetic construct
SEQUENCE: 162
QSVLTQPPSV SGAPGQRVTI SCSGSRSNIG SNTVKWYQQL PGTAPKLLIY YNDQRPSGVP    60
DRFSGSKSGT SASLAITGLQ AEDEADYYCQ SYDRYTHPAL LFGTGTKVTV LGQPKANPTV   120
TLFPPSSEEL QANKATLVCL ISDFYPGAVT VAWKADGSPV KAGVETTKPS KQSNNKYAAS   180
SYLSLTPEQW KSHRSYSCQV THEGSTVEKT VAPTECSGSS GGGGSGGGGS SGGVTGYRLF   240
EEIL                                                                244

SEQ ID NO: 163            moltype = AA   length = 217
FEATURE                   Location/Qualifiers
source                    1..217
                          mol_type = protein
                          organism = synthetic construct
SEQUENCE: 163
QSVLTQPPSV SGAPGQRVTI SCSGSRSNIG SNTVKWYQQL PGTAPKLLIY YNDQRPSGVP    60
DRFSGSKSGT SASLAITGLQ AEDEADYYCQ SYDRYTHPAL LFGTGTKVTV LGQPKANPTV   120
TLFPPSSEEL QANKATLVCL ISDFYPGAVT VAWKADGSPV KAGVETTKPS KQSNNKYAAS   180
SYLSLTPEQW KSHRSYSCQV THEGSTVEKT VAPTECS                            217

SEQ ID NO: 164            moltype = AA   length = 449
FEATURE                   Location/Qualifiers
source                    1..449
                          mol_type = protein
                          organism = synthetic construct
SEQUENCE: 164
QVQLQESGPG LVKPSQTLSL TCTVSGGSIN NNNYYWTWIR QHPGKGLEWI GYIYYSGSTF    60
YNPSLKSRVT ISVDTSKTQF SLKLSSVTAA DTAVYYCARE DTMTGLDVWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPCREEM   360
TKNQVSLWCL VKGFYPSDIA VEWESNGQPE NNYKTTPPVL DSDGSFFLYS KLTVDKSRWQ   420
QGNVFSCSVM HEALHNHYTQ KSLSLSPGK                                     449

SEQ ID NO: 165            moltype = AA   length = 213
FEATURE                   Location/Qualifiers
source                    1..213
                          mol_type = protein
                          organism = synthetic construct
SEQUENCE: 165
DIQMTQSPSS LSASVGDRVT ITCRASQSIN NYLNWYQQKP GKAPTLLIYA ASSLQSGVPS    60
RFSGSRSGTD FTLTISSLQP EDFAAYFCQQ TYSNPTFGQG TKVEVKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 166            moltype = AA   length = 450
FEATURE                   Location/Qualifiers
source                    1..450
                          mol_type = protein
                          organism = synthetic construct
SEQUENCE: 166
EVQLLESGGG LVQPGGSLRL SCAASGFTFS SYIMMWVRQA PGKGLEWVSS IYPSGGITFY    60
ADTVKGRFTI SRDNSKNTLY LQMNSLRAED TAVYYCARIK LGTVTTVDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKRVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VCTLPPSREE   360
MTKNQVSLSC AVKGFYPSDI AVEWESNGQP ENNYKTTPPV LDSDGSFFLV SKLTVDKSRW   420
QQGNVFSCSV MHEALHNHYT QKSLSLSPGK                                    450

SEQ ID NO: 167            moltype = AA   length = 216
FEATURE                   Location/Qualifiers
source                    1..216
                          mol_type = protein
                          organism = synthetic construct
SEQUENCE: 167
QSALTQPASV SGSPGQSITI SCTGTSSDVG GYNYVSWYQQ HPGKAPKLMI YDVSNRPSGV    60
SNRFSGSKSG NTASLTISGL QAEDEADYYC SSYTSSSTRV FGTGTKVTVL GQPKANPTVT   120
LFPPSSEELQ ANKATLVCLI SDFYPGAVTV AWKADGSPVK AGVETTKPSK QSNNKYAASS   180
YLSLTPEQWK SHRSYSCQVT HEGSTVEKTV APTECS                             216

SEQ ID NO: 168            moltype = AA   length = 448
FEATURE                   Location/Qualifiers
source                    1..448
                          mol_type = protein
                          organism = synthetic construct
SEQUENCE: 168
```

```
QVQLVESGGG VVQPGRSLRL SCAASGFTFS SYTMHWVRQA PGKGLEWVTF ISYDGNNKYY    60
ADSVKGRFTI SRDNSKNTLY LQMNSLRAED TAIYYCARTG WLGPFDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDKTHTCPPC PAPELLGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPCREEMT   360
KNQVSLWCLV KGFYPSDIAV EWESNGQPEN NYKTTPPVLD SDGSFFLYSK LTVDKSRWQQ   420
GNVFSCSVMH EALHNHYTQK SLSLSPGK                                     448

SEQ ID NO: 169          moltype = AA  length = 725
FEATURE                 Location/Qualifiers
source                  1..725
                        mol_type = protein
                        organism = synthetic construct
SEQUENCE: 169
QVQLVESGGG VVQPGRSLRL SCAASGFTFS SYTMHWVRQA PGKGLEWVTF ISYDGNNKYY    60
ADSVKGRFTI SRDNSKNTLY LQMNSLRAED TAIYYCARTG WLGPFDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDKTHTCPPC PAPELLGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPCREEMT   360
KNQVSLWCLV KGFYPSDIAV EWESNGQPEN NYKTTPPVLD SDGSFFLYSK LTVDKSRWQQ   420
GNVFSCSVMH EALHNHYTQK SLSLSPGKGG GGSGGGGSGG GGSEVQLVES GGGLVKPGGS   480
LRLSCAASGF TFSPYSVFWV RQAPGKGLEW VSSINTDSTY KYYADSVKGR FTISRDNAEN   540
SIFLQMNSLR AEDTAVYYCA RDRSYYAFSS GSLSDYYYGL DVWGQGTLVT VSSGGGGSGG   600
GGSGGGGSGG GGSDIVMTQS PLSLSVTPGE PASISCRSSQ SLLHTNLYNY LDWYLQKPGQ   660
SPQLLIYLAS NRASGVPDRF SGSGSGTDFT LKISRVETED VGVYYCMQAL QIPRTFGQGT   720
KLEIK                                                              725

SEQ ID NO: 170          moltype = AA  length = 445
FEATURE                 Location/Qualifiers
source                  1..445
                        mol_type = protein
                        organism = synthetic construct
SEQUENCE: 170
QVQLVESGGG VVQPGRSLRL SCAASGFTFS SYGMHWVRQA PGKGLEWVAF IRYDGSNKYY    60
ADSVKGRFTI SRDNSKNTLY LQMNSLRAED TAVYYCKTHG SHDNWGQGTM VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDK THTCPPCPAP ELLGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVCTLP PSREEMTKNQ   360
VSLSCAVKGF YPSDIAVEWE SNGQPENNYK TTPPVLDSDG SFFLVSKLTV DKSRWQQGNV   420
FSCSVMHEAL HNHYTQKSLS LSPGK                                        445

SEQ ID NO: 171          moltype = AA  length = 448
FEATURE                 Location/Qualifiers
source                  1..448
                        mol_type = protein
                        organism = synthetic construct
SEQUENCE: 171
QVQLVESGGG VVQPGRSLRL SCAASGFTFS SYTMHWVRQA PGKGLEWVTF ISYDGNNKYY    60
ADSVKGRFTI SRDNSKNTLY LQMNSLRAED TAIYYCARTG WLGPFDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDKTHTCPPC PAPELLGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPSREEMT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPGK                                     448

SEQ ID NO: 172          moltype = AA  length = 445
FEATURE                 Location/Qualifiers
source                  1..445
                        mol_type = protein
                        organism = synthetic construct
SEQUENCE: 172
QVQLVESGGG VVQPGRSLRL SCAASGFTFS SYGMHWVRQA PGKGLEWVAF IRYDGSNKYY    60
ADSVKGRFTI SRDNSKNTLY LQMNSLRAED TAVYYCKTHG SHDNWGQGTM VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDK THTCPPCPAP ELLGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSREEMTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPGK                                        445

SEQ ID NO: 173          moltype = AA  length = 365
FEATURE                 Location/Qualifiers
source                  1..365
                        mol_type = protein
                        organism = synthetic construct
```

```
SEQUENCE: 173
QSVLTQPPSV SGAPGQRVTI SCSGSRSNIG SNTVKWYQQL PGTAPKLLIY YNDQRPSGVP    60
DRFSGSKSGT SASLAITGLQ AEDEADYYCQ SYDRYTHPAL LFGTGTKVTV LGQPKANPTV   120
TLFPPSSEEL QANKATLVCL ISDFYPGAVT VAWKADGSPV KAGVETTKPS KQSNNKYAAS   180
SYLSLTPEQW KSHRSYSCQV THEGSTVEKT VAPTECSGGG GSGGGGSGGG GSAPTSSSTK   240
KTQLQLEHLL LDLQMILNGI NNYKNPKLTR MLTAKFAMPK KATELKHLQC LEEELKPLEE   300
VLNLAQSKNF HLRPRDLISN INVIVLELKG SETTFMCEYA DETATIVEFL NRWITFCQSI   360
ISTLT                                                               365

SEQ ID NO: 174          moltype = AA  length = 593
FEATURE                 Location/Qualifiers
source                  1..593
                        mol_type = protein
                        organism = synthetic construct
SEQUENCE: 174
QVQLVESGGG VVQPGRSLRL SCAASGFTFS SYGMHWVRQA PGKGLEWVAF IRYDGSNKYY    60
ADSVKGRFTI SRDNSKNTLY LQMNSLRAED TAVYYCKTHG SHDNWGQGTM VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDK THTCPPCPAP ELLGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVCTLP PSREEMTKNQ   360
VSLSCAVKGF YPSDIAVEWE SNGQPENNYK TTPPVLDSDG SFFLVSKLTV DKSRWQQGNV   420
FSCSVMHEAL HNHYTQKSLS LSPGKGGGGS GGGGSGGGGS APTSSSTKKT QLQLEHLLLD   480
LQMILNGINN YKNPKLTRML TAKFAMPKKA TELKHLQCLE EELKPLEEVL NLAQSKNFHL   540
RPRDLISNIN VIVLELKGSE TTFMCEYADE TATIVEFLNR WITFCQSIIS TLT          593

SEQ ID NO: 175          moltype = AA  length = 593
FEATURE                 Location/Qualifiers
source                  1..593
                        mol_type = protein
                        organism = synthetic construct
SEQUENCE: 175
QVQLVESGGG VVQPGRSLRL SCAASGFTFS SYGMHWVRQA PGKGLEWVAF IRYDGSNKYY    60
ADSVKGRFTI SRDNSKNTLY LQMNSLRAED TAVYYCKTHG SHDNWGQGTM VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDK THTCPPCPAP ELLGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSREEMTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPGKGGGGS GGGGSGGGGS APTSSSTKKT QLQLEHLLLD   480
LQMILNGINN YKNPKLTRML TAKFAMPKKA TELKHLQCLE EELKPLEEVL NLAQSKNFHL   540
RPRDLISNIN VIVLELKGSE TTFMCEYADE TATIVEFLNR WITFCQSIIS TLT          593

SEQ ID NO: 176          moltype = AA  length = 363
FEATURE                 Location/Qualifiers
source                  1..363
                        mol_type = protein
                        organism = synthetic construct
SEQUENCE: 176
EIVLTQSPGT LSLSPGERAT LSCRASQSVG SSYLAWYQQK PGQAPRLLIY GAFSRATGIP    60
DRFSGSGSGT DFTLTISRLE PEDFAVYYCQ QYGSSPWTFG QGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGECGGGGS GGGGSGGGGS APTSSSTKKT   240
QLQLEHLLLD LQMILNGINN YKNPKLTRML TAKFAMPKKA TELKHLQCLE EELKPLEEVL   300
NLAQSKNFHL RPRDLISNIN VIVLELKGSE TTFMCEYADE TATIVEFLNR WITFCQSIIS   360
TLT                                                                 363

SEQ ID NO: 177          moltype = AA  length = 451
FEATURE                 Location/Qualifiers
source                  1..451
                        mol_type = protein
                        organism = synthetic construct
SEQUENCE: 177
EVQLVQSGGG VERPGGSLRL SCAASGFTFD DYGMSWVRQA PGKGLEWVSG INWNGGSTGY    60
ADSVKGRVTI SRDNAKNSLY LQMNSLRAED TAVYYCAKIL GAGRGWYFDL WGKGTTVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVCTLPPSRE   360
EMTKNQVSLS CAVKGFYPSD IAVEWESNGQ PENNYKTTPP VLDSDGSFFL VSKLTVDKSR   420
WQQGNVFSCS VMHEALHNHY TQKSLSLSPG K                                  451

SEQ ID NO: 178          moltype = AA  length = 453
FEATURE                 Location/Qualifiers
source                  1..453
                        mol_type = protein
                        organism = synthetic construct
SEQUENCE: 178
QVQLVQSGGG LVQPGGSLRL SCAASGFTFD DYAMHWVRQA PGKGLEWVAG ISWDSGSTGY    60
```

```
ADSVKGRFTI SRDNAKNSLY LQMNSLRAED TALYYCARDL GAYQWVEGFD YWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCTIKPC PPCKCPAPNL   240
LGGPSVFIFP PKIKDVLMIS LSPIVTCVVV DVSEDDPDVQ ISWFVNNVEV HTAQTQTHRE   300
DYNSTLRVVS ALPIQHQDWM SGKEFKCKVN NKDLPAPIER TISKPKGSVR APQVYVLPPC   360
EEEMTKKQVT LWCMVTDFMP EDIYVEWTNN GKTELNYKNT EPVLDSDGSY FMYSKLRVEK   420
KNWVERNSYS CSVVHEGLHN HHTTKSFSRT PGK                                453

SEQ ID NO: 179           moltype = AA   length = 453
FEATURE                  Location/Qualifiers
source                   1..453
                         mol_type = protein
                         organism = synthetic construct
SEQUENCE: 179
EVQLLQSGGG LVQPGGSLRL SCAASGFMFS RYPMHWVRQA PGKGLEWVGS ISGSGGATPY    60
ADSVKGRFTI SRDNSKNTLY LQMNSLRAED TAVYYCAKDF YQILTGNAFD YWGQGTTVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKRV EPKSCTIKPC PPCKCPAPNL   240
LGGPSVFIFP PKIKDVLMIS LSPIVTCVVV DVSEDDPDVQ ISWFVNNVEV HTAQTQTHRE   300
DYNSTLRVVS ALPIQHQDWM SGKEFKCKVN NKDLPAPIER TISKPKGSVR APQVCVLPPP   360
EEEMTKKQVT LSCAVTDFMP EDIYVEWTNN GKTELNYKNT EPVLDSDGSY FMVSKLRVEK   420
KNWVERNSYS CSVVHEGLHN HHTTKSFSRT PGK                                453

SEQ ID NO: 180           moltype = AA   length = 460
FEATURE                  Location/Qualifiers
source                   1..460
                         mol_type = protein
                         organism = synthetic construct
SEQUENCE: 180
EVQLVQSGAE VKKPGSSVKV SCKASGGTFS SYAISWVRQA PGQGLEWMGG IIPIFGTANY    60
AQKFQGRVTI TADKSTSTAY MELSSLRSED TAVYYCARAP LRFLEWSTQD HYYYYYMDVW   120
GKGTTVTVSS ASTKGPSVFP LAPSSKSTSG GTAALGCLVK DYFPEPVTVS WNSGALTSGV   180
HTFPAVLQSS GLYSLSSVVT VPSSSLGTQT YICNVNHKPS NTKVDKRVEP KSCDKTHTCP   240
PCPAPELLGG PSVFLFPPKP KDTLMISRTP EVTCVVVDVS HEDPEVKFNW YVDGVEVHNA   300
KTKPREEQYN STYRVVSVLT VLHQDWLNGK EYKCKVSNKA LPAPIEKTIS KAKGQPREPQ   360
VCTLPPSREE MTKNQVSLSC AVKGFYPSDI AVEWESNGQP ENNYKTTPPV LDSDGSFFLV   420
SKLTVDKSRW QQGNVFSCSV MHEALHNHYT QKSLSLSPGK                         460

SEQ ID NO: 181           moltype = AA   length = 443
FEATURE                  Location/Qualifiers
source                   1..443
                         mol_type = protein
                         organism = synthetic construct
SEQUENCE: 181
QVQLVESGGG VVQPGRSLRL DCKASGITFS NSGMHWVRQA PGKGLEWVAV IWYDGSKRYY    60
ADSVKGRFTI SRDNSKNTLF LQMNSLRAED TAVYYCATND DYWGQGTLVT VSSASTKGPS   120
VFPLAPSSKS TSGGTAALGC LVKDYFPEPV TVSWNSGALT SGVHTFPAVL QSSGLYSLSS   180
VVTVPSSSLG TQTYICNVNH KPSNTKVDKR VEPKSCDKTH TCPPCPAPEL LGGPSVFLFP   240
PKPKDTLMIS RTPEVTCVVV DVSHEDPEVK FNWYVDGVEV HNAKTKPREE QYNSTYRVVS   300
VLTVLHQDWL NGKEYKCKVS NKALPAPIEK TISKAKGQPR EPQVYTLPPC REEMTKNQVS   360
LWCLVKGFYP SDIAVEWESN GQPENNYKTT PPVLDSDGSF FLYSKLTVDK SRWQQGNVFS   420
CSVMHEALHN HYTQKSLSLS PGK                                           443

SEQ ID NO: 182           moltype = AA   length = 214
FEATURE                  Location/Qualifiers
source                   1..214
                         mol_type = protein
                         organism = synthetic construct
SEQUENCE: 182
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ SSNWPRTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 183           moltype = AA   length = 98
FEATURE                  Location/Qualifiers
source                   1..98
                         mol_type = protein
                         organism = synthetic construct
SEQUENCE: 183
QVQLVQSGAE VKKPGASVKV SCKASGYTFT SYGISWVRQA PGQGLEWMGW ISAYNGNTNY    60
AQKLQGRVTM TTDTSTSTAY MELRSLRSDD TAVYYCAR                            98

SEQ ID NO: 184           moltype = AA   length = 98
FEATURE                  Location/Qualifiers
source                   1..98
                         mol_type = protein
                         organism = synthetic construct
SEQUENCE: 184
```

```
QVQLVQSGAE VKKPGASVKV SCKASGYTFT GYYMHWVRQA PGQGLEWMGR INPNSGGTNY   60
AQKFQGRVTS TRDTSISTAY MELSRLRSDD TVVYYCAR                          98

SEQ ID NO: 185          moltype = AA  length = 98
FEATURE                 Location/Qualifiers
source                  1..98
                        mol_type = protein
                        organism = synthetic construct
SEQUENCE: 185
QVQLVQSGAE VKKPGASVKV SCKASGYTFT SYAMHWVRQA PGQRLEWMGW INAGNGNTKY   60
SQKFQGRVTI TRDTSASTAY MELSSLRSED TAVYYCAR                          98

SEQ ID NO: 186          moltype = AA  length = 98
FEATURE                 Location/Qualifiers
source                  1..98
                        mol_type = protein
                        organism = synthetic construct
SEQUENCE: 186
QVQLVQSGAE VKKPGASVKV SCKASGYTFT SYYMHWVRQA PGQGLEWMGI INPSGGSTSY   60
AQKFQGRVTM TRDTSTSTVY MELSSLRSED TAVYYCAR                          98

SEQ ID NO: 187          moltype = AA  length = 98
FEATURE                 Location/Qualifiers
source                  1..98
                        mol_type = protein
                        organism = synthetic construct
SEQUENCE: 187
QVQLVQSGAE VKKPGSSVKV SCKASGGTFS SYAISWVRQA PGQGLEWMGG IIPIFGTANY   60
AQKFQGRVTI TADESTSTAY MELSSLRSED TAVYYCAR                          98

SEQ ID NO: 188          moltype = AA  length = 97
FEATURE                 Location/Qualifiers
source                  1..97
                        mol_type = protein
                        organism = synthetic construct
SEQUENCE: 188
EVQLVESGGG LVQPGGSLRL SCAASGFTFS SYDMHWVRQA TGKGLEWVSA IGTAGDTYYP   60
GSVKGRFTIS RENAKNSLYL QMNSLRAGDT AVYYCAR                           97

SEQ ID NO: 189          moltype = AA  length = 98
FEATURE                 Location/Qualifiers
source                  1..98
                        mol_type = protein
                        organism = synthetic construct
SEQUENCE: 189
EVQLVESGGG VVRPGGSLRL SCAASGFTFD DYGMSWVRQA PGKGLEWVSG INWNGGSTGY   60
ADSVKGRFTI SRDNAKNSLY LQMNSLRAED TALYHCAR                          98

SEQ ID NO: 190          moltype = AA  length = 98
FEATURE                 Location/Qualifiers
source                  1..98
                        mol_type = protein
                        organism = synthetic construct
SEQUENCE: 190
EVQLVESGGG LVKPGGSLRL SCAASGFTFS SYSMNWVRQA PGKGLEWVSS ISSSSSYIYY   60
ADSVKGRFTI SRDNAKNSLY LQMNSLRAED TAVYYCAR                          98

SEQ ID NO: 191          moltype = AA  length = 98
FEATURE                 Location/Qualifiers
source                  1..98
                        mol_type = protein
                        organism = synthetic construct
SEQUENCE: 191
EVQLLESGGG LVQPGGSLRL SCAASGFTFS SYAMSWVRQA PGKGLEWVSA ISGSGGSTYY   60
ADSVKGRFTI SRDNSKNTLY LQMNSLRAED TAVYYCAK                          98

SEQ ID NO: 192          moltype = AA  length = 98
FEATURE                 Location/Qualifiers
source                  1..98
                        mol_type = protein
                        organism = synthetic construct
SEQUENCE: 192
QVQLVESGGG VVQPGRSLRL SCAASGFTFS SYAMHWVRQA PGKGLEWVAV ISYDGSNKYY   60
ADSVKGRFTI SRDNSKNTLY LQMNSLRAED TAVYYCAR                          98

SEQ ID NO: 193          moltype = AA  length = 98
FEATURE                 Location/Qualifiers
source                  1..98
                        mol_type = protein
```

```
SEQUENCE: 193
QVQLVESGGG VVQPGRSLRL SCAASGFTFS SYGMHWVRQA PGKGLEWVAV IWYDGSNKYY    60
ADSVKGRFTI SRDNSKNTLY LQMNSLRAED TAVYYCAR                           98

SEQ ID NO: 194          moltype = AA   length = 97
FEATURE                 Location/Qualifiers
source                  1..97
                        mol_type = protein
                        organism = synthetic construct
SEQUENCE: 194
EVQLVESGGG LVQPGGSLRL SCAASGFTVS SNYMSWVRQA PGKGLEWVSV IYSGGSTYYA    60
DSVKGRFTIS RDNSKNTLYL QMNSLRAEDT AVYYCAR                            97

SEQ ID NO: 195          moltype = AA   length = 98
FEATURE                 Location/Qualifiers
source                  1..98
                        mol_type = protein
                        organism = synthetic construct
SEQUENCE: 195
EVQLVESGGG LVQPGGSLRL SCAASGFTFS SYWMSWVRQA PGKGLEWVAN IKQDGSEKYY    60
VDSVKGRFTI SRDNAKNSLY LQMNSLRAED TAVYYCAR                           98

SEQ ID NO: 196          moltype = AA   length = 98
FEATURE                 Location/Qualifiers
source                  1..98
                        mol_type = protein
                        organism = synthetic construct
SEQUENCE: 196
EVQLVESGGG LVQPGRSLRL SCAASGFTFD DYAMHWVRQA PGKGLEWVSG ISWNSGSIGY    60
ADSVKGRFTI SRDNAKNSLY LQMNSLRAED TALYYCAK                           98

SEQ ID NO: 197          moltype = AA   length = 98
FEATURE                 Location/Qualifiers
source                  1..98
                        mol_type = protein
                        organism = synthetic construct
SEQUENCE: 197
QVQLQESGPG LVKPPGTLSL TCAVSGGSIS SSNWWSWVRQ PPGKGLEWIG EIYHSGSTNY    60
NPSLKSRVTI SVDKSKNQFS LKLSSVTAAD TAVYCCAR                           98

SEQ ID NO: 198          moltype = AA   length = 98
FEATURE                 Location/Qualifiers
source                  1..98
                        mol_type = protein
                        organism = synthetic construct
SEQUENCE: 198
EVQLVQSGAE VKKPGESLKI SCKGSGYSFT SYWIGWVRQM PGKGLEWMGI IYPGDSDTRY    60
SPSFQGQVTI SADKSISTAY LQWSSLKASD TAMYYCAR                           98

SEQ ID NO: 199          moltype = AA   length = 88
FEATURE                 Location/Qualifiers
source                  1..88
                        mol_type = protein
                        organism = synthetic construct
SEQUENCE: 199
DIQMTQSPSS VSASVGDRVT ITCRASQGIS SWLAWYQQKP GKAPKLLIYA ASSLQSGVPS    60
RFSGSGSGTD FTLTISSLQP EDFATYYC                                      88

SEQ ID NO: 200          moltype = AA   length = 88
FEATURE                 Location/Qualifiers
source                  1..88
                        mol_type = protein
                        organism = synthetic construct
SEQUENCE: 200
DIQMTQSPSS LSASVGDRVT ITCRASQGIS NYLAWYQQKP GKVPKLLIYA ASTLQSGVPS    60
RFSGSGSGTD FTLTISSLQP EDVATYYC                                      88

SEQ ID NO: 201          moltype = AA   length = 88
FEATURE                 Location/Qualifiers
source                  1..88
                        mol_type = protein
                        organism = synthetic construct
SEQUENCE: 201
DIQMTQSPSS LSASVGDRVT ITCRASQSIS SYLNWYQQKP GKAPKLLIYA ASSLQSGVPS    60
RFSGSGSGTD FTLTISSLQP EDFATYYC                                      88

SEQ ID NO: 202          moltype = AA   length = 88
FEATURE                 Location/Qualifiers
```

```
source                  1..88
                        mol_type = protein
                        organism = synthetic construct
SEQUENCE: 202
DIQMTQSPSS LSASVGDRVT ITCRASQGIS SWLAWYQQKP EKAPKSLIYA ASSLQSGVPS  60
RFSGSGSGTD FTLTISSLQP EDFATYYC                                    88

SEQ ID NO: 203          moltype = AA   length = 93
FEATURE                 Location/Qualifiers
source                  1..93
                        mol_type = protein
                        organism = synthetic construct
SEQUENCE: 203
DIVMTQSPLS LPVTPGEPAS ISCRSSQSLL HSNGYNYLDW YLQKPGQSPQ LLIYLGSNRA  60
SGVPDRFSGS GSGTDFTLKI SRVEAEDVGV YYC                               93

SEQ ID NO: 204          moltype = AA   length = 88
FEATURE                 Location/Qualifiers
source                  1..88
                        mol_type = protein
                        organism = synthetic construct
SEQUENCE: 204
EIVLTQSPAT LSLSPGERAT LSCRASQSVS SYLAWYQQKP GQAPRLLIYD ASNRATGIPA  60
RFSGSGSGTD FTLTISSLEP EDFAVYYC                                    88

SEQ ID NO: 205          moltype = AA   length = 89
FEATURE                 Location/Qualifiers
source                  1..89
                        mol_type = protein
                        organism = synthetic construct
SEQUENCE: 205
EIVLTQSPGT LSLSPGERAT LSCRASQSVS SSYLAWYQQK PGQAPRLLIY GASSRATGIP  60
DRFSGSGSGT DFTLTISRLE PEDFAVYYC                                   89

SEQ ID NO: 206          moltype = AA   length = 89
FEATURE                 Location/Qualifiers
source                  1..89
                        mol_type = protein
                        organism = synthetic construct
SEQUENCE: 206
EIVLTQSPAT LSLSPGERAT LSCGASQSVS SSYLAWYQQK PGLAPRLLIY DASSRATGIP  60
DRFSGSGSGT DFTLTISRLE PEDFAVYYC                                   89

SEQ ID NO: 207          moltype = AA   length = 89
FEATURE                 Location/Qualifiers
source                  1..89
                        mol_type = protein
                        organism = synthetic construct
SEQUENCE: 207
QAGLTQPPSV SKGLRQTATL TCTGNSNNVG NQGAAWLQQH QGHPPKLLSY RNNNRPSGIS  60
ERLSASRSGN TASLTITGLQ PEDEADYYC                                   89

SEQ ID NO: 208          moltype = AA   length = 90
FEATURE                 Location/Qualifiers
source                  1..90
                        mol_type = protein
                        organism = synthetic construct
SEQUENCE: 208
QSVLTQPPSV SGAPGQRVTI SCTGSSSNIG AGYDVHWYQQ LPGTAPKLLI YGNSNRPSGV  60
PDRFSGSKSG TSASLAITGL QAEDEADYYC                                  90

SEQ ID NO: 209          moltype = AA   length = 89
FEATURE                 Location/Qualifiers
source                  1..89
                        mol_type = protein
                        organism = synthetic construct
SEQUENCE: 209
QSVLTQPPSA SGTPGQRVTI SCSGSSSNIG SNTVNWYQQL PGTAPKLLIY SNNQRPSGVP  60
DRFSGSKSGT SASLAISGLQ SEDEADYYC                                   89

SEQ ID NO: 210          moltype = AA   length = 90
FEATURE                 Location/Qualifiers
source                  1..90
                        mol_type = protein
                        organism = synthetic construct
SEQUENCE: 210
QSALTQPASV SGSPGQSITI SCTGTSSDVG GYNYVSWYQQ HPGKAPKLMI YEVSNRPSGV  60
SNRFSGSKSG NTASLTISGL QAEDEADYYC                                  90
```

```
SEQ ID NO: 211           moltype = AA  length = 87
FEATURE                  Location/Qualifiers
source                   1..87
                         mol_type = protein
                         organism = synthetic construct
SEQUENCE: 211
SSELTQDPAV SVALGQTVRI TCQGDSLRSY YASWYQQKPG QAPVLVIYGK NNRPSGIPDR  60
FSGSSSGNTA SLTITGAQAE DEADYYC                                     87

SEQ ID NO: 212           moltype = AA  length = 87
FEATURE                  Location/Qualifiers
source                   1..87
                         mol_type = protein
                         organism = synthetic construct
SEQUENCE: 212
SYELTQPLSV SVALGQTARI TCGGNNIGSK NVHWYQQKPG QAPVLVIYRD SNRPSGIPER  60
FSGSNSGNTA TLTISRAQAG DEADYYC                                     87

SEQ ID NO: 213           moltype = AA  length = 99
FEATURE                  Location/Qualifiers
source                   1..99
                         mol_type = protein
                         organism = synthetic construct
SEQUENCE: 213
QVQLQESGPG LVKPSQTLSL TCTVSGGSIS SGGYYWSWIR QHPGKGLEWI GYIYYSGSTY  60
YNPSLKSLVT ISVDTSKNQF SLKLSSVTAA DTAVYYCAR                        99

SEQ ID NO: 214           moltype = AA  length = 20
FEATURE                  Location/Qualifiers
source                   1..20
                         mol_type = protein
                         organism = synthetic construct
SEQUENCE: 214
METDTLLLWV LLLWVPGSTG                                             20

SEQ ID NO: 215           moltype = AA  length = 25
FEATURE                  Location/Qualifiers
source                   1..25
                         mol_type = protein
                         organism = synthetic construct
SEQUENCE: 215
QVQLVQSGAE VKKPGASVKV SCKAS                                       25

SEQ ID NO: 216           moltype = AA  length = 10
FEATURE                  Location/Qualifiers
source                   1..10
                         mol_type = protein
                         organism = synthetic construct
SEQUENCE: 216
GYTFTSYGIS                                                        10

SEQ ID NO: 217           moltype = AA  length = 14
FEATURE                  Location/Qualifiers
source                   1..14
                         mol_type = protein
                         organism = synthetic construct
SEQUENCE: 217
WVRQAPGQGL EWMG                                                   14

SEQ ID NO: 218           moltype = AA  length = 17
FEATURE                  Location/Qualifiers
source                   1..17
                         mol_type = protein
                         organism = synthetic construct
SEQUENCE: 218
WISAYNGNTN YAQKLQG                                                17

SEQ ID NO: 219           moltype = AA  length = 32
FEATURE                  Location/Qualifiers
source                   1..32
                         mol_type = protein
                         organism = synthetic construct
SEQUENCE: 219
RVTMTTDTST STAYMELRSL RSDDTAVYYC AR                               32

SEQ ID NO: 220           moltype = AA  length = 10
FEATURE                  Location/Qualifiers
source                   1..10
                         mol_type = protein
```

```
                                 -continued
                       organism = synthetic construct
SEQUENCE: 220
GYTFTGYYMH                                                              10

SEQ ID NO: 221         moltype = AA   length = 17
FEATURE                Location/Qualifiers
source                 1..17
                       mol_type = protein
                       organism = synthetic construct
SEQUENCE: 221
RINPNSGGTN YAQKFQG                                                      17

SEQ ID NO: 222         moltype = AA   length = 32
FEATURE                Location/Qualifiers
source                 1..32
                       mol_type = protein
                       organism = synthetic construct
SEQUENCE: 222
RVTSTRDTSI STAYMELSRL RSDDTVVYYC AR                                     32

SEQ ID NO: 223         moltype = AA   length = 10
FEATURE                Location/Qualifiers
source                 1..10
                       mol_type = protein
                       organism = synthetic construct
SEQUENCE: 223
GYTFTSYAMH                                                              10

SEQ ID NO: 224         moltype = AA   length = 14
FEATURE                Location/Qualifiers
source                 1..14
                       mol_type = protein
                       organism = synthetic construct
SEQUENCE: 224
WVRQAPGQRL EWMG                                                         14

SEQ ID NO: 225         moltype = AA   length = 17
FEATURE                Location/Qualifiers
source                 1..17
                       mol_type = protein
                       organism = synthetic construct
SEQUENCE: 225
WINAGNGNTK YSQKFQG                                                      17

SEQ ID NO: 226         moltype = AA   length = 32
FEATURE                Location/Qualifiers
source                 1..32
                       mol_type = protein
                       organism = synthetic construct
SEQUENCE: 226
RVTITRDTSA STAYMELSSL RSEDTAVYYC AR                                     32

SEQ ID NO: 227         moltype = AA   length = 10
FEATURE                Location/Qualifiers
source                 1..10
                       mol_type = protein
                       organism = synthetic construct
SEQUENCE: 227
GYTFTSYYMH                                                              10

SEQ ID NO: 228         moltype = AA   length = 17
FEATURE                Location/Qualifiers
source                 1..17
                       mol_type = protein
                       organism = synthetic construct
SEQUENCE: 228
IINPSGGSTS YAQKFQG                                                      17

SEQ ID NO: 229         moltype = AA   length = 32
FEATURE                Location/Qualifiers
source                 1..32
                       mol_type = protein
                       organism = synthetic construct
SEQUENCE: 229
RVTMTRDTST STVYMELSSL RSEDTAVYYC AR                                     32

SEQ ID NO: 230         moltype = AA   length = 25
FEATURE                Location/Qualifiers
source                 1..25
```

```
                    mol_type = protein
                    organism = synthetic construct
SEQUENCE: 230
QVQLVQSGAE VKKPGSSVKV SCKAS                                         25

SEQ ID NO: 231          moltype = AA  length = 10
FEATURE                 Location/Qualifiers
source                  1..10
                        mol_type = protein
                        organism = synthetic construct
SEQUENCE: 231
GGTFSSYAIS                                                          10

SEQ ID NO: 232          moltype = AA  length = 17
FEATURE                 Location/Qualifiers
source                  1..17
                        mol_type = protein
                        organism = synthetic construct
SEQUENCE: 232
GIIPIFGTAN YAQKFQG                                                  17

SEQ ID NO: 233          moltype = AA  length = 32
FEATURE                 Location/Qualifiers
source                  1..32
                        mol_type = protein
                        organism = synthetic construct
SEQUENCE: 233
RVTITADEST STAYMELSSL RSEDTAVYYC AR                                 32

SEQ ID NO: 234          moltype = AA  length = 25
FEATURE                 Location/Qualifiers
source                  1..25
                        mol_type = protein
                        organism = synthetic construct
SEQUENCE: 234
EVQLVESGGG LVQPGGSLRL SCAAS                                         25

SEQ ID NO: 235          moltype = AA  length = 10
FEATURE                 Location/Qualifiers
source                  1..10
                        mol_type = protein
                        organism = synthetic construct
SEQUENCE: 235
GFTFSSYDMH                                                          10

SEQ ID NO: 236          moltype = AA  length = 14
FEATURE                 Location/Qualifiers
source                  1..14
                        mol_type = protein
                        organism = synthetic construct
SEQUENCE: 236
WVRQATGKGL EWVS                                                     14

SEQ ID NO: 237          moltype = AA  length = 16
FEATURE                 Location/Qualifiers
source                  1..16
                        mol_type = protein
                        organism = synthetic construct
SEQUENCE: 237
AIGTAGDTYY PGSVKG                                                   16

SEQ ID NO: 238          moltype = AA  length = 32
FEATURE                 Location/Qualifiers
source                  1..32
                        mol_type = protein
                        organism = synthetic construct
SEQUENCE: 238
RFTISRENAK NSLYLQMNSL RAGDTAVYYC AR                                 32

SEQ ID NO: 239          moltype = AA  length = 25
FEATURE                 Location/Qualifiers
source                  1..25
                        mol_type = protein
                        organism = synthetic construct
SEQUENCE: 239
EVQLVESGGG VVRPGGSLRL SCAAS                                         25

SEQ ID NO: 240          moltype = AA  length = 10
FEATURE                 Location/Qualifiers
```

-continued

| | | |
|---|---|---|
| source | 1..10<br>mol_type = protein<br>organism = synthetic construct | |
| SEQUENCE: 240<br>GFTFDDYGMS | | 10 |
| SEQ ID NO: 241<br>FEATURE<br>source | moltype = AA length = 14<br>Location/Qualifiers<br>1..14<br>mol_type = protein<br>organism = synthetic construct | |
| SEQUENCE: 241<br>WVRQAPGKGL EWVS | | 14 |
| SEQ ID NO: 242<br>FEATURE<br>source | moltype = AA length = 17<br>Location/Qualifiers<br>1..17<br>mol_type = protein<br>organism = synthetic construct | |
| SEQUENCE: 242<br>GINWNGGSTG YADSVKG | | 17 |
| SEQ ID NO: 243<br>FEATURE<br>source | moltype = AA length = 32<br>Location/Qualifiers<br>1..32<br>mol_type = protein<br>organism = synthetic construct | |
| SEQUENCE: 243<br>RFTISRDNAK NSLYLQMNSL RAEDTALYHC AR | | 32 |
| SEQ ID NO: 244<br>FEATURE<br>source | moltype = AA length = 25<br>Location/Qualifiers<br>1..25<br>mol_type = protein<br>organism = synthetic construct | |
| SEQUENCE: 244<br>EVQLVESGGG LVKPGGSLRL SCAAS | | 25 |
| SEQ ID NO: 245<br>FEATURE<br>source | moltype = AA length = 10<br>Location/Qualifiers<br>1..10<br>mol_type = protein<br>organism = synthetic construct | |
| SEQUENCE: 245<br>GFTFSSYSMN | | 10 |
| SEQ ID NO: 246<br>FEATURE<br>source | moltype = AA length = 17<br>Location/Qualifiers<br>1..17<br>mol_type = protein<br>organism = synthetic construct | |
| SEQUENCE: 246<br>SISSSSSYIY YADSVKG | | 17 |
| SEQ ID NO: 247<br>FEATURE<br>source | moltype = AA length = 32<br>Location/Qualifiers<br>1..32<br>mol_type = protein<br>organism = synthetic construct | |
| SEQUENCE: 247<br>RFTISRDNAK NSLYLQMNSL RAEDTAVYYC AR | | 32 |
| SEQ ID NO: 248<br>FEATURE<br>source | moltype = AA length = 25<br>Location/Qualifiers<br>1..25<br>mol_type = protein<br>organism = synthetic construct | |
| SEQUENCE: 248<br>EVQLLESGGG LVQPGGSLRL SCAAS | | 25 |
| SEQ ID NO: 249<br>FEATURE<br>source | moltype = AA length = 10<br>Location/Qualifiers<br>1..10<br>mol_type = protein<br>organism = synthetic construct | |
| SEQUENCE: 249<br>GFTFSSYAMS | | 10 |
| SEQ ID NO: 250 | moltype = AA length = 17 | |

```
FEATURE               Location/Qualifiers
source                1..17
                      mol_type = protein
                      organism = synthetic construct
SEQUENCE: 250
AISGSGGSTY YADSVKG                                                           17

SEQ ID NO: 251        moltype = AA   length = 32
FEATURE               Location/Qualifiers
source                1..32
                      mol_type = protein
                      organism = synthetic construct
SEQUENCE: 251
RFTISRDNSK NTLYLQMNSL RAEDTAVYYC AK                                          32

SEQ ID NO: 252        moltype = AA   length = 25
FEATURE               Location/Qualifiers
source                1..25
                      mol_type = protein
                      organism = synthetic construct
SEQUENCE: 252
QVQLVESGGG VVQPGRSLRL SCAAS                                                  25

SEQ ID NO: 253        moltype = AA   length = 10
FEATURE               Location/Qualifiers
source                1..10
                      mol_type = protein
                      organism = synthetic construct
SEQUENCE: 253
GFTFSSYAMH                                                                   10

SEQ ID NO: 254        moltype = AA   length = 14
FEATURE               Location/Qualifiers
source                1..14
                      mol_type = protein
                      organism = synthetic construct
SEQUENCE: 254
WVRQAPGKGL EWVA                                                              14

SEQ ID NO: 255        moltype = AA   length = 17
FEATURE               Location/Qualifiers
source                1..17
                      mol_type = protein
                      organism = synthetic construct
SEQUENCE: 255
VISYDGSNKY YADSVKG                                                           17

SEQ ID NO: 256        moltype = AA   length = 32
FEATURE               Location/Qualifiers
source                1..32
                      mol_type = protein
                      organism = synthetic construct
SEQUENCE: 256
RFTISRDNSK NTLYLQMNSL RAEDTAVYYC AR                                          32

SEQ ID NO: 257        moltype = AA   length = 10
FEATURE               Location/Qualifiers
source                1..10
                      mol_type = protein
                      organism = synthetic construct
SEQUENCE: 257
GFTFSSYGMH                                                                   10

SEQ ID NO: 258        moltype = AA   length = 17
FEATURE               Location/Qualifiers
source                1..17
                      mol_type = protein
                      organism = synthetic construct
SEQUENCE: 258
VIWYDGSNKY YADSVKG                                                           17

SEQ ID NO: 259        moltype = AA   length = 10
FEATURE               Location/Qualifiers
source                1..10
                      mol_type = protein
                      organism = synthetic construct
SEQUENCE: 259
GFTVSSNYMS                                                                   10
```

| | | |
|---|---|---|
| SEQ ID NO: 260<br>FEATURE<br>source | moltype = AA length = 16<br>Location/Qualifiers<br>1..16<br>mol_type = protein<br>organism = synthetic construct | |
| SEQUENCE: 260<br>VIYSGGSTYY ADSVKG | | 16 |
| SEQ ID NO: 261<br>FEATURE<br>source | moltype = AA length = 10<br>Location/Qualifiers<br>1..10<br>mol_type = protein<br>organism = synthetic construct | |
| SEQUENCE: 261<br>GFTFSSYWMS | | 10 |
| SEQ ID NO: 262<br>FEATURE<br>source | moltype = AA length = 17<br>Location/Qualifiers<br>1..17<br>mol_type = protein<br>organism = synthetic construct | |
| SEQUENCE: 262<br>NIKQDGSEKY YVDSVKG | | 17 |
| SEQ ID NO: 263<br>FEATURE<br>source | moltype = AA length = 25<br>Location/Qualifiers<br>1..25<br>mol_type = protein<br>organism = synthetic construct | |
| SEQUENCE: 263<br>EVQLVESGGG LVQPGRSLRL SCAAS | | 25 |
| SEQ ID NO: 264<br>FEATURE<br>source | moltype = AA length = 10<br>Location/Qualifiers<br>1..10<br>mol_type = protein<br>organism = synthetic construct | |
| SEQUENCE: 264<br>GFTFDDYAMH | | 10 |
| SEQ ID NO: 265<br>FEATURE<br>source | moltype = AA length = 17<br>Location/Qualifiers<br>1..17<br>mol_type = protein<br>organism = synthetic construct | |
| SEQUENCE: 265<br>GISWNSGSIG YADSVKG | | 17 |
| SEQ ID NO: 266<br>FEATURE<br>source | moltype = AA length = 32<br>Location/Qualifiers<br>1..32<br>mol_type = protein<br>organism = synthetic construct | |
| SEQUENCE: 266<br>RFTISRDNAK NSLYLQMNSL RAEDTALYYC AK | | 32 |
| SEQ ID NO: 267<br>FEATURE<br>source | moltype = AA length = 25<br>Location/Qualifiers<br>1..25<br>mol_type = protein<br>organism = synthetic construct | |
| SEQUENCE: 267<br>QVQLQESGPG LVKPPGTLSL TCAVS | | 25 |
| SEQ ID NO: 268<br>FEATURE<br>source | moltype = AA length = 11<br>Location/Qualifiers<br>1..11<br>mol_type = protein<br>organism = synthetic construct | |
| SEQUENCE: 268<br>GGSISSSNWW S | | 11 |
| SEQ ID NO: 269<br>FEATURE<br>source | moltype = AA length = 14<br>Location/Qualifiers<br>1..14<br>mol_type = protein<br>organism = synthetic construct | |
| SEQUENCE: 269<br>WVRQPPGKGL EWIG | | 14 |

```
SEQ ID NO: 270           moltype = AA   length = 16
FEATURE                  Location/Qualifiers
source                   1..16
                         mol_type = protein
                         organism = synthetic construct
SEQUENCE: 270
EIYHSGSTNY NPSLKS                                                          16

SEQ ID NO: 271           moltype = AA   length = 32
FEATURE                  Location/Qualifiers
source                   1..32
                         mol_type = protein
                         organism = synthetic construct
SEQUENCE: 271
RVTISVDKSK NQFSLKLSSV TAADTAVYCC AR                                        32

SEQ ID NO: 272           moltype = AA   length = 25
FEATURE                  Location/Qualifiers
source                   1..25
                         mol_type = protein
                         organism = synthetic construct
SEQUENCE: 272
EVQLVQSGAE VKKPGESLKI SCKGS                                                25

SEQ ID NO: 273           moltype = AA   length = 10
FEATURE                  Location/Qualifiers
source                   1..10
                         mol_type = protein
                         organism = synthetic construct
SEQUENCE: 273
GYSFTSYWIG                                                                 10

SEQ ID NO: 274           moltype = AA   length = 14
FEATURE                  Location/Qualifiers
source                   1..14
                         mol_type = protein
                         organism = synthetic construct
SEQUENCE: 274
WVRQMPGKGL EWMG                                                            14

SEQ ID NO: 275           moltype = AA   length = 17
FEATURE                  Location/Qualifiers
source                   1..17
                         mol_type = protein
                         organism = synthetic construct
SEQUENCE: 275
IIYPGDSDTR YSPSFQG                                                         17

SEQ ID NO: 276           moltype = AA   length = 32
FEATURE                  Location/Qualifiers
source                   1..32
                         mol_type = protein
                         organism = synthetic construct
SEQUENCE: 276
QVTISADKSI STAYLQWSSL KASDTAMYYC AR                                        32

SEQ ID NO: 277           moltype = AA   length = 23
FEATURE                  Location/Qualifiers
source                   1..23
                         mol_type = protein
                         organism = synthetic construct
SEQUENCE: 277
DIQMTQSPSS VSASVGDRVT ITC                                                  23

SEQ ID NO: 278           moltype = AA   length = 11
FEATURE                  Location/Qualifiers
source                   1..11
                         mol_type = protein
                         organism = synthetic construct
SEQUENCE: 278
RASQGISSWL A                                                               11

SEQ ID NO: 279           moltype = AA   length = 15
FEATURE                  Location/Qualifiers
source                   1..15
                         mol_type = protein
                         organism = synthetic construct
SEQUENCE: 279
```

```
WYQQKPGKAP KLLIY                                                         15

SEQ ID NO: 280          moltype = AA   length = 7
FEATURE                 Location/Qualifiers
source                  1..7
                        mol_type = protein
                        organism = synthetic construct
SEQUENCE: 280
AASSLQS                                                                   7

SEQ ID NO: 281          moltype = AA   length = 32
FEATURE                 Location/Qualifiers
source                  1..32
                        mol_type = protein
                        organism = synthetic construct
SEQUENCE: 281
GVPSRFSGSG SGTDFTLTIS SLQPEDFATY YC                                      32

SEQ ID NO: 282          moltype = AA   length = 23
FEATURE                 Location/Qualifiers
source                  1..23
                        mol_type = protein
                        organism = synthetic construct
SEQUENCE: 282
DIQMTQSPSS LSASVGDRVT ITC                                                23

SEQ ID NO: 283          moltype = AA   length = 11
FEATURE                 Location/Qualifiers
source                  1..11
                        mol_type = protein
                        organism = synthetic construct
SEQUENCE: 283
RASQGISNYL A                                                             11

SEQ ID NO: 284          moltype = AA   length = 15
FEATURE                 Location/Qualifiers
source                  1..15
                        mol_type = protein
                        organism = synthetic construct
SEQUENCE: 284
WYQQKPGKVP KLLIY                                                         15

SEQ ID NO: 285          moltype = AA   length = 7
FEATURE                 Location/Qualifiers
source                  1..7
                        mol_type = protein
                        organism = synthetic construct
SEQUENCE: 285
AASTLQS                                                                   7

SEQ ID NO: 286          moltype = AA   length = 32
FEATURE                 Location/Qualifiers
source                  1..32
                        mol_type = protein
                        organism = synthetic construct
SEQUENCE: 286
GVPSRFSGSG SGTDFTLTIS SLQPEDVATY YC                                      32

SEQ ID NO: 287          moltype = AA   length = 11
FEATURE                 Location/Qualifiers
source                  1..11
                        mol_type = protein
                        organism = synthetic construct
SEQUENCE: 287
RASQSISSYL N                                                             11

SEQ ID NO: 288          moltype = AA   length = 15
FEATURE                 Location/Qualifiers
source                  1..15
                        mol_type = protein
                        organism = synthetic construct
SEQUENCE: 288
WYQQKPEKAP KSLIY                                                         15

SEQ ID NO: 289          moltype = AA   length = 23
FEATURE                 Location/Qualifiers
source                  1..23
                        mol_type = protein
                        organism = synthetic construct
```

```
SEQUENCE: 289
DIVMTQSPLS LPVTPGEPAS ISC                                             23

SEQ ID NO: 290          moltype = AA  length = 16
FEATURE                 Location/Qualifiers
source                  1..16
                        mol_type = protein
                        organism = synthetic construct
SEQUENCE: 290
RSSQSLLHSN GYNYLD                                                     16

SEQ ID NO: 291          moltype = AA  length = 15
FEATURE                 Location/Qualifiers
source                  1..15
                        mol_type = protein
                        organism = synthetic construct
SEQUENCE: 291
WYLQKPGQSP QLLIY                                                      15

SEQ ID NO: 292          moltype = AA  length = 7
FEATURE                 Location/Qualifiers
source                  1..7
                        mol_type = protein
                        organism = synthetic construct
SEQUENCE: 292
LGSNRAS                                                                7

SEQ ID NO: 293          moltype = AA  length = 32
FEATURE                 Location/Qualifiers
source                  1..32
                        mol_type = protein
                        organism = synthetic construct
SEQUENCE: 293
GVPDRFSGSG SGTDFTLKIS RVEAEDVGVY YC                                   32

SEQ ID NO: 294          moltype = AA  length = 23
FEATURE                 Location/Qualifiers
source                  1..23
                        mol_type = protein
                        organism = synthetic construct
SEQUENCE: 294
EIVLTQSPAT LSLSPGERAT LSC                                             23

SEQ ID NO: 295          moltype = AA  length = 11
FEATURE                 Location/Qualifiers
source                  1..11
                        mol_type = protein
                        organism = synthetic construct
SEQUENCE: 295
RASQSVSSYL A                                                          11

SEQ ID NO: 296          moltype = AA  length = 15
FEATURE                 Location/Qualifiers
source                  1..15
                        mol_type = protein
                        organism = synthetic construct
SEQUENCE: 296
WYQQKPGQAP RLLIY                                                      15

SEQ ID NO: 297          moltype = AA  length = 7
FEATURE                 Location/Qualifiers
source                  1..7
                        mol_type = protein
                        organism = synthetic construct
SEQUENCE: 297
DASNRAT                                                                7

SEQ ID NO: 298          moltype = AA  length = 32
FEATURE                 Location/Qualifiers
source                  1..32
                        mol_type = protein
                        organism = synthetic construct
SEQUENCE: 298
GIPARFSGSG SGTDFTLTIS SLEPEDFAVY YC                                   32

SEQ ID NO: 299          moltype = AA  length = 23
FEATURE                 Location/Qualifiers
source                  1..23
                        mol_type = protein
```

```
                        organism = synthetic construct
SEQUENCE: 299
EIVLTQSPGT LSLSPGERAT LSC                                        23

SEQ ID NO: 300          moltype = AA  length = 12
FEATURE                 Location/Qualifiers
source                  1..12
                        mol_type = protein
                        organism = synthetic construct
SEQUENCE: 300
RASQSVSSSY LA                                                    12

SEQ ID NO: 301          moltype = AA  length = 7
FEATURE                 Location/Qualifiers
source                  1..7
                        mol_type = protein
                        organism = synthetic construct
SEQUENCE: 301
GASSRAT                                                           7

SEQ ID NO: 302          moltype = AA  length = 32
FEATURE                 Location/Qualifiers
source                  1..32
                        mol_type = protein
                        organism = synthetic construct
SEQUENCE: 302
GIPDRFSGSG SGTDFTLTIS RLEPEDFAVY YC                               32

SEQ ID NO: 303          moltype = AA  length = 12
FEATURE                 Location/Qualifiers
source                  1..12
                        mol_type = protein
                        organism = synthetic construct
SEQUENCE: 303
GASQSVSSSY LA                                                    12

SEQ ID NO: 304          moltype = AA  length = 15
FEATURE                 Location/Qualifiers
source                  1..15
                        mol_type = protein
                        organism = synthetic construct
SEQUENCE: 304
WYQQKPGLAP RLLIY                                                 15

SEQ ID NO: 305          moltype = AA  length = 7
FEATURE                 Location/Qualifiers
source                  1..7
                        mol_type = protein
                        organism = synthetic construct
SEQUENCE: 305
DASSRAT                                                           7

SEQ ID NO: 306          moltype = AA  length = 22
FEATURE                 Location/Qualifiers
source                  1..22
                        mol_type = protein
                        organism = synthetic construct
SEQUENCE: 306
QAGLTQPPSV SKGLRQTATL TC                                         22

SEQ ID NO: 307          moltype = AA  length = 13
FEATURE                 Location/Qualifiers
source                  1..13
                        mol_type = protein
                        organism = synthetic construct
SEQUENCE: 307
TGNSNNVGNQ GAA                                                   13

SEQ ID NO: 308          moltype = AA  length = 15
FEATURE                 Location/Qualifiers
source                  1..15
                        mol_type = protein
                        organism = synthetic construct
SEQUENCE: 308
WLQQHQGHPP KLLSY                                                 15

SEQ ID NO: 309          moltype = AA  length = 7
FEATURE                 Location/Qualifiers
source                  1..7
```

```
                        mol_type = protein
                        organism = synthetic construct
SEQUENCE: 309
RNNNRPS                                                              7

SEQ ID NO: 310          moltype = AA   length = 32
FEATURE                 Location/Qualifiers
source                  1..32
                        mol_type = protein
                        organism = synthetic construct
SEQUENCE: 310
GISERLSASR SGNTASLTIT GLQPEDEADY YC                                 32

SEQ ID NO: 311          moltype = AA   length = 22
FEATURE                 Location/Qualifiers
source                  1..22
                        mol_type = protein
                        organism = synthetic construct
SEQUENCE: 311
QSVLTQPPSV SGAPGQRVTI SC                                            22

SEQ ID NO: 312          moltype = AA   length = 14
FEATURE                 Location/Qualifiers
source                  1..14
                        mol_type = protein
                        organism = synthetic construct
SEQUENCE: 312
TGSSSNIGAG YDVH                                                     14

SEQ ID NO: 313          moltype = AA   length = 15
FEATURE                 Location/Qualifiers
source                  1..15
                        mol_type = protein
                        organism = synthetic construct
SEQUENCE: 313
WYQQLPGTAP KLLIY                                                    15

SEQ ID NO: 314          moltype = AA   length = 7
FEATURE                 Location/Qualifiers
source                  1..7
                        mol_type = protein
                        organism = synthetic construct
SEQUENCE: 314
GNSNRPS                                                              7

SEQ ID NO: 315          moltype = AA   length = 32
FEATURE                 Location/Qualifiers
source                  1..32
                        mol_type = protein
                        organism = synthetic construct
SEQUENCE: 315
GVPDRFSGSK SGTSASLAIT GLQAEDEADY YC                                 32

SEQ ID NO: 316          moltype = AA   length = 22
FEATURE                 Location/Qualifiers
source                  1..22
                        mol_type = protein
                        organism = synthetic construct
SEQUENCE: 316
QSVLTQPPSA SGTPGQRVTI SC                                            22

SEQ ID NO: 317          moltype = AA   length = 13
FEATURE                 Location/Qualifiers
source                  1..13
                        mol_type = protein
                        organism = synthetic construct
SEQUENCE: 317
SGSSSNIGSN TVN                                                      13

SEQ ID NO: 318          moltype = AA   length = 7
FEATURE                 Location/Qualifiers
source                  1..7
                        mol_type = protein
                        organism = synthetic construct
SEQUENCE: 318
SNNQRPS                                                              7

SEQ ID NO: 319          moltype = AA   length = 32
FEATURE                 Location/Qualifiers
```

```
source                  1..32
                        mol_type = protein
                        organism = synthetic construct
SEQUENCE: 319
GVPDRFSGSK SGTSASLAIS GLQSEDEADY YC                              32

SEQ ID NO: 320          moltype = AA   length = 22
FEATURE                 Location/Qualifiers
source                  1..22
                        mol_type = protein
                        organism = synthetic construct
SEQUENCE: 320
QSALTQPASV SGSPGQSITI SC                                         22

SEQ ID NO: 321          moltype = AA   length = 14
FEATURE                 Location/Qualifiers
source                  1..14
                        mol_type = protein
                        organism = synthetic construct
SEQUENCE: 321
TGTSSDVGGY NYVS                                                  14

SEQ ID NO: 322          moltype = AA   length = 15
FEATURE                 Location/Qualifiers
source                  1..15
                        mol_type = protein
                        organism = synthetic construct
SEQUENCE: 322
WYQQHPGKAP KLMIY                                                 15

SEQ ID NO: 323          moltype = AA   length = 7
FEATURE                 Location/Qualifiers
source                  1..7
                        mol_type = protein
                        organism = synthetic construct
SEQUENCE: 323
EVSNRPS                                                           7

SEQ ID NO: 324          moltype = AA   length = 32
FEATURE                 Location/Qualifiers
source                  1..32
                        mol_type = protein
                        organism = synthetic construct
SEQUENCE: 324
GVSNRFSGSK SGNTASLTIS GLQAEDEADY YC                              32

SEQ ID NO: 325          moltype = AA   length = 22
FEATURE                 Location/Qualifiers
source                  1..22
                        mol_type = protein
                        organism = synthetic construct
SEQUENCE: 325
SSELTQDPAV SVALGQTVRI TC                                         22

SEQ ID NO: 326          moltype = AA   length = 11
FEATURE                 Location/Qualifiers
source                  1..11
                        mol_type = protein
                        organism = synthetic construct
SEQUENCE: 326
QGDSLRSYYA S                                                     11

SEQ ID NO: 327          moltype = AA   length = 15
FEATURE                 Location/Qualifiers
source                  1..15
                        mol_type = protein
                        organism = synthetic construct
SEQUENCE: 327
WYQQKPGQAP VLVIY                                                 15

SEQ ID NO: 328          moltype = AA   length = 7
FEATURE                 Location/Qualifiers
source                  1..7
                        mol_type = protein
                        organism = synthetic construct
SEQUENCE: 328
GKNNRPS                                                           7

SEQ ID NO: 329          moltype = AA   length = 32
```

```
FEATURE            Location/Qualifiers
source             1..32
                   mol_type = protein
                   organism = synthetic construct
SEQUENCE: 329
GIPDRFSGSS SGNTASLTIT GAQAEDEADY YC                          32

SEQ ID NO: 330     moltype = AA  length = 22
FEATURE            Location/Qualifiers
source             1..22
                   mol_type = protein
                   organism = synthetic construct
SEQUENCE: 330
SYELTQPLSV SVALGQTARI TC                                     22

SEQ ID NO: 331     moltype = AA  length = 11
FEATURE            Location/Qualifiers
source             1..11
                   mol_type = protein
                   organism = synthetic construct
SEQUENCE: 331
GGNNIGSKNV H                                                 11

SEQ ID NO: 332     moltype = AA  length = 7
FEATURE            Location/Qualifiers
source             1..7
                   mol_type = protein
                   organism = synthetic construct
SEQUENCE: 332
RDSNRPS                                                       7

SEQ ID NO: 333     moltype = AA  length = 32
FEATURE            Location/Qualifiers
source             1..32
                   mol_type = protein
                   organism = synthetic construct
SEQUENCE: 333
GIPERFSGSN SGNTATLTIS RAQAGDEADY YC                          32

SEQ ID NO: 334     moltype = AA  length = 25
FEATURE            Location/Qualifiers
source             1..25
                   mol_type = protein
                   organism = synthetic construct
SEQUENCE: 334
QVQLQESGPG LVKPSQTLSL TCTVS                                  25

SEQ ID NO: 335     moltype = AA  length = 12
FEATURE            Location/Qualifiers
source             1..12
                   mol_type = protein
                   organism = synthetic construct
SEQUENCE: 335
GGSISSGSYY WS                                                12

SEQ ID NO: 336     moltype = AA  length = 14
FEATURE            Location/Qualifiers
source             1..14
                   mol_type = protein
                   organism = synthetic construct
SEQUENCE: 336
WIRQHPGKGL EWIG                                              14

SEQ ID NO: 337     moltype = AA  length = 16
FEATURE            Location/Qualifiers
source             1..16
                   mol_type = protein
                   organism = synthetic construct
SEQUENCE: 337
YIYYSGSTYY NPSLKS                                            16

SEQ ID NO: 338     moltype = AA  length = 29
FEATURE            Location/Qualifiers
source             1..29
                   mol_type = protein
                   organism = synthetic construct
SEQUENCE: 338
RVTISVDTSK NQFSLKLSSV TAADTAVYY                              29
```

| | | |
|---|---|---|
| SEQ ID NO: 339 SEQUENCE: 339 | moltype = | length = 000 |
| SEQ ID NO: 340 SEQUENCE: 340 | moltype = | length = 000 |
| SEQ ID NO: 341 SEQUENCE: 341 | moltype = | length = 000 |
| SEQ ID NO: 342 SEQUENCE: 342 | moltype = | length = 000 |
| SEQ ID NO: 343 SEQUENCE: 343 | moltype = | length = 000 |
| SEQ ID NO: 344 SEQUENCE: 344 | moltype = | length = 000 |
| SEQ ID NO: 345 SEQUENCE: 345 | moltype = | length = 000 |
| SEQ ID NO: 346 SEQUENCE: 346 | moltype = | length = 000 |
| SEQ ID NO: 347 SEQUENCE: 347 | moltype = | length = 000 |
| SEQ ID NO: 348 SEQUENCE: 348 | moltype = | length = 000 |
| SEQ ID NO: 349 SEQUENCE: 349 | moltype = | length = 000 |
| SEQ ID NO: 350 SEQUENCE: 350 | moltype = | length = 000 |
| SEQ ID NO: 351 SEQUENCE: 351 | moltype = | length = 000 |
| SEQ ID NO: 352 SEQUENCE: 352 | moltype = | length = 000 |
| SEQ ID NO: 353 SEQUENCE: 353 | moltype = | length = 000 |
| SEQ ID NO: 354 SEQUENCE: 354 | moltype = | length = 000 |
| SEQ ID NO: 355 SEQUENCE: 355 | moltype = | length = 000 |
| SEQ ID NO: 356 SEQUENCE: 356 | moltype = | length = 000 |
| SEQ ID NO: 357 SEQUENCE: 357 | moltype = | length = 000 |
| SEQ ID NO: 358 SEQUENCE: 358 | moltype = | length = 000 |

| | | |
|---|---|---|
| SEQ ID NO: 359<br>SEQUENCE: 359<br>000 | moltype = | length = |
| SEQ ID NO: 360<br>SEQUENCE: 360<br>000 | moltype = | length = |
| SEQ ID NO: 361<br>SEQUENCE: 361<br>000 | moltype = | length = |
| SEQ ID NO: 362<br>SEQUENCE: 362<br>000 | moltype = | length = |
| SEQ ID NO: 363<br>SEQUENCE: 363<br>000 | moltype = | length = |
| SEQ ID NO: 364<br>SEQUENCE: 364<br>000 | moltype = | length = |
| SEQ ID NO: 365<br>SEQUENCE: 365<br>000 | moltype = | length = |
| SEQ ID NO: 366<br>SEQUENCE: 366<br>000 | moltype = | length = |
| SEQ ID NO: 367<br>SEQUENCE: 367<br>000 | moltype = | length = |
| SEQ ID NO: 368<br>SEQUENCE: 368<br>000 | moltype = | length = |
| SEQ ID NO: 369<br>SEQUENCE: 369<br>000 | moltype = | length = |
| SEQ ID NO: 370<br>SEQUENCE: 370<br>000 | moltype = | length = |
| SEQ ID NO: 371<br>SEQUENCE: 371<br>000 | moltype = | length = |
| SEQ ID NO: 372<br>SEQUENCE: 372<br>000 | moltype = | length = |
| SEQ ID NO: 373<br>SEQUENCE: 373<br>000 | moltype = | length = |
| SEQ ID NO: 374<br>SEQUENCE: 374<br>000 | moltype = | length = |
| SEQ ID NO: 375<br>SEQUENCE: 375<br>000 | moltype = | length = |
| SEQ ID NO: 376<br>SEQUENCE: 376<br>000 | moltype = | length = |
| SEQ ID NO: 377<br>SEQUENCE: 377<br>000 | moltype = | length = |
| SEQ ID NO: 378<br>SEQUENCE: 378 | moltype = | length = |

000

SEQ ID NO: 379         moltype =    length =
SEQUENCE: 379
000

SEQ ID NO: 380         moltype =    length =
SEQUENCE: 380
000

SEQ ID NO: 381         moltype =    length =
SEQUENCE: 381
000

SEQ ID NO: 382         moltype =    length =
SEQUENCE: 382
000

SEQ ID NO: 383         moltype =    length =
SEQUENCE: 383
000

SEQ ID NO: 384         moltype =    length =
SEQUENCE: 384
000

SEQ ID NO: 385         moltype =    length =
SEQUENCE: 385
000

SEQ ID NO: 386         moltype =    length =
SEQUENCE: 386
000

SEQ ID NO: 387         moltype =    length =
SEQUENCE: 387
000

SEQ ID NO: 388         moltype =    length =
SEQUENCE: 388
000

SEQ ID NO: 389         moltype =    length =
SEQUENCE: 389
000

SEQ ID NO: 390         moltype =    length =
SEQUENCE: 390
000

SEQ ID NO: 391         moltype =    length =
SEQUENCE: 391
000

SEQ ID NO: 392         moltype =    length =
SEQUENCE: 392
000

SEQ ID NO: 393         moltype =    length =
SEQUENCE: 393
000

SEQ ID NO: 394         moltype =    length =
SEQUENCE: 394
000

SEQ ID NO: 395         moltype =    length =
SEQUENCE: 395
000

SEQ ID NO: 396         moltype =    length =
SEQUENCE: 396
000

SEQ ID NO: 397         moltype =    length =
SEQUENCE: 397
000

SEQ ID NO: 398         moltype =    length =

```
SEQUENCE: 398
000

SEQ ID NO: 399          moltype =    length =
SEQUENCE: 399
000

SEQ ID NO: 400          moltype =    length =
SEQUENCE: 400
000

SEQ ID NO: 401          moltype = AA   length = 119
FEATURE                 Location/Qualifiers
source                  1..119
                        mol_type = protein
                        organism = synthetic construct
SEQUENCE: 401
QVQLQESGPG LVKPSQTLSL TCTVSGGSIN NNNYYWTWIR QHPGKGLEWI GYIYYSGSTF   60
YNPSLKSRVT ISVDTSKTQF SLKLSSVTAA DTAVYYCARE DTMTGLDVWG QGTTVTVSS   119

SEQ ID NO: 402          moltype = AA   length = 106
FEATURE                 Location/Qualifiers
source                  1..106
                        mol_type = protein
                        organism = synthetic construct
SEQUENCE: 402
DIQMTQSPSS LSASVGDRVT ITCRASQSIN NYLNWYQQKP GKAPTLLIYA ASSLQSGVPS   60
RFSGSRSGTD FTLTISSLQP EDFAAYFCQQ TYSNPTFGQG TKVEVK                 106

SEQ ID NO: 403          moltype = AA   length = 120
FEATURE                 Location/Qualifiers
source                  1..120
                        mol_type = protein
                        organism = synthetic construct
SEQUENCE: 403
EVQLLESGGG LVQPGGSLRL SCAASGFTFS SYIMMWVRQA PGKGLEWVSS IYPSGGITFY   60
ADTVKGRFTI SRDNSKNTLY LQMNSLRAED TAVYYCARIK LGTVTTVDYW GQGTLVTVSS  120

SEQ ID NO: 404          moltype = AA   length = 110
FEATURE                 Location/Qualifiers
source                  1..110
                        mol_type = protein
                        organism = synthetic construct
SEQUENCE: 404
QSALTQPASV SGSPGQSITI SCTGTSSDVG GYNYVSWYQQ HPGKAPKLMI YDVSNRPSGV   60
SNRFSGSKSG NTASLTISGL QAEDEADYYC SSYTSSSTRV FGTGTKVTVL             110

SEQ ID NO: 405          moltype = AA   length = 118
FEATURE                 Location/Qualifiers
source                  1..118
                        mol_type = protein
                        organism = synthetic construct
SEQUENCE: 405
QVQLVESGGG VVQPGRSLRL SCAASGFTFS SYTMHWVRQA PGKGLEWVTF ISYDGNNKYY   60
ADSVKGRFTI SRDNSKNTLY LQMNSLRAED TAIYYCARTG WLGPFDYWGQ GTLVTVSS    118

SEQ ID NO: 406          moltype = AA   length = 108
FEATURE                 Location/Qualifiers
source                  1..108
                        mol_type = protein
                        organism = synthetic construct
SEQUENCE: 406
EIVLTQSPGT LSLSPGERAT LSCRASQSVG SSYLAWYQQK PGQAPRLLIY GAFSRATGIP   60
DRFSGSGSGT DFTLTISRLE PEDFAVYYCQ QYGSSPWTFG QGTKVEIK               108

SEQ ID NO: 407          moltype = AA   length = 115
FEATURE                 Location/Qualifiers
source                  1..115
                        mol_type = protein
                        organism = synthetic construct
SEQUENCE: 407
QVQLVESGGG VVQPGRSLRL SCAASGFTFS SYGMHWVRQA PGKGLEWVAF IRYDGSNKYY   60
ADSVKGRFTI SRDNSKNTLY LQMNSLRAED TAVYYCKTHG SHDNWGQGTM VTVSS       115

SEQ ID NO: 408          moltype = AA   length = 111
FEATURE                 Location/Qualifiers
source                  1..111
                        mol_type = protein
                        organism = synthetic construct
```

```
SEQUENCE: 408
QSVLTQPPSV SGAPGQRVTI SCSGSRSNIG SNTVKWYQQL PGTAPKLLIY YNDQRPSGVP   60
DRFSGSKSGT SASLAITGLQ AEDEADYYCQ SYDRYTHPAL LFGTGTKVTV L          111

SEQ ID NO: 409           moltype = AA  length = 113
FEATURE                  Location/Qualifiers
source                   1..113
                         mol_type = protein
                         organism = synthetic construct
SEQUENCE: 409
QVQLVESGGG VVQPGRSLRL DCKASGITFS NSGMHWVRQA PGKGLEWVAV IWYDGSKRYY   60
ADSVKGRFTI SRDNSKNTLF LQMNSLRAED TAVYYCATND DYWGQGTLVT VSS         113

SEQ ID NO: 410           moltype = AA  length = 107
FEATURE                  Location/Qualifiers
source                   1..107
                         mol_type = protein
                         organism = synthetic construct
SEQUENCE: 410
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ SSNWPRTFGQ GTKVEIK               107

SEQ ID NO: 411           moltype = AA  length = 121
FEATURE                  Location/Qualifiers
source                   1..121
                         mol_type = protein
                         organism = synthetic construct
SEQUENCE: 411
EVQLVQSGGG VERPGGSLRL SCAASGFTFD DYGMSWVRQA PGKGLEWVSG INWNGGSTGY   60
ADSVKGRVTI SRDNAKNSLY LQMNSLRAED TAVYYCAKIL GAGRGWYFDL WGKGTTVTVS  120
S                                                                121

SEQ ID NO: 412           moltype = AA  length = 108
FEATURE                  Location/Qualifiers
source                   1..108
                         mol_type = protein
                         organism = synthetic construct
SEQUENCE: 412
SSELTQDPAV SVALGQTVRI TCQGDSLRSY YASWYQQKPG QAPVLVIYGK NNRPSGIPDR   60
FSGSSSGNTA SLTITGAQAE DEADYYCNSR DSSGNHVVFG GGTKLTVL              108

SEQ ID NO: 413           moltype = AA  length = 122
FEATURE                  Location/Qualifiers
source                   1..122
                         mol_type = protein
                         organism = synthetic construct
SEQUENCE: 413
EVQLVESGGG LVQPGRSLRL SCAASGFTFN DYAMHWVRQA PGKGLEWVST ISWNSGSIGY   60
ADSVKGRFTI SRDNAKKSLY LQMNSLRAED TALYYCAKDI QYGNYYYGMD VWGQGTTVTV  120
SS                                                               122

SEQ ID NO: 414           moltype = AA  length = 107
FEATURE                  Location/Qualifiers
source                   1..107
                         mol_type = protein
                         organism = synthetic construct
SEQUENCE: 414
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ RSNWPITFGQ GTRLEIK               107

SEQ ID NO: 415           moltype = AA  length = 130
FEATURE                  Location/Qualifiers
source                   1..130
                         mol_type = protein
                         organism = synthetic construct
SEQUENCE: 415
EVQLVQSGAE VKKPGSSVKV SCKASGGTFS SYAISWVRQA PGQGLEWMGG IIPIFGTANY   60
AQKFQGRVTI TADKSTSTAY MELSSLRSED TAVYYCARAP LRFLEWSTQD HYYYYYMDVW  120
GKGTTVTVSS                                                       130

SEQ ID NO: 416           moltype = AA  length = 108
FEATURE                  Location/Qualifiers
source                   1..108
                         mol_type = protein
                         organism = synthetic construct
SEQUENCE: 416
SSELTQDPAV SVALGQTVRI TCQGDSLRSY YATWYQQKPG QAPILVIYGE NKRPSGIPDR   60
FSGSSSGNTA SLTITGAQAE DEADYYCKSR DGSGQHLVFG GGTKLTVL              108
```

```
SEQ ID NO: 417         moltype = AA   length = 119
FEATURE                Location/Qualifiers
source                 1..119
                       mol_type = protein
                       organism = synthetic construct
SEQUENCE: 417
QVQLQESGPG LVKPSETLSL TCTVSGGSVS SGSYYWSWIR QPPGKGLEWI GYIYYSGSTN    60
YNPSLKSRVT ISVDTSKNQF SLKLSSVTAA DTAVYYCARE GKNGAFDIWG QGTMVTVSS    119

SEQ ID NO: 418         moltype = AA   length = 107
FEATURE                Location/Qualifiers
source                 1..107
                       mol_type = protein
                       organism = synthetic construct
SEQUENCE: 418
DIQMTQSPSS LSASVGDRVT ITCRASQSIS SYLNWYQQKP GKAPKLLIYA ASSLQSGVPS    60
GFSGSGSGTD FTLTISSLQP EDFATYYCQQ SYSTPLTFGG GTKVEIK                107
```

MULTISPECIFIC ANTIBODY MOLECULES COMPRISING LAMBDA AND KAPPA LIGHT CHAINS

CROSS-REFERENCE TO RELATED APPLICATIONS

This application is a divisional application of U.S. application Ser. No. 16/335,822, now U.S. Pat. No. 11,673,971, filed Mar. 22, 2019, which is a U.S. national phase entry of International Application No. PCT/US2017/053053 filed Sep. 22, 2017, which claims priority to U.S. Provisional Application No. 62/399,319 filed Sep. 23, 2016, and U.S. Provisional No. 62/474,569 filed Mar. 21, 2017, the entire contents of each of which are incorporated herein by reference.

REFERENCE TO SEQUENCE LISTING

This application contains a Sequence Listing which has been submitted electronically in XML format. The Sequence Listing XML is incorporated herein by reference. Said XML file, created on May 12, 2023, is named 53676-713_402_SL.xml and is 447,435 in size.

BACKGROUND

Multispecific, e.g., bispecific, antibody molecules that include a lambda chain polypeptide and a kappa light chain polypeptide, and methods of making and using the same, are disclosed. Mispairing of the light chains to the incorrect heavy chain, also known as light chain shuffling, is a problem frequently observed when preparing bispecific and other multispecific antibodies. This results in the formation of incorrect antibody pairings, leading to decreased production yield. Thus, the need exists to develop methods and compositions that reduce light chain shuffling.

SUMMARY

In one aspect, provided herein is a method of making a multispecific molecule, the method comprising expressing four non-contiguous polypeptides in a cell, wherein the four non-contiguous polypeptides comprise: (a) a first heavy chain polypeptide (HCP1) comprising a sequence having at least 85% sequence identity to the sequence of amino acids 120-449 of SEQ ID NO: 164; (b) a kappa light chain polypeptide (KLCP) comprising a sequence having at least 85% sequence identity to the sequence of amino acids 111-213 of SEQ ID NO: 165; (c) a second heavy chain polypeptide (HCP2) comprising a sequence having at least 85% sequence identity to the sequence of amino acids 121-450 of SEQ ID NO: 166; and (d) a lambda light chain polypeptide (LLCP) comprising a sequence having at least 85% sequence identity to the sequence of amino acids 111-216 of SEQ ID NO: 167; wherein the HCP1 and the HCP2 are a knob and hole pair; and wherein: (A)(i) the KLCP binds to the HCP1 with a higher affinity than the affinity of the LLCP to the HCP1 and the affinity of the KLCP to the HCP2, (ii) the LLCP binds to the HCP2 with a higher affinity than the affinity of the KLCP to the HCP2 and the affinity of the LLCP to the HCP1; or (B)(i) the LLCP binds to the HCP1 with a higher affinity than the affinity of the KLCP to the HCP1 and the affinity of the LLCP to the HCP2, and (ii) the KLCP binds to the HCP2 with a higher affinity than the affinity of the LLCP to the HCP2 and the affinity of the KLCP to the HCP1.

In some embodiments, the method comprises expressing the four non-contiguous polypeptides simultaneously in the cell, and the cell is a single cell.

In some embodiments, the method (i) does not comprise purifying the multispecific molecule away from a multispecific molecule that contains the HCP1, the HCP2 and two of the LLCPs, and (ii) does not purifying the multispecific molecule away from a multispecific molecule that contains the HCP1, the HCP2 and two of the KLCPs.

In some embodiments, the method comprises producing an amount of the multispecific molecule that is (i) at least 5.25-fold higher than the amount of a multispecific molecule produced that contains the HCP1, the HCP2 and two of the LLCPs, and (ii) at least 5.7-fold higher than the amount of a multispecific molecule produced that contains the HCP1, the HCP2 and two of the KLCPs polypeptides.

In some embodiments, the cell is a mammalian cell or an insect cell.

In some embodiments, the cell is a CHO cell, a Vero cell, a HeLa cell, a COS cell, a HEK293 cell, a BHK cell, a MDCKII cell, an SF9 cell, or an S2 cell.

In some embodiments, the method comprises introducing one or more polynucleic acids into the cell, wherein the one or more polynucleic acid molecules comprise a nucleic acid sequence encoding the HCP1, a nucleic acid sequence encoding the HCP2, a nucleic acid sequence encoding the LLCP, and a nucleic acid sequence encoding the KLCP.

In some embodiments, the one or more polynucleic acids comprise one or more plasmids; and/or the introducing comprises transfecting.

In some embodiments, the ratio of the nucleic acid sequence encoding the LLCP to the nucleic acid sequence encoding the KLCP is from 3:1 to 1:3.

In some embodiments, the method comprises: (i) isolating or purifying the multispecific molecule, and/or (ii) culturing the cell in growth media and the multispecific molecule is secreted by the cell into the growth media.

In some embodiments, the isolating or purifying comprises isolating or purifying the multispecific molecule via affinity chromatography, and/or isolating or purifying the multispecific molecule using protein A, a reagent that binds to a CH1 domain, or a reagent that binds to an affinity tag of the multispecific molecule.

In some embodiments, the multispecific molecule is a bispecific molecule.

In some embodiments, the HCP1 comprises a sequence identical to the sequence of amino acids 120-217 of SEQ ID NO: 164 and/or the HCP2 comprises a sequence identical to the sequence of amino acids 121-218 of SEQ ID NO: 166.

In some embodiments, the HCP1 comprises a sequence identical to the sequence of amino acids 351-409 of SEQ ID NO: 164, and the HCP2 comprises a sequence identical to the sequence of amino acids 352-410 of SEQ ID NO: 166.

In some embodiments, the HCP1 comprises a sequence having at least 95% sequence identity to the sequence of amino acids 120-449 of SEQ ID NO: 164.

In some embodiments, the HCP1 comprises a sequence having at least 99% sequence identity to the sequence of amino acids 120-449 of SEQ ID NO: 164.

In some embodiments, the HCP2 comprises a sequence having at least 95% sequence identity to the sequence of amino acids 121-450 of SEQ ID NO: 166.

In some embodiments, the HCP2 comprises a sequence having at least 99% sequence identity to the sequence of amino acids 121-450 of SEQ ID NO: 166.

In some embodiments, the LLCP comprises a sequence having at least 95% sequence identity to the sequence of amino acids 111-216 of SEQ ID NO: 167.

In some embodiments, the LLCP comprises a sequence having at least 96% sequence identity to the sequence of amino acids 111-216 of SEQ ID NO: 167.

In some embodiments, the LLCP comprises a sequence according to the sequence of amino acids 111-216 of SEQ ID NO: 167.

In some embodiments, the KLCP comprises a having at least 95% sequence identity to the sequence of amino acids 111-213 of SEQ ID NO: 165.

In some embodiments, the KLCP comprises a sequence according to the sequence of amino acids 111-213 of SEQ ID NO: 165.

In some embodiments, (i) the HCP1 comprises a sequence having at least 95% sequence identity to the sequence of amino acids 120-449 of SEQ ID NO: 164; (ii) the HCP2 comprises a sequence having at least 95% sequence identity to the sequence of amino acids 121-450 of SEQ ID NO: 166; (iii) the LLCP comprises a sequence having at least 95% sequence identity to the sequence of amino acids 111-216 of SEQ ID NO: 167; and (iv) the KLCP comprises a sequence having at least 95% sequence identity to the sequence of amino acids 111-213 of SEQ ID NO: 165.

In some embodiments, (i) the HCP1 comprises a sequence having at least 99% sequence identity to the sequence of amino acids 120-449 of SEQ ID NO: 164; (ii) the HCP2 comprises a sequence having at least 99% sequence identity to the sequence of amino acids 121-450 of SEQ ID NO: 166; (iii) the LLCP comprises a sequence having at least 96% sequence identity to the sequence of amino acids 111-216 of SEQ ID NO: 167; and (iv) the KLCP comprises a sequence according to the sequence of amino acids 111-213 of SEQ ID NO: 165.

In some embodiments, (i) the HCP1 comprises a sequence according to the sequence of amino acids 238-449 of SEQ ID NO: 164; (ii) the HCP2 comprises a sequence according to the sequence of amino acids 239-450 of SEQ ID NO: 166; (iii) the LLCP comprises a sequence having at least 96% sequence identity to the sequence of amino acids 111-216 of SEQ ID NO: 167; and (iv) the KLCP comprises a sequence according to the sequence of amino acids 111-213 of SEQ ID NO: 165.

In some embodiments, the HCP1 does not bind to the KLCP and the HCP2 does not bind to the LLCP, or the HCP1 does not bind to the LLCP and the HCP2 does not bind to the KLCP.

In another aspect, provided herein is a composition comprising the multispecific molecule produced according to the method as provided herein.

In another aspect, provided herein is a pharmaceutical composition comprising the multispecific molecule produced according to the method as provided herein, and a pharmaceutically acceptable diluent or excipient.

In another aspect, provided herein is a method of treating a disease or condition in a subject in need thereof, the method comprising administering to the subject a therapeutically effective amount of the pharmaceutical composition as provided herein, thereby treating the disease or condition in the subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

DETAILED DESCRIPTION OF THE INVENTION

Disclosed herein are multispecific antibody molecules (also referred to herein as "multifunctional antibody molecules") that comprise a lambda light chain polypeptide and a kappa light chain polypeptide. In embodiments, the multispecific antibody molecules include a plurality (e.g., two or more) binding specificities (or functionalities). In some embodiments, a first binding specificity selectively localizes to a cancer cell, e.g., it includes a tumor-targeting moiety; and the second (or third, or fourth) binding specificity includes one or both of: an immune cell engager (e.g., chosen from one, two, three, or all of an NK cell engager, a B cell engager, a dendritic cell engager, or a macrophage cell engager); and/or a cytokine molecule. In an embodiment, the multispecific molecule is a bispecific (or bifunctional) molecule, a trispecific (or trifunctional) molecule, or a tetraspecific (or tetrafunctional) molecule. Accordingly, provided herein are, inter alia, multispecific molecules (e.g., multispecific antibody molecules) that include the lambda light chain polypeptide and a kappa light chain polypeptide, nucleic acids encoding the same, methods of producing the aforesaid molecules, and methods of treating a disorder, e.g., cancer, using the aforesaid molecules.

In one embodiment, the multispecific antibody molecule comprises:
(i) a first heavy chain polypeptide (e.g., a heavy chain polypeptide comprising one, two, three or all of a first heavy chain variable region (first VH having a first binding specificity), a first CH1, a first heavy chain constant region (e.g., a first CH2, a first CH3, or both));
(ii) a second heavy chain polypeptide (e.g., a heavy chain polypeptide comprising one, two, three or all of a second heavy chain variable region (second VH), a second CH1, a second heavy chain constant region (e.g., a second CH2, a second CH3, or both));
(iii) a lambda light chain polypeptide (e.g., a lambda light variable region (VLλ), a lambda light constant chain (VLλ), or both) that preferentially associates with the first heavy chain polypeptide (e.g., the first VH); and
(iv) a kappa light chain polypeptide (e.g., a kappa light variable region (VLκ), a kappa light constant chain (VLκ), or both) that preferentially associates with the second heavy chain polypeptide (e.g., the second VH).

Figure 1A:
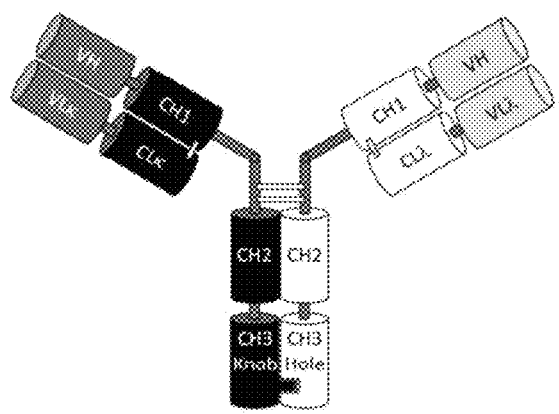
FIGS. 1A-1D depict a schematic representation of light chain shuffling.

In embodiments, the first and second heavy chain polypeptides form an Fc interface that enhances heterodimerization. An exemplary representation is depicted in FIG. 1A, which shows a multispecific antibody molecule having a first binding specificity that includes a hybrid VLκ-CLκ heterodimerized to a first heavy chain variable region connected to the Fc constant, CH2-CH3 domain (having a knob modification) and a second binding specificity that includes a hybrid VLλ-CLλ heterodimerized to a second heavy chain variable region connected to the Fc constant, CH2-CH3 domain (having a hole modification).

Figure 1B:
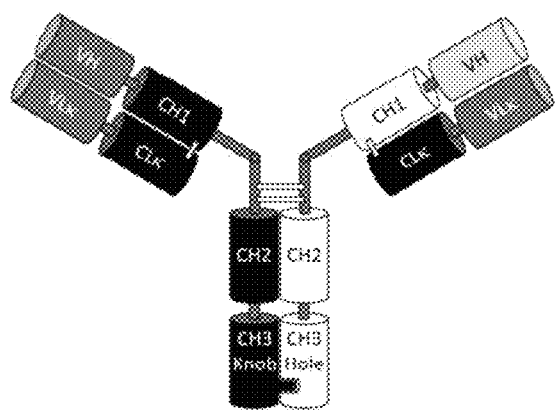
Figure 1C:
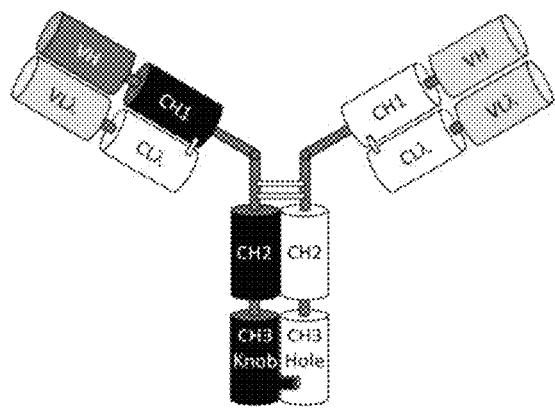
Figure 1D:
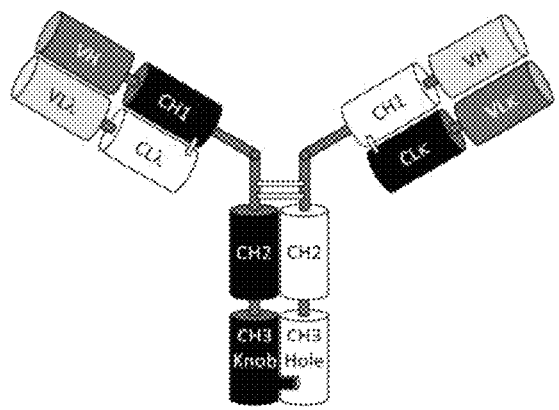

In some embodiments, disclosed herein is a novel method for generating a multispecific, e.g., a bispecific, antibody molecule. The method for generating bispecific molecules disclosed herein produces stable antibodies, while avoiding the light-chain swapping commonly described in the literature. Light chain swapping or shuffling is a common problem encountered when producing antibodies with a single kappa and a single lambda light chain. A schematic of light chain shuffling is depicted in FIGS. 1A-1D. As shown in in FIGS. 1A-1D, only 25% of the product is of the desired configuration (FIG. 1A) and the other 75% of product has the light chains mispaired (FIG. 1B-1D). The method for generating a multispecific, e.g., bispecific, antibody molecule disclosed herein uses antibodies, e.g., human antibodies, with kappa and lambda light chains to produce stable, multispecific, e.g., bispecific, antibody molecules.

Definition

Certain terms are defined below.

As used herein, the articles "a" and "an" refer to one or more than one, e.g., to at least one, of the grammatical object of the article. The use of the words "a" or "an" when used in conjunction with the term "comprising" herein may mean "one," but it is also consistent with the meaning of "one or more," "at least one," and "one or more than one."

As used herein, "about" and "approximately" generally mean an acceptable degree of error for the quantity measured given the nature or precision of the measurements. Exemplary degrees of error are within 20 percent (%), typically, within 10%, and more typically, within 5% of a given range of values.

"Antibody molecule" as used herein refers to a protein, e.g., an immunoglobulin chain or fragment thereof, comprising at least one immunoglobulin variable domain sequence. An antibody molecule encompasses antibodies (e.g., full-length antibodies) and antibody fragments. In an embodiment, an antibody molecule comprises an antigen binding or functional fragment of a full length antibody, or a full length immunoglobulin chain. For example, a full-length antibody is an immunoglobulin (Ig) molecule (e.g., an IgG antibody) that is naturally occurring or formed by normal immunoglobulin gene fragment recombinatorial processes). In embodiments, an antibody molecule refers to an immunologically active, antigen-binding portion of an immunoglobulin molecule, such as an antibody fragment. An antibody fragment, e.g., functional fragment, is a portion of an antibody, e.g., Fab, Fab', F(ab')₂, F(ab)₂, variable fragment (Fv), domain antibody (dAb), or single chain variable fragment (scFv). A functional antibody fragment binds to the same antigen as that recognized by the intact (e.g., full-length) antibody. The terms "antibody fragment" or "functional fragment" also include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). In some embodiments, an antibody fragment does not include portions of antibodies without antigen binding activity, such as Fc fragments or single amino acid residues. Exemplary antibody molecules include full length antibodies and antibody fragments, e.g., dAb (domain antibody), single chain, Fab, Fab', and F(ab')₂ fragments, and single chain variable fragments (scFvs).

As used herein, the term "molecule" as used in, e.g., antibody molecule, cytokine molecule, receptor molecule, includes full-length, naturally-occurring molecules, as well as variants, e.g., functional variants (e.g., truncations, fragments, mutated (e.g., substantially similar sequences) or derivatized form thereof), so long as at least one function and/or activity of the unmodified (e.g., naturally-occurring) molecule remains.

The term "functional variant" refers to polypeptides that have a substantially identical amino acid sequence to the naturally-occurring sequence, or are encoded by a substantially identical nucleotide sequence, and are capable of having one or more activities of the naturally-occurring sequence.

"Derived from" as used herein in reference the relationship of a first sequence, to a second sequence (e.g., in the context of nucleic acid sequence or protein sequences) imposes no process limitations and refers only to structural similarity. In embodiments a derived sequence will differ from the reference sequence by levels of homology or sequence identity described elsewhere herein.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

"Lambda light chain polypeptide (LLCP)", as that term is used herein, refers to a polypeptide comprising sufficient light chain (LC) sequence, such that when combined with a cognate heavy chain variable region, can mediate specific binding to its epitope and complex with an HCP1. In an embodiment it comprises all or a fragment of a CH1 region. In an embodiment, an LLCP comprises LC-CDR1, LC-CDR2, LC-CDR3, FR1, FR2, FR3, FR4, and CH1, or sufficient sequence therefrom to mediate specific binding of its epitope and complex with an HCP1. LLCP, together with its HCP1, provide specificity for a first epitope (while KLCP, together with its HCP2, provide specificity for a second epitope). As described elsewhere herein, LLCP has a higher affinity for HCP1 than for HCP2.

"Kappa light chain polypeptide (KLCP)", as that term is used herein, refers to a polypeptide comprising sufficient light chain (LC) sequence, such that when combined with a cognate heavy chain variable region, can mediate specific binding to its epitope and complex with an HCP2. In an embodiment, it comprises all or a fragment of a CH1 region. In an embodiment, a KLCP comprises LC-CDR1, LC-CDR2, LC-CDR3, FR1, FR2, FR3, FR4, and CH1, or sufficient sequence therefrom to mediate specific binding of its epitope and complex with an HCP2. KLCP, together with its HCP2, provide specificity for a second epitope (while LLCP, together with its HCP1, provide specificity for a first epitope).

"Heavy chain polypeptide 1 (HCP1)", as that term is used herein, refers to a polypeptide comprising sufficient heavy chain (HC) sequence, e.g., HC variable region sequence, such that when combined with a cognate LLCP, can mediate specific binding to its epitope and complex with an HCP1. In an embodiment, it comprises all or a fragment of a CH1 region. In an embodiment, it comprises all or a fragment of a CH2 and/or CH3 region. In an embodiment an HCP1 comprises HC-CDR1, HC-CDR2, HC-CDR3, FR1, FR2, FR3, FR4, CH1, CH2, and CH3, or sufficient sequence therefrom to: (i) mediate specific binding of its epitope and complex with an LLCP, (ii) to complex preferentially, as described herein to LLCP as opposed to KLCP; and (iii) to complex preferentially, as described herein, to an HCP2, as opposed to another molecule of HCP1. HCP1, together with its LLCP, provide specificity for a first epitope (while KLCP, together with its HCP2, provide specificity for a second epitope).

"Heavy chain polypeptide 2 (HCP2)", as that term is used herein, refers to a polypeptide comprising sufficient heavy chain (HC) sequence, e.g., HC variable region sequence, such that when combined with a cognate LLCP, can mediate specific binding to its epitope and complex with an HCP1. In an embodiment, it comprises all or a fragment of a CH1 region. In an embodiment, it comprises all or a fragment of a CH2 and/or CH3 region. In an embodiment an HCP1 comprises HC-CDR1, HC-CDR2, HC-CDR3, FR1, FR2, FR3, FR4, CH1, CH2, and CH3, or sufficient sequence therefrom to: (i) mediate specific binding of its epitope and complex with an KLCP, (ii) to complex preferentially, as described herein to KLCP as opposed to LLCP; and (iii) to complex preferentially, as described herein, to an HCP1, as opposed to another molecule of HCP2. HCP2, together with its KLCP, provide specificity for a second epitope (while LLCP, together with its HCP1, provide specificity for a first epitope).

In embodiments, an antibody molecule is monospecific, e.g., it comprises binding specificity for a single epitope. In some embodiments, an antibody molecule is multispecific, e.g., it comprises a plurality of immunoglobulin variable domain sequences, where a first immunoglobulin variable domain sequence has binding specificity for a first epitope and a second immunoglobulin variable domain sequence has binding specificity for a second epitope. In some embodiments, an antibody molecule is a bispecific antibody molecule. "Bispecific antibody molecule" as used herein refers to an antibody molecule that has specificity for more than one (e.g., two, three, four, or more) epitope and/or antigen.

"Multispecific antibody molecule" as that term is used herein, refers to an antibody molecule having specificity for two non-identical epitopes, e.g., having a first variable region specific for a first epitope and a second variable region specific for a second epitope, wherein the first and second epitopes are non-identical. Multispecific antibody molecules include bispecific antibody molecules.

"Antigen" (Ag) as used herein refers to a molecule that can provoke an immune response, e.g., involving activation of certain immune cells and/or antibody generation. Any macromolecule, including almost all proteins or peptides, can be an antigen. Antigens can also be derived from genomic recombinant or DNA. For example, any DNA comprising a nucleotide sequence or a partial nucleotide sequence that encodes a protein capable of eliciting an immune response encodes an "antigen." In embodiments, an antigen does not need to be encoded solely by a full length nucleotide sequence of a gene, nor does an antigen need to be encoded by a gene at all. In embodiments, an antigen can be synthesized or can be derived from a biological sample, e.g., a tissue sample, a tumor sample, a cell, or a fluid with other biological components. As used, herein a "tumor antigen" or interchangeably, a "cancer antigen" includes any molecule present on, or associated with, a cancer, e.g., a cancer cell or a tumor microenvironment that can provoke an immune response. As used, herein an "immune cell antigen" includes any molecule present on, or associated with, an immune cell that can provoke an immune response.

The "antigen-binding site," or "binding portion" of an antibody molecule refers to the part of an antibody molecule, e.g., an immunoglobulin (Ig) molecule, that participates in antigen binding. In embodiments, the antigen binding site is formed by amino acid residues of the variable (V) regions of the heavy (H) and light (L) chains. Three highly divergent stretches within the variable regions of the heavy and light chains, referred to as hypervariable regions, are disposed between more conserved flanking stretches called "framework regions," (FRs). FRs are amino acid sequences that are naturally found between, and adjacent to, hypervariable regions in immunoglobulins. In embodiments, in an antibody molecule, the three hypervariable regions of a light chain and the three hypervariable regions of a heavy chain are disposed relative to each other in three dimensional space to form an antigen-binding surface, which is complementary to the three-dimensional surface of a bound antigen. The three hypervariable regions of each of the heavy and light chains are referred to as "complementarity-determining regions," or "CDRs." The framework region and CDRs have been defined and described, e.g., in Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917. Each variable chain (e.g., variable heavy chain and variable light chain) is typically made up of three CDRs and four FRs, arranged from amino-terminus to carboxy-terminus in the amino acid order: FR1, CDR1, FR2, CDR2, FR3, CDR3, and FR4.

As used herein, preferential pairing of a heavy chain polypeptide and a light chain polypeptide refers to the condition, where the heavy chain polypeptide and the light chain polypeptide preferentially bind to each other, over an unrelated heavy chain polypeptide, or an unrelated light chain polypeptide. In one embodiment, the heavy chain polypeptide binds to the light chain polypeptide with a higher affinity than when the heavy chain polypeptide binds to an unrelated light chain polypeptide. In one embodiment, the light chain polypeptide binds to the heavy chain polypeptide with a higher affinity than when the light chain polypeptide binds to an unrelated heavy chain polypeptide.

As used here, a percent binding between a first heavy chain polypeptide and a first light chain polypeptide in the presence of a competing polypeptide (e.g., a second heavy chain polypeptide or a second light chain polypeptide) refers to the amount of binding between the first heavy chain polypeptide and the first light chain polypeptide in the presence of the competing polypeptide, relative to the amount of binding between the first heavy chain polypeptide and the first light chain polypeptide in the absence of any competing polypeptide (the latter was set to 100%). In one embodiment, the percent binding was measured when the first heavy chain polypeptide, the first light chain polypeptide, and the competing polypeptide are present at 1:1:1. In one embodiment, the percent binding was measured when the first heavy chain polypeptide, the first light chain polypeptide, and the competing polypeptide are present at 1:1:1, wherein the competing polypeptide is a second light chain polypeptide. In one embodiment, the percent binding was measured by an assay described herein, e.g., the NanoBiT assay.

"Cancer" as used herein can encompass all types of oncogenic processes and/or cancerous growths. In embodiments, cancer includes primary tumors as well as metastatic tissues or malignantly transformed cells, tissues, or organs. In embodiments, cancer encompasses all histopathologies and stages, e.g., stages of invasiveness/severity, of a cancer. In embodiments, cancer includes relapsed and/or resistant cancer. The terms "cancer" and "tumor" can be used interchangeably. For example, both terms encompass solid and liquid tumors. As used herein, the term "cancer" or "tumor" includes premalignant, as well as malignant cancers and tumors.

As used herein, an "immune cell" refers to any of various cells that function in the immune system, e.g., to protect against agents of infection and foreign matter. In embodiments, this term includes leukocytes, e.g., neutrophils, eosinophils, basophils, lymphocytes, and monocytes. Innate leukocytes include phagocytes (e.g., macrophages, neutrophils, and dendritic cells), mast cells, eosinophils, basophils, and natural killer cells. Innate leukocytes identify and eliminate pathogens, either by attacking larger pathogens through contact or by engulfing and then killing microorganisms, and are mediators in the activation of an adaptive immune response. The cells of the adaptive immune system are special types of leukocytes, called lymphocytes. B cells and T cells are important types of lymphocytes and are derived from hematopoietic stem cells in the bone marrow. B cells are involved in the humoral immune response, whereas T cells are involved in cell-mediated immune response. The term "immune cell" includes immune effector cells.

"Immune effector cell," as that term is used herein, refers to a cell that is involved in an immune response, e.g., in the promotion of an immune effector response. Examples of immune effector cells include, but are not limited to, T cells, e.g., alpha/beta T cells and gamma/delta T cells, B cells, natural killer (NK) cells, natural killer T (NK T) cells, and mast cells.

The term "effector function" or "effector response" refers to a specialized function of a cell. Effector function of a T cell, for example, may be cytolytic activity or helper activity including the secretion of cytokines.

In some embodiments, the multispecific antibody molecule includes a tumor-targeting moiety. A "tumor-targeting moiety," as used herein, refers to a binding agent that recognizes or associates with, e.g., binds to, a target in a cancer cell. The tumor-targeting moiety can be an antibody molecule, a receptor molecule (e.g., a full length receptor, receptor fragment, or fusion thereof (e.g., a receptor-Fc fusion)), or a ligand molecule (e.g., a full length ligand, ligand fragment, or fusion thereof (e.g., a ligand-Fc fusion)) that binds to the cancer antigen (e.g., the tumor and/or the stromal antigen). In embodiments, the tumor-targeting moiety specifically binds to the target tumor, e.g., binds preferentially to the target tumor. For example, when the tumor-targeting moiety is an antibody molecule, it binds to the cancer antigen (e.g., the tumor antigen and/or the stromal antigen) with a dissociation constant of less than about 10 nM. In some embodiments, the multispecific antibody molecule includes an immune cell engager. "An immune cell engager" refers to one or more binding specificities that bind and/or activate an immune cell, e.g., a cell involved in an immune response. In embodiments, the immune cell is chosen from an NK cell, a B cell, a dendritic cell, and/or the macrophage cell. The immune cell engager can be an antibody molecule, a receptor molecule (e.g., a full length receptor, receptor fragment, or fusion thereof (e.g., a receptor-Fc fusion)), or a ligand molecule (e.g., a full length ligand, ligand fragment, or fusion thereof (e.g., a ligand-Fc fusion)) that binds to the immune cell antigen (e.g., the NK cell antigen, the B cell antigen, the dendritic cell antigen, and/or the macrophage cell antigen). In embodiments, the immune cell engager specifically binds to the target immune cell, e.g., binds preferentially to the target immune cell. For example, when the immune cell engager is an antibody molecule, it binds to the immune cell antigen (e.g., the NK cell antigen, the B cell antigen, the dendritic cell antigen, and/or the macrophage cell antigen) with a dissociation constant of less than about 10 nM.

In some embodiments, the multispecific antibody molecule includes a cytokine molecule. As used herein, a "cytokine molecule" refers to full length, a fragment or a variant of a cytokine; a cytokine further comprising a receptor domain, e.g., a cytokine receptor dimerizing domain; or an agonist of a cytokine receptor, e.g., an antibody molecule (e.g., an agonistic antibody) to a cytokine receptor, that elicits at least one activity of a naturally-occurring cytokine. In some embodiments the cytokine molecule is chosen from interleukin-2 (IL-2), interleukin-12 (IL-12), interleukin-15 (IL-15), interleukin-18 (IL-18), interleukin-21 (IL-21), or interferon gamma, or a fragment or variant thereof, or a combination of any of the aforesaid cytokines. The cytokine molecule can be a monomer or a dimer. In embodiments, the cytokine molecule can further include a cytokine receptor dimerizing domain. In other embodiments, the cytokine molecule is an agonist of a cytokine receptor, e.g., an antibody molecule (e.g., an agonistic antibody) to a cytokine receptor chosen from an IL-2, IL-15Ra or IL-21R.

The compositions and methods of the present invention encompass polypeptides and nucleic acids having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%, 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) *CABIOS*, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid (e.g., SEQ ID NO: 1) molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used. See http://www.ncbi.nlm.nih.gov.

It is understood that the molecules of the present invention may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide", "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

Various aspects of the invention are described in further detail below. Additional definitions are set out throughout the specification.

Antibody Molecules

In one embodiment, the antibody molecule binds to an antigen, e.g., an immune effector cell, a tumor antigen or a stromal antigen. In some embodiments, the antigen is, e.g., a mammalian, e.g., a human, antigen. In other embodiments, the antibody molecule binds to an immune cell antigen, e.g., a mammalian, e.g., a human, immune cell antigen. For example, the antibody molecule binds specifically to an epitope, e.g., linear or conformational epitope, on the cancer antigen or the immune cell antigen.

In an embodiment, an antibody molecule is a monospecific antibody molecule and binds a single epitope. E.g., a monospecific antibody molecule having a plurality of immunoglobulin variable domain sequences, each of which binds the same epitope.

In an embodiment an antibody molecule is a multispecific antibody molecule, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a multispecific antibody molecule comprises a third, fourth or fifth immunoglobulin variable domain. In an embodiment, a multispecific antibody molecule is a bispecific antibody molecule, a trispecific antibody molecule, or a tetraspecific antibody molecule.

In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope.

In an embodiment a bispecific antibody molecule comprises a scFv or a Fab, or fragment thereof, have binding specificity for a first epitope and a scFv or a Fab, or fragment thereof, have binding specificity for a second epitope.

In an embodiment, an antibody molecule comprises a diabody, and a single-chain molecule, as well as an antigen-binding fragment of an antibody (e.g., Fab, F(ab')$_2$, and Fv). For example, an antibody molecule can include a heavy (H) chain variable domain sequence (abbreviated herein as VH), and a light (L) chain variable domain sequence (abbreviated herein as VL). In an embodiment an antibody molecule comprises or consists of a heavy chain and a light chain (referred to herein as a half antibody. In another example, an antibody molecule includes two heavy (H) chain variable domain sequences and two light (L) chain variable domain sequence, thereby forming two antigen binding sites, such as Fab, Fab', F(ab')$_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The preparation of antibody molecules can be monoclonal or polyclonal. An antibody molecule can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda. The term "immunoglobulin" (Ig) is used interchangeably with the term "antibody" herein.

Examples of antigen-binding fragments of an antibody molecule include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments are obtained using conventional techniques known to those with skill in the art, and the fragments are screened for utility in the same manner as are intact antibodies.

Antibody molecules include intact molecules as well as functional fragments thereof. Constant regions of the antibody molecules can be altered, e.g., mutated, to modify the properties of the antibody (e.g., to increase or decrease one or more of: Fc receptor binding, antibody glycosylation, the number of cysteine residues, effector cell function, or complement function).

Antibody molecules can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

The VH and VL regions can be subdivided into regions of hypervariability, termed "complementarity determining regions" (CDR), interspersed with regions that are more conserved, termed "framework regions" (FR or FW).

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., *Protein Sequence and Structure Analysis of Antibody Variable Domains*. In: Antibody Engineering Lab Manual (Ed.: Duebel, S. and Kontermann, R., Springer-Verlag, Heidelberg).

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) *JMB* 273,927-948 ("Chothia" numbering scheme). As used herein, the CDRs defined according the "Chothia" number scheme are also sometimes referred to as "hypervariable loops."

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia, the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3).

Each VH and VL typically includes three CDRs and four FRs, arranged from amino-terminus to carboxy-terminus in the following order: FR1, CDR1, FR2, CDR2, FR3, CDR3, FR4.

The antibody molecule can be a polyclonal or a monoclonal antibody.

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

The antibody can be recombinantly produced, e.g., produced by phage display or by combinatorial methods.

Phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An antibody molecule can be one in which the variable region, or a portion thereof, e.g., the CDRs, are generated in a non-human organism, e.g., a rat or mouse. Chimeric, CDR-grafted, and humanized antibodies are within the invention. Antibody molecules generated in a non-human organism, e.g., a rat or mouse, and then modified, e.g., in the variable framework or constant region, to decrease antigenicity in a human are within the invention.

An "effectively human" protein is a protein that does substantially not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., *Cancer Immunol. Immunother.*, 32:180-190 (1990)) and also because of potential allergic reactions (see, e.g., LoBuglio et al., *Hybridoma*, 5:5117-5123 (1986)).

Chimeric antibodies can be produced by recombinant DNA techniques known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDRs (of heavy and or light immuoglobulin chains) replaced with a donor CDR. The antibody may be replaced with at least a portion of a non-human CDR or only some of the CDRs may be replaced with non-human CDRs. It is only necessary to replace the number of CDRs required for binding to the antigen. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody molecule can be humanized by methods known in the art (see e.g., Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference).

Humanized or CDR-grafted antibody molecules can be produced by CDR-grafting or CDR substitution, wherein one, two, or all CDRs of an immunoglobulin chain can be replaced. See, e.g., U.S. Pat. No. 5,225,539; Jones et al. 1986 *Nature* 321:552-525; Verhoeyan et al. 1988 *Science* 239: 1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibody molecules in which specific amino acids have been substituted, deleted or added. Criteria for selecting amino acids from the donor are described in U.S. Pat. No. 5,585, 089, e.g., columns 12-16 of U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

The antibody molecule can be a single chain antibody. A single-chain antibody (scFv) may be engineered (see, for example, Colcher, D. et al. (1999) *Ann N YAcadSci* 880: 263-80; and Reiter, Y. (1996) *Clin Cancer Res* 2:245-52). The single chain antibody can be dimerized or multimerized to generate multivalent antibodies having specificities for different epitopes of the same target protein.

In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has: effector function; and can fix complement. In other embodiments the antibody does not; recruit effector cells; or fix complement. In another embodiment, the antibody has reduced or no ability to bind an Fc receptor. For example, it is an isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g., altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference). Similar type of alterations could be described which if applied to the murine, or other species immunoglobulin would reduce or eliminate these functions.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules of the invention are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

One type of derivatized antibody molecule is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Multispecific Antibody Molecules

In embodiments, multispecific antibody molecules can comprise more than one antigen-binding site, where different sites are specific for different antigens. In embodiments, multispecific antibody molecules can bind more than one (e.g., two or more) epitopes on the same antigen. In embodiments, multispecific antibody molecules comprise an antigen-binding site specific for a target cell (e.g., cancer cell) and a different antigen-binding site specific for an immune effector cell. In one embodiment, the multispecific antibody molecule is a bispecific antibody molecule. Bispecific antibody molecules can be classified into five different structural groups: (i) bispecific immunoglobulin G (BsIgG); (ii) IgG appended with an additional antigen-binding moiety; (iii) bispecific antibody fragments; (iv) bispecific fusion proteins; and (v) bispecific antibody conjugates.

BsIgG is a format that is monovalent for each antigen. Exemplary BsIgG formats include but are not limited to crossMab, DAF (two-in-one), DAF (four-in-one), DutaMab, DT-IgG, knobs-in-holes common LC, knobs-in-holes assembly, charge pair, Fab-arm exchange, SEEDbody, triomab, LUZ-Y, Fcab, κλ-body, orthogonal Fab. See Spiess et al. Mol. Immunol. 67(2015):95-106. Exemplary BsIgGs include catumaxomab (Fresenius Biotech, Trion Pharma, Neopharm), which contains an anti-CD3 arm and an anti-EpCAM arm; and ertumaxomab (Neovii Biotech, Fresenius Biotech), which targets CD3 and HER2. In some embodiments, BsIgG comprises heavy chains that are engineered for heterodimerization. For example, heavy chains can be engineered for heterodimerization using a "knobs-into-holes" strategy, a SEED platform, a common heavy chain (e.g., in κλ-bodies), and use of heterodimeric Fc regions. See Spiess et al. Mol. Immunol. 67(2015):95-106. Strategies that have been used to avoid heavy chain pairing of homodimers in BsIgG include knobs-in-holes, duobody, azymetric, charge pair, HA-TF, SEEDbody, and differential protein A affinity. See Id.

BsIgG can be produced by separate expression of the component antibodies in different host cells and subsequent purification/assembly into a BsIgG. BsIgG can also be produced by expression of the component antibodies in a single host cell. BsIgG can be purified using affinity chromatography, e.g., using protein A and sequential pH elution.

IgG appended with an additional antigen-binding moiety is another format of bispecific antibody molecules. For example, monospecific IgG can be engineered to have bispecificity by appending an additional antigen-binding unit onto the monospecific IgG, e.g., at the N- or C-terminus of either the heavy or light chain. Exemplary additional antigen-binding units include single domain antibodies (e.g., variable heavy chain or variable light chain), engineered protein scaffolds, and paired antibody variable domains (e.g., single chain variable fragments or variable fragments). See Id. Examples of appended IgG formats include dual variable domain IgG (DVD-Ig), IgG(H)-scFv, scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig, zybody, and DVI-IgG (four-in-one). See Spiess et al. Mol. Immunol. 67(2015):95-106. An example of an IgG-scFv is MM-141 (Merrimack Pharmaceuticals), which binds IGF-1R and HER3. Examples of DVD-Ig include ABT-981 (AbbVie), which binds IL-1a and IL-1β; and ABT-122 (AbbVie), which binds TNF and IL-17A.

Bispecific antibody fragments (BsAb) are a format of bispecific antibody molecules that lack some or all of the antibody constant domains. For example, some BsAb lack an Fc region. In embodiments, bispecific antibody fragments include heavy and light chain regions that are connected by a peptide linker that permits efficient expression of the BsAb in a single host cell. Exemplary bispecific antibody fragments include but are not limited to nanobody, nanobody-HAS, BiTE, Diabody, DART, TandAb, scDiabody, scDiabody-CH3, Diabody-CH3, triple body, miniantibody, minibody, TriBi minibody, scFv-CH3 KIH, Fab-scFv, scFv-CH-CL-scFv, F(ab')2, F(ab')2-scFv2, scFv-KIH, Fab-scFv-Fc, tetravalent HCAb, scDiabody-Fc, Diabody-Fc, tandem scFv-Fc, and intrabody. See Id. For example, the BiTE format comprises tandem scFvs, where the component scFvs bind to CD3 on T cells and a surface antigen on cancer cells Bispecific fusion proteins include antibody fragments linked to other proteins, e.g., to add additional specificity and/or functionality. An example of a bispecific fusion protein is an immTAC, which comprises an anti-CD3 scFv linked to an affinity-matured T-cell receptor that recognizes HLA-presented peptides. In embodiments, the dock-and-lock (DNL) method can be used to generate bispecific antibody molecules with higher valency. Also, fusions to albumin binding proteins or human serum albumin can be extend the serum half-life of antibody fragments. See Id.

CDR-Grafted Scaffolds

In embodiments, the antibody molecule is a CDR-grafted scaffold domain. In embodiments, the scaffold domain is based on a fibronectin domain, e.g., fibronectin type III domain. The overall fold of the fibronectin type III (Fn3) domain is closely related to that of the smallest functional antibody fragment, the variable domain of the antibody heavy chain. There are three loops at the end of Fn3; the positions of BC, DE and FG loops approximately correspond to those of CDR1, 2 and 3 of the VH domain of an antibody. Fn3 does not have disulfide bonds; and therefore Fn3 is stable under reducing conditions, unlike antibodies and their fragments (see, e.g., WO 98/56915; WO 01/64942; WO 00/34784). An Fn3 domain can be modified (e.g., using CDRs or hypervariable loops described herein) or varied, e.g., to select domains that bind to an antigen/marker/cell described herein.

In embodiments, a scaffold domain, e.g., a folded domain, is based on an antibody, e.g., a "minibody" scaffold created by deleting three beta strands from a heavy chain variable domain of a monoclonal antibody (see, e.g., Tramontano et al., 1994, J Mol. Recognit. 7:9; and Martin et al., 1994, EMBO J. 13:5303-5309). The "minibody" can be used to present two hypervariable loops. In embodiments, the scaffold domain is a V-like domain (see, e.g., Coia et al. WO 99/45110) or a domain derived from tendamistatin, which is a 74 residue, six-strand beta sheet sandwich held together by two disulfide bonds (see, e.g., McConnell and Hoess, 1995, J Mol. Biol. 250:460). For example, the loops of tendamistatin can be modified (e.g., using CDRs or hypervariable loops) or varied, e.g., to select domains that bind to a marker/antigen/cell described herein. Another exemplary scaffold domain is a beta-sandwich structure derived from the extracellular domain of CTLA-4 (see, e.g., WO 00/60070).

Other exemplary scaffold domains include but are not limited to T-cell receptors; MHC proteins; extracellular domains (e.g., fibronectin Type III repeats, EGF repeats); protease inhibitors (e.g., Kunitz domains, ecotin, BPTI, and so forth); TPR repeats; trifoil structures; zinc finger domains; DNA-binding proteins; particularly monomeric DNA binding proteins; RNA binding proteins; enzymes, e.g., proteases (particularly inactivated proteases), RNase; chaperones, e.g., thioredoxin, and heat shock proteins; and intracellular signaling domains (such as SH2 and SH3 domains). See, e.g., US 20040009530 and U.S. Pat. No. 7,501,121, incorporated herein by reference.

In embodiments, a scaffold domain is evaluated and chosen, e.g., by one or more of the following criteria: (1) amino acid sequence, (2) sequences of several homologous domains, (3) 3-dimensional structure, and/or (4) stability data over a range of pH, temperature, salinity, organic solvent, oxidant concentration. In embodiments, the scaffold domain is a small, stable protein domain, e.g., a protein of less than 100, 70, 50, 40 or 30 amino acids. The domain may include one or more disulfide bonds or may chelate a metal, e.g., zinc.

Exemplary structures of the multifunctional molecules defined herein are described below. Exemplary structures are further described in: Weidle U et al. (2013) The Intriguing Options of Multispecific Antibody Formats for Treatment of Cancer. *Cancer Genomics & Proteomics* 10: 1-18 (2013); and Spiess C et al. (2015) Alternative molecular formats and therapeutic applications for bispecific antibodies. *Molecular Immunology* 67: 95-106; the full contents of each of which is incorporated by reference herein).

Heterodimerized Antibody Molecules

Heterodimerized bispecific antibodies are based on the natural IgG structure, wherein the two binding arms recognize different antigens. IgG derived formats that enable defined monovalent (and simultaneous) antigen binding are generated by forced heavy chain heterodimerization, combined with technologies that minimize light chain mispairing (e.g., common light chain). Forced heavy chain heterodimerization can be obtained using, e.g., knob-in-hole OR strand exchange engineered domains (SEED).

Knob-in-Hole

Knob-in-Hole as described in U.S. Pat. Nos. 5,731,116, 7,476,724 and Ridgway, J. et al. (1996) *Prot. Engineering* 9(7): 617-621, broadly involves: (1) mutating the CH3 domain of one or both antibodies to promote heterodimerization; and (2) combining the mutated antibodies under conditions that promote heterodimerization. "Knobs" or "protuberances" are typically created by replacing a small amino acid in a parental antibody with a larger amino acid (e.g., T366Y or T366W); "Holes" or "cavities" are created by replacing a larger residue in a parental antibody with a smaller amino acid (e.g., Y407T, T366S, L368A and/or Y407V). In one embodiment, a heavy chain polypeptide containing a knob comprises T366W and S354C substitutions, numbered according to the Eu numbering system. In one embodiment, a heavy chain polypeptide containing a hole comprises T366S, L368A, Y407V and Y349C substitutions, numbered according to the Eu numbering system. In one embodiment, the multispecific antibody molecule disclosed herein comprises a first heavy chain polypeptide and a second heavy chain polypeptide, wherein the first heavy chain polypeptide comprises T366W and S354C substitutions, numbered according to the Eu numbering system, and the second heavy chain polypeptide comprises T366S, L368A, Y407V and Y349C substitutions, numbered according to the Eu numbering system.

Strand Exchange Engineered Domains (SEED)

SEED is based on sequence exchanges between IgG1 and IgA to create non-identical chains which heterodimerize preferentially. Alternating sequences from human IgA and IgG in the SEED CH3 domains generate two asymmetric but complementary domains, designated AG and GA. The SEED design allows efficient generation of AG/GA heterodimers, while disfavoring homodimerization of AG and GA SEED CH3 domains.

Common Light Chain & CrossMab

Light chain mispairing must be avoided to generate homogenous preparations of bispecific IgGs. One way to achieve this is through the use of the common light chain principle, i.e., combining two binders that share one light chain but still have separate specificities. Another option is the CrossMab technology which avoids non-specific L chain mispairing by exchanging CH1 and CL domains in the Fab of one half of the bispecific antibody. Such crossover variants retain binding specificity and affinity, but make the two arms so different that L chain mispairing is prevented.

Antibody-Based Fusions

A variety of formats can be generated which contain additional binding entities attached to the N or C terminus of antibodies. These fusions with single chain or disulfide stabilized Fvs or Fabs result in the generation of tetravalent molecules with bivalent binding specificity for each antigen. Combinations of scFvs and scFabs with IgGs enable the production of molecules which can recognize three or more different antigens.

Antibody-Fab Fusion

Antibody-Fab fusions are bispecific antibodies comprising a traditional antibody to a first target and a Fab to a second target fused to the C terminus of the antibody heavy chain. Commonly the antibody and the Fab will have a common light chain. Antibody fusions can be produced by (1) engineering the DNA sequence of the target fusion, and (2) transfecting the target DNA into a suitable host cell to express the fusion protein. It seems like the antibody-scFv fusion may be linked by a (Gly)-Ser linker between the C-terminus of the CH3 domain and the N-terminus of the scFv, as described by Coloma, J. et al. (1997) *Nature Biotech* 15:159.

Antibody-scFv Fusion

Antibody-scFv Fusions are bispecific antibodies comprising a traditional antibody and a scFv of unique specificity fused to the C terminus of the antibody heavy chain. The scFv can be fused to the C terminus through the Heavy Chain of the scFv either directly or through a linker peptide. Antibody fusions can be produced by (1) engineering the DNA sequence of the target fusion, and (2) transfecting the target DNA into a suitable host cell to express the fusion protein. It seems like the antibody-scFv fusion may be linked by a (Gly)-Ser linker between the C-terminus of the CH3 domain and the N-terminus of the scFv, as described by Coloma, J. et al. (1997) *Nature Biotech* 15:159.

Variable Domain Immunoglobulin DVD

A related format is the dual variable domain immunoglobulin (DVD), which are composed of VH and VL domains of a second specificity place upon the N termini of the V domains by shorter linker sequences.

Fc-Containing Entities (Mini-Antibodies)

Fc-containing entities, also known as mini-antibodies, can be generated by fusing scFv to the C-termini of constant heavy region domain 3 (CH3-scFv) and/or to the hinge region (scFv-hinge-Fc) of an antibody with a different specificity. Trivalent entities can also be made which have disulfide stabilized variable domains (without peptide linker) fused to the C-terminus of CH3 domains of IgGs.

Fc-Containing Multispecific Molecules

In some embodiments, the multispecific molecules disclosed herein includes an immunoglobulin constant region (e.g., an Fc region). Exemplary Fc regions can be chosen from the heavy chain constant regions of IgG1, IgG2, IgG3 or IgG4; more particularly, the heavy chain constant region of human IgG1, IgG2, IgG3, or IgG4.

In some embodiments, the immunoglobulin chain constant region (e.g., the Fc region) is altered, e.g., mutated, to increase or decrease one or more of: Fc receptor binding, antibody glycosylation, the number of cysteine residues, effector cell function, or complement function.

In other embodiments, an interface of a first and second immunoglobulin chain constant regions (e.g., a first and a second Fc region) is altered, e.g., mutated, to increase or decrease dimerization, e.g., relative to a non-engineered interface, e.g., a naturally-occurring interface. For example, dimerization of the immunoglobulin chain constant region (e.g., the Fc region) can be enhanced by providing an Fc interface of a first and a second Fc region with one or more of: a paired protuberance-cavity ("knob-in-a hole"), an electrostatic interaction, or a strand-exchange, such that a greater ratio of heteromultimer to homomultimer forms, e.g., relative to a non-engineered interface.

In some embodiments, the multispecific molecules include a paired amino acid substitution at a position chosen from one or more of 347, 349, 350, 351, 366, 368, 370, 392, 394, 395, 397, 398, 399, 405, 407, or 409, e.g., of the Fc region of human IgG1 For example, the immunoglobulin chain constant region (e.g., Fc region) can include a paired an amino acid substitution chosen from: T366S, L368A, or Y407V (e.g., corresponding to a cavity or hole), and T366W (e.g., corresponding to a protuberance or knob).

In some embodiments, the immunoglobulin chain constant region (e.g., the Fc region) is not altered, e.g., not mutated, to increase or decrease one or more of: Fc receptor binding, antibody glycosylation, the number of cysteine residues, effector cell function, or complement function. In some embodiments, the multispecific molecules does not include a paired amino acid substitution at a position chosen from one or more of 347, 349, 350, 351, 366, 368, 370, 392, 394, 395, 397, 398, 399, 405, 407, or 409, e.g., of the Fc region of human IgG1 For example, the immunoglobulin chain constant region (e.g., Fc region) does not include a paired amino acid substitution chosen from: T366S, L368A, or Y407V (e.g., corresponding to a cavity or hole), and T366W (e.g., corresponding to a protuberance or knob).

In other embodiments, the multispecific molecule includes a half-life extender, e.g., a human serum albumin or an antibody molecule to human serum albumin.

Multispecific Molecules Comprising Non-Contiguous Polypeptides

In one embodiment, the multispecific molecule is not a single polypeptide chain.

In one embodiment, the antibody molecule includes two, complete heavy chains and two, complete light chains. In one embodiment, the multispecific molecules having at least two or at least three non-contiguous polypeptide chains include a first and second immunoglobulin chain constant regions (e.g., a first and second Fc region) in at least two non-contiguous polypeptide chains, e.g., as described herein.

In embodiments, the multispecific molecule is a bispecific or bifunctional molecule, wherein the first and second polypeptides (i) and (ii) are non-contiguous, e.g., are two separate polypeptide chains. In some embodiments, the first and second polypeptides (i) and (ii) include a paired amino acid substitution at a position chosen from one or more of 347, 349, 350, 351, 366, 368, 370, 392, 394, 395, 397, 398, 399, 405, 407, or 409, e.g., of the Fc region of human IgG1. For example, the first immunoglobulin chain constant region (e.g., the first Fc region) can include an amino acid substitution chosen from: T366S, L368A, or Y407V (e.g., corresponding to a cavity or hole), and the second immunoglobulin chain constant region (e.g., the second Fc region) includes a T366W (e.g., corresponding to a protuberance or knob). In some embodiments, the first and second polypeptides are a first and second member of a heterodimeric first and second Fc region.

In embodiments, the multispecific molecule is a bispecific or bifunctional molecule, wherein the first and second polypeptides (i) and (ii) are non-contiguous, e.g., are two separate polypeptide chains. In some embodiments, the first and second polypeptides (i) and (ii) do not include a paired amino acid substitution at a position chosen from one or more of 347, 349, 350, 351, 366, 368, 370, 392, 394, 395, 397, 398, 399, 405, 407, or 409, e.g., of the Fc region of human IgG1.

In some embodiments, the first polypeptide has the following configuration from N-to-C:
(a) a first portion of a first antigen domain, e.g., a first VH-CH1 of a Fab molecule, that binds to a first antigen, e.g., a cancer antigen, e.g., a solid tumor, stromal or hematological antigen, connected, optionally via a linker to, the first immunoglobulin constant region (e.g., the CH2 connected to the CH3 region) (e.g., a first Fc region);
(b) a first portion of a second antigen domain, e.g., a first VH-CH1 of a Fab molecule, that binds to a second antigen, e.g., a cancer antigen, e.g., a solid tumor, stromal or hematological antigen, connected, optionally via a linker to, the first immunoglobulin constant region (e.g., the CH2 connected to the CH3 region) (e.g., a first Fc region);
(c) the third polypeptide has the following configuration from N-to-C: a second portion of the first antigen domain, e.g., a first VL-CL of the Fab, where the VL is of kappa subtype and binds to a first antigen, e.g., a cancer antigen, e.g., a solid tumor, stromal or hematological antigen (e.g., the same cancer antigen bound by the first VH-CH1);
(d) the fourth polypeptide has the following configuration from N-to-C: a second portion of the second antigen domain, e.g. a second VL-CL of the Fab, where the VL is of lambda subtype and binds to a second antigen, e.g., a cancer antigen, e.g., a solid tumor, stromal, or hematological antigen (e.g., the same cancer antigen bound by the second VH-CH1) (e.g. an example of this configuration is depicted in FIG. 1A).

In embodiments, the first immunoglobulin constant region (e.g., the first CH2-CH3 region) includes a protuberance or knob, e.g., as described herein. In embodiments, the first immunoglobulin constant region (e.g., the first CH2-CH3 region) does not include a protuberance or knob, e.g., as described herein.

In embodiments, the second immunoglobulin constant region (e.g., the second CH2-CH3 region) includes a cavity or hole. In embodiments, the first and second immunoglobulin constant region promote heterodimerization of the bispecific molecule. In embodiments, the second immunoglobulin constant region (e.g., the second CH2-CH3 region) does not include a cavity or hole. In embodiments, the first and second immunoglobulin constant region does not promote heterodimerization of the bispecific molecule.

Tumor Specific Targeting Moieties

In certain embodiments, the multispecific antibody molecules disclosed herein include a tumor-targeting moiety. The tumor targeting moiety can be chosen from an antibody molecule (e.g., an antigen binding domain as described herein), a receptor or a receptor fragment, or a ligand or a ligand fragment, or a combination thereof. In some embodiments, the tumor targeting moiety associates with, e.g., binds to, a tumor cell (e.g., a molecule, e.g., antigen, present on the surface of the tumor cell). In certain embodiments, the tumor targeting moiety targets, e.g., directs the multispecific molecules disclosed herein to a cancer (e.g., a cancer or tumor cells). In some embodiments, the cancer is chosen from a hematological cancer, a solid cancer, a metastatic cancer, or a combination thereof.

In some embodiments, the multispecific molecule, e.g., the tumor-targeting moiety, binds to a solid tumor antigen or a stromal antigen. The solid tumor antigen or stromal antigen can be present on a solid tumor, or a metastatic lesion thereof. In some embodiments, the solid tumor is chosen from one or more of pancreatic (e.g., pancreatic adenocarcinoma), breast, colorectal, lung (e.g., small or non-small cell lung cancer), skin, ovarian, or liver cancer. In one embodiment, the solid tumor is a fibrotic or desmoplastic solid tumor. For example, the solid tumor antigen or stromal antigen can be present on a tumor, e.g., a tumor of a class typified by having one or more of: limited tumor perfusion, compressed blood vessels, or fibrotic tumor interstitium.

In certain embodiments, the solid tumor antigen is chosen from one or more of: mesothelin, gangloside 2 (GD2), prostate stem cell antigen (PSCA), prostate specific membrane antigen (PMSA), prostate-specific antigen (PSA), carcinoembryonic antigen (CEA), Ron Kinase, c-Met, Immature laminin receptor, TAG-72, BING-4, Calcium-activated chloride channel 2, Cyclin-B1, 9D7, Ep-CAM, EphA3, Her2/neu, Telomerase, SAP-1, Survivin, NY-ESO-1/LAGE-1, PRAME, SSX-2, Melan-A/MART-1, Gp100/pmel17, Tyrosinase, TRP-1/-2, MC1R, β-catenin, BRCA1/2, CDK4, CML66, Fibronectin, p53, Ras, TGF-B receptor, AFP, ETA, MAGE, MUC-1, CA-125, BAGE, GAGE, NY-ESO-1, β-catenin, CDK4, CDC27, α actinin-4, TRP1/gp75, TRP2, gp100, Melan-A/MART1, gangliosides, WT1, EphA3, Epidermal growth factor receptor (EGFR), CD20, MART-2, MART-1, MUC1, MUC2, MUM1, MUM2, MUM3, NA88-1, NPM, OA1, OGT, RCC, RUI1, RUI2, SAGE, TRG, TRP1, or TSTA. In some embodiments, the solid tumor antigen is chosen from: Mesothelin, GD2, PMSA, PSCA, CEA, Ron Kinase, or c-Met. In some embodiments, the solid tumor antigen is Mesothelin.

Cytokine Molecules

In certain embodiments, the multispecific antibody molecules disclosed herein can further include a cytokine molecule.

Cytokines are proteinaceous signaling compounds that are mediators of the immune response. They control many different cellular functions including proliferation, differentiation and cell survival/apoptosis; cytokines are also involved in several pathophysiological processes including viral infections and autoimmune diseases. Cytokines are synthesized under various stimuli by a variety of cells of both the innate (monocytes, macrophages, dendritic cells) and adaptive (T- and B-cells) immune systems. Cytokines can be classified into two groups: pro- and anti-inflammatory. Pro-inflammatory cytokines, including IFNgamma, IL-1, IL-6 and TNF-alpha, are predominantly derived from the innate immune cells and Th1 cells. Anti-inflammatory cytokines, including IL-10, IL-4, IL-13 and IL-5, are synthesized from Th2 immune cells.

The present disclosure provides, inter alia, multi-specific (e.g., bi-, tri-, quad-specific) proteins, that include, e.g., are engineered to contain, one or more cytokine molecules, e.g., immunomodulatory (e.g., proinflammatory) cytokines and variants, e.g., functional variants, thereof. Accordingly, in some embodiments, the cytokine molecule is an interleukin or a variant, e.g., a functional variant thereof. In some embodiments the interleukin is a proinflammatory interleukin. In some embodiments the interleukin is chosen from interleukin-2 (IL-2), interleukin-12 (IL-12), interleukin-15 (IL-15), interleukin-18 (IL-18), interleukin-21 (IL-21), or interferon gamma. In some embodiments the interleukin is interleukin-2 (IL-2). In some embodiments, the cytokine molecule is a proinflammatory cytokine.

In some embodiments, the multispecific molecules disclosed herein include a cytokine molecule. In embodiments, the cytokine molecule includes a full length, a fragment or a variant of a cytokine; a cytokine receptor domain, e.g., a cytokine receptor dimerizing domain; or an agonist of a cytokine receptor, e.g., an antibody molecule (e.g., an agonistic antibody) to a cytokine receptor.

In some embodiments the cytokine molecule is chosen from IL-2, IL-12, IL-15, IL-18, IL-21, or interferon gamma, or a fragment or variant thereof, or a combination of any of the aforesaid cytokines. The cytokine molecule can be a monomer or a dimer. In embodiments, the cytokine molecule can further include a cytokine receptor dimerizing domain.

In other embodiments, the cytokine molecule is an agonist of a cytokine receptor, e.g., an antibody molecule (e.g., an agonistic antibody) to a cytokine receptor chosen from an IL-15Ra or IL-21R.

Immune Cell Engagers

In certain embodiments, the multispecific antibody molecules disclosed herein can include an immune cell engager.

The immune cell engagers of the multispecific molecules disclosed herein can mediate binding to, and/or activation of, an immune cell, e.g., an immune effector cell. In some embodiments, the immune cell is chosen from an NK cell, a B cell, a dendritic cell, or a macrophage cell engager, or a combination thereof. In some embodiments, the immune cell engager is chosen from one, two, three, or all of an NK cell engager, a B cell engager, a dendritic cell engager, or a macrophage cell engager, or a combination thereof. The immune cell engager can be an agonist of the immune system. In some embodiments, the immune cell engager can be an antibody molecule, a ligand molecule (e.g., a ligand that further comprises an immunoglobulin constant region, e.g., an Fc region), a small molecule, a nucleotide molecule.

Natural Killer Cell Engagers

Natural Killer (NK) cells recognize and destroy tumors and virus-infected cells in an antibody-independent manner. The regulation of NK cells is mediated by activating and inhibiting receptors on the NK cell surface. One family of activating receptors is the natural cytotoxicity receptors (NCRs) which include NKp30, NKp44 and NKp46. The NCRs initiate tumor targeting by recognition of heparan sulfate on cancer cells. NKG2D is a receptor that provides both stimulatory and costimulatory innate immune responses on activated killer (NK) cells, leading to cytotoxic activity. DNAM1 is a receptor involved in intercellular adhesion, lymphocyte signaling, cytotoxicity and lymphokine secretion mediated by cytotoxic T-lymphocyte (CTL) and NK cell. DAP10 (also known as HCST) is a transmembrane adapter protein which associates with KLRK1 to form an activation receptor KLRK1-HCST in lymphoid and myeloid cells; this receptor plays a major role in triggering cytotoxicity against target cells expressing cell surface ligands such as MHC class I chain-related MICA and MICB, and U(optionally L1)6-binding proteins (ULBPs); it KLRK1-HCST receptor plays a role in immune surveillance against tumors and is required for cytolysis of tumors cells; indeed, melanoma cells that do not express KLRK1 ligands escape from immune surveillance mediated by NK cells. CD16 is a receptor for the Fc region of IgG, which binds complexed or aggregated IgG and also monomeric IgG and thereby mediates antibody-dependent cellular cytotoxicity (ADCC) and other antibody-dependent responses, such as phagocytosis.

In some embodiments, the NK cell engager is a viral hemagglutinin (HA), HA is a glycoprotein found on the surface of influenza viruses. It is responsible for binding the virus to cells with sialic acid on the membranes, such as cells in the upper respiratory tract or erythrocytes. HA has at least 18 different antigens. These subtypes are named H1 through H18. NCRs can recognize viral proteins. NKp46 has been shown to be able to interact with the HA of influenza and the HA-NA of Paramyxovirus, including Sendai virus and Newcastle disease virus. Besides NKp46, NKp44 can also functionally interact with HA of different influenza subtypes.

The present disclosure provides, inter alia, multi-specific (e.g., bi-, tri-, quad-specific) proteins, that are engineered to contain one or more NK cell engager that mediate binding to and/or activation of an NK cell. Accordingly, in some embodiments, the NK cell engager is selected from an antigen binding domain or ligand that binds to (e.g., activates): NKp30, NKp40, NKp44, NKp46, NKG2D, DNAM1, DAP10, CD16 (e.g., CD16a, CD16b, or both), CRTAM, CD27, PSGL1, CD96, CD100 (SEMA4D), NKp80 or CD244 (also known as SLAMF4 or 2B4). in some embodiments, the NK cell engager is selected from an antigen binding domain or ligand that binds to (e.g., activates): NKp30 or NKp46.

In other embodiments, the NK cell engager is a ligand of NKp44 or NKp46, which is a viral HA. Viral hemagglutinins (HA) are glyco proteins which are on the surface of viruses. HA proteins allow viruses to bind to the membrane of cells via sialic acid sugar moieties which contributes to the fusion of viral membranes with the cell membranes (see e.g., Eur J Immunol. 2001 September; 31(9):2680-9 "Recognition of viral hemagglutinins by NKp44 but not by NKp30"; and Nature. 2001 Feb. 22; 409(6823):1055-60 "Recognition of haemagglutinins on virus-infected cells by NKp46 activates lysis by human NK cells" the contents of each of which are incorporated by reference herein).

In other embodiments, the NK cell engager is a ligand of NKG2D chosen from MICA, MICB, or ULBP1.

In other embodiments, the NK cell engager is a ligand of DNAM1 chosen from NECTIN2 or NECL5.

In yet other embodiments, the NK cell engager is a ligand of DAP10, which is an adapter for NKG2D (see e.g., Proc Natl Acad Sci USA. 2005 May 24; 102(21): 7641-7646; and Blood, 15 Sep. 2011 Volume 118, Number 11, the full contents of each of which is incorporated by reference herein).

In other embodiments, the NK cell engager is a ligand of CD16, which is a CD16a/b ligand, e.g., a CD16a/b ligand further comprising an antibody Fc region (see e.g., Front Immunol. 2013; 4: 76 discusses how antibodies use the Fc to trigger NK cells through CD16, the full contents of which are incorporated herein).

B Cell, Macrophage & Dendritic Cell Engagers

Broadly, B cells, also known as B lymphocytes, are a type of white blood cell of the lymphocyte subtype. They function in the humoral immunity component of the adaptive immune system by secreting antibodies. Additionally, B cells present antigen (they are also classified as professional antigen-presenting cells (APCs)) and secrete cytokines. Macrophages are a type of white blood cell that engulfs and digests cellular debris, foreign substances, microbes, cancer cells via phagocytosis. Besides phagocytosis, they play important roles in nonspecific defense (innate immunity) and also help initiate specific defense mechanisms (adaptive immunity) by recruiting other immune cells such as lymphocytes. For example, they are important as antigen presenters to T cells. Beyond increasing inflammation and stimulating the immune system, macrophages also play an important anti-inflammatory role and can decrease immune reactions through the release of cytokines. Dendritic cells (DCs) are antigen-presenting cells that function in processing antigen material and present it on the cell surface to the T cells of the immune system.

The present disclosure provides, inter alia, multi-specific (e.g., bi-, tri-, quad-specific) proteins, that include, e.g., are engineered to contain, one or more B cell, macrophage, and/or dendritic cell engager that mediate binding to and/or activation of a B cell, macrophage, and/or dendritic cell.

Accordingly, in some embodiments, the immune cell engager comprises a B cell, macrophage, and/or dendritic cell engager chosen from one or more of CD40 ligand (CD40L) or a CD70 ligand; an antibody molecule that binds to CD40 or CD70; an antibody molecule to OX40; an OX40 ligand (OX40L); an agonist of a Toll-like receptor (e.g., as described herein, e.g., a TLR4, e.g., a constitutively active TLR4 (caTLR4), or a TLR9 agonists); a 41BB; a CD2; a CD47; or a STING agonist, or a combination thereof.

In some embodiments, the B cell engager is a CD40L, an OX40L, or a CD70 ligand, or an antibody molecule that binds to OX40, CD40 or CD70.

In some embodiments, the macrophage engager is a CD2 agonist. In some embodiments, the macrophage engager is an antigen binding domain that binds to: CD40L or antigen binding domain or ligand that binds CD40, a Toll like receptor (TLR) agonist (e.g., as described herein), e.g., a TLR9 or TLR4 (e.g., caTLR4 (constitutively active TLR4), CD47, or a STING agonist. In some embodiments, the STING agonist is a cyclic dinucleotide, e.g., cyclic di-GMP (cdGMP) or cyclic di-AMP (cdAMP). In some embodiments, the STING agonist is biotinylated.

In some embodiments, the dendritic cell engager is a CD2 agonist. In some embodiments, the dendritic cell engager is a ligand, a receptor agonist, or an antibody molecule that binds to one or more of: OX40L, 41BB, a TLR agonist (e.g., as described herein) (e.g., TLR9 agonist, TLR4 agonist, caTLR4 (constitutively active TLR4)), CD47, or and a STING agonist. In some embodiments, the STING agonist is a cyclic dinucleotide, e.g., cyclic di-GMP (cdGMP) or cyclic di-AMP (cdAMP). In some embodiments, the STING agonist is biotinylated.

In other embodiments, the immune cell engager mediates binding to, or activation of, one or more of a B cell, a macrophage, and/or a dendritic cell. Exemplary B cell, macrophage, and/or dendritic cell engagers can be chosen from one or more of CD40 ligand (CD40L) or a CD70 ligand; an antibody molecule that binds to CD40 or CD70; an antibody molecule to OX40; an OX40 ligand (OX40L); a Toll-like receptor agonist (e.g., a TLR4, e.g., a constitutively active TLR4 (caTLR4) or a TLR9 agonist); a 41BB agonist; a CD2; a CD47; or a STING agonist, or a combination thereof.

In some embodiments, the B cell engager is chosen from one or more of a CD40L, an OX40L, or a CD70 ligand, or an antibody molecule that binds to OX40, CD40 or CD70.

In other embodiments, the macrophage cell engager is chosen from one or more of a CD2 agonist; a CD40L; an OX40L; an antibody molecule that binds to OX40, CD40 or CD70; a Toll-like receptor agonist or a fragment thereof (e.g., a TLR4, e.g., a constitutively active TLR4 (caTLR4)); a CD47 agonist; or a STING agonist.

In other embodiments, the dendritic cell engager is chosen from one or more of a CD2 agonist, an OX40 antibody, an OX40L, 41BB agonist, a Toll-like receptor agonist or a fragment thereof (e.g., a TLR4, e.g., a constitutively active TLR4 (caTLR4)), CD47 agonist, or a STING agonist.

In yet other embodiments, the STING agonist comprises a cyclic dinucleotide, e.g., a cyclic di-GMP (cdGMP), a cyclic di-AMP (cdAMP), or a combination thereof, optionally with 2',5' or 3',5' phosphate linkages.

Toll-Like Receptors

Toll-Like Receptors (TLRs) are evolutionarily conserved receptors are homologues of the *Drosophila* Toll protein, and recognize highly conserved structural motifs known as pathogen-associated microbial patterns (PAMPs), which are exclusively expressed by microbial pathogens, or danger-associated molecular patterns (DAMPs) that are endogenous molecules released from necrotic or dying cells. PAMPs include various bacterial cell wall components such as lipopolysaccharide (LPS), peptidoglycan (PGN) and lipopeptides, as well as flagellin, bacterial DNA and viral double-stranded RNA. DAMPs include intracellular proteins such as heat shock proteins as well as protein fragments from the extracellular matrix. Stimulation of TLRs by the corresponding PAMPs or DAMPs initiates signaling cascades leading to the activation of transcription factors, such as AP-1, NF-κB and interferon regulatory factors (IRFs). Signaling by TLRs results in a variety of cellular responses, including the production of interferons (IFNs), pro-inflammatory cytokines and effector cytokines that direct the adaptive immune response. TLRs are implicated in a number of inflammatory and immune disorders and play a role in cancer (Rakoff-Nahoum S. & Medzhitov R., 2009. Toll-like receptors and cancer. Nat Revs Cancer 9:57-63.)

TLRs are type I transmembrane proteins characterized by an extracellular domain containing leucine-rich repeats (LRRs) and a cytoplasmic tail that contains a conserved region called the Toll/IL-1 receptor (TIR) domain. Ten human and twelve murine TLRs have been characterized, TLR1 to TLR10 in humans, and TLR1 to TLR9, TLR11, TLR12 and TLR13 in mice, the homolog of TLR10 being a pseudogene. TLR2 is essential for the recognition of a variety of PAMPs from Gram-positive bacteria, including bacterial lipoproteins, lipomannans and lipoteichoic acids. TLR3 is implicated in virus-derived double-stranded RNA. TLR4 is predominantly activated by lipopolysaccharide. TLR5 detects bacterial flagellin and TLR9 is required for response to unmethylated CpG DNA. Finally, TLR7 and TLR8 recognize small synthetic antiviral molecules, and single-stranded RNA was reported to be their natural ligand. TLR11 has been reported to recognize uropathogenic E. coli and a profilin-like protein from Toxoplasma gondii. The repertoire of specificities of the TLRs is apparently extended by the ability of TLRs to heterodimerize with one another. For example, dimers of TLR2 and TLR6 are required for responses to diacylated lipoproteins while TLR2 and TLR1 interact to recognize triacylated lipoproteins. Specificities of the TLRs are also influenced by various adapter and accessory molecules, such as MD-2 and CD14 that form a complex with TLR4 in response to LPS.

TLR signaling consists of at least two distinct pathways: a MyD88-dependent pathway that leads to the production of inflammatory cytokines, and a MyD88-independent pathway associated with the stimulation of IFN-β and the maturation of dendritic cells. The MyD88-dependent pathway is common to all TLRs, except TLR3 (Adachi O. et al., 1998. Targeted disruption of the MyD88 gene results in loss of IL-1- and IL-18-mediated function. Immunity. 9(1):143-50). Upon activation by PAMPs or DAMPs, TLRs hetero- or homodimerize inducing the recruitment of adaptor proteins via the cytoplasmic TTR domain. Individual TLRs induce different signaling responses by usage of the different adaptor molecules. TLR4 and TLR2 signaling requires the adaptor TIRAP/Mal, which is involved in the MyD88-dependent pathway. TLR3 triggers the production of IFN-β in response to double-stranded RNA, in a MyD88-independent manner, through the adaptor TRIF/TICAM-1. TRAM/TICAM-2 is another adaptor molecule involved in the MyD88-independent pathway which function is restricted to the TLR4 pathway.

TLR3, TLR7, TLR8 and TLR9 recognize viral nucleic acids and induce type I IFNs. The signaling mechanisms leading to the induction of type I IFNs differ depending on the TLR activated. They involve the interferon regulatory factors, IRFs, a family of transcription factors known to play a critical role in antiviral defense, cell growth and immune regulation. Three IRFs (IRF3, IRF5 and IRF7) function as direct transducers of virus-mediated TLR signaling. TLR3 and TLR4 activate IRF3 and IRF7, while TLR7 and TLR8 activate IRF5 and IRF7 (Doyle S. et al., 2002. IRF3 mediates a TLR3/TLR4-specific antiviral gene program. Immunity. 17(3):251-63). Furthermore, type I IFN production stimulated by TLR9 ligand CpG-A has been shown to be mediated by PI(3)K and mTOR (Costa-Mattioli M. & Sonenberg N. 2008. RAPping production of type I interferon in pDCs through mTOR. Nature Immunol. 9: 1097-1099).

TLR-9

TLR9 recognizes unmethylated CpG sequences in DNA molecules. CpG sites are relatively rare (~1%) on vertebrate genomes in comparison to bacterial genomes or viral DNA. TLR9 is expressed by numerous cells of the immune system such as B lymphocytes, monocytes, natural killer (NK) cells, and plasmacytoid dendritic cells. TLR9 is expressed intracellularly, within the endosomal compartments and functions to alert the immune system of viral and bacterial infections by binding to DNA rich in CpG motifs. TLR9 signals leads to activation of the cells initiating pro-inflammatory reactions that result in the production of cytokines such as type-I interferon and IL-12.

TLR Agonists

A TLR agonist can agonize one or more TLR, e.g., one or more of human TLR-1, 2, 3, 4, 5, 6, 7, 8, 9, or 10. In some embodiments, an adjunctive agent described herein is a TLR agonist. In some embodiments, the TLR agonist specifically agonizes human TLR-9. In some embodiments, the TLR-9 agonist is a CpG moiety. As used herein, a CpG moiety, is a linear dinucleotide having the sequence: 5'-C-phosphate-G-3', that is, cytosine and guanine separated by only one phosphate.

In some embodiments, the CpG moiety comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more CpG dinucleotides. In some embodiments, the CpG moiety consists of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 CpG dinucleotides. In some embodiments, the CpG moiety has 1-5, 1-10, 1-20, 1-30, 1-40, 1-50, 5-10, 5-20, 5-30, 10-20, 10-30, 10-40, or 10-50 CpG dinucleotides.

In some embodiments, the TLR-9 agonist is a synthetic ODN (oligodeoxynucleotides). CpG ODNs are short synthetic single-stranded DNA molecules containing unmethylated CpG dinucleotides in particular sequence contexts (CpG motifs). CpG ODNs possess a partially or completely phosphorothioated (PS) backbone, as opposed to the natural phosphodiester (P0) backbone found in genomic bacterial DNA. There are three major classes of CpG ODNs: classes A, B and C, which differ in their immunostimulatory activities. CpG-A ODNs are characterized by a PO central CpG-containing palindromic motif and a PS-modified 3' poly-G string. They induce high IFN-α production from pDCs but are weak stimulators of TLR9-dependent NF-κB signaling and pro-inflammatory cytokine (e.g., IL-6) production. CpG-B ODNs contain a full PS backbone with one or more CpG dinucleotides. They strongly activate B cells and TLR9-dependent NF-κB signaling but weakly stimulate IFN-α secretion. CpG-C ODNs combine features of both classes A and B. They contain a complete PS backbone and a CpG-containing palindromic motif. C-Class CpG ODNs induce strong IFN-α production from pDC as well as B cell stimulation.

Exemplary Multispecific Antibody Molecules

Exemplary kappa and lambda multispecific antibody molecules are provided in Tables 17 and 18.

TABLE 17

Exemplary amino acid sequences of antibodies

| Target | Antibody | Heavy Chain Variable Domain Sequence | Light Chain Variable Domain Sequence |
| --- | --- | --- | --- |
| Rabphilin 3A | Ab237 | SEQ ID NO: 401 QVQLQESGPGLVKPSQTLSLTCT | SEQ ID NO 402: DIQMTQSPSSLSASVGDRVTI |

TABLE 17-continued

Exemplary amino acid sequences of antibodies

| Target | Antibody | Heavy Chain Variable Domain Sequence | Light Chain Variable Domain Sequence |
|---|---|---|---|
| | | VSGGSINNNNYYWTWIRQHPGK GLEWIGYIYYSGSTFYNPSLKSR VTISVDTSKTQFSLKLSSVTAAD TAVYYCAREDTMTGLDVWGQG TTVTVSS | TCRASQSINNYLNWYQQKPG KAPTLLIYAASSLQSGVPSRFS GSRSGTDFTLTISSLQPEDFAA YFCQQTYSNPTFGQGTKVEV K |
| PD-L1 | Avelumab | SEQ ID NO 403: EVQLLESGGGLVQPGGSLRLSC AASGFTFSSYIMMWVRQAPGKG LEWVSSIYPSGGITFYADTVKGR FTISRDNSKNTLYLQMNSLRAED TAVYYCARIKLGTVTTVDYWG QGTLVTVSS | SEQ ID NO 404: QSALTQPASVSGSPGQSITISC TGTSSDVGGYNYVSWYQQH PGKAPKLMIYDVSNRPSGVS NRFSGSKSGNTASLTISGLQA EDEADYYCSSYTSSSTRVFGT GTKVTVL |
| CTLA-4 | Ipilumumab | SEQ ID NO 405: QVQLVESGGGVVQPGRSLRLSC AASGFTFSSYTMHWVRQAPGK GLEWVTFISYDGNNKYYADSVK GRFTISRDNSKNTLYLQMNSLR AEDTAIYYCARTGWLGPFDYW GQGTLVTVSS | SEQ ID NO 406: EIVLTQSPGTLSLSPGERATLS CRASQSVGSSYLAWYQQKPG QAPRLLIYGAFSRATGIPDRFS GSGSGTDFTLTISRLEPEDFAV YYCQQYGSSPWTFGQGTKVE IK |
| IL-12/23 | Briakinumab | SEQ ID NO 407: QVQLVESGGGVVQPGRSLRLSC AASGFTFSSYGMHWVRQAPGK GLEWVAFIRYDGSNKYYADSVK GRFTISRDNSKNTLYLQMNSLR AEDTAVYYCKTHGSHDNWGQG TMVTVSS | SEQ ID NO 408: QSVLTQPPSVSGAPGQRVTIS CSGSRSNIGSNTVKWYQQLP GTAPKLLIYYNDQRPSGVPDR FSGSKSGTSASLAITGLQAED EADYYCQSYDRYTHPALLFG TGTKVTVL |
| PD-1 | Nivolumab | SEQ ID NO 409: QVQLVESGGGVVQPGRSLRLDC KASGITFSNSGMHWVRQAPGKG LEWVAVIWYDGSKRYYADSVK GRFTISRDNSKNTLFLQMNSLRA EDTAVYYCATNDDYWGQGTLV TVSS | SEQ ID NO 410: EIVLTQSPATLSLSPGERATLS CRASQSVSSYLAWYQQKPGQ APRLLIYDASNRATGIPARFS GSGSGTDFTLTISSLEPEDFAV YYCQQSSNWPRTFGQGTKVE IK |
| TRAIL-R2 | Lexatumumab | SEQ ID NO 411: EVQLVQSGGGVERPGGSLRLSC AASGFTFDDYGMSWVRQAPGK GLEWVSGINWNGGSTGYADSV KGRVTISRDNAKNSLYLQMNSL RAEDTAVYYCAKILGAGRGWY FDLWGKGTTVTVSS | SEQ ID NO 412: SSELTQDPAVSVALGQTVRIT CQGDSLRSYYASWYQQKPG QAPVLVIYGKNNRPSGIPDRF SGSSSGNTASLTITGAQAEDE ADYYCNSRDSSGNHVVFGGG TKLTVL |
| CD20 | Ofatumumab | SEQ ID NO 413: EVQLVESGGGLVQPGRSLRLSC AASGFTFNDYAMHWVRQAPGK GLEWVSTISWNSGSIGYADSVK GRFTISRDNAKKSLYLQMNSLR AEDTALYYCAKDIQYGNYYYG MDVWGQGTTVTVSS | SEQ ID NO 414: EIVLTQSPATLSLSPGERATLS CRASQSVSSYLAWYQQKPGQ APRLLIYDASNRATGIPARFS GSGSGTDFTLTISSLEPEDFAV YYCQQRSNWPITFGQGTRLEI K |
| IGF-1R | Cixutumumab | SEQ ID NO 415: EVQLVQSGAEVKKPGSSVKVSC KASGGTFSSYAISWVRQAPGQG LEWMGGIIPIFGTANYAQKFQGR VTITADKSTSTAYMELSSLRSED TAVYYCARAPLRFLEWSTQDHY YYYYMDVWGKGTTVTVSS | SEQ ID NO 416: SSELTQDPAVSVALGQTVRIT CQGDSLRSYYATWYQQKPG QAPILVIYGENKRPSGIPDRFS GSSSGNTASLTITGAQAEDEA DYYCKSRDGSGQHLVFGGGT KLTVL |
| Mesothelin | m912 | SEQ ID NO: 417 QVQLQESGPGLVKPSETLSLTCT VSGGSVSSGSYYWSWIRQPPGK GLEWIGYIYYSGSTNYNPSLKSR VTISVDTSKNQFSLKLSSVTAAD TAVYYCAREGKNGAFDIWGQG TMVTVSS | SEQ ID NO: 418 DIQMTQSPSSLSASVGDRVTI TCRASQSISSYLNWYQQKPG KAPKLLIYAASSLQSGVPSGF SGSGSGTDFTLTISSLQPEDFA TYYCQQSYSTPLTFGGGTKV EIK |

TABLE 18

Exemplary pairings of kappa and lambda antibodies

| Kappa Antibodies | Lambda Antibodies | | | |
|---|---|---|---|---|
| | Avelumab | Briakinumab | Lexatumumab | Cixutumumab |
| Ab237 | SEQ ID NO: 401, SEQ ID NO: 402, SEQ ID NO: 403, SEQ ID NO: 404 | SEQ ID NO: 401, SEQ ID NO: 402, SEQ ID NO: 407, SEQ ID NO: 408 | SEQ ID NO: 401, SEQ ID NO: 402, SEQ ID NO: 411, SEQ ID NO: 412 | SEQ ID NO: 401, SEQ ID NO: 402, SEQ ID NO: 415, SEQ ID NO: 416 |
| Ipilumumab | SEQ ID NO: 405, SEQ ID NO: 406, SEQ ID NO: 403, SEQ ID NO: 404 | SEQ ID NO: 405, SEQ ID NO: 406, SEQ ID NO: 407, SEQ ID NO: 408 | SEQ ID NO: 405, SEQ ID NO: 406, SEQ ID NO: 411, SEQ ID NO: 412 | SEQ ID NO: 405, SEQ ID NO: 406, SEQ ID NO: 415, SEQ ID NO: 416 |
| Nivolumab | SEQ ID NO: 409, SEQ ID NO: 410, SEQ ID NO: 403, SEQ ID NO: 404 | SEQ ID NO: 409, SEQ ID NO: 410, SEQ ID NO: 407, SEQ ID NO: 408 | SEQ ID NO: 409, SEQ ID NO: 410, SEQ ID NO: 411, SEQ ID NO: 412 | SEQ ID NO: 409, SEQ ID NO: 410, SEQ ID NO: 415, SEQ ID NO: 416 |
| Ofatumumab | SEQ ID NO: 413, SEQ ID NO: 414, SEQ ID NO: 403, SEQ ID NO: 404 | SEQ ID NO: 413, SEQ ID NO: 414, SEQ ID NO: 407, SEQ ID NO: 408 | SEQ ID NO: 413, SEQ ID NO: 414, SEQ ID NO: 411, SEQ ID NO: 412 | SEQ ID NO: 413, SEQ ID NO: 414, SEQ ID NO: 415, SEQ ID NO: 416 |
| m912 | SEQ ID NO: 417, SEQ ID NO: 418, SEQ ID NO: 403, SEQ ID NO: 404 | SEQ ID NO: 417, SEQ ID NO: 418, SEQ ID NO: 407, SEQ ID NO: 408 | SEQ ID NO: 417, SEQ ID NO: 418, SEQ ID NO: 411, SEQ ID NO: 412 | SEQ ID NO: 417, SEQ ID NO: 418, SEQ ID NO: 415, SEQ ID NO: 416 |

Nucleic Acids

The invention also features nucleic acids comprising nucleotide sequences that encode heavy and light chain variable regions and CDRs or hypervariable loops of the antibody molecules, as described herein. For example, the invention features a first and second nucleic acid encoding heavy and light chain variable regions, respectively, of an antibody molecule chosen from one or more of the antibody molecules disclosed herein. The nucleic acid can comprise a nucleotide sequence as set forth in the tables herein, or a sequence substantially identical thereto (e.g., a sequence at least about 85%, 90%, 95%, 99% or more identical thereto, or which differs by no more than 3, 6, 15, 30, or 45 nucleotides from the sequences shown in the tables herein.

In certain embodiments, the nucleic acid can comprise a nucleotide sequence encoding at least one, two, or three CDRs or hypervariable loops from a heavy chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In other embodiments, the nucleic acid can comprise a nucleotide sequence encoding at least one, two, or three CDRs or hypervariable loops from a light chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In yet another embodiment, the nucleic acid can comprise a nucleotide sequence encoding at least one, two, three, four, five, or six CDRs or hypervariable loops from heavy and light chain variable regions having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions).

In certain embodiments, the nucleic acid can comprise a nucleotide sequence encoding at least one, two, or three CDRs or hypervariable loops from a heavy chain variable region having the nucleotide sequence as set forth in the tables herein, a sequence substantially homologous thereto (e.g., a sequence at least about 85%, 90%, 95%, 99% or more identical thereto, and/or capable of hybridizing under the stringency conditions described herein). In another embodiment, the nucleic acid can comprise a nucleotide sequence encoding at least one, two, or three CDRs or hypervariable loops from a light chain variable region having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein). In yet another embodiment, the nucleic acid can comprise a nucleotide sequence encoding at least one, two, three, four, five, or six CDRs or hypervariable loops from heavy and light chain variable regions having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein).

In another aspect, the application features host cells and vectors containing the nucleic acids described herein. The nucleic acids may be present in a single vector or separate vectors present in the same host cell or separate host cell, as described in more detail hereinbelow.

Vectors

Further provided herein are vectors comprising the nucleotide sequences encoding an antibody molecule described herein. In one embodiment, the vectors comprise nucleotides encoding an antibody molecule described herein. In one embodiment, the vectors comprise the nucleotide sequences described herein. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity.

Methods and conditions for culturing the resulting transfected cells and for recovering the antibody molecule produced are known to those skilled in the art, and may be varied or optimized depending upon the specific expression vector and mammalian host cell employed, based upon the present description.

Cells

In another aspect, the application features host cells and vectors containing the nucleic acids described herein. The nucleic acids may be present in a single vector or separate vectors present in the same host cell or separate host cell. The host cell can be a eukaryotic cell, e.g., a mammalian cell, an insect cell, a yeast cell, or a prokaryotic cell, e.g., *E. coli*. For example, the mammalian cell can be a cultured cell or a cell line. Exemplary mammalian cells include lymphocytic cell lines (e.g., NSO), Chinese hamster ovary cells (CHO), COS cells, oocyte cells, and cells from a transgenic animal, e.g., mammary epithelial cell.

The invention also provides host cells comprising a nucleic acid encoding an antibody molecule as described herein.

In one embodiment, the host cells are genetically engineered to comprise nucleic acids encoding the antibody molecule.

In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The invention also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and VIDCKII cells. Suitable insect cells include, but are not limited to, Sf9 cells.

Methods of Making the Multispecific Molecules

The multispecific antibody molecules can be produced by recombinant expression, e.g., of at least one or more component, in a host system. Exemplary host systems include eukaryotic cells (e.g., mammalian cells, e.g., CHO cells, or insect cells, e.g., SF9 or S2 cells) and prokaryotic cells (e.g., *E. coli*). In one embodiment, the host cell is a mammalian cell, a stable mammalian cell, e.g., a CHO cell. Bispecific antibody molecules can be produced by separate expression of the components in different host cells and subsequent purification/assembly. Alternatively, the antibody molecules can be produced by expression of the components in a single host cell. Purification of bispecific antibody molecules can be performed by various methods such as affinity chromatography, e.g., using protein A and sequential pH elution. In other embodiments, affinity tags can be used for purification, e.g., histidine-containing tag, myc tag, or streptavidin tag.

In some embodiments, a method for generating bispecific antibodies disclosed herein comprises: generating a human antibody with a light chain of a lambda subtype; generating a human antibody with a light chain of kappa subtype; transfecting cells with DNA of both antibody arms; purifying the antibody with Protein A resin; confirming the presence of both lambda and kappa light chains with KappaSelect and LambdaFabSelect resin; analyzing the correct lambda and kappa heavy and light chain pairing by cleaving Fab arms with papain and running mass spectrometry. Experimental conditions for making and testing the multispecific molecules are provided in the Examples below.

Uses and Combination Therapies

Methods described herein include treating a cancer in a subject by using a multispecific molecule described herein, e.g., using a pharmaceutical composition described herein. Also provided are methods for reducing or ameliorating a symptom of a cancer in a subject, as well as methods for inhibiting the growth of a cancer and/or killing one or more cancer cells. In embodiments, the methods described herein decrease the size of a tumor and/or decrease the number of cancer cells in a subject administered with a described herein or a pharmaceutical composition described herein.

In embodiments, the cancer is a hematological cancer. In embodiments, the hematological cancer is a leukemia or a lymphoma. As used herein, a "hematologic cancer" refers to a tumor of the hematopoietic or lymphoid tissues, e.g., a tumor that affects blood, bone marrow, or lymph nodes. Exemplary hematologic malignancies include, but are not limited to, leukemia (e.g., acute lymphoblastic leukemia (ALL), acute myeloid leukemia (AML), chronic lymphocytic leukemia (CLL), chronic myelogenous leukemia (CML), hairy cell leukemia, acute monocytic leukemia (AMoL), chronic myelomonocytic leukemia (CMML), juvenile myelomonocytic leukemia (JMML), or large granular lymphocytic leukemia), lymphoma (e.g., AIDS-related lymphoma, cutaneous T-cell lymphoma, Hodgkin lymphoma (e.g., classical Hodgkin lymphoma or nodular lymphocyte-predominant Hodgkin lymphoma), mycosis fungoides, non-Hodgkin lymphoma (e.g., B-cell non-Hodgkin lymphoma (e.g., Burkitt lymphoma, small lymphocytic lymphoma (CLL/SLL), diffuse large B-cell lymphoma, follicular lymphoma, immunoblastic large cell lymphoma, precursor B-lymphoblastic lymphoma, or mantle cell lymphoma) or T-cell non-Hodgkin lymphoma (mycosis fungoides, anaplastic large cell lymphoma, or precursor T-lymphoblastic lymphoma)), primary central nervous system lymphoma, Sezary syndrome, Waldenstrom macroglobulinemia), chronic myeloproliferative neoplasm, Langerhans cell histiocytosis, multiple myeloma/plasma cell neoplasm, myelodysplastic syndrome, or myelodysplastic/myeloproliferative neoplasm.

In embodiments, the cancer is a solid cancer. Exemplary solid cancers include, but are not limited to, ovarian cancer, rectal cancer, stomach cancer, testicular cancer, cancer of the anal region, uterine cancer, colon cancer, rectal cancer, renal-cell carcinoma, liver cancer, non-small cell carcinoma of the lung, cancer of the small intestine, cancer of the esophagus, melanoma, Kaposi's sarcoma, cancer of the endocrine system, cancer of the thyroid gland, cancer of the parathyroid gland, cancer of the adrenal gland, bone cancer, pancreatic cancer, skin cancer, cancer of the head or neck, cutaneous or intraocular malignant melanoma, uterine cancer, brain stem glioma, pituitary adenoma, epidermoid cancer, carcinoma of the cervix squamous cell cancer, carcinoma of the fallopian tubes, carcinoma of the endometrium, carcinoma of the vagina, sarcoma of soft tissue, cancer of the urethra, carcinoma of the vulva, cancer of the penis, cancer of the bladder, cancer of the kidney or ureter, carcinoma of the renal pelvis, spinal axis tumor, neoplasm of the central nervous system (CNS), primary CNS lymphoma, tumor angiogenesis, metastatic lesions of said cancers, or combinations thereof.

In embodiments, the multispecific molecules (or pharmaceutical composition) are administered in a manner appropriate to the disease to be treated or prevented. The quantity and frequency of administration will be determined by such factors as the condition of the patient, and the type and severity of the patient's disease. Appropriate dosages may be determined by clinical trials. For example, when "an effective amount" or "a therapeutic amount" is indicated, the precise amount of the pharmaceutical composition (or multispecific molecules) to be administered can be determined by a physician with consideration of individual differences in tumor size, extent of infection or metastasis, age, weight, and condition of the subject. In embodiments, the pharmaceutical composition described herein can be administered at a dosage of $10^4$ to $10^9$ cells/kg body weight, e.g., $10^5$ to $10^6$ cells/kg body weight, including all integer values within those ranges. In embodiments, the pharmaceutical composition described herein can be administered multiple times at these dosages. In embodiments, the pharmaceutical composition described herein can be administered using infusion techniques described in immunotherapy (see, e.g., Rosenberg et al., New Eng. J. of Med. 319:1676, 1988).

In embodiments, the multispecific molecules or pharmaceutical composition is administered to the subject parenterally. In embodiments, the cells are administered to the subject intravenously, subcutaneously, intratumorally, intranodally, intramuscularly, intradermally, or intraperitoneally. In embodiments, the cells are administered, e.g., injected, directly into a tumor or lymph node. In embodiments, the cells are administered as an infusion (e.g., as described in Rosenberg et al., New Eng. J. of Med. 319: 1676, 1988) or an intravenous push. In embodiments, the cells are administered as an injectable depot formulation.

In embodiments, the subject is a mammal. In embodiments, the subject is a human, monkey, pig, dog, cat, cow, sheep, goat, rabbit, rat, or mouse. In embodiments, the subject is a human. In embodiments, the subject is a pediatric subject, e.g., less than 18 years of age, e.g., less than 17, 16, 15, 14, 13, 12, 11, 10, 9, 8, 7, 6, 5, 4, 3, 2, 1 or less years of age. In embodiments, the subject is an adult, e.g., at least 18 years of age, e.g., at least 19, 20, 21, 22, 23, 24, 25, 25-30, 30-35, 35-40, 40-50, 50-60, 60-70, 70-80, or 80-90 years of age.

Combination Therapies

The multispecific molecules disclosed herein can be used in combination with a second therapeutic agent or procedure.

In embodiments, the multispecific molecule and the second therapeutic agent or procedure are administered/performed after a subject has been diagnosed with a cancer, e.g., before the cancer has been eliminated from the subject. In embodiments, the multispecific molecule and the second therapeutic agent or procedure are administered/performed simultaneously or concurrently. For example, the delivery of one treatment is still occurring when the delivery of the second commences, e.g., there is an overlap in administration of the treatments. In other embodiments, the multispecific molecule and the second therapeutic agent or procedure are administered/performed sequentially. For example, the delivery of one treatment ceases before the delivery of the other treatment begins.

In embodiments, combination therapy can lead to more effective treatment than monotherapy with either agent alone. In embodiments, the combination of the first and second treatment is more effective (e.g., leads to a greater reduction in symptoms and/or cancer cells) than the first or second treatment alone. In embodiments, the combination therapy permits use of a lower dose of the first or the second treatment compared to the dose of the first or second treatment normally required to achieve similar effects when administered as a monotherapy. In embodiments, the combination therapy has a partially additive effect, wholly additive effect, or greater than additive effect.

In one embodiment, the multispecific molecule is administered in combination with a therapy, e.g., a cancer therapy (e.g., one or more of anti-cancer agents, immunotherapy, photodynamic therapy (PDT), surgery and/or radiation). The terms "chemotherapeutic," "chemotherapeutic agent," and "anti-cancer agent" are used interchangeably herein. The administration of the multispecific molecule and the therapy, e.g., the cancer therapy, can be sequential (with or without overlap) or simultaneous. Administration of the multispecific molecule can be continuous or intermittent during the course of therapy (e.g., cancer therapy). Certain therapies described herein can be used to treat cancers and non-cancerous diseases. For example, PDT efficacy can be enhanced in cancerous and non-cancerous conditions (e.g., tuberculosis) using the methods and compositions described herein (reviewed in, e.g., Agostinis, P. et al. (2011) *CA Cancer J. Clin.* 61:250-281).

Anti-Cancer Therapies

In other embodiments, the multispecific molecule is administered in combination with a low or small molecular weight chemotherapeutic agent. Exemplary low or small molecular weight chemotherapeutic agents include, but not limited to, 13-cis-retinoic acid (isotretinoin, ACCUTANE®), 2-CdA (2-chlorodeoxyadenosine, cladribine, LEUSTATIN™), 5-azacitidine (azacitidine, VIDAZA®), 5-fluorouracil (5-FU, fluorouracil, ADRUCIL®), 6-mercaptopurine (6-MP, mercaptopurine, PURINETHOL®), 6-TG (6-thioguanine, thioguanine, THIOGUANINE TABLOID®), abraxane (paclitaxel protein-bound), actinomycin-D (dactinomycin, COSMEGEN®), alitretinoin (PANRETIN®), all-transretinoic acid (ATRA, tretinoin, VESANOID®), altretamine (hexamethylmelamine, HMM, HEXALEN®), amethopterin (methotrexate, methotrexate sodium, MTX, TREXALL™, RHEUMATREX®), amifostine (ETHYOL®), arabinosylcytosine (Ara-C, cytarabine, CYTOSAR-U®), arsenic trioxide (TRISENOX®), asparaginase (*Erwinia* L-asparaginase, L-asparaginase, ELSPAR®, KIDROLASE®), BCNU (carmustine, BiCNU®), bendamustine (TREANDA®), bexarotene (TARGRETIN®), bleomycin (BLENOXANE®), busulfan (BUSULFEX®, MYLERAN®), calcium leucovorin (Citrovorum Factor, folinic acid, leucovorin), camptothecin-11 (CPT-11, irinotecan, CAMPTOSAR®), capecitabine (XELODA®), carboplatin (PARAPLATIN®), carmustine wafer (prolifeprospan 20 with carmustine implant, GLIADEL® wafer), CCI-779 (temsirolimus, TORISEL®), CCNU (lomustine, CeeNU), CDDP (cisplatin, PLATINOL®, PLATINOL-AQ®), chlorambucil (leukeran), cyclophosphamide (CYTOXAN®, NEOSAR®), dacarbazine (DIC, DTIC, imidazole carboxamide, DTIC-DOME®), daunomycin (daunorubicin, daunorubicin hydrochloride, rubidomycin hydrochloride, CERUBIDINE®), decitabine (DACOGEN®), dexrazoxane (ZINECARD®), DHAD (mitoxantrone, NOVANTRONE®), docetaxel (TAXOTERE®), doxorubicin (ADRIAMYCIN®, RUBEX®), epirubicin (ELLENCE™), estramustine (EMCYT®), etoposide (VP-16, etoposide phosphate, TOPOSAR®, VEPESID®, ETOPOPHOS®), floxuridine (FUDR®), fludarabine (FLUDARA®), fluorouracil (cream) (CARAC™, EFUDEX®, FLUOROPLEX®), gemcitabine (GEMZAR®), hydroxyurea (HYDREA®, DROXIA™, MYLOCEL™), idarubicin (IDAMYCIN®), ifosfamide (IFEX®), ixabepilone (IXEMPRA™), LCR (leurocristine, vincristine, VCR, ONCOVIN®, VINCASAR PFS®), L-PAM (L-sarcolysin, melphalan, phenylalanine mustard, ALKERAN®), mechlorethamine (mechlorethamine hydrochloride, mustine, nitrogen mustard, MUSTARGEN®), mesna (MESNEX™), mitomycin (mitomycin-C, MTC, MUTAMYCIN®), nelarabine (ARRANON®), oxaliplatin (ELOXATIN™), paclitaxel (TAXOL®, ONXAL™), pegaspargase (PEG-L-asparaginase, ONCOSPAR®), PEMETREXED (ALIMTA®), pentostatin (NIPENT®), procarbazine (MATULANE®), streptozocin (ZANOSAR®), temozolomide (TEMODAR®), teniposide (VM-26, VUMON®), TESPA (thiophosphoamide, thiotepa, TSPA, THIOPLEX®), topotecan (HYCAMTIN®), vinblastine (vinblastine sulfate, vincaleukoblastine, VLB, ALKABAN-AQ®, VELBAN®), vinorelbine (vinorelbine tartrate, NAVELBINE®), and vorinostat (ZOLINZA®).

In another embodiment, the multispecific molecule is administered in conjunction with a biologic. Biologics useful in the treatment of cancers are known in the art and a binding molecule of the invention may be administered, for example, in conjunction with such known biologics. For example, the FDA has approved the following biologics for the treatment of breast cancer: HERCEPTIN® (trastuzumab, Genentech Inc., South San Francisco, Calif.; a humanized monoclonal antibody that has anti-tumor activity in HER2-positive breast cancer); FASLODEX® (fulvestrant, AstraZeneca Pharmaceuticals, LP, Wilmington, Del.; an estrogen-receptor antagonist used to treat breast cancer); ARIMIDEX® (anastrozole, AstraZeneca Pharmaceuticals, LP; a nonsteroidal aromatase inhibitor which blocks aromatase, an enzyme needed to make estrogen); Aromasin® (exemestane, Pfizer Inc., New York, N.Y.; an irreversible, steroidal aromatase inactivator used in the treatment of breast cancer); FEMARA® (letrozole, Novartis Pharmaceuticals, East Hanover, N.J.; a nonsteroidal aromatase inhibitor approved by the FDA to treat breast cancer); and NOLVADEX® (tamoxifen, AstraZeneca Pharmaceuticals, LP; a nonsteroidal antiestrogen approved by the FDA to treat breast cancer). Other biologics with which the binding molecules of the invention may be combined include: AVASTIN® (bevacizumab, Genentech Inc.; the first FDA-approved therapy designed to inhibit angiogenesis); and ZEVALIN® (ibritumomab tiuxetan, Biogen Idec, Cambridge, Mass.; a radiolabeled monoclonal antibody currently approved for the treatment of B-cell lymphomas).

In addition, the FDA has approved the following biologics for the treatment of colorectal cancer: AVASTIN®; ERBITUX® (cetuximab, ImClone Systems Inc., New York, N.Y., and Bristol-Myers Squibb, New York, N.Y.; is a monoclonal antibody directed against the epidermal growth factor receptor (EGFR)); GLEEVEC® (imatinib mesylate; a protein kinase inhibitor); and ERGAMISOL® (levamisole hydrochloride, Janssen Pharmaceutica Products, LP, Titusville, N.J.; an immunomodulator approved by the FDA in 1990 as an adjuvant treatment in combination with 5-fluorouracil after surgical resection in patients with Dukes' Stage C colon cancer).

For the treatment of lung cancer, exemplary biologics include TARCEVA® (erlotinib HCL, OSI Pharmaceuticals Inc., Melville, N.Y.; a small molecule designed to target the human epidermal growth factor receptor 1 (HER1) pathway).

For the treatment of multiple myeloma, exemplary biologics include VELCADE® Velcade (bortezomib, Millennium Pharmaceuticals, Cambridge Mass.; a proteasome inhibitor). Additional biologics include THALIDOMID® (thalidomide, Clegene Corporation, Warren, N.J.; an immunomodulatory agent and appears to have multiple actions, including the ability to inhibit the growth and survival of myeloma cells and anti-angiogenesis).

Additional exemplary cancer therapeutic antibodies include, but are not limited to, 3F8, abagovomab, adecatumumab, afutuzumab, alacizumab pegol, alemtuzumab (CAMPATH®, MABCAMPATH®), altumomab pentetate (HYBRI-CEAKER®), anatumomab mafenatox, anrukinzumab (IMA-638), apolizumab, arcitumomab (CEA-SCAN®), bavituximab, bectumomab (LYMPHOSCAN®), belimumab (BENLYSTA®, LYMPHOSTAT-B®), besilesomab (SCINTIMUN®), bevacizumab (AVASTIN®), bivatuzumab mertansine, blinatumomab, brentuximab vedotin, cantuzumab mertansine, capromab pendetide (PROSTASCINT®), catumaxomab (REMOVAB®), CC49, cetuximab (C225, ERBITUX®), citatuzumab bogatox, cixutumumab, clivatuzumab tetraxetan, conatumumab, dacetuzumab, denosumab (PROLIA®), detumomab, ecromeximab, edrecolomab (PANOREX®), elotuzumab, epitumomab cituxetan, epratuzumab, ertumaxomab (REXOMUN®), etaracizumab, farletuzumab, figitumumab, fresolimumab, galiximab, gemtuzumab ozogamicin (MYLOTARG®), girentuximab, glembatumumab vedotin, ibritumomab (ibritumomab tiuxetan, ZEVALIN®), igovomab (INDIMACIS-125®), intetumumab, inotuzumab ozogamicin, ipilimumab, iratumumab, labetuzumab (CEA-CIDE®), lexatumumab, lintuzumab, lucatumumab, lumiliximab, mapatumumab, matuzumab, milatuzumab, minretumomab, mitumomab, nacolomab tafenatox, naptumomab estafenatox, necitumumab, nimotuzumab (THERACIM®, THERALOC®), nofetumomab merpentan (VERLUMA®), ofatumumab (ARZERRA®), olaratumab, oportuzumab monatox, oregovomab (OVAREX®), panitumumab (VECTIBIX®), pemtumomab (THERAGYN®), pertuzumab (OMNITARG®), pintumomab, pritumumab, ramucirumab, ranibizumab (LUCENTIS®), rilotumumab, rituximab (MABTHERA®, RITUXAN®), robatumumab, satumomab pendetide, sibrotuzumab, siltuximab, sontuzumab, tacatuzumab tetraxetan (AFP-CIDE®), taplitumomab paptox, tenatumomab, TGN1412, ticilimumab (tremelimumab), tigatuzumab, TNX-650, tositumomab (BEXXAR®), trastuzumab (HERCEPTIN®), tremelimumab, tucotuzumab celmoleukin, veltuzumab, volociximab, votumumab (HUMASPECT®), zalutumumab (HUMAX-EGFR®), and zanolimumab (HUMAX-CD4®).

In other embodiments, the multispecific molecule is administered in combination with a viral cancer therapeutic agent. Exemplary viral cancer therapeutic agents include, but not limited to, vaccinia virus (vvDD-CDSR), carcinoembryonic antigen-expressing measles virus, recombinant vaccinia virus (TK-deletion plus GM-CSF), Seneca Valley virus-001, Newcastle virus, coxsackie virus A21, GL-ONC1, EBNA1 C-terminal/LMP2 chimeric protein-expressing recombinant modified vaccinia Ankara vaccine, carcinoembryonic antigen-expressing measles virus, G207 oncolytic virus, modified vaccinia virus Ankara vaccine expressing p53, OncoVEX GM-CSF modified herpes-simplex 1 virus, fowlpox virus vaccine vector, recombinant vaccinia prostate-specific antigen vaccine, human papillomavirus 16/18 L1 virus-like particle/AS04 vaccine, MVA-EBNA1/LMP2 Inj. vaccine, quadrivalent HPV vaccine, quadrivalent human papillomavirus (types 6, 11, 16, 18) recombinant vaccine (GARDASTL®), recombinant fowlpox-CEA(6D)/TRICOM vaccine; recombinant vaccinia-CEA(6D)-TRICOM vaccine, recombinant modified vaccinia Ankara-5T4 vaccine, recombinant fowlpox-TRICOM vaccine, oncolytic herpes virus NV1020, HPV L1 VLP vaccine V504, human papillomavirus bivalent (types 16 and 18) vaccine (CERVARIX®), herpes simplex virus HF10, Ad5CMV-p53 gene, recombinant vaccinia DF3/MUC1 vaccine, recombinant vaccinia-MUC-1 vaccine, recombinant vaccinia-TRICOM vaccine, ALVAC MART-1 vaccine, replication-defective herpes simplex virus type I (HSV-1) vector expressing human Preproenkephalin (NP2), wild-type reovirus, reovirus type 3 Dearing (REOLYSIN®), oncolytic virus HSV1716, recombinant modified vaccinia Ankara (MVA)-based vaccine encoding Epstein-Barr virus target antigens, recombinant fowlpox-prostate specific antigen vaccine, recombinant vaccinia prostate-specific antigen vaccine, recombinant vaccinia-B7.1 vaccine, rAd-p53 gene, Ad5-delta24RGD, HPV vaccine 580299, JX-594 (thymidine kinase-deleted vaccinia virus plus GM-CSF), HPV-16/18 L1/AS04, fowlpox virus vaccine vector, vaccinia-tyrosinase vaccine, MEDI-517 HPV-16/18 VLP AS04 vaccine, adenoviral vector containing the thymidine kinase of herpes simplex virus TK99UN, HspE7, FP253/Fludarabine, ALVAC(2) melanoma multi-antigen therapeutic vaccine, ALVAC-hB7.1, canarypox-hIL-12 melanoma vaccine, Ad-REIC/Dkk-3, rAd-IFN SCH 721015, TIL-Ad-INFg, Ad-ISF35, and coxsackievirus A21 (CVA21, CAVATAK®).

In other embodiments, the multispecific molecule is administered in combination with a nanopharmaceutical. Exemplary cancer nanopharmaceuticals include, but not limited to, ABRAXANE® (paclitaxel bound albumin nanoparticles), CRLX101 (CPT conjugated to a linear cyclodextrin-based polymer), CRLX288 (conjugating docetaxel to the biodegradable polymer poly (lactic-co-glycolic acid)), cytarabine liposomal (liposomal Ara-C, DEPOCYT™) daunorubicin liposomal (DAUNOXOME®), doxorubicin liposomal (DOXIL®, CAELYX®), encapsulated-daunorubicin citrate liposome (DAUNOXOME®), and PEG anti-VEGF aptamer (MACUGEN®).

In some embodiments, the multispecific molecule is administered in combination with paclitaxel or a paclitaxel formulation, e.g., TAXOL®, protein-bound paclitaxel (e.g., ABRAXANE®). Exemplary paclitaxel formulations include, but are not limited to, nanoparticle albumin-bound paclitaxel (ABRAXANE®, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG105 (Angiopep-2 bound to three molecules of paclitaxel, marketed by ImmunoGen), paclitaxel-EC-1 (paclitaxel bound to the erbB2-recognizing peptide EC-1; see Li et al., *Biopolymers* (2007) 87:225-230), and glucose-conjugated paclitaxel (e.g., 2'-paclitaxel methyl 2-glucopyranosyl succinate, see Liu et al., *Bioorganic & Medicinal Chemistry Letters* (2007) 17:617-620).

Exemplary RNAi and antisense RNA agents for treating cancer include, but not limited to, CALAA-01, siG12D LODER (Local Drug EluteR), and ALN-VSP02.

Other cancer therapeutic agents include, but not limited to, cytokines (e.g., aldesleukin (IL-2, Interleukin-2, PROLEUKIN®), alpha Interferon (IFN-alpha, Interferon alfa, INTRON® A (Interferon alfa-2b), ROFERON-A® (Interferon alfa-2a)), Epoetin alfa (PROCRIT®), filgrastim (G-CSF, Granulocyte—Colony Stimulating Factor, NEUPOGEN®), GM-CSF (Granulocyte Macrophage Colony Stimulating Factor, sargramostim, LEUKINE™) IL-11 (Interleukin-11, oprelvekin, NEUMEGA®), Interferon alfa-2b (PEG conjugate) (PEG interferon, PEG-INTRON™), and pegfilgrastim (NEULASTA™)), hormone therapy agents (e.g., aminoglutethimide (CYTADREN®), anastrozole (ARIMIDEX®), bicalutamide (CASODEX®), exemestane (AROMASIN®), fluoxymesterone (HALOTESTIN®), flutamide (EULEXIN®), fulvestrant (FASLODEX®), goserelin (ZOLADEX®), letrozole (FEMARA®), leuprolide (ELIGARD™, LUPRON®, LUPRON DEPOT®, VIADUR™), megestrol (megestrol acetate, MEGACE®), nilutamide (ANANDRON®, NILANDRON®), octreotide (octreotide acetate, SANDOSTATIN®, SANDOSTATIN LAR®), raloxifene (EVISTA®), romiplostim (NPLATE®), tamoxifen (NOVALDEX®), and toremifene (FARESTON®)), phospholipase A2 inhibitors (e.g., anagrelide (AGRYLIN®)), biologic response modifiers (e.g., BCG (THERACYS®, TICE®), and Darbepoetin alfa (ARANESP®)), target therapy agents (e.g., bortezomib (VELCADE®), dasatinib (SPRYCEL™), denileukin diftitox (ONTAK®), erlotinib (TARCEVA®), everolimus (AFINITOR®), gefitinib (IRESSA®), imatinib mesylate (STI-571, GLEEVEC™), lapatinib (TYKERB®), sorafenib (NEXAVAR®), and SU11248 (sunitinib, SUTENT®)), immunomodulatory and antiangiogenic agents (e.g., CC-5013 (lenalidomide, REVLIMID®), and thalidomide (THALOMID®)), glucocorticosteroids (e.g., cortisone (hydrocortisone, hydrocortisone sodium phosphate, hydrocortisone sodium succinate, ALA-CORT®, HYDROCORT ACETATE®, hydrocortone phosphate LANACORT®, SOLU-CORTEF®), decadron (dexamethasone, dexamethasone acetate, dexamethasone sodium phosphate, DEXASONE®, DIODEX®, HEXADROL®, MAXIDEX®), methylprednisolone (6-methylprednisolone, methylprednisolone acetate, methylprednisolone sodium succinate, DURALONE®, MEDRALONE®, MEDROL®, M-PREDNISOL®, SOLU-MEDROL®), prednisolone (DELTA-CORTEF®, ORAPRED®, PEDIAPRED®, PRELONE®), and prednisone (DELTASONE®, LIQUID PRED®, METI-CORTEN®, ORASONE®)), and bisphosphonates (e.g., pamidronate (AREDIA®), and zoledronic acid (ZOMETA®))

In some embodiments, the multispecific molecule is used in combination with a tyrosine kinase inhibitor (e.g., a receptor tyrosine kinase (RTK) inhibitor). Exemplary tyrosine kinase inhibitor include, but are not limited to, an epidermal growth factor (EGF) pathway inhibitor (e.g., an epidermal growth factor receptor (EGFR) inhibitor), a vascular endothelial growth factor (VEGF) pathway inhibitor (e.g., an antibody against VEGF, a VEGF trap, a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-8 inhibitor)), a RAF-1 inhibitor, a KIT inhibitor and a RET inhibitor. In some embodiments, the anti-cancer agent used in combination with the AHCM agent is selected from the group consisting of: axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), alemtuzumab (CAMPATH®), gemtuzumab ozogamicin (MYLOTARG®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, XL228, AEE788, AG-490, AST-6, BMS-599626, CUDC-101, PD153035, pelitinib (EKB-569), vandetanib (zactima), WZ3146, WZ4002, WZ8040, ABT-869 (linifanib), AEE788, AP24534 (ponatinib), AV-951 (tivozanib), axitinib, BAY 73-4506 (regorafenib), brivanib alaninate (BMS-582664), brivanib (BMS-540215), cediranib (AZD2171), CHIR-258 (dovitinib), CP 673451, CYC116, E7080, Ki8751, masitinib (AB1010), MGCD-265, motesanib diphosphate (AMG-706), MP-470, OSI-930, Pazopanib Hydrochloride, PD173074, nSorafenib Tosylate (Bay 43-9006), SU 5402, TSU-68 (SU6668), vatalanib, XL880 (GSK1363089, EXEL-2880). Selected tyrosine kinase inhibitors are chosen from sunitinib, erlotinib, gefitinib, or sorafenib. In one embodiment, the tyrosine kinase inhibitor is sunitinib.

In one embodiment, the multispecific molecule is administered in combination with one of more of: an anti-angiogenic agent, or a vascular targeting agent or a vascular disrupting agent. Exemplary anti-angiogenic agents include, but are not limited to, VEGF inhibitors (e.g., anti-VEGF antibodies (e.g., bevacizumab); VEGF receptor inhibitors (e.g., itraconazole); inhibitors of cell proliferatin and/or migration of endothelial cells (e.g., carboxyamidotriazole, TNP-470); inhibitors of angiogenesis stimulators (e.g., suramin), among others. A vascular-targeting agent (VTA) or vascular disrupting agent (VDA) is designed to damage the vasculature (blood vessels) of cancer tumors causing central necrosis (reviewed in, e.g., Thorpe, P. E. (2004) Clin. Cancer Res. Vol. 10:415-427). VTAs can be small-molecule. Exemplary small-molecule VTAs include, but are not limited to, microtubule destabilizing drugs (e.g., combretastatin A-4 disodium phosphate (CA4P), ZD6126, AVE8062, Oxi 4503); and vadimezan (ASA404).

Immune Checkpoint Inhibitors

In other embodiments, methods described herein comprise use of an immune checkpoint inhibitor in combination with the multispecific molecule. The methods can be used in a therapeutic protocol in vivo.

In embodiments, an immune checkpoint inhibitor inhibits a checkpoint molecule. Exemplary checkpoint molecules include but are not limited to CTLA4, PD1, PD-L1, PD-L2, TIM3, LAG3, CD160, 2B4, CD80, CD86, B7-H3 (CD276), B7-H4 (VTCN1), HVEM (TNFRSF14 or CD270), BTLA, KIR, MHC class I, MHC class II, GAL9, VISTA, BTLA, TIGIT, LAIR1, and A2aR. See, e.g., Pardoll. Nat. Rev. Cancer 12.4(2012):252-64, incorporated herein by reference.

In embodiments, the immune checkpoint inhibitor is a PD-1 inhibitor, e.g., an anti-PD-1 antibody such as Nivolumab, Pembrolizumab or Pidilizumab. Nivolumab (also called MDX-1106, MDX-1106-04, ONO-4538, or BMS-936558) is a fully human IgG4 monoclonal antibody that specifically inhibits PD1. See, e.g., U.S. Pat. No. 8,008,449 and WO2006/121168. Pembrolizumab (also called Lambrolizumab, MK-3475, MK03475, SCH-900475 or KEYTRUDA®; Merck) is a humanized IgG4 monoclonal antibody that binds to PD-1. See, e.g., Hamid, O. et al. (2013) New England Journal of Medicine 369 (2): 134-44, U.S. Pat. No. 8,354,509 and WO2009/114335. Pidilizumab (also called CT-011 or Cure Tech) is a humanized IgG1k monoclonal antibody that binds to PD1. See, e.g., WO2009/101611. In one embodiment, the inhibitor of PD-1 is an antibody molecule having a sequence substantially identical or similar thereto, e.g., a sequence at least 85%, 90%, 95% identical or higher to the sequence of Nivolumab, Pembrolizumab or Pidilizumab. Additional anti-PD1 antibodies, e.g., AMP 514 (Amplimmune), are described, e.g., in U.S. Pat. No. 8,609,089, US 2010028330, and/or US 20120114649.

In some embodiments, the PD-1 inhibitor is an immunoadhesin, e.g., an immunoadhesin comprising an extracellular/PD-1 binding portion of a PD-1 ligand (e.g., PD-L1 or PD-L2) that is fused to a constant region (e.g., an Fc region of an immunoglobulin). In embodiments, the PD-1 inhibitor is AMP-224 (B7-DCIg, e.g., described in WO2011/066342 and WO2010/027827), a PD-L2 Fc fusion soluble receptor that blocks the interaction between B7-H1 and PD-1.

In embodiments, the immune checkpoint inhibitor is a PD-L1 inhibitor, e.g., an antibody molecule. In some embodiments, the PD-L1 inhibitor is YW243.55.570, MPDL3280A, MEDI-4736, MSB-0010718C, or MDX-1105. In some embodiments, the anti-PD-L1 antibody is MSB0010718C (also called A09-246-2; Merck Serono), which is a monoclonal antibody that binds to PD-L1. Exemplary humanized anti-PD-L1 antibodies are described, e.g., in WO2013/079174. In one embodiment, the PD-L1 inhibitor is an anti-PD-L1 antibody, e.g., YW243.55.570. The YW243.55.570 antibody is described, e.g., in WO 2010/077634. In one embodiment, the PD-L1 inhibitor is MDX-1105 (also called BMS-936559), which is described, e.g., in WO2007/005874. In one embodiment, the PD-L1 inhibitor is MDPL3280A (Genentech/Roche), which is a human Fc-optimized IgG1 monoclonal antibody against PD-L1. See, e.g., U.S. Pat. No. 7,943,743 and U.S Publication No.: 20120039906. In one embodiment, the inhibitor of PD-L1 is an antibody molecule having a sequence substantially identical or similar thereto, e.g., a sequence at least 85%, 90%, 95% identical or higher to the sequence of YW243.55.S70, MPDL3280A, MEDI-4736, MSB-0010718C, or MDX-1105.

In embodiments, the immune checkpoint inhibitor is a PD-L2 inhibitor, e.g., AMP-224 (which is a PD-L2 Fc fusion soluble receptor that blocks the interaction between PD1 and B7-H1. See, e.g., WO2010/027827 and WO2011/066342.

In one embodiment, the immune checkpoint inhibitor is a LAG-3 inhibitor, e.g., an anti LAG-3 antibody molecule. In embodiments, the anti-LAG-3 antibody is BMS-986016 (also called BMS986016; Bristol-Myers Squibb). BMS-986016 and other humanized anti-LAG-3 antibodies are described, e.g., in US 2011/0150892, WO2010/019570, and WO2014/008218.

In embodiments, the immune checkpoint inhibitor is a TIM-3 inhibitor, e.g., anti-TIM3 antibody molecule, e.g., described in U.S. Pat. No. 8,552,156, WO 2011/155607, EP 2581113 and U.S Publication No.: 2014/044728.

In embodiments, the immune checkpoint inhibitor is a CTLA-4 inhibitor, e.g., anti-CTLA-4 antibody molecule. Exemplary anti-CTLA4 antibodies include Tremelimumab (IgG2 monoclonal antibody from Pfizer, formerly known as ticilimumab, CP-675,206); and Ipilimumab (also called MDX-010, CAS No. 477202-00-9). Other exemplary anti-CTLA-4 antibodies are described, e.g., in U.S. Pat. No. 5,811,097.

EXAMPLES

The following examples are intended to be illustrative, and are not meant in any way to be limiting.

Methods

1. Construction of the Plasmids of NanoBiT Constructs.

The DNA encoding the protein sequences was optimized for expression in *Cricetulus griseus*, synthesized, and cloned into the pcDNA3.4-TOPO (Life Technologies A14697) using Gateway cloning. The nucleic acid sequences used are shown in Table 1.

TABLE 1

Nucleic acid sequences of ORFs.

| SEQ ID NO | Description | Nucleic Acid Sequence |
|---|---|---|
| SEQ ID NO: 1 | α-amyloid β heavy-LgBiT | ATGGAAACCGACACACTGCTGCTGTGGGTGCTGTTGTTGTGGGTGC CAGGATCTACAGGACAGGTGCAGCTGGTTGAATCTGGTGGCGGAG TGGTGCAGCCTGGCAGATCTCTGAGACTGTCTTGTGCCGCCTCTGG CTTCGCCTTCTCTTCTTACGGCATGCACTGGGTCCGACAGGCCCCT GGAAAAGGACTGGAATGGGTCGCCGTGATTTGGTTCGACGGCACC AAGAAGTACTACACCGACTCCGTGAAGGGCAGATTCACCATCAGC CGGGACAACTCCAAGAACACCCTGTACCTGCAGATGAATACCCTG AGAGCCGAGGACACCGCCGTGTACTACTGTGCCAGAGATAGAGGC ATCGGCGCTCGGAGAGGCCCTTACTATATGGATGTGTGGGGCAAG GGCACCACCGTGACAGTGTCCTCTGCTTCTACCAAGGGACCCAGC GTTTTCCCTCTGGCTCCATCCTCTAAGTCCACCTCTGGTGGAACCG CTGCTCTGGGCTGTCTGGTCAAGGATTACTTCCCTGAGCCTGTGAC CGTGTCCTGGAACTCTGGTGCTCTGACATCCGGCGTGCACACCTTT CCAGCTGTGCTGCAGTCCTCTGGCCTGTACTCTCTGTCCTCTGTCGT GACCGTGCCTTCTAGCTCTCTGGGCACCCAGACCTACATCTGCAAC GTGAACCACAAGCCTTCCAACACCAAAGTGGACAAGAGAGTGGA ACCCAAGTCCTGCGGATCTTCTGGCGGCGGAGGAAGCGGAGGCGG AGGATCTAGCGGCGGAGTGTTCACCCTGGAAGATTTCGTCGGCGA TTGGGAGCAGACCGCCGCCTATAATCTGGACCAGGTTCTGGAACA AGGCGGCGTGTCCTCTCTGCTGCAGAATCTGGCTGTGTCTGTGACC CCTATCCAGAGAATCGTGCGCTCTGGCGAGAACGCCCTGAAGATC GACATCCACGTGATCATCCCTTACGAGGGCCTGTCTGCCGATCAGA TGGCTCAGATCGAAGAGGTGTTCAAGGTGGTGTACCCCGTGGACG ACCACCACTTCAAAGTGATCCTGCCTTACGGCACCCTGGTCATCGA TGGCGTGACCCCAAACATGCTGAACTACTTCGGCAGACCCTACGA GGGAATCGCCGTGTTCGATGGCAAGAAAATCACCGTGACCGGCAC ACTGTGGAACGGCAACAAGATCATCGACGAGCGGCTGATCACCCC TGACGGCTCTATGCTGTTCAGAGTGACCATCAACTCCTAATGA |
| SEQ ID NO: 2 | α-amyloid β light-SmBiT | ATGGAAACCGACACACTGCTGCTGTGGGTGCTGTTGTTGTGGGTGC CAGGCTCTACCGGCGACATCCAGATGACCCAGTCTCCATCCTCTCT GTCTGCCTCTGTGGGCGACAGAGTGACCATCACCTGTAGAGCCAG CCAGTCCATCTCCTCCTACCTGAACTGGTATCAGCAGAAGCCTGGC AAGGCTCCCAAGCTGCTGATCTACGCTGCTAGCTCTCTGCAGTCTG GCGTGCCCTCTAGATTTTCCGGCTCTGGCTCTGGCACCGACTTCAC CCTGACAATCAGTTCCCTGCAGCCTGAGGACTTCGCCACCTACTAC TGCCAGCAGTCCTACAGCACACCCTTGACCTTTGGCGGAGGCACC AAGGTGGAAATCAAGAGAACCGTGGCCGCTCCTTCCGTGTTCATC TTCCCACCATCCGACGAACAGCTGAAGTCCGGCACAGCTTCTGTCG TGTGCCTGCTGAACAACTTCTACCCTCGGGAAGCCAAGGTGCAGT GGAAGGTGGACAATGCCCTGCAGTCCGGCAACTCCCAAGAGTCTG TGACCGAGCAGGACTCCAAGGACTCTACCTACAGCCTGTCCTCCA CACTGACCCTGTCTAAGGCCGACTACGAGAAGCACAAGGTGTACG CCTGTGAAGTGACCCACCAGGGACTGTCTAGCCCCGTGACCAAGT CTTTCAACAGAGGCGAGTGCGGATCTTCTGGTGGCGGAGGAAGCG GAGGCGGAGGATCATCTGGCGGAGTGACCGGCTACAGACTGTTCG AAGAGATCCTGTAATGA |
| SEQ ID NO: 3 | α-amyloid β light | ATGGAAACCGACACACTGCTGCTGTGGGTGCTGTTGTTGTGGGTGC CAGGCTCTACCGGCGACATCCAGATGACCCAGTCTCCATCCTCTCT GTCTGCCTCTGTGGGCGACAGAGTGACCATCACCTGTAGAGCCAG CCAGTCCATCTCCTCCTACCTGAACTGGTATCAGCAGAAGCCTGGC AAGGCTCCCAAGCTGCTGATCTACGCTGCTAGCTCTCTGCAGTCTG GCGTGCCCTCTAGATTTTCCGGCTCTGGCTCTGGCACCGACTTCAC |

TABLE 1-continued

Nucleic acid sequences of ORFs.

| SEQ ID NO | Description | Nucleic Acid Sequence |
|---|---|---|
| | | CCTGACAATCAGTTCCCTGCAGCCTGAGGACTTCGCCACCTACTAC<br>TGCCAGCAGTCCTACAGCACACCCTTGACCTTTGGCGGAGGCACC<br>AAGGTGGAAATCAAGAGAACCGTGGCCGCTCCTTCCGTGTTCATC<br>TTCCCACCATCCGACGAACAGCTGAAGTCCGGCACAGCTTCTGTCG<br>TGTGCCTGCTGAACAACTTCTACCCTCGGGAAGCCAAGGTGCAGT<br>GGAAGGTGGACAATGCCCTGCAGTCCGGCAACTCCCAAGAGTCTG<br>TGACCGAGCAGGACTCCAAGGACTCTACCTACAGCCTGTCCTCCA<br>CACTGACCCTGTCTAAGGCCGACTACGAGAAGCACAAGGTGTACG<br>CCTGTGAAGTGACCCACCAGGGACTGTCTAGCCCCGTGACCAAGT<br>CTTTCAACAGAGGCGAGTGCTAATGA |
| SEQ ID NO: 4 | α-Clostridium difficile toxin B heavy-LgBIT | ATGGAAACCGACACACTGCTGCTGTGGGTGCTGTTGTTGTGGGTGC<br>CAGGATCTACAGGCGAAGTGCAGTTGGTGCAGTCTGGCGCCGAAG<br>TGAAGAAGTCCGGCGAGTCCCTGAAGATCTCCTGCAAAGGCTCCG<br>GCTACTCCTTCACCTCTTACTGGATCGGCTGGGTCCGACAGATGCC<br>TGGCAAAGGACTGGAATGGATGGGCATCTTCTACCCCGGCGACTC<br>CTCTACCAGATACTCCCCTAGCTTTCAGGGCCAAGTGACCATCTCC<br>GCCGACAAGTCTGTGAACACCGCCTACCTGCAGTGGTCCTCTCTGA<br>AGGCCTCTGACACCGCCATGTACTACTGCGCCAGAAGAAGAAACT<br>GGGGCAACGCCTTCGATATCTGGGGCCAGGGAACAATGGTCACCG<br>TGTCCTCTGCTTCCACCAAGGGACCTTCCGTGTTTCCTCTGGCTCCT<br>TCCAGCAAGTCTACCTCTGGTGAACCGCTGCTCTGGGCTGCCTGG<br>TCAAGGATTACTTTCCTGAGCCTGTGACCGTGTCTTGGAACTCTGG<br>TGCTCTGACCTCCGGCGTGCACACATTTCCAGCTGTGCTGCAGTCC<br>TCCGGCCTGTACTCTCTGTCCTCTGTCGTGACCGTGCCTTCTAGCTC<br>TCTGGGCACCCAGACCTACATCTGCAACGTGAACCACAAGCCTTC<br>CAACACCAAGGTGGACAAGAGAGTGGAACCCAAGTCTTGCGGATC<br>TTCCGGTGGCGGAGGATCTGGCGGAGGTGGAAGTAGTGGCGGAGT<br>GTTCACCCTGGAAGATTTCGTCGGCGATTGGGAGCAGACCGCCGC<br>CTATAATCTGGACCAGGTTCTGGAACAAGGCGGCGTCAGCTCTCT<br>GCTGCAGAATCTGGCTGTGTCTGTGACCCCTATCCAGAGAATCGTG<br>CGCTCTGGCGAGAACGCTCTGAAGATCGACATCCACGTGATCATC<br>CCTTACGAGGGCCTGTCTGCCGATCAGATGGCTCAGATCGAAGAG<br>GTGTTCAAGGTGGTGTACCCCGTGGACGACCACCACTTCAAAGTG<br>ATCCTGCCTTACGGCACCCTGGTCATCGATGGCGTGACCCCAAACA<br>TGCTGAACTACTTCGGCAGACCCTACGAGGGAATCGCCGTGTTCG<br>ACGGCAAGAAAATCACCGTGACCGGCACACTGTGGAACGGCAAC<br>AAGATCATCGACGAGCGGCTGATCACCCCTGACGGCTCTATGCTG<br>TTCCGCGTGACCATCAACTCCTAATGA |
| SEQ ID NO: 5 | α-Clostridium difficile toxin B light-SmBiT | ATGGAAACCGACACACTGCTGCTGTGGGTGCTGTTGTTGTGGGTGC<br>CAGGATCTACAGGCGAGATCGTGCTGACCCAGTCTCCTGGCACAT<br>TGTCTCTGAGTCCTGGCGAGAGAGCTACCCTGTCTTGCAGAGCTTC<br>CCAGTCCGTGTCCTCTTCCTACCTGGCCTGGTATCAGCAGAAGCCT<br>GGACAGGCTCCCAGACTGCTGATCTACGGCGCCTCTTCTAGAGCC<br>ACAGGCATCCCTGACAGATTCTCCGGCTCTGGCTCTGGCACCGACT<br>TCACCCTGACCATCTCTAGACTGGAACCCGAGGACTTCGCCGTGTA<br>CTACTGCCAGCAGTATGGCTCCTCTACCTGGACCTTTGGACAGGGC<br>ACCAAGGTGGAAATCAAGAGAACCGTGGCCGCTCCTTCCGTGTTC<br>ATCTTCCCACCATCTGACGAGCAGCTGAAGTCCGGCACAGCTTCTG<br>TCGTGTGCCTGCTGAACAACTTCTACCCTCGGGAAGCCAAGGTGC<br>AGTGGAAGGTGGACAATGCCCTGCAGTCCGGCAACTCCCAAGAGT<br>CTGTGACCGAGCAGGACTCCAAGGACTCTACCTACAGCCTGTCCTC<br>CACACTGACCCTGTCTAAGGCCGACTACGAGAAGCACAAGGTGTA<br>CGCCTGTGAAGTGACCCACCAGGGACTGTCTAGCCCCGTGACCAA<br>GTCTTTCAACAGAGGCGAGTGCGGATCTTCTGGTGGCGGAGGATC<br>TGGCGGAGGCGGATCTAGTGGCGGAGTGACCGGCTACAGACTGTT<br>CGAAGAGATCCTGTAATGA |
| SEQ ID NO: 6 | α-Clostridium difficile toxin B light | ATGGAAACCGACACACTGCTGCTGTGGGTGCTGTTGTTGTGGGTGC<br>CAGGATCTACAGGCGAGATCGTGCTGACCCAGTCTCCTGGCACAT<br>TGTCTCTGAGTCCTGGCGAGAGAGCTACCCTGTCTTGCAGAGCTTC<br>CCAGTCCGTGTCCTCTTCCTACCTGGCCTGGTATCAGCAGAAGCCT<br>GGACAGGCTCCCAGACTGCTGATCTACGGCGCCTCTTCTAGAGCC<br>ACAGGCATCCCTGACAGATTCTCCGGCTCTGGCTCTGGCACCGACT<br>TCACCCTGACCATCTCTAGACTGGAACCCGAGGACTTCGCCGTGTA<br>CTACTGCCAGCAGTATGGCTCCTCTACCTGGACCTTTGGACAGGGC<br>ACCAAGGTGGAAATCAAGAGAACCGTGGCCGCTCCTTCCGTGTTC<br>ATCTTCCCACCATCTGACGAGCAGCTGAAGTCCGGCACAGCTTCTG<br>TCGTGTGCCTGCTGAACAACTTCTACCCTCGGGAAGCCAAGGTGC<br>AGTGGAAGGTGGACAATGCCCTGCAGTCCGGCAACTCCCAAGAGT<br>CTGTGACCGAGCAGGACTCCAAGGACTCTACCTACAGCCTGTCCTC<br>CACACTGACCCTGTCTAAGGCCGACTACGAGAAGCACAAGGTGTA<br>CGCCTGTGAAGTGACCCACCAGGGACTGTCTAGCCCCGTGACCAA<br>GTCTTTCAACAGAGGCGAGTGCTAATGA |

TABLE 1-continued

Nucleic acid sequences of ORFs.

| SEQ ID NO | Description | Nucleic Acid Sequence |
|---|---|---|
| SEQ ID NO: 7 | α-connective tissue growth factor heavy-LgBIT | ATGGAAACCGACACACTGCTGCTGTGGGTGCTGTTGTTGTGGGTGC<br>CAGGATCTACAGGCGAAGGCCAGTTGGTTCAGTCTGGCGGAGGAC<br>TTGTTCACCCTGGCGGATCTCTGAGACTGTCTTGTGCTGGCTCTGG<br>CTTCACCTTCTCCAGCTACGGCATGCACTGGGTTCGACAGGCCCCT<br>GGAAAAGGACTGGAATGGGTGTCCGGAATCGGCACCGGCGGAGG<br>CACCTATTCTACCGATTCTGTGAAGGGCAGATTCACCATCAGCCGG<br>GACAACGCCAAGAACTCCCTGTACCTGCAGATGAACAGCCTGAGA<br>GCCGAGGACATGGCCGTGTACTACTGTGCCAGAGGCGATTACTAC<br>GGCTCCGGCTCTTTCTTCGACTGTTGGGGACAGGGCACACTGGTCA<br>CCGTGTCCTCTGCTTCTACCAAGGGACCCTCTGTGTTCCCTCTGGCT<br>CCTTCCAGCAAGTCTACCTCTGGTGGAACCGCTGCTCTGGGCTGCC<br>TGGGTCAAGGATTACTTTCCTGAGCCTGTGACCGTGTCTTGGAACTC<br>TGGTGCTCTGACCTCCGGCGTGCACACATTTCCAGCTGTGCTGCAG<br>TCCTCCGGCCTGTACTCTCTGTCCTCTGTCGTGACCGTGCCTTCTAG<br>CTCTCTGGGCACCCAGACCTACATCTGCAACGTGAACCACAAGCC<br>TTCCAACACCAAGGTGGACAAGAGAGTGGAACCCAAGTCTTGCGG<br>ATCTTCTGGCGGCGGAGGAAGCGGAGGCGGAGGATCTAGTGGCGG<br>AGTGTTTACCCTGGAAGATTTCGTCGGCGATTGGGAGCAGACCGC<br>CGCCTATAATCTGGACCAGGTTCTGGAACAAGGCGGCGTCAGCTC<br>TCTGCTGCAGAATCTGGCTGTGTCTGTGACCCCTATCCAGAGAATC<br>GTGCGCTCTGGCGAGAACGCCCTGAAGATCGACATCCACGTGATC<br>ATCCCTTACGAGGGCCTGTCTGCCGATCAGATGGCTCAGATCGAA<br>GAGGTGTTCAAGGTGGTGTACCCCGTGGACGACCACCACTTCAAA<br>GTGATCCTGCCTTACGGCACCCTGGTCATCGATGGCGTGACCCCAA<br>ACATGCTGAACTACTTCGGCAGACCCTACGAGGGAATCGCCGTGT<br>TCGACGGCAAGAAAATCACCGTGACCGGCACACTGTGGAACGGCA<br>ACAAGATCATCGACGAGCGGCTGATCACCCCTGACGGCTCCATGC<br>TGTTTAGAGTGACCATCAACTCCTAATGA |
| SEQ ID NO: 8 | α-connective tissue growth factor light -SmBiT | ATGGAAACCGACACACTGCTGCTGTGGGTGCTGTTGTTGTGGGTGC<br>CAGGCTCTACCGGCGACATCCAGATGACCCAGTCTCCATCCTCTCT<br>GTCTGCCTCTGTGGGCGACAGAGTGACCATCACCTGTAGAGCCTCT<br>CAGGGCATCTCTAGCTGGCTGGCCTGGTATCAGCAGAAGCCTGAG<br>AAGGCCCCTAAGAGCCTGATCTACGCTGCCAGTTCTCTGCAGTCTG<br>GCGTGCCCTCTAGATTCTCTGGCTCTGGATCTGGCACCGACTTCAC<br>CCTGACAATCTCTAGCCTGCAGCCTGAGGACTTCGCCACCTACTAC<br>TGCCAGCAGTACAACAGCTACCCTCCTACCTTTGGCCAGGGCACC<br>AAGCTGGAAATCAAGAGAACCGTGGCCGCTCCTTCCGTGTTCATCT<br>TCCCACCATCTGACGAGCAGCTGAAGTCCGGCACAGCTTCTGTCGT<br>GTGCCTGCTGAACAACTTCTACCCTCGGGAAGCCAAGGTGCAGTG<br>GAAGGTGGACAATGCCCTGCAGTCCGGCAACTCCCAAGAGTCTGT<br>GACCGAGCAGGACTCCAAGGACTCTACCTACAGCCTGTCCTCCAC<br>ACTGACCCTGTCTAAGGCCGACTACGAGAAGCACAAGGTGTACGC<br>CTGTGAAGTGACCCACCAGGGACTGTCTAGCCCCGTGACCAAGTC<br>TTTCAACAGAGGCGAGTGCGGATCTTCTGGTGGCGGAGGATCTGG<br>CGGAGGTGGAAGTAGTGGCGGCGTGACCGGCTACAGACTGTTCGA<br>AGAGATCCTGTAATGA |
| SEQ ID NO: 9 | α-connective tissue growth factor light | ATGGAAACCGACACACTGCTGCTGTGGGTGCTGTTGTTGTGGGTGC<br>CAGGCTCTACCGGCGACATCCAGATGACCCAGTCTCCATCCTCTCT<br>GTCTGCCTCTGTGGGCGACAGAGTGACCATCACCTGTAGAGCCTCT<br>CAGGGCATCTCTAGCTGGCTGGCCTGGTATCAGCAGAAGCCTGAG<br>AAGGCCCCTAAGAGCCTGATCTACGCTGCCAGTTCTCTGCAGTCTG<br>GCGTGCCCTCTAGATTCTCTGGCTCTGGATCTGGCACCGACTTCAC<br>CCTGACAATCTCTAGCCTGCAGCCTGAGGACTTCGCCACCTACTAC<br>TGCCAGCAGTACAACAGCTACCCTCCTACCTTTGGCCAGGGCACC<br>AAGCTGGAAATCAAGAGAACCGTGGCCGCTCCTTCCGTGTTCATCT<br>TCCCACCATCTGACGAGCAGCTGAAGTCCGGCACAGCTTCTGTCGT<br>GTGCCTGCTGAACAACTTCTACCCTCGGGAAGCCAAGGTGCAGTG<br>GAAGGTGGACAATGCCCTGCAGTCCGGCAACTCCCAAGAGTCTGT<br>GACCGAGCAGGACTCCAAGGACTCTACCTACAGCCTGTCCTCCAC<br>ACTGACCCTGTCTAAGGCCGACTACGAGAAGCACAAGGTGTACGC<br>CTGTGAAGTGACCCACCAGGGACTGTCTAGCCCCGTGACCAAGTC<br>TTTCAACAGAGGCGAGTGCTAATGA |
| SEQ ID NO: 10 | α-CSF2 heavy-LgBiT | ATGGAAACCGACACACTGCTGCTGTGGGTGCTGTTGTTGTGGGTGC<br>CAGGATCTACAGGACAGGTGCAGTTGGTGCAGTCTGGCGCCGAAG<br>TGAAGAAACCTGGCGCTTCTGTGAAGGTGTCCTGCAAGGCCTCTG<br>GCTACTCCTTCACCAACTACTACATCCACTGGGTCCGACAGGCCCC<br>TGGACAGAGATTGGAGTGGATGGGCTGGATCAACGCCGGCAACGG<br>CAACACCAAGTACTCCCAGAAATTCCAGGGCAGAGTGACCATCAC<br>CAGAGACACCTCTGCCTCCACCGCCTACATGGAACTGTCCAGCCTG<br>AGATCTGAGGACACCGCCGTGTACTACTGCGTGCGGAGACAGCGG<br>TTCCCCCTACTACTTTGATTATTGGGGCCAGGGCACCCTGGTCACCG |

TABLE 1-continued

Nucleic acid sequences of ORFs.

| SEQ ID NO | Description | Nucleic Acid Sequence |
|---|---|---|
| | | TGTCCTCTGCTTCTACAAAGGGCCCCTCTGTGTTCCCTCTGGCTCCT<br>TCCTCTAAATCCACCTCTGGCGGAACAGCTGCTCTGGGCTGTCTGG<br>TCAAGGACTACTTTCCTGAGCCTGTGACCGTGTCTTGGAACTCTGG<br>TGCTCTGACATCCGGCGTGCACACCTTTCCAGCTGTGCTGCAGTCC<br>TCTGGCCTGTACTCTCTGTCCTCTGTCGTGACCGTGCCTTCTAGCTC<br>TCTGGGCACCCAGACCTACATCTGCAACGTGAACCACAAGCCTTCT<br>AACACCAAGGTGGACAAGAGAGTGGAACCCAAGTCTTGCGGATCT<br>TCTGGTGGCGGAGGATCTGGCGGAGGCGGATCTAGTGGCGGAGTG<br>TTCACCCTGGAAGATTTCGTCGGCGATTGGGAGCAGACCGCCGCC<br>TATAATCTGGACCAGGTTCTGGAACAAGGCGGGGTGTCCTCTCTGC<br>TGCAGAATCTGGCTGTGTCTGTGACCCCTATCCAGAGAATCGTGCG<br>CTCTGGCGAGAACGCCCTGAAGATCGACATCCACGTGATCATCCC<br>TTACGAGGGCCTGTCTGCCGATCAGATGGCTCAGATCGAAGAGGT<br>GTTCAAGGTGGTGTACCCCGTGGACGACCACCACTTCAAAGTGAT<br>CCTGCCTTACGGCACCCTCGTGATCGATGGCGTGACCCCAAACATG<br>CTGAACTACTTCGGCAGACCCTACGAGGGAATCGCCGTGTTCGAC<br>GGCAAGAAAATCACCGTGACCGGCACACTGTGGAACGGAAACAA<br>GATCATCGACGAGCGGCTGATCACCCCTGACGGCTCTATGCTGTTT<br>AGAGTGACAATCAACTCCTAATGA |
| SEQ ID NO: 11 | α-CSF2 light-SmBiT | ATGGAAACCGACACACTGCTGCTGTGGGTGCTGTTGTTGTGGGTGC<br>CAGGATCTACAGGCGAGATCGTGCTGACCCAGTCTCCTGCCACATT<br>GTCTGTGTCTCCCGGCGAGAGAGCTACCCTGTCTTGTAGAGCTTCT<br>CAGTCCGTGGGCACCAACGTGGCCTGGTATCAGCAGAAACCTGGA<br>CAGGCCCCTCGGGTGCTGATCTACTCTACCTCTTCTAGAGCCACCG<br>GCATCACCGACAGATTCTCTGGCTCTGGATCTGGCACCGACTTCAC<br>CCTGACCATCTCCAGACTGGAACCTGAGGACTTCGCCGTGTACTAC<br>TGCCAGCAGTTCAACAAGTCCCCTCTGACCTTTGGCGGAGGCACC<br>AAGGTGGAAATCAAGAGAACCGTGGCCGCTCCTTCCGTGTTCATC<br>TTCCCACCATCTGACGAGCAGCTGAAGTCCGGCACAGCTTCTGTCG<br>TGTGCCTGCTGAACAACTTCTACCCTCGGGAAGCCAAGGTGCAGT<br>GGAAGGTGGACAATGCCCTGCAGTCCGGCAACTCCCAAGAGTCTG<br>TGACCGAGCAGGACTCCAAGGACTCTACCTACAGCCTGTCCTCCA<br>CACTGACCCTGTCTAAGGCCGACTACGAGAAGCACAAGGTGTACG<br>CCTGTGAAGTGACCCACCAGGGACTGTCTAGCCCCGTGACCAAGT<br>CTTTCAACAGAGGCGAGTGCGGATCTTCTGGTGGCGGAGGAAGCG<br>GAGGCGGAGGATCATCTGGCGGAGTGACCGGCTACAGACTGTTCG<br>AAGAGATCCTGTAATGA |
| SEQ ID NO: 12 | α-CSF2 light | ATGGAAACCGACACACTGCTGCTGTGGGTGCTGTTGTTGTGGGTGC<br>CAGGATCTACAGGCGAGATCGTGCTGACCCAGTCTCCTGCCACATT<br>GTCTGTGTCTCCCGGCGAGAGAGCTACCCTGTCTTGTAGAGCTTCT<br>CAGTCCGTGGGCACCAACGTGGCCTGGTATCAGCAGAAACCTGGA<br>CAGGCCCCTCGGGTGCTGATCTACTCTACCTCTTCTAGAGCCACCG<br>GCATCACCGACAGATTCTCTGGCTCTGGATCTGGCACCGACTTCAC<br>CCTGACCATCTCCAGACTGGAACCTGAGGACTTCGCCGTGTACTAC<br>TGCCAGCAGTTCAACAAGTCCCCTCTGACCTTTGGCGGAGGCACC<br>AAGGTGGAAATCAAGAGAACCGTGGCCGCTCCTTCCGTGTTCATC<br>TTCCCACCATCTGACGAGCAGCTGAAGTCCGGCACAGCTTCTGTCG<br>TGTGCCTGCTGAACAACTTCTACCCTCGGGAAGCCAAGGTGCAGT<br>GGAAGGTGGACAATGCCCTGCAGTCCGGCAACTCCCAAGAGTCTG<br>TGACCGAGCAGGACTCCAAGGACTCTACCTACAGCCTGTCCTCCA<br>CACTGACCCTGTCTAAGGCCGACTACGAGAAGCACAAGGTGTACG<br>CCTGTGAAGTGACCCACCAGGGACTGTCTAGCCCCGTGACCAAGT<br>CTTTCAACAGAGGCGAGTGCTAATGA |
| SEQ ID NO: 13 | α-CTLA4 heavy-LgBiT | ATGGAAACCGACACACTGCTGCTGTGGGTGCTGCTCTTGTGGGTGC<br>CAGGATCTACAGGACAGGTGCAGCTGGTGGAATCTGGTGGCGGAG<br>TTGTGCAGCCTGGCAGATCCCTGAGACTGTCTTGTGCCGCCTCCGG<br>CTTCACCTTCTCCAGCTACACCATGCACTGGGTCCGACAGGCCCCT<br>GGCAAAGGATTGGAGTGGGTCACCTTCATCTCTTACGACGGCAAC<br>AACAAGTACTACGCCGACTCCGTGAAGGGCAGATTCACCATCTCT<br>CGGGACAACTCCAAGAACACCCTGTACCTGCAGATGAACTCCCTG<br>AGAGCCGAGGACACCGCCATCTACTACTGTGCTAGAACCGGCTGG<br>CTGGGCCCCTTTGATTATTGGGGACAGGGCACCCTGGTCACCGTGT<br>CCTCTGCTTCTACCAAGGGACCCAGCGTGTTCCCTCTGGCTCCTTC<br>CAGCAAGTCTACCTCTGGCGGAACAGCTGCTCTGGGCTGCCTGGTC<br>AAGGACTACTTTCCTGAGCCTGTGACCGTGTCTTGGAACTCTGGCG<br>CTCTGACATCCGGCGTGCACACATTTCCAGCTGTGCTGCAGTCCTC<br>CGGCCTGTACTCTCTGTCCTCTGTCGTGACCGTGCCTTCCAGCTCTC<br>TGGGAACCCAGACCTACATCTGCAATGTGAACCACAAGCCTTCCA<br>ACACCAAGGTGGACAAGAGAGTGGAACCCAAGTCCTGCGGATCTT<br>CTGGCGGCGGAGGATCTGGCGGAGGTGGTAGTTCAGGCGGAGTGT<br>CACCCCTGGAAGATTTCGTCGGCGACTGGGAGCAGACCGCCGCCT<br>ATAATCTGGACCAGGTGCTGGAACAAGGCGGCGTTAGTTCCCTGC |

TABLE 1-continued

Nucleic acid sequences of ORFs.

| SEQ ID NO | Description | Nucleic Acid Sequence |
|---|---|---|
| | | TGCAGAACCTGGCTGTGTCTGTGACCCCTATCCAGAGAATCGTGCG GAGCGGCGAGAACGCCCTGAAGATCGATATCCACGTGATCATCCC TTACGAGGGCCTGAGCGCCGATCAGATGGCTCAGATCGAAGAGGT GTTCAAGGTGGTGTACCCCGTGGACGACCACCACTTCAAAGTGAT CCTGCCTTACGGCACCCTCGTGATCGATGGCGTGACCCCAAACATG CTGAACTACTTCGGCAGACCCTACGAGGGAATCGCCGTGTTCGAC GGCAAGAAAATCACCGTGACCGGCACACTGTGGAATGGCAACAA GATCATCGACGAGCGGCTGATCACCCCTGACGGCTCCATGCTGTTC AGAGTGACCATCAACAGCTGATGA |
| SEQ ID NO: 14 | α-CTLA4 light-SmBiT | ATGGAAACCGACACACTGCTGCTGTGGGTGCTGTTGTTGTGGGTGC CAGGATCTACAGGCGAGATCGTGCTGACCCAGTCTCCTGGCACAT TGTCTCTGAGTCCTGGCGAGAGAGCTACCCTGTCTTGCAGAGCTTC CCAGTCCGTGGGATCTTCCTACCTGGCCTGGTATCAGCAGAAGCCT GGACAGGCTCCCAGACTGCTGATCTACGGCGCCTTTTCTAGAGCCA CAGGCATCCCTGACAGATTCTCCGGCTCTGGCTCTGGCACCGACTT CACCCTGACCATCTCTAGACTGGAACCCGAGGACTTCGCCGTGTAC TACTGCCAGCAGTATGGCTCCTCTCCTTGGACCTTTGGACAGGGCA CCAAGGTGGAAATCAAGAGAACCGTGGCCGCTCCTTCCGTGTTCA TCTTCCCACCATCTGACGAGCAGCTGAAGTCCGGCACAGCTTCTGT CGTGTGCCTGCTGAACAACTTCTACCCTCGGGAAGCCAAGGTGCA GTGGAAGGTGGACAATGCCCTGCAGTCCGGCAACTCCCAAGAGTC TGTGACCGAGCAGGACTCCAAGGACTCTACCTACAGCCTGTCCTCC ACACTGACCCTGTCTAAGGCCGACTACGAGAAGCACAAGGTGTAC GCCTGTGAAGTGACCCACCAGGGACTGTCTAGCCCCGTGACCAAG TCTTTCAACAGAGGCGAGTGCGGATCTTCTGGTGGCGGAGGATCT GGCGGAGGCGGATCTAGTGGCGGAGTGACCGGCTACAGACTGTTC GAAGAGATCCTGTAATGA |
| SEQ ID NO: 15 | α-CTLA4 light | ATGGAAACCGACACACTGCTGCTGTGGGTGCTGCTCTTGTGGGTGC CAGGATCTACAGGCGAGATCGTGCTGACCCAGTCTCCTGGCACAC TGTCACTGTCTCCAGGCGAGAGAGCTACCCTGTCCTGTAGAGCCTC TCAGTCCGTGGGCTCCTCTTACCTGGCTTGGTATCAGCAGAAGCCT GGCCAGGCTCCTAGACTGTTGATCTACGGCGCCTTCTCCAGAGCCA CAGGCATCCCTGATAGATTCTCCGGCTCTGGCTCTGGCACCGACTT CACCCTGACCATCTCCAGACTGGAACCCGAGGACTTCGCCGTGTA CTACTGTCAGCAGTACGGCTCCTCTCCTTGGACCTTTGGCCAGGGC ACCAAGGTGGAAATCAAGCGGACAGTGGCCGCTCCTTCCGTGTTC ATCTTCCCACCTTCCGACGAGCAGCTGAAGTCCGGCACAGCTTCTG TCGTGTGCCTGCTGAACAACTTCTACCCTCGGGAAGCCAAGGTGC AGTGGAAGGTGGACAATGCCCTGCAGTCCGGCAACTCCCAAGAGT CTGTGACCGAGCAGGACTCCAAGGACAGCACCTACAGCCTGTCCT CCACACTGACCCTGTCCAAGGCCGACTACGAGAAGCACAAGGTGT ACGCCTGCGAAGTGACCCATCAGGGCCTGTCTAGCCCTGTGACCA AGTCTTTCAACCGGGGCGAGTGCTGATGA |
| SEQ ID NO: 16 | α-IFN heavy-LgBiT | ATGGAAACCGACACACTGCTGCTGTGGGTGCTGTTGTTGTGGGTGC CAGGATCTACAGGCGAAGTGCAGTTGGTGCAGTCTGGCGCCGAAG TGAAGAAGCCTGGCGAGTCCCTGAAGATCTCCTGCAAAGGCTCCG GCTACATCTTCACCAACTACTGGATCGCCTGGGTCCGACAGATGCC TGGCAAAGGCCTGGAATCCATGGGCATCATCTACCCCGGCGACTC CGACATCAGATACAGCCCATCTTTCCAGGGCCAAGTGACCATCTCC GCCGACAAGTCTATCACCACCGCCTACCTGCAGTGGTCCTCTCTGA AGGCCTCTGACACCGCCATGTACTACTGCGCCAGACACGACATCG AGGGCTTCGATTATTGGGGCAGAGGCACCCTGGTCACCGTGTCCTC TGCTTCTACAAAGGGCCCCTCTGTGTTCCCTCTGGCTCCTTCCTCTA AATCCACCTCTGGCGGAACCGCTGCTCTGGGCTGTCTGGTCAAGG ATTACTTCCCTGAGCCTGTGACCGTGTCTTGGAACTCTGGTGCTCT GACATCCGGCGTGCACACCTTTCCAGCTGTGCTGCAGTCCTCTGGC CTGTACTCTCTGTCCTCTGTCGTGACCGTGCCTTCTAGCTCTCTGGG CACCCAGACCTACATCTGCAACGTGAACCACAAGCCTTCCAACAC CAAGGTGGACAAGAGAGTGGAACCCAAGTCTTGCGGATCTTCTGG TGGCGGAGGATCTGGCGGAGGCGGATCTAGTGGCGGAGTGTTCAC CCTGGAAGATTTCGTCGGCGATTGGGAGCAGACCGCCGCCTATAA TCTGGACCAGGTTCTGGAACAAGGCGGCGTCAGCTCTCTGCTGCA GAATCTGGCTGTGTCTGTGACCCCTATCCAGAGAATCGTGCGCTCT GGCGAGAACGCTCTGAAGATCGACATCCACGTGATCATCCCTTAC GAGGGCCTGTCTGCCGATCAGATGGCTCAGATCGAAGAGGTGTTC AAGGTGGTGTACCCCGTGGACGACCACCACTTCAAAGTGATCCTG CCTTACGGCACCCTCGTGATCGATGGCGTGACCCCAAACATGCTG AACTACTTCGGCAGACCCTACGAGGGAATCGCCGTGTTCGACGGC AAGAAAATCACCGTGACCGGCACACTGTGGAACGGCAACAAGATC ATCGACGAGCGGCTGATCACCCCTGACGGCTCTATGCTGTTCCGCG TGACCATCAACTCCTAATGA |

TABLE 1-continued

Nucleic acid sequences of ORFs.

| SEQ ID NO | Description | Nucleic Acid Sequence |
|---|---|---|
| SEQ ID NO: 17 | α-IFN light -SmBiT | ATGGAAACCGACACACTGCTGCTGTGGGTGCTGTTGTTGTGGGTGC<br>CAGGATCTACAGGCGAGATCGTGCTGACCCAGTCTCCTGGCACAT<br>TGTCTCTGAGTCCTGGCGAGAGAGCTACCCTGTCTTGCAGAGCTTC<br>CCAGTCCGTGTCCTCTAGCTTCTTCGCCTGGTATCAGCAGAAGCCC<br>GGACAGGCTCCTAGACTGCTGATCTACGGCGCCTCTTCTAGAGCCA<br>CAGGCATCCCTGATAGACTGTCCGGCTCTGGCTCTGGCACCGACTT<br>TACCCTGACCATCACCAGACTGGAACCCGAGGACTTCGCCGTGTA<br>CTACTGCCAGCAGTACGACTCCTCTGCCATCACCTTTGGCCAGGGC<br>ACAAGACTGGAAATCAAGAGAACCGTGGCCGCTCCTTCCGTGTTC<br>ATCTTCCCACCATCTGACGAGCAGCTGAAGTCCGGCACAGCTTCTG<br>TCGTGTGCCTGCTGAACAACTTCTACCCTCGGGAAGCCAAGGTGC<br>AGTGGAAGGTGGACAATGCCCTGCAGTCCGGCAACTCCCAAGAGT<br>CTGTGACCGAGCAGGACTCCAAGGACTCTACCTACAGCCTGTCCTC<br>CACACTGACCCTGTCTAAGGCCGACTACGAGAAGCACAAGGTGTA<br>CGCCTGTGAAGTGACCCACCAGGGACTGTCTAGCCCCGTGACCAA<br>GTCTTTCAACAGAGGCGAGTGCGGATCTTCTGGTGGCGGAGGATC<br>TGGCGGAGGCGGATCTAGTGGCGGAGTGACCGGCTACAGACTGTT<br>CGAAGAGATCCTGTAATGA |
| SEQ ID NO: 18 | α-IFN light | ATGGAAACCGACACACTGCTGCTGTGGGTGCTGTTGTTGTGGGTGC<br>CAGGATCTACAGGCGAGATCGTGCTGACCCAGTCTCCTGGCACAT<br>TGTCTCTGAGTCCTGGCGAGAGAGCTACCCTGTCTTGCAGAGCTTC<br>CCAGTCCGTGTCCTCTAGCTTCTTCGCCTGGTATCAGCAGAAGCCC<br>GGACAGGCTCCTAGACTGCTGATCTACGGCGCCTCTTCTAGAGCCA<br>CAGGCATCCCTGATAGACTGTCCGGCTCTGGCTCTGGCACCGACTT<br>TACCCTGACCATCACCAGACTGGAACCCGAGGACTTCGCCGTGTA<br>CTACTGCCAGCAGTACGACTCCTCTGCCATCACCTTTGGCCAGGGC<br>ACAAGACTGGAAATCAAGAGAACCGTGGCCGCTCCTTCCGTGTTC<br>ATCTTCCCACCATCTGACGAGCAGCTGAAGTCCGGCACAGCTTCTG<br>TCGTGTGCCTGCTGAACAACTTCTACCCTCGGGAAGCCAAGGTGC<br>AGTGGAAGGTGGACAATGCCCTGCAGTCCGGCAACTCCCAAGAGT<br>CTGTGACCGAGCAGGACTCCAAGGACTCTACCTACAGCCTGTCCTC<br>CACACTGACCCTGTCTAAGGCCGACTACGAGAAGCACAAGGTGTA<br>CGCCTGTGAAGTGACCCACCAGGGACTGTCTAGCCCCGTGACCAA<br>GTCTTTCAACAGAGGCGAGTGCTAATGA |
| SEQ ID NO: 19 | α-IFNa heavy- LgBiT | ATGGAAACCGACACACTGCTGCTGTGGGTGCTGTTGTTGTGGGTGC<br>CAGGATCTACAGGACAGGTGCAGTTGGTGCAGTCTGGCGCCGAAG<br>TGAAGAAACCTGGCGCTTCTGTGAAGGTGTCCTGCAAGGCCTCTG<br>GCTACACCTTTACCAGCTACTCCATCTCCTGGGTCCGACAGGCTCC<br>TGGACAAGGATTGGAGTGGATGGGCTGGATCTCCGTGTACAACGG<br>CAACACCAACTACGCCCAGAAATTCCAGGGCAGAGTGACCATGAC<br>CACCGACACCTCTACCTCCACCGCCTACCTGGAACTGAGATCCCTG<br>AGATCTGACGACACCGCCGTGTACTACTGCGCCAGAGATCCTATC<br>GCTGCTGGCTATTGGGGACAGGGCACACTGGTTACCGTGTCCTCTG<br>CTTCTACCAAGGGACCCTCTGTGTTCCCTCTGGCTCCTTCCAGCAA<br>GTCTACCTCTGGTGGAACCGCTGCTCTGGGCTGTCTGGTCAAGGAT<br>TACTTCCCTGAGCCTGTGACCGTGTCTTGGAACTCTGGTGCTCTGA<br>CCTCCGGCGTGCACACATTTCCAGCTGTGCTGCAGTCCTCCGGCCT<br>GTACTCTCTGTCCTCTGTCGTGACCGTGCCTTCTAGCTCTCTGGGCA<br>CCCAGACCTACATCTGCAACGTGAACCACAAGCCTTCCAACACCA<br>AGGTGGACAAGAGAGTGGAACCCAAGTCTTGCGGATCTTCTGGTG<br>GCGGAGGATCTGGCGGAGGTGGAAGTAGTGGCGGAGTGTTCACCC<br>TGGAAGATTTCGTCGGCGATTGGGAGCAGACCGCCGCCTATAATC<br>TGGACCAGGTTCTGGAACAAGGCGGCGTCAGCTCTCTGCTGCAGA<br>ATCTGGCTGTGTCTGTGACCCCTATCCAGAGAATTGTGCGCTCTGG<br>CGAGAACGCCCTGAAGATCGACATCCACGTGATCATCCCTTACGA<br>GGGCCTGTCTGCCGATCAGATGGCTCAGATCGAAGAGGTGTTCAA<br>GGTGGTGTACCCCGTGGACGACCACCACTTCAAAGTGATCCTGCCT<br>TACGGCACCCTGGTCATCGATGCGTGACCCCAAACATGCTGAAC<br>TACTTCGGCAGACCCTACGAGGGAATCGCCGTGTTCGACGGCAAG<br>AAAATCACCGTGACCGGCACACTGTGGAACGGAAACAAGATCATC<br>GACGAGCGGCTGATCACCCCTGACGGCTCTATGCTGTTCCGCGTGA<br>CCATCAACTCCTAATGA |
| SEQ ID NO: 20 | α-IFNa light- SmBiT | ATGGAAACCGACACACTGCTGCTGTGGGTGCTGTTGTTGTGGGTGC<br>CAGGATCTACAGGCGAGATCGTGCTGACCCAGTCTCCTGGCACAT<br>TGTCTCTGAGTCCTGGCGAGAGAGCTACCCTGTCTTGCAGAGCTTC<br>CCAGTCCGTGTCCTCTACCTACCTGGCTGGTATCAGCAGAAGCCT<br>GGACAGGCTCCCAGACTGCTGATCTACGGCGCCTCTTCTAGAGCCA<br>CAGGCATCCCTGACAGATTCTCCGGCTCTGGCTCTGGCACCGACT<br>TCACCCTGACCATCTCTAGACTGGAACCCGAGGACTTCGCCGTGTA<br>CTACTGCCAGCAGTATGGCTCCTCTCCTCGGACCTTTGGACAGGGC<br>ACCAAGGTGGAAATCAAGAGAACCGTGGCCGCTCCTTCCGTGTTC<br>ATCTTCCCACCATCTGACGAGCAGCTGAAGTCCGGCACAGCTTCTG |

TABLE 1-continued

Nucleic acid sequences of ORFs.

| SEQ ID NO | Description | Nucleic Acid Sequence |
|---|---|---|
| | | TCGTGTGCCTGCTGAACAACTTCTACCCTCGGGAAGCCAAGGTGC<br>AGTGGAAGGTGGACAATGCCCTGCAGTCCGGCAACTCCCAAGAGT<br>CTGTGACCGAGCAGGACTCCAAGGACTCTACCTACAGCCTGTCCTC<br>CACACTGACCCTGTCTAAGGCCGACTACGAGAAGCACAAGGTGTA<br>CGCCTGTGAAGTGACCCACCAGGGACTGTCTAGCCCCGTGACCAA<br>GTCTTTCAACAGAGGCGAGTGCGGATCTTCTGGTGGCGGAGGATC<br>TGGCGGAGGCGGATCTAGTGGCGGAGTGACCGGCTACAGACTGTT<br>CGAAGAGATCCTGTAATGA |
| SEQ ID NO: 21 | α-IFNa LgBiT | ATGGAAACCGACACACTGCTGCTGTGGGTGCTGTTGTTGTGGGTGC<br>CAGGATCTACAGGCGAGATCGTGCTGACCCAGTCTCCTGGCACAT<br>TGTCTCTGAGTCCTGGCGAGAGAGCTACCCCTGTCTTGCAGAGCTTC<br>CCAGTCCGTGTCCTCTACCTACCTGGCCTGGTATCAGCAGAAGCCT<br>GGACAGGCTCCCAGACTGCTGATCTACGGCGCCTCTTCTAGAGCC<br>ACAGGCATCCCTGACAGATTCTCCGGCTCTGGCTCTGGCACCGACT<br>TCACCCTGACCATCTCTAGACTGGAACCCGAGGACTTCGCCGTGTA<br>CTACTGCCAGCAGTATGGCCTCTCCTCGGACCTTTGGACAGGGC<br>ACCAAGGTGGAAATCAAGAGAACCGTGGCCGCTCCTTCCGTGTTC<br>ATCTTCCCACCATCTGACAGCAGCTGAAGTCCGGCACAGCTTCTG<br>TCGTGTGCCTGCTGAACAACTTCTACCCTCGGGAAGCCAAGGTGC<br>AGTGGAAGGTGGACAATGCCCTGCAGTCCGGCAACTCCCAAGAGT<br>CTGTGACCGAGCAGGACTCCAAGGACTCTACCTACAGCCTGTCCTC<br>CACACTGACCCTGTCTAAGGCCGACTACGAGAAGCACAAGGTGTA<br>CGCCTGTGAAGTGACCCACCAGGGACTGTCTAGCCCCGTGACCAA<br>GTCTTTCAACAGAGGCGAGTGCTAATGA |
| SEQ ID NO: 22 | α-IGF1R heavy-light | ATGGAAACCGACACACTGCTGCTGTGGGTGCTGTTGTTGTGGGTGC<br>CAGGATCTACAGGCCAGGTCCAGCTGCAAGAATCTGGCCCTGGAC<br>TGGTCAAGCCTTCTGGCACCCTGTCTCTGACATGTGCTGTGTCCGG<br>CGGCTCCATCTCCTCCTCTAATTGGTGGTCTTGGGTCGACAGCCT<br>CCTGGCAAAGGACTGGAATGGATCGGCGAGATCTACCACTCCGGC<br>TCCACCAACTACAACCCCAGCCTGAAGTCCAGAGTGACCATCTCC<br>GTGGACAAGTCCAAGAACCAGTTCTCCCTGAAGCTGTCCTCTGTGA<br>CCGCTGCCGATACCGCCGTGTACTACTGTGCTAGATGGACCGGCA<br>GAACCGACGCCTTTGATATCTGGGGCCAGGGCACAATGGTCACCG<br>TGTCCTCTGCTTCTACCAAGGGACCCTCTGTGTTCCCTCTGGCTCCT<br>TCCAGCAAGTCTACCTCTGGTGGAACCGCTGCTCTGGGCTGCCTGG<br>TCAAGGATTACTTTCCTGAGCCTGTGACCGTGTCTTGGAACTCTGG<br>TGCTCTGACCTCCGGCGTGCACACATTTCCAGCTGTGCTGCAGTCT<br>AGCGGCCTGTACTCTCTGTCTAGCGTCGTGACCGTGCCTTCTAGCT<br>CTCTGGGCACCCAGACCTACATCTGCAACGTGAACCACAAGCCTT<br>CCAACACCAAGGTGGACAAGAGAGTGGAACCCAAGTCTTGCGGAT<br>CTTCTGGTGGCGGAGGATCTGGCGGAGGTGGAAGTAGTGGCGGAG<br>TGTTCACCCTGGAAGATTTCGTCGGCGATTGGGAGCAGACCGCCG<br>CCTATAATCTGGACCAGGTTCTGGAACAAGGCGGCGTCAGCTCTCT<br>GCTGCAGAATCTCGCTGTGTCTGTGACCCCTATCCAGAGAATCGTG<br>CGCTCTGGCGAGAACGCCCTGAAGATCGACATCCACGTGATCATC<br>CCTTACGAGGGCCTGTCTGCCGATCAGATGGCTCAGATCGAAGAG<br>GTGTTCAAGGTGGTGTACCCCGTGGACGACCACCACTTCAAAGTG<br>ATCCTGCCTTACGGCACCCTGGTCATCGATGGCGTGACCCCAAACA<br>TGCTGAACTACTTCGGCAGACCCTACGAGGGAATCGCCGTGTTCG<br>ACGGCAAGAAAATCACCGTGACCGGCACACTGTGGAACGGCAAC<br>AAGATCATCGACGAGCGGCTGATCACCCCTGACGGCTCTATGCTG<br>TTCCGCGTGACCATCAACTCCTAATGA |
| SEQ ID NO: 23 | α-IGF1R light-SmBiT | ATGGAAACCGACACACTGCTGCTGTGGGTGCTGTTGTTGTGGGTGC<br>CAGGATCTACAGGCGACGTCGTGATGACCCAGTCTCCTCTGTCTCT<br>GCCTGTGACACCTGGCGAGCCTGCCTCCATCTCTTGCAGATCTTCT<br>CAGTCCCTGCTGCACTCCAACGGCTACAACTACCTGGACTGGTATC<br>TGCAGAAGCCCGGCCAGTCTCCACAGCTGCTGATCTACCTGGGCTC<br>TAACAGAGCCTCTGGCGTGCCCGATAGATTCTCTGGCTCTGGATCT<br>GGCACCGACTTCACCCTGAAGATCTCCAGAGTGGAAGCCGAGGAC<br>GTGGGCGTGTACTACTGTATGCAGGGCACCCACTGGCCTCTGACCT<br>TTGGACAGGGCACCAAGGTGGAAATCAAGAGAACCGTGGCCGCTC<br>CTTCCGTGTTCATCTTCCCACCATCTGACAGCAGCTGAAGTCCGG<br>CACAGCTTCTGTCGTGTGCCTGCTGAACAACTTCTACCCTCGGGAA<br>GCCAAGGTGCAGTGGAAGGTGGACAATGCCCTGCAGTCCGGCAAC<br>TCCCAAGAGTCTGTGACCGAGCAGGACTCCAAGGACTCTACCTAC<br>AGCCTGTCCTCCACACTGACCCTGTCTAAGGCCGACTACGAGAAG<br>CACAAGGTGTACGCCTGTGAAGTGACCCACCAGGGACTGTCTAGC<br>CCCGTGACCAAGTCTTTCAACAGAGGCGAGTGCGGATCTTCTGGT<br>GGCGGAGGATCTGGCGGAGGTGGAAGTAGTGGCGGCGTGACCGG<br>CTACAGACTGTTCGAAGAGATCCTGTAATGA |

TABLE 1-continued

Nucleic acid sequences of ORFs.

| SEQ ID NO | Description | Nucleic Acid Sequence |
|---|---|---|
| SEQ ID NO: 24 | α-IGF1R light | ATGGAAACCGACACACTGCTGCTGTGGGTGCTGTTGTTGTGGGTGC CAGGATCTACAGGCGACGTCGTGATGACCCAGTCTCCTCTGTCTCT GCCTGTGACACCTGGCGAGCCTGCCTCCATCTCTTGCAGATCTTCT CAGTCCCTGCTGCACTCCAACGGCTACAACTACCTGGACTGGTATC TGCAGAAGCCCGGCCAGTCTCCACAGCTGCTGATCTACCTGGGCTC TAACAGAGCCTCTGGCGTGCCCGATAGATTCTCTGGCTCTGGATCT GGCACCGACTTCACCCTGAAGATCTCCAGAGTGGAAGCCGAGGAC GTGGGCGTGTACTACTGTATGCAGGGCACCCACTGGCCTCTGACCT TTGGACAGGGCACCAAGGTGGAAATCAAGAGAACCGTGGCCGCTC CTTCCGTGTTCATCTTCCCACCATCTGACGAGCAGCTGAAGTCCGG CACAGCTTCTGTCGTGTGCCTGCTGAACAACTTCTACCCTCGGGAA GCCAAGGTGCAGTGGAAGGTGGACAATGCCCTGCAGTCCGGCAAC TCCCAAGAGTCTGTGACCGAGCAGGACTCCAAGGACTCTACCTAC AGCCTGTCCTCCACACTGACCCTGTCTAAGGCCGACTACGAGAAG CACAAGGTGTACGCCTGTGAAGTGACCCACCAGGGACTGTCTAGC CCCGTGACCAAGTCTTTCAACAGAGGCGAGTGCTAATGA |
| SEQ ID NO 25 | α-IGF1R heavy-LgBiT | ATGGAAACCGACACACTGCTGCTGTGGGTGCTGTTGTTGTGGGTGC CAGGATCTACAGGCGAAGTGCAGTTGTTGCAGTCTGGCGGAGGAT TGGTTCAGCCTGGCGGATCTCTGAGACTGTCTTGTGCCGCCTCCGG CTTCATGTTCAGCAGATACCCTATGCACTGGGTCCGACAGGCCCCT GGAAAAGGACTGGAATGGGTCGGATCTATCTCTGGCAGTGGCGGC GCTACCCCTTACGCTGATTCTGTGAAGGGCAGATTCACCATCAGCC GGGACAACTCCAAGAACACCCTGTACCTGCAGATGAACTCCCTGA GAGCCGAGGACACCGCCGTGTACTACTGCGCCAAGGACTTCTATC AGATCCTGACCGGCAACGCCTTCGATTATTGGGGCCAGGGCACAA CCGTGACCGTGTCCTCTGCTTCTACCAAGGGACCCTCTGTGTTCCC TCTGGCTCCTTCCAGCAAGTCTACCTCTGGTGGAACCGCTGCTCTG GGCTGCCTGGTCAAGGATTACTTTCCTGAGCCTGTGACAGTGTCCT GGAACTCTGGTGCTCTGACCTCCGGCGTGCACACATTTCCAGCTGT GCTGCAGTCCTCCGGCCTGTACTCTCTGTCCTCTGTCGTGACAGTG CCTTCCAGCTCTCTGGGCACCCAGACCTACATCTGCAACGTGAACC ACAAGCCTTCCAACACCAAGGTGGACAAGAGAGTGGAACCCAAGT CTTTGCGGATCTTCTGGTGGCGGTGGAAGTGGCGGAGGTGGAAGTT CAGGCGGAGTGTTCACCCTGGAAGATTTCGTCGGCGATTGGGAGC AGACCGCCGCCTATAATCTGGACCAGGTTCTGGAACAAGGCGGCG TTAGCTCTCTGCTGCAGAATCTGGCTGTGTCTGTGACCCCTATCCA GAGAATCGTGCGCTCTGGCGAGAACGCCCTGAAGATCGACATCCA CGTGATCATCCCTTACGAGGGCCTGTCTGCCGATCAGATGGCTCAG ATCGAAGAGGTGTTCAAGGTGGTGTACCCCGTGGACGACCACCAC TTCAAAGTGATCCTGCCTTACGGCACCCTGGTCATCGATGGCGTGA CCCCAAACATGCTGAACTACTTCGGCAGACCCTACGAGGGAATCG CCGTGTTCGACGGCAAGAAAATCACCGTGACAGGCACCCTGTGGA ACGGCAACAAGATCATCGACGAGCGGCTGATCACCCCTGACGGCT CTATGCTGTTCAGAGTGACCATCAACTCCTAATGA |
| SEQ ID NO: 26 | α-IGF1R light-SmBiT | ATGGAAACCGACACACTGCTGCTGTGGGTGCTGTTGTTGTGGGTGC CAGGCTCTACCGGCGACATCCAGATGACCCAGTCTCCAAGCTCTCT GTCTGCCTCTCTGGGCGACAGAGTGACCATCACCTGTAGAGCCTCT CAGGGCATCTCCTCCTACCTGGCCTGGTATCAGCAGAAGCCTGGC AAGGCTCCCAAGCTGCTGATCTACGCTAAGTCTACCCTGCAGTCCG GCGTGCCCTCTAGATTTTCTGGCTCTGGATCTGGCACCGACTTCAC CCTGACCATCAGTTCTCTGCAGCCTGAGGACTCCGCCACCTACTAC TGTCAGCAGTACTGGACCTTTCCTCTGACCTTCGGCGGAGGCACCA AGGTGGAAATCAAGAGAACCGTGGCCGCTCCTTCCGTGTTCATCTT CCCACCATCTGACGAGCAGCTGAAGTCCGGCACAGCTTCTGTCGT GTGCCTGCTGAACAACTTCTACCCTCGGGAAGCCAAGGTGCAGTG GAAGGTGGACAATGCCCTGCAGAGCGGCAACTCCCAAGAGTCTGT GACCGAGCAGGACTCCAAGGACTCTACCTACAGCCTGTCCTCCAC ACTGACCCTGTCTAAGGCCGACTACGAGAAGCACAAGGTGTACGC CTGTGAAGTGACCCACCAGGGACTGTCTAGCCCCGTGACCAAGTC TTTCAACAGAGGCGAGTGCGGATCTTCTGGCGGCGGAGGAAGCGG AGGCGGAGGATCTAGCGGCGGAGTTACCGGCTACAGACTGTTCGA AGAGATCCTGTAATGA |
| SEQ ID NO: 27 | α-IGF1R light | ATGGAAACCGACACACTGCTGCTGTGGGTGCTGCTCTTGTGGGTGC CAGGATCTACCGGCGACATCCAGATGACCCAGTCTCCATCCTCTCT GTCTGCCAGCCTGGGCGACAGAGTGACCATCACCTGTAGAGCCTC TCAGGGCATCTCCTCCTACCTGGCCTGGTATCAGCAGAAGCCTGGC AAGGCTCCCAAGCTGCTGATCTACGCCAAGAGCACACTGCAGTCT GGCGTGCCCTCTAGATTCTCCGGCTCTGGCTCTGGCACCGACTTTA CCCTGACAATCTCCAGCCTGCAGCCTGAGGACTCCGCCACCTACTA CTGTCAGCAGTACTGGACCTTTCCACTGACCTTCGGCGGAGGCACC AAGGTGGAAATCAAGAGAACCGTGGCCGCTCCTTCCGTGTTCATC |

TABLE 1-continued

Nucleic acid sequences of ORFs.

| SEQ ID NO | Description | Nucleic Acid Sequence |
|---|---|---|
| | | TTCCCACCTTCCGACGAGCAGCTGAAGTCCGGCACAGCTTCTGTCG<br>TGTGCCTGCTGAACAACTTCTACCCTCGGGAAGCCAAAGTGCAGT<br>GGAAGGTGGACAACGCTCTGCAGTCCGGCAACTCCCAAGAGTCTG<br>TGACCGAGCAGGACTCCAAGGACAGCACCTACAGCCTGTCCTCCA<br>CACTGACCCTGTCCAAGGCCGACTACGAGAAGCACAAGGTGTACG<br>CCTGCGAAGTGACCCATCAGGGCCTGTCTAGCCCTGTGACCAAGT<br>CTTTCAACCGGGGCGAGTGCTGATGA |
| SEQ ID NO: 28 | α-IGF1R heavy-LgBiT | ATGGAAACCGACACACTGCTGCTGTGGGTGCTGTTGTTGTGGGTGC<br>CAGGATCTACAGGCGAAGTGCAGTTGGTTCAGTCTGGCGGAGGAC<br>TGGTTAAGCCTGGCGGATCTCTGAGACTGTCTTGTGCCGCCTCTGG<br>CTTCACCTTCTCTAGCTTTGCCATGCACTGGGTCCGACAGGCCCCT<br>GGAAAAGGCCTGGAATGGATCTCCGTGATCGATACCAGAGGCGCC<br>ACCTACTACGCCGACTCTGTGAAGGGCAGATTCACCATCTCTCGGG<br>ACAACGCCAAGAACTCCCTGTACCTGCAGATGAACAGCCTGAGAG<br>CCGAGGACACCGCCGTGTACTATTGTGCCAGACTGGGCAACTTCT<br>ACTACGGCATGGATGTGTGGGGCCAGGGCACAACAGTGACCGTGT<br>CCTCTGCTTCTACCAAGGGACCCTCTGTGTTCCCTCTGGCTCCTTCC<br>AGCAAGTCTACCTCTGGTGGAACCGCTGCTCTGGGCTGCCTGGTCA<br>AGGATTACTTTCCTGAGCCTGTGACAGTGTCCTGGAACTCTGGTGC<br>TCTGACCTCCGGCGTGCACACATTTCCAGCTGTGCTGCAGTCCTCT<br>GGCCTGTACTCTCTGTCCTCTGTCGTGACCGTGCCTTCTAGCTCTCT<br>GGGCACCCAGACCTACATCTGCAACGTGAACCACAAGCCTTCCAA<br>CACCAAGGTGGACAAGAGAGTGGAACCCAAGTCTTGCGGATCTTC<br>TGGTGGCGGTGGAAGCGGAGGCGGAGGATCTAGTGGCGGAGTGTT<br>CACCCTGGAAGATTTCGTCGGCGATTGGGAGCAGACCGCCGCCTA<br>TAATCTGGACCAGGTTCTGGAACAAGGCGGCGTCAGCTCTCTGCT<br>GCAGAATCTGGCTGTGTCTGTGACCCCTATCCAGAGAATCGTGCGC<br>TCTGGCGAGAACGCCCTGAAGATCGACATCCACGTGATCATCCCTT<br>ACGAGGGCCTGTCTGCCGATCAGATGGCTCAGATCGAAGAGGTGT<br>TCAAGGTGGTGTACCCCGTGGACGACCACCACTTCAAAGTGATCC<br>TGCCTTACGGCACCCTGGTCATCGATGGCGTGACCCCAAACATGCT<br>GAACTACTTCGGCAGACCCTACGAGGGAATCGCCGTGTTCGACGG<br>CAAGAAAATCACCGTGACCGGCACACTGTGGAACGGCAACAAGAT<br>CATCGACGAGCGGCTGATCACCCCTGACGGCTCCATGCTGTTTAGA<br>GTGACCATCAACTCCTAATGA |
| SEQ ID NO: 29 | α-IGF1R light-SmBiT | ATGGAAACCGACACACTGCTGCTGTGGGTGCTGTTGTTGTGGGTGC<br>CAGGATCTACAGGCGAGATCGTGCTGACCCAGTCTCCTGGCACAT<br>TGTCTGTGTCTCCCGGCGAGAGAGCTACCCTGTCTTGTAGAGCTTC<br>CCAGTCCATCGGCTCCAGCCTGCACTGGTATCAGCAGAAACCTGG<br>ACAGGCCCCTCGGCTGCTGATTAAGTACGCCTCTCAGTCCCTGTCT<br>GGCATCCCTGACAGATTCTCTGGCTCTGGCTCCGGCACCGACTTCA<br>CCCTGACAATCTCTAGACTGGAACCCGAGGACTTCGCCGTGTACTA<br>CTGCCACCAGTCTAGCAGACTGCCTCACACCTTTGGCCAGGGCACC<br>AAGGTGGAAATCAAGAGAACCGTGGCCGCTCCTTCCGTGTTCATC<br>TTCCCACCATCTGACGAGCAGCTGAAGTCTGGCACCGCTTCTGTCG<br>TGTGCCTGCTGAACAACTTCTACCCTCGGGAAGCCAAGGTGCAGT<br>GGAAGGTGGACAATGCCCTGCAGTCCGGCAACTCCCAAGAGTCTG<br>TGACCGAGCAGGACTCCAAGGACTCTACCTACAGCCTGTCCTCCA<br>CACTGACCCTGTCTAAGGCCGACTACGAGAAGCACAAGGTGTACG<br>CCTGTGAAGTGACCCACCAGGGACTGTCTAGCCCCGTGACCAAGT<br>CTTTCAACAGAGGCGAGTGCGGATCTTCTGGTGGCGGAGGATCTG<br>GCGGAGGTGGAAGTAGTGGCGGCGTGACCGGCTACAGACTGTTCG<br>AAGAGATCCTGTAATGA |
| SEQ ID NO: 30 | α-IGF1R light | ATGGAAACCGACACACTGCTGCTGTGGGTGCTGTTGTTGTGGGTGC<br>CAGGATCTACAGGCGAGATCGTGCTGACCCAGTCTCCTGGCACAT<br>TGTCTGTGTCTCCCGGCGAGAGAGCTACCCTGTCTTGTAGAGCTTC<br>CCAGTCCATCGGCTCCAGCCTGCACTGGTATCAGCAGAAACCTGG<br>ACAGGCCCCTCGGCTGCTGATTAAGTACGCCTCTCAGTCCCTGTCT<br>GGCATCCCTGACAGATTCTCTGGCTCTGGCTCCGGCACCGACTTCA<br>CCCTGACAATCTCTAGACTGGAACCCGAGGACTTCGCCGTGTACTA<br>CTGCCACCAGTCTAGCAGACTGCCTCACACCTTTGGCCAGGGCACC<br>AAGGTGGAAATCAAGAGAACCGTGGCCGCTCCTTCCGTGTTCATC<br>TTCCCACCATCTGACGAGCAGCTGAAGTCTGGCACCGCTTCTGTCG<br>TGTGCCTGCTGAACAACTTCTACCCTCGGGAAGCCAAGGTGCAGT<br>GGAAGGTGGACAATGCCCTGCAGTCCGGCAACTCCCAAGAGTCTG<br>TGACCGAGCAGGACTCCAAGGACTCTACCTACAGCCTGTCCTCCA<br>CACTGACCCTGTCTAAGGCCGACTACGAGAAGCACAAGGTGTACG<br>CCTGTGAAGTGACCCACCAGGGACTGTCTAGCCCCGTGACCAAGT<br>CTTTCAACAGAGGCGAGTGCTAATGA |
| SEQ ID | α-IGF1R heavy- | ATGGAAACCGACACACTGCTGCTGTGGGTGCTGTTGTTGTGGGTGC<br>CAGGATCTACCGGACAGGTGGAACTGGTTGAATCTGGTGGCGGAG |

TABLE 1-continued

Nucleic acid sequences of ORFs.

| SEQ ID NO | Description | Nucleic Acid Sequence |
|---|---|---|
| SEQ ID NO: 31 | LgBiT | TGGTGCAGCCTGGCAGATCTCAGAGACTGTCTTGTGCCGCCTCTGG<br>CTTCACCTTCTCCTCTTACGGCATGCACTGGGTCCGACAGGCCCCT<br>GGAAAAGGACTGGAATGGGTCGCCATCATTTGGTTCGACGGCTCC<br>TCTACCTACTACGCCGATTCTGTGCGGGGCAGATTCACCATCTCTC<br>GGGACAACTCCAAGAACACCCTGTACCTGCAGATGAACTCCCTGA<br>GAGCCGAGGATACCGCCGTGTACTTCTGTGCCAGAGAGCTGGGGA<br>GAAGATACTTCGATCTGTGGGGCAGAGGCACCCTGGTGTCTGTGT<br>CCTCTGCTTCTACCAAGGGACCCAGCGTTTTCCCTCTGGCTCCATC<br>CTCTAAGTCCACCTCTGGTGGAACCGCTGCTCTGGGCTGTCTGGTC<br>AAGGATTACTTCCCTGAGCCTGTGACCGTGTCCTGGAACTCTGGTG<br>CTCTGACATCCGGCGTGCACACCTTTCCAGCTGTGCTGCAGTCCTC<br>TGGCCTGTACTCTCTGTCCTCTGTCGTGACCGTGCCTTCTTCTAGCC<br>TGGGCACCCAGACCTACATCTGCAACGTGAACCACAAGCCTTCCA<br>ACACCAAAGTGGACAAGAGAGTGGAACCCAAGTCTTGCGGATCTT<br>CTGGCGGCGGAGGAAGCGGAGGCGGAGGATCTAGCGGCGGAGTG<br>TTCACCCTGGAAGATTTCGTCGGCGATTGGGAGCAGACCGCCGCC<br>TATAATCTGGACCAGGTTCTGGAACAAGGCGGCGTGTCCTCTCTGC<br>TGCAGAATCTGGCTGTGTCTGTGACCCCTATCCAGAGAATCGTGCG<br>CTCTGGCGAGAACGCCCTGAAGATCGACATCCACGTGATCATCCC<br>TTACGAGGGCCTGTCTGCCGATCAGATGGCCCAGATTGAAGAGGT<br>GTTCAAGGTGGTGTACCCCGTGGACGACCACCACTTCAAAGTGAT<br>CCTGCCTTACGGCACCCTCGTGATCGATGGCGTGACCCCAAACATG<br>CTGAACTACTTCGGCAGACCCTACGAGGGAATCGCCGTGTTCGAT<br>GGCAAGAAAATCACCGTGACCGGCACACTGTGGAACGGCAACAA<br>GATCATCGACGAGCGGCTGATCACCCCTGACGGCTCTATGCTGTTC<br>AGAGTGACCATCAACTCCTAATGA |
| SEQ ID NO: 32 | α-IGF1R light-SmBiT | ATGGAAACCGACACACTGCTGCTGTGGGTGCTGTTGTTGTGGGTGC<br>CAGGATCTACAGGCGAGATCGTGCTGACCCAGTCTCCTGCCACATT<br>GTCTCTGAGTCCTGGCGAGAGAGCTACCCTGTCTTGCAGAGCTTCC<br>CAGTCCGTGTCCTCCTACCTGGCCTGGTATCAGCAGAAACCTGGAC<br>AGGCCCCTCGGCTGCTGATCTACGATGCTTCTAAGAGAGCCACAG<br>GCATCCCCGCCAGATTTTCTGGCTCTGGATCTGGCACCGACTTCAC<br>CCTGACCATCTCTAGCCTGGAACCTGAGGACTTCGCCGTGTACTAC<br>TGCCAGCAGAGATCCAAGTGGCCTCCTTGGACCTTTGGACAGGGC<br>ACCAAGGTGGAATCTAAGAGAACCGTGGCCGCTCCTTCCGTGTTC<br>ATCTTCCCCACCATCTGACGAGCAGCTGAAGTCCGGCACAGCTTCTG<br>TCGTGTGCCTGCTGAACAACTTCTACCCTCGGGAAGCCAAGGTGC<br>AGTGGAAGGTGGACAATGCCCTGCAGTCCGGCAACTCCCAAGAGT<br>CTGTGACCGAGCAGGACTCCAAGGACTCTACCTACAGCCTGTCCTC<br>CACACTGACCCTGTCTAAGGCCGACTACGAGAAGCACAAGGTGTA<br>CGCCTGTGAAGTGACCCACCAGGGACTGTCTAGCCCCGTGACCAA<br>GTCTTTCAACAGAGGCGAGTGCGGATCTTCTGGTGGCGGAGGATC<br>TGGCGGAGGCGGATCTAGTGGCGGAGTGACCGGCTACAGACTGTT<br>CGAAGAGATCCTGTAATGA |
| SEQ ID NO: 33 | α-IGF1R LgBiT | ATGGAAACCGACACACTGCTGCTGTGGGTGCTGTTGTTGTGGGTGC<br>GTCTCTGAGTCCTGGCGAGAGAGCTACCCTGTCTTGCAGAGCTTCC<br>CAGTCCGTGTCCTCCTACCTGGCCTGGTATCAGCAGAAACCTGGAC<br>AGGCCCCTCGGCTGCTGATCTACGATGCTTCTAAGAGAGCCACAG<br>GCATCCCCGCCAGATTTTCTGGCTCTGGATCTGGCACCGACTTCAC<br>CCTGACCATCTCTAGCCTGGAACCTGAGGACTTCGCCGTGTACTAC<br>TGCCAGCAGAGATCCAAGTGGCCTCCTTGGACCTTTGGACAGGGC<br>ACCAAGGTGGAATCTAAGAGAACCGTGGCCGCTCCTTCCGTGTTC<br>ATCTTCCCCACCATCTGACGAGCAGCTGAAGTCCGGCACAGCTTCTG<br>TCGTGTGCCTGCTGAACAACTTCTACCCTCGGGAAGCCAAGGTGC<br>AGTGGAAGGTGGACAATGCCCTGCAGTCCGGCAACTCCCAAGAGT<br>CTGTGACCGAGCAGGACTCCAAGGACTCTACCTACAGCCTGTCCTC<br>CACACTGACCCTGTCTAAGGCCGACTACGAGAAGCACAAGGTGTA<br>CGCCTGTGAAGTGACCCACCAGGGACTGTCTAGCCCCGTGACCAA<br>GTCTTTCAACAGAGGCGAGTGCTAATGA |
| SEQ ID NO: 34 | α-IL6R heavy-light | ATGGAAACCGACACACTGCTGCTGTGGGTGCTGTTGTTGTGGGTGC<br>CAGGATCTACAGGCGAGGTGCAGTTGGTTGAATCTGGCGGAGGAC<br>TGGTGCAGCCTGGCAGATCTCTGAGACTGTCTTGCGCCGCCTCCAG<br>ATTCACCTTCGACGATTACGCCATGCACTGGGTCCGACAGGCCCCT<br>GGAAAAGGATTGGAGTGGGTGTCCGGCATCTCCTGGAACTCTGGC<br>AGAATCGGCTACGCCGACTCCGTGAAGGGCAGATTCACAATCTCC<br>CGGGACAACGCCGAGAACTCCCTGTTCCTGCAGATGAATGGCCTG<br>AGAGCCGAGGACACCGCTCTGTACTATTGCGCCAAGGGCAGAGAC<br>TCCTTCGATATCTGGGGCCAGGGCACCATGGTCACCGTGTCCTCTG<br>CTTCTACCAAGGGACCCTCTGTGTTCCCTCTGGCTCCTTCCAGCAA<br>GTCTACCTCTGGTGGAACCGCTGCTCTGGGCTGCCTGGTCAAGGAT<br>TACTTTCCTGAGCCTGTGACCGTGTCTTGGAACTCCGGTGCTCTGA<br>CATCCGGCGTGCACACATTTCCAGCTGTGCTGCAGTCCTCTGGCCT |

TABLE 1-continued

Nucleic acid sequences of ORFs.

| SEQ ID NO | Description | Nucleic Acid Sequence |
|---|---|---|
| | | GTACTCTCTGTCCTCTGTCGTGACCGTGCCTTCTAGCTCTCTGGGCA CCCAGACCTACATCTGCAACGTGAACCACAAGCCTTCCAACACCA AGGTGGACAAGAGAGTGGAACCCAAGTCTTGCGGATCTTCTGGTG GCGGTGGAAGCGGAGGCGGAGGATCTAGTGGCGGAGTGTTCACCC TGGAAGATTTCGTCGGCGATTGGGAGCAGACCGCCGCCTATAATC TGGACCAGGTTCTGGAACAAGGCGGCGTCAGCTCTCTGCTGCAGA ATCTGGCTGTGTCTGTGACCCCTATCCAGAGAATCGTGCGCTCTGG CGAGAACGCCCTGAAGATCGACATCCACGTGATCATCCCTTACGA GGGCCTGTCTGCCGATCAGATGGCTCAGATCGAAGAGGTGTTCAA GGTGGTGTACCCCGTGGACGACCACCACTTCAAAGTGATCCTGCCT TACGGCACCCTGGTCATCGATGGCGTGACCCCAAACATGCTGAAC TACTTCGGCAGACCCTACGAGGAATCGCCGTGTTCGACGGCAAG AAAATCACCGTGACCGGCACACTGTGGAACGGCAACAAGATCATC GACGAGCGGCTGATCACCCCTGACGGCTCTATGCTGTTCAGAGTG ACCATCAACTCCTAATGA |
| SEQ ID NO: 35 | α-IL6R light-SmBiT | ATGGAAACCGACACACTGCTGCTGTGGGTGCTGTTGTTGTGGGTGC CAGGCTCTACCGGCGACATCCAGATGACCCAGTCTCCATCCTCTGT GTCTGCCTCTGTGGGCGACAGAGTGACCATCACCTGTAGAGCCTCT CAGGGCATCTCTAGCTGGCTGGCCTGGTATCAGCAGAAGCCTGGA AAGGCCCCTAAGCTGCTGATCTACGGCGCCTCTTCTCTGGAATCTG GCGTGCCCTCTAGATTCTCCGGCTCTGGCTCTGGCACCGACTTTAC CCTGACAATCAGCTCCCTGCAGCCTGAGGACTTCGCCTCTTACTAC TGCCAGCAGGCCAACAGCTTCCCCTATACCTTTGGCCAGGGCACC AAGCTGGAAATCAAGAGAACCGTGGCCGCTCCTTCCGTGTTCATCT TCCCACCATCTGACGAGCAGCTGAAGTCCGGCACAGCTTCTGTCGT GTGCCTGCTGAACAACTTCTACCCTCGGGAAGCCAAGGTGCAGTG GAAGGTGGACAATGCCCTGCAGTCCGGCAACTCCCAAGAGTCTGT GACCGAGCAGGACTCCAAGGACTCTACCTACAGCCTGTCCTCCAC ACTGACCCTGTCTAAGGCCGACTACGAGAAGCACAAGGTGTACGC CTGTGAAGTGACCCACCAGGGACTGTCTAGCCCCGTGACCAAGTC TTTCAACAGAGGCGAGTGCGGATCTTCTGGTGGCGGAGGATCTGG CGGAGGTGGAAGTAGTGGCGGCGTGACCGGCTACAGACTGTTCGA AGAGATCCTGTAATGA |
| SEQ ID NO: 36 | α-IL6R light | ATGGAAACCGACACACTGCTGCTGTGGGTGCTGTTGTTGTGGGTGC CAGGCTCTACCGGCGACATCCAGATGACCCAGTCTCCATCCTCTGT GTCTGCCTCTGTGGGCGACAGAGTGACCATCACCTGTAGAGCCTCT CAGGGCATCTCTAGCTGGCTGGCCTGGTATCAGCAGAAGCCTGGA AAGGCCCCTAAGCTGCTGATCTACGGCGCCTCTTCTCTGGAATCTG GCGTGCCCTCTAGATTCTCCGGCTCTGGCTCTGGCACCGACTTTAC CCTGACAATCAGCTCCCTGCAGCCTGAGGACTTCGCCTCTTACTAC TGCCAGCAGGCCAACAGCTTCCCCTATACCTTTGGCCAGGGCACC AAGCTGGAAATCAAGAGAACCGTGGCCGCTCCTTCCGTGTTCATCT TCCCACCATCTGACGAGCAGCTGAAGTCCGGCACAGCTTCTGTCGT GTGCCTGCTGAACAACTTCTACCCTCGGGAAGCCAAGGTGCAGTG GAAGGTGGACAATGCCCTGCAGTCCGGCAACTCCCAAGAGTCTGT GACCGAGCAGGACTCCAAGGACTCTACCTACAGCCTGTCCTCCAC ACTGACCCTGTCTAAGGCCGACTACGAGAAGCACAAGGTGTACGC CTGTGAAGTGACCCACCAGGGACTGTCTAGCCCCGTGACCAAGTC TTTCAACAGAGGCGAGTGCTAATGA |
| SEQ ID NO: 37 | α-LINGO-1 heavy-LgBiT | ATGGAAACCGACACACTGCTGCTGTGGGTGCTGTTGTTGTGGGTGC CAGGATCTACAGGCGAGGTGCAGTTGTTGGAATCTGGCGGAGGAT TGGTGCAGCCTGGCGGATCTCTGAGACTGTCTTGTGCCGCCTCTGG CTTCACCTTCTCCGCCTATGAGATGAAGTGGGTCCGACAGGCTCCT GGCAAAGGACTGGAATGGGTGTCCGTGATTGGCCCTTCTGGCGGC TTTACCTTTTACGCCGACTCCGTGAAGGGCAGATTCACCATCTCTC GGGACAACTCCAAGAACACCCTGTACCTGCAGATGAACTCCCTGA GAGCCGAGGACACCGCCGTGTACTATTGTGCCACCGAGGGCGACA ACGACGCCTTTGATATTTGGGGCCAGGGCACCACCGTGACCGTGT CCTCTGCTTCTACAAAGGGCCCCTCTGTGTTCCCTCTGGCTCCTTCC TCTAAATCCACCTCTGGCGGAACCGCTGCTCTGGGCTGTCTGGTCA AGGATTACTTCCCTGAGCCTGTGACAGTGTCCTGGAACTCTGGTGC TCTGACATCCGGCGTGCACACCTTTCCAGCTGTGCTGCAGTCCTCT GGCCTGTACTCTCTGTCCTCTGTCGTGACAGTGCCTTCCAGCTCTCT GGGCACCCAGACCTACATCTGCAACGTGAACCACAAGCCTTCCAA CACCAAGGTGGACAAGAGAGTGGAACCCAAGTCTTGCGGATCTTC CGGCGGAGGTGGAAGTGGCGGAGGCGGATCAAGCGGCGGAGTGT TCACACTGGAAGATTTCGTCGGCGATTGGGAGCAGACCGCCGCCT ATAATCTGGACCAGGTTCTGGAACAAGGCGGCGTTAGCTCTCTGCT GCAGAATCTGGCTGTGTCTGTGACCCCTATCCAGAGAATCGTGCGC TCTGGCGAGAACGCCCTGAAGATCGACATCCACGTGATCATCCCTT ACGAGGGCCTGTCTGCCGATCAGATGGCTCAGATCGAAGAGGTGT TCAAGGTGGTGTACCCCGTGGACGACCACCACTTCAAAGTGATCC |

TABLE 1-continued

Nucleic acid sequences of ORFs.

| SEQ ID NO | Description | Nucleic Acid Sequence |
|---|---|---|
| | | TGCCTTACGGCACCCTGGTCATCGATGGCGTGACCCCAAACATGCT
GAACTACTTCGGCAGACCCTACGAGGGAATCGCCGTGTTCGACGG
CAAGAAAATCACCGTGACAGGCACCCTGTGGAACGGCAACAAGAT
CATCGACGGCGGCTGATCACCCCTGACGGCTCTATGCTGTTCAGA
GTGACCATCAACTCCTAATGA |
| SEQ ID NO: 38 | α-LINGO-1 light-SmBiT | ATGGAAACCGACACACTGCTGCTGTGGGTGCTGTTGTTGTGGGTGC
CAGGATCTACAGGCGATATCCAGATGACCCAGTCTCCTGCCACATT
GTCTCTGAGTCCTGGCGAGAGAGCTACCCTGTCTTGCAGAGCTTCC
CAGTCCGTGTCCTCCTACCTGGCCTGGTATCAGCAGAAACCTGGAC
AGGCCCCTCGGCTGCTGATCTACGATGCCTCTAATAGAGCCACAG
GCATCCCCGCCAGATTCTCTGGCTCTGGATCTGGCACCGACTTCAC
CCTGACCATCTCTAGCCTGGAACCTGAGGACTTCGCCGTGTACTAC
TGCCAGCAGAGATCCAACTGGCCTATGTACACCTTCGGCCAGGGC
ACCAAGCTGGAAATCAAGAGAACCGTGGCCGCTCCTTCCGTGTTC
ATCTTCCCACCATCTGACGAGCAGCTGAAGTCCGGCACAGCTTCTG
TCGTGTGCCTGCTGAACAACTTCTACCCTCGGGAAGCCAAGGTGC
AGTGGAAGGTGGACAATGCCCTGCAGTCCGGCAACTCCCAAGAGT
CTGTGACCGAGCAGGACTCCAAGGACTCTACCTACAGCCTGTCCTC
CACACTGACCCTGTCTAAGGCCGACTACGAGAAGCACAAGGTGTA
CGCCTGTGAAGTGACCCACCAGGGACTGTCTAGCCCCGTGACCAA
GTCTTTCAACAGAGGCGAGTGCGGATCTTCTGGTGGCGGAGGAAG
CGGAGGCGGAGGATCATCTGGCGGAGTGACCGGCTACAGACTGTT
CGAAGAGATCCTGTAATGA |
| SEQ ID NO: 39 | α-LINGO-1 light | ATGGAAACCGACACACTGCTGCTGTGGGTGCTGTTGTTGTGGGTGC
CAGGATCTACAGGCGATATCCAGATGACCCAGTCTCCTGCCACATT
GTCTCTGAGTCCTGGCGAGAGAGCTACCCTGTCTTGCAGAGCTTCC
CAGTCCGTGTCCTCCTACCTGGCCTGGTATCAGCAGAAACCTGGAC
AGGCCCCTCGGCTGCTGATCTACGATGCCTCTAATAGAGCCACAG
GCATCCCCGCCAGATTCTCTGGCTCTGGATCTGGCACCGACTTCAC
CCTGACCATCTCTAGCCTGGAACCTGAGGACTTCGCCGTGTACTAC
TGCCAGCAGAGATCCAACTGGCCTATGTACACCTTCGGCCAGGGC
ACCAAGCTGGAAATCAAGAGAACCGTGGCCGCTCCTTCCGTGTTC
ATCTTCCCACCATCTGACGAGCAGCTGAAGTCCGGCACAGCTTCTG
TCGTGTGCCTGCTGAACAACTTCTACCCTCGGGAAGCCAAGGTGC
AGTGGAAGGTGGACAATGCCCTGCAGTCCGGCAACTCCCAAGAGT
CTGTGACCGAGCAGGACTCCAAGGACTCTACCTACAGCCTGTCCTC
CACACTGACCCTGTCTAAGGCCGACTACGAGAAGCACAAGGTGTA
CGCCTGTGAAGTGACCCACCAGGGACTGTCTAGCCCCGTGACCAA
GTCTTTCAACAGAGGCGAGTGCTAATGA |
| SEQ ID NO: 40 | α-neuropilin 1 heavy-LgBiT | ATGGAAACCGACACACTGCTGCTGTGGGTGCTGTTGTTGTGGGTGC
CAGGATCTACAGGCGAGGTGCAGTTGGTTGAATCTGGCGGAGGAT
TGGTGCAGCCTGGCGGATCTCTGAGACTGTCTTGTGCCGCTCCGG
CTTCACCTTCTCCTCTTACGCTATGTCCTGGGTCCGACAGGCTCCTG
GCAAAGGATTGGAGTGGGTGTCCCAGATTTCTCCCGCTGGCGGCT
ACACCAACTACGCCGATTCTGTGAAGGGCAGATTCACCATCTCCG
CCGACACCTCCAAGAACACCGCCTACCTGCAGATGAACTCCCTGA
GAGCTGAGGACACCGCCGTGTACTATTGTGCTAGAGGCGAGCTGC
CCTACTACCGGATGTCCAAAGTGATGGATGTGTGGGGCCAGGGCA
CACTGGTTACCGTGTCCTCTGCTTCTACCAAGGGACCCTCTGTGTT
CCCTCTGGCTCCTTCCAGCAAGTCTACCTCTGGTGGAACCGCTGCT
CTGGGCTGCCTGGTCAAGGATTACTTTCCTGAGCCTGTGACCGTGT
CTTGGAACTCTGGTGCTCTGACCTCCGGCGTGCACACATTCCAGC
TGTGCTGCAGTCCTCCGGCCTGTACTCTCTGTCCTCTGTCGTGACC
GTGCCTTCTAGCTCTCTGGGCACCCAGACCTACATCTGCAACGTGA
ACCACAAGCCTTCCAACACCAAGGTGGACAAGAGAGTGGAACCCA
AGTCTTGCGGATCTTCTGGTGGCGGTGGAAGTGGCGGAGGTGGAA
GTTCAGGCGGAGTGTTCACCCTGGAAGATTTCGTCGGCGATTGGG
AGCAGACCGCCGCCTATAATCTGGACCAGGTTCTGGAACAAGGCG
GCGTCAGCTCTCTGCTGCAGAATCTGGCTGTGTCTGTGACCCCTAT
CCAGAGAATCGTGCGCTCTGGCGAGAACGCCCTGAAGATCGACAT
CCACGTGATCATCCCTTACGAGGGCCTGTCTGCCGATCAGATGGCT
CAGATCGAAGAGGTGTTCAAGGTGGTGTACCCCGTGGACGACCAC
CACTTCAAAGTGATCCTGCCTTACGGCACCCTGGTCATCGATGGCG
TGACCCCAAACATGCTGAACTACTTCGGCAGACCCTACGAGGGAA
TCGCCGTGTTCGACGGCAAGAAAATCACCGTGACCGGCACACTGT
GGAACGGCAACAAGATCATCGACGAGCGGCTGATCACCCCTGACG
GCTCTATGCTGTTCAGAGTGACCATCAACTCCTAATGA |
| SEQ ID NO: 41 | α-neuropilin 1 light-SmBiT | ATGGAAACCGACACACTGCTGCTGTGGGTGCTGTTGTTGTGGGTGC
CAGGCTCTACCGGCGACATCCAGATGACCCAGTCTCCATCCTCTCT
GTCTGCCTCTGTGGGCGACAGAGTGACCATCACCTGTCGGGCCTCT
CAGTACTTCTCCTCCTACCTGGCCTGGTATCAGCAGAAAGCCTGGCA |

TABLE 1-continued

Nucleic acid sequences of ORFs.

| SEQ ID NO | Description | Nucleic Acid Sequence |
|---|---|---|
| | | AGGCTCCCAAGCTGCTGATCTACGGCGCCTCTTCTAGAGCCTCTGG<br>CGTGCCATCTAGATTCTCCGGCTCTGGCTCTGGCACCGACTTTACC<br>CTGACAATCAGCTCCCTGCAGCCTGAGGACTTCGCCACCTACTACT<br>GTCAGCAGTACCTGGGCTCTCCTCCAACCTTTGGCCAGGGCACCAA<br>GGTGGAAATCAAGAGAACCGTGGCCGCTCCTTCCGTGTTCATCTTC<br>CCACCATCTGACGAGCAGCTGAAGTCCGGCACAGCTTCTGTCGTGT<br>GCCTGCTGAACAACTTCTACCCTCGGGAAGCCAAGGTGCAGTGGA<br>AGGTGGACAATGCCCTGCAGTCCGGCAACTCCCAAGAGTCTGTGA<br>CCGAGCAGGACTCCAAGGACTCTACCTACAGCCTGTCCTCCACACT<br>GACCCTGTCTAAGGCCGACTACGAGAAGCACAAGGTGTACGCCTG<br>TGAAGTGACCCACCAGGGACTGTCTAGCCCCGTGACCAAGTCTTTC<br>AACAGAGGCGAGTGCGGATCTTCTGGTGGCGGAGGATCTGGCGGA<br>GGTGGAAGTAGTGGCGGCGTGACCGGCTACAGACTGTTCGAAGAG<br>ATCCTGTAATGA |
| SEQ ID NO: 42 | α-neuropilin 1 light | ATGGAAACCGACACACTGCTGCTGTGGGTGCTGTTGTTGTGGGTGC<br>CAGGCTCTACCGGCGACATCCAGATGACCCAGTCTCCATCCTCTCT<br>GTCTGCCTCTGTGGGCGACAGAGTGACCATCACCTGTCGGGCCTCT<br>CAGTACTTCTCCTCCTACCTGGCCTGGTATCAGCAGAAGCCTGGCA<br>AGGCTCCCAAGCTGCTGATCTACGGCGCCTCTTCTAGAGCCTCTGG<br>CGTGCCATCTAGATTCTCCGGCTCTGGCTCTGGCACCGACTTTACC<br>CTGACAATCAGCTCCCTGCAGCCTGAGGACTTCGCCACCTACTACT<br>GTCAGCAGTACCTGGGCTCTCCTCCAACCTTTGGCCAGGGCACCAA<br>GGTGGAAATCAAGAGAACCGTGGCCGCTCCTTCCGTGTTCATCTTC<br>CCACCATCTGACGAGCAGCTGAAGTCCGGCACAGCTTCTGTCGTGT<br>GCCTGCTGAACAACTTCTACCCTCGGGAAGCCAAGGTGCAGTGGA<br>AGGTGGACAATGCCCTGCAGTCCGGCAACTCCCAAGAGTCTGTGA<br>CCGAGCAGGACTCCAAGGACTCTACCTACAGCCTGTCCTCCACACT<br>GACCCTGTCTAAGGCCGACTACGAGAAGCACAAGGTGTACGCCTG<br>TGAAGTGACCCACCAGGGACTGTCTAGCCCCGTGACCAAGTCTTTC<br>AACAGAGGCGAGTGCTAATGA |
| SEQ ID NO: 43 | α-CD221 heavy-LgBiT | ATGGAAACCGATACATTGCTTGCTGTGGGTGCTGTTGTTGTGGGTGC<br>CAGGATCTACAGGCGAAGTGCAGTTGGTGCAGTCTGGCGCCGAAG<br>TGAAGAAACCTGGCTCCTCTGTGAAGGTGTCCTGCAAGGCTTCTGG<br>CGGCACCTTCTCCTCTTACGCCATCTCTTGGGTCCGACAGGCTCCT<br>GGACAAGGCTTGGAGTGGATGGGCGGCATCATCCCTATCTTCGGC<br>ACCGCCAACTACGCCCAGAAATTCCAGGGCAGAGTGACCATCACC<br>GCCGACAAGTCTACCTCCACCGCCTACATGGAACTGTCCAGCCTG<br>AGATCTGAGGACACCGCCGTGTACTACTGTGCTAGAGCCCCTCTGC<br>GGTTCCTGGAATGGTCTACCCAGGACCACTACTACTATTACTACAT<br>GGACGTGTGGGGCAAGGGCACCACCGTGACAGTTTCTTCCGCTTC<br>CACCAAGGGACCCAGCGTTTTCCCTCTGGCTCCATCCTCCAAGTCC<br>ACCTCTGGTGGAACAGCTGCTCTGGGCTGCCTGGTCAAGGATTACT<br>TTCCTGAGCCTGTGACCGTGTCCTGGAACTCTGGTGCTCTGACATC<br>CGGCGTGCACACCTTTCCAGCTGTGCTGCAGTCCTCTGGCCTGTAC<br>TCTCTGTCCTCTGTCGTGACCGTGCCTTCTAGCTCTCTGGGCACCCA<br>GACCTACATCTGCAACGTGAACCACAAGCCTTCCAACACCAAAGT<br>GGACAAGAGAGTGGAACCCAAGTCTTGCGGATCTTCCGGTGGCGG<br>AGGATCTGGCGGAGGTGGAAGTAGTGGCGGAGTGTTCACCCTGGA<br>AGATTTCGTCGGCGATTGGGAGCAGACCGCCGCCTATAATCTGGA<br>CCAGGTTCTGGAACAAGGCGGCGTGTCCTCTCTGCTGCAGAATCTG<br>GCTGTGTCTGTGACCCCTATCCAGAGAATCGTGCGCTCTGGCGAGA<br>ACGCCCTGAAGATCGACATCCACGTGATCATCCCTTACGAGGGCC<br>TGTCTGCCGATCAGATGGCTCAGATCGAAGAGGTGTTCAAGGTGG<br>TGTACCCCGTGGACGACCACCACTTCAAAGTGATCCTGCCTTACGG<br>CACCCTGGTCATCGATGGCGTGACCCCAAACATGCTGAACTACTTC<br>GGCAGACCCTACGAGGGAATCGCCGTGTTCGACGGCAAGAAAATC<br>ACCGTGACCGGCACACTGTGGAACGGCAACAAGATCATCGACGAG<br>CGGCTGATCACCCCTGACGGCTCTATGCTGTTTAGAGTGACAATCA<br>ACTCCTAATGA |
| SEQ ID NO: 44 | α-CD221 light-SmBiT | ATGGAAACCGACACACTGCTGCTGTGGGTGCTGTTGTTGTGGGTGC<br>CAGGCTCTACCGGATCCTCTGAGTTGACACAGGACCCTGCTGTGTC<br>TGTGGCTCTGGGACAGACAGTGCGGATTACCTGTCAGGGCGACTC<br>CCTGAGATCTTACTACGCCACCTGGTATCAGCAGAAGCCCGGACA<br>GGCTCCCATCCTGGTTATCTACGGCGAGAACAAGCGGCCCTCTGG<br>CATCCCTGATAGATTCTCTGGCTCCTCCTCCGGCAATACCGCCTCT<br>CTGACAATTACTGGCGCCCAGGCTGAGGACGAGGCCGACTACTAT<br>TGCAAGTCCAGAGATGGCTCTGGCCAGCACTTGGTGTTTGCGGC<br>GGAACAAAACTGACCGTGCTGGGCCAGCCTAAGGCCAATCCTACA<br>GTGACCCTGTTTCCTCCATCCTCCGAGGAACTGCAGGCCAACAAG<br>GCTACCCTCGTGTGCCTGATCTCTGACTTTTACCCTGGCGCTGTGA<br>CCGTGGCTTGGAAGGCTGATGGATCTCCTGTGAAGGCCGGCGTGG<br>AAACCACCAAGCCTAGCAAGCAGTCCAACAACAAATACGCCGCCT |

TABLE 1-continued

Nucleic acid sequences of ORFs.

| SEQ ID NO | Description | Nucleic Acid Sequence |
|---|---|---|
| | | CCTCCTACCTGTCTCTGACCCCTGAACAGTGGAAGTCCCACCGGTC<br>CTACTCTTGCCAAGTGACCCATGAGGGCTCCACCGTGGAAAAGAC<br>AGTGGCCCCTACCGAGTGCTCTGGATCTTCTGGTGGCGGAGGATCT<br>GGCGGAGGTGGAAGTAGTGGCGGCGTGACCGGCTACAGACTGTTC<br>GAAGAGATCCTGTAATGA |
| SEQ ID NO: 45 | α-CD221 light | ATGGAAACCGACACACTGCTGCTGTGGGTGCTGCTCTTGTGGGTGC<br>CAGGCTCTACCGGATCCTCTGAGCTGACACAGGACCCTGCTGTGTC<br>TGTGGCTCTGGGCCAGACAGTGCGGATTACCTGTCAGGGCGACTC<br>CCTGAGATCCTACTACGCCACCTGGTATCAGCAGAAGCCTGGACA<br>GGCTCCCATCCTGGTCATCTACGGCGAGAACAAGCGGCCCTCTGG<br>CATCCCTGATAGATTCTCCGGCTCCTCCAGCGGCAATACCGCCTCT<br>CTGACAATTACCGGCGCTCAGGCTGAGGACGAGGCCGACTACTAC<br>TGCAAGTCCAGAGATGGCTCCGGCCAGCACCTGGTTTTTGGCGGA<br>GGAACAAAGCTGACCGTGCTGGGCCAGCCTAAGGCCAATCCTACC<br>GTGACACTGTTCCCTCCATCCTCCGAGGAACTGCAGGCCAACAAG<br>GCTACCCTCGTGTGCCTGATCTCCGACTTTTACCCTGGCGCTGTGA<br>CCGTGGCCTGGAAGGCTGATGGATCTCCTGTGAAGGCTGGCGTGG<br>AAACCACCAAGCCTTCCAAGCAGTCCAACAACAAATACGCCGCCT<br>CCTCCTACCTGTCTCTGACCCCTGAACAGTGGAAGTCCCACCGGTC<br>CTACAGCTGCCAAGTGACCCATGAGGGCTCCACCGTGGAAAAGAC<br>CGTGGCTCCTACCGAGTGCTCCTGATGA |
| SEQ ID NO: 46 | α-death receptor 5 heavy-LgBiT | ATGGAAACCGACACACTGCTGCTGTGGGTGCTGTTGTTGTGGGTGC<br>CAGGATCTACAGGCGAAGTGCAGTTGGTTCAGTCTGGCGGCGGAG<br>TTGAAAGACCTGGCGGATCTCTGAGACTGTCTTGTGCCGCCTCTGG<br>CTTCACCTTCGACGACTACGCTATGTCCTGGGTCCGACAGGCTCCT<br>GGCAAAGGATTGGAATGGGTGTCCGGCATCAACTGGCAAGGCGGC<br>TCTACCGGCTACGCCGATTCTGTGAAGGGCAGAGTGACCATCTCTC<br>GGGACAACGCCAAGAACTCCCTGTACCTGCAGATGAACAGCCTGA<br>GAGCCGAGGACACCGCCGTGTACTACTGTGCTAAGATCCTCGGCG<br>CTGGCCAGAGGCTGGTACTTCGATTATTGGGGCAAGGGCACCACCG<br>TGACCGTGTCCTCTGCTTCTACAAAGGGCCCCTCTGTGTTCCCTCT<br>GGCTCCTTCCTCTAAATCCACCTCTGGCGGAACCGCTGCTCTGGGC<br>TGTCTGGTCAAGGATTACTTCCCTGAGCCTGTGACAGTGTCCTGGA<br>ACTCTGGTGCTCTGACATCCGGCGTGCACACCTTTCCAGCTGTGCT<br>GCAGTCCTCTGGCCTGTACTCTCTGTCCTCTGTCGTGACAGTGCCTT<br>CCAGCTCTCTGGGCACCCAGACCTACATCTGCAACGTGAACCACA<br>AGCCTTCCAACACCAAGGTGGACAAGAGAGTGGAACCCAAGTCTT<br>GTGGATCTTCTGGCGGAGGTGGAAGCGGAGGCGGAGGATCAAGTG<br>GCGGAGTGTTCACCCTGGAAGATTTCGTCGGCGATTGGGAGCAGA<br>CCGCCGCCTATAATCTGGACCAGGTTCTGGAACAAGGCGGCGTTA<br>GCTCTCTGCTGCAGAATCTGGCTGTGTCTGTGACCCCTATCCAGAG<br>AATCGTGCGCTCTGGCGAGAACGCCCTGAAGATCGACATCCACGT<br>GATCATCCCTTACGAGGGCCTGTCTGCCGATCAGATGGCTCAGATC<br>GAAGAGGTGTTCAAGGTGGTATACCCCGTGGACGACCACCACTTC<br>AAAGTGATCCTGCCTTACGGCACCCTGGTCATCGATGCGTGACCC<br>CAAACATGCTGAACTACTTCGGCAGACCCTACGAGGGAATCGCCG<br>TGTTCGACGGCAAGAAAATCACCGTGACAGGCACCCTGTGGAACG<br>GCAACAAGATCATCGACGAGCGGCTGATCACCCCTGACGGCTCCA<br>TGCTGTTTCGCGTGACCATCAACTCCTAATGA |
| SEQ ID NO: 47 | α-death receptor 5 light-SmBiT | ATGGAAACCGACACACTGCTGCTGTGGGTGCTGTTGTTGTGGGTGC<br>CAGGCTCTACCGGATCCTCTGAGTTGACACAGGACCCTGCTGTGTC<br>TGTGGCTCTGGGACAGACAGTGCGGATCACCTGTTCCGGCGACTC<br>CCTGAGATCTTACTACGCCTCCTGGTATCAGCAGAAGCCTGGACA<br>GGCTCCCGTGCTGGTTATCTACGGCGCCAACAACAGACCTTCTGGC<br>ATCCCTGACAGATTCTCCGGCTCCAGCTCTGGCAATACCGCCTCTC<br>TGACAATTACCGGCGCTCAGGCTGAGGACGAGGCCGACTACTACT<br>GCAACTCTGCCGACTCTTCCGGCAATCACGTTGTGTTTGGCGGAGG<br>CACCAAGCTGACAGTGCTGGGCCAACCTAAGGCCAATCCTACCGT<br>GACACTGTTCCCTCCATCCTCCGAGGAACTGCAGGCTAACAAGGC<br>TACCCTCGTGTGCCTGATCTCCGATTTTTACCCTGGCGCTGTGACC<br>GTGGCTTGGAAGGCTGATGGATCTCCTGTGAAGGCCGGCGTGGAA<br>ACCACCAAGCCTAGCAAGCAGTCCAACAACAAATACGCCGCCTCC<br>TCCTACCTGTCTCTGACCCCTGAACAGTGGAAGTCCCACCGGTCCT<br>ACTCTTGCCAAGTGACCCATGAGGGCTCCACCGTGGAAAAGACAG<br>TGGCCCCTACCGAGTGCTCTGGATCTTCTGGTGGCGGAGGAAGCG<br>GAGGCGGAGGATCATCTGGCGGAGTGACCGGCTACAGACTGTTCG<br>AAGAGATCCTGTAATGA |
| SEQ ID NO: 48 | α-death receptor 5 light | ATGGAAACCGACACACTGCTGCTGTGGGTGCTGTTGTTGTGGGTGC<br>CAGGCTCTACCGGATCCTCTGAGTTGACACAGGACCCTGCTGTGTC<br>TGTGGCTCTGGGACAGACAGTGCGGATCACCTGTTCCGGCGACTC<br>CCTGAGATCTTACTACGCCTCCTGGTATCAGCAGAAGCCTGGACA |

TABLE 1-continued

Nucleic acid sequences of ORFs.

| SEQ ID NO | Description | Nucleic Acid Sequence |
|---|---|---|
| | | GGCTCCCGTGCTGGTTATCTACGGCGCCAACAACAGACCTTCTGGC<br>ATCCCTGACAGATTCTCCGGCTCCAGCTCTGGCAATACCGCCTCTC<br>TGACAATTACCGGCGCTCAGGCTGAGGACGAGGCCGACTACTACT<br>GCAACTCTGCCGACTCTTCCGGCAATCACGTTGTGTTTGGCGGAGG<br>CACCAAGCTGACAGTGCTGGGCCAACCTAAGGCCAATCCTACCGT<br>GACACTGTTCCCTCCATCCTCCGAGGAACTGCAGGCTAACAAGGC<br>TACCCTCGTGTGCCTGATCTCCGATTTTTACCCTGGCGCTGTGACC<br>GTGGCTTGGAAGGCTGATGGATCTCCTGTGAAGGCCGGCGTGGAA<br>ACCACCAAGCCTAGCAAGCAGTCCAACAACAAATACGCCGCCTCC<br>TCCTACCTGTCTCTGACCCCTGAACAGTGGAAGTCCCACCGGTCCT<br>ACTCTTGCCAAGTGACCCATGAGGGCTCCACCGTGGAAAAGACAG<br>TGGCCCCTACCGAGTGCTCTTAATGA |
| SEQ ID NO: 49 | α-IL23 heavy-LgBiT | ATGGAAACCGACACACTGCTGCTGTGGGTGCTGTTGTTGTGGGTGC<br>CAGGATCTACAGGCGAAGTGCAGTTGGTGCAGTCTGGCGCCGAAG<br>TGAAGAAGCCTGGCGAGTCCCTGAAGATCTCCTGCAAAGGCTCCG<br>GCTACTCCTTCTCCAACTACTGGATCGGCTGGGTCCGACAGATGCC<br>TGGCAAAGGACTGGAATGGATGGGCATCATCGACCCCTCCAACAG<br>CTACACCAGATACAGCCCTAGCTTCCAGGGCCAAGTGACCATCTC<br>CGCCGACAAGTCTATCTCCACCGCCTACCTGCAGTGGTCCTCTCTG<br>AAGGCCTCTGACACCGCCATGTACTACTGCGCCAGATGGTACTAC<br>AAGCCCTTCGATGTGTGGGGCCAGGGCACACTGGTTACCGTGTCCT<br>CTGCTTCTACCAAGGGACCCTCTGTGTTCCCTCTGGCTCCTTCCAG<br>CAAGTCTACCTCTGGTGGAACCGCTGCTCTGGGCTGCCTGGTCAAG<br>GATTACTTTCCTGAGCCTGTGACCGTGTCTTGGAACTCTGGTGCTC<br>TGACCTCCGGCGTGCACACATTTCCAGCTGTGCTGCAGTCCTCCGG<br>CCTGTACTCTCTGTCCTCTGTCGTGACCGTGCCTTCTAGCTCTCTGG<br>GCACCCAGAGACCTACATCTGCAACGTGAACCACAAGCCTTCCAACA<br>CCAAGGTGGACAAGAGAGTGGAACCCAAGTCTTGCGGATCTTCTG<br>GTGGCGGAGGATCTGGCGGAGGTGGAAGTAGTGGCGGAGTGTTCA<br>CCCTGGAAGATTTCGTCGGCGATTGGGAGCAGACCGCCGCCTATA<br>ATCTGGACCAGGTTCTGGAACAAGGCGGCGTCAGCTCTCTGCTGC<br>AGAATCTGGCTGTGTCTGTGACCCCTATCCAGAGAATCGTGCGCTC<br>TGGCGAGAACGCTCTGAAGATCGACATCCACGTGATCATCCCTTA<br>CGAGGGCCTGTCTGCCGATCAGATGGCTCAGATCGAAGAGGTGTT<br>CAAGGTGGTGTACCCCGTGGACGACCACCACTTCAAAGTGATCCT<br>GCCTTACGGCACCCTGGTCATCGATGGCGTGACCCCAAACATGCT<br>GAACTACTTCGGCAGACCCTACGAGGGAATCGCCGTGTTCGACGG<br>CAAGAAAATCACCGTGACCGGCACACTGTGGAACGGCAACAAGAT<br>CATCGACGAGCGGCTGATCACCCCTGACGGCTCTATGCTGTTCCGC<br>GTGACCATCAACTCCTAATGA |
| SEQ ID NO: 50 | α-IL23 light-SmBiT | ATGGAAACCGACACACTGCTGCTGTGGGTGCTGTTGTTGTGGGTGC<br>CAGGCTCTACAGGCCAGTCTGTTCTGACTCAGCCTCCTTCTGTTTCT<br>GGCGCTCCTGGCCAGAGAGTGACCATCTCCTGTACCGGCTCCTCCT<br>CTAACATCGGCTCTGGCTACGACGTGCACTGGTATCAGCAGCTGCC<br>TGGCACAGCCCCTAAACTGCTGATCTACGGCAACTCCAAGAGGCC<br>TTCTGGCGTGCCCGATAGATTCTCCGGCTCTAAGTCTGGCACCTCT<br>GCTTCTCTGGCTATCACCGGCCTGCAGTCTGAGGACGAGGCCGATT<br>ACTACTGCGCTTCTTGGACCGATGGCCTGAGCCTGGTTGTGTTTGG<br>CGGCGGAACAAAGCTGACAGTGCTGGGCCAGCCTAAGGCCAATCC<br>TACCGTGACACTGTTCCCTCCATCCTCCGAGGAACTGCAGGCTAAC<br>AAGGCTACCCTCGTGTGCCTGATCTCCGATTTTTACCCTGGCGCTG<br>TGACCGTGGCTTGGAAGGCTGATGGATCTCCTGTGAAGGCCGGCG<br>TGGAAACCACCAAGCCTAGCAAGCAGTCCAACAACAAATACGCCG<br>CCTCCTCCTACCTGTCTCTGACCCCTGAACAGTGGAAGTCCCACCG<br>GTCCTACTCTTGCCAAGTGACCCATGAGGGCTCCACCGTGGAAAA<br>GACAGTGGCCCCTACCGAGTGCTCTGGATCTTCTGGTGGCGGAGG<br>ATCTGGCGGAGGTGGAAGTAGTGGCGGCGTGACCGGCTACAGACT<br>GTTCGAAGAGATCCTGTAATGA |
| SEQ ID NO: 51 | α-IL23 light | ATGGAAACCGACACACTGCTGCTGTGGGTGCTGTTGTTGTGGGTGC<br>CAGGCTCTACAGGCCAGTCTGTTCTGACTCAGCCTCCTTCTGTTTCT<br>GGCGCTCCTGGCCAGAGAGTGACCATCTCCTGTACCGGCTCCTCCT<br>CTAACATCGGCTCTGGCTACGACGTGCACTGGTATCAGCAGCTGCC<br>TGGCACAGCCCCTAAACTGCTGATCTACGGCAACTCCAAGAGGCC<br>TTCTGGCGTGCCCGATAGATTCTCCGGCTCTAAGTCTGGCACCTCT<br>GCTTCTCTGGCTATCACCGGCCTGCAGTCTGAGGACGAGGCCGATT<br>ACTACTGCGCTTCTTGGACCGATGGCCTGAGCCTGGTTGTGTTTGG<br>CGGCGGAACAAAGCTGACAGTGCTGGGCCAGCCTAAGGCCAATCC<br>TACCGTGACACTGTTCCCTCCATCCTCCGAGGAACTGCAGGCTAAC<br>AAGGCTACCCTCGTGTGCCTGATCTCCGATTTTTACCCTGGCGCTG<br>TGACCGTGGCTTGGAAGGCTGATGGATCTCCTGTGAAGGCCGGCG<br>TGGAAACCACCAAGCCTAGCAAGCAGTCCAACAACAAATACGCCG<br>CCTCCTCCTACCTGTCTCTGACCCCTGAACAGTGGAAGTCCCACCG |

TABLE 1-continued

Nucleic acid sequences of ORFs.

| SEQ ID NO | Description | Nucleic Acid Sequence |
|---|---|---|
| | | GTCCTACTCTTGCCAAGTGACCCATGAGGGCTCCACCGTGGAAAA<br>GACAGTGGCCCCTACCGAGTGCTCTTAATGA |
| SEQ ID NO: 52 | α-HER3 heavy-LgBiT | ATGGAAACCGACACACTGCTGCTGTGGGTGCTGTTGTTGTGGGTGC<br>CAGGATCTACAGGACAGGTGCAGTTGGTTCAGTCTGGCGGAGGAC<br>TTGTTCAGCCAGGCGGATCTCTGAGACTGTCTTGTGCCGCCTCTGG<br>CTTCACCTTCGACGATTACGCTATGCACTGGGTCCGACAGGCCCCT<br>GGAAAAGGATTGGAATGGGTGGCCGGCATCTCCTGGGATTCTGGC<br>TCTACCGGCTACGCCGATTCCGTGAAGGGCAGATTCACCATCTCTC<br>GGGACAACGCCAAGAACTCCCTGTACCTGCAGATGAACAGCCTGA<br>GAGCCGAGGACACCGCTCTGTACTACTGTGCTAGAGATCTGGGCG<br>CCTACCAGTGGGTGGAAGGCTTTGATTATTGGGGCCAGGGCACCC<br>TGGTCACCGTGTCCTCTGCTTCTACAAAGGGCCCCTCTGTGTTCCC<br>TCTGGCTCCTTCCTCTAAATCCACCTCTGGCGGAACCGCTGCTCTG<br>GGCTGTCTGGTCAAGGATTACTTCCCTGAGCCTGTGACCGTGTCTT<br>GGAACTCTGGTGCTCTGACATCCGGCGTGCACACCTTTCCAGCTGT<br>GCTGCAGTCCTCTGGCCTGTACTCTCTGTCCTCTGTCGTGACCGTG<br>CCTTCTAGCTCTCTGGGCACCCAGACCTACATCTGCAACGTGAACC<br>ACAAGCCTAGCAACACCAAGGTGGACAAGAGAGTGGAACCCAAG<br>TCTTGCGGATCTTCTGGCGGCGGAGGAAGCGGAGGCGGAGGATCT<br>AGTGGCGGAGTGTTCACCCTGGAAGATTTCGTCGGCGATTGGGAG<br>CAGACCGCCGCCTATAATCTGGACCAGGTTCTGGAACAAGGCGGC<br>GTCAGCTCTCTGCTGCAGAATCTGGCTGTGTCTGTGACCCCTATCC<br>AGAGAATCGTGCGCTCTGGCGAGAACGCCCTGAAGATCGACATCC<br>ACGTGATCATCCCTTACGAGGGCCTGTCTGCCGATCAGATGGCTCA<br>GATCGAAGAGGTGTTCAAGGTGGTGTACCCCGTGGACGACCACCA<br>CTTCAAAGTGATCCTGCCTTACGGCACCCTCGTGATCGATGGCGTG<br>ACCCCAAACATGCTGAACTACTTCGGCAGACCCTACGAGGGAATC<br>GCCGTGTTCGACGGCAAGAAAATCACCGTGACCGGCACACTGTGG<br>AACGGCAACAAGATCATCGACGAGCGGCTGATCACCCCTGACGGC<br>TCCATGCTGTTTAGAGTGACCATCAACTCCTAATGA |
| SEQ ID NO: 53 | α-HER3 light-SmBiT | ATGGAAACCGACACACTGCTGCTGTGGGTGCTGTTGTTGTGGGTGC<br>CAGGCTCTACCGGCTCTTACGAGTTGACACAGGACCCTGCTGTGTC<br>TGTGGCTCTGGGACAGACAGTGCGGATTACCTGTCAGGGCGACTC<br>CCTGAGATCCTACTACGCCTCCTGGTATCAGCAGAAGCCTGGACA<br>GGCTCCCGTGCTGGTCATCTACGGCAAGAACAACAGACCCTCTGG<br>CATCCCTGACCGGTTCTCTGGCTCTACCTCTGGCAATTCCGCCAGC<br>CTGACAATTACTGGCGCTCAGGCTGAGGACGAGGCCGACTACTAC<br>TGCAACTCTAGAGACTCCCCTGGCAACCAGTGGGTGTTCGGCGGA<br>GGAACAAAAGTGACAGTGCTCGGCGGCCAGCCTAAGGCCAATCCT<br>ACAGTGACCCTGTTTCCTCCATCCTCCGAGGAACTGCAGGCCAACA<br>AGGCTACCCTCGTGTGCCTGATCTCTGACTTTTACCCTGGCGCTGT<br>GACCGTGGCTTGGAAGGCTGATGGATCTCCTGTGAAGGCCGGCGT<br>GGAAACCACCAAGCCTAGCAAGCAGTCCAACAACAAATACGCCGC<br>CTCCTCCTACCTGTCTCTGACCCCTGAACAGTGGAAGTCCCACCGG<br>TCCTACTCTTGCCAAGTGACCCATGAGGGCTCCACCGTGGAAAG<br>ACAGTGGCCCCTACCGAGTGCTCTGGATCTTCTGGTGGCGGAGGA<br>TCTGGCGGAGGTGGAAGTAGTGGCGGCGTGACCGGCTACAGACTG<br>TTCGAAGAGATCCTGTAATGA |
| SEQ ID NO: 54 | α-HER3 light | ATGGAAACCGACACACTGCTGCTGTGGGTGCTGCTCTTGTGGGTGC<br>CAGGCTCTACCGGCTCTTACGAGCTGACACAGGACCCTGCTGTGTC<br>TGTGGCTCTGGGCCAGACAGTGCGGATTACCTGTCAGGGCGACTC<br>CCTGAGATCCTACTACGCCTCCTGGTATCAGCAGAAGCCTGGACA<br>GGCTCCCGTGCTGGTCATCTACGGCAAGAACAACCGGCCTAGCGG<br>CATCCCTGACAGATTCTCCGGCTCTACCTCCGGCAACTCTGCCAGC<br>CTGACAATTACTGGCGCCCAGGCTGAGGACGAGGCCGACTACTAC<br>TGCAACTCCAGAGACTCCCCTGGCAACCAGTGGGTTTTCGGCGGA<br>GGCACCAAAGTGACAGTGCTCGGAGGACAGCCCAAGGCCAATCCT<br>ACCGTGACACTGTTCCCTCCATCCTCCGAGGAACTGCAGGCCAAC<br>AAGGCTACCCTCGTGTGCCTGATCTCCGACTTTTACCCTGGCGCTG<br>TGACCGTGGCCTGGAAGGCTGATGGATCTCCTGTGAAGGCTGGCG<br>TGGAAACCACCAAGCCTTCCAAGCAGTCCAACAACAAATACGCCG<br>CCTCCTCCTACCTGTCTCTGACCCCTGAACAGTGGAAGTCCCACCG<br>GTCCTACAGCTGCCAAGTGACCCATGAGGGCTCCACCGTGGAAAA<br>GACCGTGGCTCCTACCGAGTGCTCCTGATGA |
| SEQ ID NO: 55 | α-TRAILR2 heavy-LgBiT | ATGGAAACCGACACACTGCTGCTGTGGGTGCTGTTGTTGTGGGTGC<br>CAGGATCTACAGGCGAAGTGCAGTTGGTTCAGTCTGGCGGCGAG<br>TTGAAAGACCTGGCCGGATCTCTGAGACTGTCTTGTGCCGCCTCTGG<br>CTTCACCTTCGACGACTATGGCATGTCCTGGGTCCGACAGGCTCCT<br>GGCAAAGGATTGGAATGGGTGTCCGGCATCAACTGGAATGGCGGC<br>TCTACCGGCTACGCCGATTCCGTGAAGGGCAGAGTGACCATCTCTC<br>GGGACAACGCCAAGAACTCCCTGTACCTGCAGATGAACAGCCTGA |

TABLE 1-continued

Nucleic acid sequences of ORFs.

| SEQ ID NO | Description | Nucleic Acid Sequence |
|---|---|---|
| | | GAGCCGAGGACACCGCCGTGTACTACTGTGCTAAGATCCTCGGCG CTGGCAGAGGCTGGTATTTCGATCTGTGGGGCAAGGGCACCACCG TGACAGTGTCCTCTGCTTCTACCAAGGGACCCAGCGTTTTCCCTCT GGCTCCATCCTCTAAGTCCACCTCTGGTGGAACCGCTGCTCTGGGC TGTCTGGTCAAGGATTACTTCCCTGAGCCTGTGACCGTGTCCTGGA ACTCTGGTGCTCTGACATCCGGCGTGCACACCTTTCCAGCTGTGCT GCAGTCCTCTGGCCTGTACTCTCTGTCCTCTGTCGTGACCGTGCCTT CTAGCTCTCTGGGCACCCAGACCTACATCTGCAACGTGAACCACA AGCCTTCCAACACCAAAGTGGACAAGAGAGTGGAACCCAAGTCCT GCGGATCTTCTGGTGGCGGAGGATCTGGCGGAGGTGGAAGTAGTG GCGGAGTGTTCACCCTGGAAGATTTCGTCGGCGATTGGGAGCAGA CCGCCGCCTATAATCTGGACCAGGTTCTGGAACAAGGCGGCGTGT CCTCTCTGCTGCAGAATCTGGCTGTGTCTGTGACCCCTATCCAGAG AATCGTGCGCTCTGGCGAGAACGCCCTGAAGATCGACATCCACGT GATCATCCCTTACGAGGGCCTGTCTGCCGATCAGATGGCTCAGATC GAAGAGGTGTTCAAGGTGGTATACCCCGTGGACGACCACCACTTC AAAGTGATCCTGCCTTACGGCACCCTGGTCATCGATGGCGTGACCC CAAACATGCTGAACTACTTCGGCAGACCCTACGAGGGAATCGCCG TGTTCGACGGCAAGAAAATCACCGTGACCGGCACACTGTGGAACG GCAACAAGATCATCGACGAGCGGCTGATCACCCCTGACGGCTCCA TGCTGTTTCGCGTGACCATCAACTCCTAATGA |
| SEQ ID NO: 56 | α-TRAILR2 light-SmBiT | ATGGAAACCGACACACTGCTGCTGTGGGTGCTGTTGTTGTGGGTGC CAGGCTCTACCGGATCCTCTGAGTTGACACAGGACCCTGCTGTGTC TGTGGCTCTGGGACAGACAGTGCGGATTACCTGTCAGGGCGACTC CCTGAGATCCTACTACGCCTCCTGGTATCAGCAGAAGCCTGGACA GGCTCCCGTGCTGGTCATCTACGGCAAGAACAACAGACCCTCTGG CATCCCTGACCGGTTCTCCGGATCTAGCTCTGGCAATACCGCCAGC CTGACAATTACTGGCGCTCAGGCTGAGGACGAGGCCGACTACTAC TGCAACTCCAGAGACTCTTCCGGCAATCACGTGGTGTTTGGCGGCG GAACAAAGCTGACAGTGCTGGGCCAGCCTAAGGCCAATCCTACCG TGACACTGTTCCCTCCATCCTCCGAGGAACTGCAGGCTAACAAGG CTACCCTCGTGTGCCTGATCTCCGATTTTTACCCTGGCGCTGTGAC CGTGGCTTGGAAGGCTGATGGATCTCCTGTGAAGGCCGGCGTGGA AACCACCAAGCCTAGCAAGCAGTCCAACAACAAATACGCCGCCTC CTCCTACCTGTCTCTGACCCCTGAACAGTGGAAGTCCCACCGGTCC TACTCTTGCCAAGTGACCCATGAGGGCTCCACCGTGGAAAAGACA GTGGCCCCTACCGAGTGCTCTGGATCTTCTGGTGGCGGAGGATCTG GCGGAGGTGGAAGTAGTGGCGGCGTGACCGGCTACAGACTGTTCG AAGAGATCCTGTAATGA |
| SEQ ID NO: 57 | α-TRAILR2 light | ATGGAAACCGACACACTGCTGCTGTGGGTGCTGCTCTTGTGGGTGC CAGGCTCTACCGGATCCTCTGAGCTGACACAGGACCCTGCTGTGTC TGTGGCTCTGGGCCAGACAGTGCGGATTACCTGTCAGGGCGACTC CCTGAGATCCTACTACGCCTCCTGGTATCAGCAGAAGCCTGGACA GGCTCCCGTGCTGGTCATCTACGGCAAGAACAACCGGCCTAGCGG CATCCCTGACAGATTCTCCGGATCTTCCAGCGGCAATACCGCCAGC CTGACAATTACTGGCGCCCAGGCTGAGGACGAGGCCGACTACTAC TGCAACTCCAGAGACTCCTCCGGCAATCACGTGGTGTTTGGCGGC GGAACAAAGCTGACAGTGCTGGGCCAGCCTAAGGCCAATCCTACC GTGACACTGTTCCCTCCATCCTCCGAGGAACTGCAGGCCAACAAG GCTACCCTCGTGTGCCTGATCTCCGACTTTTACCCTGGCGCTGTGA CCGTGGCCTGGAAGGCTGATGGATCTCCTGTGAAGGCTGGCGTGG AAACCACCAAGCCTTCCAAGCAGTCCAACAACAAATACGCCGCCT CCTCCTACCTGTCTCTGACCCCTGAACAGTGGAAGTCCCACCGGTC CTACAGCTGCCAAGTGACCCATGAGGGCTCCACCGTGGAAAAGAC CGTGGCTCCTACCGAGTGCTCCTGATGA |
| SEQ ID NO: 58 | α-activin receptors heavy-LgBiT | ATGGAAACCGACACACTGCTGCTGTGGGTGCTGTTGTTGTGGGTGC CAGGATCTACAGGACAGGTGCAGTTGGTGCAGTCTGGCGCCGAAG TGAAGAAACCTGGCGCTTCTGTGAAGGTGTCCTGCAAGGCCTCTG GCTACACCTTTACCTCCAGCTACATCAACTGGGTCCGACAGGCTCC TGGACAGGGACTTGAGTGGATGGGCACCATCAATCCTGTGTCCGG CTCTACCAGCTACGCCCAGAAATTCCAGGGCAGAGTGACCATGAC CAGAGACACCTCCATCTCCACCGCCTACATGGAACTGTCCCGGCTG AGATCTGACGACACCGCCGTGTACTATTGTGCCAGAGGCGGATGG TTCGATTACTGGGGACAGGGCACACTGGTCACCGTGTCCTCTGCTT CTACCAAGGGACCCTCTGTGTTCCCTCTGGCTCCTTCCAGCAAGTC TACCTCTGGTGGAACCGCTGCTCTGGGCTGCCTGGTCAAGGATTAC TTTCCTGAGCCTGTGACCGTGTCTTGGAACTCTGGTGCTCTGACCT CCGGCGTGCACACATTTCCAGCTGTGCTGCAGTCCTCTCCGGCCTGTA CTCTCTGTCCTCTGTCGTGACCGTGCCTTCTAGCTCTCTGGGCACCC AGACCTACATCTGCAACGTGAACCACAAGCCTTCCAACACCAAGG TGGACAAGAGAGTGGAACCCAAGTCTTGCGGATCTTCTGGTGGCG GAGGATCTGGCGGAGGTGGAAGTAGTGGCGGAGTGTTCACCCTGG |

TABLE 1-continued

Nucleic acid sequences of ORFs.

| SEQ ID NO | Description | Nucleic Acid Sequence |
|---|---|---|
| | | AAGATTTCGTCGGCGATTGGGAGCAGACCGCCGCCTATAATCTGG<br>ACCAGGTTCTGGAACAAGGCGGCGTCAGCTCTCTGCTGCAGAATC<br>TGGCTGTGTCTGTGACCCCTATCCAGAGAATTGTGCGCTCTGGCGA<br>GAACGCCCTGAAGATCGACATCCACGTGATCATCCCTTACGAGGG<br>CCTGTCTGCCGATCAGATGGCTCAGATCGAAGAGGTGTTCAAGGT<br>GGTGTACCCCGTGGACGACCACCACTTCAAAGTGATCCTGCCTTAC<br>GGCACCCTGGTCATCGATGGCGTGACCCCAAACATGCTGAACTAC<br>TTCGGCAGACCCTACGAGGGAATCGCCGTGTTCGACGGCAAGAAA<br>ATCACCGTGACCGGCACACTGTGGAACGGCAACAAGATCATCGAC<br>GAGCGGCTGATCACCCCTGACGGCTCTATGCTGTTCCGCGTGACCA<br>TCAACTCCTAATGA |
| SEQ ID NO: 59 | α-activin receptors light-SmBiT | ATGGAAACCGACACACTGCTGCTGTGGGTGCTGTTGTTGTGGGTGC<br>CAGGCTCTACAGGCCAGTCTGCTTTGACTCAGCCTGCCTCTGTGTC<br>TGGCTCCCCTGGCCAGTCTATCACCATCTCTTGTACCGGCACCTCC<br>TCCGACGTGGGCTCCTACAACTACGTGAACTGGTATCAGCAGCAC<br>CCCGGCAAGGCCCCTAAGCTGATGATCTACGGCGTGTCCAAACGG<br>CCCAGCGGAGTGTCTAACAGATTCTCCGGCTCCAAGTCTGGCAAC<br>ACCGCTTCTCTGACAATCAGCGGACTGCAGGCCGAGGACGAGGCT<br>GATTACTACTGTGGCACCTTCGCTGGCGGCTCCTACTATGGTGTTT<br>TTGGCGGCGGAACAAAGCTGACCGTGCTGGGCCAACCTAAGGCCA<br>ATCCTACCGTGACACTGTTCCCTCCATCCTCCGAGGAACTGCAGGC<br>TAACAAGGCTACCCTCGTGTGCCTGATCTCCGATTTTTACCCTGGC<br>GCTGTGACCGTGGCTTGGAAGGCTGATGGATCTCCTGTGAAGGCC<br>GGCGTGGAAACCACCAAGCCTAGCAAGCAGTCCAACAACAAATAC<br>GCCGCCTCCTCCTACCTGTCTCTGACCCCTGAACAGTGGAAGTCCC<br>ACCGGTCCTACTCTTGCCAAGTGACCCATGAGGGCTCCACCGTGG<br>AAAAGACAGTGGCCCCTACCGAGTGCTGGATCTTCTGGTGGCG<br>GAGGATCTGGCGGAGGTGGAAGTAGTGGCGGCGTGACCGGCTACA<br>GACTGTTCGAAGAGATCCTGTAATGA |
| SEQ ID NO: 60 | α-activin receptors light | ATGGAAACCGACACACTGCTGCTGTGGGTGCTGTTGTTGTGGGTGC<br>CAGGCTCTACAGGCCAGTCTGCTTTGACTCAGCCTGCCTCTGTGTC<br>TGGCTCCCCTGGCCAGTCTATCACCATCTCTTGTACCGGCACCTCC<br>TCCGACGTGGGCTCCTACAACTACGTGAACTGGTATCAGCAGCAC<br>CCCGGCAAGGCCCCTAAGCTGATGATCTACGGCGTGTCCAAACGG<br>CCCAGCGGAGTGTCTAACAGATTCTCCGGCTCCAAGTCTGGCAAC<br>ACCGCTTCTCTGACAATCAGCGGACTGCAGGCCGAGGACGAGGCT<br>GATTACTACTGTGGCACCTTCGCTGGCGGCTCCTACTATGGTGTTT<br>TTGGCGGCGGAACAAAGCTGACCGTGCTGGGCCAACCTAAGGCCA<br>ATCCTACCGTGACACTGTTCCCTCCATCCTCCGAGGAACTGCAGGC<br>TAACAAGGCTACCCTCGTGTGCCTGATCTCCGATTTTTACCCTGGC<br>GCTGTGACCGTGGCTTGGAAGGCTGATGGATCTCCTGTGAAGGCC<br>GGCGTGGAAACCACCAAGCCTAGCAAGCAGTCCAACAACAAATAC<br>GCCGCCTCCTCCTACCTGTCTCTGACCCCTGAACAGTGGAAGTCCC<br>ACCGGTCCTACTCTTGCCAAGTGACCCATGAGGGCTCCACCGTGG<br>AAAAGACAGTGGCCCCTACCGAGTGCTCTTAATGA |
| SEQ ID NO: 61 | complement C5 heavy-LgBiT | ATGGAAACCGACACACTGCTGCTGTGGGTGCTGTTGTTGTGGGTGC<br>CAGGATCTACAGGCGAAGTGCAGTTGGTGCAGTCTGGCGCCGAAG<br>TGAAGAAACCTGGCTCCTCTGTGAAGGTGTCCTGCAAGGCTTCTGG<br>CGGCACCTTCTCCTCTTACGCCATCTCTTGGGTCCGACAGGCTCCT<br>GGACAAGGCTTGGAGTGGATGGGCGGCATCGGCCCTTTTTCGGC<br>ACCGCCAACTACGCCCAGAAATTCCAGGGCAGAGTGACCATCACC<br>GCCGACGAGTCTACCTCCACCGCTTACATGGAACTGTCCAGCCTGA<br>GATCTGAGGACACCGCCGTGTACTACTGCGCCAGAGACACCCCTT<br>ACTTCGATTATTGGGGCCAGGGCACCCTGGTCACCGTGTCCTCTGC<br>TTCTACAAAGGGCCCCTCTGTGTTCCCTCTGGCTCCTAGCTCTAAG<br>TCTACATCTGGCGGAACCGCTGCTCTGGGCTGCCTGGTCAAGGATT<br>ACTTTCCTGAGCCTGTGACCGTGTCTTGGAACTCTGGTGCTCTGAC<br>CTCCGGCGTGCACACATTTCCAGCTGTGCTGCAGTCCTCCGGCCTG<br>TACTCTCTGTCCTCTGTCGTGACCGTGCCTTCTAGCTCTCTGGGCAC<br>CCAGACCTACATCTGCAACGTGAACCACAAGCCTTCCAACACCAA<br>GGTGGACAAGAGAGTGGAACCCAAGTCTTGCGGATCTTCCGGTGG<br>CGGAGGAAGCGGAGGCGGAGGATCTAGTGGCGGAGTGTTCACCCT<br>GGAAGATTTCGTCGGCGATTGGGAGCAGACCGCCGCCTATAATCT<br>GGACCAGGTTCTGGAACAAGGCGGGGTGCCTCTCTGCTGCAGAA<br>TCTGGCTGTGTCTGTGACCCCTATCCAGAGAATCGTGCGCTCTGGC<br>GAGAACGCCCTGAAGATCGACATCCACGTGATCATCCCTTACGAG<br>GGCCTGTCTGCCGATCAGATGGCTCAGATCGAAGAGGTGTTCAAG<br>GTGGTGTACCCCGTGGACGACCACCACTTCAAAGTGATCCTGCCTT<br>ACGGCACCCTCGTGATCGATGGCGTGACCCCAAACATGCTGAACT<br>ACTTCGGCAGACCCTACGAGGGAATCGCCGTGTTCGACGGCAAGA<br>AAATCACCGTGACCGGCACACTGTGGAACGGCAACAAGATCATCG |

TABLE 1-continued

Nucleic acid sequences of ORFs.

| SEQ ID NO | Description | Nucleic Acid Sequence |
|---|---|---|
| | | ACGAGCGGCTGATCACCCCTGACGGCTCTATGCTGTTTAGAGTGAC<br>AATCAACTCCTAATGA |
| SEQ ID NO: 62 | α-complement C5 light-SmBiT | ATGGAAACCGACACACTGCTGCTGTGGGTGCTGTTGTTGTGGGTGC<br>CAGGCTCTACCGGCTCTTATGAGCTGACACAGCCTCTGTCTGTGTC<br>TGTGGCTCTGGGCCAGACCGCCAGAATCACCTGTTCTGGCGACAG<br>CATCCCCAACTACTACGTGTACTGGTATCAGCAGAAGCCCGGCCA<br>GGCTCCTGTGCTGGTCATCTACGACGACTCCAACAGACCCAGCGG<br>CATCCCTGAGAGATTCTCCGGCTCTAACTCTGGCAACACCGCCACA<br>CTGACCATCTCTAGAGCACAGGCTGGCGACGAGGCCGACTACTAC<br>TGCCAGTCTTTCGACAGCTCTCTGAACGCCGAAGTGTTCGGCGGAG<br>GCACAAAACTGACAGTGCTGGGCCAGCCTAAGGCCAATCCTACCG<br>TGACACTGTTCCCTCCATCCTCCGAGGAACTGCAGGCTAACAAGG<br>CTACCCTCGTGTGCCTGATCTCCGATTTTTACCCTGGCGCTGTGAC<br>CGTGGCTTGGAAGGCTGATGGATCTCCTGTGAAGGCCGGCGTGGA<br>AACCACCAAGCCTAGCAAGCAGTCCAACAACAAATACGCCGCCTC<br>CTCCTACCTGTCTCTGACCCCTGAACAGTGGAAGTCCCACCGGTCC<br>TACTCTTGCCAAGTGACCCATGAGGGCTCCACCGTGGAAAAGACA<br>GTGGCCCCTACCGAGTGCTCTGGATCTTCTGGTGGCGGAGGATCTG<br>GCGGAGGTGGAAGTAGTGGCGGCGTGACCGGCTACAGACTGTTCG<br>AAGAGATCCTGTAATGA |
| SEQ ID NO: 63 | α-complement C5 light | ATGGAAACCGACACACTGCTGCTGTGGGTGCTGTTGTTGTGGGTGC<br>CAGGCTCTACCGGCTCTTATGAGCTGACACAGCCTCTGTCTGTGTC<br>TGTGGCTCTGGGCCAGACCGCCAGAATCACCTGTTCTGGCGACAG<br>CATCCCCAACTACTACGTGTACTGGTATCAGCAGAAGCCCGGCCA<br>GGCTCCTGTGCTGGTCATCTACGACGACTCCAACAGACCCAGCGG<br>CATCCCTGAGAGATTCTCCGGCTCTAACTCTGGCAACACCGCCACA<br>CTGACCATCTCTAGAGCACAGGCTGGCGACGAGGCCGACTACTAC<br>TGCCAGTCTTTCGACAGCTCTCTGAACGCCGAAGTGTTCGGCGGAG<br>GCACAAAACTGACAGTGCTGGGCCAGCCTAAGGCCAATCCTACCG<br>TGACACTGTTCCCTCCATCCTCCGAGGAACTGCAGGCTAACAAGG<br>CTACCCTCGTGTGCCTGATCTCCGATTTTTACCCTGGCGCTGTGAC<br>CGTGGCTTGGAAGGCTGATGGATCTCCTGTGAAGGCCGGCGTGGA<br>AACCACCAAGCCTAGCAAGCAGTCCAACAACAAATACGCCGCCTC<br>CTCCTACCTGTCTCTGACCCCTGAACAGTGGAAGTCCCACCGGTCC<br>TACTCTTGCCAAGTGACCCATGAGGGCTCCACCGTGGAAAAGACA<br>GTGGCCCCTACCGAGTGCTCTTAATGA |
| SEQ ID NO: 64 | α-CCR2 heavy-LgBiT | ATGGAAACCGACACACTGCTGCTGTGGGTGCTGTTGTTGTGGGTGC<br>CAGGATCTACAGGCGAAGTGCAGTTGGTGCAGTCTGGCGCTGAAG<br>TGAAGAAACCTGGCGCTTCTGTGAAGGTGTCCTGCAAGGCCTCTG<br>GCTACACCTTTACCGGCTACCACATGCACTGGGTCCGACAGGCTCC<br>AGGACAAGGATTGGAGTGGATGGGCTGGATCAACCCCAACTCCGG<br>CGTGACCAAATACGCCCAGAAATTCCAGGGCAGAGTGACCATGAC<br>CAGAGACACCTCCATCAACACCGCCTACATGGAACTGTCCCGGCT<br>GAGATTCGACGACACCGACGTGTACTATTGTGCCACCGGCGGCTTT<br>GGCTATTGGGGAGAGGGAACACTGGTCACCGTGTCCTCTGCTTCTA<br>CCAAGGGACCCTCCGTGTTTCCTCTGGCTCCTTCCAGCAAGTCTAC<br>CTCTGGTGGAACCGCTGCTCTGGGCTGCCTGGTCAAGGATTACTTT<br>CCTGAGCCTGTGACCGTGTCTTGGAACTCTGGTGCTCTGACCAGCG<br>GCGTGCACACATTTCCAGCTGTGCTGCAGTCCTCCGGCCTGTACTC<br>TCTGTCCTCTGTCGTGACCGTGCCTTCTAGCTCTCTGGGCACCCAG<br>ACCTACATCTGCAACGTGAACCACAAGCCTTCCAACACCAAGGTG<br>GACAAGAGAGTGGAACCCAAGTCTTGCGGATCTTCTGGTGGCGGA<br>GGATCTGGCGGAGGTGGAAGTAGTGGCGGAGTGTTCACCCTGGAA<br>GATTTCGTCGGCGATTGGGAGCAGACCGCCGCCTATAATCTGGAC<br>CAGGTTCTGGAACAAGGCGGCGTCAGCTCTCTGCTGCAGAATCTG<br>GCTGTGTCTGTGACCCCTATCCAGAGAATCGTGCGCTCTGGCGAGA<br>ACGCCCTGAAGATCGACATCCACGTGATCATCCCTTACGAGGGCC<br>TGTCTGCCGATCAGATGGCTCAGATCGAAGAGGTGTTCAAGGTGG<br>TGTACCCCGTGGACGACCACCACTTCAAAGTGATCCTGCCTTACGG<br>CACCCTGGTCATCGATGGCGTGACCCCAAACATGCTGAACTACTTC<br>GGCAGACCCTACGAGGGAATCGCCGTGTTCGACGGCAAGAAAATC<br>ACCGTGACCGGCACACTGTGGAACGGCAACAAGATCATCGACGAG<br>CGGCTGATCACCCCTGACGGCTCTATGCTGTTCCGCGTGACCATCA<br>ACTCCTAATGA |
| SEQ ID NO: 65 | α-CCR2 light-SmBiT | ATGGAAACCGACACACTGCTGCTGTGGGTGCTGTTGTTGTGGGTGC<br>CAGGATCTACAGGCGATGTGGTCATGACCCAGACTCCTCTGAGTCT<br>TCCAGTCACACCAGGGGAGCCTGCCTCCATTAGCTGTAGATCCTCT<br>CAAGGGCCTGAGACAGACCGCTACACTGACCTGCACCGGCAACTC<br>TAACAACGTGGGAAATCAGGGCGCTGCCTGGTTGCAGCAGCATCA<br>GGGACAACCTCCAAAGCTGCTGTCCTACCGGAACCACAATAGACC<br>TTCCGGCGTGTCCGAGCGGTTCAGCCCTTCTAGATCTGGCGACACC<br>TCTAGCCTGACCATCACTGGACTGCAGCCTGAGGACGAGGCCGAT |

TABLE 1-continued

Nucleic acid sequences of ORFs.

| SEQ ID NO | Description | Nucleic Acid Sequence |
|---|---|---|
| | | TACTACTGTCTGGCCTGGGATTCTTCTCTGCGGGCCTTTGTGTTTGG<br>CACCGGCACAAAACTGACCGTGCTGGGCCAGCCTAAGGCCAATCC<br>TACCAGTGACCCTGTTTCCTCCATCCTCCGAGGAACTGCAGGCCAAC<br>AAGGCTACCCTCGTGTGCCTGATCTCTGACTTTTACCCTGGCGCTG<br>TGACCGTGGCTTGGAAGGCTGATGGATCTCCTGTGAAGGCCGGCG<br>TGGAAACCACCAAGCCTAGCAAGCAGTCCAACAACAAATACGCCG<br>CCTCCTCCTACCTGTCTCTGACCCCTGAACAGTGGAAGTCCCACCG<br>GTCCTACTCTTGCCAAGTGACCCATGAGGGCTCCACCGTGGAAAA<br>GACAGTGGCCCCTACCGAGTGCTCTGGATCTTCTGGTGGCGGAGG<br>ATCTGGCGGAGGTGGAAGTAGTGGCGGCGTGACCGGCTACAGACT<br>GTTCGAAGAGATCCTGTAATGA |
| SEQ ID NO: 66 | α-CCR2 light | ATGGAAACCGACACACTGCTGCTGTGGGTGCTGCTCTTGTGGGTGC<br>CAGGATCTACAGGACTGCCCGTGTTGACCCAGCCTCCTAGCGTTTC<br>CAAGGGCCTGAGACAGACCGCCACACTGACCTGTACCGGCAACTC<br>TAACAACGTGGGCAATCAGGGCGCTGCCTGGTTGCAGCAGCATCA<br>GGGACAGCCTCCAAAGCTGCTGTCCTACCGGAACCACAACAGACC<br>TAGCGGCGTGTCCGAGCGGTTCAGCCCTTCTAGATCTGGCGACACC<br>TCCAGCCTGACCATCACTGGACTGCAGCCTGAGGACGAGGCCGAC<br>TACTATTGTCTGGCCTGGGACAGCTCCCTGCGGGCCTTTGTTTTTG<br>GCACCGGCACCAAGCTGACCGTGCTGGGACAACCTAAGGCCAATC<br>CTACCGTGACACTGTTCCCTCCATCCTCCGAGGAACTGCAGGCCAA<br>CAAGGCTACCCTCGTGTGCCTGATCTCCGACTTTTACCCTGGCGCT<br>GTGACCGTGGCCTGGAAGGCTGATGGATCTCCTGTGAAGGCTGGC<br>GTGGAAACCACCAAGCCTTCCAAGCAGTCCAACAACAAATACGCC<br>GCCTCCTCCTACCTGTCTCTGACCCCTGAACAGTGGAAGTCCCACC<br>GGTCCTACAGCTGCCAAGTGACCCATGAGGGCTCCACCGTGGAAA<br>AGACCGTGGCTCCTACCGAGTGCTCCTGATGA |
| SEQ ID NO: 67 | α-CCR2 heavy-LgBiT | ATGGAAACCGACACACTGCTGCTGTGGGTGCTGTTGTTGTGGGTGC<br>CAGGATCTACAGGCGAGGTGCAGTTGGTTGAATCTGGCGGAGGAT<br>TGGTGCAGCCTGGCGGATCTCTGAGACTGTCTTGTGTGGCCTTCCGG<br>CTTCACCTTCTCCGACTACTGGATGTCCTGGGTCCGACAGGCTCCT<br>GGCAAAGGACTGGAATGGGTCGCCAACATCAAGAAAGACGGCTC<br>CGTGAACTACTACGTGGACTCCGTGAAGGGCAGATTCACCATCTCT<br>CGGGACAACGCCAAGAACTCCCTGTACCTGCAGATGAACAGCCTG<br>AGAGCCGAGGACACCGCCGTGTACTACTGCACCAGATTCGATTAT<br>TGGGGCCAGGGCACCCTGGTCACCGTGTCCTCTGCTTCTACAAAGG<br>GCCCCTCTGTGTTCCCTCTGGCTCCTTCCTCTAAATCACCTCTGGC<br>GGAACCGCTGCTCTGGGCTGTCTGGTCAAGGATTACTTCCCTGAGC<br>CTGTGACCGTGTCTTGGAACTCTGGTGCTCTGACATCCGGCGTGCA<br>CACCTTTCCAGCTGTGCTGCAGTCCTCTGGCCTGTACTCTCTGTCCT<br>CTGTCGTGACCGTGCCTTCTAGCTCTCTGGGCACCCAGACCTACAT<br>CTGCAACGTGAACCACAAGCCTTCCAACACCAAGGTGGACAAGAG<br>AGTGGAACCCAAGTCTTGCGGATCTTCTGGTGGTGGTGGAAGTGG<br>CGGAGGCGGTTCTTCAGGCGGAGTGTTCACCCTGGAAGATTTCGTC<br>GGCGATTGGGAGCAGACCGCCGCCTATAATCTGGACCAGGTTCTG<br>GAACAAGGCGGCGTCAGCTCTCTGCTGCAGAATCTGGCTGTGTCT<br>GTGACCCCTATCCAGAGAATCGTGCGCTCTGGCGAGAACGCCCTG<br>AAGATCGACATCCACGTGATCATCCCTTACGAGGGCCTGTCTGCCG<br>ATCAGATGGCTCAGATCGAAGAGGTGTTCAAGGTGGTGTACCCCG<br>TGGACGACCACCACTTCAAAGTGATCCTGCCTTACGGCACCCTCGT<br>GATCGATGGCGTGACCCCAAACATGCTGAACTACTTCGGCAGACC<br>CTACGAGGGAATCGCCGTGTTCGACGGCAAGAAAATCACCGTGAC<br>CGGCACACTGTGGAACGGCAACAAGATCATCGACGAGCGGCTGAT<br>CACCCCTGACGGCTCCATGCTGTTTAGAGTGACCATCAACTCCTAA<br>TGA |
| SEQ ID NO: 68 | α-CCR2 light-SmBiT | ATGGAAACCGACACACTGCTGCTGTGGGTGCTGTTGTTGTGGGTGC<br>CAGGATCTACAGGCCAGGCTGGATTGACACAGCCTCCTAGCGTGT<br>CCAAGGGCCTGAGACAGACCGCTACACTGACCTGCACCGGCAACT<br>CTAACAACGTGGGAAATCAGGGCGCTGCCTGGTTGCAGCAGCATC<br>AGGGACATCCTCCAAAGCTGCTGTTCTACCGGAACAACAATAGAG<br>CCTCCGGCATCTCCGAGCGGCTGTCTGCTTCTAGATCTGGCAATAC<br>CGCCAGCCTGACCATCACTGGACTGCAGCCTGAGGACGAGGCCGA<br>CTACTATTGCCTGACCTGGGACTCCTCTCTGTCCGTGGTTGTGTTTG<br>GCGGCGGAACAAAGCTGACAGTGCTGGGCCAGCCTAAGGCCAATC<br>CTACCGTGACACTGTTCCCTCCATCCTCCGAGGAACTGCAGGCTAA<br>CAAGGCTACCCTCGTGTGCCTGATCTCCGATTTTTACCCTGGCGCT<br>GTGACCGTGGCTTGGAAGGCTGATGGATCTCCTGTGAAGGCCGGC<br>GTGGAAACCACCAAGCCTAGCAAGCAGTCCAACAACAAATACGCC<br>GCCTCCTCCTACCTGTCTCTGACCCCTGAACAGTGGAAGTCCCACC<br>GGTCCTACTCTTGCCAAGTGACCCATGAGGGCTCCACCGTGGAAA<br>AGACAGTGGCCCCTACCGAGTGCTCTGGATCTTCTGGTGGCGGAG |

TABLE 1-continued

Nucleic acid sequences of ORFs.

| SEQ ID NO | Description | Nucleic Acid Sequence |
|---|---|---|
| | | GATCTGGCGGAGGTGGAAGTAGTGGCGGCGTGACCGGCTACAGAC<br>TGTTCGAAGAGATCCTGTAATGA |
| SEQ ID NO: 69 | α-CCR2 light | ATGGAAACCGACACACTGCTGCTGTGGGTGCTGCTCTTGTGGGTGC<br>CAGGATCTACAGGACAGGCTGGCTTGACCCAGCCTCCTAGCGTTTC<br>CAAGGGCCTGAGACAGACCGCCACACTGACCTGTACCGGCAACTC<br>TAACAACGTGGGCAATCAGGGCGCTGCCTGGTTGCAGCAGCATCA<br>GGGACATCCTCCAAAGCTGCTGTTCTACCGGAACAACAACAGAGC<br>CTCCGGCATCTCCGAGCGGCTGTCTGCTTCTAGATCCGGCAATACC<br>GCCAGCCTGACCATCACTGGACTGCAGCCTGAGGACGAGGCCGAC<br>TACTATTGCCTGACCTGGGACTCCTCTCTGTCCGTGGTGGTTTTTGG<br>CGGAGGCACCAAGCTGACAGTGCTGGGACAGCCTAAGGCCAATCC<br>TACCGTGACACTGTTCCCTCCATCCTCCGAGGAACTGCAGGCCAAC<br>AAGGCTACCCTCGTGTGCCTGATCTCCGACTTTTACCCTGGCGCTG<br>TGACCGTGGCCTGGAAGGCTGATGGATCTCCTGTGAAGGCTGGCG<br>TGGAAAACACCAAGCCTTCCAAGCAGTCCAACAACAAATACGCCG<br>CCTCCTCCTACCTGTCTCTGACCCCTGAACAGTGGAAGTCCCACCG<br>GTCCTACAGCTGCCAAGTGACCCATGAGGGCTCCACCGTGGAAAA<br>GACCGTGGCTCCTACCGAGTGCTCCTGATGA |
| SEQ ID NO: 70 | α-IL12β heavy-LgBiT | ATGGAAACCGACACACTGCTGCTGTGGGTGCTGCTCTTGTGGGTGC<br>CAGGATCTACAGGACAGGTGCAGCTGGTGGAATCTGGTGGCGGAG<br>TTGTGCAGCCTGGCAGATCCCTGAGACTGTCTTGTGCCGCCTCCGG<br>CTTCACCTTCTCCTCTTACGGAATGCACTGGGTCCGACAGGCCCCT<br>GGCAAAGGATTGGAGTGGGTCGCCTTCATCAGATACGACGGCTCC<br>AACAAGTACTACGCCGACTCCGTGAAGGGCAGATTCACCATCTCT<br>CGGGACAACTCCAAGAACACCCTGTACCTGCAGATGAACTCCCTG<br>AGAGCCGAGGACACCGCCGTGTACTACTGCAAGACCCACGGCTCT<br>CACGACAATTGGGGCCAGGGCACAATGGTCACCGTGTCCTCTGCT<br>TCCACCAAGGGACCCTCTGTGTTCCCTCTGGCTCCTTCCAGCAAGT<br>CTACCTCTGGCGGAACAGCTGCTCTGGGCTGCCTGGTCAAGGACT<br>ACTTTCCTGAGCCTGTGACCGTGTCTTGGAACTCTGGCGCTCTGAC<br>ATCCGGCGTGCACACCTTTCCAGCTGTGCTGCAATCCTCCGGCCTG<br>TACTCTCTGTCCTCCGTCGTGACCGTGCCTTCTAGCTCTCTGGGCAC<br>CCAGACCTACATCTGCAATGTGAACCACAAGCCTTCCAACACCAA<br>GGTGGACAAGAGAGTGGAACCCAAGTCCTGCGGATCTTCTGGCGG<br>CGGAGGATCTGGCGGAGGTGGTAGTTCAGGCGGAGTGTTCACCCT<br>GGAAGATTTCGTCGGCGACTGGGAGCAGACCGCCGCCTATAATCT<br>GGACCAGGTGCTGGAACAAGGCGGCGTCAGTTCTCTGCTGCAGAA<br>CCTGGCTGTGTCTGTGACCCCTATCCAGAGAATCGTGCGGAGCGG<br>CGAGAACGCCCTGAAGATCGATATCCACGTGATCATCCCTTACGA<br>GGGCCTGAGCGCCGATCAGATGGCTCAGATCGAAGAGGTGTTCAA<br>GGTGGTGTACCCCGTGGACGACCACCACTTCAAAGTGATCCTGCCT<br>TACGGCACCCTGGTCATCGATGGCGTGACCCCAAACATGCTGAAC<br>TACTTCGGCAGACCCTACGAGGGAATCGCCGTGTTCGACGGCAAG<br>AAAATCACCGTGACCGGCACACTGTGGAACGGCAACAAGATCATC<br>GACGAGCGGCTGATCACCCCTGACGGCTCTATGCTGTTCAGAGTG<br>ACCATCAACAGCTGATGA |
| SEQ ID NO: 71 | α-IL12β light-SmBiT | ATGGAAACCGACACACTGCTGCTGTGGGTGCTGCTCTTGTGGGTGC<br>CAGGATCTACCGGACAGTCCGTGTTGACCCAGCCTCCTTCTGTTTC<br>TGGCGCTCCTGGCCAGAGAGTGACCATCTCTTGCTCCGGCTCTCGG<br>TCCAACATCGGCTCCAATACCGTGAAGTGGTATCAGCAGCTGCCC<br>GGCACAGCTCCCAAACTGCTGATCTACTACAACGACCAGCGGCCT<br>TCTGGCGTGCCCGATAGATTCTCTGGCTCCAAGTCTGGCACCTCTG<br>CCAGCCTGGCTATTACCGGACTGCAGGCTGAGGACGAGGCCGACT<br>ACTACTGCCAGTCTTACGACCGGTACACCCATCCTGCTCTGCTGTT<br>TGGCACCGGCACCAAAGTGACAGTGCTGGGCCAGCCTAAGGCCAA<br>TCCTACCGTGACACTGTTCCCTCCATCCTCCGAAGAACTGCAGGCC<br>AACAAGGCTACCCTCGTGTGCCTGATCTCCGACTTTTACCCTGGCG<br>CTGTGACCGTGGCCTGGAAGGCTGATGGATCTCCTGTGAAGGCTG<br>GCGTGGAAAACACCAAGCCTTCCAAGCAGTCCAACAACAAATACG<br>CCGCCTCCTCCTACCTGTCTCTGACCCCTGAACAGTGGAAGTCCCA<br>CCGGTCCTACAGCTGCCAAGTGACCCATGAGGGCTCCACCGTGGA<br>AAAGACCGTGGCTCCTACCGAGTGCTCCGGATCTTCTGGTGGCGG<br>AGGATCTGGCGGAGGCGGTTCTTCAGGCGGAGTGACCGGCTACAG<br>ACTGTTCGAAGAGATCCTGTGATGA |
| SEQ ID NO: 72 | α-IL12β light | ATGGAAACCGACACACTGCTGCTGTGGGTGCTGCTCTTGTGGGTGC<br>CAGGATCTACCGGACAGTCCGTGTTGACCCAGCCTCCTTCTGTTTC<br>TGGCGCTCCTGGCCAGAGAGTGACCATCTCTTGCTCCGGCTCTCGG<br>TCCAACATCGGCTCCAATACCGTGAAGTGGTATCAGCAGCTGCCC<br>GGCACAGCTCCCAAACTGCTGATCTACTACAACGACCAGCGGCCT<br>TCTGGCGTGCCCGATAGATTCTCTGGCTCCAAGTCTGGCACCTCTG<br>CCAGCCTGGCTATTACCGGACTGCAGGCTGAGGACGAGGCCGACT |

TABLE 1-continued

Nucleic acid sequences of ORFs.

| SEQ ID NO | Description | Nucleic Acid Sequence |
|---|---|---|
| | | ACTACTGCCAGTCTTACGACCGGTACACCCATCCTGCTCTGCTGTT<br>TGGCACCGGCACCAAAGTGACAGTGCTGGGCCAGCCTAAGGCCAA<br>TCCTACCGTGACACTGTTCCCTCCATCCTCCGAAGAACTGCAGGCC<br>AACAAGGCTACCCTCGTGTGCCTGATCTCCGACTTTTACCCTGGCG<br>CTGTGACCGTGGCCTGGAAGGCTGATGGATCTCCTGTGAAGGCTG<br>GCGTGGAAACCACCAAGCCTTCCAAGCAGTCCAACAACAAATACG<br>CCGCCTCCTCCTACCTGTCTCTGACCCCTGAACAGTGGAAGTCCCA<br>CCGGTCCTACAGCTGCCAAGTGACCCATGAGGGCTCCACCGTGGA<br>AAAGACCGTGGCTCCTACCGAGTGCTCCTGATGA |
| SEQ ID NO: 73 | α-CTLA4 heavy-hCHIg | ATGGAAACCGACACACTGCTGCTGTGGGTGCTGCTCTTGTGGGTGC<br>CAGGATCTACAGGACAGGTGCAGCTGGTGGAATCTGGTGGCGGAG<br>TTGTGCAGCCTGGCAGATCCCTGAGACTGTCTTGTGCCGCCTCCGG<br>CTTCACCTTCTCCAGCTACACCATGCACTGGGTCCGACAGGCCCCT<br>GGCAAAGGATTGGAGTGGGTCACCTTCATCTCTTACGACGGCAAC<br>AACAAGTACTACGCCGACTCCGTGAAGGGCAGATTCACCATCTCT<br>CGGGACAACTCCAAGAACACCCTGTACCTGCAGATGAACTCCCTG<br>AGAGCCGAGGACACCGCCATCTACTACTGTGCTAGAACCGGCTGG<br>CTGGGCCCCTTTGATTATTGGGGACAGGGCACCCTGGTCACCGTGT<br>CCTCTGCTTCTACCAAGGGACCCAGCGTGTTCCCTCTGGCTCCTTC<br>CAGCAAGTCTACCTCTGGCGGAACAGCTGCTCTGGGCTGCCTGGTC<br>AAGGACTACTTTCCTGAGCCTGTGACCGTGTCTTGGAACTCTGGCG<br>CTCTGACATCCGGCGTGCACACATTTCCAGCTGTGCTGCAGTCCTC<br>CGGCCTGTACTCTCTGTCCTCTGTCGTGACCGTGCCTTCCAGCTCTC<br>TGGGAACCCAGACCTACATCTGCAATGTGAACCACAAGCCTTCCA<br>ACACCAAGGTGGACAAGAGAGTGGAACCCAAGTCCTGCGACAAG<br>ACCCACACCTGTCCACCATGTCCTGCTCCAGAACTGCTCGGCGGAC<br>CTTCCGTGTTCCTGTTTCCTCCAAAGCCTAAGGACACCCTGATGAT<br>CTCTCGGACCCCTGAAGTGACCTGCGTGGTGGTGGATGTGTCTCAC<br>GAGGATCCCGAAGTGAAGTTCAATTGGTACGTGGACGGCGTGGAA<br>GTGCACAACGCCAAGACCAAGCCTAGAGAGGAACAGTACAACTCC<br>ACCTACAGAGTGGTGTCCGTGCTGACCGTGCTGCACCAGGATTGG<br>CTGAACGGCAAAGAGTACAAGTGCAAGGTGTCCAACAAGGCCCTG<br>CCTGCTCCTATCGAAAAGACCATCTCCAAGGCCAAGGGCCAGCCT<br>AGGGAACCCCAGGTTTACACCCTGCCTCCAAGCCGGGAAGAGATG<br>ACCAAGAACCAGGTGTCCCTGACCTGCCTCGTGAAGGGATTCTAC<br>CCCTCCGATATCGCCGTGGAATGGGAGTCTAATGGCCAGCCTGAG<br>AACAACTACAAGACAACCCCTCCTGTGCTGGACTCCGACGGCTCA<br>TTCTTCCTGTACTCCAAGCTGACAGTGGACAAGTCCAGATGGCAGC<br>AGGGCAACGTGTTCTCCTGCTCCGTGATGCACGAGGCCCTGCACA<br>ATCACTACACCCAGAAGTCCCTGTCTCTGAGCCCCGGCAAGTGAT<br>GA |
| SEQ ID NO: 74 | α-IL12β heavy-hCHIg | ATGGAAACCGACACACTGCTGCTGTGGGTGCTGCTCTTGTGGGTGC<br>CAGGATCTACAGGACAGGTGCAGCTGGTGGAATCTGGTGGCGGAG<br>TTGTGCAGCCTGGCAGATCCCTGAGACTGTCTTGTGCCGCCTCCGG<br>CTTCACCTTCTCCTCTTACGGAATGCACTGGGTCCGACAGGCCCCT<br>GGCAAAGGATTGGAGTGGGTCGCCTTCATCAGATACGACGGCTCC<br>AACAAGTACTACGCCGACTCCGTGAAGGGCAGATTCACCATCTCT<br>CGGGACAACTCCAAGAACACCCTGTACCTGCAGATGAACTCCCTG<br>AGAGCCGAGGACACCGCCGTGTACTACTGCAAGACCCACGGCTCT<br>CACGACAATTGGGGCCAGGGCACAATGGTCACCGTGTCCTCTGCT<br>TCCACCAAGGGACCCTCTGTGTTCCCTCTGGCTCCTTCCAGCAAGT<br>CTACCTCTGGCGGAACAGCTGCTCTGGGCTGCCTGGTCAAGGACT<br>ACTTTCCTGAGCCTGTGACCGTGTCTTGGAACTCTGGCGCTCTGAC<br>ATCCGGCGTGCACACCTTTCCAGCTGTGCTGCAATCCTCCGGCCTG<br>TACTCTCTGTCCTCCGTCGTGACCGTGCCTTCTAGCTCTCTGGGCAC<br>CCAGACCTACATCTGCAATGTGAACCACAAGCCTTCCAACACCAA<br>GGTGGACAAGAGAGTGGAACCCAAGTCCTGCGATAAGACCCACAC<br>CTGTCCACCATGTCCTGCTCCAGAACTGCTCGGCGGACCTTCCGTG<br>TTCCTGTTTCCTCCAAAGCCTAAGGACACCCTGATGATCTCTCGGA<br>CCCCTGAAGTGACCTGCGTGGTGGTGGATGTGTCTCACGAGGATC<br>CCGAAGTGAAGTTCAATTGGTACGTGGACGGCGTGGAAGTGCACA<br>ACGCCAAGACCAAGCCTAGAGAGGAACAGTACAACTCCACCTACA<br>GAGTGGTGTCCGTGCTGACCGTGCTGCACCAGGATTGGCTGAACG<br>GCAAAGAGTACAAGTGCAAGGTGTCCAACAAGGCCCTGCCTGCTC<br>CTATCGAAAAGACCATCTCCAAGGCCAAGGGCCAGCCTAGGGAAC<br>CCCAGGTTTACACCCTGCCTCCAAGCCGGGAAGAGATGACCAAGA<br>ACCAGGTGTCCCTGACCTGCCTCGTGAAGGGATTCTACCCCTCCGA<br>TATCGCCGTGGAATGGGAGTCTAATGGCCAGCCTGAGAACAACTA<br>CAAGACCACACCTCCTGTGCTGGACTCCGACGGCTCATTCTTCCTG<br>TACTCCAAGCTGACAGTGGACAAGTCCAGATGGCAGCAGGGCAAC<br>GTGTTCTCCTGCTCCGTGATGCACGAGGCCCTGCACAATCACTACA<br>CCCAGAAGTCCCTGTCTCTGAGCCCCGGCAAGTGATGA |

TABLE 1-continued

Nucleic acid sequences of ORFs.

| SEQ ID NO | Description | Nucleic Acid Sequence |
|---|---|---|
| SEQ ID NO: 75 | α-IL12β light-hCLIg_vl-IL2 | ATGGAAACCGACACACTGCTGCTGTGGGTGCTGCTCTTGTGGGTGC CAGGATCTACCGGACAGTCCGTGTTGACCCAGCCTCCTTCTGTTTC TGGCGCTCCTGGCCAGAGAGTGACCATCTCTTGCTCCGGCTCCGG TCCAACATCGGCTCCAATACCGTGAAGTGGTATCAGCAGCTGCCC GGCACAGCTCCCAAACTGCTGATCTACTACAACGACCAGCGGCCT TCTGGCGTGCCCGATAGATTCTCTGGCTCCAAGTCTGGCACCTCTG CCAGCCTGGCTATTACCGGACTGCAGGCTGAGGACGAGGCCGACT ACTACTGCCAGTCTTACGACCGGTACACCCATCCTGCTCTGCTGTT TGGCACCGGCACCAAAGTGACAGTGCTGGGCCAGCCTAAGGCCAA TCCTACCGTGACACTGTTCCCTCCATCCTCCGAAGAACTGCAGGCC AACAAGGCTACCCTCGTGTGCCTGATCTCCGACTTTTACCCTGGCG CTGTGACCGTGGCCTGGAAGGCTGATGGATCTCCTGTGAAGGCTG GCGTGGAAACCACCAAGCCTTCCAAGCAGTCCAACAACAAATACG CCGCCTCCTCCTACCTGTCTCTGACCCCTGAACAGTGGAAGTCCCA CCGGTCCTACAGCTGCCAAGTGACCCATGAGGGCTCCACCGTGGA AAAGACCGTGGCTCCTACAGAGTGTTCTGGCGGCGGAGGATCTGG CGGAGGTGGAAGCGGAGGCGGTGGATCTGCTCCTACCTCCTCCAG CACCAAGAAAACCCAGCTGCAGTTGGAGCATCTGCTGCTGGACCT GCAGATGATCCTGAACGGCATCAACAACTACAAGAACCCCAAGCT GACCCGGATGCTGACCGCCAAGTTTGCCATGCCTAAGAAGGCCAC CGAGCTGAAACATCTGCAGTGCCTGGAAGAGGAACTGAAGCCCCT GGAAGAAGTGCTGAATCTGGCCCAGTCCAAGAACTTCCACCTGAG GCCTCGGGACCTGATCAGCAACATCAACGTGATCGTGCTCGAGCT GAAGGGCTCCGAGACAACCTTCATGTGCGAGTACGCCGACGAGAC AGCTACCATCGTGGAATTTCTGAACCGGTGGATCACCTTCTGCCAG TCCATCATCAGCACCCTGACCTGATGA |
| SEQ ID NO: 76 | α-IL12β heavy-hCHIg_Hole_Cys | ATGGAAACCGACACACTGCTGCTGTGGGTGCTGCTCTTGTGGGTGC CAGGATCTACAGGACAGGTGCAGCTGGTGGAATCTGGTGGCGGAG TTGTGCAGCCTGGCAGATCCCTGAGACTGTCTTGTGCCGCCTCCGG CTTCACCTTCTCCTCTTACGGAATGCACTGGGTCCGACAGGCCCCT GGCAAAGGATTGGAGTGGGTCGCCTTCATCAGATACGACGGCTCC AACAAGTACTACGCCGACTCCGTGAAGGGCAGATTCACCATCTCT CGGGACAACTCCAAGAACACCCTGTACCTGCAGATGAACTCCCTG AGAGCCGAGGACACCGCCGTGTACTACTGCAAGACCCACGGCTCT CACGACAATTGGGGCCAGGGCACAATGGTCACCGTGTCCTCTGCT TCCACCAAGGGACCCTCTGTGTTCCCTCTGGCTCCTTCCAGCAAGT CTACCTCTGGCGGAACAGCTGCTCTGGGCTGCCTGGTCAAGGACT ACTTTCCTGAGCCTGTGACCGTGTCTTGGAACTCTGGCGCTCTGAC ATCCGGCGTGCACACCTTTCCAGCTGTGCTGCAATCCTCCGGCCTG TACTCTCTGTCCTCCGTCGTGACCGTGCCTTCTAGCTCTCTGGGCAC CCAGACCTACATCTGCAATGTGAACCACAAGCCTTCCAACACCAA GGTGGACAAGAGAGTGGAACCCAAGTCCTGCGATAAGACCCACAC CTGTCCACCATGTCCTGCTCCAGAACTGCTCGGCGGACCTTCCGTG TTCCTGTTTCCTCCAAAGCCTAAGGACACCCTGATGATCTCTCGGA CCCCTGAAGTGACCTGCGTGGTGGTGGATGTGTCTCACGAGGATC CCGAAGTGAAGTTCAATTGGTACGTGGACGGCGTGGAAGTGCACA ACGCCAAGACCAAGCCTAGAGAGGAACAGTACAACTCCACCTACA GAGTGGTGTCCGTGCTGACCGTGCTGCACCAGGATTGGCTGAACG GCAAAGAGTACAAGTGCAAGGTGTCCAACAAGGCCCTGCCTGCTC CTATCGAAAAGACCATCTCCAAGGCCAAGGGCCAGCCTCGGGAAC CTCAAGTCTGTACCCTGCCTCCTAGCCGGGAAGAGATGACCAAGA ACCAGGTGTCCCTGTCCTGCGCTGTGAAGGGCTTCTACCCTTCCGA TATCGCCGTGGAATGGGAGAGCAATGGCCAGCCTGAGAACAACTA CAAGACCACACCTCCTGTGCTGGACTCCGACGGCTCATTCTTCCTG GTGTCCAAGCTGACAGTGGACAAGTCCAGATGGCAGCAGGGCAAC GTGTTCTCCTGCTCCGTGATGCACGAGGCCCTGCACAATCACTACA CCCAGAAGTCCCTGTCTCTGTCTCCCGGAAAAGGCGGCGGAGGAT CTGGCGGAGGTGGTAGCGGAGGCGGTGGATCTGCTCCTACCTCCT CCAGCACCAAGAAAACCCAGCTGCAGTTGGAGCATCTGCTGCTGG ACCTCCAGATGATCCTGAATGGCATCAACAATTACAAGAACCCCA AGCTCACCCGGATGCTGACCGCCAAGTTTGCCATGCCTAAGAAGG CCACCGAGCTGAAACATCTGCAGTGCCTGGAAGAGGAACTGAAGC CCCTGGAAGAAGTGCTGAATCTGGCCCAGTCCAAGAACTTCCACC TGAGGCCTCGGGACCTGATCTCCAACATCAACGTGATCGTGCTCG AGCTGAAGGGCTCCGAGACAACCTTCATGTGCGAGTACGCCGACG AGACAGCTACCATCGTGGAATTTCTGAACCGGTGGATCACCTTCTG CCAGTCCATCATCAGCACCCTGACCTGATGA |
| SEQ ID NO: 77 | α-IL12β heavy-hCHIg | ATGGAAACCGACACACTGCTGCTGTGGGTGCTGCTCTTGTGGGTGC CAGGATCTACAGGACAGGTGCAGCTGGTGGAATCTGGTGGCGGAG TTGTGCAGCCTGGCAGATCCCTGAGACTGTCTTGTGCCGCCTCCGG CTTCACCTTCTCCTCTTACGGAATGCACTGGGTCCGACAGGCCCCT GGCAAAGGATTGGAGTGGGTCGCCTTCATCAGATACGACGGCTCC AACAAGTACTACGCCGACTCCGTGAAGGGCAGATTCACCATCTCT |

TABLE 1-continued

Nucleic acid sequences of ORFs.

| SEQ ID NO | Description | Nucleic Acid Sequence |
|---|---|---|
| | | CGGGACAACTCCAAGAACACCCTGTACCTGCAGATGAACTCCCTG<br>AGAGCCGAGGACACCGCCGTGTACTACTGCAAGACCCACGGCTCT<br>CACGACAATTGGGGCCAGGGCACAATGGTCACCGTGTCCTCTGCT<br>TCCACCAAGGGACCCTCTGTGTTCCCTCTGGCTCCTTCCAGCAAGT<br>CTACCTCTGGCGGAACAGCTGCTCTGGGCTGCCTGGTCAAGGACT<br>ACTTTCCTGAGCCTGTGACCGTGTCTTGGAACTCTGGCGCTCTGAC<br>ATCCGGCGTGCACACCTTTCCAGCTGTGCTGCAATCCTCCGGCCTG<br>TACTCTCTGTCCTCCGTCGTGACCGTGCCTTCTAGCTCTCTGGGCAC<br>CCAGACCTACATCTGCAATGTGAACCACAAGCCTTCCAACACCAA<br>GGTGGACAAGAGAGTGGAACCCAAGTCCTGCGATAAGACCCACAC<br>CTGTCCACCATGTCCTGCTCCAGAACTGCTCGGCGGACCTTCCGTG<br>TTCCTGTTTCCTCCAAAGCCTAAGGACACCCTGATGATCTCTCGGA<br>CCCCTGAAGTGACCTGCGTGGTGGTGGATGTGTCTCACGAGGATC<br>CCGAAGTGAAGTTCAATTGGTACGTGGACGGCGTGGAAGTGCACA<br>ACGCCAAGACCAAGCCTAGAGAGGAACAGTACAACTCCACCTACA<br>GAGTGGTGTCCGTGCTGACCGTGCTGCACCAGGATTGGCTGAACG<br>GCAAAGAGTACAAGTGCAAGGTGTCCAACAAGGCCCTGCCTGCTC<br>CTATCGAAAAGACCATCTCCAAGGCCAAGGGCCAGCCTAGGGAAC<br>CCCAGGTTTACACCCTGCCTCCAAGCCGGGAAGAGATGACCAAGA<br>ACCAGGTGTCCCTGACCTGCCTCGTGAAGGGATTCTACCCCTCCGA<br>TATCGCCGTGGAATGGGAGTCTAATGGCCAGCCTGAGAACAACTA<br>CAAGACCACACCTCCTGTGCTGGACTCCGACGGCTCATTCTTCCTG<br>TACTCCAAGCTGACAGTGGACAAGTCCAGATGGCAGCAGGGCAAC<br>GTGTTCTCCTGCTCCGTGATGCACGAGGCCCTGCACAATCACTACA<br>CCCAGAAGTCCCTGTCTCTGTCTCCCGGAAAAGGCGGCGGAGGAT<br>CTGGCGGAGGTGGTAGCGGAGGCGGTGGATCTGCTCCTACCTCCT<br>CCAGCACCAAGAAAACCCAGCTGCAGTTGGAGCATCTGCTGCTGG<br>ACCTCCAGATGATCCTGAATGGCATCAACAATTACAAGAACCCCA<br>AGCTCACCCGGATGCTGACCGCCAAGTTTGCCATGCCTAAGAAGG<br>CCACCGAGCTGAAACATCTGCAGTGCCTGGAAGAGGAACTGAAGC<br>CCCTGGAAGAAGTGCTGAATCTGGCCCAGTCCAAGAACTTCCACC<br>TGAGGCCTCGGGACCTGATCTCCAACATCAACGTGATCGTGCTCG<br>AGCTGAAGGGCTCCGAGACAACCTTCATGTGCGAGTACGCCGACG<br>AGACAGCTACCATCGTGGAATTTCTGAACCGGTGGATCACCTTCTG<br>CCAGTCCATCATCTCCACACTGACCTGATGA |
| SEQ ID NO: 78 | α-CTLA4 heavy-hCHIg_Knob_Cys | ATGGAAACCGACACACTGCTGCTGTGGGTGCTGCTCTTGTGGGTGC<br>CAGGATCTACAGGACAGGTGCAGCTGGTGGAATCTGGTGGCGGAG<br>TTGTGCAGCCTGGCAGATCCCTGAGACTGTCTTGTGCCGCCTCCGG<br>CTTCACCTTCTCCAGCTACACCATGCACTGGGTCCGACAGGCCCCT<br>GGCAAAGGATTGGAGTGGGTCACCTTCATCTCTTACGACGGCAAC<br>AACAAGTACTACGCCGACTCCGTGAAGGGCAGATTCACCATCTCT<br>CGGGACAACTCCAAGAACACCCTGTACCTGCAGATGAACTCCCTG<br>AGAGCCGAGGACACCGCCATCTACTACTGTGCTAGAACCGGCTGG<br>CTGGGCCCCTTTGATTATTGGGGACAGGGCACCCTGGTCACCGTGT<br>CCTCTGCTTCTACCAAGGGACCCAGCGTGTTCCCTCTGGCTCCTTC<br>CAGCAAGTCTACCTCTGGCGGAACAGCTGCTCTGGGCTGCCTGGTC<br>AAGGACTACTTTCCTGAGCCTGTGACCGTGTCTTGGAACTCTGGCG<br>CTCTGACATCCGGCGTGCACACATTTCCAGCTGTGCTGCAGTCCTC<br>CGGCCTGTACTCTCTGTCCTCTGTCGTGACCGTGCCTTCCAGCTCTC<br>TGGGAACCCAGACCTACATCTGCAATGTGAACCACAAGCCTTCCA<br>ACACCAAGGTGGACAAGAGAGTGGAACCCAAGTCCTGCGACAAG<br>ACCCACACCTGTCCACCATGTCCTGCTCCAGAACTGCTCGGCGGAC<br>CTTCCGTGTTCCTGTTTCCTCCAAAGCCTAAGGACACCCTGATGAT<br>CTCTCGGACCCCTGAAGTGACCTGCGTGGTGGTGGATGTGTCTCAC<br>GAGGATCCCGAAGTGAAGTTCAATTGGTACGTGGACGGCGTGGAA<br>GTGCACAACGCCAAGACCAAGCCTAGAGAGGAACAGTACAACTCC<br>ACCTACAGAGTGGTGTCCGTGCTGACCGTGCTGCACCAGGATTGG<br>CTGAACGGCAAAGAGTACAAGTGCAAGGTGTCCAACAAGGCCCTG<br>CCTGCTCCTATCGAAAAGACCATCTCCAAGGCCAAGGGCCAGCCT<br>AGGGAACCCCAGGTTTACACCCTGCCTCCATGCCGGGAAGAGATG<br>ACCAAGAACCAGGTGTCCCTGTGGTGCCTGGTTAAGGGCTTCTACC<br>CCTCCGATATCGCCGTGGAATGGGAGTCTAATGGCCAGCCTGAGA<br>ACAACTACAAGACAACCCCTCCTGTGCTGGACTCCGACGGCTCATT<br>CTTCCTGTACTCCAAGCTGACAGTGGACAAGTCCAGATGGCAGCA<br>GGGCAACGTGTTCTCCTGCTCCGTGATGCACGAGGCCCTGCACAAT<br>CACTACACCCAGAAGTCCCTGTCTCTGAGCCCCGGCAAGTGATGA |
| SEQ ID NO: 79 | α-CTLA4 heavy-hCHIg_Knob_Cys-GH scFv | ATGGAAACCGACACACTGCTGCTGTGGGTGCTGCTCTTGTGGGTGC<br>CAGGATCTACAGGACAGGTGCAGCTGGTGGAATCTGGTGGCGGAG<br>TTGTGCAGCCTGGCAGATCCCTGAGACTGTCTTGTGCCGCCTCCGG<br>CTTCACCTTCTCCAGCTACACCATGCACTGGGTCCGACAGGCCCCT<br>GGCAAAGGATTGGAGTGGGTCACCTTCATCTCTTACGACGGCAAC<br>AACAAGTACTACGCCGACTCCGTGAAGGGCAGATTCACCATCTCT<br>CGGGACAACTCCAAGAACACCCTGTACCTGCAGATGAACTCCCTG |

TABLE 1-continued

Nucleic acid sequences of ORFs.

| SEQ ID NO | Description | Nucleic Acid Sequence |
|---|---|---|
| | | AGAGCCGAGGACACCGCCATCTACTACTGTGCTAGAACCGGCTGG CTGGGCCCCTTTGATTATTGGGGACAGGGCACCCTGGTCACCGTGT CCTCTGCTTCTACCAAGGGACCCAGCGTGTTCCCTCTGGCTCCTTC CAGCAAGTCTACCTCTGGCGGAACAGCTGCTCTGGGCTGCCTGGTC AAGGACTACTTTCCTGAGCCTGTGACCGTGTCTTGGAACTCTGGCG CTCTGACATCCGGCGTGCACACATTTCCAGCTGTGCTGCAGTCCTC CGGCCTGTACTCTCTGTCCTCTGTCGTGACCGTGCCTTCCAGCTCTC TGGGAACCCAGACCTACATCTGCAATGTGAACCACAAGCCTTCCA ACACCAAGGTGGACAAGAGAGTGGAACCCAAGTCCTGCGACAAG ACCCACACCTGTCCACCATGTCCTGCTCCAGAACTGCTCGGCGGAC CTTCCGTGTTCCTGTTTCCTCCAAAGCCTAAGGACACCCTGATGAT CTCTCGGACCCCTGAAGTGACCTGCGTGGTGGTGGATGTGTCTCAC GAGGATCCCGAAGTGAAGTTCAATTGGTACGTGGACGGCGTGGAA GTGCACAACGCCAAGACCAAGCCTAGAGAGGAACAGTACAACTCC ACCTACAGAGTGGTGTCCGTGCTGACCGTGCTGCACCAGGATTGG CTGAACGGCAAAGAGTACAAGTGCAAGGTGTCCAACAAGGCCCTG CCTGCTCCTATCGAAAAGACCATCTCCAAGGCCAAGGGCCAGCCT AGGGAACCCCAGGTTTACACCCTGCCTCCATGCCGGGAAGAGATG ACCAAGAACCAGGTGTCCCTGTGGTGCCTGGTTAAGGGCTTCTACC CCTCCGATATCGCCGTGGAATGGGAGTCTAATGGCCAGCCTGAGA ACAACTACAAGACAACCCCTCCTGTGCTGGACTCCGACGGCTCATT CTTCCTGTACTCCAAGCTGACAGTGGACAAGTCCAGATGGCAGCA GGGCAACGTGTTCTCCTGCTCCGTGATGCACGAGGCCCTGCACAAT CACTACACCCAGAAGTCCCTGTCTCTGTCTCCCGGAAAAGGCGGC GGAGGATCTGGCGGAGGTGGTAGCGGAGGCGGTGGATCTGAAGTT CAGCTGGTTGAGAGTGGCGGCGACTGGTTAAGCCTGGTGGTTCT CTGAGACTGAGCTGCGCCGCTTCTGGCTTCACATTCAGCCCCTACT CCGTGTTCTGGGTTCGACAAGCTCCAGGCAAGGGCCTCGAATGGG TGTCCTCTATCAACACCGACAGCACCTACAAGTATTACGCTGACAG CGTGAAAGGCCGGTTTACCATCAGCAGAGACAACGCCGAGAACTC CATCTTCCTCCAGATGAATTCTCTGCGCGCTGAGGATACCGCTGTG TACTACTGCGCCAGAGACAGATCCTACTACGCCTTCTCCTCCGGCT CTCTGTCTGACTACTACTACGGCCTGGATGTGTGGGGCCAGGGAA CACTTGTGACAGTGTCAAGTGGCGGTGGCGGTAGTGGCGGAGGCG GTTCTGGTGGTGGTGGTTCAGGCGGTGGTGGCAGCGATATCGTGA TGACCCAGTCTCCACTGAGCCTGAGCGTGACACCTGGCGAGCCTG CCTCTATCTCCTGCAGATCCTCTCAGTCCCTGCTGCACACCAACCT GTACAACTACCTGGATTGGTATGTGCAGAAGCCCGGCCAGTCTCCT CAGCTGCTGATCTACCTGGCCTCCAACAGAGCTTCTGGCGTGCCCG ATAGATTCTCCGGTTCTGGCTCTGGCACCGACTTCACCCTGAAGAT TTCCAGAGTGGAAACAGAGGACGTGGGCGTGTACTATTGCATGCA GGCTCTGCAGATTCCCCGGACCTTCGGCCAGGGCACCAAACTGGA AATCAAGTGATGA |
| SEQ ID NO: 80 | α-CTLA4 light- hCLIg_vk- IL2 | ATGGAAACCGACACACTGCTGCTGTGGGTGCTGCTCTTGTGGGTGC CAGGATCTACAGGCGAGATCGTGCTGACCCAGTCTCCTGGCACAC TGTCACTGTCTCCAGGCGAGAGAGCTACCCTGTCCTGTAGAGCCTC TCAGTCCGTGGGCTCCTCTTACCTGGCTTGGTATCAGCAGAAGCCC GGCCAGGCTCCTAGACTGTTGATCTACGGCGCCTTCTCCAGAGCCA CAGGCATCCCTGATAGATTCTCCGGCTCTGGCTCTGGCACCGACTT CACCCTGACCATCTCCAGACTGGAACCCGAGGACTTCGCCGTGTA CTACTGTCAGCAGTACGGCTCCTCTCCTTGGACCTTTGGCCAGGGC ACCAAGGTGGAAATCAAGCGGACAGTGGCCGCTCCTTCCGTGTTC ATCTTCCCACCTTCCGACGAGCAGCTGAAGTCCGGCACAGCTTCTG TCGTGTGCCTGCTGAACAACTTCTACCCTCGGGAAGCCAAGGTGC AGTGGAAGGTGGACAATGCCCTGCAGTCCGGCAACTCCCAAGAGT CTGTGACCGAGCAGGACTCCAAGGACAGCACCTACAGCCTGTCCT CCACACTGACCCTGTCCAAGGCCGACTACGAGAAGCACAAGGTGT ACGCCTGCGAAGTGACCCATCAGGGCCTGTCTAGCCCTGTGACCA AGTCTTTCAACAGAGGCGAGTGTGGCGGCGGAGGATCTGGCGGAG GTGGAAGCGGAGGCGGTGGATCTGCTCCTACCTCCTCCAGCACCA AGAAAACCCAGCTGCAGTTGGAGCATCTGCTGCTGGACCTGCAGA TGATCCTGAACGGCATCAACAACTACAAGAACCCCAAGCTGACCC GGATGCTGACCGCCAAGTTTGCCATGCCTAAGAAGGCCACCGAGC TGAAACATCTGCAGTGCCTGGAAGAGGAACTGAAGCCCCTGGAAG AAGTGCTGAATCTGGCCCAGTCCAAGAACTTCCACCTGAGGCCTC GGGACCTGATCTCCAACATCAACGTGATCGTGCTCGAGCTGAAGG GCTCCGAGACAACCTTCATGTGCGAGTACGCCGACGAGACTGCTA CCATCGTGGAATTTCTGAACCGGTGGATCACCTTCTGCCAGTCCAT CATCTCTACCCTGACCTGATGA |
| SEQ ID NO: | α- TRAILR2 heavy- | ATGGAAACCGACACACTGCTGCTGTGGGTGCTGCTCTTGTGGGTGC CAGGATCTACAGGCGAAGTGCAGCTGGTTCAATCTGGCGGCGAG TGGAAAGACCTGGCGGATCTCTGAGACTGTCTTGTGCCGCCTCTGG |

TABLE 1-continued

Nucleic acid sequences of ORFs.

| SEQ ID NO | Description | Nucleic Acid Sequence |
|---|---|---|
| 81 | hCHIg_Hole_Cys | CTTCACCTTCGACGACTACGGAATGTCCTGGGTCCGACAGGCTCCT<br>GGCAAAGGACTGGAATGGGTGTCCGGCATCAATTGGAACGGCGGC<br>TCTACCGGCTACGCCGACTCTGTGAAGGGCAGAGTGACCATCTCC<br>AGAGACAACGCCAAGAACTCCCTGTACCTGCAGATGAACAGCCTG<br>AGAGCCGAGGACACCGCCGTGTACTACTGTGCTAAGATCCTCGGC<br>GCTGGCAGAGGCTGGTACTTTGATCTGTGGGGCAAGGGCACCACC<br>GTGACCGTTTCTTCCGCTTCCACCAAGGGACCCAGCGTGTTCCCTC<br>TGGCTCCTTCCAGCAAGTCTACCTCTGGCGGAACAGCTGCTCTGGG<br>CTGCCTGGTCAAGGACTACTTTCCTGAGCCTGTGACCGTGTCCTGG<br>AACTCTGGCGCTCTGACATCTGGCGTGCACACCTTTCCAGCTGTGC<br>TGCAGTCCTCCGGCCTGTACTCTCTGTCCTCTGTCGTGACCGTGCCT<br>TCCAGCTCTCTGGGAACCCAGACCTACATCTGCAATGTGAACCAC<br>AAGCCTTCCAACACCAAGGTGGACAAGAGAGTGGAACCCAAGTCC<br>TGCGACAAGACCCACACCTGTCCTCCATGTCCTGCTCCAGAACTGC<br>TCGGCGGACCTTCCGTGTTCCTGTTTCCTCCAAAGCCTAAGGACAC<br>CCTGATGATCTCTCGGACCCCTGAAGTGACCTGCGTGGTGGTGGAT<br>GTGTCTCACGAGGATCCCGAAGTGAAGTTCAATTGGTACGTGGAC<br>GGCGTGGAAGTGCACAATGCCAAGACCAAGCCTAGAGAGGAACA<br>GTACAACTCCACCTACAGAGTGGTGTCCGTGCTGACCGTGCTGCAC<br>CAGGATTGGCTGAACGGCAAAGAGTACAAGTGCAAGGTGTCCAAC<br>AAGGCCCTGCCTGCTCCTATCGAAAAGACCATCAGCAAGGCCAAG<br>GGCCAGCCTCGGGAACCTCAAGTCTGTACCCTGCCTCCTAGCCGG<br>GAAGAGATGACCAAGAACCAGGTGTCCCTGTCCTGTGCCGTGAAG<br>GGCTTCTACCCTTCCGATATCGCCGTGGAATGGGAGAGCAATGGC<br>CAGCCAGAGAACAACTACAAGACAACCCCTCCTGTGCTGGACTCC<br>GACGGCTCATTCTTCCTGGTGTCCAAGCTGACAGTGGACAAGTCCA<br>GATGGCAGCAGGGCAACGTGTTCTCCTGCTCCGTGATGCACGAGG<br>CCCTGCACAATCACTACACCCAGAAGTCCCTGTCTCTGAGCCCCGG<br>CAAGTGATGA |
| SEQ ID NO: 82 | α-meso AB237 heavy-hCHIg_Knob_Cys | ATGGAAACCGATACACTGCTGCTGTGGGTGCTGCTCCTCTGGGTGC<br>CAGGATCTACAGGCCAGGTCCAGCTGCAGGAAAAGCGGCCCTGGAC<br>TGGTCAAGCCTAGCCAGACCCTGAGCCTGACCTGTACCGTGTCG<br>GCGGCAGCATCAACAACAACAATTACTACTGGACATGGATCCGGC<br>AGCACCCCGGCAAGGGCCTGGAATGGATCGGCTACATCTACTACA<br>GCGGCTCCACCTTCTACAACCCCAGCCTGAAGTCCAGAGTGACCA<br>TCAGCGTGGACACCAGCAAGACCCAGTTCTCCCTGAAGCTGAGCA<br>GCGTGACAGCCGCCGACACAGCCGTGTACTACTGCGCCAGAGAAG<br>ATACCATGACCGGCCTGGATGTGTGGGGCCAGGGCACCACAGTGA<br>CAGTGTCTAGCGCCAGCACCAAGGGCCCTAGCGTGTTCCCTCTGGC<br>CCCTAGCTCTAAGAGCACATCTGGCGGAACAGCCGCCCTGGGCTG<br>CCTGGTCAAGGATTACTTTCCTGAGCCCGTGACCGTGTCCTGGAAC<br>TCTGGTGCTCTGACCAGCGGCGTGCACACCTTTCCAGCTGTGCTGC<br>AGAGCAGCGGCCTGTACAGCCTGTCTAGCGTGGTCACAGTGCCTA<br>GCAGCAGCCTGGGCACACAGACCTACATCTGCAACGTGAACCACA<br>AGCCCAGCAACACCAAGGTGGACAAGCGGGTGGAACCCAAGAGC<br>TGCGACAAGACCCACACCTGTCCTCCCTGTCCTGCCCCTGAACTGC<br>TGGGCGGACCTTCCGTGTTCCTGTTTCCTCCAAAGCCCAAGGACAC<br>CCTGATGATCAGCCGGACCCCTGAAGTGACCTGCGTGGTGGTGGA<br>TGTGTCCCACGAGGATCCCGAAGTGAAGTTCAATTGGTACGTGGA<br>CGGCGTGGAAGTGCACAACGCCAAGACCAAGCCCAGAGAGGAAC<br>AGTACAACAGCACCTACCGGGTGGTGTCCGTGCTGACCGTGCTGC<br>ACCAGGACTGGCTGAACGGCAAAGAGTACAAGTGCAAGGTGTCCA<br>ACAAGGCCCTGCCAGCCCCTATCGAGAAAACCATCAGCAAGGCCA<br>AGGGCCAGCCCCGCGAACCTCAGGTGTACACACTGCCTCCCTGCC<br>GGGAAGAGATGACCAAGAACCAGGTGTCCCTGTGGTGTCTCGTGA<br>AGGGCTTCTACCCCTCCGATATCGCCGTGGAATGGGAGAGCAACG<br>GCCAGCCCGAGAACAACTACAAGACCACCCCTCCCGTGCTGGACA<br>GCGACGGCAGCTTCTTCCTGTACTCCAAACTGACCGTGGACAAGA<br>GCCGGTGGCAGCAGGGCAATGTGTTCAGCTGTAGCGTGATGCACG<br>AGGCCCTGCACAACCACTACACCCAGAAGTCCCTGTCCCTGAGCC<br>CTGGCAAGTAATGA |
| SEQ ID NO: 83 | α-meso AB237 light-hCLIg_vk | ATGGAAACCGATACACTGCTGCTGTGGGTGCTGCTCCTCTGGGTGC<br>CAGGCAGCACCGGCGATATCCAGATGACACAGAGCCCTAGCAGCC<br>TGAGCGCCAGCGTGGGCGATAGAGTGACCATCACCTGTCGGGCCA<br>GCCAGAGCATCAACAACTACCTGAACTGGTATCAGCAGAAGCCCG<br>GCAAGGCCCCTACCCTGCTGATCTATGCCGCTTCTAGCCTGCAGAG<br>CGGCGTGCCCAGCAGATTTTCTGGCAGCAGATCCGGCACCGACTT<br>CACCCTGACAATCAGCAGCCTGCAGCCCGAGGACTTCGCCGCCTA<br>CTTCTGCCAGCAGACCTACAGCAATCCCACCTTCGGCCAGGGCAC<br>CAAGGTGGAAGTGAAGAGAACAGTGGCCGCTCCCAGCGTGTTCAT<br>CTTCCCACCCAGCGACGAGCAGCTGAAGTCTGGCACAGCCAGCGT<br>CGTGTGCCTGCTGAACAACTTCTACCCCAGAGAAGCCAAGGTGCA<br>GTGGAAGGTGGACAACGCCCTGCAGTCCGGCAACAGCCAGGAA |

TABLE 1-continued

Nucleic acid sequences of ORFs.

| SEQ ID NO | Description | Nucleic Acid Sequence |
|---|---|---|
| | | GCGTCACCGAGCAGGACAGCAAGGACTCCACCTACAGCCTGTCCA
GCACCCTGACCCTGAGCAAGGCCGACTACGAGAAGCACAAAGTGT
ACGCCTGCGAAGTGACCCACCAGGGCCTGAGCAGCCCCGTGACCA
AGAGCTTCAATAGAGGCGAGTGCTAATGA |
| SEQ ID NO: 84 | α-PDL1 heavy-hCHIg_Hole_Cys | ATGGAAACCGATACCCTGCTGCTGTGGGTGCTGCTCCTCTGGGTGC
CAGGATCTACAGGCGAGGTGCAGCTGCTGGAATCTGGCGGAGGAC
TGGTGCAGCCTGGCGGCTCTCTGAGACTGTCTTGTGCCGCCTCCGG
CTTCACCTTCTCCAGCTATATCATGATGTGGGTCCGACAGGCCCCT
GGCAAGGGCCTGGAATGGGTGTCCTCTATCTACCCCTCCGGCGGC
ATCACCTTTTACGCCGACACCGTGAAGGGCCGGTTCACCATCTCCC
GGGACAACTCCAAGAACACCCTGTACCTGCAGATGAACTCCCTGC
GGGCCGAGGACACCGCCGTGTACTACTGCGCTAGAATCAAGCTGG
GCACCGTGACCACCGTGGACTATTGGGGCCAGGGCACCCTGGTCA
CCGTGTCCTCTGCTTCTACCAAGGGCCCCTCCGTGTTCCCTCTGGC
CCCTTCCAGCAAGTCCACCTCTGGCGGAACCGCTGCTCTGGGCTGC
CTGGTCAAGGACTACTTCCCCGAGCCCGTGACCGTGTCTTGGAACT
CTGGCGCCCTGACCAGCGGCGTGCACACATTTCCAGCCGTGCTGC
AGTCCAGCGGCCTGTACTCTCTGTCCTCCGTCGTGACAGTGCCCTC
CAGCTCTCTGGGCACACAGACCTACATCTGCAACGTGAACCACAA
GCCCTCCAACACCAAGGTGGACAAGCGGGTGGAACCCAAGTCCTG
CGACAAGACCCACACCTGTCCTCCCTGTCCTGCCCCTGAACTGCTG
GGCGGACCCAGCGTGTTCCTGTTCCCTCCAAAGCCTAAGGACACC
CTGATGATCTCCCGGACCCCTGAAGTGACCTGCGTGGTGGTGGAC
GTGTCCCACGAGGATCCCGAAGTGAAGTTCAATTGGTACGTGGAC
GGCGTGGAAGTGCACAACGCCAAGACCAAGCCTAGAGAGGAACA
GTACAACTCCACCTACCGGGTGGTGTCCGTGCTGACAGTGCTGCAT
CAGGACTGGCTGAACGGCAAAGAGTACAAGTGCAAGGTGTCCAAC
AAGGCCCTGCCAGCCCCTATCGAAAAGACCATCTCCAAGGCCAAG
GGCCAGCCAAGAGAGCCTCAAGTCTGCACACTGCCTCCCAGCCGG
GAAGAGATGACCAAGAACCAGGTGTCCCTGAGCTGCGCTGTGAAG
GGCTTCTACCCTTCCGATATCGCCGTGGAATGGGAGAGCAACGGC
CAGCCCGAGAACAATTACAAGACCACCCCTCCCGTGCTGGACTCC
GACGGCTCATTCTTCCTGGTGTCCAAGCTGACCGTGGACAAGTCCC
GGTGGCAGCAGGGCAACGTGTTCTCCTGCTCTGTGATGCACGAGG
CCCTGCACAACCACTACACCCAGAAGTCCCTGTCCCTGTCTCCCGG
CAAGTAATGA |
| SEQ ID NO: 85 | α-PDL1 light-hCLIg_v1 | ATGGAAACCGATACCCTGCTGCTGTGGGTGCTGCTCCTCTGGGTGC
CAGGCTCTACCGGCCAGTCTGCTCTGACCCAGCCTGCCTCTGTGTC
TGGCTCCCCTGGCCAGTCCATCACCATCAGCTGTACCGGCACCTCC
TCCGACGTGGGCGGCTACAACTACGTGTCCTGGTATCAGCAGCAT
CCCGGCAAGGCCCCTAAGCTGATGATCTACGACGTGTCCAACCGG
CCCTCCGGCGTGTCCAATCGGTTCTCTGGCTCCAAGTCCGGCAACA
CCGCCTCCCTGACAATCAGCGGACTGCAGGCCGAGGACGAGGCCG
ACTACTACTGCTCCTCCTACACCTCCAGCTCTACCCGGGTGTTCGG
CACCGGCACCAAAGTGACAGTGCTGGGCCAGCCCAAGGCCAACCC
CACCGTGACCCTGTTCCCTCCATCCTCCGAGGAACTGCAGGCTAAC
AAGGCCACCCTCGTGTGCCTGATCTCCGACTTCTACCCTGGCGCCG
TGACCGTGGCTTGGAAGGCTGATGGCTCTCCTGTGAAGGCCGGCG
TGGAAACCACCAAGCCCTCCAAGCAGTCCAACAACAAATACGCCG
CCTCCAGCTACCTGTCCCTGACCCCTGAGCAGTGGAAGTCCCACCG
GTCCTACAGCTGCCAGGTCACACATGAGGGCTCCACCGTGGAAAA
GACCGTGGCCCCTACCGAGTGCTCCTAATGA |
| SEQ ID NO: 86 | α-HER3 heavy-mFc Knob_Cys | ATGGAAACCGACACACTGCTGCTGTGGGTGCTGCTCTTGTGGGTGC
CAGGATCTACAGGACAGGTGCAGCTGGTTCAGTCTGGCGGAGGAT
TGGTTCAGCCAGGCGGATCCCTGAGACTGTCTTGTGCCGCCTCTGG
CTTCACCTTCGACGACTACGCTATGCACTGGGTCCGACAGGCCCCT
GGCAAGGATTGGAATGGGTGGCCGGCATCTCTTGGGACTCTGGC
TCTACCGGCTACGCCGACTCTGTGAAGGGCAGATTCACCATCTCTC
GGGACAACGCCAAGAACTCCCTGTACCTGCAGATGAACAGCCTGA
GAGCCGAGGACACCGCTCTGTACTACTGCGCTAGAGATCTGGGCG
CCTACCAGTGGGTGGAAGGCTTTGATTATTGGGGCCAGGGCACCC
TGGTCACCGTGTCCTCTGCTTCTACCAAGGGACCCAGCGTGTTCCC
TCTGGCTCCTTCCAGCAAGTCTACCTCTGGCGGAACAGCTGCTCTG
GGCTGCCTGGTCAAGGACTACTTTCCTGAGCCTGTGACCGTGTCTT
GGAACTCCGGCGCTCTGACATCTGGCGTGCACACCTTTCCAGCTGT
GCTGCAGTCCTCCGGCCTGTACTCTCTGTCCTCTGTCGTGACCGTG
CCTTCCAGCTCTCTGGGAACCCAGACCTACATCTGCAATGTGAACC
ACAAGCCTAGCAACACCAAGGTGGACAAGAGAGTGGAACCCAAG
TCCTGCGACAAGACCCACACCTGTCCTCCATGCAAGTCCCCGCTCCTA
ATCTGCTCGGAGGCCCTTCCGTGTTCATCTTCCCACCTAAGATCAA
GGACGTGCTGATGATCTCCCTGTCTCCTATCGTGACCTGCGTGGTG
GTGGACGTGTCCGAGGATGATCCTGACGTGCAGATCAGTTGGTTC TABLE 1-continued Nucleic acid sequences of ORFs.

| SEQ ID NO | Description | Nucleic Acid Sequence |
|---|---|---|
| | | GTGAACAACGTGGAAGTGCACACCGCTCAGACCCAGACACACAGA<br>GAGGACTACAACAGCACCCTGAGAGTGGTGTCTGCCCTGCCTATC<br>CAGCACCAGGATTGGATGTCCGGCAAAGAATTCAAGTGCAAAGTC<br>AACAACAAGGACCTGCCTGCTCCAATCGAGCGGACCATCTCTAAG<br>CCTAAGGGCTCTGTCAGGGCCCCTCAGGTGTACGTTCTGCCTCCTT<br>GCGAGGAAGAGATGACCAAGAAACAAGTGACCCTGTGGTGCATG<br>GTCACCGACTTCATGCCCGAGGACATCTACGTGGAATGGACCAAC<br>AACGGCAAGACCGAGCTGAACTACAAGAACACCGAGCCTGTGCTG<br>GACTCCGACGGCTCCTACTTCATGTACTCCAAGCTGCGCGTCGAGA<br>AGAAGAACTGGGTCGAGAGAAACTCCTACTCCTGCTCCGTGGTGC<br>ACGAGGGCCTGCACAATCACCACACCACCAAGTCCTTCTCTCGGA<br>CCCCTGGAAAGTGATGA |
| SEQ ID NO: 87 | α-IGF1R heavy-mFc_Hole Cys | ATGGAAACCGACACACTGCTGCTGTGGGTGCTGCTCTTGTGGGTGC<br>CAGGATCTACAGGCGAAGTGCAGCTGTTGCAGTCTGGCGGAGGAT<br>TGGTTCAGCCTGGCGGATCCCTGAGACTGTCTTGTGCCGCCTCTG<br>CTTCATGTTCAGCAGATACCCCATGCACTGGGTCCGACAGGCCCCT<br>GGAAAAGGACTGGAATGGGTCGGATCCATCTCCGGAAGTGGCGGC<br>GCTACCCCTTACGCCGATTCTGTGAAGGGCAGATTCACCATCAGCC<br>GGGACAACTCCAAGAACACCCTGTACCTGCAGATGAACTCCCTGA<br>GAGCCGAGGACACCGCCGTGTACTACTGCGCCAAGGACTTCTACC<br>AGATCCTGACCGGCAACGCCTTCGACTATTGGGGCCAGGGCACAA<br>CCGTGACCGTGTCCTCTGCTTCTACCAAGGGACCCAGCGTGTTCCC<br>TCTGGCTCCTTCCAGCAAGTCTACCTCTGGCGGAACAGCTGCTCTG<br>GGCTGCCTGGTCAAGGACTACTTTCCTGAGCCTGTGACAGTGTCCT<br>GGAACTCTGGCGCTCTGACATCCGGCGTGCACACCTTTCCAGCTGT<br>GCTGCAATCCAGCGGCCTGTACTCTCTGTCCTCCGTCGTGACAGTG<br>CCTTCCAGCTCTCTGGGAACCCAGACCTACATCTGCAATGTGAACC<br>ACAAGCCTTCCAACACCAAGGTGGACAAGAGAGTGGAACCCAAGT<br>CCTGCACCATCAAGCCCTGTCCTCCATGCAAGTGCCCCGCTCCTAA<br>TCTGCTCGGAGGCCCTTCCGTGTTCATCTTCCCACCTAAGATCAAG<br>GACGTGCTGATGATCTCCCTGTCTCCTATCGTGACCTGCGTGGTGG<br>TGGACGTGTCCGAGGATGATCCTGACGTGCAGATCAGTTGGTTCGT<br>GAACAACGTGGAAGTGCACACCGCTCAGACCCAGACACACAGAG<br>AGGACTACAACAGCACCCTGAGAGTGGTGTCTGCCCTGCCTATCC<br>AGCACCAGGATTGGATGTCCGGCAAAGAATTCAAGTGCAAAGTCA<br>ACAACAAGGACCTGCCTGCTCCAATCGAGCGGACCATCTCTAAGC<br>CTAAGGGCTCTGTGCGGGCTCCCCAAGTTTGTGTTCTGCCTCCACC<br>TGAGGAAGAGATGACCAAGAAACAAGTGACCCTGTCCTGCGCCGT<br>GACCGACTTCATGCCTGAGGACATCTACGTGGAATGGACCAACAA<br>CGGCAAGACCGAGCTGAATTACAAGAACACAGAGCCTGTGCTGGA<br>CTCCGACGGCTCCTACTTCATGGTGTCTAAGCTGCGCGTCGAGAAG<br>AAGAACTGGGTCGAGAGAAACTCCTACTCCTGCTCCGTGGTGCAC<br>GAGGGCCTGCACAATCACCACACCACCAAGTCCTTCTCTCGGACC<br>CCTGGCAAGTGATGA |
| SEQ ID NO: 88 | α-CD221 heavy-hCHIg_Hole_Cys | ATGGAAACCGACACACTGCTGCTGTGGGTGCTGCTCTTGTGGGTGC<br>CAGGATCTACAGGCGAAGTGCAGCTGGTTCAGTCTGGCGCCGAAG<br>TGAAGAAACCTGGCTCCTCCGTGAAGGTGTCCTGCAAGGCTTCTG<br>GCGGCACCTTCTCCTCTTACGCCATCTCCTGGGTCCGACAGGCTCC<br>TGGACAAGGCTTGGAATGGATGGGCGGCATCATCCCCATCTTCGG<br>CACCGCCAATTACGCCCAGAAATTCCAGGGCAGAGTGACCATCAC<br>CGCCGACAAGTCTACCTCCACCGCCTACATGGAACTGTCCAGCCTG<br>AGATCTGAGGACACCGCCGTGTACTACTGCGCTAGAGCCCCTCTG<br>AGATTCCTGGAATGGTCTACCCAGGACCACTACTACTATTACTACA<br>TGGACGTGTGGGGCAAGGGCACCACCGTGACAGTTTCTTCCGCCT<br>CCACCAAGGGACCCAGCGTTTTCCCTCTGGCTCCATCCTCCAAGTC<br>CACCTCTGGTGGAACAGCTGCTCTGGGCTGCCTGGTCAAGGACTA<br>CTTTCCTGAGCCTGTGACCGTGTCCTGGAACTCTGGCGCTCTGACA<br>TCTGGCGTGCACACCTTTCCAGCTGTGCTGCAGTCCTCCGGCCTGT<br>ACTCTCTGTCCTCTGTCGTGACCGTGCCTTCCAGCTCTCTGGGAAC<br>CCAGACCTACATCTGCAATGTGAACCACAAGCCTTCCAACACCAA<br>GGTCGACAAGAGAGTGGAACCCAAGTCCTGCGACAAGACCCACAC<br>CTGTCCTCCATGTCCTGCTCCAGAACTGCTCGGCGGACCTTCCGTG<br>TTCCTGTTTCCTCCAAAGCCTAAGGACACCCTGATGATCTCTCGGA<br>CCCCTGAAGTGACCTGCGTGGTGGTGGATGTGTCTCACGAGGACC<br>CAGAAGTGAAGTTCAATTGGTACGTGGACGGCGTGGAAGTGCACA<br>ACGCCAAGACCAAGCCTAGAGAGGAACAGTACAACTCCACCTACA<br>GAGTGGTGTCCGTGCTGACCGTGCTGCACCAGGATTGGCTGAACG<br>GCAAAGAGTACAAGTGCAAGGTGTCCAACAAGGCCCTGCCTGCTC<br>CTATCGAAAAGACCATCTCCAAGGCCAAGGGCCAGCCTCGGGAAC<br>CTCAAGTCTGTACCCTGCCTCCTAGCCGGGAAGAGATGACCAAGA<br>ACCAGGTGTCCCTGTCCTGTGCCGTGAAGGGCTTCTACCCTTCCGA<br>TATCGCCGTGGAATGGGAGAGCAATGGCCAGCCAGAGAACAACTA<br>CAAGACAACCCCTCCTGTGCTGGACTCCGACGGCTCATTCTTCCTG |

TABLE 1-continued

Nucleic acid sequences of ORFs.

| SEQ ID NO | Description | Nucleic Acid Sequence |
|---|---|---|
| | | GTGTCCAAGCTGACAGTGGACAAGTCCAGATGGCAGCAGGGCAAC<br>GTGTTCTCCTGCTCCGTGATGCACGAGGCCCTGCACAATCACTACA<br>CACAGAAGTCCCTGTCTCTGAGCCCCGGCAAGTGATGA |
| SEQ ID NO: 89 | α-PD1 heavy-hCHIg_Knob_Cys | ATGGAAACCGACACACTGCTGCTGTGGGTGCTGCTCTTGTGGGTGC<br>CAGGATCTACAGGACAGGTGCAGCTGGTGGAATCTGGTGGCGGAG<br>TTGTGCAGCCTGGCAGATCTCTGAGACTGGACTGCAAGGCCTCCG<br>GCATCACCTTCTCCAACTCTGGCATGCACTGGGTCCGACAGGCCCC<br>TGGAAAAGGACTGGAATGGGTCGCCGTGATTTGGTACGACGGCTC<br>CAAGAGGTACTACGCCGACTCCGTGAAGGGCAGATTCACCATCTC<br>TCGGGACAACTCCAAGAACACCCTGTTTCTGCAGATGAACTCCCTG<br>AGAGCCGAGGACACCGCCGTGTACTACTGTGCCACCAACGACGAT<br>TATTGGGGCCAGGGCACACTGGTCACCGTGTCCTCTGCTTCTACCA<br>AGGGACCCAGCGTGTTCCCTCTGGCTCCTTCCAGCAAGTCTACCTC<br>TGGCGGAACAGCTGCTCTGGGCTGCCTGGTCAAGGACTACTTTCCT<br>GAGCCTGTGACCGTGTCTTGGAACTCTGGCGCTCTGACATCCGGCG<br>TGCACACCTTTCCAGCTGTGCTGCAATCCTCCGGCCTGTACTCTCT<br>GTCCTCCGTCGTGACCGTGCCTTCTAGCTCTCTGGGCACCCAGACC<br>TACATCTGCAATGTGAACCACAAGCCTTCCAACACCAAGGTGGAC<br>AAGAGAGTGGAACCCAAGTCCTGCGACAAGACCCACACCTGTCCA<br>CCATGTCCTGCTCCAGAACTGCTCGGCGGACCTTCCGTGTTCCTGT<br>TCCTCCAAAGCCTAAGGACACCCTGATGATCTCTCGGACCCCTGA<br>AGTGACCTGCGTGGTGGTGGATGTGTCTCACGAGGATCCCGAAGT<br>GAAGTTCAATTGGTACGTGGACGGCGTGGAAGTGCACAACGCCAA<br>GACCAAGCCTAGAGAGGAACAGTACAACTCCACCTACAGAGTGGT<br>GTCCGTGCTGACCGTGCTGCACCAGGATTGGCTGAACGGCAAAGA<br>GTACAAGTGCAAGGTGTCCAACAAGGCCCTGCCTGCTCCTATCGA<br>AAAGACCATCTCCAAGGCCAAGGGCCAGCCTAGGGAACCCCAGGT<br>TTACACCCTGCCTCCATGCGGGAAGAGATGACCAAGAACCAGGT<br>GTCCCTGTGGTGCCTGGTTAAGGGCTTCTACCCCTCCGATATCGCC<br>GTGGAATGGGAGTCTAATGGCCAGCCTGAGAACAACTACAAGACA<br>ACCCCTCCTGTGCTGGACTCCGACGGCTCATTCTTCCTGTACTCCA<br>AGCTGACAGTGGACAAGTCCAGATGGCAGCAGGGCAACGTGTTCT<br>CCTGCTCCGTGATGCACGAGGCCCTGCACAATCACTACACCCAGA<br>AGTCCCTGTCTCTGTCCCTGGCAAGTGATGA |
| SEQ ID NO: 90 | α-PD1 light-hCLIg_vk | ATGGAAACCGACACACTGCTGCTGTGGGTGCTGCTCTTGTGGGTGC<br>CAGGATCTACAGGCGAGATCGTGCTGACCCAGTCTCCTGCCACAC<br>TGTCACTGTCTCCAGGCGAGAGAGCTACCCTGTCCTGTAGAGCCTC<br>TCAGTCCGTGTCCTCTTACCTGGCCTGGTATCAGCAGAAGCCTGGA<br>CAGGCTCCCCGGCTGCTGATCTACGATGCCTCTAATAGAGCCACA<br>GGCATCCCCGCCAGATTCTCCGGATCTGGCTCTGGCACAGACTTTA<br>CCCTGACCATCTCCAGCCTGGAACCTGAGGACTTCGCCGTGTACTA<br>CTGCCAGCAGTCCTCTAACTGGCCTCGGACCTTTGGCCAGGGCACC<br>AAGGTGGAAATCAAGCGGACAGTGGCCGCTCCTTCCGTGTTCATC<br>TTCCCACCTTCCGACGAGCAGCTGAAGTCTGGCACCGCTTCTGTCG<br>TGTGCCTGCTGAACAACTTCTACCCTCGGGAAGCCAAGGTGCAGT<br>GGAAGGTGGACAATGCCCTGCAGTCCGGCAACTCCCAAGAGTCTG<br>TGACCGAGCAGGACTCCAAGGACAGCACCTACAGCCTGTCCTCCA<br>CACTGACCCTGTCCAAGGCCGACTACGAGAAGCACAAGGTGTACG<br>CCTGCGAAGTGACCCATCAGGGCCTGTCTAGCCCTGTGACCAAGT<br>CTTTCAACCGGGGCGAGTGCTGATGA |
| SEQ ID NO: 91 | α-IL12β heavy-hCHIg_Hole_Cys | ATGGAAACCGACACACTGCTGCTGTGGGTGCTGCTCTTGTGGGTGC<br>CAGGATCTACAGGACAGGTGCAGCTGGTGGAATCTGGTGGCGGAG<br>TTGTGCAGCCTGGCAGATCCCTGAGACTGTCTTGTGCCGCCTCCGG<br>CTTCACCTTCTCCTCTTACGGAATGCACTGGGTCCGACAGGCCCCT<br>GGCAAAGGATTGGAGTGGGTCGCCTTCATCAGATACGACGGCTCC<br>AACAAGTACTACGCCGACTCCGTGAAGGGCAGATTCACCATCTCT<br>CGGGACAACTCCAAGAACACCCTGTACCTGCAGATGAACTCCCTG<br>AGAGCCGAGGACACCGCCGTGTACTACTGCAAGACCCACGGCTCT<br>CACGACAATTGGGGCCAGGGCACAATGGTCACCGTGTCCTCTGCT<br>TCCACCAAGGGACCCTCTGTGTTCCCTCTGGCTCCTTCCAGCAAGT<br>CTACCTCTGGCGGAACAGCTGCTCTGGGCTGCCTGGTCAAGGACT<br>ACTTTCCTGAGCCTGTGACCGTGTCTTGGAACTCTGGCGCTCTGAC<br>ATCCGGCGTGCACACCTTTCCAGCTGTGCTGCAATCCTCCGGCCTG<br>TACTCTCTGTCCTCCGTCGTGACCGTGCCTTCTAGCTCTCTGGGCAC<br>CCAGACCTACATCTGCAATGTGAACCACAAGCCTTCCAACACCAA<br>GGTGGACAAGAGAGTGGAACCCAAGTCCTGCGATAAGACCCACAC<br>CTGTCCACCATGTCCTGCTCCAGAACTGCTCGGCGGACCTTCCGTG<br>TTCCTGTTTCCTCCAAAGCCTAAGGACACCCTGATGATCTCTCGGA<br>CCCCTGAAGTGACCTGCGTGGTGGTGGATGTGTCTCACGAGGATC<br>CCGAAGTGAAGTTCAATTGGTACGTGGACGGCGTGGAAGTGCACA<br>ACGCCAAGACCAAGCCTAGAGAGGAACAGTACAACTCCACCTACA<br>GAGTGGTGTCCGTGCTGACCGTGCTGCACCAGGATTGGCTGAACG |

TABLE 1-continued

Nucleic acid sequences of ORFs.

| SEQ ID NO | Description | Nucleic Acid Sequence |
|---|---|---|
| | | GCAAAGAGTACAAGTGCAAGGTGTCCAACAAGGCCCTGCCTGCTC<br>CTATCGAAAAGACCATCTCCAAGGCCAAGGGCCAGCCTCGGGAAC<br>CTCAAGTCTGTACCCTGCCTCCTAGCCGGGAAGAGATGACCAAGA<br>ACCAGGTGTCCCTGTCCTGCGCTGTGAAGGGCTTCTACCCTTCCGA<br>TATCGCCGTGGAATGGGAGAGCAATGGCCAGCCTGAGAACAACTA<br>CAAGACCACACCTCCTGTGCTGGACTCCGACGGCTCATTCTTCCTG<br>GTGTCCAAGCTGACAGTGGACAAGTCCAGATGGCAGCAGGGCAAC<br>GTGTTCTCCTGCTCCGTGATGCACGAGGCCCTGCACAATCACTACA<br>CCCAGAAGTCCCTGTCTCTGAGCCCCGGCAAGTGATGA |

2. Expression and Purification of NanoBiT Constructs.

The plasmids were co-transfected into ExpiCHO cells (Life Technologies A29127). Transfections were performed using 1 mg of total DNA per liter for a multispecific construct with a 1:1:1 heavy chain to light chain to competing light chain ratio. The ExpiCHO transfection was performed according to the manufacturer's instructions. ExpiCHO cells were grown for 7 days at 32° C. with 5% $CO_2$ after transfection. The cells were pelleted by centrifugation at 3000 x g. CaptureSelect CH1-XL affinity resin (GE 2943452010) was added to the supernatant and incubated for 1-3 hours at room temperature. The resin was packed into a fritted filter plate (Nunc fritted deepwell filter plates 278011), washed with 3×1 mL of Dulbecco's phosphate-buffered saline (DPBS, Life Technologies 14190-144). The bound protein was eluted from the column with 20 mM citrate, 100 mM NaCl, pH 2.9. The elution fractions were neutralized using 1 M Tris-HCl, pH 8.0. Table 2 shows the amino acid sequences for all the NanoBiT constructs.

TABLE 2

Amino Acid sequences for NanoBiT constructs. All constructs contained an Ig Kappa leader sequence (SEQ ID NO 214: METDTLLLWVLLLWVPGSTG).

| SEQ ID NO | Amino Acid Sequence | Description | Germline | Corresponding DNA SEQ ID NO |
|---|---|---|---|---|
| SEQ ID NO: 92 | QVQLVESGGGVVQPGRSLRLSCAASGFAFSS YGMHWVRQAPGKGLEWVAVIWFDGTKKYYTD SVKGRFTISRDNSKNTLYLQMNTLRAEDTAV YYCARDRGIGARRGPYYMDVWGKGTTVTVSS ASTKGPSVFPLAPSSKSTSGGTAALGCLVKD YFPEPVTVSWNSGALTSGVHTFPAVLQSSGL YSLSSVVTVPSSSLGTQTYICNVNHKPSNTK VDKRVEPKSCGSSGGGGSGGGGSSGGVFTLE DFVGDWEQTAAYNLDQVLEQGGVSSLLQNLA VSVTPIQRIVRSGENALKIDIHVIIPYEGLS ADQMAQIEEVFKVVYPVDDHHFKVILPYGTL VIDGVTPNMLNYFGRPYEGIAVFDGKKITVT GTLWNGNKIIDERLITPDGSMLFRVTINS | α-amyloid β heavy-LgBiT | VH3-33*01 (SEQ ID NO: 193) | SEQ ID NO: 1 |
| SEQ ID NO: 93 | DIQMTQSPSSLSASVGDRVTITCRASQSISS YLNWYQQKPGKAPKLLIYAASSLQSGVPSRF SGSGSGTDFTLTISSLQPEDFATYYCQQSYS TPLTFGGGTKVEIKRTVAAPSVFIFPPSDEQ LKSGTASVVCLLNNFYPREAKVQWKVDNALQ SGNSQESVTEQDSKDSTYSLSSTLTLSKADY EKHKVYACEVTHQGLSSPVTKSFNRGECGSS GGGGSGGGGSSGGVTGYRLFEEIL | α-amyloid ß light-SmBiT | Vk1-39*01 (SEQ ID NO: 201) | SEQ ID NO: 2 |
| SEQ ID NO: 94 | DIQMTQSPSSLSASVGDRVTITCRASQSISS YLNWYQQKPGKAPKLLIYAASSLQSGVPSRF SGSGSGTDFTLTISSLQPEDFATYYCQQSYS TPLTFGGGTKVEIKRTVAAPSVFIFPPSDEQ LKSGTASVVCLLNNFYPREAKVQWKVDNALQ SGNSQESVTEQDSKDSTYSLSSTLTLSKADY EKHKVYACEVTHQGLSSPVTKSFNRGEC | α-amyloid ß light | Vk1-39*01 (SEQ ID NO: 201) | SEQ ID NO: 3 |
| SEQ ID NO: 95 | EVQLVQSGAEVKKSGESLKISCKGSGYSFTS YWIGWVRQMPGKGLEWMGIFYPGDSSTRYSP SFQGQVTISADKSVNTAYLQWSSLKASDTAM YYCARRRNWGNAFDIWGQGTMVTVSSASTKG PSVFPLAPSSKSTSGGTAALGCLVKDYFPEP VTVSWNSGALTSGVHTFPAVLQSSGLYSLSS VVTVPSSSLGTQTYICNVNHKPSNTKVDKRV EPKSCGSSGGGGSGGGGSSGGVFTLEDFVGD WEQTAAYNLDQVLEQGGVSSLLQNLAVSVTP IQRIVRSGENALKIDIHVIIPYEGLSADQMA | α-Clostridium difficile toxin B heavy-LgBiT | VH5-51*01 (SEQ ID NO: 198) | SEQ ID NO: 4 |

TABLE 2-continued

Amino Acid sequences for NanoBiT constructs. All constructs contained an Ig Kappa leader sequence (SEQ ID NO 214: METDTLLLWVLLLWVPGSTG).

| SEQ ID NO | Amino Acid Sequence | Description | Germline | Corresponding DNA SEQ ID NO |
|---|---|---|---|---|
| | QIEEVFKVVYPVDDHHFKVILPYGTLVIDGV TPNMLNYFGRPYEGIAVFDGKKITVTGTLWN GNKIIDERLITPDGSMLFRVTINS | | | |
| SEQ ID NO: 96 | EIVLTQSPGTLSLSPGERATLSCRASQSVSS SYLAWYQQKPGQAPRLLIYGASSRATGIPDR FSGSGSGTDFTLTISRLEPEDFAVYYCQQYG SSTWTFGQGTKVEIKRTVAAPSVFIFPPSDE QLKSGTASVVCLLNNFYPREAKVQWKVDNAL QSGNSQESVTEQDSKDSTYSLSSTLTLSKAD YEKHKVYACEVTHQGLSSPVTKSFNRGECGS SGGGGSGGGGSSGGVTGYRLFEEIL | α-Clostridium difficile toxin B light-SmBiT | Vk3-20*01 (SEQ ID NO: 205) | SEQ ID NO: 5 |
| SEQ ID NO: 97 | EIVLTQSPGTLSLSPGERATLSCRASQSVSS SYLAWYQQKPGQAPRLLIYGASSRATGIPDR FSGSGSGTDFTLTISRLEPEDFAVYYCQQYG SSTWTFGQGTKVEIKRTVAAPSVFIFPPSDE QLKSGTASVVCLLNNFYPREAKVQWKVDNAL QSGNSQESVTEQDSKDSTYSLSSTLTLSKAD YEKHKVYACEVTHQGLSSPVTKSFNRGEC | α-Clostridium difficile toxin B light | Vk3-20*01 (SEQ ID NO: 205) | SEQ ID NO: 6 |
| SEQ ID NO: 98 | EGQLVQSGGGLVHPGGSLRLSCAGSGFTSS YGMHWVRQAPGKGLEWVSGIGTGGGTYSTDS VKGRFTISRDNAKNSLYLQMNSLRAEDMAVY YCARGDYYGSGSFFDCWGQGTLVTVSSASTK GPSVFPLAPSSKSTSGGTAALGCLVKDYFPE PVTVSWNSGALTSGVHTFPAVLQSSGLYSLS SVVTVPSSSLGTQTYICNVNHKPSNTKVDKR VEPKSCGSSGGGGSGGGGSSGGVFTLEDFVG DWEQTAAYNLDQVLEQGGVSSLLQNLAVSVT PIQRIVRSGENALKIDIHVIIPYEGLSADQM AQIEEVFKVVYPVDDHHFKVILPYGTLVIDG VTPNMLNYFGRPYEGIAVFDGKKITVTGTLW NGNKIIDERLITPDGSMLFRVTINS | α-connective tissue growth factor heavy-LgBiT | VH3-13*01 (SEQ ID NO: 188) | SEQ IDNO: 7 |
| SEQ ID NO: 99 | DIQMTQSPSSLSASVGDRVTITCRASQGISS WLAWYQQKPEKAPKSLIYAASSLQSGVPSRF SGSGSGTDFTLTISSLQPEDFATYYCQQYNS YPPTFGQGTKLEIKRTVAAPSVFIFPPSDEQ LKSGTASVVCLLNNFYPREAKVQWKVDNALQ SGNSQESVTEQDSKDSTYSLSSTLTLSKADY EKHKVYACEVTHQGLSSPVTKSFNRGECGSS GGGGSGGGGSSGGVTGYRLFEEIL | α-connective tissue growth factor light-SmBiT | Vk1D-16*01 (SEQ ID NO: 202) | SEQ ID NO: 8 |
| SEQ ID NO: 100 | DIQMTQSPSSLSASVGDRVTITCRASQGISS WLAWYQQKPEKAPKSLIYAASSLQSGVPSRF SGSGSGTDFTLTISSLQPEDFATYYCQQYNS YPPTFGQGTKLEIKRTVAAPSVFIFPPSDEQ LKSGTASVVCLLNNFYPREAKVQWKVDNALQ SGNSQESVTEQDSKDSTYSLSSTLTLSKADY EKHKVYACEVTHQGLSSPVTKSFNRGEC | α-connective tissue growth factor light | Vk1D-16*01 (SEQ ID NO: 202) | SEQ ID NO: 9 |
| SEQ ID NO: 101 | QVQLVQSGAEVKKPGASVKVSCKASGYSFTN YYIHWVRQAPGQRLEWMGWINAGNGNTKYSQ KFQGRVTITRDTSASTAYMELSSLRSEDTAV YYCVRRQRFPYYFDYWGQGTLVTVSSASTKG PSVFPLAPSSKSTSGGTAALGCLVKDYFPEP VTVSWNSGALTSGVHTFPAVLQSSGLYSLSS VVTVPSSSLGTQTYICNVNHKPSNTKVDKRV EPKSCGSSGGGGSGGGGSSGGVFTLEDFVGD WEQTAAYNLDQVLEQGGVSSLLQNLAVSVTP IQRIVRSGENALKIDIHVIIPYEGLSADQMA QIEEVFKVVYPVDDHHFKVILPYGTLVIDGV TPNMLNYFGRPYEGIAVFDGKKITVTGTLWN GNKIIDERLITPDGSMLFRVTINS | α-CSF2 heavy-LgBiT | VH1-3*01 (SEQ ID NO: 185) | SEQ ID NO: 10 |
| SEQ ID NO: 102 | EIVLTQSPATLSVSPGERATLSCRASQSVGT NVAWYQQKPGQAPRVLIYSTSSRATGITDRF SGSGSGTDFTLTISRLEPEDFAVYYCQQFNK SPLTFGGGTKVEIKRTVAAPSVFIFPPSDEQ LKSGTASVVCLLNNFYPREAKVQWKVDNALQ SGNSQESVTEQDSKDSTYSLSSTLTLSKADY | α-CSF2 light-SmBiT | Vk3D-20*01 (SEQ ID NO: 206) | SEQ ID NO: 11 |

TABLE 2-continued

Amino Acid sequences for NanoBiT constructs. All constructs contained an Ig Kappa leader sequence (SEQ ID NO 214: METDTLLLWVLLLWVPGSTG).

| SEQ ID NO | Amino Acid Sequence | Description | Germline | Corresponding DNA SEQ ID NO |
|---|---|---|---|---|
| | EKHKVYACEVTHQGLSSPVTKSFNRGECGSSGGGGSGGGGSSGGVTGYRLFEEIL | | | |
| SEQ ID NO: 103 | EIVLTQSPATLSVSPGERATLSCRASQSVGTNVAWYQQKPGQAPRVLIYSTSSRATGITDRFSGSGSGTDFTLTISRLEPEDFAVYYCQQFNKSPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | α-CSF2 light | Vk3D-20*01 (SEQ ID NO: 206) | SEQ ID NO: 12 |
| SEQ ID NO: 104 | QVQLVESGGGVVQPGRSLRLSCAASGFTFSSYTMHWVRQAPGKGLEWVTFISYDGNNKYYADSVKGRFTISRDNSKNTLYLQMNSLRAEDTAIYYCARTGWLGPFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCGSSGGGGSGGGGSSGGVFTLEDFVGDWEQTAAYNLDQVLEQGGVSSLLQNLAVSVTPIQRIVRSGENALKIDIHVIIPYEGLSADQMAQIEEVFKVVYPVDDHHFKVILPYGTLVIDGVTPNMLNYFGRPYEGIAVFDGKKITVTGTLWNGNKIIDERLITPDGSMLFRVTINS | α-CTLA4 heavy-LgBiT | VH3-30*01 (SEQ ID NO: 192) | SEQ ID NO: 13 |
| SEQ ID NO: 105 | EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGSSGGGGSGGGGSSGGVTGYRLFEEIL | α-CTLA4 light SmBiT | Vk3-20*01 (SEQ ID NO: 205) | SEQ ID NO: 14 |
| SEQ ID NO: 106 | EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | α-CTLA4 light | Vk3-20*01 (SEQ ID NO: 205) | SEQ ID NO: 15 |
| SEQ ID NO: 107 | EVQLVQSGAEVKKPGESLKISCKGSGYIFTNYWIAWVRQMPGKGLESMGIIYPGDSDIRYSPSFQGQVTISADKSITTAYLQWSSLKASDTAMYYCARHDIEGFDYWGRGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCGSSGGGGSGGGGSSGGVFTLEDFVGDWEQTAAYNLDQVLEQGGVSSLLQNLAVSVTPIQRIVRSGENALKIDIHVIIPYEGLSADQMAQIEEVFKVVYPVDDHHFKVILPYGTLVIDGVTPNMLNYFGRPYEGIAVFDGKKITVTGTLWNGNKIIDERLITPDGSMLFRVTINS | α-IFN heavy-LgBiT | VH5-51*01 (SEQ ID NO: 198) | SEQ ID NO: 16 |
| SEQ ID NO: 108 | EIVLTQSPGTLSLSPGERATLSCRASQSVSSSFFAWYQQKPGQAPRLLIYGASSRATGIPDRLSGSGSGTDFTLTITRLEPEDFAVYYCQQYDSSAITFGQGTRLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGSSGGGGSGGGGSSGGVTGYRLFEEIL | α-IFN light-SmBiT | Vk3-20*01 (SEQ ID NO: 205) | SEQ ID NO: 17 |
| SEQ ID NO: 109 | EIVLTQSPGTLSLSPGERATLSCRASQSVSSSFFAWYQQKPGQAPRLLIYGASSRATGIPDRLSGSGSGTDFTLTITRLEPEDFAVYYCQQYDSSAITFGQGTRLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | α-IFN light | Vk3-20*01 (SEQ ID NO: 205) | SEQ ID NO: 18 |

TABLE 2-continued

Amino Acid sequences for NanoBiT constructs. All constructs contained an Ig Kappa leader sequence (SEQ ID NO 214: METDTLLLWVLLLWVPGSTG).

| SEQ ID NO | Amino Acid Sequence | Description | Germline | Corresponding DNA SEQ ID NO |
|---|---|---|---|---|
| SEQ ID NO: 110 | QVQLVQSGAEVKKPGASVKVSCKASGYTFTS YSISWVRQAPGQGLEWMGWISVYNGNTNYAQ KFQGRVTMTTDTSTSTAYLELRSLRSDDTAV YYCARDPIAAGYWGQGTLVTVSSASTKGPSV FPLAPSSKSTSGGTAALGCLVKDYFPEPVTV SWNSGALTSGVHTFPAVLQSSGLYSLSSVVT VPSSSLGTQTYICNVNHKPSNTKVDKRVEPK SCGSSGGGGSGGGGSSGGVFTLEDFVGDWEQ TAAYNLDQVLEQGGVSSLLQNLAVSVTPIQR IVRSGENALKIDIHVIIPYEGLSADQMAQIE EVFKVVYPVDDHHFKVILPYGTLVIDGVTPN MLNYFGRPYEGIAVFDGKKITVTGTLWNGNK IIDERLITPDGSMLFRVTINS | α-IFNα heavy-LgBiT | VH1-18*01 (SEQ ID NO: 183) | SEQ ID NO: 19 |
| SEQ ID NO: 111 | EIVLTQSPGTLSLSPGERATLSCRASQSVSS TYLAWYQQKPGQAPRLLIYGASSRATGIPDR FSGSGSGTDFTLTISRLEPEDFAVYYCQQYG SSPRTFGQGTKVEIKRTVAAPSVFIFPPSDE QLKSGTASVVCLLNNFYPREAKVQWKVDNAL QSGNSQESVTEQDSKDSTYSLSSTLTLSKAD YEKHKVYACEVTHQGLSSPVTKSFNRGECGS SGGGGSGGGGSSGGVTGYRLFEEIL | α-IFNα light-SmBiT | Vk3-20*01 (SEQ ID NO: 205) | SEQ ID NO: 20 |
| SEQ ID NO: 112 | EIVLTQSPGTLSLSPGERATLSCRASQSVSS TYLAWYQQKPGQAPRLLIYGASSRATGIPDR FSGSGSGTDFTLTISRLEPEDFAVYYCQQYG SSPRTFGQGTKVEIKRTVAAPSVFIFPPSDE QLKSGTASVVCLLNNFYPREAKVQWKVDNAL QSGNSQESVTEQDSKDSTYSLSSTLTLSKAD YEKHKVYACEVTHQGLSSPVTKSFNRGEC | α-IFNα light | Vk3-20*01 (SEQ ID NO: 205) | SEQ ID NO: 21 |
| SEQ ID NO: 113 | QVQLQESGPGLVKPSGTLSLTCAVSGGSISS SNWWSWVRQPPGKGLEWIGEIYHSGSTNYNP SLKSRVTISVDKSKNQFSLKLSSVTAADTAV YYCARWTGRTDAFDIWGQGTMVTVSSASTKG PSVFPLAPSSKSTSGGTAALGCLVKDYFPEP VTVSWNSGALTSGVHTFPAVLQSSGLYSLSS VVTVPSSSLGTQTYICNVNHKPSNTKVDKRV EPKSCGSSGGGGSGGGGSSGGVFTLEDFVGD WEQTAAYNLDQVLEQGGVSSLLQNLAVSVTP IQRIVRSGENALKIDIHVIIPYEGLSADQMA QIEEVFKVVYPVDDHHFKVILPYGTLVIDGV TPNMLNYFGRPYEGIAVFDGKKITVTGTLWN GNKIIDERLITPDGSMLFRVTINS | α-IGF1R heavy-LgBiT | VH4-4*01 (SEQ ID NO: 197) | SEQ ID NO: 22 |
| SEQ ID NO: 114 | DVVMTQSPLSLPVTPGEPASISCRSSQSLLH SNGYNYLDWYLQKPGQSPQLLIYLGSNRASG VPDRFSGSGSGTDFTLKISRVEAEDVGVYYC MQGTHWPLTFGQGTKVEIKRTVAAPSVFIFP PSDEQLKSGTASVVCLLNNFYPREAKVQWKV DNALQSGNSQESVTEQDSKDSTYSLSSTLTL SKADYEKHKVYACEVTHQGLSSPVTKSFNRG ECGSSGGGGSGGGGSSGGVTGYRLFEEIL | α-IGF1R light-SmBiT | Vk2-28*01 (SEQ ID NO: 203) | SEQ ID NO: 23 |
| SEQ ID NO: 115 | DVVMTQSPLSLPVTPGEPASISCRSSQSLLH SNGYNYLDWYLQKPGQSPQLLIYLGSNRASG VPDRFSGSGSGTDFTLKISRVEAEDVGVYYC MQGTHWPLTFGQGTKVEIKRTVAAPSVFIFP PSDEQLKSGTASVVCLLNNFYPREAKVQWKV DNALQSGNSQESVTEQDSKDSTYSLSSTLTL SKADYEKHKVYACEVTHQGLSSPVTKSFNRG EC | α-IGF1R light | Vk2-28*01 (SEQ ID NO: 203) | SEQ ID NO: 24 |
| SEQ ID NO: 116 | EVQLLQSGGGLVQPGGSLRLSCAASGFMFSR YPMHWVRQAPGKGLEWVGSISGSGGATPYAD SVKGRFTISRDNSKNTLYLQMNSLRAEDTAV YYCAKDFYQILTGNAFDYWGQGTTVTVSSAS TKGPSVFPLAPSSKSTSGGTAALGCLVKDYF PEPVTVSWNSGALTSGVHTFPAVLQSSGLYS LSSVVTVPSSSLGTQTYICNVNHKPSNTKVD KRVEPKSCGSSGGGGSGGGGSSGGVFTLEDF VGDWEQTAAYNLDQVLEQGGVSSLLQNLAVS VTPIQRIVRSGENALKIDIHVIIPYEGLSAD | α-IGF1R heavy-LgBiT | VH3-23*01 (SEQ ID NO: 191) | SEQ ID NO: 25 |

TABLE 2-continued

Amino Acid sequences for NanoBiT constructs. All constructs contained an Ig Kappa leader sequence (SEQ ID NO 214: METDTLLLWVLLLWVPGSTG).

| SEQ ID NO | Amino Acid Sequence | Description | Germline | Corresponding DNA SEQ ID NO |
|---|---|---|---|---|
| | QMAQIEEVFKVVYPVDDHHFKVILPYGTLVI DGVTPNMLNYFGRPYEGIAVFDGKKITVTGT LWNGNKIIDERLITPDGSMLFRVTINS | | | |
| SEQ ID NO: 117 | DIQMTQSPSSLSASLGDRVTITCRASQGISS YLAWYQQKPGKAPKLLIYAKSTLQSGVPSRF SGSGSGTDFTLTISSLQPEDSATYYCQQYWT FPLTFGGGTKVEIKRTVAAPSVFIFPPSDEQ LKSGTASVVCLLNNFYPREAKVQWKVDNALQ SGNSQESVTEQDSKDSTYSLSSTLTLSKADY EKHKVYACEVTHQGLSSPVTKSFNRGECGSS GGGGSGGGGSSGGVTGYRLFEEIL | α-IGF1R light-SmBiT | Vk1-27*01 (SEQ ID NO: 200) | SEQ ID NO: 26 |
| SEQ ID NO: 118 | DIQMTQSPSSLSASLGDRVTITCRASQGISS YLAWYQQKPGKAPKLLIYAKSTLQSGVPSRF SGSGSGTDFTLTISSLQPEDSATYYCQQYWT FPLTFGGGTKVEIKRTVAAPSVFIFPPSDEQ LKSGTASVVCLLNNFYPREAKVQWKVDNALQ SGNSQESVTEQDSKDSTYSLSSTLTLSKADY EKHKVYACEVTHQGLSSPVTKSFNRGEC | α-IGF1R light | Vk1-27*01 (SEQ ID NO: 200) | SEQ ID NO: 27 |
| SEQ ID NO: 119 | EVQLVQSGGGLVKPGGSLRLSCAASGFTFSS FAMHWVRQAPGKGLEWISVIDTRGATYYADS VKGRFTISRDNAKNSLYLQMNSLRAEDTAVY YCARLGNFYYGMDVWGQGTTVTVSSASTKGP SVFPLAPSSKSTSGGTAALGCLVKDYFPEPV TVSWNSGALTSGVHTFPAVLQSSGLYSLSSV VTVPSSSLGTQTYICNVNHKPSNTKVDKRVE PKSCGSSGGGGSGGGGSSGGVFTLEDFVGDW EQTAAYNLDQVLEQGGVSSLLQNLAVSVTPI QRIVRSGENALKIDIHVIIPYEGLSADQMAQ IEEVFKVVYPVDDHHFKVILPYGTLVIDGVT PNMLNYFGRPYEGIAVFDGKKITVTGTLWNG NKIIDERLITPDGSMLFRVTINS | α-IGF1R heavy-LgBiT | VH3-21*01 (SEQ ID NO: 190) | SEQ ID NO: 28 |
| SEQ ID NO: 120 | EIVLTQSPGTLSVSPGERATLSCRASQSIGS SLHWYQQKPGQAPRLLIKYASQSLSGIPDRF SGSGSGTDFTLTISRLEPEDFAVYYCHQSSR LPHTFGQGTKVEIKRTVAAPSVFIFPPSDEQ LKSGTASVVCLLNNFYPREAKVQWKVDNALQ SGNSQESVTEQDSKDSTYSLSSTLTLSKADY EKHKVYACEVTHQGLSSPVTKSFNRGECGSS GGGGSGGGGSSGGVTGYRLFEEIL | α-IGF1R light-SmBiT | Vk3-20*01 (SEQ ID NO: 205) | SEQ ID NO: 29 |
| SEQ ID NO: 121 | EIVLTQSPGTLSVSPGERATLSCRASQSIGS SLHWYQQKPGQAPRLLIKYASQSLSGIPDRF SGSGSGTDFTLTISRLEPEDFAVYYCHQSSR LPHTFGQGTKVEIKRTVAAPSVFIFPPSDEQ LKSGTASVVCLLNNFYPREAKVQWKVDNALQ SGNSQESVTEQDSKDSTYSLSSTLTLSKADY EKHKVYACEVTHQGLSSPVTKSFNRGEC | α-IGF1R light | Vk3-20*01 (SEQ ID NO: 205) | SEQ ID NO: 30 |
| SEQ ID NO: 122 | QVELVESGGGVVQPGRSQRLSCAASGFTFSS YGMHWVRQAPGKGLEWVAIIWFDGSSTYYAD SVRGRFTISRDNSKNTLYLQMNSLRAEDTAV YFCARELGRRYFDLWGRGTLVSVSSASTKGP SVFPLAPSSKSTSGGTAALGCLVKDYFPEPV TVSWNSGALTSGVHTFPAVLQSSGLYSLSSV VTVPSSSLGTQTYICNVNHKPSNTKVDKRVE PKSCGSSGGGGSGGGGSSGGVFTLEDFVGDW EQTAAYNLDQVLEQGGVSSLLQNLAVSVTPI QRIVRSGENALKIDIHVIIPYEGLSADQMAQ IEEVFKVVYPVDDHHFKVILPYGTLVIDGVT PNMLNYFGRPYEGIAVFDGKKITVTGTLWNG NKIIDERLITPDGSMLFRVTINS | α-IGF1R heavy-LgBiT | VH3-33*01 (SEQ ID NO: 193) | SEQ ID NO: 31 |
| SEQ ID NO: 123 | EIVLTQSPATLSLSPGERATLSCRASQSVSS YLAWYQQKPGQAPRLLIYDASKRATGIPARF SGSGSGTDFTLTISSLEPEDFAVYYCQQRSK WPPWTFGQGTKVESKRTVAAPSVFIFPPSDE QLKSGTASVVCLLNNFYPREAKVQWKVDNAL QSGNSQESVTEQDSKDSTYSLSSTLTLSKAD | α-IGF1R light-SmBiT | Vk3-11*01 (SEQ ID NO: 204) | SEQ ID NO: 32 |

TABLE 2-continued

Amino Acid sequences for NanoBiT constructs. All constructs contained an Ig Kappa leader sequence (SEQ ID NO 214: METDTLLLWVLLLWVPGSTG).

| SEQ ID NO | Amino Acid Sequence | Description | Germline | Corresponding DNA SEQ ID NO |
|---|---|---|---|---|
| | YEKHKVYACEVTHQGLSSPVTKSFNRGECGS SGGGGSGGGGSSGGVTGYRLFEEIL | | | |
| SEQ ID NO: 124 | EIVLTQSPATLSLSPGERATLSCRASQSVSS YLAWYQQKPGQAPRLLIYDASKRATGIPARF SGSGSGTDFTLTISSLEPEDFAVYYCQQRSK WPPWTFGQGTKVESKRTVAAPSVFIFPPSDE QLKSGTASVVCLLNNFYPREAKVQWKVDNAL QSGNSQESVTEQDSKDSTYSLSSTLTLSKAD YEKHKVYACEVTHQGLSSPVTKSFNRGEC | α-IGF1R light | Vk3-11*01 (SEQ ID NO: 204) | SEQ ID NO: 33 |
| SEQ ID NO: 125 | EVQLVESGGGLVQPGRSLRLSCAASRFTFDD YAMHWVRQAPGKGLEWVSGISWNSGRIGYAD SVKGRFTISRDNAENSLFLQMNGLRAEDTAL YYCAKGRDSFDIWGQGTMVTVSSASTKGPSV FPLAPSSKSTSGGTAALGCLVKDYFPEPVTV SWNSGALTSGVHTFPAVLQSSGLYSLSSVVT VPSSSLGTQTYICNVNHKPSNTKVDKRVEPK SCGSSGGGGSGGGGSSGGVFTLEDFVGDWEQ TAAYNLDQVLEQGGVSSLLQNLAVSVTPIQR IVRSGENALKIDIHVIIPYEGLSADQMAQIE EVFKVVYPVDDHHFKVILPYGTLVIDGVTPN MLNYFGRPYEGIAVFDGKKITVTGTLWNGNK IIDERLITPDGSMLFRVTINS | α-IL6R heavy-LgBiT | VH3-9*01 (SEQ ID NO: 196) | SEQ ID NO: 34 |
| SEQ ID NO: 126 | DIQMTQSPSSVSASVGDRVTITCRASQGISS WLAWYQQKPGKAPKLLIYGASSLESGVPSRF SGSGSGTDFTLTISSLQPEDFASYYCQQANS FPYTFGQGTKLEIKRTVAAPSVFIFPPSDEQ LKSGTASVVCLLNNFYPREAKVQWKVDNALQ SGNSQESVTEQDSKDSTYSLSSTLTLSKADY EKHKVYACEVTHQGLSSPVTKSFNRGECGSS GGGGSGGGGSSGGVTGYRLFEEIL | α-IL6R light-SmBiT | Vk1-12*01 (SEQ ID NO: 199) | SEQ ID NO: 35 |
| SEQ ID NO: 127 | DIQMTQSPSSVSASVGDRVTITCRASQGISS WLAWYQQKPGKAPKLLIYGASSLESGVPSRF SGSGSGTDFTLTISSLQPEDFASYYCQQANS FPYTFGQGTKLEIKRTVAAPSVFIFPPSDEQ LKSGTASVVCLLNNFYPREAKVQWKVDNALQ SGNSQESVTEQDSKDSTYSLSSTLTLSKADY EKHKVYACEVTHQGLSSPVTKSFNRGEC | α-IL6R light | Vk1-12*01 (SEQ ID NO: 199) | SEQ ID NO: 36 |
| SEQ ID NO: 128 | EVQLLESGGGLVQPGGSLRLSCAASGFTFSA YEMKWVRQAPGKGLEWVSVIGPSGGFTFYAD SVKGRFTISRDNSKNTLYLQMNSLRAEDTAV YYCATEGDNDAFDIWGQGTTVTVSSASTKGP SVFPLAPSSKSTSGGTAALGCLVKDYFPEPV TVSWNSGALTSGVHTFPAVLQSSGLYSLSSV VTVPSSSLGTQTYICNVNHKPSNTKVDKRVE PKSCGSSGGGGSGGGGSSGGVFTLEDFVGDW EQTAAYNLDQVLEQGGVSSLLQNLAVSVTPI QRIVRSGENALKIDIHVIIPYEGLSADQMAQ IEEVFKVVYPVDDHHFKVILPYGTLVIDGVT PNMLNYFGRPYEGIAVFDGKKITVTGTLWNG NKIIDERLITPDGSMLFRVTINS | α-LINGO-1 heavy-LgBiT | VH3-23*01 (SEQ ID NO: 191) | SEQ ID NO: 37 |
| SEQ ID NO: 129 | DIQMTQSPATLSLSPGERATLSCRASQSVSS YLAWYQQKPGQAPRLLIYDASNRATGIPARF SGSGSGTDFTLTISSLEPEDFAVYYCQQRSN WPMYTFGQGTKLEIKRTVAAPSVFIFPPSDE QLKSGTASVVCLLNNFYPREAKVQWKVDNAL QSGNSQESVTEQDSKDSTYSLSSTLTLSKAD YEKHKVYACEVTHQGLSSPVTKSFNRGECGS SGGGGSGGGGSSGGVTGYRLFEEIL | α-LINGO-1 light-SmBiT | Vk3-11*01 (SEQ ID NO: 204) | SEQ ID NO: 38 |
| SEQ ID NO: 130 | DIQMTQSPATLSLSPGERATLSCRASQSVSS YLAWYQQKPGQAPRLLIYDASNRATGIPARF SGSGSGTDFTLTISSLEPEDFAVYYCQQRSN WPMYTFGQGTKLEIKRTVAAPSVFIFPPSDE QLKSGTASVVCLLNNFYPREAKVQWKVDNAL QSGNSQESVTEQDSKDSTYSLSSTLTLSKAD YEKHKVYACEVTHQGLSSPVTKSFNRGEC | α-LINGO-1 light | Vk3-11*01 (SEQ ID NO: 204) | SEQ ID NO: 39 |

TABLE 2-continued

Amino Acid sequences for NanoBiT constructs. All constructs contained an Ig Kappa leader sequence (SEQ ID NO 214: METDTLLLWVLLLWVPGSTG).

| SEQ ID NO | Amino Acid Sequence | Description | Germline | Corresponding DNA SEQ ID NO |
|---|---|---|---|---|
| SEQ ID NO: 131 | EVQLVESGGGLVQPGGSLRLSCAASGFTFSS YAMSWVRQAPGKGLEWVSQISPAGGYTNYAD SVKGRFTISADTSKNTAYLQMNSLRAEDTAV YYCARGELPYYRMSKVMDVWGQGTLVTVSSA STKGPSVFPLAPSSKSTSGGTAALGCLVKDY FPEPVTVSWNSGALTSGVHTFPAVLQSSGLY SLSSVVTVPSSSLGTQTYICNVNHKPSNTKV DKRVEPKSCGSSGGGGSGGGGSSGGVFTLED FVGDWEQTAAYNLDQVLEQGGVSSLLQNLAV SVTPIQRIVRSGENALKIDIHVIIPYEGLSA DQMAQIEEVFKVVYPVDDHHFKVILPYGTLV IDGVTPNMLNYFGRPYEGIAVFDGKKITVTG TLWNGNKIIDERLITPDGSMLFRVTINS | α-neuropilin 1 heavy-LgBiT | VH3-66*01 (SEQ ID NO: 194) | SEQ ID NO: 40 |
| SEQ ID NO: 132 | DIQMTQSPSSLSASVGDRVTITCRASQYFSS YLAWYQQKPGKAPKLLIYGASSRASGVPSRF SGSGSGTDFTLTISSLQPEDFATYYCQQYLG SPPTFGQGTKVEIKRTVAAPSVFIFPPSDEQ LKSGTASVVCLLNNFYPREAKVQWKVDNALQ SGNSQESVTEQDSKDSTYSLSSTLTLSKADY EKHKVYACEVTHQGLSSPVTKSFNRGECGSS GGGGSGGGGSSGGVTGYRLFEEIL | α-neuropilin 1 light-SmBiT | Vk1-39*01 (SEQ ID NO: 201) | SEQ ID NO: 41 |
| SEQ ID NO: 133 | DIQMTQSPSSLSASVGDRVTITCRASQYFSS YLAWYQQKPGKAPKLLIYGASSRASGVPSRF SGSGSGTDFTLTISSLQPEDFATYYCQQYLG SPPTFGQGTKVEIKRTVAAPSVFIFPPSDEQ LKSGTASVVCLLNNFYPREAKVQWKVDNALQ SGNSQESVTEQDSKDSTYSLSSTLTLSKADY EKHKVYACEVTHQGLSSPVTKSFNRGEC | α-neuropilin 1 light | Vk1-39*01 (SEQ ID NO: 201) | SEQ ID NO: 42 |
| SEQ ID NO: 134 | EVQLVQSGAEVKKPGSSVKVSCKASGGTFSS YAISWVRQAPGQGLEWMGGIIPIFGTANYAQ KFQGRVTITADKSTSTAYMELSSLRSEDTAV YYCARAPLRFLEWSTQDHYYYYMDVWGKGT TVTVSSASTKGPSVFPLAPSSKSTSGGTAAL GCLVKDYFPEPVTVSWNSGALTSGVHTFPAV LQSSGLYSLSSVVTVPSSSLGTQTYICNVNH KPSNTKVDKRVEPKSCGSSGGGGSGGGGSSG GVFTLEDFVGDWEQTAAYNLDQVLEQGGVSS LLQNLAVSVTPIQRIVRSGENALKIDIHVII PYEGLSADQMAQIEEVFKVVYPVDDHHFKVI LPYGTLVIDGVTPNMLNYFGRPYEGIAVFDG KKITVTGTLWNGNKIIDERLITPDGSMLFRV TINS | α-CD221 heavy-LgBiT | VH1-69*01 (SEQ ID NO: 187) | SEQ ID NO: 43 |
| SEQ ID NO: 135 | SSELTQDPAVSVALGQTVRITCQGDSLRSYY ATWYQQKPGQAPILVIYGENKRPSGIPDRFS GSSSGNTASLTITGAQAEDEADYYCKSRDGS GQHLVFGGGTKLTVLGQPKANPTVTLFPPSS EELQANKATLVCLISDFYPGAVTVAWKADGS PVKAGVETTKPSKQSNNKYAASSYLSLTPEQ WKSHRSYSCQVTHEGSTVEKTVAPTECSGSS GGGGSGGGGSSGGVTGYRLFEEIL | α-CD221 light-SmBiT | V13-19*01 (SEQ ID NO: 211) | SEQ ID NO: 44 |
| SEQ ID NO: 136 | SSELTQDPAVSVALGQTVRITCQGDSLRSYY ATWYQQKPGQAPILVIYGENKRPSGIPDRFS GSSSGNTASLTITGAQAEDEADYYCKSRDGS GQHLVFGGGTKLTVLGQPKANPTVTLFPPSS EELQANKATLVCLISDFYPGAVTVAWKADGS PVKAGVETTKPSKQSNNKYAASSYLSLTPEQ WKSHRSYSCQVTHEGSTVEKTVAPTECS | α-CD221 light | V13-19*01 (SEQ ID NO: 211) | SEQ ID NO: 45 |
| SEQ ID NO: 137 | EVQLVQSGGGVERPGGSLRLSCAASGFTFDD YAMSWVRQAPGKGLEWVSGINWQGGSTGYAD SVKGRVTISRDNAKNSLYLQMNSLRAEDTAV YYCAKILGAGRGWYFDYWGKGTTVTVSSAST KGPSVFPLAPSSKSTSGGTAALGCLVKDYFP EPVTVSWNSGALTSGVHTFPAVLQSSGLYSL SSVVTVPSSSLGTQTYICNVNHKPSNTKVDK RVEPKSCGSSGGGGSGGGGSSGGVFTLEDFV GDWEQTAAYNLDQVLEQGGVSSLLQNLAVSV TPIQRIVRSGENALKIDIHVIIPYEGLSADQ | α-death receptor 5 heavy-LgBiT | VH3-20*01 (SEQ ID NO: 189) | SEQ ID NO: 46 |

TABLE 2-continued

Amino Acid sequences for NanoBiT constructs. All constructs contained an Ig Kappa leader sequence (SEQ ID NO 214: METDTLLLWVLLLWVPGSTG).

| SEQ ID NO | Amino Acid Sequence | Description | Germline | Corresponding DNA SEQ ID NO |
|---|---|---|---|---|
| | MAQIEEVFKVVYPVDDHHFKVILPYGTLVID GVTPNMLNYFGRPYEGIAVFDGKKITVTGTL WNGNKIIDERLITPDGSMLFRVTINS | | | |
| SEQ ID NO: 138 | SSELTQDPAVSVALGQTVRITCSGDSLRSYY ASWYQQKPGQAPVLVIYGANNRPSGIPDRFS GSSSGNTASLTITGAQAEDEADYYCNSADSS GNHVVFGGGTKLTVLGQPKANPTVTLFPPSS EELQANKATLVCLISDFYPGAVTVAWKADGS PVKAGVETTKPSKQSNNKYAASSYLSLTPEQ WKSHRSYSCQVTHEGSTVEKTVAPTECSGSS GGGGSGGGGSSGGVTGYRLFEEIL | α-death receptor 5 light-S SmBiT | V13-19*01 (SEQ ID NO: 211) | SEQ ID NO: 47 |
| SEQ ID NO: 139 | SSELTQDPAVSVALGQTVRITCSGDSLRSYY ASWYQQKPGQAPVLVIYGANNRPSGIPDRFS GSSSGNTASLTITGAQAEDEADYYCNSADSS GNHVVFGGGTKLTVLGQPKANPTVTLFPPSS EELQANKATLVCLISDFYPGAVTVAWKADGS PVKAGVETTKPSKQSNNKYAASSYLSLTPEQ WKSHRSYSCQVTHEGSTVEKTVAPTECS | α-death receptor 5 light | V13-19*01 (SEQ ID NO: 211) | SEQ ID NO: 48 |
| SEQ ID NO: 140 | EVQLVQSGAEVKKPGESLKISCKGSGYSFSN YWIGWVRQMPGKGLEWMGIIDPSNSYTRYSP SFQGQVTISADKSISTAYLQWSSLKASDTAM YYCARWYYKPFDVWGQGTLVTVSSASTKGPS VFPLAPSSKSTSGGTAALGCLVKDYFPEPVT VSWNSGALTSGVHTFPAVLQSSGLYSLSSVV TVPSSSLGTQTYICNVNHKPSNTKVDKRVEP KSCGSSGGGGSGGGGSSGGVFTLEDFVGDWE QTAAYNLDQVLEQGGVSSLLQNLAVSVTPIQ RIVRSGENALKIDIHVIIPYEGLSADQMAQI EEVFKVVYPVDDHHFKVILPYGTLVIDGVTP NMLNYFGRPYEGIAVFDGKKITVTGTLWNGN KIIDERLITPDGSMLFRVTINS | α-IL23 heavy-LgBiT | VH5-51*01 (SEQ ID NO: 198) | SEQ ID NO: 49 |
| SEQ ID NO: 141 | QSVLTQPPSVSGAPGQRVTISCTGSSSNIGS GYDVHWYQQLPGTAPKLLIYGNSKRPSGVPD RFSGSKSGTSASLAITGLQSEDEADYYCASW TDGLSLVVFGGGTKLTVLGQPKANPTVTLFP PSSEELQANKATLVCLISDFYPGAVTVAWKA DGSPVKAGVETTKPSKQSNNKYAASSYLSLT PEQWKSHRSYSCQVTHEGSTVEKTVAPTECS GSSGGGGSGGGGSSGGVTGYRLFEEIL | α-IL23 light-SmBiT | V11-40*01 (SEQ ID NO: 208) | SEQ ID NO: 50 |
| SEQ ID NO: 142 | QSVLTQPPSVSGAPGQRVTISCTGSSSNIGS GYDVHWYQQLPGTAPKLLIYGNSKRPSGVPD RFSGSKSGTSASLAITGLQSEDEADYYCASW TDGLSLVVFGGGTKLTVLGQPKANPTVTLFP PSSEELQANKATLVCLISDFYPGAVTVAWKA DGSPVKAGVETTKPSKQSNNKYAASSYLSLT PEQWKSHRSYSCQVTHEGSTVEKTVAPTECS | α-IL23 light | V11-40*01 (SEQ ID NO: 208) | SEQ ID NO: 51 |
| SEQ ID NO: 143 | QVQLVQSGGGLVQPGGSLRLSCAASGFTFDD YAMHWVRQAPGKGLEWVAGISWDSGSTGYAD SVKGRFTISRDNAKNSLYLQMNSLRAEDTAL YYCARDLGAYQWVEGFDYWGQGTLVTVSSAS TKGPSVFPLAPSSKSTSGGTAALGCLVKDYF PEPVTVSWNSGALTSGVHTFPAVLQSSGLYS LSSVVTVPSSSLGTQTYICNVNHKPSNTKVD KRVEPKSCGSSGGGGSGGGGSSGGVFTLEDF VGDWEQTAAYNLDQVLEQGGVSSLLQNLAVS VTPIQRIVRSGENALKIDIHVIIPYEGLSAD QMAQIEEVFKVVYPVDDHHFKVILPYGTLVI DGVTPNMLNYFGRPYEGIAVFDGKKITVTGT LWNGNKIIDERLITPDGSMLFRVTINS | α-HER3 heavy-LgBiT | VH3-9*01 (SEQ ID NO: 196) | SEQ ID NO: 52 |
| SEQ ID NO: 144 | SYELTQDPAVSVALGQTVRITCQGDSLRSYY ASWYQQKPGQAPVLVIYGKNNRPSGIPDRFS GSTSGNSASLTITGAQAEDEADYYCNSRDSP GNQWVFGGGTKVTVLGGQPKANPTVTLFPPS SEELQANKATLVCLISDFYPGAVTVAWKADG SPVKAGVETTKPSKQSNNKYAASSYLSLTPE | α-HER3 light-SmBiT | V13-19*01 (SEQ ID NO: 211) | SEQ ID NO: 53 |

TABLE 2-continued

Amino Acid sequences for NanoBiT constructs. All constructs contained an Ig Kappa leader sequence (SEQ ID NO 214: METDTLLLWVLLLWVPGSTG).

| SEQ ID NO | Amino Acid Sequence | Description | Germline | Corresponding DNA SEQ ID NO |
|---|---|---|---|---|
| | QWKSHRSYSCQVTHEGSTVEKTVAPTECSGS SGGGGSGGGGSSGGVTGYRLFEEIL | | | |
| SEQ ID NO: 145 | SYELTQDPAVSVALGQTVRITCQGDSLRSYY ASWYQQKPGQAPVLVIYGKNNRPSGIPDRFS GSTSGNSASLTITGAQAEDEADYYCNSRDSP GNQWVFGGGTKVTVLGGQPKANPTVTLFPPS SEELQANKATLVCLISDFYPGAVTVAWKADG SPVKAGVETTKPSKQSNNKYAASSYLSLTPE QWKSHRSYSCQVTHEGSTVEKTVAPTECS | α-HER3 light | V13-19*01 (SEQ ID NO: 211) | SEQ ID NO: 54 |
| SEQ ID NO: 146 | EVQLVQSGGGVERPGGSLRLSCAASGFTFDD YGMSWVRQAPGKGLEWVSGINWNGGSTGYAD SVKGRVTISRDNAKNSLYLQMNSLRAEDTAV YYCAKILGAGRGWYFDLWGKGTTVTVSSAST KGPSVFPLAPSSKSTSGGTAALGCLVKDYFP EPVTVSWNSGALTSGVHTFPAVLQSSGLYSL SSVVTVPSSSLGTQTYICNVNHKPSNTKVDK RVEPKSCGSSGGGGSGGGGSSGGVFTLEDFV GDWEQTAAYNLDQVLEQGGVSSLLQNLAVSV TPIQRIVRSGENALKIDIHVIIPYEGLSADQ MAQIEEVFKVVYPVDDHHFKVILPYGTLVID GVTPNMLNYFGRPYEGIAVFDGKKITVTGTL WNGNKIIDERLITPDGSMLFRVTINS | α-TRAILR2 heavy-LgBiT | VH3-20*01 (SEQ ID NO: 189) | SEQ ID NO: 55 |
| SEQ ID NO: 147 | SSELTQDPAVSVALGQTVRITCQGDSLRSYY ASWYQQKPGQAPVLVIYGKNNRPSGIPDRFS GSSSGNTASLTITGAQAEDEADYYCNSRDSS GNHVVFGGGTKLTVLGQPKANPTVTLFPPSS EELQANKATLVCLISDFYPGAVTVAWKADGS PVKAGVETTKPSKQSNNKYAASSYLSLTPEQ WKSHRSYSCQVTHEGSTVEKTVAPTECSGSS GGGGSGGGGSSGGVTGYRLFEEIL | α-TRAILR2 light-SmBiT | V13-19*01 (SEQ ID NO: 211) | SEQ ID NO: 56 |
| SEQ ID NO: 148 | SSELTQDPAVSVALGQTVRITCQGDSLRSYY ASWYQQKPGQAPVLVIYGKNNRPSGIPDRFS GSSSGNTASLTITGAQAEDEADYYCNSRDSS GNHVVFGGGTKLTVLGQPKANPTVTLFPPSS EELQANKATLVCLISDFYPGAVTVAWKADGS PVKAGVETTKPSKQSNNKYAASSYLSLTPEQ WKSHRSYSCQVTHEGSTVEKTVAPTECS | α-TRAILR2 light | V13-19*01 (SEQ ID NO: 211) | SEQ ID NO: 57 |
| SEQ ID NO: 149 | QVQLVQSGAEVKKPGASVKVSCKASGYTFTS SYINWVRQAPGQGLEWMGTINPVSGSTSYAQ KFQGRVTMTRDTSISTAYMELSRLRSDDTAV YYCARGGWFDYWGQGTLVTVSSASTKGPSVF PLAPSSKSTSGGTAALGCLVKDYFPEPVTVS WNSGALTSGVHTFPAVLQSSGLYSLSSVVTV PSSSLGTQTYICNVNHKPSNTKVDKRVEPKS CGSSGGGGSGGGGSSGGVFTLEDFVGDWEQT AAYNLDQVLEQGGVSSLLQNLAVSVTPIQRI VRSGENALKIDIHVIIPYEGLSADQMAQIEE VFKVVYPVDDHHFKVILPYGTLVIDGVTPNM LNYFGRPYEGIAVFDGKKITVTGTLWNGNKI IDERLITPDGSMLFRVTINS | α-activin receptors heavy-LgBiT | VH1-46*01 (SEQ ID NO: 186) | SEQ ID NO: 58 |
| SEQ ID NO: 150 | QSALTQPASVSGSPGQSITISCTGTSSDVGS YNYVNWYQQHPGKAPKLMIYGVSKRPSGVSN RFSGSKSGNTASLTISGLQAEDEADYYCGTF AGGSYYGVFGGGTKLTVLGQPKANPTVTLFP PSSEELQANKATLVCLISDFYPGAVTVAWKA DGSPVKAGVETTKPSKQSNNKYAASSYLSLT PEQWKSHRSYSCQVTHEGSTVEKTVAPTECS GSSGGGGSGGGGSSGGVTGYRLFEEIL | α-activin receptors light-SmBiT | V12-14*01 (SEQ ID NO: 210) | SEQ ID NO: 59 |
| SEQ ID NO: 151 | QSALTQPASVSGSPGQSITISCTGTSSDVGS YNYVNWYQQHPGKAPKLMIYGVSKRPSGVSN RFSGSKSGNTASLTISGLQAEDEADYYCGTF AGGSYYGVFGGGTKLTVLGQPKANPTVTLFP PSSEELQANKATLVCLISDFYPGAVTVAWKA DGSPVKAGVETTKPSKQSNNKYAASSYLSLT PEQWKSHRSYSCQVTHEGSTVEKTVAPTECS | α-activin receptors light | V12-14*01 (SEQ ID NO: 210) | SEQ ID NO: 60 |

TABLE 2-continued

Amino Acid sequences for NanoBiT constructs. All constructs contained an Ig Kappa leader sequence (SEQ ID NO 214: METDTLLLWVLLLWVPGSTG).

| SEQ ID NO | Amino Acid Sequence | Description | Germline | Corresponding DNA SEQ ID NO |
|---|---|---|---|---|
| SEQ ID NO: 152 | EVQLVQSGAEVKKPGSSVKVSCKASGGTFSSYAISWVRQAPGQGLEWMGGIGPFFGTANYAQKFQGRVTITADESTSTAYMELSSLRSEDTAVYYCARDTPYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCGSSGGGGSGGGGSSGGVFTLEDFVGDWEQTAAYNLDQVLEQGGVSSLLQNLAVSVTPIQRIVRSGENALKIDIHVIIPYEGLSADQMAQIEEVFKVVYPVDDHHFKVILPYGTLVIDGVTPNMLNYFGRPYEGIAVFDGKKITVTGTLWNGNKIIDERLITPDGSMLFRVTINS | α-complement C5 heavy-LgBiT | VH1-69*01 (SEQ ID NO: 187) | SEQ ID NO: 61 |
| SEQ ID NO: 153 | SYELTQPLSVSVALGQTARITCSGDSIPNYYVYWYQQKPGQAPVLVIYDDSNRPSGIPERFSGSNSGNTATLTISRAQAGDEADYYCQSFDSSLNAEVFGGGTKLTVLGQPKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECSGSSGGGGSGGGGSSGGVTGYRLFEEIL | α-complement C5 light-SmBiT | V13-9*01 (SEQ ID NO: 212) | SEQ ID NO: 62 |
| SEQ ID NO: 154 | SYELTQPLSVSVALGQTARITCSGDSIPNYYVYWYQQKPGQAPVLVIYDDSNRPSGIPERFSGSNSGNTATLTISRAQAGDEADYYCQSFDSSLNAEVFGGGTKLTVLGQPKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS | α-complement C5 light | V13-9*01 (SEQ ID NO: 212) | SEQ ID NO: 63 |
| SEQ ID NO: 155 | EVQLVQSGAEVKKPGASVKVSCKASGYTFTGYHMHWVRQAPGQGLEWMGWINPNSGVTKYAQKFQGRVTMTRDTSINTAYMELSRLRFDDTDVYYCATGFGYWGEGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCGSSGGGGSGGGGSSGGVFTLEDFVGDWEQTAAYNLDQVLEQGGVSSLLQNLAVSVTPIQRIVRSGENALKIDIHVIIPYEGLSADQMAQIEEVFKVVYPVDDHHFKVILPYGTLVIDGVTPNMLNYFGRPYEGIAVFDGKKITVTGTLWNGNKIIDERLITPDGSMLFRVTINS | α-CCR2 heavy-LgBiT | VH1-2*01 (SEQ ID NO: 184) | SEQ ID NO: 64 |
| SEQ ID NO: 156 | LPVLTQPPSVSKGLRQTATLTCTGNSNNVGNQGAAWLQQHQGQPPKLLSYRNHNRPSGVSERFSPSRSGDTSSLTITGLQPEDEADYYCLAWDSSLRAFVFGTGTKLTVLGQPKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECSGSSGGGGSGGGGSSGGVTGYRLFEEIL | α-CCR2 light-SmBiT | V110-54*01 (SEQ ID NO: 207) | SEQ ID NO: 65 |
| SEQ ID NO: 157 | LPVLTQPPSVSKGLRQTATLTCTGNSNNVGNQGAAWLQQHQGQPPKLLSYRNHNRPSGVSERFSPSRSGDTSSLTITGLQPEDEADYYCLAWDSSLRAFVFGTGTKLTVLGQPKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS | α-CCR2 light | V110-54*01 (SEQ ID NO: 207) | SEQ ID NO: 66 |
| SEQ ID NO: 158 | EVQLVESGGGLVQPGGSLRLSCVASGFTFSDYWMSWVRQAPGKGLEWVANIKKDGSVNYYVDSVKGRFTISRDNAKNSLYLQMNSLRAEDTAVYYCTRFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCGSSGGGGSGGGGSSGGVFTLEDFVGDWEQTAAYNLDQVLEQGGVSSLLQNLAVSVTPIQRIVRSGENALKIDIHVIIPYEGLSADQMAQIEEVFKVVYPVDDHHFKVILPYGTLVIDGVTPNMLNY | α-CCR2 heavy-LgBiT | VH3-7*01 (SEQ ID NO: 195) | SEQ ID NO: 67 |

TABLE 2-continued

Amino Acid sequences for NanoBiT constructs. All constructs contained an Ig Kappa leader sequence (SEQ ID NO 214: METDTLLLWVLLLWVPGSTG).

| SEQ ID NO | Amino Acid Sequence | Description | Germline | Corresponding DNA SEQ ID NO |
|---|---|---|---|---|
|  | FGRPYEGIAVFDGKKITVTGTLWNGNKIIDE RLITPDGSMLFRVTINS |  |  |  |
| SEQ ID NO: 159 | QAGLTQPPSVSKGLRQTATLTCTGNSNNVGN QGAAWLQQHQGHPPKLLFYRNNNRASGISER LSASRSGNTASLTITGLQPEDEADYYCLTWD SSLSVVVFGGGTKLTVLGQPKANPTVTLFPP SSEELQANKATLVCLISDFYPGAVTVAWKAD GSPVKAGVETTKPSKQSNNKYAASSYLSLTP EQWKSHRSYSCQVTHEGSTVEKTVAPTECSG SSGGGGSGGGGSSGGVTGYRLFEEIL | α-CCR2 light-SmBiT | V110-54*01 (SEQ ID NO: 207) | SEQ ID NO: 68 |
| SEQ ID NO: 160 | QAGLTQPPSVSKGLRQTATLTCTGNSNNVGN QGAAWLQQHQGHPPKLLFYRNNNRASGISER LSASRSGNTASLTITGLQPEDEADYYCLTWD SSLSVVVFGGGTKLTVLGQPKANPTVTLFPP SSEELQANKATLVCLISDFYPGAVTVAWKAD GSPVKAGVETTKPSKQSNNKYAASSYLSLTP EQWKSHRSYSCQVTHEGSTVEKTVAPTECS | α-CCR2 light | V110-54*01 (SEQ ID NO: 207) | SEQ ID NO: 69 |
| SEQ ID NO: 161 | QVQLVESGGGVVQPGRSLRLSCAASGFTFSS YGMHWVRQAPGKGLEWVAFIRYDGSNKYYAD SVKGRFTISRDNSKNTLYLQMNSLRAEDTAV YYCKTHGSHDNWGQGTMVTVSSASTKGPSVF PLAPSSKSTSGGTAALGCLVKDYFPEPVTVS WNSGALTSGVHTFPAVLQSSGLYSLSSVVTV PSSSLGTQTYICNVNHKPSNTKVDKRVEPKS CGSSGGGGSGGGGSSGGVFTLEDFVGDWEQT AAYNLDQVLEQGGVSSLLQNLAVSVTPIQRI VRSGENALKIDIHVIIPYEGLSADQMAQIEE VFKVVYPVDDHHFKVILPYGTLVIDGVTPNM LNYFGRPYEGIAVFDGKKITVTGTLWNGNKI IDERLITPDGSMLFRVTINS | α-IL12ß heavy-LgBiT | VH3-33*01 (SEQ ID NO: 193) | SEQ ID NO: 70 |
| SEQ ID NO: 162 | QSVLTQPPSVSGAPGQRVTISCSGSRSNIGS NTVKWYQQLPGTAPKLLIYYNDQRPSGVPDR FSGSKSGTSASLAITGLQAEDEADYYCQSYD RYTHPALLFGTGTKVTVLGQPKANPTVTLFP PSSEELQANKATLVCLISDFYPGAVTVAWKA DGSPVKAGVETTKPSKQSNNKYAASSYLSLT PEQWKSHRSYSCQVTHEGSTVEKTVAPTECS GSSGGGGSGGGGSSGGVTGYRLFEEIL | α-IL12ß light-SmBiT | V11-44*01 SEQ ID NO: 209 | SEQ ID NO: 71 |
| SEQ ID NO: 163 | QSVLTQPPSVSGAPGQRVTISCSGSRSNIGS NTVKWYQQLPGTAPKLLIYYNDQRPSGVPDR FSGSKSGTSASLAITGLQAEDEADYYCQSYD RYTHPALLFGTGTKVTVLGQPKANPTVTLFP PSSEELQANKATLVCLISDFYPGAVTVAWKA DGSPVKAGVETTKPSKQSNNKYAASSYLSLT PEQWKSHRSYSCQVTHEGSTVEKTVAPTECS | α-IL12ß light | V11-44*01 SEQ ID NO: 209 | SEQ ID NO: 72 |

3. NanoBiT Competition Assay.

Figure 3A:
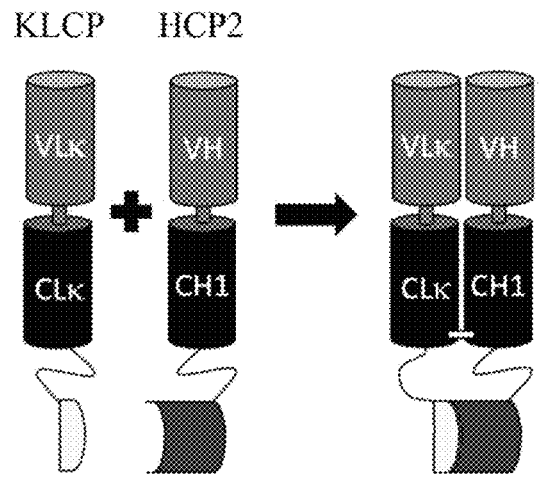
FIGS. 3A-3C depict the competition of a lambda light chain polypeptide (LLCP) and a kappa light chain polypeptide (KLCP) for a heavy chain polypeptide (HCP2) when mixed at a 1:1:1 molar ratio utilizing the NanoBiT® Protein: Protein Interaction System (ACS Chem Biol. 2016 Feb. 19; 11(2):400-8.). HCP2 has the LgBiT as a C-terminal fusion, KLCP has the SmBiT as a C-terminal fusion, and LLCP is a native light chain. When HCP2 and KLCP form a Fab region, the LgBiT and SmBiT create a fully functional NanoLuc domain (FIG. 3A). When HCP2 and LLCP form a Fab region, the NanoLuc is not complete and is inactive (FIG. 3B). A 1:1:1 competition of LLCP and KLCP for HCP2 purified by CH1 affinity results in the HCP2/KLCP functional NanoLuc and the HCP2/LLCP nonfunctional NanoLuc Fab regions (FIG. 3C).
Figure 3B:
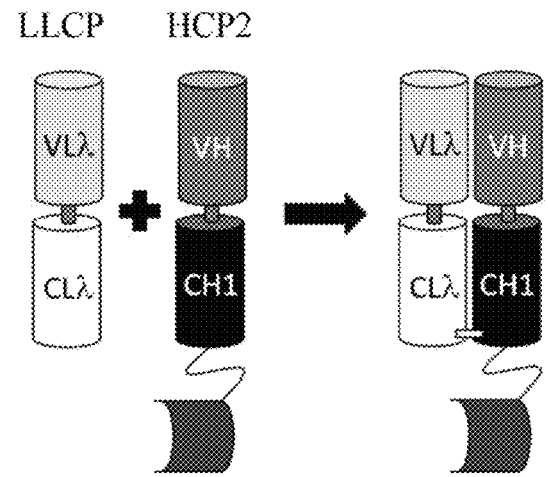
Figure 3C:
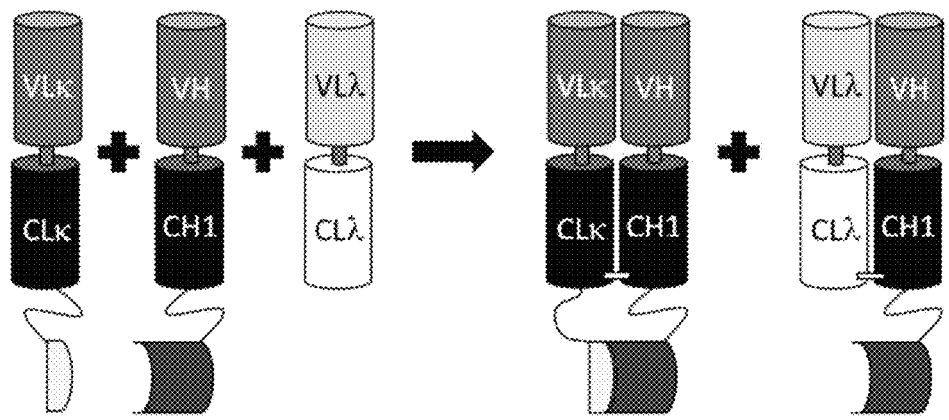

First, a NanoBiT assay was conducted to test the binding between a heavy chain polypeptide (HCP2) and its cognate kappa light chain polypeptide (KLCP) in the presence of a competing lambda light chain polypeptide (LLCP). As shown in FIGS. 3A-3C, a LgBiT was fused to the C-terminus of the HCP2 and a SmBiT was fused to the C-terminus of the KLCP. The competing LLCP was expressed as an un-modified chain. When HCP2 and KLCP form a Fab, the LgBiT and SmBiT generate a fully functional NanoLuc domain, which has luciferase activity (FIG. 3A). When HCP2 and LLCP form a Fab, the NanoLuc is not complete and is inactive (FIG. 3B). A 1:1:1 competition of LLCP and KLCP for HCP2 results in the HCP2/KLCP Fab with a functional NanoLuc and the HCP2/LLCP Fab with a non-functional NanoLuc (FIG. 3C). Each testing included a positive control where the competing light chain was absent, as well as a negative control where the competing light chain was the same KLCP without the SmBiT fusion. The positive control represented 100% pairing; whereas, the negative control represented 50% pairing. The luminescence readings for the positive and negative controls (100% and 50%, respectively) and the luminescence readings for each test pair in the presence of a competing light chain, were compared to quantify the percent pairing for each test pair.

Figure 4A:
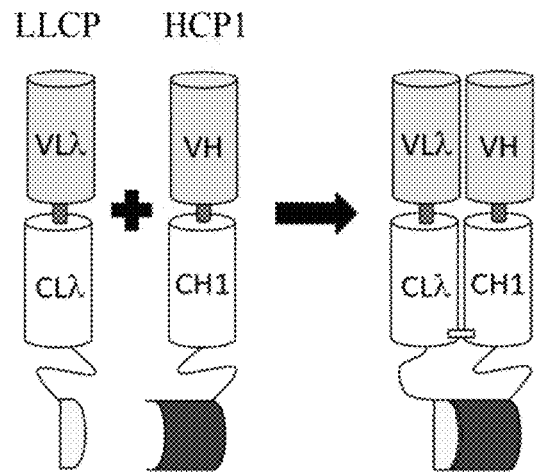
FIGS. 4A-4C depict the competition of a lambda light chain polypeptide (LLCP) and a kappa light chain polypeptide (KLCP) for a heavy chain polypeptide (HCP1) when mixed at a 1:1:1 molar ratio utilizing the NanoBiT® Protein: Protein Interaction System. HCP1 has the LgBiT as a C-terminal fusion, LLCP has the SmBiT as a C-terminal fusion, and KLCP is a native light chain. When HCP1 and LLCP form a Fab region, the LgBiT and SmBiT create a fully functional NanoLuc domain (FIG. 4A). When HCP1 and KLCP form a Fab region, the NanoLuc is not complete and is inactive (FIG. 4B). A 1:1:1 competition of LLCP and KLCP for HCP1 purified by CH1 affinity results in the HCP1/LLCP functional NanoLuc and the HCP1/KLCP nonfunctional NanoLuc Fab regions (FIG. 4C).
Figure 4B:
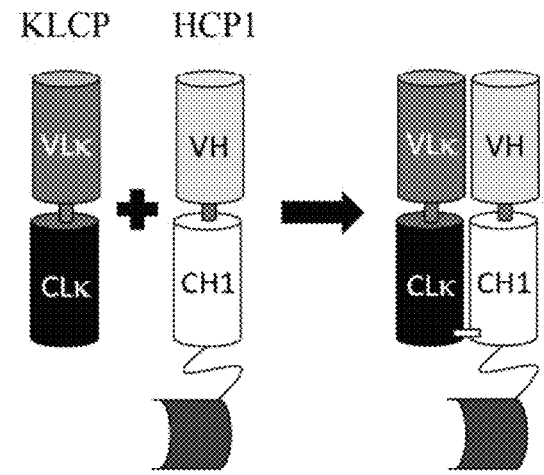
Figure 4C:
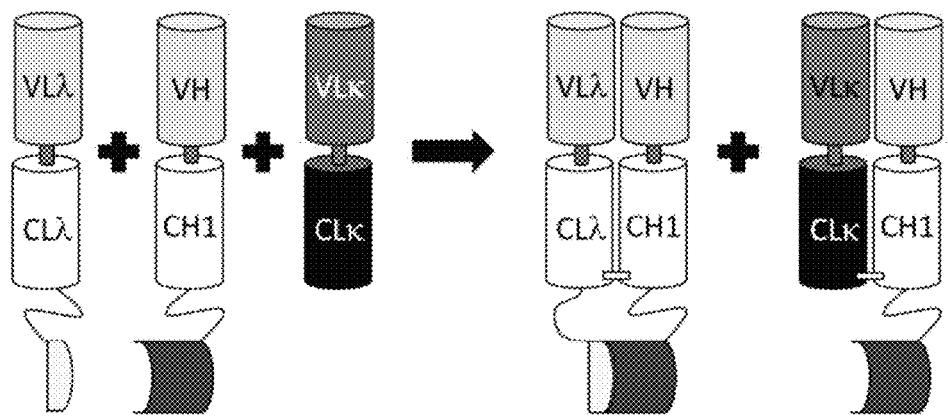

A similar NanoBiT assay was used to test the binding between a heavy chain polypeptide (HCP1) and a lambda light chain polypeptide (LLCP) in the presence of a competing kappa chain polypeptide (KLCP) (FIGS. 4A-4C). In this assay, a LgBiT was fused to the C-terminus of the HCP1 and a SmBiT was fused to the C-terminus of the LLCP. The competing KLCP was expressed as an un-modified light chain. Expression of the HCP1, LLCP, and KLCP at 1:1:1 leads to formation of the HCP1/LLCP Fab with a functional NanoLuc, and the HCP1/KLCP Fab with a nonfunctional NanoLuc (FIG. 4C). Similarly, luminescence readings for each test pair in the presence of a competing light chain were compared with those for positive controls (the competing light chain was absent; 100% pairing) and negative controls (the competing light chain was the same LLCP without the SmBiT fusion; 50% pairing) to determine the percent pairing for each test pair.

The NanoBiT competition assays were performed with 100 µL of protein at 1 g/mL in 96 well plates. A 5× stock solution was made of the Promega Nano-Glo (N1110) assay system following the manufacturer's instructions. Each well received 20 µL of 5× NanoLuc stock solution and the luminescence of the plate was immediately read using a SpectraMax i3x plate reader.

4. Expression and Purification of Multispecific Molecules.

The plasmids were co-transfected into either Expi293 cells (Life Technologies A14527) or ExpiCHO cells (Life Technologies A29127). Transfections were performed using 1 mg of total DNA for a multispecific construct with a 1:1 knob to hole heavy chain ratio and 3:2 light chain to heavy chain ratio. To investigate possible misbalance in expression of the chains, the transfections were performed using varying ratios of heavy chain DNA ranging from 3:1 to 1:3 of knob to hole heavy chain DNA, with the same 3:2 light chain to heavy chain ratio. Transfection in Expi293 cells was done using linear 25,000 Da polyethylenimine (PEI, Polysciences Inc 23966) in a 3:1 ratio with the total DNA. The DNA and PEI were each added to 50 mL of OptiMem (Life Technologies 31985088) medium and sterile filtered. The DNA and PEI were combined for 10 minutes and added to the Expi293 cells with a cell density of $1.8-2.8 \times 10^6$ cells/mL and a viability of at least 95%. The ExpiCHO transfection was performed according to the manufacturer's instructions. Expi293 cells were grown in a humidified incubator at 37° C. with 8% $CO_2$ for 5-7 days after transfection and ExpiCHO cells were grown for 14 days at 32° C. with 5% $CO_2$. The cells were pelleted by centrifugation at 18,000×g and the supernatant was filtered through a 0.2 µm membrane. Protein A resin (GE 17-1279-03) was added to the filtered supernatant and incubated for 1-3 hours at room temperature. The resin was packed into a column, washed with 3×10 column volumes of Dulbecco's phosphate-buffered saline (DPBS, Life Technologies 14190-144). The bound protein was eluted from the column with 20 mM citrate, 100 mM NaCl, pH 2.9. When necessary, the proteins were further purified using size exclusion chromatography on a Superdex 200 column with a running buffer of DPBS.

Table 4 contains the sequences unique to the multispecific constructs. Some of the light chain sequences shown in Table 2 were also used to express the multispecific constructs. A total of 12 multispecific molecules were expressed as described above. The amino acid sequences of these molecules are provided in Table 5a. Table 5b provides the corresponding germline sequences for the multispecific molecules.

TABLE 4

Amino acid sequences used to construct multispecific constructs.

| SEQ ID NO | Amino Acid Sequence | Description | Germline | Corresponding DNA SEQ ID NO |
|---|---|---|---|---|
| SEQ ID NO: 164 | QVQLQESGPGLVKPSQTLSLTCTVSGGSIN NNNYYWTWIRQHPGKGLEWIGYIYYSGST FYNPSLKSRVTISVDTSKTQFSLKLSSVTAA DTAVYYCAREDTMTGLDVWGQGTTVTVS SASTKGPSVFPLAPSSKSTSGGTAALGCLV KDYFPEPVTVSWNSGALTSGVHTFPAVLQS SGLYSLSSVVTVPSSSLGTQTYICNVNHKPS NTKVDKRVEPKSCDKTHTCPPCPAPELLGG PSVFLFPPKPKDTLMISRTPEVTCVVVDVSH EDPEVKFNWYVDGVEVHNAKTKPREEQY NSTYRVVSVLTVLHQDWLNGKEYKCKVS NKALPAPIEKTISKAKGQPREPQVYTLPPCR EEMTKNQVSLWCLVKGFYPSDIAVEWESN GQPENNYKTTPPVLDSDGSFFLYSKLTVDK SRWQQGNVFSCSVMHEALHNHYTQKSLSL SPGK | α-mesothelin AB237 heavy-hCHIg_Knob_Cys | VH4-31*01 (SEQ ID NO: 213) | SEQ ID NO: 82 |
| SEQ ID NO: 165 | DIQMTQSPSSLSASVGDRVTITCRASQSINN YLNWYQQKPGKAPTLLIYAASSLQSGVPSR FSGSRSGTDFTLTISSLQPEDFAAYFCQQTY SNPTFGQGTKVEVKRTVAAPSVFIFPPSDEQ LKSGTASVVCLLNNFYPREAKVQWKVDN ALQSGNSQESVTEQDSKDSTYSLSSTLTLS KADYEKHKVYACEVTHQGLSSPVTKSFNR GEC | α-mesothelin AB237 light-hCLIg_vk | Vk1-39*01 (SEQ ID NO: 201) | SEQ ID NO: 83 |
| SEQ ID NO: 166 | EVQLLESGGGLVQPGGSLRLSCAASGFTFS SYIMMWVRQAPGKGLEWVSSIYPSGGITFY ADTVKGRFTISRDNSKNTLYLQMNSLRAE DTAVYYCARIKLGTVTTVDYWGQGTLVTV SSASTKGPSVFPLAPSSKSTSGGTAALGCLV KDYFPEPVTVSWNSGALTSGVHTFPAVLQS SGLYSLSSVVTVPSSSLGTQTYICNVNHKPS NTKVDKRVEPKSCDKTHTCPPCPAPELLGG PSVFLFPPKPKDTLMISRTPEVTCVVVDVSH EDPEVKFNWYVDGVEVHNAKTKPREEQY NSTYRVVSVLTVLHQDWLNGKEYKCKVS NKALPAPIEKTISKAKGQPREPQVCTLPPSR | α-PDL1 heavy-hCHIg_Hole_Cys | VH3-66*01 (SEQ ID NO: 194) | SEQ ID NO: 84 |

TABLE 4-continued

Amino acid sequences used to construct multispecific constructs.

| SEQ ID NO | Amino Acid Sequence | Description | Germline | Corresponding DNA SEQ ID NO |
|---|---|---|---|---|
| | EEMTKNQVSLSCAVKGFYPSDIAVEWESN GQPENNYKTTPPVLDSDGSFFLVSKLTVDK SRWQQGNVFSCSVMHEALHNHYTQKSLSL SPGK | | | |
| SEQ ID NO: 167 | QSALTQPASVSGSPGQSITISCTGTSSDVGG YNYVSWYQQHPGKAPKLMIYDVSNRPSG VSNRFSGSKSGNTASLTISGLQAEDEADYY CSSYTSSSTRVFGTGTKVTVLGQPKANPTV TLFPPSSEELQANKATLVCLISDFYPGAVTV AWKADGSPVKAGVETTKPSKQSNNKYAA SSYLSLTPEQWKSHRSYSCQVTHEGSTVEK TVAPTECS | α-PDL1 light-hCLIg_vl | Vl2-14*01 (SEQ ID NO: 210) | SEQ ID NO: 85 |
| SEQ ID NO: 168 | QVQLVESGGGVVQPGRSLRLSCAASGFTFS SYTMHWVRQAPGKGLEWVTFISYDGNNK YYADSVKGRFTISRDNSKNTLYLQMNSLR AEDTAIYYCARTGWLGPFDYWGQGTLVTV SSASTKGPSVFPLAPSSKSTSGGTAALGCLV KDYFPEPVTVSWNSGALTSGVHTFPAVLQS SGLYSLSSVVTVPSSSLGTQTYICNVNHKPS NTKVDKRVEPKSCDKTHTCPPCPAPELLGG PSVFLFPPKPKDTLMISRTPEVTCVVVDVSH EDPEVKFNWYVDGVEVHNAKTKPREEQY NSTYRVVSVLTVLHQDWLNGKEYKCKVS NKALPAPIEKTISKAKGQPREPQVYTLPPCR EEMTKNQVSLWCLVKGFYPSDIAVEWESN GQPENNYKTTPPVLDSDGSFFLYSKLTVDK SRWQQGNVFSCSVMHEALHNHYTQKSLSL SPGK | α-CTLA4 heavy-hCHIg_Knob_Cys | VH3-30*01 (SEQ ID NO: 192) | SEQ ID NO: 78 |
| SEQ ID NO: 169 | QVQLVESGGGVVQPGRSLRLSCAASGFTFS SYTMHWVRQAPGKGLEWVTFISYDGNNK YYADSVKGRFTISRDNSKNTLYLQMNSLR AEDTAIYYCARTGWLGPFDYWGQGTLVTV SSASTKGPSVFPLAPSSKSTSGGTAALGCLV KDYFPEPVTVSWNSGALTSGVHTFPAVLQS SGLYSLSSVVTVPSSSLGTQTYICNVNHKPS NTKVDKRVEPKSCDKTHTCPPCPAPELLGG PSVFLFPPKPKDTLMISRTPEVTCVVVDVSH EDPEVKFNWYVDGVEVHNAKTKPREEQY NSTYRVVSVLTVLHQDWLNGKEYKCKVS NKALPAPIEKTISKAKGQPREPQVYTLPPCR EEMTKNQVSLWCLVKGFYPSDIAVEWESN GQPENNYKTTPPVLDSDGSFFLYSKLTVDK SRWQQGNVFSCSVMHEALHNHYTQKSLSL SPGKGGGGSGGGGSGGGGSEVQLVESGGG LVKPGGSLRLSCAASGFTFSPYSVFWRQA PGKGLEWVSSINTDSTYKYYADSVKGRFTI SRDNAENSIFLQMNSLRAEDTAVYYCARD RSYYAFSSGSLSDYYYGLDVWGQGTLVTV SSGGGGSGGGGSGGGGSGGGGSDIVMTQS PLSLSVTPGEPASISCRSSQSLLHTNLYNYL DWYVQKPGQSPQLLIYLASNRASGVPDRFS GSGSGTDFTLKISRVETEDVGVYYCMQAL QIPRTFGQGTKLEIK | α-CTLA4 heavy-hCHIg_Knob_Cys-GH_scFv | VH3-30*01 (SEQ ID NO: 192) | SEQ ID NO: 79 |
| SEQ ID NO: 170 | QVQLVESGGGVVQPGRSLRLSCAASGFTFS SYGMHWVRQAPGKGLEWVAFIRYDGSNK YYADSVKGRFTISRDNSKNTLYLQMNSLR AEDTAVYYCKTHGSHDNWGQGTMVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKRVEPKSCDKTHTCPPCPAPELLGG PSVFLFPPKPKDTLMISRTPEVTCVVVDVSH EDPEVKFNWYVDGVEVHNAKTKPREEQY NSTYRVVSVLTVLHQDWLNGKEYKCKVS NKALPAPIEKTISKAKGQPREPQVCTLPPSR EEMTKNQVSLSCAVKGFYPSDIAVEWESN GQPENNYKTTPPVLDSDGSFFLVSKLTVDK SRWQQGNVFSCSVMHEALHNHYTQKSLSL SPGK | α-IL12β heavy-hCHIg_Hole_Cys | VH3-33*01 (SEQ ID NO: 193) | SEQ ID NO: 91 |

TABLE 4-continued

Amino acid sequences used to construct multispecific constructs.

| SEQ ID NO | Amino Acid Sequence | Description | Germline | Corresponding DNA SEQ ID NO |
|---|---|---|---|---|
| SEQ ID NO: 171 | QVQLVESGGGVVQPGRSLRLSCAASGFTFS SYTMHWVRQAPGKGLEWVTFISYDGNNK YYADSVKGRFTISRDNSKNTLYLQMNSLR AEDTAIYYCARTGWLGPFDYWGQGTLVTV SSASTKGPSVFPLAPSSKSTSGGTAALGCLV KDYFPEPVTVSWNSGALTSGVHTFPAVLQS SGLYSLSSVVTVPSSSLGTQTYICNVNHKPS NTKVDKRVEPKSCDKTHTCPPCPAPELLGG PSVFLFPPKPKDTLMISRTPEVTCVVVDVSH EDPEVKFNWYVDGVEVHNAKTKPREEQY NSTYRVVSVLTVLHQDWLNGKEYKCKVS NKALPAPIEKTISKAKGQPREPQVYTLPPSR EEMTKNQVSLTCLVKGFYPSDIAVEWESN GQPENNYKTTPPVLDSDGSFFLYSKLTVDK SRWQQGNVFSCSVMHEALHNHYTQKSLSL SPGK | α-CTLA4 heavy- hCHIg | VH3- 30*01 (SEQ ID NO: 192) | SEQ ID NO: 73 |
| SEQ ID NO: 172 | QVQLVESGGGVVQPGRSLRLSCAASGFTFS SYGMHWVRQAPGKGLEWVAFIRYDGSNK YYADSVKGRFTISRDNSKNTLYLQMNSLR AEDTAVYYCKTHGSHDNWGQGTMVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKRVEPKSCDKTHTCPPCPAPELLGG PSVFLFPPKPKDTLMISRTPEVTCVVVDVSH EDPEVKFNWYVDGVEVHNAKTKPREEQY NSTYRVVSVLTVLHQDWLNGKEYKCKVS NKALPAPIEKTISKAKGQPREPQVYTLPPSR EEMTKNQVSLTCLVKGFYPSDIAVEWESN GQPENNYKTTPPVLDSDGSFFLYSKLTVDK SRWQQGNVFSCSVMHEALHNHYTQKSLSL SPGK | α-IL12β heavy- hCHIg | VH3- 33*01 (SEQ ID NO: 193) | SEQ ID NO: 74 |
| SEQ ID NO: 173 | QSVLTQPPSVSGAPGQRVTISCSGSRSNIGS NTVKWYQQLPGTAPKLLIYYNDQRPSGVP DRFSGSKSGTSASLAITGLQAEDEADYYCQ SYDRYTHPALLFGTGTKVTVLGQPKANPT VTLFPPSSEELQANKATLVCLISDFYPGAVT VAWKADGSPVKAGVETTKPSKQSNNKYA ASSYLSLTPEQWKSHRSYSCQVTHEGSTVE KTVAPTECSGGGGSGGGGSGGGGSAPTSSS TKKTQLQLEHLLLDLQMILNGINNYKNPKL TRMLTAKFAMPKKATELKHLQCLEEELKP LEEVLNLAQSKNFHLRPRDLISNINVIVLEL KGSETTFMCEYADETATIVEFLNRWITFCQ SIISTLT | α-IL12β light- hCLIg_vl- IL2 | Vl1- 44*01 (SEQ ID NO: 209) | SEQ ID NO: 75 |
| SEQ ID NO: 174 | QVQLVESGGGVVQPGRSLRLSCAASGFTFS SYGMHWVRQAPGKGLEWVAFIRYDGSNK YYADSVKGRFTISRDNSKNTLYLQMNSLR AEDTAVYYCKTHGSHDNWGQGTMVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKRVEPKSCDKTHTCPPCPAPELLGG PSVFLFPPKPKDTLMISRTPEVTCVVVDVSH EDPEVKFNWYVDGVEVHNAKTKPREEQY NSTYRVVSVLTVLHQDWLNGKEYKCKVS NKALPAPIEKTISKAKGQPREPQVCTLPPSR EEMTKNQVSLSCAVKGFYPSDIAVEWESN GQPENNYKTTPPVLDSDGSFFLVSKLTVDK SRWQQGNVFSCSVMHEALHNHYTQKSLSL SPGKGGGGSGGGGSGGGGSAPTSSSTKKT QLQLEHLLLDLQMILNGINNYKNPKLTRML TAKFAMPKKATELKHLQCLEEELKPLEEVL NLAQSKNFHLRPRDLISNINVIVLELKGSET TFMCEYADETATIVEFLNRWITFCQSIISTLT | α-IL12β heavy- hCHIg_ Hole_Cys | VH3- 33*01 (SEQ ID NO: 193) | SEQ ID NO: 76 |
| SEQ ID NO: 175 | QVQLVESGGGVVQPGRSLRLSCAASGFTFS SYGMHWVRQAPGKGLEWVAFIRYDGSNK YYADSVKGRFTISRDNSKNTLYLQMNSLR AEDTAVYYCKTHGSHDNWGQGTMVTVSS ASTKGPSVFPLAPSSKSTSGGTAALGCLVK | α-IL12β heavy- hCHIg | VH3- 33*01 (SEQ ID NO: 193) | SEQ ID NO: 77 |

TABLE 4-continued

Amino acid sequences used to construct multispecific constructs.

| SEQ ID NO | Amino Acid Sequence | Description | Germline | Corresponding DNA SEQ ID NO |
|---|---|---|---|---|
| | DYFPEPVTVSWNSGALTSGVHTFPAVLQSS GLYSLSSVVTVPSSSLGTQTYICNVNHKPS NTKVDKRVEPKSCDKTHTCPPCPAPELLGG PSVFLFPPKPKDTLMISRTPEVTCVVVDVSH EDPEVKFNWYVDGVEVHNAKTKPREEQY NSTYRVVSVLTVLHQDWLNGKEYKCKVS NKALPAPIEKTISKAKGQPREPQVYTLPPSR EEMTKNQVSLTCLVKGFYPSDIAVEWESN GQPENNYKTTPPVLDSDGSFFLYSKLTVDK SRWQQGNVFSCSVMHEALHNHYTQKSLSL SPGKGGGGSGGGGSGGGGSAPTSSSTKKT QLQLEHLLLDLQMILNGINNYKNPKLTRML TAKFAMPKKATELKHLQCLEEELKPLEEVL NLAQSKNFHLRPRDLISNINVIVLELKGSET TFMCEYADETATIVEFLNRWITFCQSIISTLT | | | |
| SEQ ID NO: 176 | EIVLTQSPGTLSLSPGERATLSCRASQSVGS SYLAWYQQKPGQAPRLLIYGAFSRATGIPD RFSGSGSGTDFTLTISRLEPEDFAVYYCQQY GSSPWTFGQGTKVEIKRTVAAPSVFIFPPSD EQLKSGTASVVCLLNNFYPREAKVQWKVD NALQSGNSQESVTEQDSKDSTYSLSSTLTL SKADYEKHKVYACEVTHQGLSSPVTKSFN RGECGGGGSGGGGSGGGGSAPTSSSTKKT QLQLEHLLLDLQMILNGINNYKNPKLTRML TAKFAMPKKATELKHLQCLEEELKPLEEVL NLAQSKNFHLRPRDLISNINVIVLELKGSET TFMCEYADETATIVEFLNRWITFCQSIISTLT | α-CTLA4 light-hCLIg_vk-IL2 | Vk3-20*01 (SEQ ID NO: 205) | SEQ ID NO: 80 |
| SEQ ID NO: 177 | EVQLVQSGGGVERPGGSLRLSCAASGFTFD DYGMSWVRQAPGKGLEWVSGINWNGGST GYADSVKGRVTISRDNAKNSLYLQMNSLR AEDTAVYYCAKILGAGRGWYFDLWGKGT TVTVSSASTKGPSVFPLAPSSKSTSGGTAAL GCLVKDYFPEPVTVSWNSGALTSGVHTFP AVLQSSGLYSLSSVVTVPSSSLGTQTYICNV NHKPSNTKVDKRVEPKSCDKTHTCPPCPAP ELLGGPSVFLFPPKPKDTLMISRTPEVTCVV VDVSHEDPEVKFNWYVDGVEVHNAKTKP REEQYNSTYRVVSVLTVLHQDWLNGKEY KCKVSNKALPAPIEKTISKAKGQPREPQVC TLPPSREEMTKNQVSLSCAVKGFYPSDIAV EWESNGQPENNYKTTPPVLDSDGSFFLVSK LTVDKSRWQQGNVFSCSVMHEALHNHYT QKSLSLSPGK | α-TNFR10β heavy-hCHIg_Hole_Cys | Vk3-20*01 (SEQ ID NO: 205) | SEQ ID NO: 81 |
| SEQ ID NO: 178 | QVQLVQSGGGLVQPGGSLRLSCAASGFTF DDYAMHWVRQAPGKGLEWVAGISWDSGS TGYADSVKGRFTISRDNAKNSLYLQMNSL RAEDTALYYCARDLGAYQWVEGFDYWGQ GTLVTVSSASTKGPSVFPLAPSSKSTSGGTA ALGCLVKDYFPEPVTVSWNSGALTSGVHT FPAVLQSSGLYSLSSVVTVPSSSLGTQTYIC NVNHKPSNTKVDKRVEPKSCTIKPCPPCKC PAPNLLGGPSVFIFPPKIKDVLMISLSPIVTC VVVDVSEDDPDVQISWFVNNVEVHTAQTQ THREDYNSTLRVVSALPIQHQDWMSGKEF KCKVNNKDLPAPIERTISKPKGSVRAPQVY VLPPCEEEMTKKQVTLWCMVTDFMPEDIY VEWTNNGKTELNYKNTEPVLDSDGSYFMY SKLRVEKKNWVERNSYSCSVVHEGLHNH HTTKSFSRTPGK | α-HER3 heavy-mFc_Knob_Cys | VH3-9*01 (SEQ ID NO: 196) | SEQ ID NO: 86 |
| SEQ ID NO: 179 | EVQLLQSGGGLVQPGGSLRLSCAASGFMFS RYPMHWVRQAPGKGLEWVGSISGSGGATP YADSVKGRFTISRDNSKNTLYLQMNSLRA EDTAVYYCAKDFYQILTGNAFDYWGQGTT VTVSSASTKGPSVFPLAPSSKSTSGGTAALG CLVKDYFPEPVTVSWNSGALTSGVHTFPA VLQSSGLYSLSSVVTVPSSSLGTQTYICNVN HKPSNTKVDKRVEPKSCTIKPCPPCKCPAP NLLGGPSVFIFPPKIKDVLMISLSPIVTCVVV DVSEDDPDVQISWFVNNVEVHTAQTQTHR EDYNSTLRVVSALPIQHQDWMSGKEFKCK | α-IGF1R heavy-mFc_Hole_Cys | VH3-23*01 (SEQ ID NO: 191) | SEQ ID NO: 87 |

TABLE 4-continued

Amino acid sequences used to construct multispecific constructs.

| SEQ ID NO | Amino Acid Sequence | Description | Germline | Corresponding DNA SEQ ID NO |
|---|---|---|---|---|
| | VNNKDLPAPIERTISKPKGSVRAPQVCVLPP PEEEMTKKQVTLSCAVTDFMPEDIYVEWT NNGKTELNYKNTEPVLDSDGSYFMVSKLR VEKKNWVERNSYSCSVVHEGLHNHHTTKS FSRTPGK | | | |
| SEQ ID NO: 180 | EVQLVQSGAEVKKPGSSVKVSCKASGGTF SSYAISWVRQAPGQGLEWMGGIIPIFGTAN YAQKFQGRVTITADKSTSTAYMELSSLRSE DTAVYYCARAPLRFLEWSTQDHYYYYM DVWGKGTTVTVSSASTKGPSVFPLAPSSKS TSGGTAALGCLVKDYFPEPVTVSWNSGAL TSGVHTFPAVLQSSGLYSLSSVVTVPSSSLG TQTYICNVNHKPSNTKVDKRVEPKSCDKT HTCPPCPAPELLGGPSVFLFPPKPKDTLMIS RTPEVTCVVVDVSHEDPEVKFNWYVDGVE VHNAKTKPREEQYNSTYRVVSVLTVLHQD WLNGKEYKCKVSNKALPAPIEKTISKAKG QPREPQVCTLPPSREEMTKNQVSLSCAVKG FYPSDIAVEWESNGQPENNYKTTPPVLDSD GSFFLVSKLTVDKSRWQQGNVFSCSVMHE ALHNHYTQKSLSLSPGK | α-CD221 heavy-hCHIg_Hole_Cys | VH1-69*01 (SEQ ID NO: 187) | SEQ ID NO: 88 |
| SEQ ID NO: 181 | QVQLVESGGGVVQPGRSLRLDCKASGITFS NSGMHWVRQAPGKGLEWVAVIWYDGSK RYYADSVKGRFTISRDNSKNTLFLQMNSLR AEDTAVYYCATNDDYWGQGTLVTVSSAS TKGPSVFPLAPSSKSTSGGTAALGCLVKDY FPEPVTVSWNSGALTSGVHTFPAVLQSSGL YSLSSVVTVPSSSLGTQTYICNVNHKPSNT KVDKRVEPKSCDKTHTCPPCPAPELLGGPS VFLFPPKPKDTLMISRTPEVTCVVVDVSHE DPEVKFNWYVDGVEVHNAKTKPREEQYN STYRVVSVLTVLHQDWLNGKEYKCKVSN KALPAPIEKTISKAKGQPREPQVYTLPPCRE EMTKNQVSLWCLVKGFYPSDIAVEWESNG QPENNYKTTPPVLDSDGSFFLYSKLTVDKS RWQQGNVFSCSVMHEALHNHYTQKSLSLS PGK | α-PD1 heavy-hCHIg_Knob_Cys | VH3-33*01 (SEQ ID NO: 193) | SEQ ID NO: 89 |
| SEQ ID NO: 182 | EIVLTQSPATLSLSPGERATLSCRASQSVSS YLAWYQQKPGQAPRLLIYDASNRATGIPA RFSGSGSGTDFTLTISSLEPEDFAVYYCQQS SNWPRTFGQGTKVEIKRTVAAPSVFIFPPSD EQLKSGTASVVCLLNNFYPREAKVQWKVD NALQSGNSQESVTEQDSKDSTYSLSSTLTL SKADYEKHKVYACEVTHQGLSSPVTKSFN RGEC | α-PD1 light-hCLIg_vk | Vk3-11*01 (SEQ ID NO: 204) | SEQ ID NO: 90 |

TABLE 15

Germline sequences shown in Tables 2 and 4 (full-length sequences).

| SEQ ID NO | Description | Amino acid sequences |
|---|---|---|
| 183 | VH1-18*01 | QVQLVQSGAEVKKPGASVKVSCKASGYTFTSYGISWVRQAPGQGLEWMG WISAYNGNTNYAQKLQGRVTMTTDTSTSTAYMELRSLRSDDTAVYYCAR |
| 184 | VH1-2*01 | QVQLVQSGAEVKKPGASVKVSCKASGYTFTGYYMHWVRQAPGQGLEWMG RINPNSGGTNYAQKFQGRVTSTRDTSISTAYMELSRLRSDDTVVYYCAR |
| 185 | VH1-3*01 | QVQLVQSGAEVKKPGASVKVSCKASGYTFTSYAMHWVRQAPGQRLEWMG WINAGNGNTKYSQKFQGRVTITRDTSASTAYMELSSLRSEDTAVYYCAR |
| 186 | VH1-46*01 | QVQLVQSGAEVKKPGASVKVSCKASGYTFTSYYMHWVRQAPGQGLEWMG IINPSGGSTSYAQKFQGRVTMTRDTSTSTVYMELSSLRSEDTAVYYCAR |

TABLE 15-continued

Germline sequences shown in
Tables 2 and 4 (full-length sequences).

| SEQ ID NO | Description | Amino acid sequences |
|---|---|---|
| 187 | VH1-69*01 | QVQLVQSGAEVKKPGSSVKVSCKASGGTFSSYAISWVRQAPGQGLEWMG GIIPIFGTANYAQKFQGRVTITADESTSTAYMELSSLRSEDTAVYYCAR |
| 188 | VH3-13*01 | EVQLVESGGGLVQPGGSLRLSCAASGFTFSSYDMHWVRQATGKGLEWVS AIGTAGDTYYPGSVKGRFTISRENAKNSLYLQMNSLRAGDTAVYYCAR |
| 189 | VH3-20*01 | EVQLVESGGGVVRPGGSLRLSCAASGFTFDDYGMSWVRQAPGKGLEWVS GINWNGGSTGYADSVKGRFTISRDNAKNSLYLQMNSLRAEDTALYHCAR |
| 190 | VH3-21*01 | EVQLVESGGGLVKPGGSLRLSCAASGFTFSSYSMNWVRQAPGKGLEWVS SISSSSSYIYYADSVKGRFTISRDNAKNSLYLQMNSLRAEDTAVYYCAR |
| 191 | VH3-23*01 | EVQLLESGGGLVQPGGSLRLSCAASGFTFSSYAMSWVRQAPGKGLEWVS AISGSGGSTYYADSVKGRFTISRDNSKNTLYLQMNSLRAEDTAVYYCAK |
| 192 | VH3-30*01 | QVQLVESGGGVVQPGRSLRLSCAASGFTFSSYAMHWVRQAPGKGLEWVA VISYDGSNKYYADSVKGRFTISRDNSKNTLYLQMNSLRAEDTAVYYCAR |
| 193 | VH3-33*01 | QVQLVESGGGVVQPGRSLRLSCAASGFTFSSYGMHWVRQAPGKGLEWVA VIWYDGSNKYYADSVKGRFTISRDNSKNTLYLQMNSLRAEDTAVYYCAR |
| 194 | VH3-66*01 | EVQLVESGGGLVQPGGSLRLSCAASGFTVSSNYMSWVRQAPGKGLEWVS VIYSGGSTYYADSVKGRFTISRDNSKNTLYLQMNSLRAEDTAVYYCAR |
| 195 | VH3-7*01 | EVQLVESGGGLVQPGGSLRLSCAASGFTFSSYWMSWVRQAPGKGLEWVA NIKQDGSEKYYVDSVKGRFTISRDNAKNSLYLQMNSLRAEDTAVYYCAR |
| 196 | VH3-9*01 | EVQLVESGGGLVQPGRSLRLSCAASGFTFDDYAMHWVRQAPGKGLEWVS GISWNSGSIGYADSVKGRFTISRDNAKNSLYLQMNSLRAEDTALYYCAK |
| 197 | VH4-4*01 | QVQLQESGPGLVKPPGTLSLTCAVSGGSISSSNWWSWVRQPPGKGLEWI GEIYHSGSTNYNPSLKSRVTISVDKSKNQFSLKLSSVTAADTAVYCCAR |
| 198 | VH5-51*01 | EVQLVQSGAEVKKPGESLKISCKGSGYSFTSYWIGWVRQMPGKGLEWMG IIYPGDSDTRYSPSFQGQVTISADKSISTAYLQWSSLKASDTAMYYCAR |
| 199 | Vk1-12*01 | DIQMTQSPSSVSASVGDRVTITCRASQGISSWLAWYQQKPGKAPKLLIY AASSLQSGVPSRFSGSGSGTDFTLTISSLQPEDFATYYC |
| 200 | Vk1-27*01 | DIQMTQSPSSLSASVGDRVTITCRASQGISNYLAWYQQKPGKVPKLLIY AASTLQSGVPSRFSGSGSGTDFTLTISSLQPEDVATYYC |
| 201 | Vk1-39*01 | DIQMTQSPSSLSASVGDRVTITCRASQSISSYLNWYQQKPGKAPKLLIY AASSLQSGVPSRFSGSGSGTDFTLTISSLQPEDFATYYC |
| 202 | Vk1D-16*01 | DIQMTQSPSSLSASVGDRVTITCRASQGISSWLAWYQQKPEKAPKSLIY AASSLQSGVPSRFSGSGSGTDFTLTISSLQPEDFATYYC |
| 203 | Vk2-28*01 | DIVMTQSPLSLPVTPGEPASISCRSSQSLLHSNGYNYLDWYLQKPGQSP QLLIYLGSNRASGVPDRFSGSGSGTDFTLKISRVEAEDVGVYYC |
| 204 | Vk3-11*01 | EIVLTQSPATLSLSPGERATLSCRASQSVSSYLAWYQQKPGQAPRLLIY DASNRATGIPARFSGSGSGTDFTLTISSLEPEDFAVYYC |
| 205 | Vk3-20*01 | EIVLTQSPGTLSLSPGERATLSCRASQSVSSSYLAWYQQKPGQAPRLLI YGASSRATGIPDRFSGSGSGTDFTLTISRLEPEDFAVYYC |
| 206 | Vk3D-20*01 | EIVLTQSPATLSLSPGERATLSCGASQSVSSSYLAWYQQKPGLAPRLLI YDASSRATGIPDRFSGSGSGTDFTLTISRLEPEDFAVYYC |
| 207 | Vl10-54*01 | QAGLTQPPSVSKGLRQTATLTCTGNSNNVGNQGAAWLQQHQGHPPKLLS YRNNNRPSGISERLSASRSGNTASLTITGLQPEDEADYYC |
| 208 | Vl1-40*01 | QSVLTQPPSVSGAPGQRVTISCTGSSSNIGAGYDVHWYQQLPGTAPKLL IYGNSNRPSGVPDRFSGSKSGTSASLAITGLQAEDEADYYC |
| 209 | Vl1-44*01 | QSVLTQPPSASGTPGQRVTISCSGSSSNIGSNTVNWYQQLPGTAPKLLI YSNNQRPSGVPDRFSGSKSGTSASLAISGLQSEDEADYYC |
| 210 | Vl2-14*01 | QSALTQPASVSGSPGQSITISCTGTSSDVGGYNYVSWYQQHPGKAPKLM IYEVSNRPSGVSNRFSGSKSGNTASLTISGLQAEDEADYYC |

TABLE 15-continued

Germline sequences shown in
Tables 2 and 4 (full-length sequences).

| SEQ ID NO | Description | Amino acid sequences |
|---|---|---|
| 211 | Vl3-19*01 | SSELTQDPAVSVALGQTVRITCQGDSLRSYYASWYQQKPGQAPVLVIYG KNNRPSGIPDRFSGSSSGNTASLTITGAQAEDEADYYC |
| 212 | Vl3-9*01 | SYELTQPLSVSVALGQTARITCGGNNIGSKNVHWYQQKPGQAPVLVIYR DSNRPSGIPERFSGSNSGNTATLTISRAQAGDEADYYC |
| 213 | VH4-31*01 | QVQLQESGPGLVKPSQTLSLTCTVSGGSISSGGYYWSWIRQHPGKGLEW IGYIYYSGSTYYNPSLKSLVTISVDTSKNQFSLKLSSVTAADTAVYYCA R |

TABLE 16

Germline sequences shown in Tables 2 and 4
(framework 1, CDR1, framework 2, CDR2, and
framework 3 sequences).

| Germline | Framework 1 | Kabat CDR 1 | Framework 2 | Kabat CDR 2 | Framework 3 |
|---|---|---|---|---|---|
| VH1-18*01 (SEQ ID NO: 183) | QVQLVQSGA EVKKPGASV KVSCKAS (SEQ ID NO: 215) | GYTFTSYGIS (SEQ ID NO: 216) | WVRQAPGQG LEWMG (SEQ ID NO: 217) | WISAYNGNT NYAQKLQG (SEQ ID NO: 218) | RVTMTTDTST STAYMELRSL RSDDTAVYY CAR (SEQ ID NO: 219) |
| VH1-2*01 (SEQ ID NO: 184) | QVQLVQSGA EVKKPGASV KVSCKAS (SEQ ID NO: 215) | GYTFTGYYM H (SEQ ID NO: 220) | WVRQAPGQG LEWMG (SEQ ID NO: 217) | RINPNSGGTN YAQKFQG (SEQ ID NO: 221) | RVTSTRDTSIS TAYMELSRL RSDDTVVYY CAR (SEQ ID NO: 222) |
| VH1-3*01 (SEQ ID NO: 185) | QVQLVQSGA EVKKPGASV KVSCKAS (SEQ ID NO: 215) | GYTFTSYAM H (SEQ ID NO: 223) | WVRQAPGQR LEWMG (SEQ ID NO: 224) | WINAGNGNT KYSQKFQG (SEQ ID NO: 225) | RVTITRDTSA STAYMELSSL RSEDTAVYY CAR (SEQ ID NO: 226) |
| VH1-46*01 (SEQ ID NO: 186) | QVQLVQSGA EVKKPGASV KVSCKAS (SEQ ID NO: 215) | GYTFTSYYM H (SEQ ID NO: 227) | WVRQAPGQG LEWMG (SEQ ID NO: 217) | IINPSGGSTSY AQKFQG (SEQ ID NO: 228) | RVTMTRDTS TSTVYMELSS LRSEDTAVY YCAR (SEQ ID NO: 229) |
| VH1-69*01 (SEQ ID NO: 187) | QVQLVQSGA EVKKPGSSVK VSCKAS (SEQ ID NO: 230) | GGTFSSYAIS (SEQ ID NO: 231) | WVRQAPGQG LEWMG (SEQ ID NO: 217) | GIIPIFGTANY AQKFQG (SEQ ID NO: 232) | RVTITADEST STAYMELSSL RSEDTAVYY CAR (SEQ ID NO: 233) |
| VH3-13*01 (SEQ ID NO: 188) | EVQLVESGG GLVQPGGSLR LSCAAS (SEQ ID NO: 234) | GFTFSSYDMH (SEQ ID NO: 235) | WVRQATGKG LEWVS (SEQ ID NO: 236) | AIGTAGDTYY PGSVKG (SEQ ID NO: 237) | RFTISRENAK NSLYLQMNS LRAGDTAVY YCAR (SEQ ID NO: 238) |
| VH3-20*01 (SEQ ID NO: 189) | EVQLVESGG GVVRPGGSL RLSCAAS (SEQ ID NO: 239) | GFTFDDYGM S (SEQ ID NO: 240) | WVRQAPGKG LEWVS (SEQ ID NO: 241) | GINWNGGST GYADSVKG (SEQ ID NO: 242) | RFTISRDNAK NSLYLQMNS LRAEDTALY HCAR (SEQ ID NO: 243) |
| VH3-21*01 (SEQ ID NO: 190) | EVQLVESGG GLVKPGGSLR LSCAAS (SEQ ID NO: 244) | GFTFSSYSMN (SEQ ID NO: 245) | WVRQAPGKG LEWVS (SEQ ID NO: 241) | SISSSSSYIYY ADSVKG (SEQ ID NO: 246) | RFTISRDNAK NSLYLQMNS LRAEDTAVY YCAR (SEQ ID NO: 247) |
| VH3-23*01 (SEQ ID NO: 191) | EVQLLESGGG LVQPGGSLRL SCAAS (SEQ ID NO: 249) | GFTFSSYAMS (SEQ ID NO: 249) | WVRQAPGKG LEWVS (SEQ ID NO: 241) | AISGSGGSTY YADSVKG (SEQ ID NO: | RFTISRDNSK NTLYLQMNS LRAEDTAVY |

TABLE 16-continued

Germline sequences shown in Tables 2 and 4 (framework 1, CDR1, framework 2, CDR2, and framework 3 sequences).

| Germline | Framework 1 | Kabat CDR 1 | Framework 2 | Kabat CDR 2 | Framework 3 |
|---|---|---|---|---|---|
| | ID NO: 248) | | | 250) | YCAK (SEQ ID NO: 251) |
| VH3-30*01 (SEQ ID NO: 192) | QVQLVESGG GVVQPGRSL RLSCAAS (SEQ ID NO: 252) | GFTFSSYAMH (SEQ ID NO: 253) | WVRQAPGKG LEWVA (SEQ ID NO: 254) | VISYDGSNKY YADSVKG (SEQ ID NO: 255) | RFTISRDNSK NTLYLQMNS LRAEDTAVY YCAR (SEQ ID NO: 256) |
| VH3-33*01 (SEQ ID NO: 193) | QVQLVESGG GVVQPGRSL RLSCAAS (SEQ ID NO: 252) | GFTFSSYGMH (SEQ ID NO: 257) | WVRQAPGKG LEWVA (SEQ ID NO: 254) | VIWYDGSNK YYADSVKG (SEQ ID NO: 258) | RFTISRDNSK NTLYLQMNS LRAEDTAVY YCAR (SEQ ID NO: 256) |
| VH3-66*01 (SEQ ID NO: 194) | EVQLVESGG GLVQPGGSLR LSCAAS (SEQ ID NO: 234) | GFTVSSNYMS (SEQ ID NO: 259) | WVRQAPGKG LEWVS (SEQ ID NO: 241) | VIYSGGSTYY ADSVKG (SEQ ID NO: 260) | RFTISRDNSK NTLYLQMNS LRAEDTAVY YCAR (SEQ ID NO: 256) |
| VH3-7*01 (SEQ ID NO: 195) | EVQLVESGG GLVQPGGSLR LSCAAS (SEQ ID NO: 234) | GFTFSSYWM S (SEQ ID NO: 261) | WVRQAPGKG LEWVA (SEQ ID NO: 254) | NIKQDGSEKY YVDSVKG (SEQ ID NO: 262) | RFTISRDNAK NSLYLQMNS LRAEDTAVY YCAR (SEQ ID NO: 247) |
| VH3-9*01 (SEQ ID NO: 196) | EVQLVESGG GLVQPGRSLR LSCAAS (SEQ ID NO: 263) | GFTFDDYAM H (SEQ ID NO: 264) | WVRQAPGKG LEWVS (SEQ ID NO: 241) | GISWNSGSIG YADSVKG (SEQ ID NO: 265) | RFTISRDNAK NSLYLQMNS LRAEDTALY YCAK (SEQ ID NO: 266) |
| VH4-4*01 (SEQ ID NO: 197) | QVQLQESGP GLVKPPGTLS LTCAVS (SEQ ID NO: 267) | GGSISSSNWW S (SEQ ID NO: 268) | WVRQPPGKG LEWIG (SEQ ID NO: 269) | EIYHSGSTNY NPSLKS (SEQ ID NO: 270) | RVTISVDKSK NQFSLKLSSV TAADTAVYC CAR (SEQ ID NO: 271) |
| VH5-51*01 (SEQ ID NO: 198) | EVQLVQSGA EVKKPGESLK ISCKGS (SEQ ID NO: 272) | GYSFTSYWIG (SEQ ID NO: 273) | WVRQMPGK GLEWMG (SEQ ID NO: 274) | IIYPGDSDTR YSPSFQG (SEQ ID NO: 275) | QVTISADKSIS TAYLQWSSL KASDTAMYY CAR (SEQ ID NO: 276) |
| Vk1-12*01 (SEQ ID NO: 199) | DIQMTQSPSS VSASVGDRV TITC (SEQ ID NO: 277) | RASQGISSWL A (SEQ ID NO: 278) | WYQQKPGKA PKLLIY (SEQ ID NO: 279) | AASSLQS (SEQ ID NO: 280) | GVPSRFSGSG SGTDFTLTISS LQPEDFATYY C (SEQ ID NO: 281) |
| Vk1-27*01 (SEQ ID NO: 200) | DIQMTQSPSS LSASVGDRVT ITC (SEQ ID NO: 282) | RASQGISNYL A (SEQ ID NO: 283) | WYQQKPGKV PKLLIY (SEQ ID NO: 284) | AASTLQS (SEQ ID NO: 285) | GVPSRFSGSG SGTDFTLTISS LQPEDVATY YC (SEQ ID NO: 286) |
| Vk1-39*01 (SEQ ID NO: 201) | DIQMTQSPSS LSASVGDRVT ITC (SEQ ID NO: 282) | RASQSISSYL N (SEQ ID NO: 287) | WYQQKPGKA PKLLIY (SEQ ID NO: 279) | AASSLQS (SEQ ID NO: 280) | GVPSRFSGSG SGTDFTLTISS LQPEDFATYY C (SEQ ID NO: 281) |
| Vk1D-16*01 (SEQ ID NO: 202) | DIQMTQSPSS LSASVGDRVT ITC (SEQ ID NO: 282) | RASQGISSWL A (SEQ ID NO: 278) | WYQQKPEKA PKSLIY (SEQ ID NO: 288) | AASSLQS (SEQ ID NO: 280) | GVPSRFSGSG SGTDFTLTISS LQPEDFATYY C (SEQ ID NO: 281) |
| Vk2-28*01 (SEQ ID NO: 203) | DIVMTQSPLS LPVTPGEPASI SC (SEQ ID NO: 289) | RSSQSLLHSN GYNLD (SEQ ID NO: 290) | WYLQKPGQS PQLLIY (SEQ ID NO: 291) | LGSNRAS (SEQ ID NO: 292) | GVPDRFSGSG SGTDFTLKIS RVEAEDVGV YYC (SEQ ID NO: 293) |

TABLE 16-continued

Germline sequences shown in Tables 2 and 4 (framework 1, CDR1, framework 2, CDR2, and framework 3 sequences).

| Germline | Framework 1 | Kabat CDR 1 | Framework 2 | Kabat CDR 2 | Framework 3 |
|---|---|---|---|---|---|
| Vk3-11*01 (SEQ ID NO: 204) | EIVLTQSPAT LSLSPGERAT LSC (SEQ ID NO: 294) | RASQSVSSYL A (SEQ ID NO: 295) | WYQQKPGQA PRLLIY (SEQ ID NO: 296) | DASNRAT (SEQ ID NO: 297) | GIPARFSGSG SGTDFTLTISS LEPEDFAVYY C (SEQ ID NO: 298) |
| Vk3-20*01 (SEQ ID NO: 205) | EIVLTQSPGT LSLSPGERAT LSC (SEQ ID NO: 299) | RASQSVSSSY LA (SEQ ID NO: 300) | WYQQKPGQA PRLLIY (SEQ ID NO: 296) | GASSRAT (SEQ ID NO: 301) | GIPDRFSGSG SGTDFTLTISR LEPEDFAVYY C (SEQ ID NO: 302) |
| Vk3D-20*01 (SEQ ID NO: 206) | EIVLTQSPAT LSLSPGERAT LSC (SEQ ID NO: 294) | GASQSVSSSY LA (SEQ ID NO: 303) | WYQQKPGLA PRLLIY (SEQ ID NO: 304) | DASSRAT (SEQ ID NO: 305) | GIPDRFSGSG SGTDFTLTISR LEPEDFAVYY C (SEQ ID NO: 302) |
| Vl10-54*01 (SEQ ID NO: 207) | QAGLTQPPSV SKGLRQTATL TC (SEQ ID NO: 306) | TGNSNNVGN QGAA (SEQ ID NO: 307) | WLQQHQGHP PKLLSY (SEQ ID NO: 308) | RNNNRPS (SEQ ID NO: 309) | GISERLSASRS GNTASLTITG LQPEDEADY YC (SEQ ID NO: 310) |
| Vl1-40*01 (SEQ ID NO: 208) | QSVLTQPPSV SGAPGQRVTI SC (SEQ ID NO: 311) | TGSSSNIGAG YDVH (SEQ ID NO: 312) | WYQQLPGTA PKLLIY (SEQ ID NO: 313) | GNSNRPS (SEQ ID NO: 314) | GVPDRFSGSK SGTSASLAIT GLQAEDEAD YYC (SEQ ID NO: 315) |
| Vl1-44*01 (SEQ ID NO: 209) | QSVLTQPPSA SGTPGQRVTI SC (SEQ ID NO: 316) | SGSSSNIGSNT VN (SEQ ID NO: 317) | WYQQLPGTA PKLLIY (SEQ ID NO: 313) | SNNQRPS (SEQ ID NO: 318) | GVPDRFSGSK SGTSASLAIS GLQSEDEAD YYC (SEQ ID NO: 319) |
| Vl2-14*01 (SEQ ID NO: 210) | QSALTQPASVS GSPGQSITISC (SEQ ID NO: 320) | TGTSSDVGG YNYVS (SEQ ID NO: 321) | WYQQHPGKA PKLMIY (SEQ ID NO: 322) | EVSNRPS (SEQ ID NO: 323) | GVSNRFSGSK SGNTASLTIS GLQAEDEAD YYC (SEQ ID NO: 324) |
| Vl3-19*01 (SEQ ID NO: 211) | SSELTQDPAV SVALGQTVRI TC (SEQ ID NO: 325) | QGDSLRSYY AS (SEQ ID NO: 326) | WYQQKPGQA PVLVIY (SEQ ID NO: 327) | GKNNRPS (SEQ ID NO: 328) | GIPDRFSGSSS GNTASLTITG AQAEDEADY YC (SEQ ID NO: 329) |
| Vl3-9*01 (SEQ ID NO: 212) | SYELTQPLSV SVALGQTARI TC (SEQ ID NO: 330) | GGNNIGSKN VH (SEQ ID NO: 331) | WYQQKPGQA PVLVIY (SEQ ID NO: 327) | RDSNRPS (SEQ ID NO: 332) | GIPERFSGSNS GNTATLTISR AQAGDEADY YC (SEQ ID NO: 333) |
| VH4-31*01 (SEQ ID NO: 213) | QVQLQESGP GLVKPSQTLS LTCTVS (SEQ ID NO: 334) | GGSISSGSYY WS (SEQ ID NO: 335) | WIRQHPGKG LEWIG (SEQ ID NO: 336) | YIYYSGSTYY NPSLKS (SEQ ID NO: 337) | RVTISVDTSK NQFSLKLSSV TAADTAVYY (SEQ ID NO: 338) |

TABLE 5a

Sequences used to construct multispecific molecules.

| Column 1: Construct | Column 2: heavy chain polypeptide 1 (HCP1) | Column 3: lambda light chain polypeptide (LLCP) | Column 4: heavy chain polypeptide 2 (HCP2) | Column 5: kappa light chain polypeptide (KLCP) |
|---|---|---|---|---|
| Multispecific molecule 1 | SEQ ID NO: 178 | SEQ ID NO: 145 | SEQ ID NO: 179 | SEQ ID NO: 118 |
| Multispecific molecule 2 | SEQ ID NO: 166 | SEQ ID NO: 167 | SEQ ID NO: 164 | SEQ ID NO: 165 |
| Multispecific molecule 3 | SEQ ID NO: 170 | SEQ ID NO: 163 | SEQ ID NO: 168 | SEQ ID NO: 106 |
| Multispecific molecule 4 | SEQ ID NO: 177 | SEQ ID NO: 148 | SEQ ID NO: 168 | SEQ ID NO: 106 |
| Multispecific molecule 5 | SEQ ID NO: 180 | SEQ ID NO: 136 | SEQ ID NO: 168 | SEQ ID NO: 106 |
| Multispecific molecule 6 | SEQ ID NO: 177 | SEQ ID NO: 148 | SEQ ID NO: 181 | SEQ ID NO: 182 |
| Multispecific molecule 7 | SEQ ID NO: 166 | SEQ ID NO: 167 | SEQ ID NO: 181 | SEQ ID NO: 182 |
| Multispecific molecule 8 | SEQ ID NO: 172 | SEQ ID NO: 173 | SEQ ID NO: 171 | SEQ ID NO: 106 |
| Multispecific molecule 9 | SEQ ID NO: 170 | SEQ ID NO: 173 | SEQ ID NO: 168 | SEQ ID NO: 106 |
| Multispecific molecule 10 | SEQ ID NO: 175 | SEQ ID NO: 173 | SEQ ID NO: 171 | SEQ ID NO: 106 |
| Multispecific molecule 11 | SEQ ID NO: 174 | SEQ ID NO: 173 | SEQ ID NO: 168 | SEQ ID NO: 106 |
| Multispecific molecule 12 | SEQ ID NO: 177 | SEQ ID NO: 148 | SEQ ID NO: 169 | SEQ ID NO: 176 |

TABLE 5b

Corresponding germline sequences of multispecific molecules.

| Column 1: Construct | Column 2: heavy chain polypeptide 1 (HCP1) corresponding germline sequence | Column 3: lambda light chain polypeptide (LLCP) corresponding germline sequence | Column 4: heavy chain polypeptide 2 (HCP2) corresponding germline sequence | Column 5: kappa light chain polypeptide (KLCP) corresponding germline sequence |
|---|---|---|---|---|
| Multispecific molecule 1 | VH3-9*01 (SEQ ID NO: 196) | Vl3-19*01 (SEQ ID NO: 211) | VH3-23*01 (SEQ ID NO: 191) | Vk1-27*01 (SEQ ID NO: 200) |
| Multispecific molecule 2 | VH3-66*01 (SEQ ID NO: 194) | Vl2-14*01 (SEQ ID NO: 210) | VH4-31*01 (SEQ ID NO: 213) | Vk1-39*01 (SEQ ID NO: 201) |
| Multispecific molecule 3 | VH3-33*01 (SEQ ID NO: 193) | Vl1-44*01 (SEQ ID NO: 209) | VH3-30*01 (SEQ ID NO: 192) | Vk3-20*01 (SEQ ID NO: 205) |
| Multispecific molecule 4 | Vk3-20*01 (SEQ ID NO: 205) | Vl3-19*01 (SEQ ID NO: 211) | VH3-30*01 (SEQ ID NO: 192) | Vk3-20*01 (SEQ ID NO: 205) |
| Multispecific molecule 5 | VH1-69*01 (SEQ ID NO: 187) | Vl3-19*01 (SEQ ID NO: 211) | VH3-30*01 (SEQ ID NO: 192) | Vk3-20*01 (SEQ ID NO: 205) |
| Multispecific molecule 6 | Vk3-20*01 (SEQ ID NO: 205) | Vl3-19*01 (SEQ ID NO: 211) | VH3-33*01 (SEQ ID NO: 193) | Vk3-11*01 (SEQ ID NO: 204) |
| Multispecific molecule 7 | VH3-66*01 (SEQ ID NO: 194) | Vl2-14*01 (SEQ ID NO: 210) | VH3-33*01 (SEQ ID NO: 193) | Vk3-11*01 (SEQ ID NO: 204) |
| Multispecific molecule 8 | VH3-33*01 (SEQ ID NO: 193) | Vl1-44*01 (SEQ ID NO: 209) | VH3-30*01 (SEQ ID NO: 192) | Vk3-20*01 (SEQ ID NO: 205) |
| Multispecific molecule 9 | VH3-33*01 (SEQ ID NO: 193) | Vl1-44*01 (SEQ ID NO: 209) | VH3-30*01 (SEQ ID NO: 192) | Vk3-20*01 (SEQ ID NO: 205) |
| Multispecific molecule 10 | VH3-33*01 (SEQ ID NO: 193) | Vl1-44*01 (SEQ ID NO: 209) | VH3-30*01 (SEQ ID NO: 192) | Vk3-20*01 (SEQ ID NO: 205) |
| Multispecific molecule 11 | VH3-33*01 (SEQ ID NO: 193) | Vl1-44*01 (SEQ ID NO: 209) | VH3-30*01 (SEQ ID NO: 192) | Vk3-20*01 (SEQ ID NO: 205) |

TABLE 5b-continued

Corresponding germline sequences of multispecific molecules.

| Column 1: Construct | Column 2: heavy chain polypeptide 1 (HCP1) corresponding germline sequence | Column 3: lambda light chain polypeptide (LLCP) corresponding germline sequence | Column 4: heavy chain polypeptide 2 (HCP2) corresponding germline sequence | Column 5: kappa light chain polypeptide (KLCP) corresponding germline sequence |
|---|---|---|---|---|
| Multispecific molecule 12 | Vk3-20*01 (SEQ ID NO: 205) | Vl3-19*01 (SEQ ID NO: 211) | VH3-30*01 (SEQ ID NO: 192) | Vk3-20*01 (SEQ ID NO: 205) |

5. Kappa/Lambda Select Resin Analysis of Chain Pairing.

The kappa and lambda light chain pairing of bispecific constructs was analyzed by incubating 1 mg of protein with 100 μL of either KappaSelect (GE 17-5458-01) or Lambda-FabSelect (GE 17-5482-01) resin. After incubating for 1-3 hours, the resin was packed into a column, washed with 3×10 column volumes of Dulbecco's phosphate-buffered saline (DPBS, Life Technologies 14190-144). The bound protein was eluted from the column with 100 mM citrate, pH 2.46. The content of the load, flow-through, and elution fractions was analyzed using gels of samples reduced with 200 mM Bond-Breaker TCEP (Thermo Scientific 77720), allowing for the identification of the various chains. For quantitative assessment of the chain pairing, the amount of protein in the load and flow-through fractions was assessed using the absorbance at 280 nm with a NanoDrop.

The KappaSelect resin is an affinity resin that binds to the constant light chain of kappa antibodies. The elution from the KappaSelect will contain molecules with both a lambda and kappa light chain, where there are three possibilities (FIGS. 1A, 1B, and 1D). The LambdaFabSelect resin is an affinity resin that binds to the constant light chain of lambda antibodies. The elution from the LambdaFabSelect will contain molecules with both lambda and kappa light chain, where there are three possibilities (FIGS. 1A, 1C, and 1D).

6. Mass Spectrometry for Analysis of Chain Pairing.

Figure 2:
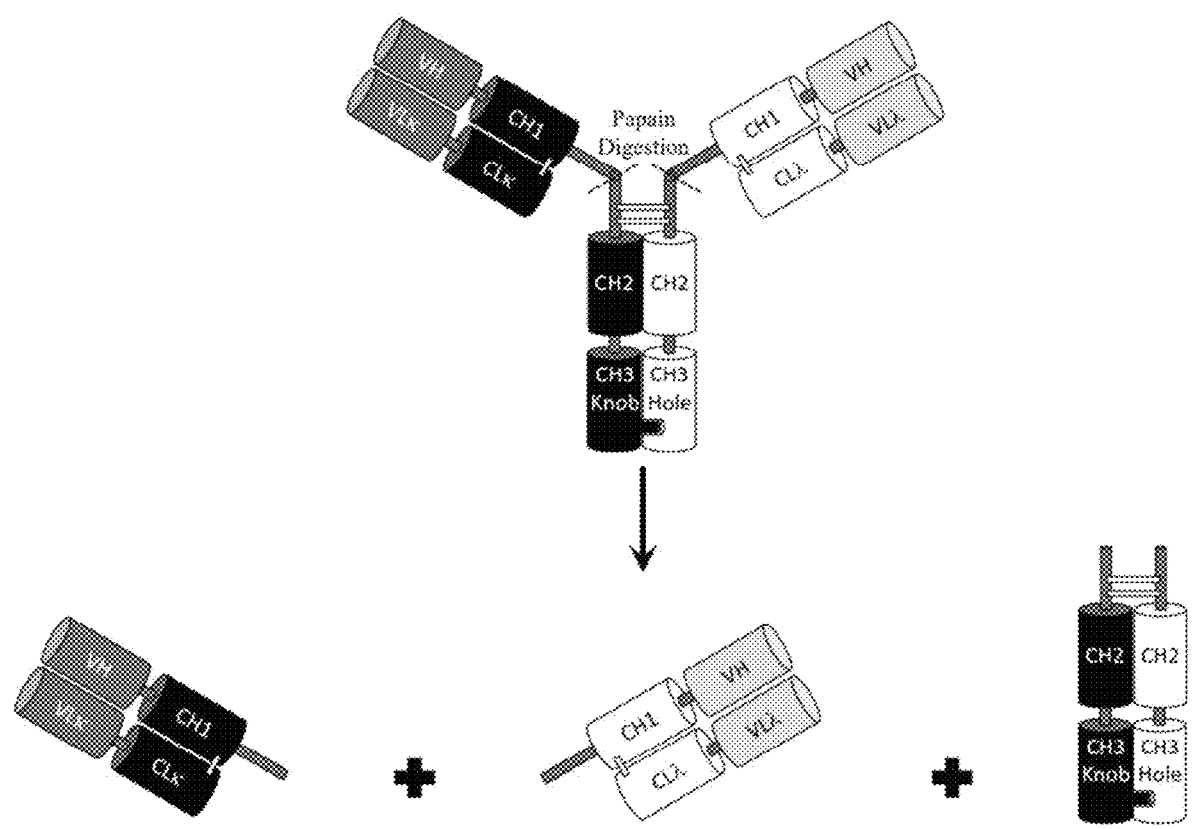
FIG. 2 depicts a schematic representation of a papain-cleaved bispecific antibody showing the location of cleavage in the hinge region by a dotted line. In embodiments, the multispecific antibody molecule having a first binding specificity that includes a hybrid VLλ-CLλ heterodimerized to a first heavy chain variable region-CH1 connected to the Fc constant, CH2-CH3 domain (having a hole modification) and a second binding specificity that includes a hybrid VLκ-CLκ heterodimerized to a second heavy chain variable region-CH1 connected to the Fc constant, CH2-CH3 domain (having a knob modification). Two Fab fragments are released after papain treatment.

To characterize the chain pairing in multispecific molecules, the purified samples were digested with immobilized papain (Thermo Scientific 20341) according to the manufacturer's instructions. Papain cleaves after the hinge region (FIG. 2), yielding two Fab arms. The digested molecules were run on a mass spectrometer, allowing identification of the two Fab arms based on the intact masses measured. The MS analysis allows for the discrimination of the different configurations (FIG. 1A vs. FIG. 1D), and the characterization of the extent of light-chain swapping.

Results

Example 1

NanoBiT based constructs were expressed by co-transfecting cells with DNA in a 1:1:1 heavy chain to light chain to competing light chain ratio. Table 3 shows individual combinations of a heavy chain (column 2), a light chain (column 3), and a competing light chain (column 4). Column 1 in Table 3 provides identifiers for each sequence combination. The molecules were purified and the luminescence assay was performed using the Nano-Glo reagent. The positive controls and negative controls are indicated. Positive controls represented 100% perfect pairing and the negative controls represented 50% perfect pairing. These values were used to quantify the pairing of the test constructs.

Table 6 shows the percent pairing for heavy chains and kappa light chains in the presence of competing lambda light chains (only the sequence combinations with a percent pairing of 75% or greater were included). Table 7 shows the percent pairing for heavy chains and lambda light chains in the presence of competing kappa light chains (only the sequence combinations with a percent pairing of 75% or greater were included). The identifiers shown in column 1 of Tables 6 and 7 correspond to the identifiers in column 1 of Table 3. In addition, Tables 6 and 7 also provide the corresponding germline sequences for the heavy chains (column 3), the light chains (column 4), and the competing light chains (column 5) used in each sequence combination.

Table 8a is a compilation of Tables 6 and 7 with samples that were successful in both directions. Each row of Table 8a shows a heavy chain/kappa light chain pair and a heavy chain/lambda light chain pair (indicated by the ID number), where the swapping of light chains between these two pairs is low based on the NanoBiT assay. Table 8b provides the corresponding germline sequences for the heavy chain/light chain pairs included in Table 8a. The identifiers shown in Tables 8a and 8b correspond to the identifiers in column 1 of Table 3.

TABLE 3

Sequences used to generate competition constructs.

| Identifier for sequence combinations | Heavy chain | Light chain | Competing light chain |
|---|---|---|---|
| ID183 (positive control) | SEQ ID NO: 92 | SEQ ID NO: 93 | |
| ID184 (negative control) | SEQ ID NO: 92 | SEQ ID NO: 93 | SEQ ID NO: 94 |
| ID185 | SEQ ID NO: 92 | SEQ ID NO: 93 | SEQ ID NO: 136 |
| ID186 | SEQ ID NO: 92 | SEQ ID NO: 93 | SEQ ID NO: 139 |
| ID187 | SEQ ID NO: 92 | SEQ ID NO: 93 | SEQ ID NO: 142 |
| ID188 | SEQ ID NO: 92 | SEQ ID NO: 93 | SEQ ID NO: 145 |
| ID189 | SEQ ID NO: 92 | SEQ ID NO: 93 | SEQ ID NO: 148 |
| ID190 | SEQ ID NO: 92 | SEQ ID NO: 93 | SEQ ID NO: 151 |
| ID191 | SEQ ID NO: 92 | SEQ ID NO: 93 | SEQ ID NO: 154 |
| ID192 | SEQ ID NO: 92 | SEQ ID NO: 93 | SEQ ID NO: 157 |

TABLE 3-continued

Sequences used to generate competition constructs.

| Identifier for sequence combinations | Heavy chain | Light chain | Competing light chain |
|---|---|---|---|
| ID193 | SEQ ID NO: 92 | SEQ ID NO: 93 | SEQ ID NO: 160 |
| ID194 | SEQ ID NO: 92 | SEQ ID NO: 93 | SEQ ID NO: 163 |
| ID195 (positive control) | SEQ ID NO: 95 | SEQ ID NO: 96 | |
| ID196 (negative control) | SEQ ID NO: 95 | SEQ ID NO: 96 | SEQ ID NO: 97 |
| ID197 | SEQ ID NO: 95 | SEQ ID NO: 96 | SEQ ID NO: 136 |
| ID198 | SEQ ID NO: 95 | SEQ ID NO: 96 | SEQ ID NO: 139 |
| ID199 | SEQ ID NO: 95 | SEQ ID NO: 96 | SEQ ID NO: 142 |
| ID200 | SEQ ID NO: 95 | SEQ ID NO: 96 | SEQ ID NO: 145 |
| ID201 | SEQ ID NO: 95 | SEQ ID NO: 96 | SEQ ID NO: 148 |
| ID202 | SEQ ID NO: 95 | SEQ ID NO: 96 | SEQ ID NO: 151 |
| ID203 | SEQ ID NO: 95 | SEQ ID NO: 96 | SEQ ID NO: 154 |
| ID204 | SEQ ID NO: 95 | SEQ ID NO: 96 | SEQ ID NO: 157 |
| ID205 | SEQ ID NO: 95 | SEQ ID NO: 96 | SEQ ID NO: 160 |
| ID206 | SEQ ID NO: 95 | SEQ ID NO: 96 | SEQ ID NO: 163 |
| ID207 (positive control) | SEQ ID NO: 98 | SEQ ID NO: 99 | |
| ID208 (negative control) | SEQ ID NO: 98 | SEQ ID NO: 99 | SEQ ID NO: 100 |
| ID209 | SEQ ID NO: 98 | SEQ ID NO: 99 | SEQ ID NO: 136 |
| ID210 | SEQ ID NO: 98 | SEQ ID NO: 99 | SEQ ID NO: 139 |
| ID211 | SEQ ID NO: 98 | SEQ ID NO: 99 | SEQ ID NO: 142 |
| ID212 | SEQ ID NO: 98 | SEQ ID NO: 99 | SEQ ID NO: 145 |
| ID213 | SEQ ID NO: 98 | SEQ ID NO: 99 | SEQ ID NO: 148 |
| ID214 | SEQ ID NO: 98 | SEQ ID NO: 99 | SEQ ID NO: 151 |
| ID215 | SEQ ID NO: 98 | SEQ ID NO: 99 | SEQ ID NO: 154 |
| ID216 | SEQ ID NO: 98 | SEQ ID NO: 99 | SEQ ID NO: 157 |
| ID217 | SEQ ID NO: 98 | SEQ ID NO: 99 | SEQ ID NO: 160 |
| ID218 | SEQ ID NO: 98 | SEQ ID NO: 99 | SEQ ID NO: 163 |
| ID219 (positive control) | SEQ ID NO: 101 | SEQ ID NO: 102 | |
| ID220 (negative control) | SEQ ID NO: 101 | SEQ ID NO: 102 | SEQ ID NO: 103 |
| ID221 | SEQ ID NO: 101 | SEQ ID NO: 102 | SEQ ID NO: 136 |
| ID222 | SEQ ID NO: 101 | SEQ ID NO: 102 | SEQ ID NO: 139 |
| ID223 | SEQ ID NO: 101 | SEQ ID NO: 102 | SEQ ID NO: 142 |
| ID224 | SEQ ID NO: 101 | SEQ ID NO: 102 | SEQ ID NO: 145 |
| ID225 | SEQ ID NO: 101 | SEQ ID NO: 102 | SEQ ID NO: 148 |
| ID226 | SEQ ID NO: 101 | SEQ ID NO: 102 | SEQ ID NO: 151 |
| ID227 | SEQ ID NO: 101 | SEQ ID NO: 102 | SEQ ID NO: 154 |
| ID228 | SEQ ID NO: 101 | SEQ ID NO: 102 | SEQ ID NO: 157 |
| ID229 | SEQ ID NO: 101 | SEQ ID NO: 102 | SEQ ID NO: 160 |
| ID230 | SEQ ID NO: 101 | SEQ ID NO: 102 | SEQ ID NO: 163 |
| ID231 (positive control) | SEQ ID NO: 104 | SEQ ID NO: 105 | |
| ID232 (negative control) | SEQ ID NO: 104 | SEQ ID NO: 105 | SEQ ID NO: 106 |
| ID233 | SEQ ID NO: 104 | SEQ ID NO: 105 | SEQ ID NO: 136 |
| ID234 | SEQ ID NO: 104 | SEQ ID NO: 105 | SEQ ID NO: 139 |
| ID235 | SEQ ID NO: 104 | SEQ ID NO: 105 | SEQ ID NO: 142 |
| ID236 | SEQ ID NO: 104 | SEQ ID NO: 105 | SEQ ID NO: 145 |
| ID237 | SEQ ID NO: 104 | SEQ ID NO: 105 | SEQ ID NO: 148 |
| ID238 | SEQ ID NO: 104 | SEQ ID NO: 105 | SEQ ID NO: 151 |
| ID239 | SEQ ID NO: 104 | SEQ ID NO: 105 | SEQ ID NO: 154 |
| ID240 | SEQ ID NO: 104 | SEQ ID NO: 105 | SEQ ID NO: 157 |
| ID241 | SEQ ID NO: 104 | SEQ ID NO: 105 | SEQ ID NO: 160 |
| ID242 | SEQ ID NO: 104 | SEQ ID NO: 105 | SEQ ID NO: 163 |
| ID243 (positive control) | SEQ ID NO: 107 | SEQ ID NO: 108 | |
| ID244 (negative control) | SEQ ID NO: 107 | SEQ ID NO: 108 | SEQ ID NO: 109 |
| ID245 | SEQ ID NO: 107 | SEQ ID NO: 108 | SEQ ID NO: 136 |
| ID246 | SEQ ID NO: 107 | SEQ ID NO: 108 | SEQ ID NO: 139 |
| ID247 | SEQ ID NO: 107 | SEQ ID NO: 108 | SEQ ID NO: 142 |
| ID248 | SEQ ID NO: 107 | SEQ ID NO: 108 | SEQ ID NO: 145 |
| ID249 | SEQ ID NO: 107 | SEQ ID NO: 108 | SEQ ID NO: 148 |
| ID250 | SEQ ID NO: 107 | SEQ ID NO: 108 | SEQ ID NO: 151 |
| ID251 | SEQ ID NO: 107 | SEQ ID NO: 108 | SEQ ID NO: 154 |
| ID252 | SEQ ID NO: 107 | SEQ ID NO: 108 | SEQ ID NO: 157 |
| ID253 | SEQ ID NO: 107 | SEQ ID NO: 108 | SEQ ID NO: 160 |
| ID254 | SEQ ID NO: 107 | SEQ ID NO: 108 | SEQ ID NO: 163 |
| ID255 (positive control) | SEQ ID NO: 110 | SEQ ID NO: 111 | |
| ID256 (negative control) | SEQ ID NO: 110 | SEQ ID NO: 111 | SEQ ID NO: 112 |
| ID257 | SEQ ID NO: 110 | SEQ ID NO: 111 | SEQ ID NO: 136 |
| ID258 | SEQ ID NO: 110 | SEQ ID NO: 111 | SEQ ID NO: 139 |
| ID259 | SEQ ID NO: 110 | SEQ ID NO: 111 | SEQ ID NO: 142 |
| ID260 | SEQ ID NO: 110 | SEQ ID NO: 111 | SEQ ID NO: 145 |
| ID261 | SEQ ID NO: 110 | SEQ ID NO: 111 | SEQ ID NO: 148 |
| ID262 | SEQ ID NO: 110 | SEQ ID NO: 111 | SEQ ID NO: 151 |
| ID263 | SEQ ID NO: 110 | SEQ ID NO: 111 | SEQ ID NO: 154 |
| ID264 | SEQ ID NO: 110 | SEQ ID NO: 111 | SEQ ID NO: 157 |
| ID265 | SEQ ID NO: 110 | SEQ ID NO: 111 | SEQ ID NO: 160 |
| ID266 | SEQ ID NO: 110 | SEQ ID NO: 111 | SEQ ID NO: 163 |
| ID267 (positive control) | SEQ ID NO: 113 | SEQ ID NO: 114 | |

TABLE 3-continued

Sequences used to generate competition constructs.

| Identifier for sequence combinations | Heavy chain | Light chain | Competing light chain |
|---|---|---|---|
| ID268 (negative control) | SEQ ID NO: 113 | SEQ ID NO: 114 | SEQ ID NO: 115 |
| ID269 | SEQ ID NO: 113 | SEQ ID NO: 114 | SEQ ID NO: 136 |
| ID270 | SEQ ID NO: 113 | SEQ ID NO: 114 | SEQ ID NO: 139 |
| ID271 | SEQ ID NO: 113 | SEQ ID NO: 114 | SEQ ID NO: 142 |
| ID272 | SEQ ID NO: 113 | SEQ ID NO: 114 | SEQ ID NO: 145 |
| ID273 | SEQ ID NO: 113 | SEQ ID NO: 114 | SEQ ID NO: 148 |
| ID274 | SEQ ID NO: 113 | SEQ ID NO: 114 | SEQ ID NO: 151 |
| ID275 | SEQ ID NO: 113 | SEQ ID NO: 114 | SEQ ID NO: 154 |
| ID276 | SEQ ID NO: 113 | SEQ ID NO: 114 | SEQ ID NO: 157 |
| ID277 | SEQ ID NO: 113 | SEQ ID NO: 114 | SEQ ID NO: 160 |
| ID278 | SEQ ID NO: 113 | SEQ ID NO: 114 | SEQ ID NO: 163 |
| ID279 (positive control) | SEQ ID NO: 116 | SEQ ID NO: 117 | |
| ID280 (negative control) | SEQ ID NO: 116 | SEQ ID NO: 117 | SEQ ID NO: 118 |
| ID281 | SEQ ID NO: 116 | SEQ ID NO: 117 | SEQ ID NO: 136 |
| ID282 | SEQ ID NO: 116 | SEQ ID NO: 117 | SEQ ID NO: 139 |
| ID283 | SEQ ID NO: 116 | SEQ ID NO: 117 | SEQ ID NO: 142 |
| ID284 | SEQ ID NO: 116 | SEQ ID NO: 117 | SEQ ID NO: 145 |
| ID285 | SEQ ID NO: 116 | SEQ ID NO: 117 | SEQ ID NO: 148 |
| ID286 | SEQ ID NO: 116 | SEQ ID NO: 117 | SEQ ID NO: 151 |
| ID287 | SEQ ID NO: 116 | SEQ ID NO: 117 | SEQ ID NO: 154 |
| ID288 | SEQ ID NO: 116 | SEQ ID NO: 117 | SEQ ID NO: 157 |
| ID289 | SEQ ID NO: 116 | SEQ ID NO: 117 | SEQ ID NO: 160 |
| ID290 | SEQ ID NO: 116 | SEQ ID NO: 117 | SEQ ID NO: 163 |
| ID291 (positive control) | SEQ ID NO: 119 | SEQ ID NO: 120 | |
| ID292 (negative control) | SEQ ID NO: 119 | SEQ ID NO: 120 | SEQ ID NO: 121 |
| ID293 | SEQ ID NO: 119 | SEQ ID NO: 120 | SEQ ID NO: 136 |
| ID294 | SEQ ID NO: 119 | SEQ ID NO: 120 | SEQ ID NO: 139 |
| ID295 | SEQ ID NO: 119 | SEQ ID NO: 120 | SEQ ID NO: 142 |
| ID296 | SEQ ID NO: 119 | SEQ ID NO: 120 | SEQ ID NO: 145 |
| ID297 | SEQ ID NO: 119 | SEQ ID NO: 120 | SEQ ID NO: 148 |
| ID298 | SEQ ID NO: 119 | SEQ ID NO: 120 | SEQ ID NO: 151 |
| ID299 | SEQ ID NO: 119 | SEQ ID NO: 120 | SEQ ID NO: 154 |
| ID300 | SEQ ID NO: 119 | SEQ ID NO: 120 | SEQ ID NO: 157 |
| ID301 | SEQ ID NO: 119 | SEQ ID NO: 120 | SEQ ID NO: 160 |
| ID302 | SEQ ID NO: 119 | SEQ ID NO: 120 | SEQ ID NO: 163 |
| ID303 (positive control) | SEQ ID NO: 122 | SEQ ID NO: 123 | |
| ID304 (negative control) | SEQ ID NO: 122 | SEQ ID NO: 123 | SEQ ID NO: 124 |
| ID305 | SEQ ID NO: 122 | SEQ ID NO: 123 | SEQ ID NO: 136 |
| ID306 | SEQ ID NO: 122 | SEQ ID NO: 123 | SEQ ID NO: 139 |
| ID307 | SEQ ID NO: 122 | SEQ ID NO: 123 | SEQ ID NO: 142 |
| ID308 | SEQ ID NO: 122 | SEQ ID NO: 123 | SEQ ID NO: 145 |
| ID309 | SEQ ID NO: 122 | SEQ ID NO: 123 | SEQ ID NO: 148 |
| ID310 | SEQ ID NO: 122 | SEQ ID NO: 123 | SEQ ID NO: 151 |
| ID311 | SEQ ID NO: 122 | SEQ ID NO: 123 | SEQ ID NO: 154 |
| ID312 | SEQ ID NO: 122 | SEQ ID NO: 123 | SEQ ID NO: 157 |
| ID313 | SEQ ID NO: 122 | SEQ ID NO: 123 | SEQ ID NO: 160 |
| ID314 | SEQ ID NO: 122 | SEQ ID NO: 123 | SEQ ID NO: 163 |
| ID315 (positive control) | SEQ ID NO: 125 | SEQ ID NO: 126 | |
| ID316 (negative control) | SEQ ID NO: 125 | SEQ ID NO: 126 | SEQ ID NO: 127 |
| ID317 | SEQ ID NO: 125 | SEQ ID NO: 126 | SEQ ID NO: 136 |
| ID318 | SEQ ID NO: 125 | SEQ ID NO: 126 | SEQ ID NO: 139 |
| ID319 | SEQ ID NO: 125 | SEQ ID NO: 126 | SEQ ID NO: 142 |
| ID320 | SEQ ID NO: 125 | SEQ ID NO: 126 | SEQ ID NO: 145 |
| ID321 | SEQ ID NO: 125 | SEQ ID NO: 126 | SEQ ID NO: 148 |
| ID322 | SEQ ID NO: 125 | SEQ ID NO: 126 | SEQ ID NO: 151 |
| ID323 | SEQ ID NO: 125 | SEQ ID NO: 126 | SEQ ID NO: 154 |
| ID324 | SEQ ID NO: 125 | SEQ ID NO: 126 | SEQ ID NO: 157 |
| ID325 | SEQ ID NO: 125 | SEQ ID NO: 126 | SEQ ID NO: 160 |
| ID326 | SEQ ID NO: 125 | SEQ ID NO: 126 | SEQ ID NO: 163 |
| ID327 (positive control) | SEQ ID NO: 128 | SEQ ID NO: 129 | |
| ID328 (negative control) | SEQ ID NO: 128 | SEQ ID NO: 129 | SEQ ID NO: 130 |
| ID329 | SEQ ID NO: 128 | SEQ ID NO: 129 | SEQ ID NO: 136 |
| ID330 | SEQ ID NO: 128 | SEQ ID NO: 129 | SEQ ID NO: 139 |
| ID331 | SEQ ID NO: 128 | SEQ ID NO: 129 | SEQ ID NO: 142 |
| ID332 | SEQ ID NO: 128 | SEQ ID NO: 129 | SEQ ID NO: 145 |
| ID333 | SEQ ID NO: 128 | SEQ ID NO: 129 | SEQ ID NO: 148 |
| ID334 | SEQ ID NO: 128 | SEQ ID NO: 129 | SEQ ID NO: 151 |
| ID335 | SEQ ID NO: 128 | SEQ ID NO: 129 | SEQ ID NO: 154 |
| ID336 | SEQ ID NO: 128 | SEQ ID NO: 129 | SEQ ID NO: 157 |
| ID337 | SEQ ID NO: 128 | SEQ ID NO: 129 | SEQ ID NO: 160 |
| ID338 | SEQ ID NO: 128 | SEQ ID NO: 129 | SEQ ID NO: 163 |
| ID339 (positive control) | SEQ ID NO: 131 | SEQ ID NO: 132 | |
| ID340 (negative control) | SEQ ID NO: 131 | SEQ ID NO: 132 | SEQ ID NO: 133 |
| ID341 | SEQ ID NO: 131 | SEQ ID NO: 132 | SEQ ID NO: 136 |
| ID342 | SEQ ID NO: 131 | SEQ ID NO: 132 | SEQ ID NO: 139 |

TABLE 3-continued

Sequences used to generate competition constructs.

| Identifier for sequence combinations | Heavy chain | Light chain | Competing light chain |
|---|---|---|---|
| ID343 | SEQ ID NO: 131 | SEQ ID NO: 132 | SEQ ID NO: 142 |
| ID344 | SEQ ID NO: 131 | SEQ ID NO: 132 | SEQ ID NO: 145 |
| ID345 | SEQ ID NO: 131 | SEQ ID NO: 132 | SEQ ID NO: 148 |
| ID346 | SEQ ID NO: 131 | SEQ ID NO: 132 | SEQ ID NO: 151 |
| ID347 | SEQ ID NO: 131 | SEQ ID NO: 132 | SEQ ID NO: 154 |
| ID348 | SEQ ID NO: 131 | SEQ ID NO: 132 | SEQ ID NO: 157 |
| ID349 | SEQ ID NO: 131 | SEQ ID NO: 132 | SEQ ID NO: 160 |
| ID350 | SEQ ID NO: 131 | SEQ ID NO: 132 | SEQ ID NO: 163 |
| ID351 (positive control) | SEQ ID NO: 134 | SEQ ID NO: 135 | |
| ID352 (negative control) | SEQ ID NO: 134 | SEQ ID NO: 135 | SEQ ID NO: 136 |
| ID353 | SEQ ID NO: 134 | SEQ ID NO: 135 | SEQ ID NO: 94 |
| ID354 | SEQ ID NO: 134 | SEQ ID NO: 135 | SEQ ID NO: 97 |
| ID355 | SEQ ID NO: 134 | SEQ ID NO: 135 | SEQ ID NO: 100 |
| ID356 | SEQ ID NO: 134 | SEQ ID NO: 135 | SEQ ID NO: 103 |
| ID357 | SEQ ID NO: 134 | SEQ ID NO: 135 | SEQ ID NO: 106 |
| ID358 | SEQ ID NO: 134 | SEQ ID NO: 135 | SEQ ID NO: 109 |
| ID359 | SEQ ID NO: 134 | SEQ ID NO: 135 | SEQ ID NO: 112 |
| ID360 | SEQ ID NO: 134 | SEQ ID NO: 135 | SEQ ID NO: 115 |
| ID361 | SEQ ID NO: 134 | SEQ ID NO: 135 | SEQ ID NO: 118 |
| ID362 | SEQ ID NO: 134 | SEQ ID NO: 135 | SEQ ID NO: 121 |
| ID363 | SEQ ID NO: 134 | SEQ ID NO: 135 | SEQ ID NO: 124 |
| ID364 | SEQ ID NO: 134 | SEQ ID NO: 135 | SEQ ID NO: 127 |
| ID365 | SEQ ID NO: 134 | SEQ ID NO: 135 | SEQ ID NO: 130 |
| ID366 | SEQ ID NO: 134 | SEQ ID NO: 135 | SEQ ID NO: 133 |
| ID367 (positive control) | SEQ ID NO: 137 | SEQ ID NO: 138 | |
| ID368 (negative control) | SEQ ID NO: 137 | SEQ ID NO: 138 | SEQ ID NO: 139 |
| ID369 | SEQ ID NO: 137 | SEQ ID NO: 138 | SEQ ID NO: 94 |
| ID370 | SEQ ID NO: 137 | SEQ ID NO: 138 | SEQ ID NO: 97 |
| ID371 | SEQ ID NO: 137 | SEQ ID NO: 138 | SEQ ID NO: 100 |
| ID372 | SEQ ID NO: 137 | SEQ ID NO: 138 | SEQ ID NO: 103 |
| ID373 | SEQ ID NO: 137 | SEQ ID NO: 138 | SEQ ID NO: 106 |
| ID374 | SEQ ID NO: 137 | SEQ ID NO: 138 | SEQ ID NO: 109 |
| ID375 | SEQ ID NO: 137 | SEQ ID NO: 138 | SEQ ID NO: 112 |
| ID376 | SEQ ID NO: 137 | SEQ ID NO: 138 | SEQ ID NO: 115 |
| ID377 | SEQ ID NO: 137 | SEQ ID NO: 138 | SEQ ID NO: 118 |
| ID378 | SEQ ID NO: 137 | SEQ ID NO: 138 | SEQ ID NO: 121 |
| ID379 | SEQ ID NO: 137 | SEQ ID NO: 138 | SEQ ID NO: 124 |
| ID380 | SEQ ID NO: 137 | SEQ ID NO: 138 | SEQ ID NO: 127 |
| ID381 | SEQ ID NO: 137 | SEQ ID NO: 138 | SEQ ID NO: 130 |
| ID382 | SEQ ID NO: 137 | SEQ ID NO: 138 | SEQ ID NO: 133 |
| ID383 (positive control) | SEQ ID NO: 140 | SEQ ID NO: 141 | |
| ID384 (negative control) | SEQ ID NO: 140 | SEQ ID NO: 141 | SEQ ID NO: 142 |
| ID385 | SEQ ID NO: 140 | SEQ ID NO: 141 | SEQ ID NO: 94 |
| ID386 | SEQ ID NO: 140 | SEQ ID NO: 141 | SEQ ID NO: 97 |
| ID387 | SEQ ID NO: 140 | SEQ ID NO: 141 | SEQ ID NO: 100 |
| ID388 | SEQ ID NO: 140 | SEQ ID NO: 141 | SEQ ID NO: 103 |
| ID389 | SEQ ID NO: 140 | SEQ ID NO: 141 | SEQ ID NO: 106 |
| ID390 | SEQ ID NO: 140 | SEQ ID NO: 141 | SEQ ID NO: 109 |
| ID391 | SEQ ID NO: 140 | SEQ ID NO: 141 | SEQ ID NO: 112 |
| ID392 | SEQ ID NO: 140 | SEQ ID NO: 141 | SEQ ID NO: 115 |
| ID393 | SEQ ID NO: 140 | SEQ ID NO: 141 | SEQ ID NO: 118 |
| ID394 | SEQ ID NO: 140 | SEQ ID NO: 141 | SEQ ID NO: 121 |
| ID395 | SEQ ID NO: 140 | SEQ ID NO: 141 | SEQ ID NO: 124 |
| ID396 | SEQ ID NO: 140 | SEQ ID NO: 141 | SEQ ID NO: 127 |
| ID397 | SEQ ID NO: 140 | SEQ ID NO: 141 | SEQ ID NO: 130 |
| ID398 | SEQ ID NO: 140 | SEQ ID NO: 141 | SEQ ID NO: 133 |
| ID399 (positive control) | SEQ ID NO: 143 | SEQ ID NO: 144 | |
| ID400 (negative control) | SEQ ID NO: 143 | SEQ ID NO: 144 | SEQ ID NO: 145 |
| ID401 | SEQ ID NO: 143 | SEQ ID NO: 144 | SEQ ID NO: 94 |
| ID402 | SEQ ID NO: 143 | SEQ ID NO: 144 | SEQ ID NO: 97 |
| ID403 | SEQ ID NO: 143 | SEQ ID NO: 144 | SEQ ID NO: 100 |
| ID404 | SEQ ID NO: 143 | SEQ ID NO: 144 | SEQ ID NO: 103 |
| ID405 | SEQ ID NO: 143 | SEQ ID NO: 144 | SEQ ID NO: 106 |
| ID406 | SEQ ID NO: 143 | SEQ ID NO: 144 | SEQ ID NO: 109 |
| ID407 | SEQ ID NO: 143 | SEQ ID NO: 144 | SEQ ID NO: 112 |
| ID408 | SEQ ID NO: 143 | SEQ ID NO: 144 | SEQ ID NO: 115 |
| ID409 | SEQ ID NO: 143 | SEQ ID NO: 144 | SEQ ID NO: 118 |
| ID410 | SEQ ID NO: 143 | SEQ ID NO: 144 | SEQ ID NO: 121 |
| ID411 | SEQ ID NO: 143 | SEQ ID NO: 144 | SEQ ID NO: 124 |
| ID412 | SEQ ID NO: 143 | SEQ ID NO: 144 | SEQ ID NO: 127 |
| ID413 | SEQ ID NO: 143 | SEQ ID NO: 144 | SEQ ID NO: 130 |
| ID414 | SEQ ID NO: 143 | SEQ ID NO: 144 | SEQ ID NO: 133 |
| ID415 (positive control) | SEQ ID NO: 146 | SEQ ID NO: 147 | |
| ID416 (negative control) | SEQ ID NO: 146 | SEQ ID NO: 147 | SEQ ID NO: 148 |
| ID417 | SEQ ID NO: 146 | SEQ ID NO: 147 | SEQ ID NO: 94 |

TABLE 3-continued

Sequences used to generate competition constructs.

| Identifier for sequence combinations | Heavy chain | Light chain | Competing light chain |
|---|---|---|---|
| ID418 | SEQ ID NO: 146 | SEQ ID NO: 147 | SEQ ID NO: 97 |
| ID419 | SEQ ID NO: 146 | SEQ ID NO: 147 | SEQ ID NO: 100 |
| ID420 | SEQ ID NO: 146 | SEQ ID NO: 147 | SEQ ID NO: 103 |
| ID421 | SEQ ID NO: 146 | SEQ ID NO: 147 | SEQ ID NO: 106 |
| ID422 | SEQ ID NO: 146 | SEQ ID NO: 147 | SEQ ID NO: 109 |
| ID423 | SEQ ID NO: 146 | SEQ ID NO: 147 | SEQ ID NO: 112 |
| ID424 | SEQ ID NO: 146 | SEQ ID NO: 147 | SEQ ID NO: 115 |
| ID425 | SEQ ID NO: 146 | SEQ ID NO: 147 | SEQ ID NO: 118 |
| ID426 | SEQ ID NO: 146 | SEQ ID NO: 147 | SEQ ID NO: 121 |
| ID427 | SEQ ID NO: 146 | SEQ ID NO: 147 | SEQ ID NO: 124 |
| ID428 | SEQ ID NO: 146 | SEQ ID NO: 147 | SEQ ID NO: 127 |
| ID429 | SEQ ID NO: 146 | SEQ ID NO: 147 | SEQ ID NO: 130 |
| ID430 | SEQ ID NO: 146 | SEQ ID NO: 147 | SEQ ID NO: 133 |
| ID431 (positive control) | SEQ ID NO: 149 | SEQ ID NO: 150 | |
| ID432 (negative control) | SEQ ID NO: 149 | SEQ ID NO: 150 | SEQ ID NO: 151 |
| ID433 | SEQ ID NO: 149 | SEQ ID NO: 150 | SEQ ID NO: 94 |
| ID434 | SEQ ID NO: 149 | SEQ ID NO: 150 | SEQ ID NO: 97 |
| ID435 | SEQ ID NO: 149 | SEQ ID NO: 150 | SEQ ID NO: 100 |
| ID436 | SEQ ID NO: 149 | SEQ ID NO: 150 | SEQ ID NO: 103 |
| ID437 | SEQ ID NO: 149 | SEQ ID NO: 150 | SEQ ID NO: 106 |
| ID438 | SEQ ID NO: 149 | SEQ ID NO: 150 | SEQ ID NO: 109 |
| ID439 | SEQ ID NO: 149 | SEQ ID NO: 150 | SEQ ID NO: 112 |
| ID440 | SEQ ID NO: 149 | SEQ ID NO: 150 | SEQ ID NO: 115 |
| ID441 | SEQ ID NO: 149 | SEQ ID NO: 150 | SEQ ID NO: 118 |
| ID442 | SEQ ID NO: 149 | SEQ ID NO: 150 | SEQ ID NO: 121 |
| ID443 | SEQ ID NO: 149 | SEQ ID NO: 150 | SEQ ID NO: 124 |
| ID444 | SEQ ID NO: 149 | SEQ ID NO: 150 | SEQ ID NO: 127 |
| ID445 | SEQ ID NO: 149 | SEQ ID NO: 150 | SEQ ID NO: 130 |
| ID446 | SEQ ID NO: 149 | SEQ ID NO: 150 | SEQ ID NO: 133 |
| ID447 (positive control) | SEQ ID NO: 152 | SEQ ID NO: 153 | |
| ID448 (negative control) | SEQ ID NO: 152 | SEQ ID NO: 153 | SEQ ID NO: 154 |
| ID449 | SEQ ID NO: 152 | SEQ ID NO: 153 | SEQ ID NO: 94 |
| ID450 | SEQ ID NO: 152 | SEQ ID NO: 153 | SEQ ID NO: 97 |
| ID451 | SEQ ID NO: 152 | SEQ ID NO: 153 | SEQ ID NO: 100 |
| ID452 | SEQ ID NO: 152 | SEQ ID NO: 153 | SEQ ID NO: 103 |
| ID453 | SEQ ID NO: 152 | SEQ ID NO: 153 | SEQ ID NO: 106 |
| ID454 | SEQ ID NO: 152 | SEQ ID NO: 153 | SEQ ID NO: 109 |
| ID455 | SEQ ID NO: 152 | SEQ ID NO: 153 | SEQ ID NO: 112 |
| ID456 | SEQ ID NO: 152 | SEQ ID NO: 153 | SEQ ID NO: 115 |
| ID457 | SEQ ID NO: 152 | SEQ ID NO: 153 | SEQ ID NO: 118 |
| ID458 | SEQ ID NO: 152 | SEQ ID NO: 153 | SEQ ID NO: 121 |
| ID459 | SEQ ID NO: 152 | SEQ ID NO: 153 | SEQ ID NO: 124 |
| ID460 | SEQ ID NO: 152 | SEQ ID NO: 153 | SEQ ID NO: 127 |
| ID461 | SEQ ID NO: 152 | SEQ ID NO: 153 | SEQ ID NO: 130 |
| ID462 | SEQ ID NO: 152 | SEQ ID NO: 153 | SEQ ID NO: 133 |
| ID463 (positive control) | SEQ ID NO: 155 | SEQ ID NO: 156 | |
| ID464 (negative control) | SEQ ID NO: 155 | SEQ ID NO: 156 | SEQ ID NO: 157 |
| ID465 | SEQ ID NO: 155 | SEQ ID NO: 156 | SEQ ID NO: 94 |
| ID466 | SEQ ID NO: 155 | SEQ ID NO: 156 | SEQ ID NO: 97 |
| ID467 | SEQ ID NO: 155 | SEQ ID NO: 156 | SEQ ID NO: 100 |
| ID468 | SEQ ID NO: 155 | SEQ ID NO: 156 | SEQ ID NO: 103 |
| ID469 | SEQ ID NO: 155 | SEQ ID NO: 156 | SEQ ID NO: 106 |
| ID470 | SEQ ID NO: 155 | SEQ ID NO: 156 | SEQ ID NO: 109 |
| ID471 | SEQ ID NO: 155 | SEQ ID NO: 156 | SEQ ID NO: 112 |
| ID472 | SEQ ID NO: 155 | SEQ ID NO: 156 | SEQ ID NO: 115 |
| ID473 | SEQ ID NO: 155 | SEQ ID NO: 156 | SEQ ID NO: 118 |
| ID474 | SEQ ID NO: 155 | SEQ ID NO: 156 | SEQ ID NO: 121 |
| ID475 | SEQ ID NO: 155 | SEQ ID NO: 156 | SEQ ID NO: 124 |
| ID476 | SEQ ID NO: 155 | SEQ ID NO: 156 | SEQ ID NO: 127 |
| ID477 | SEQ ID NO: 155 | SEQ ID NO: 156 | SEQ ID NO: 130 |
| ID478 | SEQ ID NO: 155 | SEQ ID NO: 156 | SEQ ID NO: 133 |
| ID479 (positive control) | SEQ ID NO: 158 | SEQ ID NO: 159 | |
| ID480 (negative control) | SEQ ID NO: 158 | SEQ ID NO: 159 | SEQ ID NO: 160 |
| ID481 | SEQ ID NO: 158 | SEQ ID NO: 159 | SEQ ID NO: 94 |
| ID482 | SEQ ID NO: 158 | SEQ ID NO: 159 | SEQ ID NO: 97 |
| ID483 | SEQ ID NO: 158 | SEQ ID NO: 159 | SEQ ID NO: 100 |
| ID484 | SEQ ID NO: 158 | SEQ ID NO: 159 | SEQ ID NO: 103 |
| ID485 | SEQ ID NO: 158 | SEQ ID NO: 159 | SEQ ID NO: 106 |
| ID486 | SEQ ID NO: 158 | SEQ ID NO: 159 | SEQ ID NO: 109 |
| ID487 | SEQ ID NO: 158 | SEQ ID NO: 159 | SEQ ID NO: 112 |
| ID488 | SEQ ID NO: 158 | SEQ ID NO: 159 | SEQ ID NO: 115 |
| ID489 | SEQ ID NO: 158 | SEQ ID NO: 159 | SEQ ID NO: 118 |
| ID490 | SEQ ID NO: 158 | SEQ ID NO: 159 | SEQ ID NO: 121 |
| ID491 | SEQ ID NO: 158 | SEQ ID NO: 159 | SEQ ID NO: 124 |
| ID492 | SEQ ID NO: 158 | SEQ ID NO: 159 | SEQ ID NO: 127 |

TABLE 3-continued

Sequences used to generate competition constructs.

| Identifier for sequence combinations | Heavy chain | Light chain | Competing light chain |
|---|---|---|---|
| ID493 | SEQ ID NO: 158 | SEQ ID NO: 159 | SEQ ID NO: 130 |
| ID494 | SEQ ID NO: 158 | SEQ ID NO: 159 | SEQ ID NO: 133 |
| ID495 (positive control) | SEQ ID NO: 161 | SEQ ID NO: 162 | |
| ID496 (negative control) | SEQ ID NO: 161 | SEQ ID NO: 162 | SEQ ID NO: 163 |
| ID497 | SEQ ID NO: 161 | SEQ ID NO: 162 | SEQ ID NO: 94 |
| ID498 | SEQ ID NO: 161 | SEQ ID NO: 162 | SEQ ID NO: 97 |
| ID499 | SEQ ID NO: 161 | SEQ ID NO: 162 | SEQ ID NO: 100 |
| ID500 | SEQ ID NO: 161 | SEQ ID NO: 162 | SEQ ID NO: 103 |
| ID501 | SEQ ID NO: 161 | SEQ ID NO: 162 | SEQ ID NO: 106 |
| ID502 | SEQ ID NO: 161 | SEQ ID NO: 162 | SEQ ID NO: 109 |
| ID503 | SEQ ID NO: 161 | SEQ ID NO: 162 | SEQ ID NO: 112 |
| ID504 | SEQ ID NO: 161 | SEQ ID NO: 162 | SEQ ID NO: 115 |
| ID505 | SEQ ID NO: 161 | SEQ ID NO: 162 | SEQ ID NO: 118 |
| ID506 | SEQ ID NO: 161 | SEQ ID NO: 162 | SEQ ID NO: 121 |
| ID507 | SEQ ID NO: 161 | SEQ ID NO: 162 | SEQ ID NO: 124 |
| ID508 | SEQ ID NO: 161 | SEQ ID NO: 162 | SEQ ID NO: 127 |
| ID509 | SEQ ID NO: 161 | SEQ ID NO: 162 | SEQ ID NO: 130 |
| ID510 | SEQ ID NO: 161 | SEQ ID NO: 162 | SEQ ID NO: 133 |

TABLE 6

Percent pairing for heavy chains and kappa light chains in the presence of competing lambda light chains as measured by the NanoBiT assay.

| Column 1: Identifier for sequence combinations | Column 2: Percent pairing | Column 3: heavy chain polypeptide 2 (HCP2) corresponding germline | Column 4: kappa light chain polypeptide (KLCP) corresponding germline | Column 5: competing lambda light chain polypeptide (LLCP) corresponding germline |
|---|---|---|---|---|
| ID185 | 98 | VH3-33*01 (SEQ ID NO: 193) | Vk1-39*01 (SEQ ID NO: 201) | Vl3-19*01 (SEQ ID NO: 211) |
| ID189 | 82 | VH3-33*01 (SEQ ID NO: 193) | Vk1-39*01 (SEQ ID NO: 201) | Vl3-19*01 (SEQ ID NO: 211) |
| ID190 | 100 | VH3-33*01 (SEQ ID NO: 193) | Vk1-39*01 (SEQ ID NO: 201) | Vl2-14*01 (SEQ ID NO: 210) |
| ID191 | 100 | VH3-33*01 (SEQ ID NO: 193) | Vk1-39*01 (SEQ ID NO: 201) | Vl3-9*01 (SEQ ID NO: 212) |
| ID192 | 87 | VH3-33*01 (SEQ ID NO: 193) | Vk1-39*01 (SEQ ID NO: 201) | Vl10-54*01 (SEQ ID NO: 207) |
| ID198 | 93 | VH5-51*01 (SEQ ID NO: 198) | Vk3-20*01 (SEQ ID NO: 205) | Vl3-19*01 (SEQ ID NO: 211) |
| ID205 | 100 | VH5-51*01 (SEQ ID NO: 198) | Vk3-20*01 (SEQ ID NO: 205) | Vl10-54*01 (SEQ ID NO: 207) |
| ID206 | 93 | VH5-51*01 (SEQ ID NO: 198) | Vk3-20*01 (SEQ ID NO: 205) | Vl1-44*01 (SEQ ID NO: 209) |
| ID209 | 95 | VH3-13*01 (SEQ ID NO: 188) | Vk1D-16*01 (SEQ ID NO: 202) | Vl3-19*01 (SEQ ID NO: 211) |
| ID211 | 93 | VH3-13*01 (SEQ ID NO: 188) | Vk1D-16*01 (SEQ ID NO: 202) | Vl1-40*01 (SEQ ID NO: 208) |
| ID213 | 90 | VH3-13*01 (SEQ ID NO: 188) | Vk1D-16*01 (SEQ ID NO: 202) | Vl3-19*01 (SEQ ID NO: 211) |
| ID214 | 100 | VH3-13*01 (SEQ ID NO: 188) | Vk1D-16*01 (SEQ ID NO: 202) | Vl2-14*01 (SEQ ID NO: 210) |
| ID215 | 95 | VH3-13*01 (SEQ ID NO: 188) | Vk1D-16*01 (SEQ ID NO: 202) | Vl3-9*01 (SEQ ID NO: 212) |
| ID216 | 96 | VH3-13*01 (SEQ ID NO: 188) | Vk1D-16*01 (SEQ ID NO: 202) | Vl10-54*01 (SEQ ID NO: 207) |

TABLE 6-continued

Percent pairing for heavy chains and kappa light chains in the presence of competing lambda light chains as measured by the NanoBiT assay.

| Column 1: Identifier for sequence combinations | Column 2: Percent pairing | Column 3: heavy chain polypeptide 2 (HCP2) corresponding germline | Column 4: kappa light chain polypeptide (KLCP) corresponding germline | Column 5: competing lambda light chain polypeptide (LLCP) corresponding germline |
|---|---|---|---|---|
| ID217 | 100 | VH3-13*01 (SEQ ID NO: 188) | Vk1D-16*01 (SEQ ID NO: 202) | Vl10-54*01 (SEQ ID NO: 207) |
| ID218 | 100 | VH3-13*01 (SEQ ID NO: 188) | Vk1D-16*01 (SEQ ID NO: 202) | Vl1-44*01 (SEQ ID NO: 209) |
| ID222 | 100 | VH1-3*01 (SEQ ID NO: 185) | Vk3D-20*01 (SEQ ID NO: 206) | Vl3-19*01 (SEQ ID NO: 211) |
| ID229 | 98 | VH1-3*01 (SEQ ID NO: 185) | Vk3D-20*01 (SEQ ID NO: 206) | Vl10-54*01 (SEQ ID NO: 207) |
| ID230 | 83 | VH1-3*01 (SEQ ID NO: 185) | Vk3D-20*01 (SEQ ID NO: 206) | Vl1-44*01 (SEQ ID NO: 209) |
| ID228 | 93 | VH1-3*01 (SEQ ID NO: 185) | Vk3D-20*01 (SEQ ID NO: 206) | Vl10-54*01 (SEQ ID NO: 207) |
| ID235 | 90 | VH3-30*01 (SEQ ID NO: 192) | Vk3-20*01 (SEQ ID NO: 205) | Vl1-40*01 (SEQ ID NO: 208) |
| ID236 | 100 | VH3-30*01 (SEQ ID NO: 192) | Vk3-20*01 (SEQ ID NO: 205) | Vl3-19*01 (SEQ ID NO: 211) |
| ID242 | 100 | VH3-30*01 (SEQ ID NO: 192) | Vk3-20*01 (SEQ ID NO: 205) | Vl1-44*01 (SEQ ID NO: 209) |
| ID241 | 100 | VH3-30*01 (SEQ ID NO: 192) | Vk3-20*01 (SEQ ID NO: 205) | Vl10-54*01 (SEQ ID NO: 207) |
| ID259 | 75 | VH1-18*01 (SEQ ID NO: 183) | Vk3-20*01 (SEQ ID NO: 205) | Vl1-40*01 (SEQ ID NO: 208) |
| ID262 | 90 | VH1-18*01 (SEQ ID NO: 183) | Vk3-20*01 (SEQ ID NO: 205) | Vl2-14*01 (SEQ ID NO: 210) |
| ID288 | 95 | VH3-23*01 (SEQ ID NO: 191) | Vk1-27*01 (SEQ ID NO: 200) | Vl10-54*01 (SEQ ID NO: 207) |
| ID289 | 100 | VH3-23*01 (SEQ ID NO: 191) | Vk1-27*01 (SEQ ID NO: 200) | Vl10-54*01 (SEQ ID NO: 207) |
| ID284 | 84 | VH3-23*01 (SEQ ID NO: 191) | Vk1-27*01 (SEQ ID NO: 200) | Vl3-19*01 (SEQ ID NO: 211) |
| ID286 | 81 | VH3-23*01 (SEQ ID NO: 191) | Vk1-27*01 (SEQ ID NO: 200) | Vl2-14*01 (SEQ ID NO: 210) |
| ID290 | 96 | VH3-23*01 (SEQ ID NO: 191) | Vk1-27*01 (SEQ ID NO: 200) | Vl1-44*01 (SEQ ID NO: 209) |
| ID295 | 95 | VH3-21*01 (SEQ ID NO: 190) | Vk3-20*01 (SEQ ID NO: 205) | Vl1-40*01 (SEQ ID NO: 208) |
| ID299 | 99 | VH3-21*01 (SEQ ID NO: 190) | Vk3-20*01 (SEQ ID NO: 205) | Vl3-9*01 (SEQ ID NO: 212) |
| ID302 | 100 | VH3-21*01 (SEQ ID NO: 190) | Vk3-20*01 (SEQ ID NO: 205) | Vl1-44*01 (SEQ ID NO: 209) |
| ID301 | 100 | VH3-21*01 (SEQ ID NO: 190) | Vk3-20*01 (SEQ ID NO: 205) | Vl10-54*01 (SEQ ID NO: 207) |
| ID306 | 94 | VH3-33*01 (SEQ ID NO: 193) | Vk3-11*01 (SEQ ID NO: 204) | Vl3-19*01 (SEQ ID NO: 211) |
| ID307 | 98 | VH3-33*01 (SEQ ID NO: 193) | Vk3-11*01 (SEQ ID NO: 204) | Vl1-40*01 (SEQ ID NO: 208) |
| ID308 | 100 | VH3-33*01 (SEQ ID NO: 193) | Vk3-11*01 (SEQ ID NO: 204) | Vl3-19*01 (SEQ ID NO: 211) |

TABLE 6-continued

Percent pairing for heavy chains and kappa light chains in the presence of competing lambda light chains as measured by the NanoBiT assay.

| Column 1: Identifier for sequence combinations | Column 2: Percent pairing | Column 3: heavy chain polypeptide 2 (HCP2) corresponding germline | Column 4: kappa light chain polypeptide (KLCP) corresponding germline | Column 5: competing lambda light chain polypeptide (LLCP) corresponding germline |
|---|---|---|---|---|
| ID309 | 93 | VH3-33*01 (SEQ ID NO: 193) | Vk3-11*01 (SEQ ID NO: 204) | Vl3-19*01 (SEQ ID NO: 211) |
| ID310 | 94 | VH3-33*01 (SEQ ID NO: 193) | Vk3-11*01 (SEQ ID NO: 204) | Vl2-14*01 (SEQ ID NO: 210) |
| ID312 | 88 | VH3-33*01 (SEQ ID NO: 193) | Vk3-11*01 (SEQ ID NO: 204) | Vl10-54*01 (SEQ ID NO: 207) |
| ID313 | 100 | VH3-33*01 (SEQ ID NO: 193) | Vk3-11*01 (SEQ ID NO: 204) | Vl10-54*01 (SEQ ID NO: 207) |
| ID314 | 100 | VH3-33*01 (SEQ ID NO: 193) | Vk3-11*01 (SEQ ID NO: 204) | Vl1-44*01 (SEQ ID NO: 209) |
| ID317 | 100 | VH3-9*01 (SEQ ID NO: 196) | Vk1-12*01 (SEQ ID NO: 199) | Vl3-19*01 (SEQ ID NO: 211) |
| ID318 | 99 | VH3-9*01 (SEQ ID NO: 196) | Vk1-12*01 (SEQ ID NO: 199) | Vl3-19*01 (SEQ ID NO: 211) |
| ID320 | 100 | VH3-9*01 (SEQ ID NO: 196) | Vk1-12*01 (SEQ ID NO: 199) | Vl3-19*01 (SEQ ID NO: 211) |
| ID324 | 100 | VH3-9*01 (SEQ ID NO: 196) | Vk1-12*01 (SEQ ID NO: 199) | Vl10-54*01 (SEQ ID NO: 207) |
| ID323 | 84 | VH3-9*01 (SEQ ID NO: 196) | Vk1-12*01 (SEQ ID NO: 199) | Vl3-9*01 (SEQ ID NO: 212) |
| ID246 | 100 | VH5-51*01 (SEQ ID NO: 198) | Vk3-20*01 (SEQ ID NO: 205) | Vl3-19*01 (SEQ ID NO: 211) |
| ID253 | 80 | VH5-51*01 (SEQ ID NO: 198) | Vk3-20*01 (SEQ ID NO: 205) | Vl10-54*01 (SEQ ID NO: 207) |
| ID254 | 100 | VH5-51*01 (SEQ ID NO: 198) | Vk3-20*01 (SEQ ID NO: 205) | Vl1-44*01 (SEQ ID NO: 209) |
| ID274 | 79 | VH4-4*01 (SEQ ID NO: 197) | Vk2-28*01 (SEQ ID NO: 203) | Vl2-14*01 (SEQ ID NO: 210) |
| ID278 | 79 | VH4-4*01 (SEQ ID NO: 197) | Vk2-28*01 (SEQ ID NO: 203) | Vl1-44*01 (SEQ ID NO: 209) |
| ID336 | 76 | VH3-23*01 (SEQ ID NO: 191) | Vk3-11*01 (SEQ ID NO: 204) | Vl10-54*01 (SEQ ID NO: 207) |
| ID341 | 100 | VH3-66*01 (SEQ ID NO: 194) | Vk1-39*01 (SEQ ID NO: 201) | Vl3-19*01 (SEQ ID NO: 211) |
| ID349 | 100 | VH3-66*01 (SEQ ID NO: 194) | Vk1-39*01 (SEQ ID NO: 201) | Vl10-54*01 (SEQ ID NO: 207) |
| ID344 | 100 | VH3-66*01 (SEQ ID NO: 194) | Vk1-39*01 (SEQ ID NO: 201) | Vl3-19*01 (SEQ ID NO: 211) |
| ID342 | 100 | VH3-66*01 (SEQ ID NO: 194) | Vk1-39*01 (SEQ ID NO: 201) | Vl3-19*01 (SEQ ID NO: 211) |
| ID343 | 84 | VH3-66*01 (SEQ ID NO: 194) | Vk1-39*01 (SEQ ID NO: 201) | Vl1-40*01 (SEQ ID NO: 208) |
| ID347 | 100 | VH3-66*01 (SEQ ID NO: 194) | Vk1-39*01 (SEQ ID NO: 201) | Vl3-9*01 (SEQ ID NO: 212) |
| ID348 | 100 | VH3-66*01 (SEQ ID NO: 194) | Vk1-39*01 (SEQ ID NO: 201) | Vl10-54*01 (SEQ ID NO: 207) |

TABLE 6-continued

Percent pairing for heavy chains and kappa light chains in the presence of competing lambda light chains as measured by the NanoBiT assay.

| Column 1: Identifier for sequence combinations | Column 2: Percent pairing | Column 3: heavy chain polypeptide 2 (HCP2) corresponding germline | Column 4: kappa light chain polypeptide (KLCP) corresponding germline | Column 5: competing lambda light chain polypeptide (LLCP) corresponding germline |
|---|---|---|---|---|
| ID350 | 100 | VH3-66*01 (SEQ ID NO: 194) | Vk1-39*01 (SEQ ID NO: 201) | Vl1-44*01 (SEQ ID NO: 209) |

TABLE 7

Percent pairing for heavy chains and lambda light chains in the presence of competing kappa light chains as measured by the NanoBiT assay.

| Column 1: Identifier for sequence combinations | Column 2: Percent pairing | Column 3: heavy chain polypeptide 1 (HCP1) corresponding germline | Column 4: lambda light chain polypeptide (LLCP) corresponding germline | Column 5: Competing kappa light chain polypeptide (KLCP) corresponding germline |
|---|---|---|---|---|
| ID357 | 96 | VH1-69*01 (SEQ ID NO: 187) | Vl3-19*01 (SEQ ID NO: 211) | Vk3-20*01 (SEQ ID NO: 205) |
| ID359 | 95 | VH1-69*01 (SEQ ID NO: 187) | Vl3-19*01 (SEQ ID NO: 211) | Vk3-20*01 (SEQ ID NO: 205) |
| ID363 | 100 | VH1-69*01 (SEQ ID NO: 187) | Vl3-19*01 (SEQ ID NO: 211) | Vk3-11*01 (SEQ ID NO: 204) |
| ID366 | 100 | VH1-69*01 (SEQ ID NO: 187) | Vl3-19*01 (SEQ ID NO: 211) | Vk1-39*01 (SEQ ID NO: 201) |
| ID378 | 94 | VH3-20*01 (SEQ ID NO: 189) | Vl3-19*01 (SEQ ID NO: 211) | Vk3-20*01 (SEQ ID NO: 205) |
| ID379 | 100 | VH3-20*01 (SEQ ID NO: 189) | Vl3-19*01 (SEQ ID NO: 211) | Vk3-11*01 (SEQ ID NO: 204) |
| ID372 | 100 | VH3-20*01 (SEQ ID NO: 189) | Vl3-19*01 (SEQ ID NO: 211) | Vk3D-20*01 (SEQ ID NO: 206) |
| ID374 | 100 | VH3-20*01 (SEQ ID NO: 189) | Vl3-19*01 (SEQ ID NO: 211) | Vk3-20*01 (SEQ ID NO: 205) |
| ID380 | 95 | VH3-20*01 (SEQ ID NO: 189) | Vl3-19*01 (SEQ ID NO: 211) | Vk1-12*01 (SEQ ID NO: 199) |
| ID386 | 96 | VH5-51*01 (SEQ ID NO: 198) | Vl1-40*01 (SEQ ID NO: 208) | Vk3-20*01 (SEQ ID NO: 205) |
| ID392 | 93 | VH5-51*01 (SEQ ID NO: 198) | Vl1-40*01 (SEQ ID NO: 208) | Vk2-28*01 (SEQ ID NO: 203) |
| ID393 | 91 | VH5-51*01 (SEQ ID NO: 198) | Vl1-40*01 (SEQ ID NO: 208) | Vk1-27*01 (SEQ ID NO: 200) |
| ID395 | 100 | VH5-51*01 (SEQ ID NO: 198) | Vl1-40*01 (SEQ ID NO: 208) | Vk3-11*01 (SEQ ID NO: 204) |
| ID462 | 79 | VH1-69*01 (SEQ ID NO: 187) | Vl3-9*01 (SEQ ID NO: 212) | Vk1-39*01 (SEQ ID NO: 201) |
| ID472 | 90 | VH1-2*01 (SEQ ID NO: 184) | Vl10-54*01 (SEQ ID NO: 207) | Vk2-28*01 (SEQ ID NO: 203) |
| ID475 | 80 | VH1-2*01 (SEQ ID NO: 184) | Vl10-54*01 (SEQ ID NO: 207) | Vk3-11*01 (SEQ ID NO: 204) |
| ID476 | 77 | VH1-2*01 (SEQ ID NO: 184) | Vl10-54*01 (SEQ ID NO: 207) | Vk1-12*01 (SEQ ID NO: 199) |
| ID477 | 100 | VH1-2*01 (SEQ ID NO: 184) | Vl10-54*01 (SEQ ID NO: 207) | Vk3-11*01 (SEQ ID NO: 204) |

TABLE 7-continued

Percent pairing for heavy chains and lambda light chains in the presence of competing kappa light chains as measured by the NanoBiT assay.

| Column 1: Identifier for sequence combinations | Column 2: Percent pairing | Column 3: heavy chain polypeptide 1 (HCP1) corresponding germline | Column 4: lambda light chain polypeptide (LLCP) corresponding germline | Column 5: Competing kappa light chain polypeptide (KLCP) corresponding germline |
|---|---|---|---|---|
| ID478 | 100 | VH1-2*01 (SEQ ID NO: 184) | Vl10-54*01 (SEQ ID NO: 207) | Vk1-39*01 (SEQ ID NO: 201) |
| ID481 | 100 | VH3-7*01 (SEQ ID NO: 195) | Vl10-54*01 (SEQ ID NO: 207) | Vk1-39*01 (SEQ ID NO: 201) |
| ID482 | 89 | VH3-7*01 (SEQ ID NO: 195) | Vl10-54*01 (SEQ ID NO: 207) | Vk3-20*01 (SEQ ID NO: 205) |
| ID483 | 99 | VH3-7*01 (SEQ ID NO: 195) | Vl10-54*01 (SEQ ID NO: 207) | Vk1D-16*01 (SEQ ID NO: 202) |
| ID484 | 100 | VH3-7*01 (SEQ ID NO: 195) | Vl10-54*01 (SEQ ID NO: 207) | Vk3D-20*01 (SEQ ID NO: 206) |
| ID485 | 98 | VH3-7*01 (SEQ ID NO: 195) | Vl10-54*01 (SEQ ID NO: 207) | Vk3-20*01 (SEQ ID NO: 205) |
| ID486 | 95 | VH3-7*01 (SEQ ID NO: 195) | Vl10-54*01 (SEQ ID NO: 207) | Vk3-20*01 (SEQ ID NO: 205) |
| ID488 | 97 | VH3-7*01 (SEQ ID NO: 195) | Vl10-54*01 (SEQ ID NO: 207 | Vk2-28*01 (SEQ ID NO: 203) |
| ID493 | 99 | VH3-7*01 (SEQ ID NO: 195) | Vl10-54*01 (SEQ ID NO: 207) | Vk3-11*01 (SEQ ID NO: 204) |
| ID494 | 99 | VH3-7*01 (SEQ ID NO: 195) | Vl10-54*01 (SEQ ID NO: 207) | Vk1-39*01 (SEQ ID NO: 201) |
| ID402 | 100 | VH3-9*01 (SEQ ID NO: 196) | Vl3-19*01 (SEQ ID NO: 211) | Vk3-20*01 (SEQ ID NO: 205) |
| ID404 | 80 | VH3-9*01 (SEQ ID NO: 196) | Vl3-19*01 (SEQ ID NO: 211) | Vk3D-20*01 (SEQ ID NO: 206) |
| ID405 | 93 | VH3-9*01 (SEQ ID NO: 196) | Vl3-19*01 (SEQ ID NO: 211) | Vk3-20*01 (SEQ ID NO: 205) |
| ID407 | 100 | VH3-9*01 (SEQ ID NO: 196) | Vl3-19*01 (SEQ ID NO: 211) | Vk3-20*01 (SEQ ID NO: 205) |
| ID408 | 86 | VH3-9*01 (SEQ ID NO: 196) | Vl3-19*01 (SEQ ID NO: 211) | Vk2-28*01 (SEQ ID NO: 203) |
| ID409 | 90 | VH3-9*01 (SEQ ID NO: 196) | Vl3-19*01 (SEQ ID NO: 211) | Vk1-27*01 (SEQ ID NO: 200) |
| ID411 | 100 | VH3-9*01 (SEQ ID NO: 196) | Vl3-19*01 (SEQ ID NO: 211) | Vk3-11*01 (SEQ ID NO: 204) |
| ID412 | 100 | VH3-9*01 (SEQ ID NO: 196) | Vl3-19*01 (SEQ ID NO: 211) | Vk1-12*01 (SEQ ID NO: 199) |
| ID414 | 100 | VH3-9*01 (SEQ ID NO: 196) | Vl3-19*01 (SEQ ID NO: 211) | Vk1-39*01 (SEQ ID NO: 201) |
| ID418 | 100 | VH3-20*01 (SEQ ID NO: 189) | Vl3-19*01 (SEQ ID NO: 211) | Vk3-20*01 (SEQ ID NO: 205) |
| ID420 | 84 | VH3-20*01 (SEQ ID NO: 189) | Vl3-19*01 (SEQ ID NO: 211) | Vk3D-20*01 (SEQ ID NO: 206) |
| ID421 | 77 | VH3-20*01 (SEQ ID NO: 189) | Vl3-19*01 (SEQ ID NO: 211) | Vk3-20*01 (SEQ ID NO: 205) |
| ID422 | 100 | VH3-20*01 (SEQ ID NO: 189) | Vl3-19*01 (SEQ ID NO: 211) | Vk3-20*01 (SEQ ID NO: 205) |

TABLE 7-continued

Percent pairing for heavy chains and lambda light chains in the presence of competing kappa light chains as measured by the NanoBiT assay.

| Column 1: Identifier for sequence combinations | Column 2: Percent pairing | Column 3: heavy chain polypeptide 1 (HCP1) corresponding germline | Column 4: lambda light chain polypeptide (LLCP) corresponding germline | Column 5: Competing kappa light chain polypeptide (KLCP) corresponding germline |
|---|---|---|---|---|
| ID423 | 100 | VH3-20*01 (SEQ ID NO: 189) | Vl3-19*01 (SEQ ID NO: 211) | Vk3-20*01 (SEQ ID NO: 205) |
| ID424 | 81 | VH3-20*01 (SEQ ID NO: 189) | Vl3-19*01 (SEQ ID NO: 211) | Vk2-28*01 (SEQ ID NO: 203) |
| ID430 | 100 | VH3-20*01 (SEQ ID NO: 189) | Vl3-19*01 (SEQ ID NO: 211) | Vk1-39*01 (SEQ ID NO: 201) |
| ID434 | 90 | VH1-46*01 (SEQ ID NO: 186) | Vl2-14*01 (SEQ ID NO: 210) | Vk3-20*01 (SEQ ID NO: 205) |
| ID435 | 90 | VH1-46*01 (SEQ ID NO: 186) | Vl2-14*01 (SEQ ID NO: 210) | Vk1D-16*01 (SEQ ID NO: 202) |
| ID436 | 81 | VH1-46*01 (SEQ ID NO: 186) | Vl2-14*01 (SEQ ID NO: 210) | Vk3D-20*01 (SEQ ID NO: 206) |
| ID440 | 75 | VH1-46*01 (SEQ ID NO: 186) | Vl2-14*01 (SEQ ID NO: 210) | Vk2-28*01 (SEQ ID NO: 203) |
| ID441 | 79 | VH1-46*01 (SEQ ID NO: 186) | Vl2-14*01 (SEQ ID NO: 210) | Vk1-27*01 (SEQ ID NO: 200) |
| ID443 | 100 | VH1-46*01 (SEQ ID NO: 186) | Vl2-14*01 (SEQ ID NO: 210) | Vk3-11*01 (SEQ ID NO: 204) |
| ID446 | 87 | VH1-46*01 (SEQ ID NO: 186) | Vl2-14*01 (SEQ ID NO: 210) | Vk1-39*01 (SEQ ID NO: 201) |
| ID498 | 100 | VH3-33*01 (SEQ ID NO: 193) | Vl1-44*01 (SEQ ID NO: 209) | Vk3-20*01 (SEQ ID NO: 205) |
| ID499 | 100 | VH3-33*01 (SEQ ID NO: 193) | Vl1-44*01 (SEQ ID NO: 209) | Vk1D-16*01 (SEQ ID NO: 202) |
| ID500 | 100 | VH3-33*01 (SEQ ID NO: 193) | Vl1-44*01 (SEQ ID NO: 209) | Vk3D-20*01 (SEQ ID NO: 206) |
| ID501 | 100 | VH3-33*01 (SEQ ID NO: 193) | Vl1-44*01 (SEQ ID NO: 209) | Vk3-20*01 (SEQ ID NO: 205) |
| ID502 | 80 | VH3-33*01 (SEQ ID NO: 193) | Vl1-44*01 (SEQ ID NO: 209) | Vk3-20*01 (SEQ ID NO: 205) |
| ID506 | 100 | VH3-33*01 (SEQ ID NO: 193) | Vl1-44*01 (SEQ ID NO: 209) | Vk3-20*01 (SEQ ID NO: 205) |

TABLE 8a

Two-way pairs based on NanoBiT data.

| Identifier for sequence combinations | Percent pairing | Identifier for sequence combinations | Percent pairing | Identifier for sequence combinations | Percent pairing | Identifier for sequence combinations | Percent pairing |
|---|---|---|---|---|---|---|---|
| ID205 | 100 | ID482 | 89 | ID284 | 84 | ID409 | 90 |
| ID206 | 93 | ID498 | 100 | ID286 | 81 | ID441 | 79 |
| ID214 | 100 | ID435 | 90 | ID302 | 100 | ID506 | 100 |
| ID217 | 100 | ID483 | 99 | ID306 | 94 | ID379 | 100 |
| ID218 | 100 | ID499 | 100 | ID307 | 98 | ID395 | 100 |
| ID222 | 100 | ID372 | 100 | ID308 | 100 | ID411 | 100 |
| ID229 | 98 | ID484 | 100 | ID310 | 94 | ID443 | 100 |
| ID230 | 83 | ID500 | 100 | ID312 | 88 | ID475 | 80 |
| ID236 | 100 | ID405 | 93 | ID318 | 99 | ID380 | 95 |
| ID242 | 100 | ID501 | 100 | ID320 | 100 | ID412 | 100 |
| ID241 | 100 | ID485 | 98 | ID324 | 100 | ID476 | 77 |
| ID259 | 75 | ID392 | 93 | ID246 | 100 | ID374 | 100 |

TABLE 8a-continued

Two-way pairs based on NanoBiT data.

| Identifier for sequence combinations | Percent pairing | Identifier for sequence combinations | Percent pairing |
|---|---|---|---|
| ID253 | 80 | ID486 | 95 |
| ID254 | 100 | ID502 | 80 |
| ID274 | 79 | ID440 | 75 |
| ID336 | 76 | ID477 | 100 |
| ID341 | 100 | ID366 | 100 |
| ID349 | 100 | ID494 | 99 |
| ID344 | 100 | ID414 | 100 |
| ID347 | 100 | ID462 | 79 |
| ID348 | 100 | ID478 | 100 |

TABLE 8b

Corresponding germline sequences of two-way pairs based on NanoBiT data

| Column 1: Identifier for sequence combinations | Column 2: heavy chain polypeptide 1 (HCP1) corresponding germline | Column 3: lambda light chain polypeptide (LLCP) corresponding germline | Column 4: Identifier for sequence combinations | Column 5: heavy chain polypeptide 2 (HCP2) corresponding germline | Column 6: kappa light chain polypeptide (KLCP) corresponding germline |
|---|---|---|---|---|---|
| ID205 | VH5-51*01 (SEQ ID NO: 198) | VK3-20*01 (SEQ ID NO: 205) | ID482 | VH3-7*01 (SEQ ID NO: 195) | Vl10-54*01 (SEQ ID NO: 207) |
| ID206 | VH5-51*01 (SEQ ID NO: 198) | VK3-20*01 (SEQ ID NO: 205) | ID498 | VH3-33*01 (SEQ ID NO: 193) | Vl1-44*01 (SEQ ID NO: 209) |
| ID214 | VH3-13*01 (SEQ ID NO: 188) | VK1D-16*01 (SEQ ID NO: 202) | ID435 | VH1-46*01 (SEQ ID NO: 186) | Vl2-14*01 (SEQ ID NO: 210) |
| ID217 | VH3-13*01 (SEQ ID NO: 188) | VK1D-16*01 (SEQ ID NO: 202) | ID483 | VH3-7*01 (SEQ ID NO: 195) | Vl10-54*01 (SEQ ID NO: 207) |
| ID218 | VH3-13*01 (SEQ ID NO: 188) | VKID-16*01 (SEQ ID NO: 202) | ID499 | VH3-33*01 (SEQ ID NO: 193) | Vl1-44*01 (SEQ ID NO: 209) |
| ID222 | VH1-3*01 (SEQ ID NO: 185) | VK3D-20*01 (SEQ ID NO: 206) | ID372 | VH3-20*01 (SEQ ID NO: 189) | Vl3-19*01 (SEQ ID NO: 211) |
| ID229 | VH1-3*01 (SEQ ID NO: 185) | VK3D-20*01 (SEQ ID NO: 206) | ID484 | VH3-7*01 (SEQ ID NO: 195) | Vl10-54*01 (SEQ ID NO: 207) |
| ID230 | VH1-3*01 (SEQ ID NO: 185) | VK3D-20*01 (SEQ ID NO: 206) | ID500 | VH3-33*01 (SEQ ID NO: 193) | Vl1-44*01 (SEQ ID NO: 209) |
| ID236 | VH3-30*01 (SEQ ID NO: 192) | VK3-20*01 (SEQ ID NO: 205) | ID405 | VH3-9*01 (SEQ ID NO: 196) | Vl3-19*01 (SEQ ID NO: 211) |
| ID242 | VH3-30*01 (SEQ ID NO: 192) | VK3-20*01 (SEQ ID NO: 205) | ID501 | VH3-33*01 (SEQ ID NO: 193) | Vl1-44*01 (SEQ ID NO: 209) |
| ID241 | VH3-30*01 (SEQ ID NO: 192) | VK3-20*01 (SEQ ID NO: 205) | ID485 | VH3-7*01 (SEQ ID NO: 195) | Vl10-54*01 (SEQ ID NO: 207) |
| ID259 | VH1-18*01 (SEQ ID NO: 183) | VK3-20*01 (SEQ ID NO: 205) | ID392 | VH5-51*01 (SEQ ID NO: 198) | Vl1-40*01 (SEQ ID NO: 208) |
| ID284 | VH3-23*01 (SEQ ID NO: 191) | VK1-27*01 (SEQ ID NO: 200) | ID409 | VH3-9*01 (SEQ ID NO: 196) | Vl3-19*01 (SEQ ID NO: 211) |
| ID286 | VH3-23*01 (SEQ ID NO: 191) | VK1-27*01 (SEQ ID NO: 200) | ID441 | VH1-46*01 (SEQ ID NO: 186) | Vl2-14*01 (SEQ ID NO: 210) |

TABLE 8b-continued

Corresponding germline sequences of two-way pairs based on NanoBiT data

| Column 1: Identifier for sequence combinations | Column 2: heavy chain polypeptide 1 (HCP1) corresponding germline | Column 3: lambda light chain polypeptide (LLCP) corresponding germline | Column 4: Identifier for sequence combinations | Column 5: heavy chain polypeptide 2 (HCP2) corresponding germline | Column 6: kappa light chain polypeptide (KLCP) corresponding germline |
|---|---|---|---|---|---|
| ID302 | VH3-21*01 (SEQ ID NO: 190) | VK3-20*01 (SEQ ID NO: 205) | ID506 | VH3-33*01 (SEQ ID NO: 193) | Vl1-44*01 (SEQ ID NO: 209) |
| ID306 | VH3-33*01 (SEQ ID NO: 193) | Vk3-11*01 (SEQ ID NO: 204) | ID379 | VH3-20*01 (SEQ ID NO: 189) | Vl3-19*01 (SEQ ID NO: 211) |
| ID307 | VH3-33*01 (SEQ ID NO: 193) | Vk3-11*01 (SEQ ID NO: 204) | ID395 | VH5-51*01 (SEQ ID NO: 198) | Vl1-40*01 (SEQ ID NO: 208) |
| ID308 | VH3-33*01 (SEQ ID NO: 193) | Vk3-11*01 (SEQ ID NO: 204) | ID411 | VH3-9*01 (SEQ ID NO: 196) | Vl3-19*01 (SEQ ID NO: 211) |
| ID310 | VH3-33*01 (SEQ ID NO: 193) | Vk3-11*01 (SEQ ID NO: 204) | ID443 | VH1-46*01 (SEQ ID NO: 186) | Vl2-14*01 (SEQ ID NO: 210) |
| ID312 | VH3-33*01 (SEQ ID NO: 193) | Vk3-11*01 (SEQ ID NO: 204) | ID475 | VH1-2*01 (SEQ ID NO: 184) | Vl10-54*01 (SEQ ID NO: 207) |
| ID318 | VH3-9*01 (SEQ ID NO: 196) | Vk1-12*01 (SEQ ID NO: 199) | ID380 | VH3-20*01 (SEQ ID NO: 189) | Vl3-19*01 (SEQ ID NO: 211) |
| ID320 | VH3-9*01 (SEQ ID NO: 196) | Vk1-12*01 (SEQ ID NO: 199) | ID412 | VH3-9*01 (SEQ ID NO: 196) | Vl3-19*01 (SEQ ID NO: 211) |
| ID324 | VH3-9*01 (SEQ ID NO: 196) | Vk1-12*01 (SEQ ID NO: 199) | ID476 | VH1-2*01 (SEQ ID NO: 184) | Vl10-54*01 (SEQ ID NO: 207) |
| ID246 | VH5-51*01 (SEQ ID NO: 198) | VK3-20*01 (SEQ ID NO: 205) | ID374 | VH3-20*01 (SEQ ID NO: 189) | Vl3-19*01 (SEQ ID NO: 211) |
| ID253 | VH5-51*01 (SEQ ID NO: 198) | VK3-20*01 (SEQ ID NO: 205) | ID486 | VH3-7*01 (SEQ ID NO: 195) | Vl10-54*01 (SEQ ID NO: 207) |
| ID254 | VH5-51*01 (SEQ ID NO: 198) | VK3-20*01 (SEQ ID NO: 205) | ID502 | VH3-33*01 (SEQ ID NO: 193) | Vl1-44*01 (SEQ ID NO: 209) |
| ID274 | VH4-4*01 (SEQ ID NO: 197) | VK2-28*01 (SEQ ID NO: 203 | ID440 | VH1-46*01 (SEQ ID NO: 186) | Vl2-14*01 (SEQ ID NO: 210) |
| ID336 | VH3-23*01 (SEQ ID NO: 191 | Vk3-11*01 (SEQ ID NO: 204) | ID477 | VH1-2*01 (SEQ ID NO: 184) | Vl10-54*01 (SEQ ID NO: 207) |
| ID341 | VH3-66*01 (SEQ ID NO: 194) | Vk1-39*01 (SEQ ID NO: 201) | ID366 | VH1-69*01 (SEQ ID NO: 187) | Vl3-19*01 (SEQ ID NO: 211) |
| ID349 | VH3-66*01 (SEQ ID NO: 194) | Vk1-39*01 (SEQ ID NO: 201) | ID494 | VH3-7*01 (SEQ ID NO: 195) | Vl10-54*01 (SEQ ID NO: 207) |
| ID344 | VH3-66*01 (SEQ ID NO: 194 | Vk1-39*01 (SEQ ID NO: 201) | ID414 | VH3-9*01 (SEQ ID NO: 196) | Vl3-19*01 (SEQ ID NO: 211) |

TABLE 8b-continued

Corresponding germline sequences of two-way pairs based on NanoBiT data

| Column 1: Identifier for sequence combinations | Column 2: heavy chain polypeptide 1 (HCP1) corresponding germline | Column 3: lambda light chain polypeptide (LLCP) corresponding germline | Column 4: Identifier for sequence combinations | Column 5: heavy chain polypeptide 2 (HCP2) corresponding germline | Column 6: kappa light chain polypeptide (KLCP) corresponding germline |
|---|---|---|---|---|---|
| ID347 | VH3-66*01 (SEQ ID NO: 194) | Vk1-39*01 (SEQ ID NO: 201) | ID462 | VH1-69*01 (SEQ ID NO: 187) | Vl3-9*01 (SEQ ID NO: 212) |
| ID348 | VH3-66*01 (SEQ ID NO: 194) | Vk1-39*01 (SEQ ID NO: 201) | ID478 | VH1-2*01 (SEQ ID NO: 184) | Vl10-54*01 (SEQ ID NO: 207) |

Example 2

Figure 5:
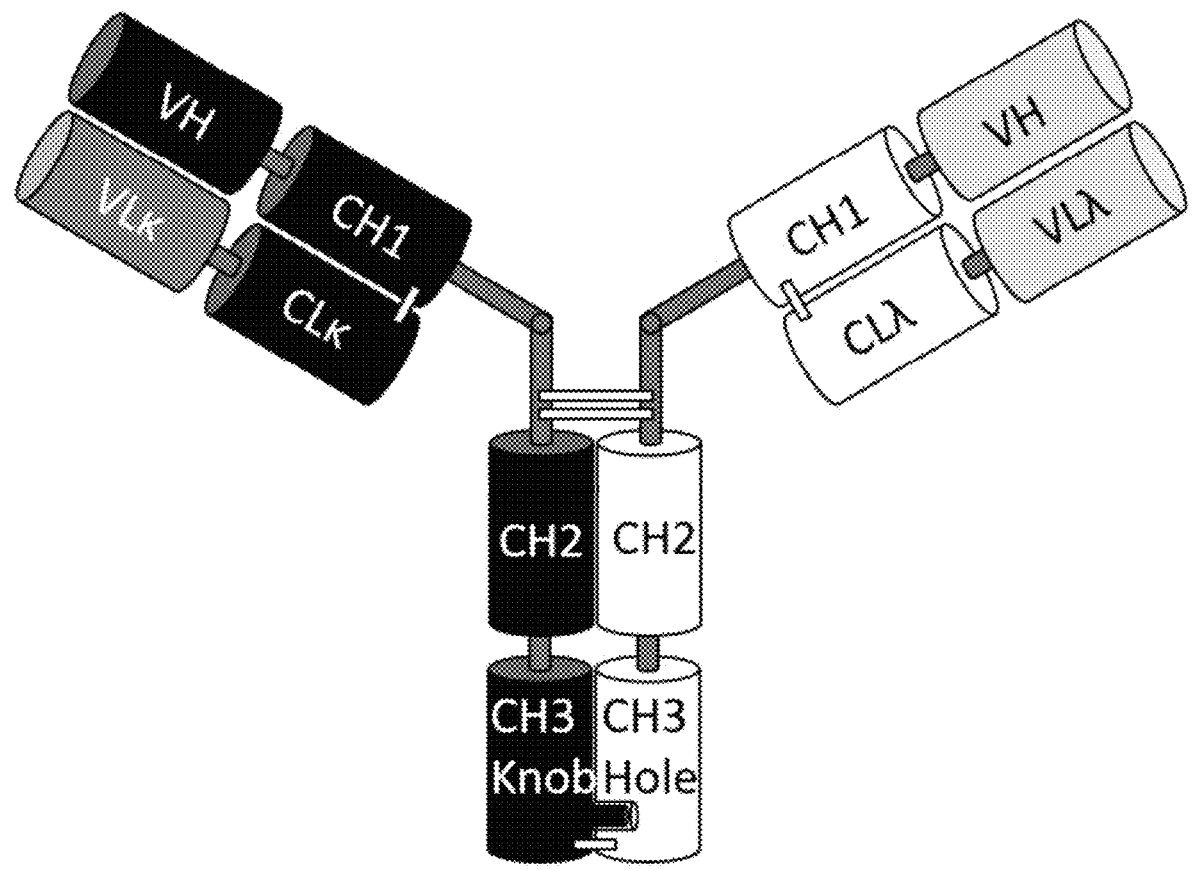
FIG. 5 depicts a schematic representation of an exemplary multispecific antibody molecule of the present invention. The multispecific antibody molecule comprises a first Fab comprising a kappa light chain polypeptide; a second Fab comprising a lambda light chain polypeptide; and an Fc domain, wherein the Fc domain contains a paired protuberance/cavity, e.g., knob and hole pair. In one embodiment, the first Fab binds to IGF1R and the second Fab binds to HER3 (e.g., multispecific molecule 1 described in Example 2). In one embodiment, the first Fab binds to mesothelin and the second Fab binds to PD-L1 (e.g., multispecific molecule 2 described in Example 3). In one embodiment, the first Fab binds to CTLA-4 and the second Fab binds to IL12β (e.g., multispecific molecule 3 described in Example 4). In one embodiment, the first Fab binds to CTLA-4 and the second Fab binds to TRAILR2 (e.g., multispecific molecule 4 described in Example 5). In one embodiment, the first Fab binds to CTLA-4 and the second Fab binds to CD221 (e.g., multispecific molecule 5 described in Example 6). In one embodiment, the first Fab binds to PD-1 and the second Fab binds to TRAILR2 (e.g., multispecific molecule 6 described in Example 7). In one embodiment, the first Fab binds to PD-1 and the second Fab binds to PDL1 (e.g., multispecific molecule 7 described in Example 8).

Multispecific molecule 1 comprises an α-IGF1R arm and an α-HER3 arm. The α-IGF1IR arm comprises a first chain of the amino acid sequence of SEQ TD NO: 179 and a second chain of the amino acid sequence of SEQ TD NO: 118. The α-HER3 arm comprises a first chain of the amino acid sequence of SEQ ID NO: 178 and a second chain of the amino acid sequence of SEQ ID NO: 145. The configuration of multispecific molecule 1 is shown in FIG. 5.

Figure 11:
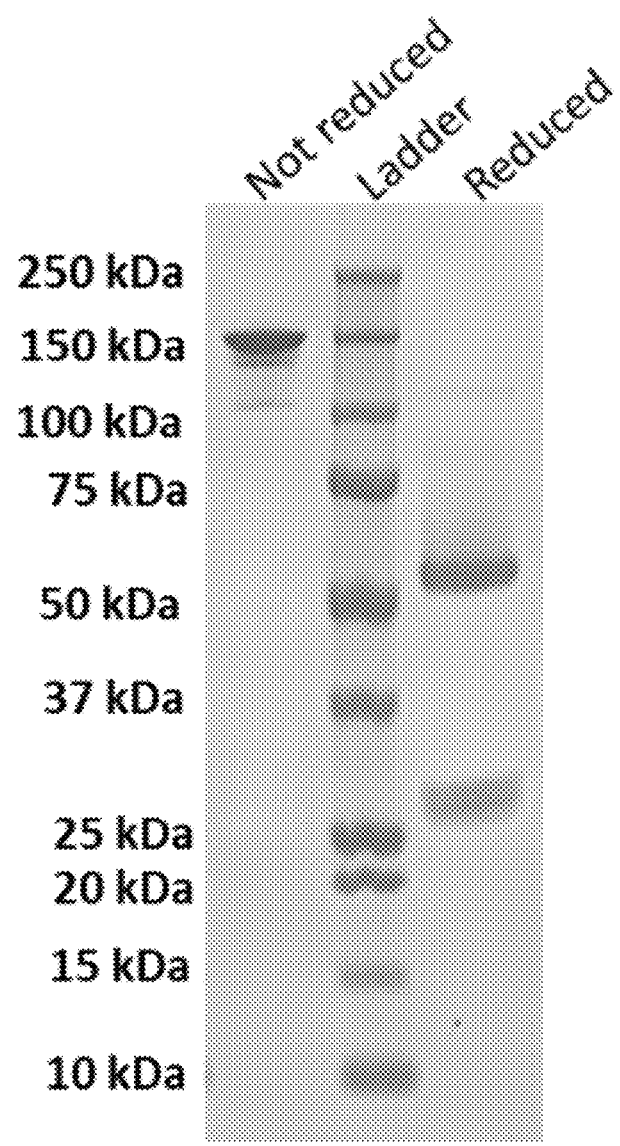
FIG. 11. Gel of multispecific molecule 1.
Figure 19:
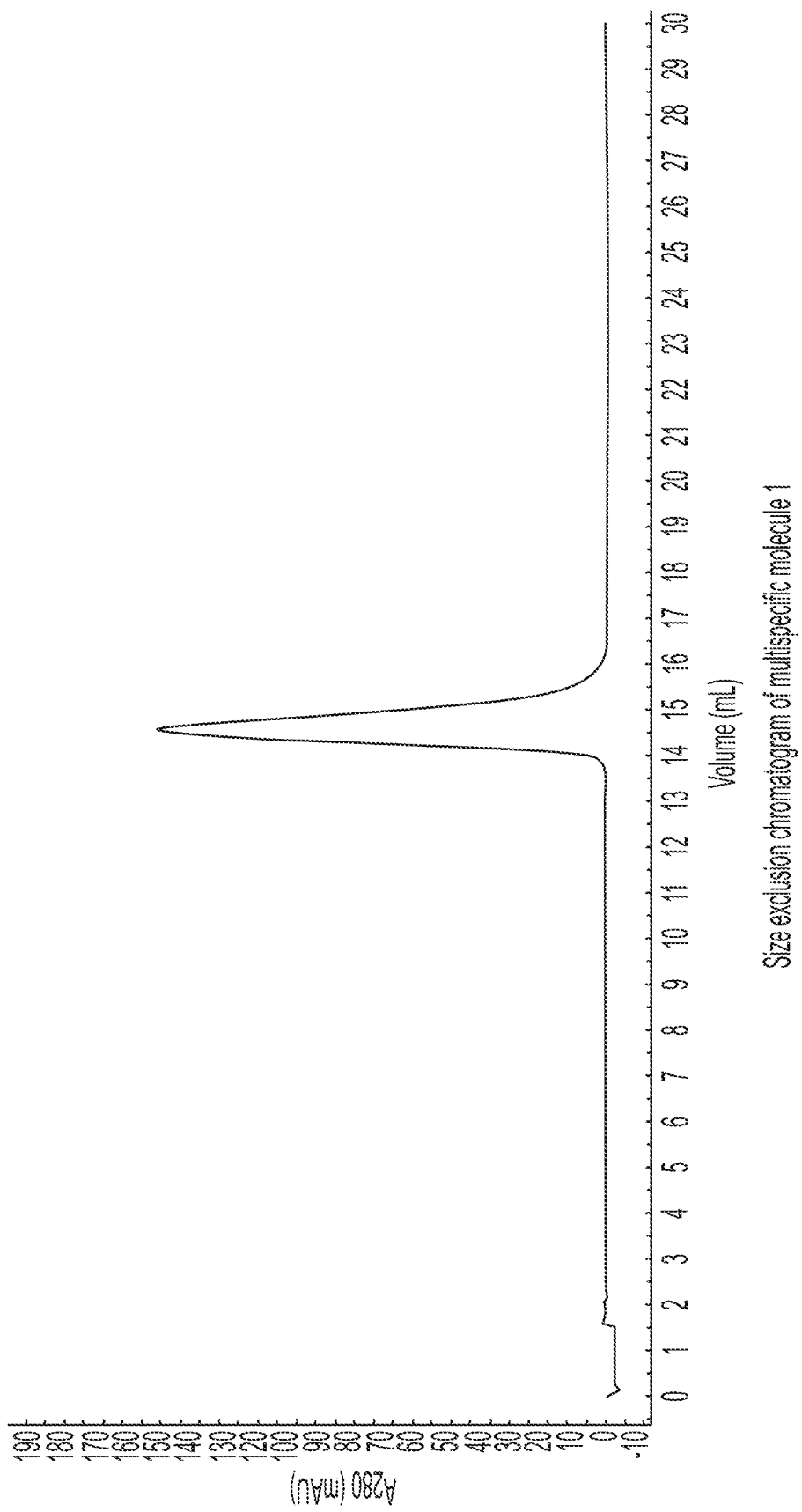
FIG. 19. Size exclusion chromatogram of multispecific molecule 1.
Figure 24:
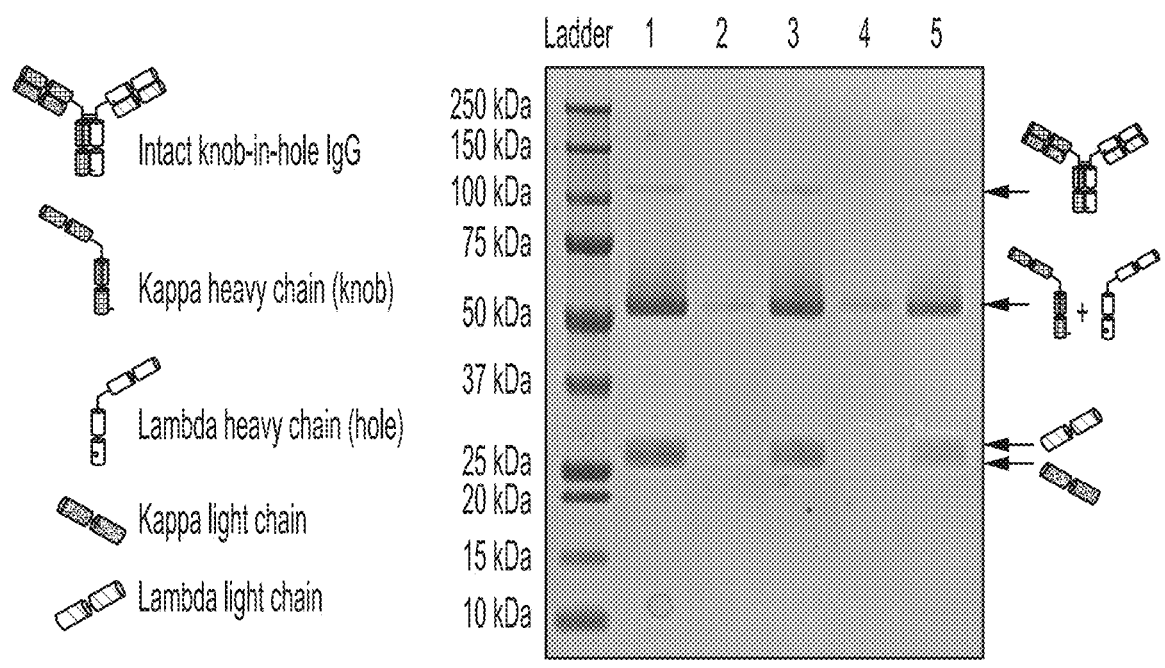
FIG. 24. Gel of reduced samples of multispecific molecule 1 following kappa/lambda select analysis. Lane 1 is the load, lane 2 is the flow-through from the KappaSelect column, lane 3 is the elution from the KappaSelect column, lane 4 is the flow-through from the LambdaFabSelect column, and lane 5 is the elution from the LambdaFabSelect column.

Multispecific molecule 1 was expressed by co-transfecting cells with expression vectors comprising polynucleotide sequences of SEQ ID NO: 86, SEQ TD NO: 54, SEQ ID NO: 87, and SEQ TD NO: 27. Multispecific molecule 1 was purified and a SDS-PAGE gel of the final product is shown in FIG. 11. FIG. 19 shows the size exclusion chromatogram of multispecific molecule 1. A KappaSelect and Lambda-FabSelect analysis was performed with multispecific molecule 1, shown in FIG. 24. The gel shows a small amount of protein in the flow-through from the KappaSelect and LambdaFab columns. The quantitative results of this analysis are shown in Table 9, giving 85% fidelity for the kappa chain and 85% fidelity for the lambda chain. These results correlate with the NanoBiT data of ID284 and ID409, which have the same Fab arms, with 84% and 90% fidelity, respectively.

TABLE 9

Results of quantitative kappa/lambda select analysis.

| Construct | Percent pairing from KappaSelect column | Percent pairing from LambdaFabSelect |
|---|---|---|
| Multispecific molecule 1 | 85 | 85 |
| Multispecific molecule 2 | 88 | 86 |

Example 3

Multispecific molecule 2 comprises an α-mesothelin arm and an α-PDL1 arm. The α-mesothelin arm comprises a first chain of the amino acid sequence of SEQ ID NO: 164 and a second chain of the amino acid sequence of SEQ ID NO: 165. The α-PDL1 arm comprises a first chain of the amino acid sequence of SEQ ID NO: 166 and a second chain of the amino acid sequence of SEQ ID NO: 167. The configuration of multispecific molecule 2 is shown in FIG. 5.

Figure 23:
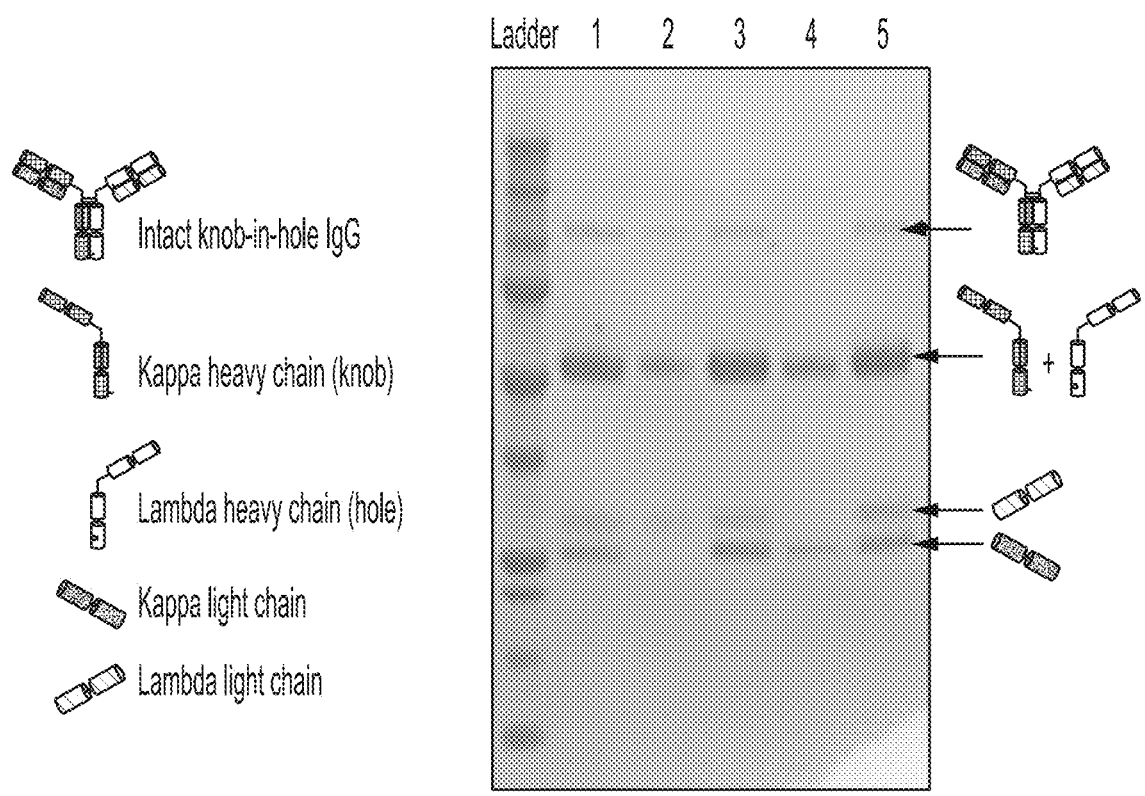
FIG. 23. Gel of reduced samples of multispecific molecule 2 following kappa/lambda select analysis. Lane 1 is the load, lane 2 is the flow-through from the KappaSelect column, lane 3 is the elution from the KappaSelect column, lane 4 is the flow-through from the LambdaFabSelect column, and lane 5 is the elution from the LambdaFabSelect column.

Multispecific molecule 2 was expressed by co-transfecting cells with expression vectors comprising polynucleotide sequences of SEQ ID NO: 82, SEQ ID NO: 83, SEQ ID NO: 84, and SEQ ID NO: 85. A KappaSelect and LambdaFab-Select analysis was performed with multispecific molecule 2, shown in FIG. 23. The gel shows a small amount of protein in the flow-through from the KappaSelect and LambdaFab columns. The quantitative results of this analysis are shown in Table 9. The fidelity for the KappaSelect column is 88% and the fidelity for the LambdaFabSelect column is 86%.

Example 4

Multispecific molecule 3 comprises an α-CTLA4 arm and an α-IL12β arm. The α-CTLA4 arm comprises a first chain of the amino acid sequence of SEQ ID NO: 168 and a second chain of the amino acid sequence of SEQ ID NO: 106. The α-IL12β arm comprises a first chain of the amino acid sequence of SEQ ID NO: 170 and a second chain of the amino acid sequence of SEQ ID NO: 163. The configuration of multispecific molecule 3 is shown in FIG. 5.

Figure 12:
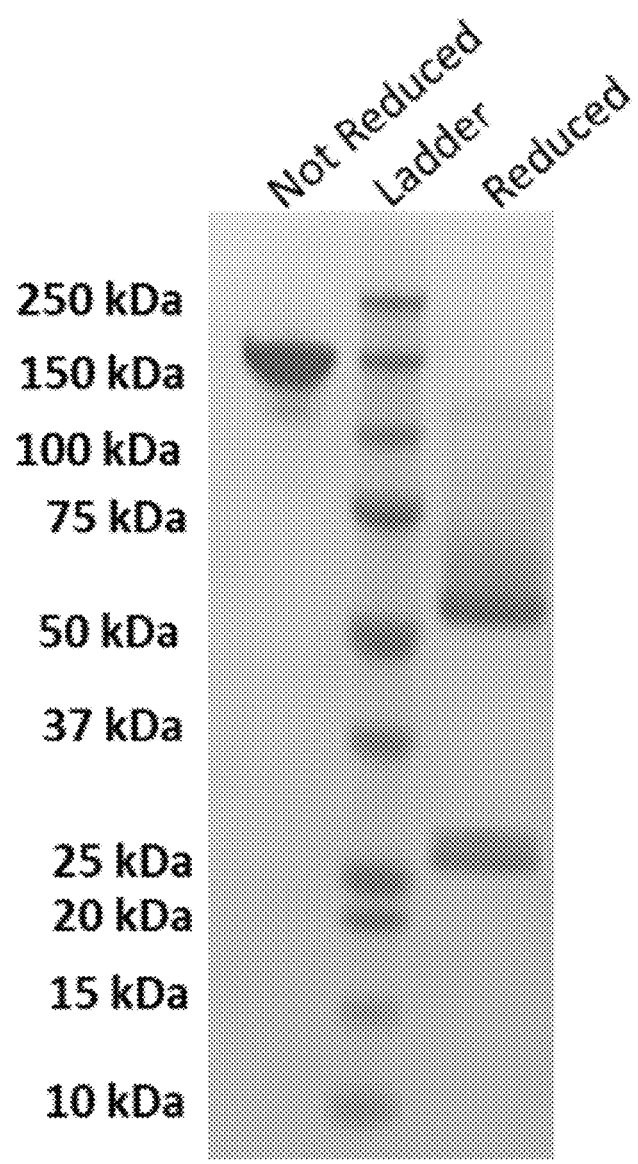
FIG. 12. Gel of multispecific molecule 3.
Figure 20:
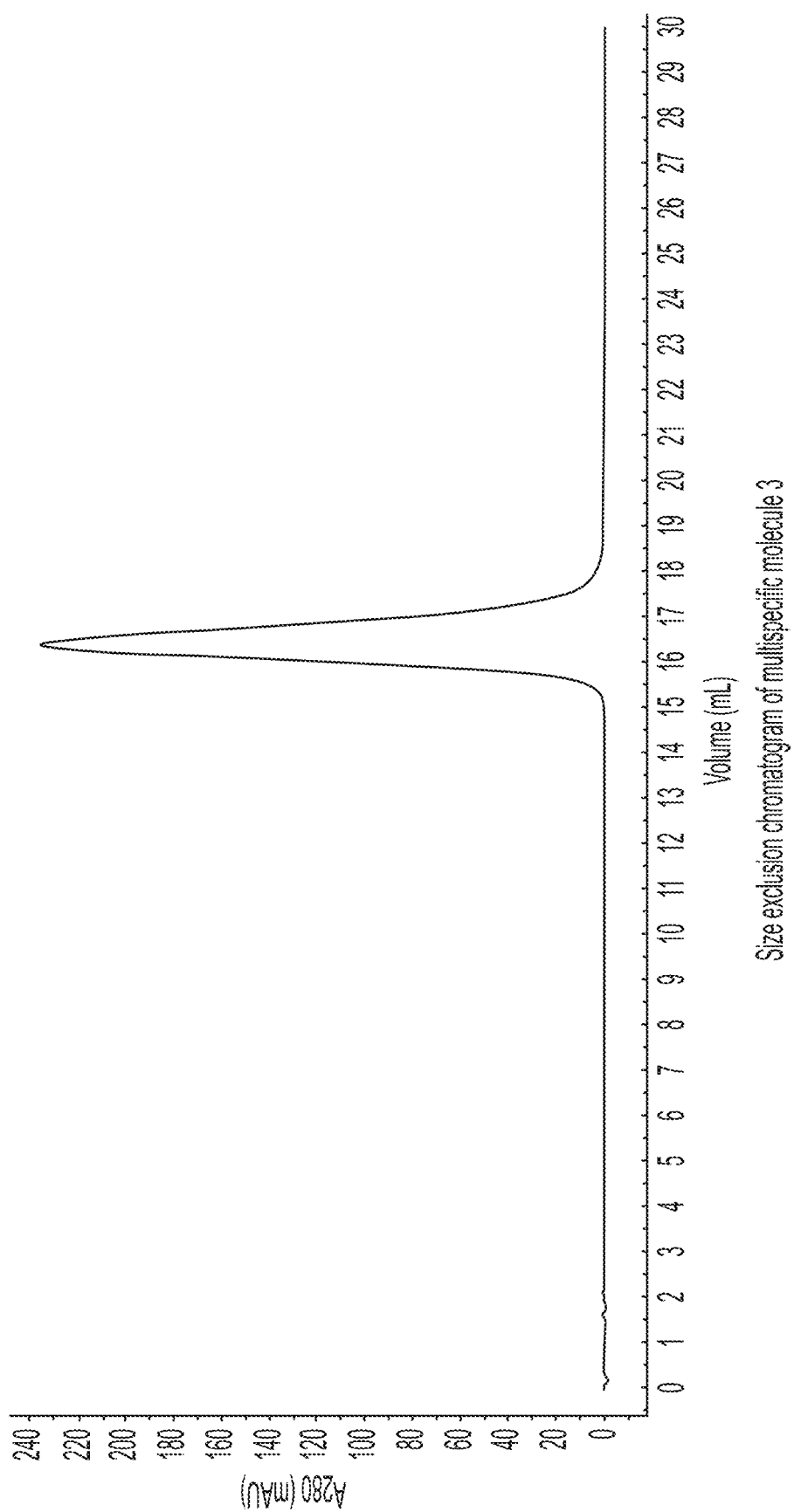
FIG. 20. Size exclusion chromatogram of multispecific molecule 3.
Figure 25:
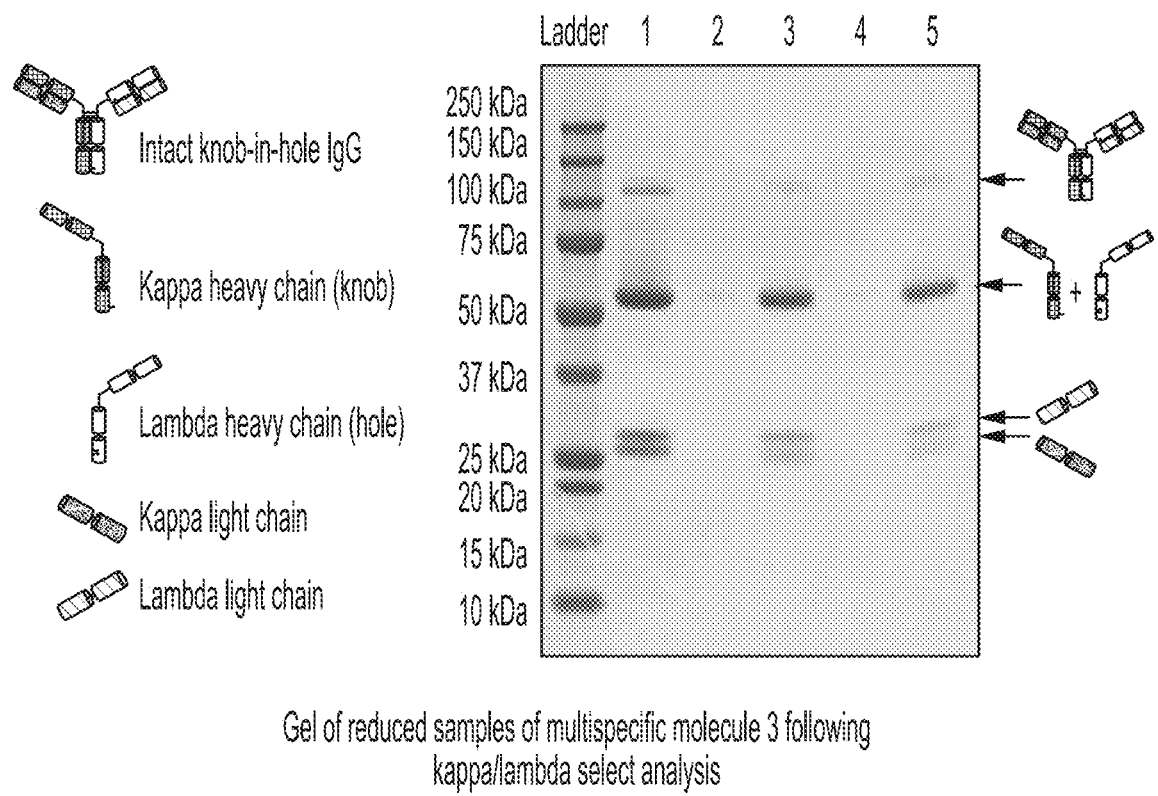
FIG. 25. Gel of reduced samples of multispecific molecule 3 following kappa/lambda select analysis. Lane 1 is the load, lane 2 is the flow-through from the KappaSelect column, lane 3 is the elution from the KappaSelect column, lane 4 is the flow-through from the LambdaFabSelect column, and lane 5 is the elution from the LambdaFabSelect column.
Figure 31:
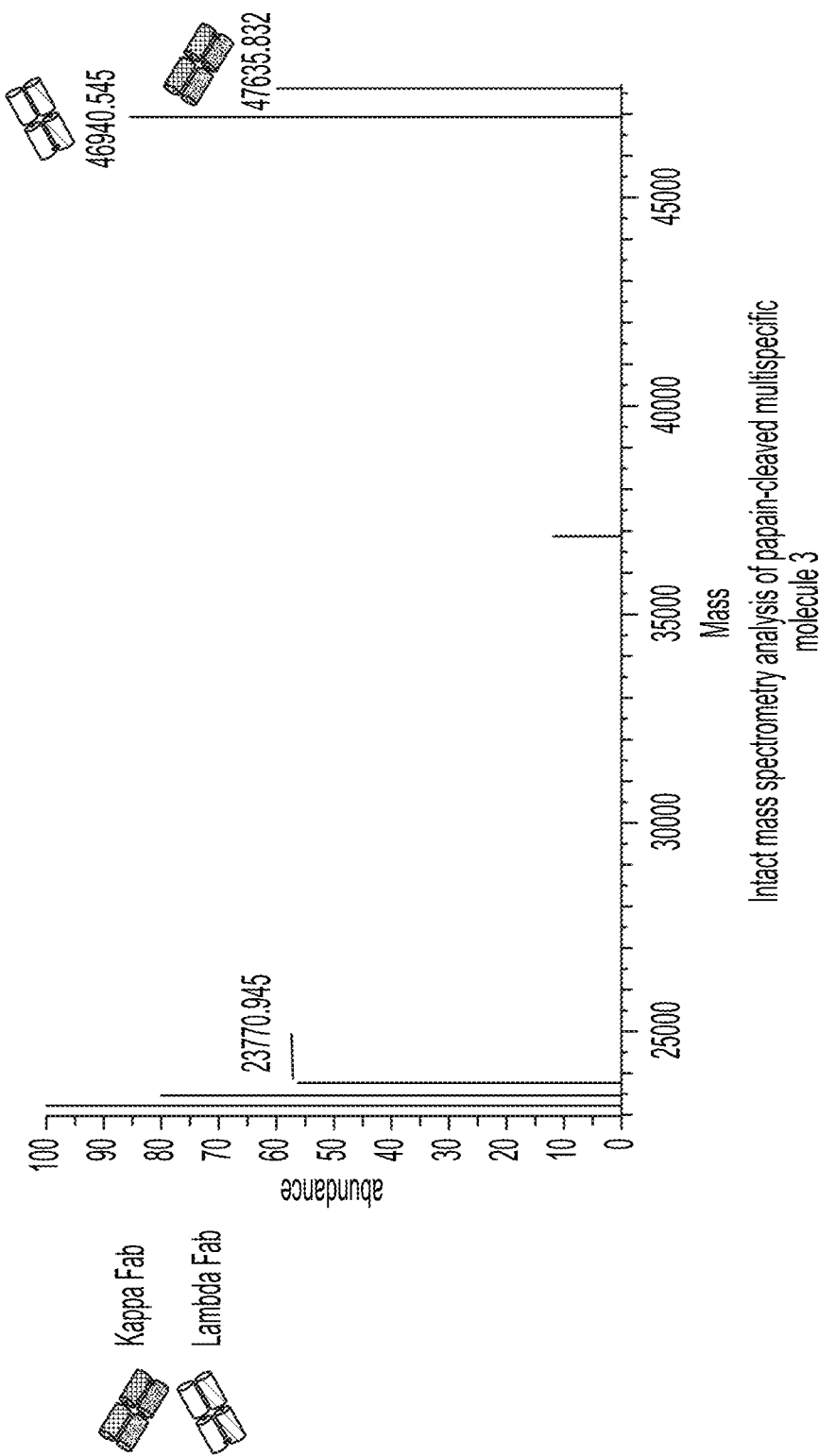
FIG. 31. Intact mass spectrometry analysis of papain-cleaved multispecific molecule 3.
Figure 32:
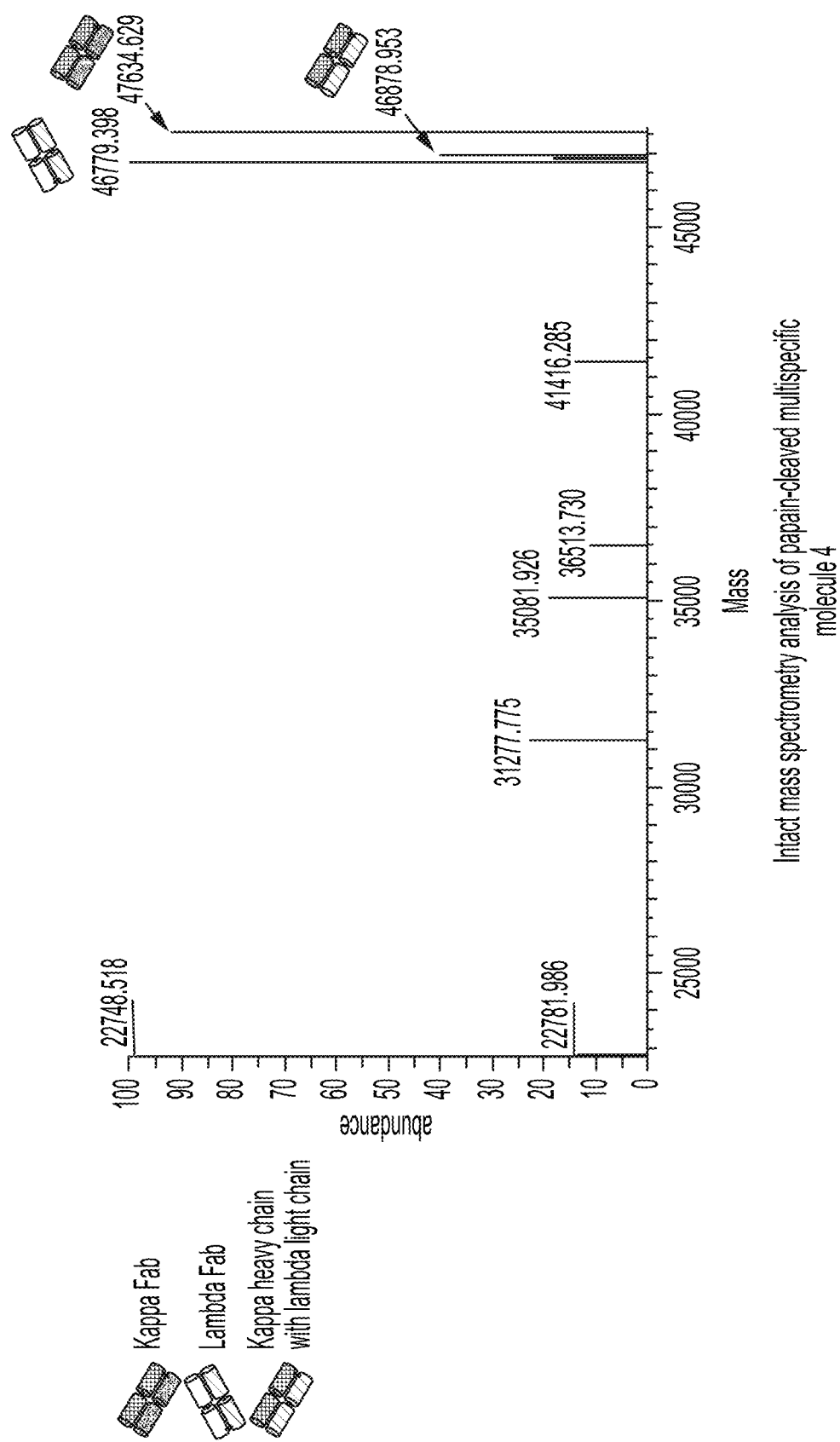
FIG. 32. Intact mass spectrometry analysis of papain-cleaved multispecific molecule 4.

Multispecific molecule 3 was expressed by co-transfecting cells with expression vectors comprising polynucleotide sequences of SEQ ID NO: 78, SEQ ID NO: 15, SEQ ID NO: 91, and SEQ ID NO: 72. Multispecific molecule 3 was purified and a SDS-PAGE gel of the final product is shown in FIG. 12. FIG. 20. shows the size exclusion chromatogram of multispecific molecule 3. A KappaSelect and Lambda-FabSelect analysis was performed with multispecific molecule 3, shown in FIG. 25. The gel shows no protein in the flow-through of the KappaSelect or LambdaFabSelect columns, suggesting correct light chain pairing. The mass spectrometry data of the papain cleavage of multispecific molecule 3 is shown in FIG. 31 and summarized in Table 10. This data only shows correctly paired Fabs, further illustrating that there is no mispairing for these kappa and lambda chains. These results also correlate with the Nano-BiT data of ID242 and ID501, which have the same Fab arms, and both showed 100% chain fidelity.

TABLE 10

Mass spectrometry results for multispecific molecule 3.

| Fab Pairing | Predicted Mass (Da) | Observed Mass (Da) |
|---|---|---|
| Kappa heavy chain/kappa light chain | 47652.9 | 47634.9 |
| Kappa heavy chain/lambda light chain | 47390.4 | N/A |
| Lambda heavy chain/lambda light chain | 46974.6 | 46940.4 |
| Lambda heavy chain/kappa light chain | 47237.2 | N/A |

Example 5

Multispecific molecule 4 comprises an α-CTLA4 arm and an α-TRAILR2 arm. The α-CTLA4 arm comprises a first chain of the amino acid sequence of SEQ ID NO: 168 and a second chain of the amino acid sequence of SEQ ID NO: 106. The α-TRAILR2 arm comprises a first chain of the amino acid sequence of SEQ ID NO: 177 and a second chain of the amino acid sequence of SEQ ID NO: 148. The configuration of multispecific molecule 4 is shown in FIG. 5.

Figure 13:
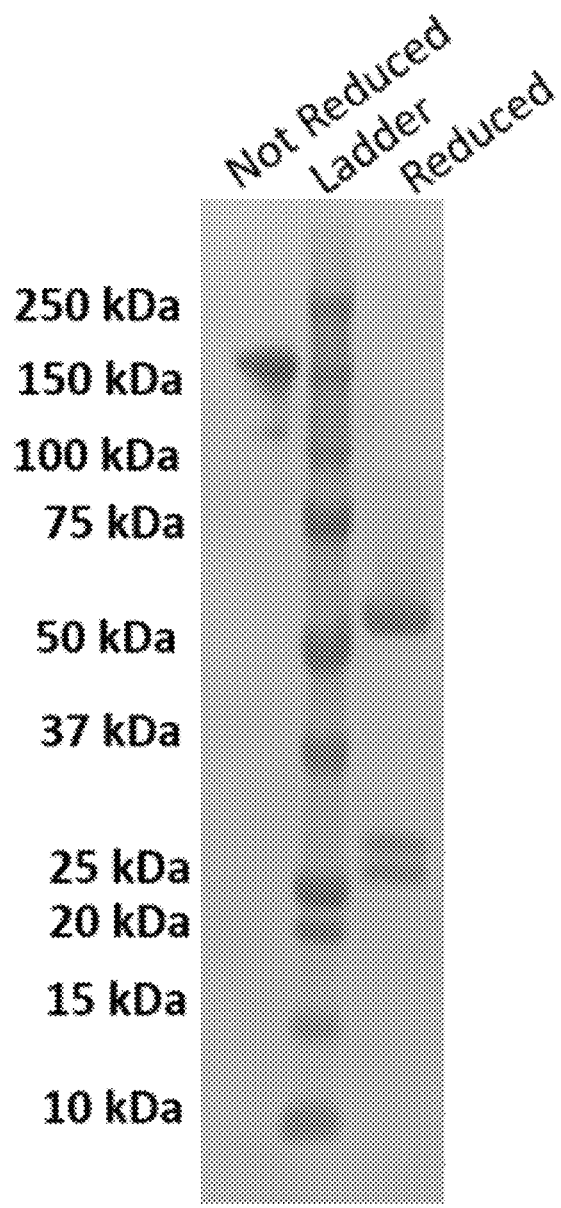
FIG. 13. Gel of multispecific molecule 4.

Multispecific molecule 4 was expressed by co-transfecting cells with expression vectors comprising polynucleotide sequences of SEQ ID NO: 78, SEQ ID NO: 15, SEQ ID NO: 81, and SEQ ID NO: 57. Multispecific molecule 4 was purified and a SDS-PAGE gel of the final product is shown in FIG. 13. The mass spectrometry data of the papain cleavage of multispecific molecule 4 is shown in FIG. 31 and summarized in Table 11. This data shows one incorrect Fab pairing where the kappa heavy chain is paired with the lambda light chain. This correlates with the NanoBiT data of ID237 and ID421, which have the same Fab arms as multispecific molecule 4, where chain fidelity is seen in one direction: the lambda heavy chain with the competing kappa light chain.

TABLE 11

Mass spectrometry results for multispecific molecule 4.

| Fab Pairing | Predicted Mass (Da) | Observed Mass (Da) |
|---|---|---|
| Kappa heavy chain/kappa light chain | 47634.9 | 47634.6 |
| Kappa heavy chain/lambda light chain | 46880.4 | 46879.0 |
| Lambda heavy chain/lambda light chain | 46779.2 | 46779.4 |
| Lambda heavy chain/kappa light chain | 47481.7 | N/A |

Example 6

Multispecific molecule 5 comprises an α-CTLA4 arm and an α-CD221 arm. The α-CTLA4 arm comprises a first chain of the amino acid sequence of SEQ ID NO: 168 and a second chain of the amino acid sequence of SEQ ID NO: 106. The α-TRAILR2 arm comprises a first chain of the amino acid sequence of SEQ ID NO: 180 and a second chain of the amino acid sequence of SEQ ID NO: 136. The configuration of multispecific molecule 5 is shown in FIG. 5.

Figure 14:
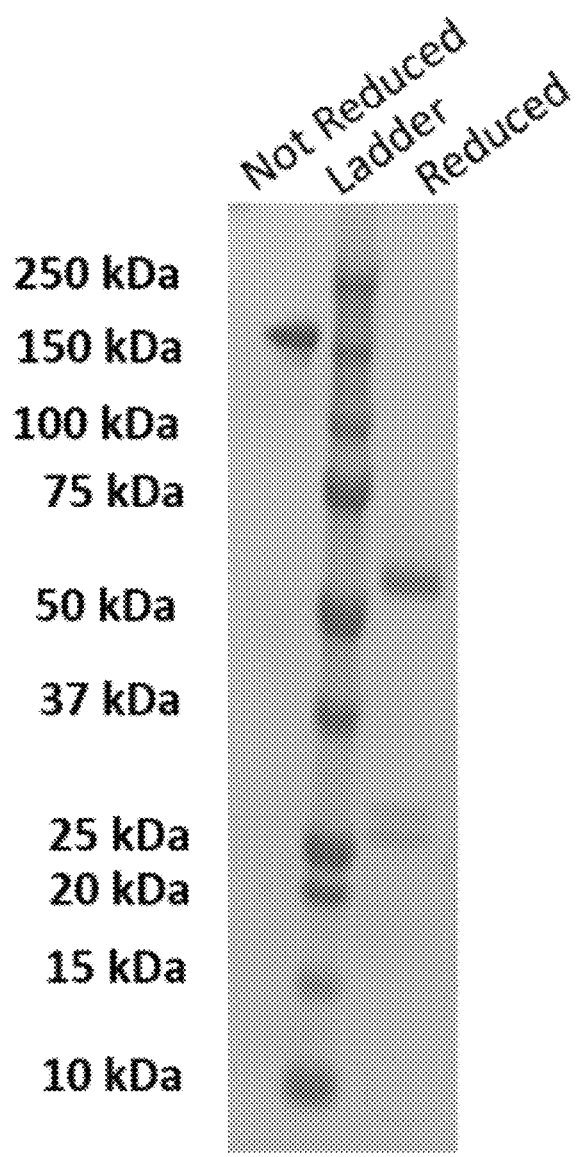
FIG. 14. Gel of multispecific molecule 5.
Figure 33:
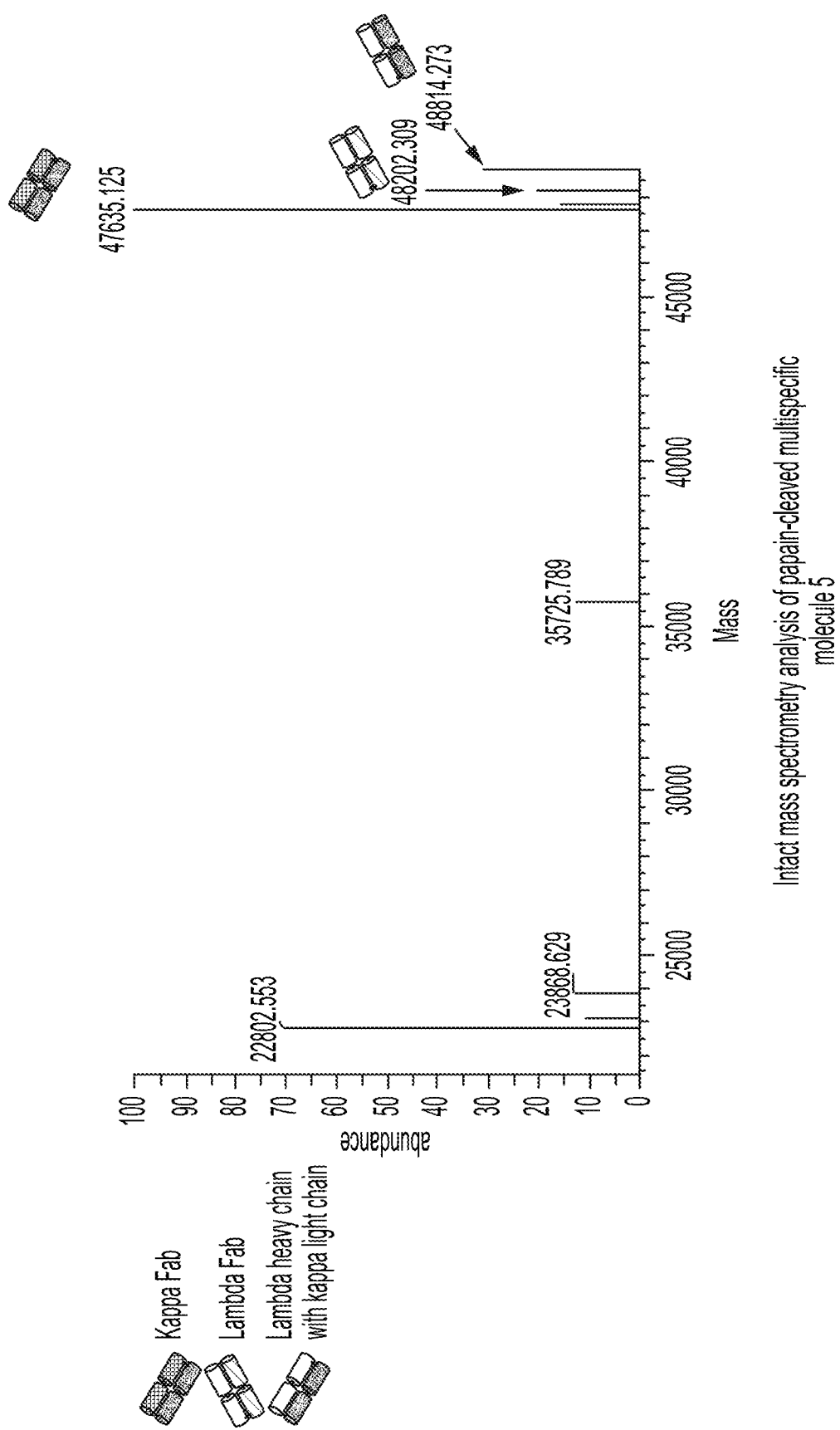
FIG. 33. Intact mass spectrometry analysis of papain-cleaved multispecific molecule 5.

Multispecific molecule 5 was expressed by co-transfecting cells with expression vectors comprising polynucleotide sequences of SEQ ID NO: 78, SEQ ID NO: 15, SEQ ID NO: 88, and SEQ ID NO: 45. Multispecific molecule 5 was purified and a SDS-PAGE gel of the final product is shown in FIG. 14. The mass spectrometry data of the papain cleavage of multispecific molecule 5 is shown in FIG. 33 and summarized in Table 12, where there is one incorrect Fab pairing with the lambda heavy chain paired with the kappa light chain.

TABLE 12

Mass spectrometry results for multispecific molecule 5.

| Fab Pairing | Predicted Mass (Da) | Observed Mass (Da) |
|---|---|---|
| Kappa heavy chain/kappa light chain | 47634.9 | 47635.1 |
| Kappa heavy chain/lambda light chain | 47652.9 | N/A |
| Lambda heavy chain/lambda light chain | 48205.1 | 48202.3 |
| Lambda heavy chain/kappa light chain | 48817.2 | 48814.3 |

Example 7

Multispecific molecule 6 comprises an α-PD1 arm and an α-TRAILR2 arm. The α-PD1 arm comprises a first chain of the amino acid sequence of SEQ ID NO: 181 and a second chain of the amino acid sequence of SEQ ID NO: 182. The α-TRAILR2 arm comprises a first chain of the amino acid sequence of SEQ ID NO: 177 and a second chain of the amino acid sequence of SEQ ID NO: 148. The configuration of multispecific molecule 6 is shown in FIG. 5.

Figure 15:
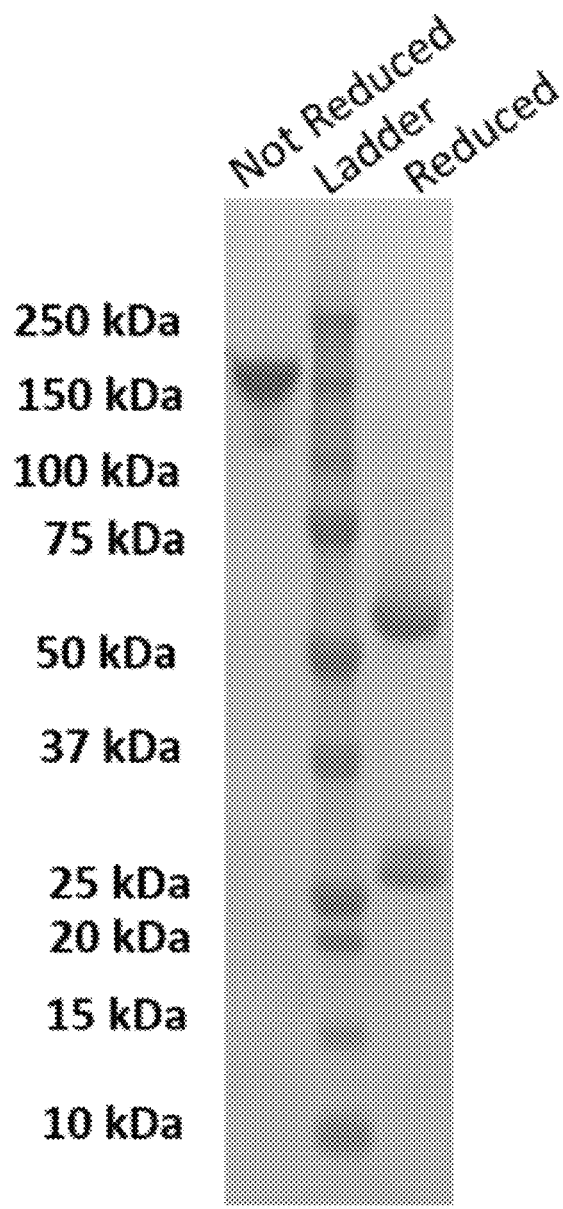
FIG. 15. Gel of multispecific molecule 6.
Figure 34:
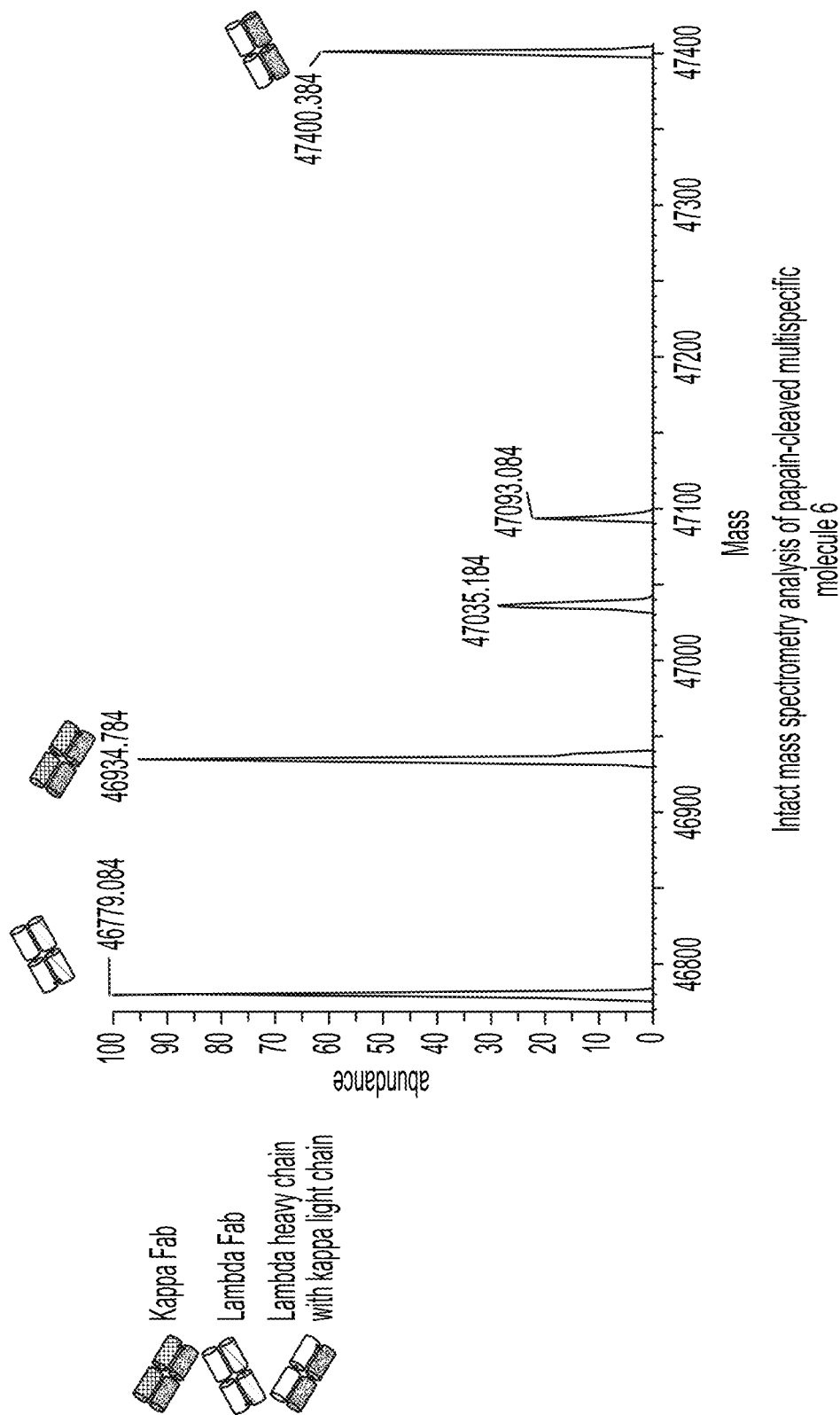
FIG. 34. Intact mass spectrometry analysis of papain-cleaved multispecific molecule 6.

Multispecific molecule 6 was expressed by co-transfecting cells with expression vectors comprising polynucleotide sequences of SEQ ID NO: 89, SEQ ID NO: 90, SEQ ID NO: 81, and SEQ ID NO: 57. Multispecific molecule 6 was purified and a SDS-PAGE gel of the final product is shown in FIG. 15. The mass spectrometry data of the papain cleavage of multispecific molecule 6 is shown in FIG. 34 and summarized in Table 13, where there is one incorrect Fab pairing with the lambda heavy chain paired with the kappa light chain.

TABLE 13

Mass spectrometry results for multispecific molecule 6.

| Fab Pairing | Predicted Mass (Da) | Observed Mass (Da) |
| --- | --- | --- |
| Kappa heavy chain/kappa light chain | 46933.9 | 46934.8 |
| Kappa heavy chain/lambda light chain | 46329.6 | N/A |
| Lambda heavy chain/lambda light chain | 46779.2 | 46779.0 |
| Lambda heavy chain/kappa light chain | 47400.5 | 47400.4 |

Example 8

Multispecific molecule 7 comprises an α-PD1 arm and an α-PDL1 arm. The α-PD1 arm comprises a first chain of the amino acid sequence of SEQ ID NO: 181 and a second chain of the amino acid sequence of SEQ ID NO: 182. The α-PDL1 arm comprises a first chain of the amino acid sequence of SEQ ID NO: 166 and a second chain of the amino acid sequence of SEQ ID NO: 167. The configuration of multispecific molecule 7 is shown in FIG. 5.

Figure 16:
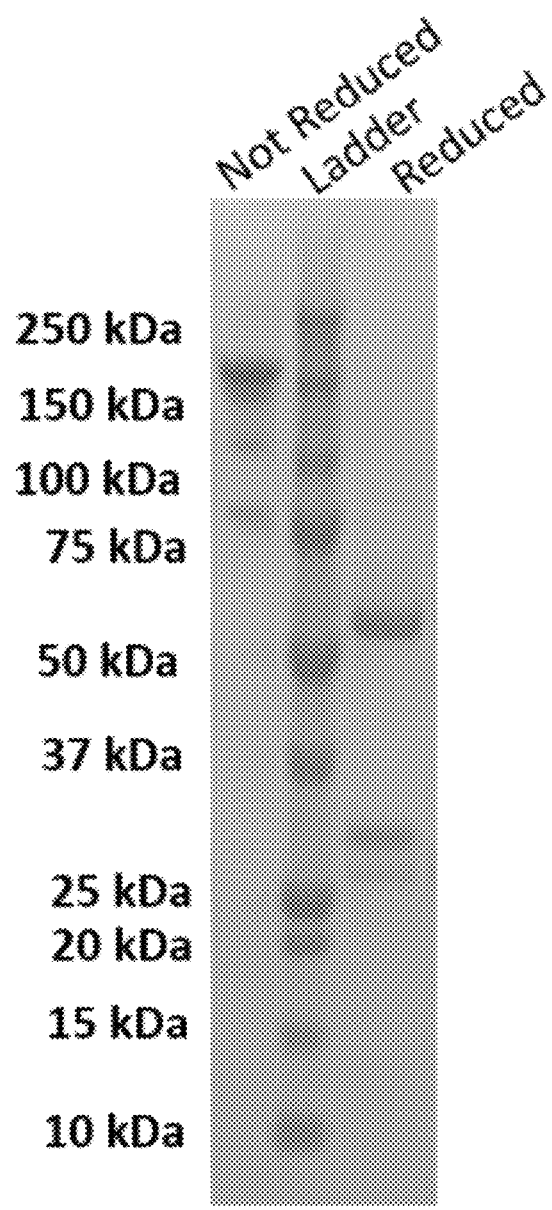
FIG. 16. Gel of multispecific molecule 7.
Figure 35:
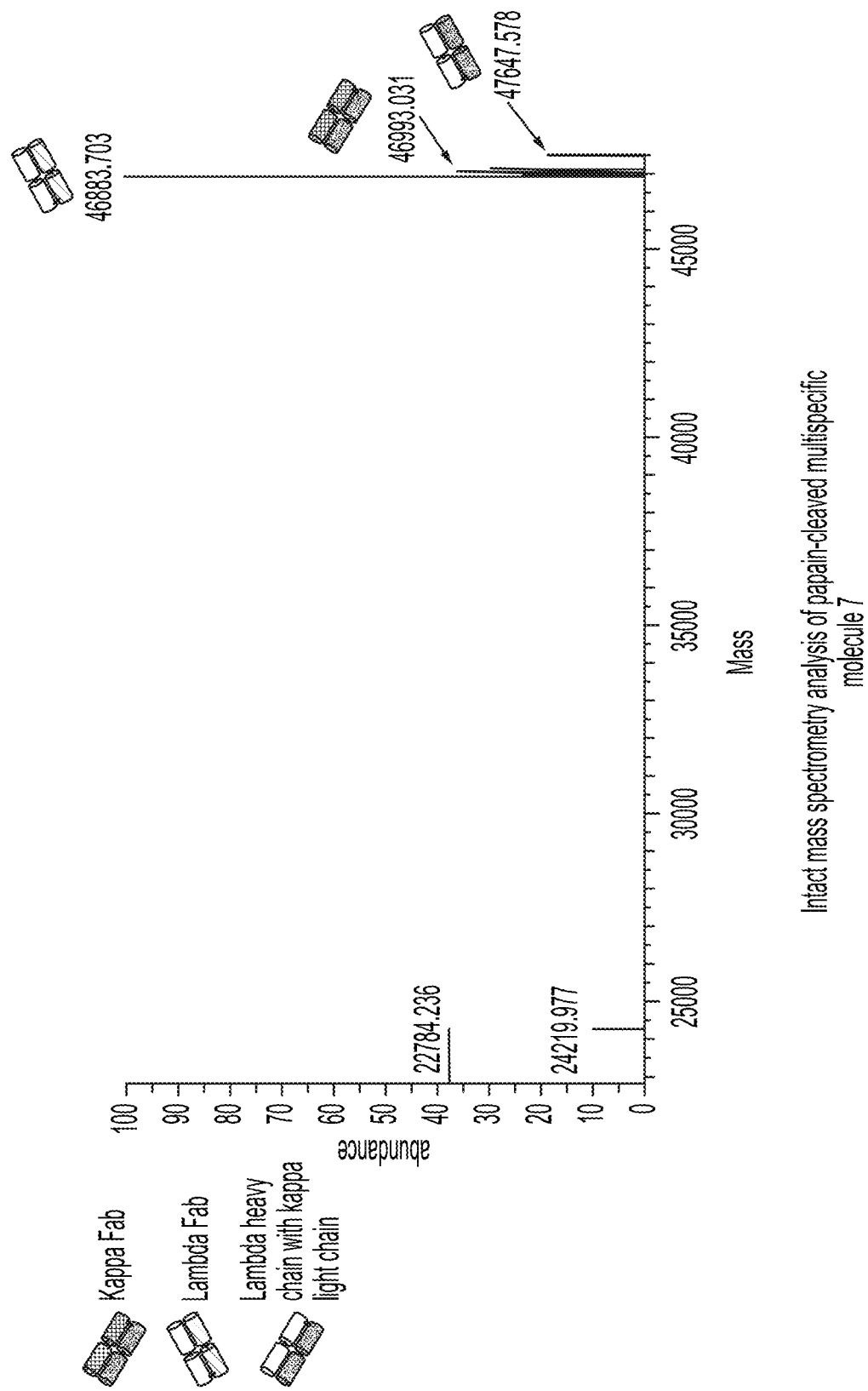
FIG. 35. Intact mass spectrometry analysis of papain-cleaved multispecific molecule 7.

Multispecific molecule 7 was expressed by co-transfecting cells with expression vectors comprising polynucleotide sequences of SEQ ID NO: 89, SEQ ID NO: 90, SEQ ID NO: 84, and SEQ ID NO: 85. Multispecific molecule 7 was purified and a SDS-PAGE gel of the final product is shown in FIG. 16. The mass spectrometry data of the papain cleavage of multispecific molecule 7 is shown in FIG. 35 and summarized in Table 14, where there is one incorrect Fab pairing with the lambda heavy chain paired with the kappa light chain.

TABLE 14

Mass spectrometry results for multispecific molecule 7.

| Fab Pairing | Predicted Mass (Da) | Observed Mass (Da) |
| --- | --- | --- |
| Kappa heavy chain/kappa light chain | 46933.9 | 46933.0 |
| Kappa heavy chain/lambda light chain | 46382.56 | N/A |
| Lambda heavy chain/lambda light chain | 46882.7 | 46883.7 |
| Lambda heavy chain/kappa light chain | 47469.0 | 47467.6 |

Example 9

Figure 7:
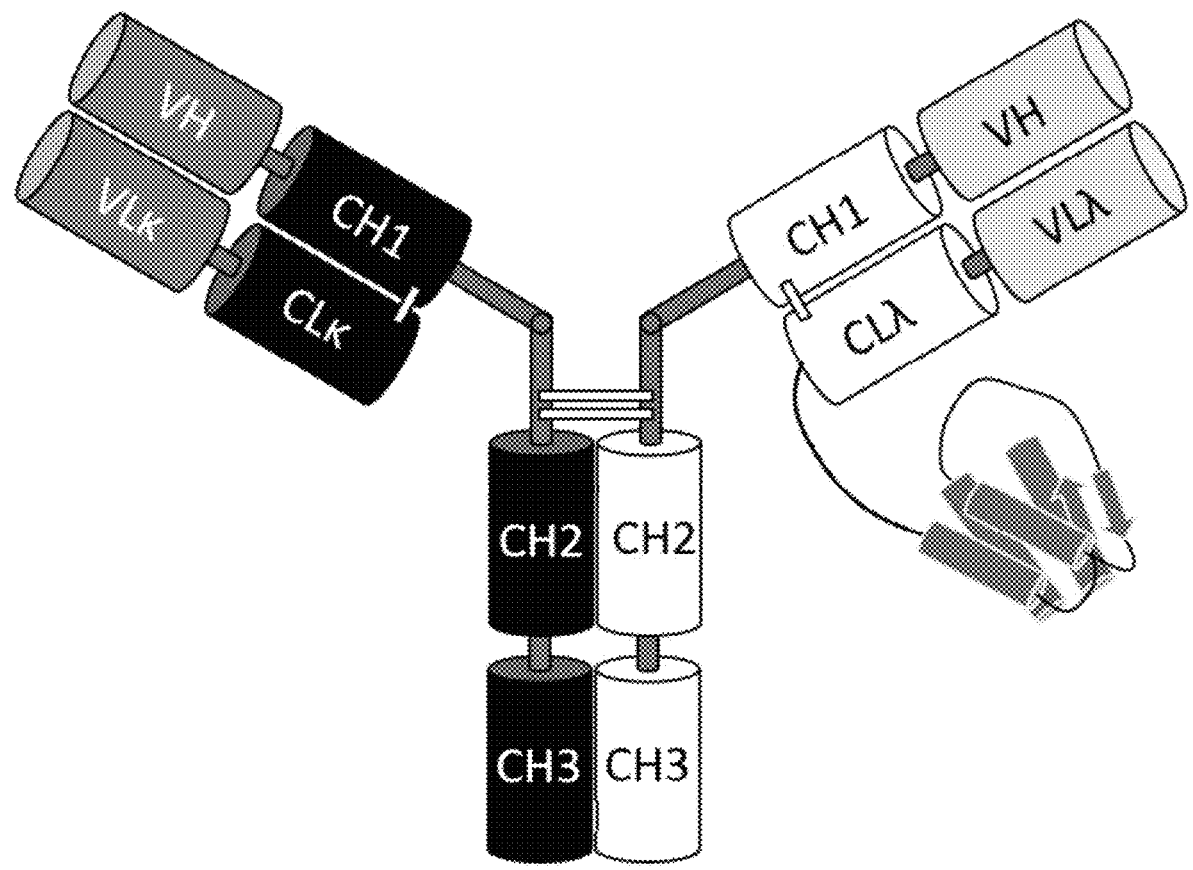
FIG. 7 depicts a schematic representation of an exemplary multispecific antibody molecule of the present invention. The multispecific antibody molecule comprises a first Fab comprising a kappa light chain polypeptide; a second Fab comprising a lambda light chain polypeptide; a polypeptide attached to the C terminus of the lambda light chain polypeptide; and an Fc domain, wherein the Fc domain does not contain a paired protuberance/cavity, e.g., knob and hole pair (e.g., the Fc domain is a naturally existing Fc domain). In one embodiment, the first Fab binds to CTLA4, the second Fab binds to IL12β, and the polypeptide that is attached to the C terminus of the lambda light chain polypeptide comprises interleukin 2, or fragment or variant thereof (e.g., multispecific molecule 8 described in Example 9).

Multispecific molecule 8 comprises an α-CTLA4 arm, an α-IL12β arm, and an IL-2 polypeptide. The IL-2 polypeptide is fused to the C-terminus of the lambda light chain of the α-IL12β arm. The α-CTLA4 arm comprises a first chain of the amino acid sequence of SEQ ID NO: 171 and a second chain of the amino acid sequence of SEQ ID NO: 106. The α-IL12β arm, together with the fused IL-2 polypeptide, comprises a first chain of the amino acid sequence of SEQ ID NO: 172 and a second chain of the amino acid sequence of SEQ ID NO: 173. The two heavy chains of multispecific molecule 8 do not comprise the knobs-into-holes mutations. The configuration of multispecific molecule 8 is shown in FIG. 7.

Figure 17:
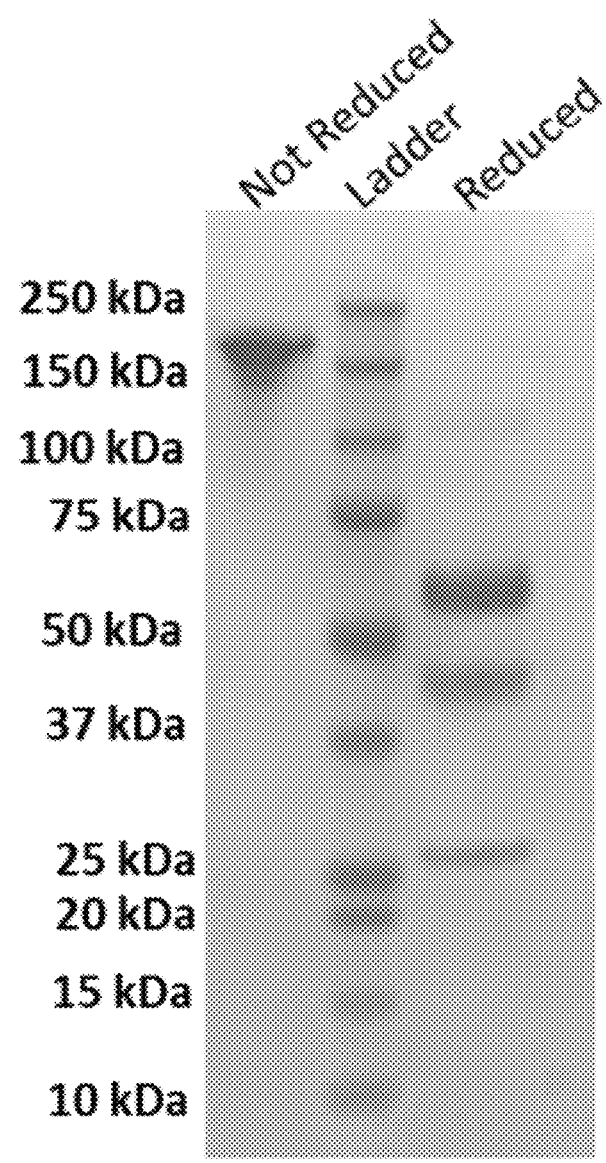
FIG. 17. Gel of multispecific molecule 8.
Figure 21:
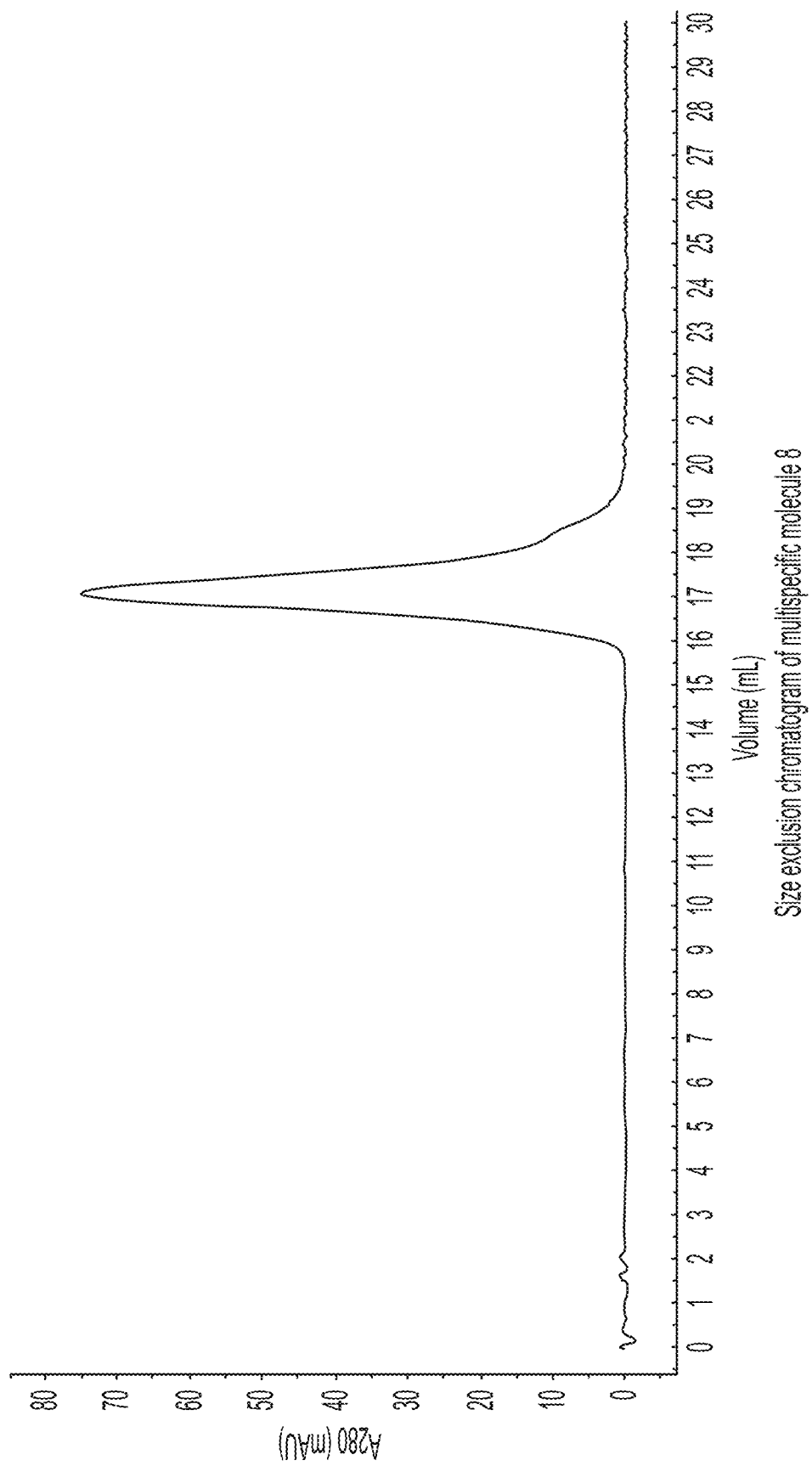
FIG. 21. Size exclusion chromatogram of multispecific molecule 8.
Figure 26:
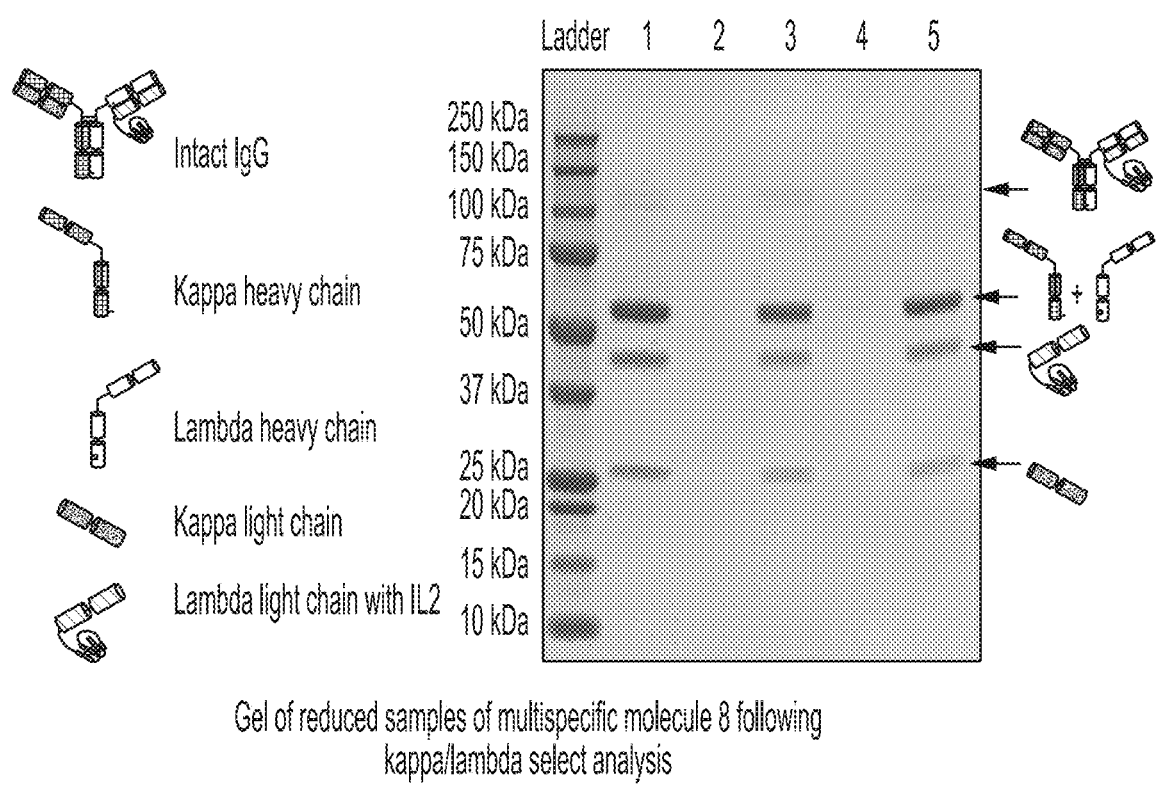
FIG. 26. Gel of reduced samples of multispecific molecule 8 following kappa/lambda select analysis. Lane 1 is the load, lane 2 is the flow-through from the KappaSelect column, lane 3 is the elution from the KappaSelect column, lane 4 is the flow-through from the LambdaFabSelect column, and lane 5 is the elution from the LambdaFabSelect column.

Multispecific molecule 8 was expressed by co-transfecting cells with expression vectors comprising polynucleotide sequences of SEQ ID NO: 73, SEQ ID NO: 15, SEQ ID NO: 74, and SEQ ID NO: 75. Multispecific molecule 8 was purified and a SDS-PAGE gel of the final product is shown in FIG. 17. FIG. 21 shows the size exclusion chromatogram of multispecific molecule 8. A KappaSelect and LambdaFabSelect analysis was performed with multispecific molecule 8, shown in FIG. 26. Both the KappaSelect and LambdaFabSelect flow-through fractions contained no protein, suggesting good chain fidelity.

Example 10

Figure 6:
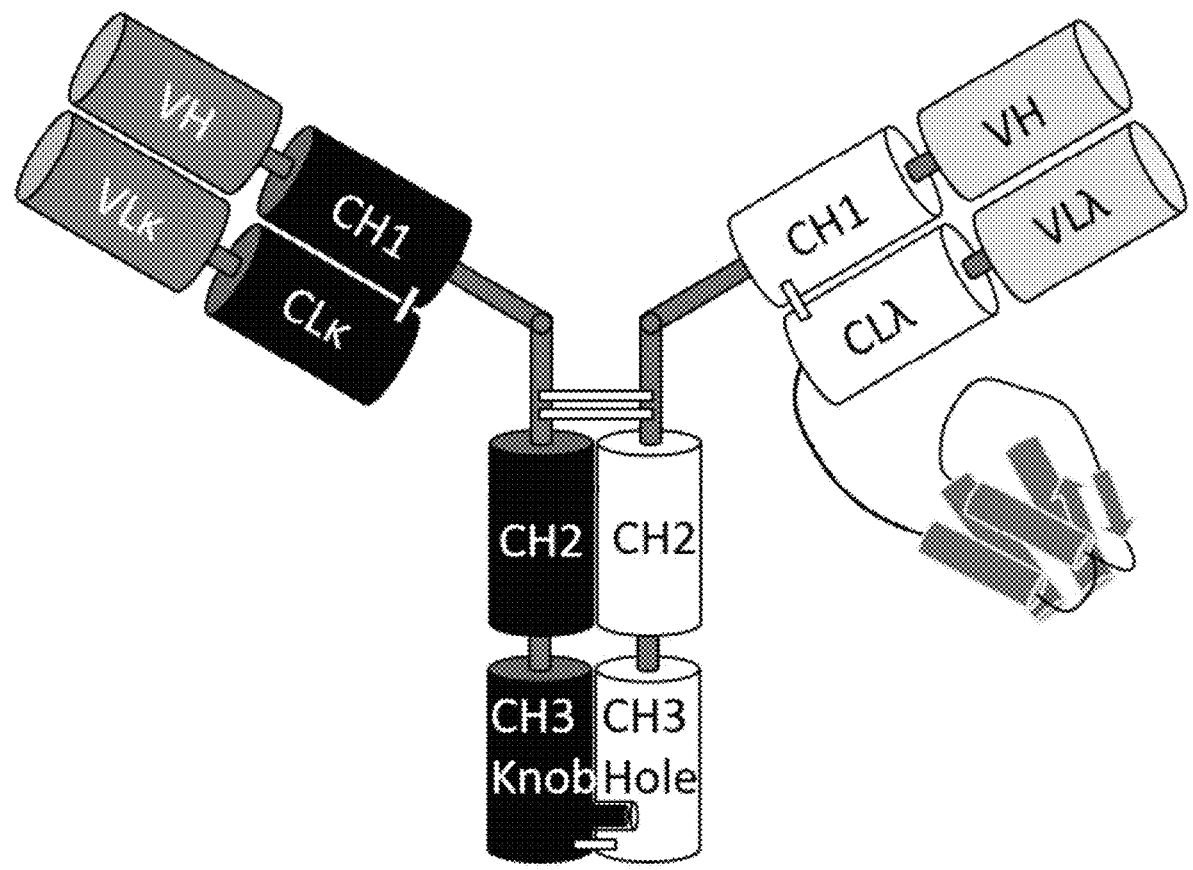
FIG. 6 depicts a schematic representation of an exemplary multispecific antibody molecule of the present invention. The multispecific antibody molecule comprises a first Fab comprising a kappa light chain polypeptide; a second Fab comprising a lambda light chain polypeptide; a polypeptide attached to the C terminus of the lambda light chain polypeptide; and an Fc domain, wherein the Fc domain contains a paired protuberance/cavity, e.g., knob and hole pair. In one embodiment, the first Fab binds to CTLA4, the second Fab binds to IL12β, and the polypeptide that is attached to the C terminus of the lambda light chain polypeptide comprises interleukin 2, or fragment or variant thereof (e.g., multispecific molecule 9 described in Example 10).

Multispecific molecule 9 comprises an α-CTLA4 arm, an α-IL12β arm, and an IL-2 polypeptide. The IL-2 polypeptide is fused to the C-terminus of the lambda light chain of the α-IL12β arm. The α-CTLA4 arm comprises a first chain of the amino acid sequence of SEQ ID NO: 168 and a second chain of the amino acid sequence of SEQ ID NO: 106. The α-IL12β arm, together with the fused IL-2 polypeptide, comprises a first chain of the amino acid sequence of SEQ ID NO: 170 and a second chain of the amino acid sequence of SEQ ID NO: 173. Different from multispecific molecule 8, the two heavy chains of multispecific molecule 9 comprise the knobs-into-holes mutations. The configuration of multispecific molecule 9 is shown in FIG. 6.

Figure 18:
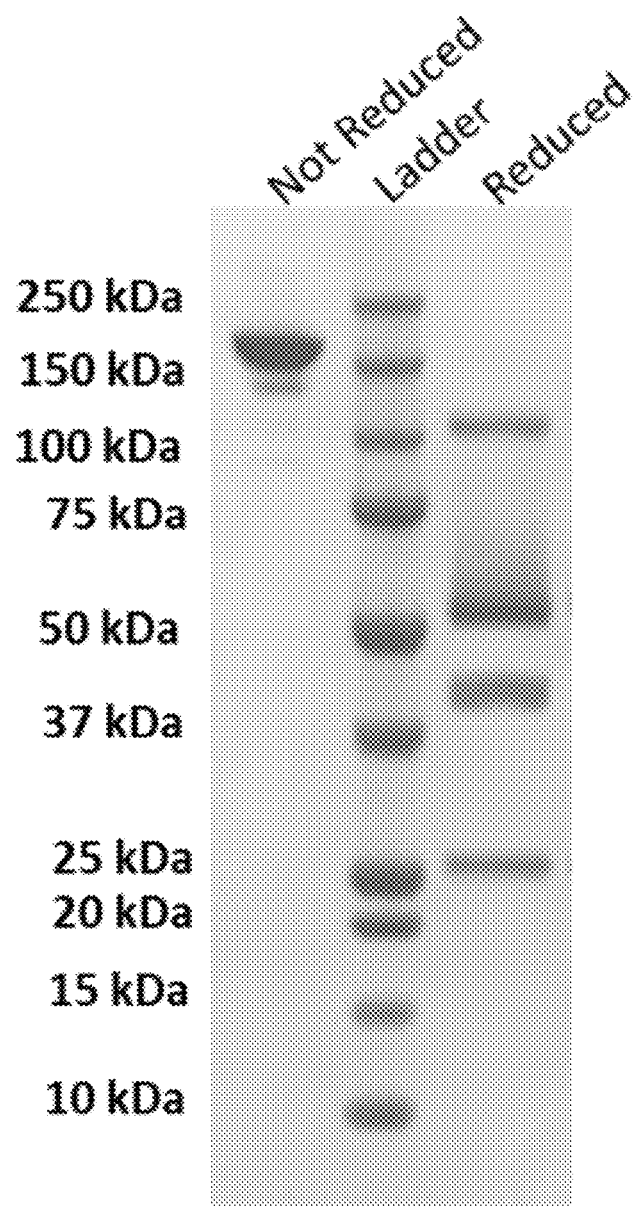
FIG. 18. Gel of multispecific molecule 9.
Figure 22:
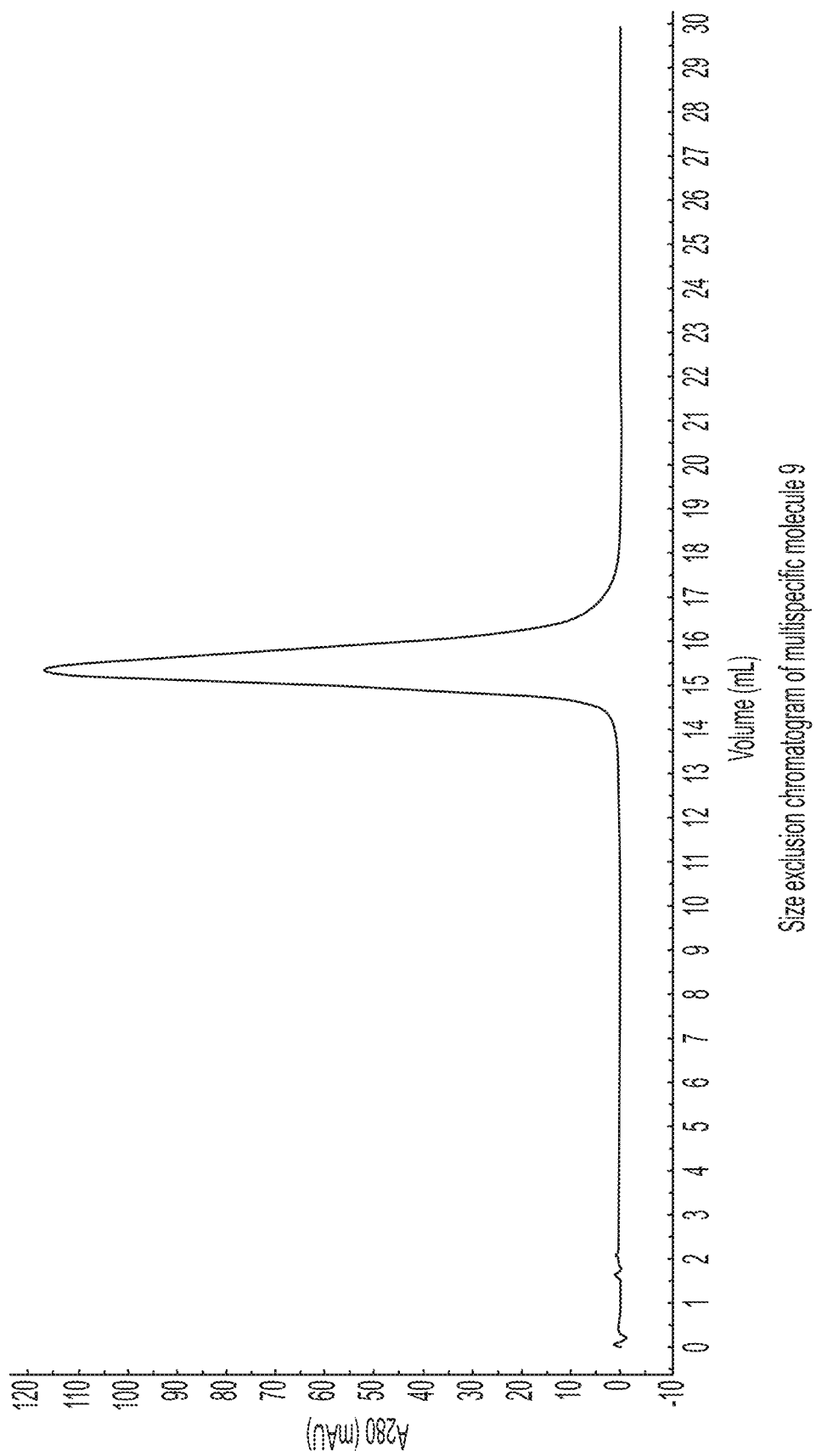
FIG. 22. Size exclusion chromatogram of multispecific molecule 9.
Figure 27:
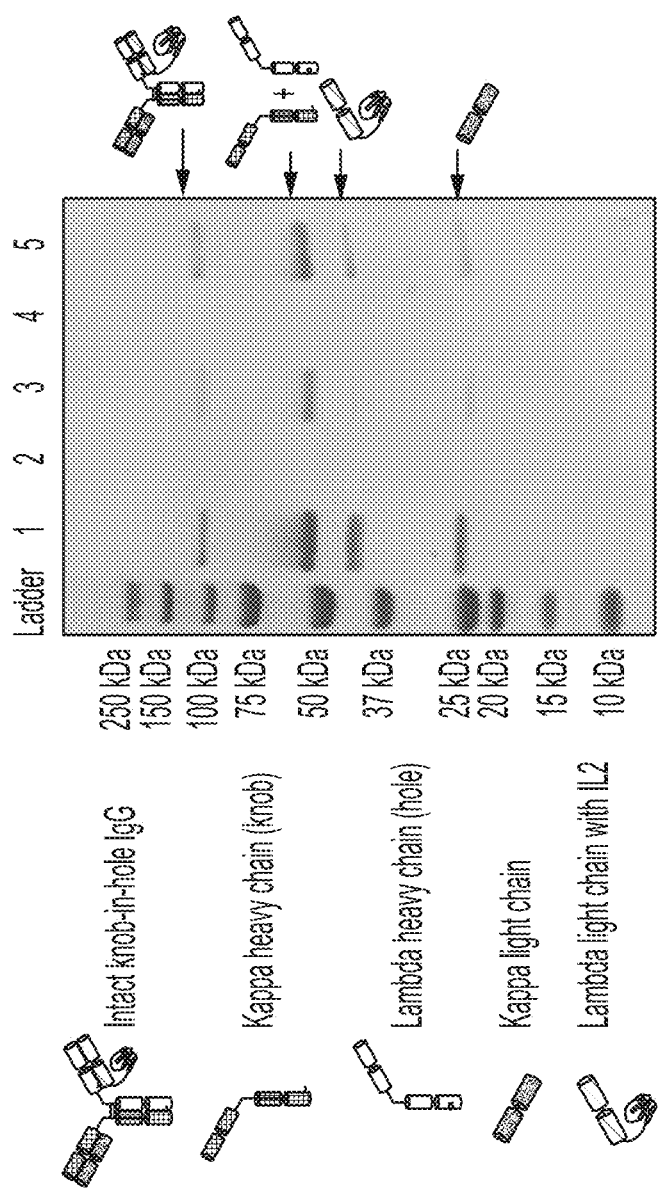
FIG. 27. Gel of reduced samples of multispecific molecule 9 following kappa/lambda select analysis. Lane 1 is the load, lane 2 is the flow-through from the KappaSelect column, lane 3 is the elution from the KappaSelect column, lane 4 is the flow-through from the LambdaFabSelect column, and lane 5 is the elution from the LambdaFabSelect column.

Multispecific molecule 9 was expressed by co-transfecting cells with expression vectors comprising polynucleotide sequences of SEQ ID NO: 78, SEQ ID NO: 15, SEQ ID NO: 91, and SEQ ID NO: 75. Multispecific molecule 9 was purified and a SDS-PAGE gel of the final product is shown in FIG. 18. FIG. 22 shows the size exclusion chromatogram of multispecific molecule 9. A KappaSelect and LambdaFabSelect analysis was performed with multispecific molecule 9, shown in FIG. 27. Both the KappaSelect and LambdaFabSelect flow-through fractions contained no protein, suggesting good chain fidelity.

Example 11

Figure 9:
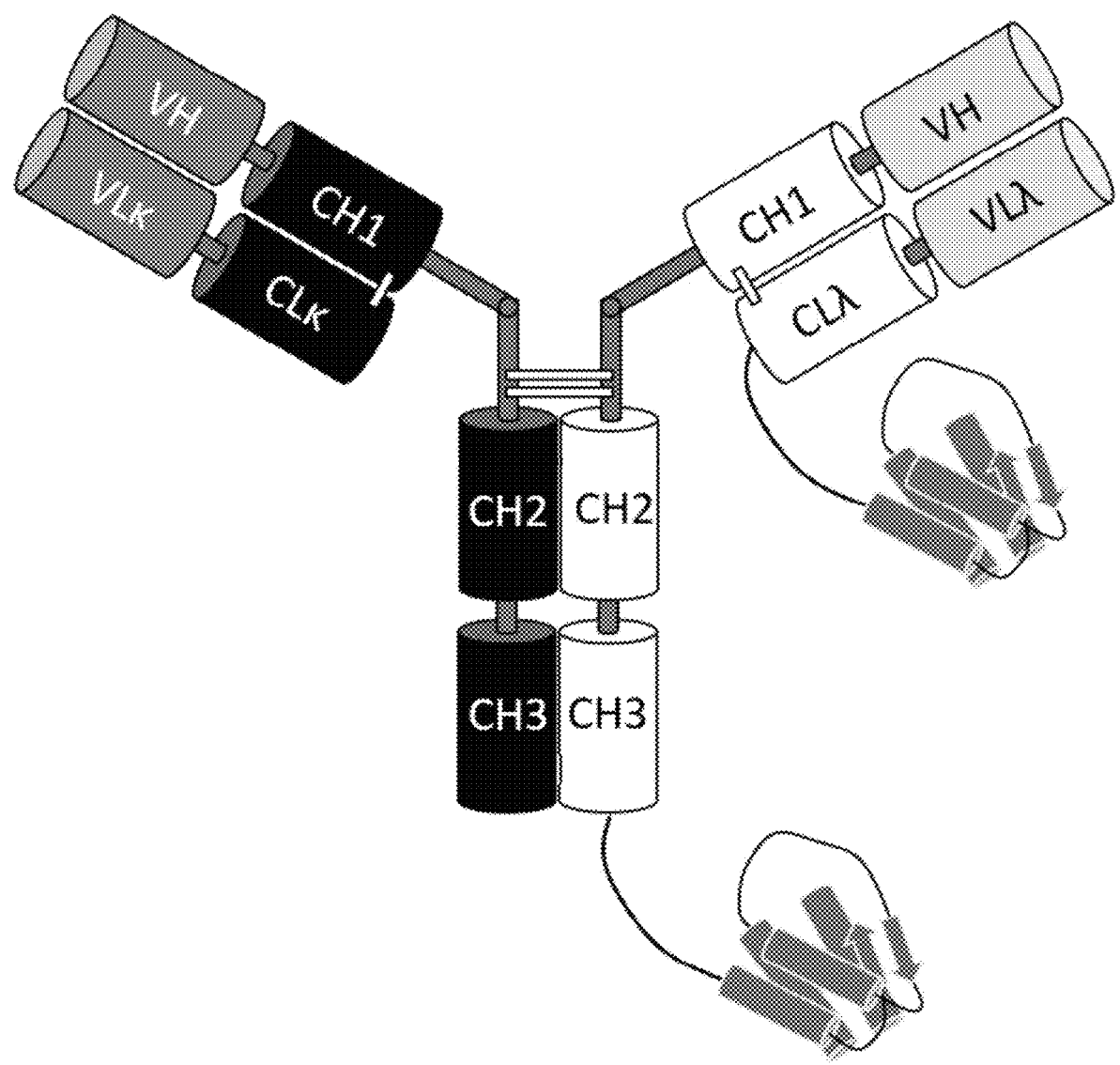
FIG. 9 depicts a schematic representation of an exemplary multispecific antibody molecule of the present invention. The multispecific antibody molecule comprises a first Fab comprising a kappa light chain polypeptide; a second Fab comprising a lambda light chain polypeptide; a first polypeptide attached to the C terminus of the lambda light chain polypeptide; a second polypeptide attached to the C terminus of the heavy chain polypeptide that associates with the lambda light chain polypeptide; and an Fc domain, wherein the Fc domain does not contain a paired protuberance/cavity, e.g., knob and hole pair (e.g., the Fc domain is a naturally existing Fc domain). In one embodiment, the first Fab binds to CTLA4, the second Fab binds to IL12β, the first polypeptide comprises interleukin 2, or fragment or variant thereof, and the second polypeptide comprises interleukin 2, or fragment or variant thereof (e.g., multispecific molecule 10 described in Example 11).

Multispecific molecule 10 comprises an α-CTLA4 arm, an α-IL12β arm, and two IL-2 polypeptides. The first IL-2 polypeptide is fused to the C-terminus of the lambda light chain of the α-IL12β arm. The second IL-2 polypeptide is fused to the C-terminus of the heavy chain of the α-IL12β arm. The α-CTLA4 arm comprises a first chain of the amino acid sequence of SEQ ID NO: 171 and a second chain of the amino acid sequence of SEQ ID NO: 106. The α-IL12β arm, together with the two fused IL-2 polypeptides, comprises a first chain of the amino acid sequence of SEQ ID NO: 175 and a second chain of the amino acid sequence of SEQ ID NO: 173. The two heavy chains of multispecific molecule 10 do not comprise the knobs-into-holes mutations. The configuration of multispecific molecule 10 is shown in FIG. 9.

Figure 29:
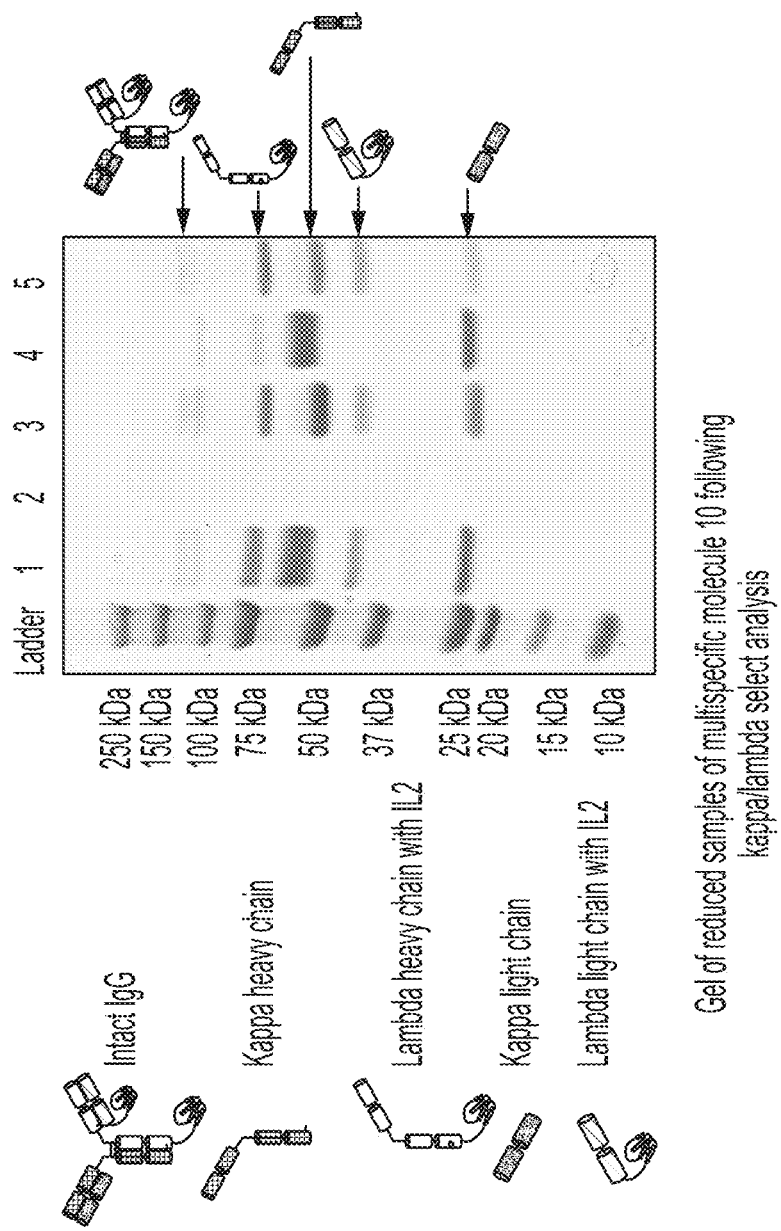
FIG. 29. Gel of reduced samples of multispecific molecule 10 following kappa/lambda select analysis. Lane 1 is the load, lane 2 is the flow-through from the KappaSelect column, lane 3 is the elution from the KappaSelect column, lane 4 is the flow-through from the LambdaFabSelect column, and lane 5 is the elution from the LambdaFabSelect column.

Multispecific molecule 10 was expressed by co-transfecting cells with expression vectors comprising polynucleotide sequences of SEQ ID NO: 73, SEQ ID NO: 15, SEQ ID NO: 77, and SEQ ID NO: 75. A KappaSelect and LambdaFabSelect analysis was performed with multispecific molecule 10, shown in FIG. 29. The flow-through from the KappaSelect column contained no protein, while the flow-through from the LambdaFabSelect column had protein primarily composed of the kappa heavy chain (knob) and kappa light chain. This suggests that the expression for the kappa pieces was greater than that of the lambda chains, rather than an issue with chain fidelity.

Example 12

Figure 8:
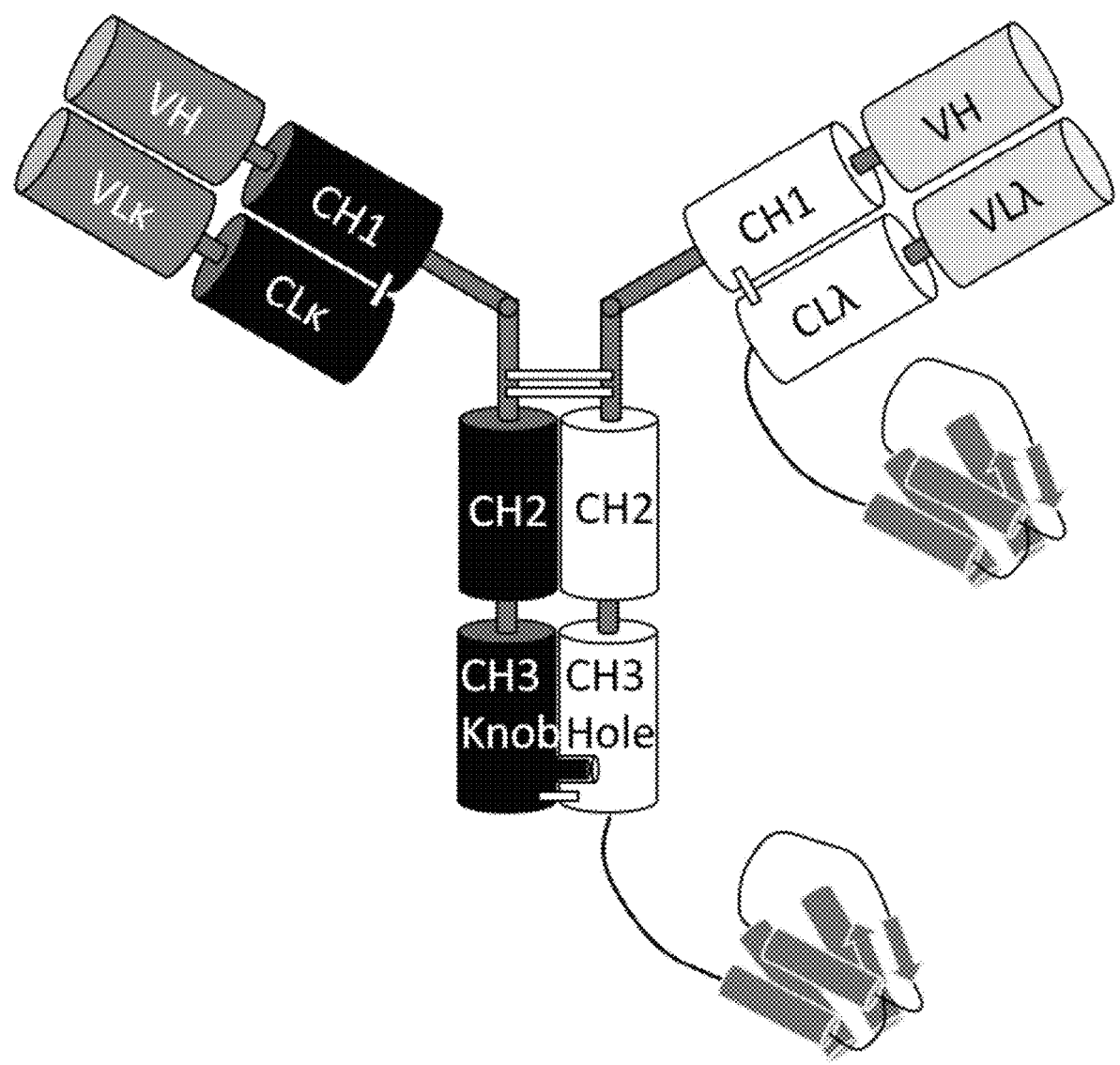
FIG. 8 depicts a schematic representation of an exemplary multispecific antibody molecule of the present invention. The multispecific antibody molecule comprises a first Fab comprising a kappa light chain polypeptide; a second Fab comprising a lambda light chain polypeptide; a first polypeptide attached to the C terminus of the lambda light chain polypeptide; a second polypeptide attached to the C terminus of the heavy chain polypeptide that associates with the lambda light chain polypeptide; and an Fc domain, wherein the Fc domain contains a paired protuberance/cavity, e.g., knob and hole pair. In one embodiment, the first Fab binds to CTLA4, the second Fab binds to IL12β, the first polypeptide comprises interleukin 2, or fragment or variant thereof, and the second polypeptide comprises interleukin 2, or fragment or variant thereof (e.g., multispecific molecule 11 described in Example 12).

Multispecific molecule 11 comprises an α-CTLA4 arm, an α-IL12β arm, and two IL-2 polypeptides. The first IL-2 polypeptide is fused to the C-terminus of the lambda light chain of the α-IL12β arm. The second IL-2 polypeptide is fused to the C-terminus of the heavy chain of the α-IL12β arm. The α-CTLA4 arm comprises a first chain of the amino acid sequence of SEQ ID NO: 168 and a second chain of the amino acid sequence of SEQ ID NO: 106. The α-IL12β arm, together with the two fused IL-2 polypeptides, comprises a first chain of the amino acid sequence of SEQ ID NO: 174 and a second chain of the amino acid sequence of SEQ ID NO: 173. Different from multispecific molecule 10, the two heavy chains of multispecific molecule 11 comprise the knobs-into-holes mutations. The configuration of multispecific molecule 11 is shown in FIG. 8.

Figure 28:
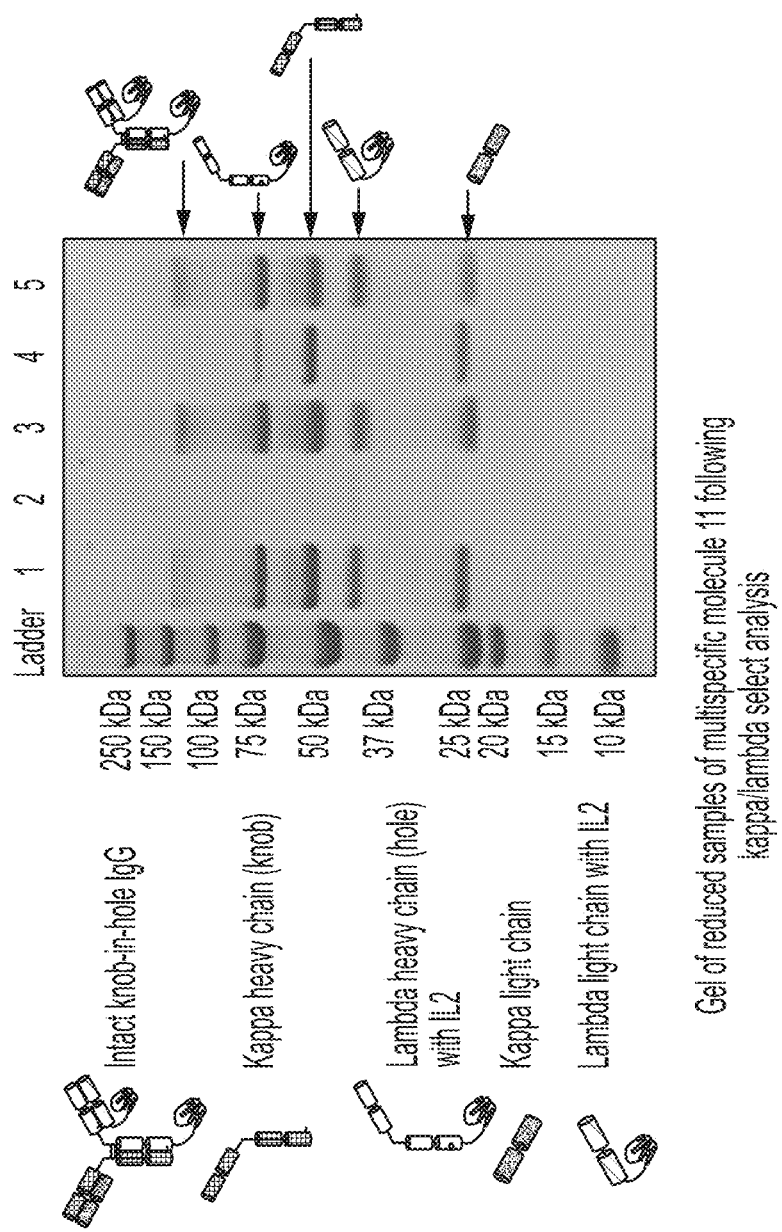
FIG. 28. Gel of reduced samples of multispecific molecule 11 following kappa/lambda select analysis. Lane 1 is the load, lane 2 is the flow-through from the KappaSelect column, lane 3 is the elution from the KappaSelect column, lane 4 is the flow-through from the LambdaFabSelect column, and lane 5 is the elution from the LambdaFabSelect column.

Multispecific molecule 11 was expressed by co-transfecting cells with expression vectors comprising polynucleotide sequences of SEQ ID NO: 78, SEQ ID NO: 15, SEQ ID NO: 76, and SEQ ID NO: 75. A KappaSelect and LambdaFabSelect analysis was performed with multispecific molecule 11, shown in FIG. 28. The flow-through from the KappaSelect column contained no protein, while the flow-through from the LambdaFabSelect column had protein primarily composed of the kappa heavy chain (knob) and kappa light chain. This suggests that the expression for the kappa pieces was greater than that of the lambda chains, rather than an issue with chain fidelity. This agrees with the what was seen with multispecific molecule 10, which is the same molecule except for the absence of the knob-in-hole mutations.

Example 13

Figure 10:
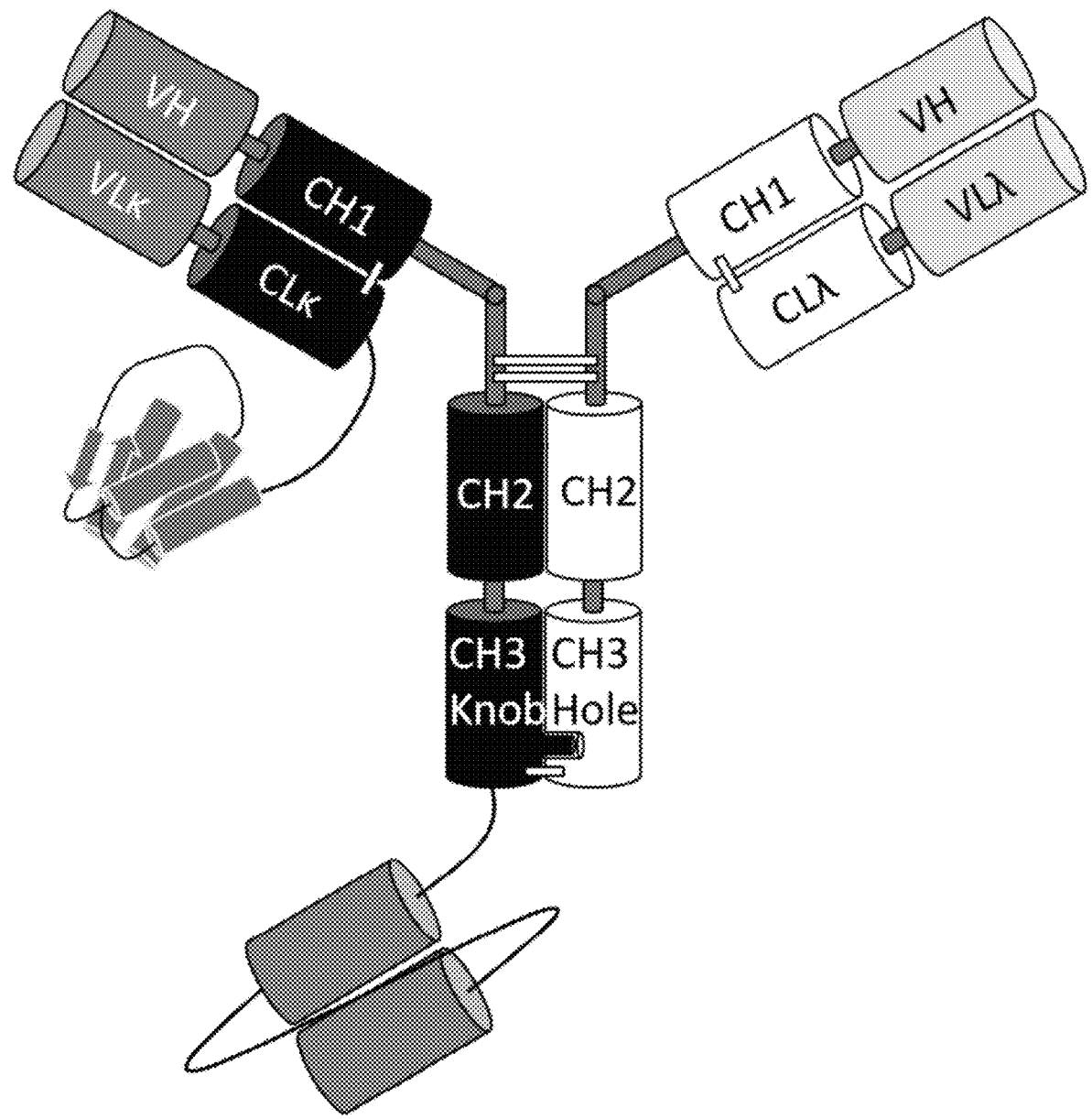
FIG. 10 depicts a schematic representation of an exemplary multispecific antibody molecule of the present invention. The multispecific antibody molecule comprises a first Fab comprising a kappa light chain polypeptide; a second Fab comprising a lambda light chain polypeptide; a first polypeptide attached to the C terminus of the kappa light chain polypeptide; a second polypeptide attached to the C terminus of the heavy chain polypeptide that associates with the kappa light chain polypeptide; and an Fc domain, wherein the Fc domain contains a paired protuberance/cavity, e.g., knob and hole pair. In one embodiment, the first Fab binds to CTLA4, the second Fab binds to TRAILR2, the first polypeptide comprises interleukin 2, or fragment or variant thereof, and the second polypeptide comprises an scFv (e.g., multispecific molecule 12 described in Example 13).

Multispecific molecule 12 comprises an α-CTLA4 arm, an α-TRAILR2 arm, a scFv targeting arm, and an IL-2 polypeptide. The IL-2 polypeptide is fused to the C-terminus of the kappa light chain of the α-CTLA4 arm. The scFv is fused to the C-terminus of the heavy chain of the α-CTLA4 arm. The α-CTLA4 arm, together with the fused IL-2 polypeptide and the scFv, comprises a first chain of the amino acid sequence of SEQ ID NO: 169 and a second chain of the amino acid sequence of SEQ ID NO: 176. The α-TRAILR2 arm comprises a first chain of the amino acid sequence of SEQ ID NO: 177 and a second chain of the amino acid sequence of SEQ ID NO: 148. The two heavy chains of multispecific molecule 12 comprise the knobs-into-holes mutations. The configuration of multispecific molecule 12 is shown in FIG. 10.

Figure 30:
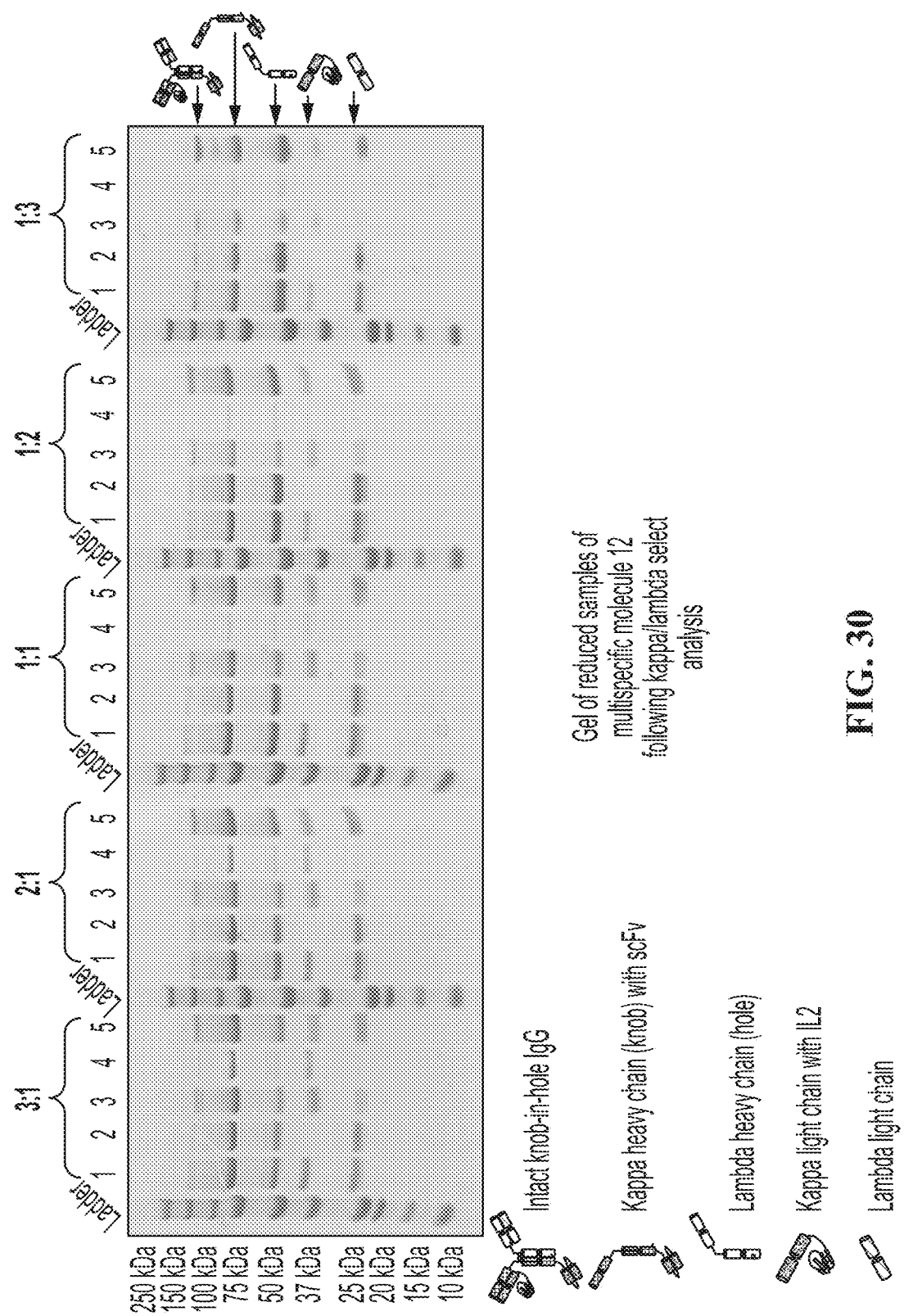
FIG. 30. Gel of reduced samples of multispecific molecule 12 following kappa/lambda select analysis. Lane 1 is the load, lane 2 is the flow-through from the KappaSelect column, lane 3 is the elution from the KappaSelect column, lane 4 is the flow-through from the LambdaFabSelect column, and lane 5 is the elution from the LambdaFabSelect column. The ratios indicate the DNA ratio used in the transfection from 3:1 to 1:3 of knob to hole.

Multispecific molecule 12 was expressed by co-transfecting cells with expression vectors comprising polynucleotide sequences of SEQ ID NO: 79, SEQ ID NO: 80, SEQ ID NO: 81, and SEQ ID NO: 57. A KappaSelect and LambdaFabSelect analysis was performed with multispecific molecule 12, shown in FIG. 30. The ratios indicate the ratios of DNA used at the time of transfection, varying from 3:1 to 1:3 of kappa to lambda. In all cases, there is protein in the flow-through of both the KappaSelect and LambdaFabSelect columns. The protein in the KappaSelect flow-through is composed of the kappa heavy chain, lambda heavy chain, and lambda light chain. The protein in the LambdaFabSelect flow-through is composed of the kappa heavy and light chains and diminishes as the ratio of the lambda chains increases. These data are in agreement with the data from multispecific molecule 4, which has the same Fab components and only shows the lambda light chain pairing with the kappa heavy chain and not vice versa.

EXEMPLARY EMBODIMENTS

Exemplary Embodiments 1

The present application is based, at least in part, on the unexpected finding that light chain shuffle in the context of a multispecific antibody molecule, e.g., a bispecific IgG molecule, can be prevented by using one kappa light chain polypeptide and one lambda light chain polypeptide. This is based, in part, on the observation that kappa light chains do not pair with a heavy chain from a lambda antibody and vice versa. Thus, described herein are novel multispecific, e.g., bispecific, antibody molecules that include a kappa light chain polypeptide and a lambda light chain polypeptide, and methods of making and using the multispecific antibody molecules.

Accordingly, in one aspect, disclosed herein is a multispecific antibody molecule, e.g., an antibody molecule comprising two binding specificities, e.g., a bispecific antibody molecule. The multispecific antibody molecule comprises: i) a first antigen-binding domain that binds to a first antigen, wherein the first antigen-binding domain comprises: a) a first heavy chain polypeptide (HCP1) comprising: a first heavy chain variable region sequence (HCVRS) sufficient that, when paired with i) b) allows the first antigen-binding domain to bind to the first antigen; and b) a lambda light chain polypeptide (LLCP) comprising: a lambda light chain variable region sequence (LLCVRS) sufficient that, when paired with i) a) allows the first antigen-binding domain to bind to the first antigen; and ii) a second antigen-binding domain that binds to a second antigen, wherein the second antigen-binding domain comprises: a) a second heavy chain polypeptide (HCP2) comprising: a second heavy chain variable region sequence (HCVRS) sufficient that, when paired with ii) b) allows the second antigen-binding domain to bind to the second antigen; and b) a kappa light chain polypeptide (KLCP) comprising: a kappa light chain variable region sequence (KLCVRS) sufficient that, when paired with ii) a) allows the second antigen-binding domain to bind to the second antigen.

In one embodiment, the first HCVRS comprises one, two, or all of framework 1 sequence, framework 2 sequence, or framework 3 sequence. In one embodiment, the framework 1 sequence, framework 2 sequence, or framework 3 sequence of the first HCVRS has at least 75, 80, 85, 90, 95, 98, or 100% sequence identity with a corresponding region in a first heavy chain germline sequence selected from column 3 of Table 7, column 2 of Table 8b, or column 2 of Table 5b. In one embodiment, the framework 1 sequence, framework 2 sequence, or framework 3 sequence of the first HCVRS comprises no more than 1, 2, 3, 4, 5, 6, 7, or 8 amino acid mutations (e.g., substitutions, insertions, or deletions, e.g., conserved substitutions) relative to a corresponding region in a first heavy chain germline sequence selected from column 3 of Table 7, column 2 of Table 8b, or column 2 of Table 5b. In one embodiment, the first HCVRS comprises a framework sequence selected from Table 16.

In one embodiment, the LLCVRS comprises one, two, or all of framework 1 sequence, framework 2 sequence, or framework 3 sequence. In one embodiment, the framework 1 sequence, framework 2 sequence, or framework 3 sequence of the LLCVRS has at least 75, 80, 85, 90, 95, 98, or 100% sequence identity with a corresponding region in a lambda light chain germline sequence selected from column 4 of Table 7, column 3 of Table 8b; or column 3 of Table 5b. In one embodiment, the framework 1 sequence, framework 2 sequence, or framework 3 sequence of the LLCVRS comprises no more than 1, 2, 3, 4, 5, 6, 7, or 8 amino acid mutations (e.g., substitutions, insertions, or deletions, e.g., conserved substitutions) relative to a corresponding region in a lambda light chain germline sequence selected from column 4 of Table 7, column 3 of Table 8b; or column 3 of Table 5b. In one embodiment, the LLCVRS comprises a framework sequence selected from Table 16.

In one embodiment, the second HCVRS comprises one, two, or all of framework 1 sequence, framework 2 sequence, or framework 3 sequence. In one embodiment, the framework 1 sequence, framework 2 sequence, or framework 3 sequence of the first HCVRS has at least 75, 80, 85, 90, 95, 98, or 100% sequence identity with a corresponding region in a second heavy chain germline sequence selected from column 3 of Table 6, column 5 of Table 8b, or column 4 of Table 5b. In one embodiment, the framework 1 sequence, framework 2 sequence, or framework 3 sequence of the second HCVRS comprises no more than 1, 2, 3, 4, 5, 6, 7, or 8 amino acid mutations (e.g., substitutions, insertions, or deletions, e.g., conserved substitutions) relative to a corresponding region in a second heavy chain germline sequence selected from column 3 of Table 6, column 5 of Table 8b, or column 4 of Table 5b. In one embodiment, the second HCVRS comprises a framework sequence selected from Table 16.

In one embodiment, the KLCVRS comprises one, two, or all of framework 1 sequence, framework 2 sequence, or framework 3 sequence. In one embodiment, the framework 1 sequence, framework 2 sequence, or framework 3 sequence of the LLCVRS has at least 75, 80, 85, 90, 95, 98, or 100% sequence identity with a corresponding region in a kappa light chain germline sequence selected from column 4 of Table 6, column 6 of Table 8b, or column 5 of Table 5b. In one embodiment, the framework 1 sequence, framework 2 sequence, or framework 3 sequence of the KLCVRS comprises no more than 1, 2, 3, 4, 5, 6, 7, or 8 amino acid mutations (e.g., substitutions, insertions, or deletions, e.g., conserved substitutions) relative to a corresponding region in a kappa light chain germline sequence selected from column 4 of Table 6, column 6 of Table 8b, or column 5 of Table 5b. In one embodiment, the KLCVRS comprises a framework sequence selected from Table 16.

In one embodiment, 1) the first HCVRS has at least 75, 80, 85, 90, 95, 98, or 100% sequence identity with a first heavy chain germline sequence selected from column 3 of Table 7, column 2 of Table 8b, or column 2 of Table 5b; 2) the LLCVRS has at least 75, 80, 85, 90, 95, 98, or 100% sequence identity with a lambda light chain germline sequence selected from column 4 of Table 7, column 3 of Table 8b; or column 3 of Table 5b; 3) the second HCVRS has at least 75, 80, 85, 90, 95, 98, or 100% sequence identity with a second heavy chain germline sequence selected from column 3 of Table 6, column 5 of Table 8b, or column 4 of Table 5b; or 4) the KLCVRS has at least 75, 80, 85, 90, 95, 98, or 100% sequence identity with a kappa light chain germline sequence selected from column 4 of Table 6, column 6 of Table 8b, or column 5 of Table 5b.

In one embodiment, the first HCVRS has at least 75, 80, 85, 90, 95, 98, or 100% sequence identity with a first heavy chain germline sequence selected from column 3 of Table 7, column 2 of Table 8b, or column 2 of Table 5b. In one embodiment, the first heavy chain germline sequence and the lambda light chain germline sequence are selected from a single row of Table 7, Table 8b, or Table 5b. In one embodiment, the first heavy chain germline sequence, the lambda light chain germline sequence, and the kappa light chain germline sequence are selected from a single row of Table 7, Table 8b, or Table 5b. In one embodiment, the second heavy chain germline sequence and the kappa light chain germline sequence are selected from a single row of Table 6, Table 8b, or Table 5b. In one embodiment, the second heavy chain germline sequence, the kappa light chain germline sequence, and the lambda light chain germline sequence are selected from a single row of Table 6, Table 8b, or Table 5b. In one embodiment, at least two (e.g., two, three, or all) of the following: the first heavy chain germline sequence, the lambda light chain germline sequence, the second heavy chain germline sequence, and the kappa light chain germline sequence, are selected from a single row of Table 8b or Table 5b.

In one embodiment, the LLCVRS has at least 75, 80, 85, 90, 95, 98, or 100% sequence identity with a lambda light chain germline sequence selected from column 4 of Table 7, column 3 of Table 8b; or column 3 of Table 5b. In one embodiment, the first heavy chain germline sequence and the lambda light chain germline sequence are selected from a single row of Table 7, Table 8b, or Table 5b. In one embodiment, the first heavy chain germline sequence, the lambda light chain germline sequence, and the kappa light chain germline sequence are selected from a single row of Table 7, Table 8b, or Table 5b. In one embodiment, the second heavy chain germline sequence and the kappa light chain germline sequence are selected from a single row of Table 6, Table 8b, or Table 5b. In one embodiment, the second heavy chain germline sequence, the kappa light chain germline sequence, and the lambda light chain germline sequence are selected from a single row of Table 6, Table 8b, or Table 5b. In one embodiment, at least two (e.g., two, three, or all) of the following: the first heavy chain germline sequence, the lambda light chain germline sequence, the second heavy chain germline sequence, and the kappa light chain germline sequence, are selected from a single row of Table 8b or Table 5b.

In one embodiment, the second HCVRS has at least 75, 80, 85, 90, 95, 98, or 100% sequence identity with a second heavy chain germline sequence selected from column 3 of Table 6, column 5 of Table 8b, or column 4 of Table 5b. In one embodiment, the first heavy chain germline sequence and the lambda light chain germline sequence are selected from a single row of Table 7, Table 8b, or Table 5b. In one embodiment, the first heavy chain germline sequence, the lambda light chain germline sequence, and the kappa light chain germline sequence are selected from a single row of Table 7, Table 8b, or Table 5b. In one embodiment, the second heavy chain germline sequence and the kappa light chain germline sequence are selected from a single row of Table 6, Table 8b, or Table 5b. In one embodiment, the second heavy chain germline sequence, the kappa light chain germline sequence, and the lambda light chain germline sequence are selected from a single row of Table 6, Table 8b, or Table 5b. In one embodiment, at least two (e.g., two, three, or all) of the following: the first heavy chain germline sequence, the lambda light chain germline sequence, the second heavy chain germline sequence, and the kappa light chain germline sequence, are selected from a single row of Table 8b or Table 5b.

In one embodiment, the KLCVRS has at least 75, 80, 85, 90, 95, 98, or 100% sequence identity with a kappa light chain germline sequence selected from column 4 of Table 6, column 6 of Table 8b, or column 5 of Table 5b. In one embodiment, the first heavy chain germline sequence and the lambda light chain germline sequence are selected from a single row of Table 7, Table 8b, or Table 5b. In one embodiment, the first heavy chain germline sequence, the lambda light chain germline sequence, and the kappa light chain germline sequence are selected from a single row of Table 7, Table 8b, or Table 5b. In one embodiment, the second heavy chain germline sequence and the kappa light chain germline sequence are selected from a single row of Table 6, Table 8b, or Table 5b. In one embodiment, the second heavy chain germline sequence, the kappa light chain germline sequence, and the lambda light chain germline sequence are selected from a single row of Table 6, Table 8b, or Table 5b. In one embodiment, at least two (e.g., two, three, or all) of the following: the first heavy chain germline sequence, the lambda light chain germline sequence, the second heavy chain germline sequence, and the kappa light chain germline sequence, are selected from a single row of Table 8b or Table 5b.

In one embodiment, the first heavy chain germline sequence and the lambda light chain germline sequence are selected from a single row of Table 8b or Table 5b. In one embodiment, the first heavy chain germline sequence and the second heavy chain germline sequence are selected from a single row of Table 8b or Table 5b. In one embodiment, the first heavy chain germline sequence and the kappa light chain germline sequence are selected from a single row of Table 8b or Table 5b. In one embodiment, the lambda light chain germline sequence and the second heavy chain germline sequence are selected from a single row of Table 8b or Table 5b. In one embodiment, the lambda light chain germline sequence and the kappa light chain germline sequence are selected from a single row of Table 8b or Table 5b. In one embodiment, the second heavy chain germline sequence and the kappa light chain germline sequence are selected from a single row of Table 8b or Table 5b. In one embodiment, the first heavy chain germline sequence, the lambda light chain germline sequence, and the second heavy chain germline sequence are selected from a single row of Table 8b or Table 5b. In one embodiment, the first heavy chain germline sequence, the lambda light chain germline sequence, and the kappa light chain germline sequence are selected from a single row of Table 8b or Table 5b. In one embodiment, the first heavy chain germline sequence, the second heavy chain germline sequence, and the kappa light chain germline sequence are selected from a single row of Table 8b or Table 5b. In one embodiment, the lambda light chain germline sequence, the second heavy chain germline sequence, and the kappa light chain germline sequence are selected from a single row of Table 8b or Table 5b. In one embodiment, the first heavy chain germline sequence, the lambda light chain germline sequence, the second heavy chain germline sequence, and the kappa light chain germline sequence are selected from a single row of Table 8b or Table 5b.

In certain embodiments of the foregoing aspects, the multispecific antibody molecule further comprises an accessory moiety, wherein the accessory moiety has a property chosen from: 1) the accessory moiety has a molecular weight of at least 10, 20, 30, 40, 50, 60, 70, 80, 90, or 100 kDa; 2) the accessory moiety comprises a polypeptide having at least 30, 40, 50, 60, 70, 80, 90, or 100 amino acid residues; 3) the accessory moiety comprises a polypeptide having the ability to modulate the activity of an immune cell, e.g., a T cell, a B cell, an antigen presenting cell (APC), or an NK cell; or 4) the accessory moiety is chosen from one or more of an immune cell engager (e.g., a CD40 agonist, e.g., a CD40L polypeptide or an agonistic anti-CD40 antibody molecule, or a PD-1 binding moiety, e.g., a PD-1 binding sequence of PDL-1 or an anti-PD-1 antibody molecule), a cytokine molecule (e.g. an IL-2 molecule), a cytokine antagonist (e.g., a TGF-β antagonist), an enzyme, a toxin, or a labeling agent.

In one aspect, disclosed herein is a multispecific antibody molecule comprising: i) a first antigen-binding domain that binds to a first antigen, wherein the first antigen-binding domain comprises: a) a first heavy chain polypeptide (HCP1) comprising: a first heavy chain variable region sequence (HCVRS) sufficient that, when paired with i) b) allows the first antigen-binding domain to bind to the first antigen; and b) a lambda light chain polypeptide (LLCP) comprising: a lambda light chain variable region sequence (LLCVRS) sufficient that, when paired with i) a) allows the first antigen-binding domain to bind to the first antigen; and ii) a second antigen-binding domain that binds to a second antigen, wherein the second antigen-binding domain comprises: a) a second heavy chain polypeptide (HCP2) comprising: a second heavy chain variable region sequence (HCVRS) sufficient that, when paired with ii) b) allows the second antigen-binding domain to bind to the second antigen; and b) a kappa light chain polypeptide (KLCP) comprising: a kappa light chain variable region sequence (KLCVRS) sufficient that, when paired with ii) a) allows the second antigen-binding domain to bind to the second antigen, wherein: the multispecific antibody molecule further comprises an accessory moiety, wherein the accessory moiety has a property chosen from: 1) the accessory moiety has a molecular weight of at least 10, 20, 30, 40, 50, 60, 70, 80, 90, or 100 kDa; 2) the accessory moiety comprises a polypeptide having at least 30, 40, 50, 60, 70, 80, 90, or 100 amino acid residues; 3) the accessory moiety comprises a polypeptide having the ability to modulate the activity of an immune cell, e.g., a T cell, a B cell, an antigen presenting cell (APC), or an NK cell; or 4) the accessory moiety is chosen from one or more of an immune cell engager (e.g., a CD40 agonist, e.g., a CD40L polypeptide or an agonistic anti-CD40 antibody molecule, or a PD-1 binding moiety, e.g., a PD-1 binding sequence of PDL-1 or an anti-PD-1 antibody molecule), a cytokine molecule (e.g. an IL-2 molecule), a cytokine antagonist (e.g., a TGF-β antagonist), an enzyme, a toxin, or a labeling agent.

Exemplary multispecific antibody molecules with one or more accessory moieties are shown in FIGS. 6-10 and described in Examples (e.g., multispecific molecule 8 described in Example 9, multispecific molecule 9 described in Example 10, multispecific molecule 10 described in Example 11, multispecific molecule 11 described in Example 12, multispecific molecule 12 described in Example 13).

In one embodiment, the accessory moiety has a molecular weight of at least 10, 20, 30, 40, 50, 60, 70, 80, 90, or 100 kDa. In one embodiment, the accessory moiety comprises a polypeptide having at least 30, 40, 50, 60, 70, 80, 90, or 100 amino acid residues. In one embodiment, the accessory moiety comprises a polypeptide having the ability to modulate the activity of an immune cell, e.g., a T cell, a B cell, an antigen presenting cell (APC), or an NK cell. In one embodiment, the accessory moiety is chosen from one or more of an immune cell engager (e.g., a CD40 agonist, e.g., a CD40L polypeptide or an agonistic anti-CD40 antibody molecule, or a PD-1 binding moiety, e.g., a PD-1 binding sequence of PDL-1 or an anti-PD-1 antibody molecule), a cytokine molecule (e.g. an IL-2 molecule), a cytokine antagonist (e.g., a TGF-β antagonist), an enzyme, a toxin, or a labeling agent.

In one embodiment, the accessory moiety is fused to the polypeptide of a, b, c, or d of the multispecific antibody molecule. In one embodiment, the accessory moiety is fused to any of the following: the HCP1, first HCVRS, LLCP, LLCVRS, HCP2, second HCVRS, KLCP, or KLCVRS of the multispecific antibody molecule, e.g., the C-terminus or N-terminus of HCP1, first HCVRS, LLCP, LLCVRS, HCP2, second HCVRS, KLCP, or KLCVRS of the multispecific antibody molecule. In one embodiment, the accessory moiety is fused to the HCP1. In one embodiment, the accessory moiety is fused to the first HCVRS (e.g., the C-terminus or N-terminus of the first HCVRS). In one embodiment, the accessory moiety is fused to the LLCP (e.g., the C-terminus or N-terminus of the LLCP). In one embodiment, the accessory moiety is fused to the LLCVRS (e.g., the C-terminus or N-terminus of the LLCVRS). In one embodiment, the accessory moiety is fused to the HCP2 (e.g., the C-terminus or N-terminus of the HCP2). In one embodiment, the accessory moiety is fused to the second HCVRS (e.g., the C-terminus or N-terminus of the second HCVRS). In one embodiment, the accessory moiety is fused to the KLCP (e.g., the C-terminus or N-terminus of the KLCP). In one embodiment, the accessory moiety is fused to the KLCVRS (e.g., the C-terminus or N-terminus of the KLCVRS). In one embodiment, the HCP1 comprises a first heavy chain constant region sequence (HCCRS) (e.g., CH1, CH2, and CH3 sequences), wherein the accessory moiety is fused to the first HCCRS, e.g., the C-terminus of the first HCCRS. In one embodiment, the HCP2 comprises a second heavy chain constant region sequence (HCCRS) (e.g., CH1, CH2, and CH3 sequences), wherein the accessory moiety is fused to the second HCCRS, e.g., the C-terminus of the second HCCRS. In one embodiment, the LLCP comprises a lambda light chain constant region sequence (LLCCRS), wherein the accessory moiety is fused to the LLCCRS, e.g., the C-terminus of the LLCCRS. In one embodiment, the KLCP comprises a kappa light chain constant region sequence (KLCCRS), wherein the accessory moiety is fused to the KLCCRS, e.g., the C-terminus of the KLCCRS.

In one embodiment, the multispecific antibody molecule comprises one or more (e.g., two, three, four, five, or more) accessory molecule. In one embodiment, the multispecific antibody molecule comprises a first accessory moiety and a second accessory moiety, wherein the first or second accessory moiety has a property chosen from: 1) the first or second accessory moiety has a molecular weight of at least 10, 20, 30, 40, 50, 60, 70, 80, 90, or 100 kDa; 2) the first or second accessory moiety comprises a polypeptide having at least 30, 40, 50, 60, 70, 80, 90, or 100 amino acid residues; 3) the first or second accessory moiety comprises a polypeptide having the ability to modulate the active of an immune cell, e.g., a T cell, a B cell, an antigen presenting cell (APC), or an NK cell; or 4) the first or second accessory moiety is chosen from one or more of an immune cell engager (e.g., a CD40 agonist, e.g., a CD40L polypeptide or an agonistic anti-CD40 antibody molecule, or a PD-1 binding moiety, e.g., a PD-1 binding sequence of PDL-1 or an anti-PD-1 antibody molecule), a cytokine molecule (e.g. an IL-2 molecule), a cytokine antagonist (e.g., a TGF-β antagonist), an enzyme, a toxin, or a labeling agent.

In one embodiment, the first and second accessory moieties are the same. In one embodiment, the first and second accessory moieties are different. In one embodiment, i) the first accessory moiety is fused to the HCP1 or HCP2, e.g., the C-terminus of the HCP1 or HCP2; and ii) the second accessory moiety is fused to the LLCP or KLCP, e.g., the C-terminus of the LLCP or KLCP. In one embodiment, i) the first accessory moiety is fused to the HCP1, e.g., the C-terminus of the HCP1; and ii) the second accessory moiety is fused to the LLCP, e.g., the C-terminus of the LLCP. In one embodiment, i) the first accessory moiety is fused to the HCP1, e.g., the C-terminus of the HCP1; and ii) the second accessory moiety is fused to the KLCP, e.g., the C-terminus of the KLCP. In one embodiment, i) the first accessory moiety is fused to the HCP2, e.g., the C-terminus of the HCP2; and ii) the second accessory moiety is fused to the LLCP, e.g., the C-terminus of the LLCP. In one embodiment, i) the first accessory moiety is fused to the HCP2, e.g., the C-terminus of the HCP2; and ii) the second accessory moiety is fused to the KLCP, e.g., the C-terminus of the KLCP. In one embodiment, i) the first accessory moiety is fused to the KLCP, e.g., the C-terminus of the KLCP; and ii) the second accessory moiety is fused to the LLCP, e.g., the C-terminus of the LLCP. In one embodiment, i) the first accessory moiety is fused to the LLCP, e.g., the C-terminus of the LLCP; and ii) the second accessory moiety is fused to the KLCP, e.g., the C-terminus of the KLCP. In one embodiment, i) the HCP1 comprises a first heavy chain constant region sequence (HCCRS) (e.g., CH1, CH2, and CH3 sequences), wherein the first accessory moiety is fused to the first HCCRS, e.g., the C-terminus of the first HCCRS; and ii) the LLCP comprises a lambda light chain constant region sequence (LLCCRS), wherein the second accessory moiety is fused to the LLCCRS, e.g., the C-terminus of the LLCCRS. In one embodiment, i) the HCP2 comprises a second heavy chain constant region sequence (HCCRS) (e.g., CH1, CH2, and CH3 sequences), wherein the accessory moiety is fused to the second HCCRS, e.g., the C-terminus of the second HCCRS; and ii) the KLCP comprises a kappa light chain constant region sequence (KLCCRS), wherein the accessory moiety is fused to the KLCCRS, e.g., the C-terminus of the KLCCRS. In one embodiment, i) the HCP1 comprises a first heavy chain constant region sequence (HCCRS) (e.g., CH1, CH2, and CH3 sequences), wherein the first accessory moiety is fused to the first HCCRS, e.g., the C-terminus of the first HCCRS; and ii) the KLCP comprises a kappa light chain constant region sequence (KLCCRS), wherein the accessory moiety is fused to the KLCCRS, e.g., the C-terminus of the KLCCRS. In one embodiment, i) the HCP2 comprises a second heavy chain constant region sequence (HCCRS) (e.g., CH1, CH2, and CH3 sequences), wherein the accessory moiety is fused to the second HCCRS, e.g., the C-terminus of the second HCCRS; and ii) the LLCP comprises a lambda light chain constant region sequence (LLCCRS), wherein the second accessory moiety is fused to the LLCCRS, e.g., the C-terminus of the LLCCRS.

In certain embodiments of the foregoing aspects, the multispecific antibody molecule comprises: i) a) the HCP1 comprises a first heavy chain constant region sequence (HCCRS) (e.g., a first CH1 sequence), i) b) the LLCP comprises a lambda light chain constant region sequence (LLCCRS), ii) a) the HCP2 comprises a second heavy chain constant region sequence (HCCRS) (e.g., a second CH1 sequence), and ii) b) the KLCP comprises a kappa light chain constant region sequence (KLCCRS), wherein: 1) the multispecific antibody molecule does not comprise a mutation in the first HCCRS (e.g., a mutation relative to a naturally existing heavy chain constant region sequence) that promotes the preferential pairing of the HCP1 and the LLCP, compared with pairing of the HCP1 and the LLCP without the mutation, or the multispecific antibody molecule does not comprise a mutation in the LLCCRS (e.g., a mutation relative to a naturally existing lambda light chain constant region sequence) that promotes the preferential pairing of the HCP1 and the LLCP, compared with pairing of the HCP1 and the LLCP without the mutation; and 2) the multispecific antibody molecule does not comprise a mutation in the second HCCRS (e.g., a mutation relative to a naturally existing heavy chain constant region sequence) that promotes the preferential pairing of the HCP2 and the KLCP, compared with pairing of the HCP2 and the KLCP without the mutation, or the multispecific antibody molecule does not comprise a mutation in the KLCCRS (e.g., a mutation relative to a naturally existing kappa light chain constant region sequence) that promotes the preferential pairing of the HCP2 and the KLCP, compared with pairing of the HCP2 and the KLCP without the mutation.

In one aspect, disclosed herein is a multispecific antibody comprising: i) a first antigen-binding domain that binds to a first antigen, wherein the first antigen-binding domain comprises: a) a first heavy chain polypeptide (HCP1) comprising: a first heavy chain variable region sequence (HCVRS) sufficient that, when paired with i) b) allows the first antigen-binding domain to bind to the first antigen; and a first heavy chain constant region sequence (HCCRS) (e.g., a first CH1 sequence), and b) a lambda light chain polypeptide (LLCP) comprising: a lambda light chain variable region sequence (LLCVRS) sufficient that, when paired with i) a) allows the first antigen-binding domain to bind to the first antigen; and a lambda light chain constant region sequence (LLCCRS), and ii) a second antigen-binding domain that binds to a second antigen, wherein the second antigen-binding domain comprises: a) a second heavy chain polypeptide (HCP2) comprising: a second heavy chain variable region sequence (HCVRS) sufficient that, when paired with ii) b) allows the second antigen-binding domain to bind to the second antigen; and a second heavy chain constant region sequence (HCCRS) (e.g., a second CH1 sequence) and b) a kappa light chain polypeptide (KLCP) comprising: a kappa light chain variable region sequence (KLCVRS) sufficient that, when paired with ii) a) allows the second antigen-binding domain to bind to the second antigen; and a kappa light chain constant region sequence (KLCCRS), wherein: 1) the multispecific antibody molecule does not comprise a mutation in the first HCCRS (e.g., a mutation relative to a naturally existing heavy chain constant region sequence) that promotes the preferential pairing of the HCP1 and the LLCP, compared with pairing of the HCP1 and the LLCP without the mutation, or the multispecific antibody molecule does not comprise a mutation in the LLCCRS (e.g., a mutation relative to a naturally existing lambda light chain constant region sequence) that promotes the preferential pairing of the HCP1 and the LLCP, compared with pairing of the HCP1 and the LLCP without the mutation; and 2) the multispecific antibody molecule does not comprise a mutation in the second HCCRS (e.g., a mutation relative to a naturally existing heavy chain constant region sequence) that promotes the preferential pairing of the HCP2 and the KLCP, compared with pairing of the HCP2 and the KLCP without the mutation, or the multispecific antibody molecule does not comprise a mutation in the KLCCRS (e.g., a mutation relative to a naturally existing kappa light chain constant region sequence) that promotes the preferential pairing of the HCP2 and the KLCP, compared with pairing of the HCP2 and the KLCP without the mutation.

In one embodiment, 1) the multispecific antibody molecule does not comprise a mutation in the first HCCRS (e.g., a mutation relative to a naturally existing heavy chain constant region sequence) that promotes the preferential pairing of the HCP1 and the LLCP, compared with pairing of the HCP1 and the LLCP without the mutation; and 2) the multispecific antibody molecule does not comprise a mutation in the second HCCRS (e.g., a mutation relative to a naturally existing heavy chain constant region sequence) that promotes the preferential pairing of the HCP2 and the KLCP, compared with pairing of the HCP2 and the KLCP without the mutation.

In one embodiment, 1) the multispecific antibody molecule does not comprise a mutation in the first HCCRS (e.g., a mutation relative to a naturally existing heavy chain constant region sequence) that promotes the preferential pairing of the HCP1 and the LLCP, compared with pairing of the HCP1 and the LLCP without the mutation; and 2) the multispecific antibody molecule does not comprise a mutation in the KLCCRS (e.g., a mutation relative to a naturally existing kappa light chain constant region sequence) that promotes the preferential pairing of the HCP2 and the KLCP, compared with pairing of the HCP2 and the KLCP without the mutation.

In one embodiment, 1) the multispecific antibody molecule does not comprise a mutation in the LLCCRS (e.g., a mutation relative to a naturally existing lambda light chain constant region sequence) that promotes the preferential pairing of the HCP1 and the LLCP, compared with pairing of the HCP1 and the LLCP without the mutation; and 2) the multispecific antibody molecule does not comprise a mutation in the second HCCRS (e.g., a mutation relative to a naturally existing heavy chain constant region sequence) that promotes the preferential pairing of the HCP2 and the KLCP, compared with pairing of the HCP2 and the KLCP without the mutation.

In one embodiment, 1) the multispecific antibody molecule does not comprise a mutation in the LLCCRS (e.g., a mutation relative to a naturally existing lambda light chain constant region sequence) that promotes the preferential pairing of the HCP1 and the LLCP, compared with pairing of the HCP1 and the LLCP without the mutation; and 2) the multispecific antibody molecule does not comprise a mutation in the KLCCRS (e.g., a mutation relative to a naturally existing kappa light chain constant region sequence) that promotes the preferential pairing of the HCP2 and the KLCP, compared with pairing of the HCP2 and the KLCP without the mutation.

In one embodiment, 1) the multispecific antibody molecule does not comprise a mutation in the first HCCRS (e.g., a mutation relative to a naturally existing heavy chain constant region sequence) that promotes the preferential pairing of the HCP1 and the LLCP, compared with pairing of the HCP1 and the LLCP without the mutation, and the multispecific antibody molecule does not comprise a mutation in the LLCCRS (e.g., a mutation relative to a naturally existing lambda light chain constant region sequence) that promotes the preferential pairing of the HCP1 and the LLCP, compared with pairing of the HCP1 and the LLCP without the mutation; and 2) the multispecific antibody molecule does not comprise a mutation in the second HCCRS (e.g., a mutation relative to a naturally existing heavy chain constant region sequence) that promotes the preferential pairing of the HCP2 and the KLCP, compared with pairing of the HCP2 and the KLCP without the mutation, or the multispecific antibody molecule does not comprise a mutation in the KLCCRS (e.g., a mutation relative to a naturally existing kappa light chain constant region sequence) that promotes the preferential pairing of the HCP2 and the KLCP, compared with pairing of the HCP2 and the KLCP without the mutation.

In one embodiment, 1) the multispecific antibody molecule does not comprise a mutation in the first HCCRS (e.g., a mutation relative to a naturally existing heavy chain constant region sequence) that promotes the preferential pairing of the HCP1 and the LLCP, compared with pairing of the HCP1 and the LLCP without the mutation, or the multispecific antibody molecule does not comprise a mutation in the LLCCRS (e.g., a mutation relative to a naturally existing lambda light chain constant region sequence) that promotes the preferential pairing of the HCP1 and the LLCP, compared with pairing of the HCP1 and the LLCP without the mutation; and 2) the multispecific antibody molecule does not comprise a mutation in the second HCCRS (e.g., a mutation relative to a naturally existing heavy chain constant region sequence) that promotes the preferential pairing of the HCP2 and the KLCP, compared with pairing of the HCP2 and the KLCP without the mutation, and the multispecific antibody molecule does not comprise a mutation in the KLCCRS (e.g., a mutation relative to a naturally existing kappa light chain constant region sequence) that promotes the preferential pairing of the HCP2 and the KLCP, compared with pairing of the HCP2 and the KLCP without the mutation.

In one embodiment, 1) the multispecific antibody molecule does not comprise a mutation in the first HCCRS (e.g., a mutation relative to a naturally existing heavy chain constant region sequence) that promotes the preferential pairing of the HCP1 and the LLCP, compared with pairing of the HCP1 and the LLCP without the mutation, and the multispecific antibody molecule does not comprise a mutation in the LLCCRS (e.g., a mutation relative to a naturally existing lambda light chain constant region sequence) that promotes the preferential pairing of the HCP1 and the LLCP, compared with pairing of the HCP1 and the LLCP without the mutation; and 2) the multispecific antibody molecule does not comprise a mutation in the second HCCRS (e.g., a mutation relative to a naturally existing heavy chain constant region sequence) that promotes the preferential pairing of the HCP2 and the KLCP, compared with pairing of the HCP2 and the KLCP without the mutation, and the multispecific antibody molecule does not comprise a mutation in the KLCCRS (e.g., a mutation relative to a naturally existing kappa light chain constant region sequence) that promotes the preferential pairing of the HCP2 and the KLCP, compared with pairing of the HCP2 and the KLCP without the mutation.

In one embodiment, the multispecific antibody molecule does not comprise a mutation in the first HCCRS (e.g., a mutation relative to a naturally existing heavy chain constant region sequence) that increases the preferential pairing of the HCP1 and the LLCP by at least 1.5, 2, 3, 4, 5, 6, 7, 8, 9, 10, 20, 30, 40, or 50 folds, compared with pairing of the HCP1 and the LLCP without the mutation. In one embodiment, the multispecific antibody molecule does not comprise a mutation in the LLCCRS (e.g., a mutation relative to a naturally existing lambda light chain constant region sequence) that increases the preferential pairing of the HCP1 and the LLCP by at least 1.5, 2, 3, 4, 5, 6, 7, 8, 9, 10, 20, 30, 40, or 50 folds, compared with pairing of the HCP1 and the LLCP without the mutation.

In one embodiment, the multispecific antibody molecule does not comprise a mutation in the second HCCRS (e.g., a mutation relative to a naturally existing heavy chain constant region sequence) that increases the preferential pairing of the HCP2 and the KLCP by at least 1.5, 2, 3, 4, 5, 6, 7, 8, 9, 10, 20, 30, 40, or 50 folds, compared with pairing of the HCP2 and the KLCP without the mutation. In one embodiment, the multispecific antibody molecule does not comprise a mutation in the KLCCRS (e.g., a mutation relative to a naturally existing kappa light chain constant region sequence) that increases the preferential pairing of the HCP2 and the KLCP by at least 1.5, 2, 3, 4, 5, 6, 7, 8, 9, 10, 20, 30, 40, or 50 folds, compared with pairing of the HCP2 and the KLCP without the mutation.

In certain embodiments of the foregoing aspects, the multispecific antibody molecule comprises: i) a) the HCP1 comprises a first heavy chain constant region sequence (HCCRS) (e.g., a first CH1 sequence), i) b) the LLCP comprises a lambda light chain constant region sequence (LLCCRS), ii) a) the HCP2 comprises a second heavy chain constant region sequence (HCCRS) (e.g., a second CH1 sequence), and ii) b) the KLCP comprises a kappa light chain constant region sequence (KLCCRS), wherein: 1) the multispecific antibody molecule does not comprise a mutation in the first HCCRS (e.g., a mutation relative to a naturally existing heavy chain constant region sequence), or the multispecific antibody molecule does not comprise a mutation in the LLCCRS (e.g., a mutation relative to a naturally existing lambda light chain constant region sequence); and 2) the multispecific antibody molecule does not comprise a mutation in the second HCCRS (e.g., a mutation relative to a naturally existing heavy chain constant region sequence), or the multispecific antibody molecule does not comprise a mutation in the KLCCRS (e.g., a mutation relative to a naturally existing kappa light chain constant region sequence).

In one aspect, disclosed herein is a multispecific antibody comprising: i) a first antigen-binding domain that binds to a first antigen, wherein the first antigen-binding domain comprises: a) a first heavy chain polypeptide (HCP1) comprising: a first heavy chain variable region sequence (HCVRS) sufficient that, when paired with i) b) allows the first antigen-binding domain to bind to the first antigen; and a first heavy chain constant region sequence (HCCRS) (e.g., a first CH1 sequence), and b) a lambda light chain polypeptide (LLCP) comprising: a lambda light chain variable region sequence (LLCVRS) sufficient that, when paired with i) a) allows the first antigen-binding domain to bind to the first antigen; and a lambda light chain constant region sequence (LLCCRS), and ii) a second antigen-binding domain that binds to a second antigen, wherein the second antigen-binding domain comprises: a) a second heavy chain polypeptide (HCP2) comprising: a second heavy chain variable region sequence (HCVRS) sufficient that, when paired with ii) b) allows the second antigen-binding domain to bind to the second antigen; and a second heavy chain constant region sequence (HCCRS) (e.g., a second CH1 sequence) and b) a kappa light chain polypeptide (KLCP) comprising: a kappa light chain variable region sequence (KLCVRS) sufficient that, when paired with ii) a) allows the second antigen-binding domain to bind to the second antigen; and a kappa light chain constant region sequence (KLCCRS), wherein: 1) the multispecific antibody molecule does not comprise a mutation in the first HCCRS (e.g., a mutation relative to a naturally existing heavy chain constant region sequence), or the multispecific antibody molecule does not comprise a mutation in the LLCCRS (e.g., a mutation relative to a naturally existing lambda light chain constant region sequence); and 2) the multispecific antibody molecule does not comprise a mutation in the second HCCRS (e.g., a mutation relative to a naturally existing heavy chain constant region sequence), or the multispecific antibody molecule does not comprise a mutation in the KLCCRS (e.g., a mutation relative to a naturally existing kappa light chain constant region sequence).

In one embodiment, the multispecific antibody molecule does not comprise a mutation in the first HCCRS (e.g., a mutation relative to a naturally existing heavy chain constant region sequence), and the multispecific antibody molecule does not comprise a mutation in the second HCCRS (e.g., a mutation relative to a naturally existing heavy chain constant region sequence).

In one embodiment, the multispecific antibody molecule does not comprise a mutation in the first HCCRS (e.g., a mutation relative to a naturally existing heavy chain constant region sequence), and the multispecific antibody molecule does not comprise a mutation in the KLCCRS (e.g., a mutation relative to a naturally existing kappa light chain constant region sequence).

In one embodiment, the multispecific antibody molecule does not comprise a mutation in the LLCCRS (e.g., a mutation relative to a naturally existing lambda light chain constant region sequence), and the multispecific antibody molecule does not comprise a mutation in the second HCCRS (e.g., a mutation relative to a naturally existing heavy chain constant region sequence).

In one embodiment, the multispecific antibody molecule does not comprise a mutation in the LLCCRS (e.g., a mutation relative to a naturally existing lambda light chain constant region sequence), and the multispecific antibody molecule does not comprise a mutation in the KLCCRS (e.g., a mutation relative to a naturally existing kappa light chain constant region sequence).

In one embodiment, 1) the multispecific antibody molecule does not comprise a mutation in the first HCCRS (e.g., a mutation relative to a naturally existing heavy chain constant region sequence), and the multispecific antibody molecule does not comprise a mutation in the LLCCRS (e.g., a mutation relative to a naturally existing lambda light chain constant region sequence); and 2) the multispecific antibody molecule does not comprise a mutation in the second HCCRS (e.g., a mutation relative to a naturally existing heavy chain constant region sequence), or the multispecific antibody molecule does not comprise a mutation in the KLCCRS (e.g., a mutation relative to a naturally existing kappa light chain constant region sequence).

In one embodiment, 1) the multispecific antibody molecule does not comprise a mutation in the first HCCRS (e.g., a mutation relative to a naturally existing heavy chain constant region sequence), or the multispecific antibody molecule does not comprise a mutation in the LLCCRS (e.g., a mutation relative to a naturally existing lambda light chain constant region sequence); and 2) the multispecific antibody molecule does not comprise a mutation in the second HCCRS (e.g., a mutation relative to a naturally existing heavy chain constant region sequence), and the multispecific antibody molecule does not comprise a mutation in the KLCCRS (e.g., a mutation relative to a naturally existing kappa light chain constant region sequence).

In one embodiment, 1) the multispecific antibody molecule does not comprise a mutation in the first HCCRS (e.g., a mutation relative to a naturally existing heavy chain constant region sequence), and the multispecific antibody molecule does not comprise a mutation in the LLCCRS (e.g., a mutation relative to a naturally existing lambda light chain constant region sequence); and 2) the multispecific antibody molecule does not comprise a mutation in the second HCCRS (e.g., a mutation relative to a naturally existing heavy chain constant region sequence), and the multispecific antibody molecule does not comprise a mutation in the KLCCRS (e.g., a mutation relative to a naturally existing kappa light chain constant region sequence).

In one embodiment, the multispecific antibody molecule does not comprise a mutation in any of the following: the first HCCRS, the LLCCRS, the second HCCRS, and the KLCCRS (e.g., a mutation relative to a naturally existing heavy chain constant region sequence, a naturally existing lambda light chain constant region sequence, or a naturally existing kappa light chain constant region sequence).

In one embodiment, the multispecific antibody molecule does not comprise a mutation disclosed in WO2017059551.

In certain embodiments of the foregoing aspects, the multispecific antibody molecule comprises: i) a) the HCP1 comprises a first heavy chain constant region sequence (HCCRS) (e.g., a first CH1 sequence), i) b) the LLCP comprises a lambda light chain constant region sequence (LLCCRS), ii) a) the HCP2 comprises a second heavy chain constant region sequence (HCCRS) (e.g., a second CH1 sequence) and ii) b) the KLCP comprises a kappa light chain constant region sequence (KLCCRS), wherein: 1) the first HCCRS comprises a naturally existing heavy chain constant region sequence, or the LLCCRS comprises a naturally existing lambda light chain constant region sequence; and 2) the second HCCRS comprises a naturally existing heavy chain constant region sequence, or the KLCCRS comprises a naturally existing kappa light chain constant region sequence.

In one aspect, disclosed herein is a multispecific antibody molecule comprising: i) a first antigen-binding domain that binds to a first antigen, wherein the first antigen-binding domain comprises: a) a first heavy chain polypeptide (HCP1) comprising: a first heavy chain variable region sequence (HCVRS) sufficient that, when paired with i) b) allows the first antigen-binding domain to bind to the first antigen; and a first heavy chain constant region sequence (HCCRS) (e.g., a first CH1 sequence), and b) a lambda light chain polypeptide (LLCP) comprising: a lambda light chain variable region sequence (LLCVRS) sufficient that, when paired with i) a) allows the first antigen-binding domain to bind to the first antigen; and a lambda light chain constant region sequence (LLCCRS), and ii) a second antigen-binding domain that binds to a second antigen, wherein the second antigen-binding domain comprises: a) a second heavy chain polypeptide (HCP2) comprising: a second heavy chain variable region sequence (HCVRS) sufficient that, when paired with ii) b) allows the second antigen-binding domain to bind to the second antigen; and a second heavy chain constant region sequence (HCCRS) (e.g., a second CH1 sequence) and b) a kappa light chain polypeptide (KLCP) comprising: a kappa light chain variable region sequence (KLCVRS) sufficient that, when paired with ii) a) allows the second antigen-binding domain to bind to the second antigen; and a kappa light chain constant region sequence (KLCCRS), wherein: 1) the first HCCRS comprises a naturally existing heavy chain constant region sequence, or the LLCCRS comprises a naturally existing lambda light chain constant region sequence; and 2) the second HCCRS comprises a naturally existing heavy chain constant region sequence, or the KLCCRS comprises a naturally existing kappa light chain constant region sequence.

In one embodiment, 1) the first HCCRS comprises a naturally existing heavy chain constant region sequence; and 2) the second HCCRS comprises a naturally existing heavy chain constant region sequence. In one embodiment, 1) the first HCCRS comprises a naturally existing heavy chain constant region sequence; and 2) the KLCCRS comprises a naturally existing kappa light chain constant region sequence. In one embodiment, 1) the LLCCRS comprises a naturally existing lambda light chain constant region sequence; and 2) the second HCCRS comprises a naturally existing heavy chain constant region sequence. In one embodiment, 1) the LLCCRS comprises a naturally existing lambda light chain constant region sequence; and 2) the KLCCRS comprises a naturally existing kappa light chain constant region sequence. In one embodiment, 1) the first HCCRS comprises a naturally existing heavy chain constant region sequence, and the LLCCRS comprises a naturally existing lambda light chain constant region sequence; and 2) the second HCCRS comprises a naturally existing heavy chain constant region sequence, or the KLCCRS comprises a naturally existing kappa light chain constant region sequence. In one embodiment, 1) the first HCCRS comprises a naturally existing heavy chain constant region sequence, or the LLCCRS comprises a naturally existing lambda light chain constant region sequence; and 2) the second HCCRS comprises a naturally existing heavy chain constant region sequence, and the KLCCRS comprises a naturally existing kappa light chain constant region sequence.

In one embodiment, i) the first HCCRS comprises a naturally existing heavy chain constant region sequence, ii) the LLCCRS comprises a naturally existing lambda light chain constant region sequence, iii) the second HCCRS comprises a naturally existing heavy chain constant region sequence, and iv) the KLCCRS comprises a naturally existing kappa light chain constant region sequence.

In certain embodiments of the foregoing aspects, the HCP1 preferentially binds to the LLCP over the KLCP. In certain embodiments of the foregoing aspects, the LLCP preferentially binds to the HCP1 over the HCP2. In certain embodiments of the foregoing aspects, the HCP2 preferentially binds to the KLCP over the LLCP. In certain embodiments of the foregoing aspects, the KLCP preferentially binds to the HCP2 over the HCP1. In one embodiment, the HCP1 has a higher affinity, e.g., a substantially higher affinity, for the LLCP than for the KLCP (e.g., the KD for the binding between the HCP1 and the LLCP is no more than 50%, 40%, 30%, 20%, 10%, 1%, 0.1%, or 0.01% of the KD for the binding between the HCP1 and the KLCP). In one embodiment, the LLCP has a higher affinity, e.g., a substantially higher affinity, for the HCP1 than for the HCP2 (e.g., the KD for the binding between the LLCP and the HCP1 is no more than 50%, 40%, 30%, 20%, 10%, 1%, 0.1%, or 0.01% of the KD for the binding between the LLCP and the first HCP2). In one embodiment, the HCP2 has a higher affinity, e.g., a substantially higher affinity, for the KLCP than for the LLCP (e.g., the KD for the binding between the HCP2 and the KLCP is no more than 50%, 40%, 30%, 20%, 10%, 1%, 0.1%, or 0.01% of the KD for the binding between the HCP2 and the LLCP). In one embodiment, the KLCP has a higher affinity, e.g., a substantially higher affinity, for the HCP2 than for the HCP1 (e.g., the KD for the binding between the KLCP and the HCP2 is no more than 50%, 40%, 30%, 20%, 10%, 1%, 0.1%, or 0.01% of the KD for the binding between the KLCP and the HCP1).

In one embodiment, the percent binding between the HCP1 and the LLCP in the presence of the KLCP is at least 75, 80, 90, 95, 98, 99, or 99.5%. In one embodiment, when the HCP1, LLCP, and KLCP are present at 1:1:1, the percent binding between the HCP1 and the LLCP in the presence of the KLCP is at least 75, 80, 90, 95, 98, 99, or 99.5% (setting the binding between the HCP1 and the LLCP in the absence of any competing peptide to 100%, and the binding between the HCP1 and the LLCP in the presence of LLCP to 50%). In one embodiment, the percent binding was measured by an assay described herein, e.g., the NanoBiT assay.

In one embodiment, the percent binding between the HCP1 and the LLCP in the presence of the HCP2 is at least 75, 80, 90, 95, 98, 99, or 99.5%. In one embodiment, when HCP1, LLCP, and HCP2 are present at 1:1:1, the percent binding between the HCP1 and the LLCP in the presence of the HCP2 is at least 75, 80, 90, 95, 98, 99, or 99.5% (setting the binding between the HCP1 and the LLCP in the absence of any competing peptide to 100%, and the binding between the HCP1 and the LLCP in the presence of HCP1 to 50%). In one embodiment, the percent binding was measured by an assay described herein, e.g., the NanoBiT assay.

In one embodiment, the percent binding between the HCP2 and the KLCP in the presence of the LLCP is at least 75, 80, 90, 95, 98, 99, or 99.5%. In one embodiment, when HCP2, KLCP, and LLCP are present at 1:1:1, the percent binding between the HCP2 and the KLCP in the presence of the LLCP is at least 75, 80, 90, 95, 98, 99, or 99.5% (setting the binding between the HCP2 and the KLCP in the absence of any competing peptide to 100%, and the binding between the HCP2 and the KLCP in the presence of KLCP to 50%). In one embodiment, the percent binding was measured by an assay described herein, e.g., the NanoBiT assay.

In one embodiment, the percent binding between the HCP2 and the KLCP in the presence of the HCP1 is at least 75, 80, 90, 95, 98, 99, or 99.5%. In one embodiment, when HCP2, KLCP, and HCP1 are present at 1:1:1, the percent binding between the HCP2 and the KLCP in the presence of the HCP1 is at least 75, 80, 90, 95, 98, 99, or 99.5% (setting the binding between the HCP2 and the KLCP in the absence of any competing peptide to 100%, and the binding between the HCP2 and the KLCP in the presence of HCP2 to 50%). In one embodiment, the percent binding was measured by an assay described herein, e.g., the NanoBiT assay.

In one embodiment, when the HCP1, LLCP, HCP2, and KLCP are present under preselected conditions, e.g., in aqueous buffer, e.g., at pH 7, in saline, e.g., at pH 7, or under physiological conditions: at least 70, 75, 80, 90, 95, 98, 99, 99.5, or 99.9% of the HCP1 is complexed, or interfaced with, the LLCP. In one embodiment, when the HCP1, LLCP, HCP2, and KLCP are present under preselected conditions, e.g., in aqueous buffer, e.g., at pH 7, in saline, e.g., at pH 7, or under physiological conditions: at least 70, 75, 80, 90, 95, 98, 99, 99.5, or 99.9% of the LLCP is complexed, or interfaced with, the HCP1. In one embodiment, when the HCP1, LLCP, HCP2, and KLCP are present under preselected conditions, e.g., in aqueous buffer, e.g., at pH 7, in saline, e.g., at pH 7, or under physiological conditions: at least 70, 75, 80, 90, 95, 98, 99, 99.5, or 99.9% of the HCP2 is complexed, or interfaced with, the KLCP. In one embodiment, when the HCP1, LLCP, HCP2, and KLCP are present under preselected conditions, e.g., in aqueous buffer, e.g., at pH 7, in saline, e.g., at pH 7, or under physiological conditions: at least 70, 75, 80, 90, 95, 98, 99, 99.5, or 99.9% of the KLCP is complexed, or interfaced with, the HCP2.

In certain embodiments of the foregoing aspects, the multispecific antibody molecule comprises: i) a) the HCP1 comprises a first heavy chain constant region sequence (HCCRS) (e.g., a first CH1 sequence), i) b) the LLCP comprises a lambda light chain constant region sequence (LLCCRS), ii) a) the HCP2 comprises a second heavy chain constant region sequence (HCCRS) (e.g., a second CH1 sequence) and ii) b) the KLCP comprises a kappa light chain constant region sequence (KLCCRS), wherein: 1) the first HCCRS is complexed, or interfaced with, LLCCRS, and 2) the second HCCRS is complexed, or interfaced with, KLCCRS.

In certain embodiments of the foregoing aspects, the HCP1 is complexed, or interfaced with, the HCP2. In one embodiment, the HCP1 has a greater affinity, e.g., a substantially greater affinity, for HCP2, than for a second molecule of HCP1. In one embodiment, the HCP2 has a greater affinity, e.g., a substantially greater affinity, for HCP1, than for a second molecule of HCP2. In one embodiment, the HCP1 comprises a sequence element that increases the ratio of HCP1-HCP2: HCP1-HCP1 pairings, compared to the ratio that would be seen in the absence of the sequence element, e.g., where a naturally occurring sequence replaces the sequence element. In one embodiment, the HCP2 comprises a sequence element that increases the ratio of HCP1-HCP2: HCP2-HCP2 pairings, compared to the ratio that would be seen in the absence of the sequence element, e.g., where a naturally occurring sequence replaces the sequence element. In one embodiment, the sequence element is not a naturally occurring constant region sequence. In one embodiment, the sequence element is disposed in CH3. In one embodiment, one or both of HCP1 and HCP2 were selected to minimize self-dimerization (e.g., HCP1-HCP1) as opposed to heterodimerization (e.g., HCP2-HCP2). In one embodiment, HCP1 and HCP2 are members of a paired protuberance/cavity, e.g., knob and hole pair. In one embodiment, HCP1-HCP2 paring is promoted by an electrostatic interaction. In one embodiment, HCP1-HCP2 paring is promoted by strand exchange. In one embodiment, HCP1 and HCP2 are not members of a paired protuberance/cavity, e.g., knob and hole pair. In one embodiment, the HCP1 comprises a first heavy chain constant region sequence (HCCRS), wherein the first HCCRS does not comprise a mutation (e.g., a mutation relative to a naturally existing heavy chain constant region sequence). In one embodiment, the HCP2 comprises a second heavy chain constant region sequence (HCCRS), wherein the second HCCRS does not comprise a mutation (e.g., a mutation relative to a naturally existing heavy chain constant region sequence). In one embodiment, i) the HCP1 comprises a first heavy chain constant region sequence (HCCRS), wherein the first HCCRS does not comprise a mutation (e.g., a mutation relative to a naturally existing heavy chain constant region sequence); and ii) the HCP2 comprises a second heavy chain constant region sequence (HCCRS), wherein the second HCCRS does not comprise a mutation (e.g., a mutation relative to a naturally existing heavy chain constant region sequence). In one embodiment, the HCP1 comprises a first CH2 domain sequence and a first CH3 domain sequence, wherein the first CH2 domain sequence and the first CH3 domain sequence do not comprise a mutation (e.g., a mutation relative to a naturally existing CH2 domain sequence or a naturally existing CH3 domain sequence). In one embodiment, the HCP2 comprises a second CH2 domain sequence and a second CH3 domain sequence, wherein the second CH2 domain sequence and the second CH3 domain sequence do not comprise a mutation (e.g., a mutation relative to a naturally existing CH2 domain sequence or a naturally existing CH3 domain sequence). In one embodiment, i) the HCP1 comprises a first CH2 domain sequence and a first CH3 domain sequence, wherein the first CH2 domain sequence and the first CH3 domain sequence do not comprise a mutation (e.g., a mutation relative to a naturally existing CH2 domain sequence or a naturally existing CH3 domain sequence); and ii) the HCP2 comprises a second CH2 domain sequence and a second CH3 domain sequence, wherein the second CH2 domain sequence and the second CH3 domain sequence do not comprise a mutation (e.g., a mutation relative to a naturally existing CH2 domain sequence or a naturally existing CH3 domain sequence).

In certain embodiments of the foregoing aspects, the HCP1 is derived from an antibody arising, either in vivo or in vitro, as a lambda antibody. In certain embodiments of the foregoing aspects, the HCP2 is derived from an antibody arising, either in vivo or in vitro, as a kappa antibody.

In one embodiment, the HCP1 and LLCP comprise amino acid sequences selected from Table 18 (e.g., as paired in Table 18) or Table 5a (e.g., as paired in Table 5a), or functional variant or fragment thereof. In one embodiment, the HCP2 and KLCP comprise amino acid sequences selected from Table 18 (e.g., as paired in Table 18) or Table 5a (e.g., as paired in Table 5a), or functional variant or fragment thereof. In one embodiment, the HCP1, LLCP, HCP2, and KLCP comprise amino acid sequences selected from Table 18 (e.g., a single cell of Table 18) or Table 5a (e.g., a single row of Table 5a), or functional variant or fragment thereof.

In one embodiment, the first or second antigen is a tumor antigen, e.g., a pancreatic, lung, or colorectal tumor antigen. In one embodiment, the first or second antigen is chosen from: PD-L1, HER3, TROP2, mesothelin, IGF-1R, or CA19-9. In one embodiment, the first or second antigen is chosen from: PD-L1, HER3, TROP2, VEGF-A, EGFR, MUC1, DLL4, or HGF. In one embodiment, the first or second antigen is chosen from: PD-L1, HER3, TROP2, VEGF-A, EGFR, MUC1, MAGE-A3, gpA33, NY-ESO-1, ANG2, RSPO3, HER2, CEACAM5, or CEA. In one embodiment, the first or second antigen is an antigen of an immune effector cell, e.g., a T cell, an NK cell, or a myeloid cell. In one embodiment, the first or second antigen is chosen from: CD3, PD-1, LAG-3, TIM-3, CTLA-4, VISTA, TIGIT, PD-L1, B7-H3, 4-1BB, or ICOS. In one embodiment, the first antigen is a tumor antigen, e.g., mesothelin, and the second antigen is an antigen chosen from NKP30, PD-L1, CD3, NKG2D, CD47, 4-1BB, or NKP46; or the second antigen is a tumor antigen, e.g., mesothelin, and the first antigen is an antigen chosen from NKP30, PD-L1, CD3, NKG2D, CD47, 4-1BB, or NKP46. In one embodiment, the first antigen is IGF1R and the second antigen is HER3, or the second antigen is IGF1R and the first antigen is HER3. In one embodiment, the first antigen is mesothelin and the second antigen is PD-L1, or the second antigen is mesothelin and the first antigen is PD-L1. In one embodiment, the first antigen is CTLA4 and the second antigen is IL12β, or the second antigen is CTLA4 and the first antigen is IL12β. In one embodiment, the first antigen is CTLA4 and the second antigen is TRAILR2, or the second antigen is CTLA4 and the first antigen is TRAILR2. In one embodiment, the first antigen is CTLA4 and the second antigen is CD221, or the second antigen is CTLA4 and the first antigen is CD221. In one embodiment, the first antigen is PD1 and the second antigen is TRAILR2, or the second antigen is PD1 and the first antigen is TRAILR2. In one embodiment, the first antigen is PD1 and the second antigen is PDL1, or the second antigen is PD1 and the first antigen is PDL1. In one embodiment, the first antigen is PD1 and the second antigen is PDL1, or the second antigen is PD1 and the first antigen is PDL1. In one embodiment, the multispecific antibody molecule further comprises an IL-2 molecule. In one embodiment, the multispecific antibody molecule further comprises a CD40 agonist, e.g., a CD40L polypeptide or an agonistic anti-CD40 antibody molecule.

In one aspect, disclosed herein is a multispecific antibody molecule, e.g., an antibody molecule comprising two binding specificities, e.g., a bispecific antibody molecule. The multispecific antibody molecule includes: a lambda light chain polypeptide (LLCP) specific for a first epitope; a heavy chain polypeptide 1 (HCP1) specific for the first epitope; a kappa light chain polypeptide (KLCP) specific for a second epitope; and a heavy chain polypeptide 2 (HCP2) specific for the second epitope.

In another aspect, disclosed herein is a multispecific, e.g., a bispecific, antibody molecule that includes: (i) a first heavy chain polypeptide (HCP1) (e.g., a heavy chain polypeptide comprising one, two, three or all of a first heavy chain variable region (first VH), a first CH1, a first heavy chain constant region (e.g., a first CH2, a first CH3, or both)), e.g., wherein the HCP1 binds to a first epitope; (ii) a second heavy chain polypeptide (HCP2) (e.g., a heavy chain polypeptide comprising one, two, three or all of a second heavy chain variable region (second VH), a second CH1, a second heavy chain constant region (e.g., a second CH2, a second CH3, or both)), e.g., wherein the HCP2 binds to a second epitope; (iii) a lambda light chain polypeptide (LLCP) (e.g., a lambda light variable region (VLλ), a lambda light constant chain (VLλ), or both) that preferentially associates with the first heavy chain polypeptide (e.g., the first VH), e.g., wherein the LLCP binds to a first epitope; and (iv) a kappa light chain polypeptide (KLCP) (e.g., a kappa light variable region (VLK), a kappa light constant chain (VLK), or both) that preferentially associates with the second heavy chain polypeptide (e.g., the second VH), e.g., wherein the KLCP binds to a second epitope. In embodiments, the first and second heavy chain polypeptides form an Fc interface that enhances heterodimerization.

In some embodiments of the multispecific antibody molecule disclosed herein: LLCP has a higher affinity for HCP1 than for HCP2; and/or KLCP has a higher affinity for HCP2 than for HCP1.

In embodiments, the affinity of LLCP for HCP1 is sufficiently greater than its affinity for HCP2, such that under preselected conditions, e.g., in aqueous buffer, e.g., at pH 7, in saline, e.g., at pH 7, or under physiological conditions, at least 75%, 80, 90, 95, 98, 99, 99.5, or 99.9% of the multispecific antibody molecule molecules have a LLCP complexed, or interfaced with, a HCP1.

In some embodiments of the multispecific antibody molecule disclosed herein: the HCP1 has a greater affinity for HCP2, than for a second molecule of HCP1; and/or the HCP2 has a greater affinity for HCP1, than for a second molecule of HCP2.

In embodiments, the affinity of HCP1 for HCP2 is sufficiently greater than its affinity for a second molecule of HCP1, such that under preselected conditions, e.g., in aqueous buffer, e.g., at pH 7, in saline, e.g., at pH 7, or under physiological conditions, at least 75%, 80, 90, 95, 98, 99 99.5 or 99.9% of the multispecific antibody molecule molecules have a HCP1complexed, or interfaced with, a HCP2.

In another aspect, disclosed herein is a method for making, or producing, a multispecific antibody molecule. The method includes: (i) providing a first heavy chain polypeptide (e.g., a heavy chain polypeptide comprising one, two, three or all of a first heavy chain variable region (first VH), a first CH1, a first heavy chain constant region (e.g., a first CH2, a first CH3, or both)); (ii) providing a second heavy chain polypeptide (e.g., a heavy chain polypeptide comprising one, two, three or all of a second heavy chain variable region (second VH), a second CH1, a second heavy chain constant region (e.g., a second CH2, a second CH3, or both)); (iii) providing a lambda chain polypeptide (e.g., a lambda light variable region (VLλ), a lambda light constant chain (VLλ), or both) that preferentially associates with the first heavy chain polypeptide (e.g., the first VH); and (iv) providing a kappa chain polypeptide (e.g., a kappa light variable region (VLκ), a kappa light constant chain (VLκ), or both) that preferentially associates with the second heavy chain polypeptide (e.g., the second VH), under conditions where (i)-(iv) associate.

In embodiments, the first and second heavy chain polypeptides form an Fc interface that enhances heterodimerization.

In another aspect, disclosed herein is a method for making, or producing, a multispecific antibody molecule. The method includes: (i) providing a first heavy chain polypeptide (e.g., a heavy chain polypeptide comprising one, two, three or all of a first heavy chain variable region (first VH), a first CH1, a first heavy chain constant region (e.g., a first CH2, a first CH3, or both)); (ii) providing a second heavy chain polypeptide (e.g., a heavy chain polypeptide comprising one, two, three or all of a second heavy chain variable region (second VH), a second CH1, a second heavy chain constant region (e.g., a second CH2, a second CH3, or both)); (iii) providing a lambda chain polypeptide (e.g., a lambda light variable region (VLλ), a lambda light constant chain (VLλ), or both) that preferentially associates with the first heavy chain polypeptide (e.g., the first VH), and further comprising an effector moiety (e.g., IL2); and (iv) providing a kappa chain polypeptide (e.g., a kappa light variable region (VLκ), a kappa light constant chain (VLκ), or both) that preferentially associates with the second heavy chain polypeptide (e.g., the second VH), and optionally further comprising an antigen binding moiety (e.g., a scFv), under conditions where (i)-(iv) associate. In embodiments, (i)-(iv) (e.g., nucleic acid encoding (i)-(iv)) are introduced in a single cell, e.g., a single mammalian cell, e.g., a CHO cell. In embodiments, (i)-(iv) are expressed in the cell.

In embodiments, (i)-(iv) (e.g., nucleic acid encoding (i)-(iv)) are introduced in different cells, e.g., different mammalian cells, e.g., two or more CHO cell. In embodiments, (i)-(iv) are expressed in the cells.

In embodiments, the method further comprises purifying a cell-expressed antibody molecule, e.g., using a lambda- and/or-kappa-specific purification, e.g., affinity chromatography.

In embodiments, the method further comprises evaluating the cell-expressed multispecific antibody molecule. For example, the purified cell-expressed multispecific antibody molecule can be analyzed by techniques known in the art, include mass spectrometry. In one embodiment, the purified cell-expressed antibody molecule is cleaved, e.g., digested with papain to yield the Fab moieties and evaluated using mass spectrometry.

In embodiments, the method produces correctly paired kappa/lambda multispecific, e.g., bispecific, antibody molecules in a high yield, e.g., at least 75%, 80, 90, 95, 98, 99 99.5 or 99.9%.

Nucleic acid molecules, vectors and host cells encoding the aforesaid multispecific molecules are also disclosed.

Pharmaceutical compositions comprising the aforesaid multispecific molecules and a pharmaceutical acceptable carrier are also disclosed.

In another aspect, the invention features a method of treating a subject having a disorder, e.g., cancer, using the multispecific antibody molecules disclosed herein.

Additional features and embodiments of the multispecific antibody molecules and methods disclosed herein include one or more of the following.

In some embodiments, the multispecific antibody molecule is isolated or purified. In some embodiments, an interface of a first and second heavy chain polypeptide of the multispecific antibody molecule, e.g., the first and second heavy chain constant regions (e.g., a first and a second Fc region) is altered, e.g., mutated, to increase heterodimerization, e.g., relative to a non-engineered interface, e.g., a naturally-occurring interface. In one embodiment, heterodimerization of the first and second heavy chain polypeptides is enhanced by providing an Fc interface of a first and a second Fc region with one or more of: a paired protuberance-cavity ("knob-in-a hole"), an electrostatic interaction, or a strand-exchange, such that a greater ratio of heteromultimer to homomultimer forms, e.g., relative to a non-engineered interface. In some embodiments, the multispecific antibody molecules include a paired amino acid substitution at a position chosen from one or more of 347, 349, 350, 351, 366, 368, 370, 392, 394, 395, 397, 398, 399, 405, 407, or 409, e.g., of the Fc region of human IgG1 For example, the first immunoglobulin chain constant region (e.g., Fc region) can include a paired an amino acid substitution chosen from: T366S, L368A, or Y407V (e.g., corresponding to a cavity or hole), and the second immunoglobulin chain constant region comprises a T366W (e.g., corresponding to a protuberance or knob).

In some embodiments, an interface of a first and second heavy chain polypeptide of the multispecific antibody molecule, e.g., the first and second heavy chain constant regions (e.g., a first and a second Fc region) is not altered, e.g., not mutated, to increase heterodimerization, e.g., relative to a non-engineered interface, e.g., a naturally-occurring interface. In one embodiment, heterodimerization of the first and second heavy chain polypeptides is not enhanced by providing an Fc interface of a first and a second Fc region with one or more of: a paired protuberance-cavity ("knob-in-a hole").

In some embodiments, one or more (e.g., all) of a CH1 chain, a lambda light constant chain (VLλ), and a kappa light constant chain (VLκ) is not altered, e.g., not mutated, to increase heterodimerization, e.g., relative to a non-engineered interface, e.g., a naturally-occurring interface. In some embodiments, one or more (e.g., all) of a CH1 chain, a lambda light constant chain (VLλ), and a kappa light constant chain (VLκ) is naturally occurring.

In some embodiments, the heavy chain variable region (VH, e.g., FR1, FR2, FR3, and optionally, CDRs 1-2) is derived from a germline family described by IMGT®, the international ImMunoGeneTics (Lefranc, M.-P., "IMGT, the international ImMunoGeneTics database" *Nucl. Acids Res.*, 29, 207-209 (2001) and Scaviner, D., Barbié, V., Ruiz, M. and Lefranc, M.-P., "Protein displays of the human immunoglobulin heavy, kappa and lambda variable and joining regions", *Exp. Clin. Immunogenet.*, 16, 234-240 (1999)), or an amino acid sequence substantially identical thereto.

In some embodiments, the light chain variable region (VL kappa or lambda, e.g., FR1, FR2, FR3, and optionally, CDRs 1-2) is derived from a germline family described by IMGT, or an amino acid sequence substantially identical thereto.

In embodiments, the multispecific antibody molecules include a plurality (e.g., two, three or more) binding specificities (or functionalities).

In an embodiment, the multispecific antibody molecule is a bispecific (or bifunctional) molecule, a trispecific (or trifunctional) molecule, or a tetraspecific (or tetrafunctional) molecule.

In some embodiments, the multispecific antibody molecules include a first binding specificity to a first epitope, and a second binding specificity to a second epitope. In some embodiments, the first and second epitopes are on the same antigen, e.g., the same polypeptide. In other embodiments, the first and second epitopes are on different antigens, e.g., different polypeptide. In some embodiments, the first epitope is on a first antigen, e.g., a first polypeptide and the second epitope is on a second antigen, e.g., a second polypeptide. In some embodiments, the antigen, or polypeptide, is selected an antigen recognized by an antibody from Tables 2, 4, 5a, 17 and 18, e.g., a first and second antigen recognized by a lambda and kappa antibody disclosed in Tables 2, 4, 5a, 17 and 18. Exemplary pairings of lambda and kappa antibodies are depicted in Tables 5a and 18.

In some embodiments the multispecific antibody molecule includes a first binding specificity to a first epitope, wherein the first epitope is on a tumor antigen, e.g., a pancreatic, lung, or colorectal tumor antigen. In some embodiments, the first epitope is on an antigen chosen from: PD-L1, HER3, TROP2, mesothelin, IGF-1R, or CA19-9. In other embodiments, the first epitope is on an antigen chosen from PD-L1, HER3, TROP2, VEGF-A, EGFR, MUC1, DLL4, or HGF. In yet other embodiments, the first epitope is on an antigen chosen from PD-L1, HER3, TROP2, VEGF-A, EGFR, MUC1, MAGE-A3, gpA33, NY-ESO-1, ANG2, RSPO3, HER2, CEACAM5, or CEA.

In some embodiments, the multispecific antibody molecule includes a second binding specificity to a second epitope, wherein the second epitope is on an antigen of an immune effector cell, e.g., a T cell, an NK cell, or a myeloid cell. In some embodiments, the second epitope is chosen from CD3, PD-1, LAG-3, TIM-3, CTLA-4, VISTA, TIGIT, PD-L1, B7-H3, 4-1BB, or ICOS.

In some embodiments, the multispecific antibody molecule binds to a first epitope on a tumor antigen, e.g., mesothelin, and a second epitope on an antigen chosen from NKP30, PD-L1, CD3, NKG2D, CD47, 4-1BB, or NKP46. In some embodiments, the multispecific antibody molecule binds mesothelin and PD-L1. In some embodiments, the multispecific antibody molecule binds mesothelin and PDL1, and further comprises a cytokine (e.g., IL2). In some embodiments, the multispecific antibody molecule binds mesothelin; PDL1; and NKp30, and further comprises a cytokine (e.g., IL2).

In some embodiments, the multispecific antibody molecules include a plurality (e.g., two or more) binding specificities (or functionalities). In some embodiments, a first binding specificity selectively localizes to a cancer cell, e.g., it includes a tumor-targeting moiety; and the second (or third, or fourth) binding specificity includes one or both of: an immune cell engager (e.g., chosen from one, two, three, or all of an NK cell engager, a B cell engager, a dendritic cell engager, or a macrophage cell engager); and/or a cytokine molecule. Exemplary tumor-targeting moieties, immune cell engagers and cytokine molecules are described in the

DETAILED DESCRIPTION

Exemplary Embodiments 2

In one aspect, provided herein is a multispecific antibody molecule comprising: i) a first antigen-binding domain that binds to a first antigen, wherein the first antigen-binding domain comprises: a) a first heavy chain polypeptide (HCP1) comprising: a first heavy chain variable region sequence (HCVRS) sufficient that, when paired with i) b) allows the first antigen-binding domain to bind to the first antigen; and b) a lambda light chain polypeptide (LLCP) comprising: a lambda light chain variable region sequence (LLCVRS) sufficient that, when paired with i) a) allows the first antigen-binding domain to bind to the first antigen; and ii) a second antigen-binding domain that binds to a second antigen, wherein the second antigen-binding domain comprises: a) a second heavy chain polypeptide (HCP2) comprising: a second heavy chain variable region sequence (HCVRS) sufficient that, when paired with ii) b) allows the second antigen-binding domain to bind to the second antigen; and b) a kappa light chain polypeptide (KLCP) comprising: a kappa light chain variable region sequence (KLCVRS) sufficient that, when paired with ii) a) allows the second antigen-binding domain to bind to the second antigen, wherein: 1) the first HCVRS has at least 75, 80, 85, 90, 95, 98, or 100% sequence identity with a first heavy chain germline sequence selected from column 3 of Table 7, column 2 of Table 8b, or column 2 of Table 5b; 2) the LLCVRS has at least 75, 80, 85, 90, 95, 98, or 100% sequence identity with a lambda light chain germline sequence selected from column 4 of Table 7, column 3 of Table 8b; or column 3 of Table 5b; 3) the second HCVRS has at least 75, 80, 85, 90, 95, 98, or 100% sequence identity with a second heavy chain germline sequence selected from column 3 of Table 6, column 5 of Table 8b, or column 4 of Table 5b; or 4) the KLCVRS has at least 75, 80, 85, 90, 95, 98, or 100% sequence identity with a kappa light chain germline sequence selected from column 4 of Table 6, column 6 of Table 8b, or column 5 of Table 5b.

In some embodiments, 1) the first HCVRS has at least 75, 80, 85, 90, 95, 98, or 100% sequence identity with a first heavy chain germline sequence selected from column 3 of Table 7, column 2 of Table 8b, or column 2 of Table 5b.

In some embodiments, 2) the LLCVRS has at least 75, 80, 85, 90, 95, 98, or 100% sequence identity with a lambda light chain germline sequence selected from column 4 of Table 7, column 3 of Table 8b; or column 3 of Table 5b.

In some embodiments, 3) the second HCVRS has at least 75, 80, 85, 90, 95, 98, or 100% sequence identity with a second heavy chain germline sequence selected from column 3 of Table 6, column 5 of Table 8b, or column 4 of Table 5b.

In some embodiments, 4) the KLCVRS has at least 75, 80, 85, 90, 95, 98, or 100% sequence identity with a kappa light chain germline sequence selected from column 4 of Table 6, column 6 of Table 8b, or column 5 of Table 5b.

In some embodiments, the first heavy chain germline sequence and the lambda light chain germline sequence are selected from a single row of Table 7, Table 8b, or Table 5b.

In some embodiments, the first heavy chain germline sequence, the lambda light chain germline sequence, and the kappa light chain germline sequence are selected from a single row of Table 7, Table 8b, or Table 5b.

In some embodiments, the second heavy chain germline sequence and the kappa light chain germline sequence are selected from a single row of Table 6, Table 8b, or Table 5b.

In some embodiments, the second heavy chain germline sequence, the kappa light chain germline sequence, and the lambda light chain germline sequence are selected from a single row of Table 6, Table 8b, or Table 5b.

In some embodiments, at least two (e.g., two, three, or all) of the following: the first heavy chain germline sequence, the lambda light chain germline sequence, the second heavy chain germline sequence, and the kappa light chain germline sequence, are selected from a single row of Table 8b or Table 5b.

In some embodiments, 2) the LLCVRS has at least 75, 80, 85, 90, 95, 98, or 100% sequence identity with a lambda light chain germline sequence selected from column 4 of Table 7, column 3 of Table 8b; or column 3 of Table 5b.

In some embodiments, 1) the first HCVRS has at least 75, 80, 85, 90, 95, 98, or 100% sequence identity with a first heavy chain germline sequence selected from column 3 of Table 7, column 2 of Table 8b, or column 2 of Table 5b.

In some embodiments, 3) the second HCVRS has at least 75, 80, 85, 90, 95, 98, or 100% sequence identity with a second heavy chain germline sequence selected from column 3 of Table 6, column 5 of Table 8b, or column 4 of Table 5b.

In some embodiments, 4) the KLCVRS has at least 75, 80, 85, 90, 95, 98, or 100% sequence identity with a kappa light chain germline sequence selected from column 4 of Table 6, column 6 of Table 8b, or column 5 of Table 5b.

In some embodiments, the first heavy chain germline sequence and the lambda light chain germline sequence are selected from a single row of Table 7, Table 8b, or Table 5b.

In some embodiments, the second heavy chain germline sequence and the kappa light chain germline sequence are selected from a single row of Table 6, Table 8b, or Table 5b.

In some embodiments, the second heavy chain germline sequence, the kappa light chain germline sequence, and the lambda light chain germline sequence are selected from a single row of Table 6, Table 8b, or Table 5b.

In some embodiments, at least two (e.g., two, three, or all) of the following: the first heavy chain germline sequence, the lambda light chain germline sequence, the second heavy chain germline sequence, and the kappa light chain germline sequence, are selected from a single row of Table 8b or Table 5b.

In some embodiments, 3) the second HCVRS has at least 75, 80, 85, 90, 95, 98, or 100% sequence identity with a second heavy chain germline sequence selected from column 3 of Table 6, column 5 of Table 8b, or column 4 of Table 5b.

In some embodiments, 1) the first HCVRS has at least 75, 80, 85, 90, 95, 98, or 100% sequence identity with a first heavy chain germline sequence selected from column 3 of Table 7, column 2 of Table 8b, or column 2 of Table 5b.

In some embodiments, 2) the LLCVRS has at least 75, 80, 85, 90, 95, 98, or 100% sequence identity with a lambda light chain germline sequence selected from column 4 of Table 7, column 3 of Table 8b; or column 3 of Table 5b.

In some embodiments, 4) the KLCVRS has at least 75, 80, 85, 90, 95, 98, or 100% sequence identity with a kappa light chain germline sequence selected from column 4 of Table 6, column 6 of Table 8b, or column 5 of Table 5b.

In some embodiments, the first heavy chain germline sequence and the lambda light chain germline sequence are selected from a single row of Table 7, Table 8b, or Table 5b.

In some embodiments, the first heavy chain germline sequence, the lambda light chain germline sequence, and the kappa light chain germline sequence are selected from a single row of Table 7, Table 8b, or Table 5b.

In some embodiments, the second heavy chain germline sequence and the kappa light chain germline sequence are selected from a single row of Table 6, Table 8b, or Table 5b.

In some embodiments, the second heavy chain germline sequence, the kappa light chain germline sequence, and the lambda light chain germline sequence are selected from a single row of Table 6, Table 8b, or Table 5b.

In some embodiments, at least two (e.g., two, three, or all) of the following: the first heavy chain germline sequence, the lambda light chain germline sequence, the second heavy chain germline sequence, and the kappa light chain germline sequence, are selected from a single row of Table 8b or Table 5b.

In some embodiments, 4) the KLCVRS has at least 75, 80, 85, 90, 95, 98, or 100% sequence identity with a kappa light chain germline sequence selected from column 4 of Table 6, column 6 of Table 8b, or column 5 of Table 5b.

In some embodiments, 1) the first HCVRS has at least 75, 80, 85, 90, 95, 98, or 100% sequence identity with a first heavy chain germline sequence selected from column 3 of Table 7, column 2 of Table 8b, or column 2 of Table 5b.

In some embodiments, 2) the LLCVRS has at least 75, 80, 85, 90, 95, 98, or 100% sequence identity with a lambda light chain germline sequence selected from column 4 of Table 7, column 3 of Table 8b; or column 3 of Table 5b.

In some embodiments, 3) the second HCVRS has at least 75, 80, 85, 90, 95, 98, or 100% sequence identity with a second heavy chain germline sequence selected from column 3 of Table 6, column 5 of Table 8b, or column 4 of Table 5b.

In some embodiments, the first heavy chain germline sequence and the lambda light chain germline sequence are selected from a single row of Table 7, Table 8b, or Table 5b.

In some embodiments, the first heavy chain germline sequence, the lambda light chain germline sequence, and the kappa light chain germline sequence are selected from a single row of Table 7, Table 8b, or Table 5b.

In some embodiments, the second heavy chain germline sequence and the kappa light chain germline sequence are selected from a single row of Table 6, Table 8b, or Table 5b.

In some embodiments, the second heavy chain germline sequence, the kappa light chain germline sequence, and the lambda light chain germline sequence are selected from a single row of Table 6, Table 8b, or Table 5b.

In some embodiments, at least two (e.g., two, three, or all) of the following: the first heavy chain germline sequence, the lambda light chain germline sequence, the second heavy chain germline sequence, and the kappa light chain germline sequence, are selected from a single row of Table 8b or Table 5b.

In some embodiments, the first heavy chain germline sequence, the lambda light chain germline sequence, the second heavy chain germline sequence, and the kappa light chain germline sequence are selected from a single row of Table 8b or Table 5b.

In another aspect, provided herein is a multispecific antibody molecule comprising: i) a first antigen-binding domain that binds to a first antigen, wherein the first antigen-binding domain comprises: a) a first heavy chain polypeptide (HCP1) comprising: a first heavy chain variable region sequence (HCVRS) sufficient that, when paired with i) b) allows the first antigen-binding domain to bind to the first antigen; and b) a lambda light chain polypeptide (LLCP) comprising: a lambda light chain variable region sequence (LLVRS) sufficient that, when paired with i) a) allows the first antigen-binding domain to bind to the first antigen; and ii) a second antigen-binding domain that binds to a second antigen, wherein the second antigen-binding domain comprises: a) a second heavy chain polypeptide (HCP2) comprising: a second heavy chain variable region sequence (HCVRS) sufficient that, when paired with ii) b) allows the second antigen-binding domain to bind to the second antigen; and b) a kappa light chain polypeptide (KLCP) comprising: a kappa light chain variable region sequence (KLCVRS) sufficient that, when paired with ii) a) allows the second antigen-binding domain to bind to the second antigen, wherein: the multispecific antibody molecule further comprises an accessory moiety, wherein the accessory moiety has a property chosen from: 1) the accessory moiety has a molecular weight of at least 10, 20, 30, 40, 50, 60, 70, 80, 90, or 100 kDa; 2) the accessory moiety comprises a polypeptide having at least 30, 40, 50, 60, 70, 80, 90, or 100 amino acid residues; 3) the accessory moiety comprises a polypeptide having the ability to modulate the activity of an immune cell, e.g., a T cell, a B cell, an antigen presenting cell (APC), or an NK cell; or 4) the accessory moiety is chosen from one or more of an immune cell engager (e.g., a CD40 agonist, e.g., a CD40L polypeptide or an agonistic anti-CD40 antibody molecule, or a PD-1 binding moiety, e.g., a PD-1 binding sequence of PDL-1 or an anti-PD-1 antibody molecule), a cytokine molecule (e.g. an IL-2 molecule), a cytokine antagonist (e.g., a TGF-β antagonist), an enzyme, a toxin, or a labeling agent.

In some embodiments, the multispecific antibody molecule further comprises an accessory moiety, wherein the accessory moiety has a property chosen from: 1) the accessory moiety has a molecular weight of at least 10, 20, 30, 40, 50, 60, 70, 80, 90, or 100 kDa; 2) the accessory moiety comprises a polypeptide having at least 30, 40, 50, 60, 70, 80, 90, or 100 amino acid residues; 3) the accessory moiety comprises a polypeptide having the ability to modulate the active of an immune cell, e.g., a T cell, a B cell, an antigen presenting cell (APC), or an NK cell; or 4) the accessory moiety is chosen from one or more of an immune cell engager (e.g., a CD40 agonist, e.g., a CD40L polypeptide or an agonistic anti-CD40 antibody molecule, or a PD-1 binding moiety, e.g., a PD-1 binding sequence of PDL-1 or an anti-PD-1 antibody molecule), a cytokine molecule (e.g. an IL-2 molecule), a cytokine antagonist (e.g., a TGF-β antagonist), an enzyme, a toxin, or a labeling agent.

In some embodiments, the accessory moiety is fused to the polypeptide of a, b, c, or d of the multispecific antibody molecule.

In some embodiments, the accessory moiety is fused to any of the following: the HCP1, first HCVRS, LLCP, LLCVRS, HCP2, second HCVRS, KLCP, or KLCVRS of the multispecific antibody molecule, e.g., the C-terminus or N-terminus of HCP1, first HCVRS, LLCP, LLCVRS, HCP2, second HCVRS, KLCP, or KLCVRS of the multispecific antibody molecule.

In some embodiments, the HCP1 comprises a first heavy chain constant region sequence (HCCRS) (e.g., CH1, CH2, and CH3 sequences), wherein the accessory moiety is fused to the first HCCRS, e.g., the C-terminus of the first HCCRS.

In some embodiments, the HCP2 comprises a second heavy chain constant region sequence (HCCRS) (e.g., CH1, CH2, and CH3 sequences), wherein the accessory moiety is fused to the second HCCRS, e.g., the C-terminus of the second HCCRS.

In some embodiments, the LLCP comprises a lambda light chain constant region sequence (LLCCRS), wherein the accessory moiety is fused to the LLCCRS, e.g., the C-terminus of the LLCCRS.

In some embodiments, the KLCP comprises a kappa light chain constant region sequence (KLCCRS), wherein the accessory moiety is fused to the KLCCRS, e.g., the C-terminus of the KLCCRS.

In some embodiments, the multispecific antibody molecule as provided herein comprises a first accessory moiety and a second accessory moiety, wherein the first or second accessory moiety has a property chosen from: 1) the first or second accessory moiety has a molecular weight of at least 10, 20, 30, 40, 50, 60, 70, 80, 90, or 100 kDa; 2) the first or second accessory moiety comprises a polypeptide having at least 30, 40, 50, 60, 70, 80, 90, or 100 amino acid residues; 3) the first or second accessory moiety comprises a polypeptide having the ability to modulate the active of an immune cell, e.g., a T cell, a B cell, an antigen presenting cell (APC), or an NK cell; or 4) the first or second accessory moiety is chosen from one or more of an immune cell engager (e.g., a CD40 agonist, e.g., a CD40L polypeptide or an agonistic anti-CD40 antibody molecule, or a PD-1 binding moiety, e.g., a PD-1 binding sequence of PDL-1 or an anti-PD-1 antibody molecule), a cytokine molecule (e.g. an IL-2 molecule), a cytokine antagonist (e.g., a TGF-β antagonist), an enzyme, a toxin, or a labeling agent.

In some embodiments, the first and second accessory moieties are the same.

In some embodiments, the first and second accessory moieties are different.

In some embodiments, i) the first accessory moiety is fused to the HCP1 or HCP2, e.g., the C-terminus of the HCP1 or HCP2; and ii) the second accessory moiety is fused to the LLCP or KLCP, e.g., the C-terminus of the LLCP or KLCP.

In some embodiments, i) the HCP1 comprises a first heavy chain constant region sequence (HCCRS) (e.g., CH1, CH2, and CH3 sequences), wherein the first accessory moiety is fused to the first HCCRS, e.g., the C-terminus of the first HCCRS; and ii) the LLCP comprises a lambda light chain constant region sequence (LLCCRS), wherein the second accessory moiety is fused to the LLCCRS, e.g., the C-terminus of the LLCCRS.

In some embodiments, i) the HCP2 comprises a second heavy chain constant region sequence (HCCRS) (e.g., CH1, CH2, and CH3 sequences), wherein the accessory moiety is fused to the second HCCRS, e.g., the C-terminus of the second HCCRS; and ii) the KLCP comprises a kappa light chain constant region sequence (KLCCRS), wherein the accessory moiety is fused to the KLCCRS, e.g., the C-terminus of the KLCCRS.

In another aspect, provided herein is a multispecific antibody molecule comprising: i) a first antigen-binding domain that binds to a first antigen, wherein the first antigen-binding domain comprises: a) a first heavy chain polypeptide (HCP1) comprising: a first heavy chain variable region sequence (HCVRS) sufficient that, when paired with i) b) allows the first antigen-binding domain to bind to the first antigen; and a first heavy chain constant region sequence (HCCRS) (e.g., a first CH1 sequence), and b) a lambda light chain polypeptide (LLCP) comprising: a lambda light chain variable region sequence (LLCVRS) sufficient that, when paired with i) a) allows the first antigen-binding domain to bind to the first antigen; and a lambda light chain constant region sequence (LLCCRS), and ii) a second antigen-binding domain that binds to a second antigen, wherein the second antigen-binding domain comprises: a) a second heavy chain polypeptide (HCP2) comprising: a second heavy chain variable region sequence (HCVRS) sufficient that, when paired with ii) b) allows the second antigen-binding domain to bind to the second antigen; and a second heavy chain constant region sequence (HCCRS) (e.g., a second CH1 sequence) and b) a kappa light chain polypeptide (KLCP) comprising: a kappa light chain variable region sequence (KLCVRS) sufficient that, when paired with ii) a) allows the second antigen-binding domain to bind to the second antigen; and a kappa light chain constant region sequence (KLCCRS), wherein: 1) the multispecific antibody molecule does not comprise a mutation in the first HCCRS (e.g., a mutation relative to a naturally existing heavy chain constant region sequence) that promotes the preferential pairing of the HCP1 and the LLCP, compared with pairing of the HCP1 and the LLCP without the mutation, or the multispecific antibody molecule does not comprise a mutation in the LLCCRS (e.g., a mutation relative to a naturally existing lambda light chain constant region sequence) that promotes the preferential pairing of the HCP1 and the LLCP, compared with pairing of the HCP1 and the LLCP without the mutation; and 2) the multispecific antibody molecule does not comprise a mutation in the second HCCRS (e.g., a mutation relative to a naturally existing heavy chain constant region sequence) that promotes the preferential pairing of the HCP2 and the KLCP, compared with pairing of the HCP2 and the KLCP without the mutation, or the multispecific antibody molecule does not comprise a mutation in the KLCCRS (e.g., a mutation relative to a naturally existing kappa light chain constant region sequence) that promotes the preferential pairing of the HCP2 and the KLCP, compared with pairing of the HCP2 and the KLCP without the mutation.

In some embodiments, i) a) the HCP1 comprises a first heavy chain constant region sequence (HCCRS) (e.g., a first CH1 sequence), i) b) the LLCP comprises a lambda light chain constant region sequence (LLCCRS), ii) a) the HCP2 comprises a second heavy chain constant region sequence (HCCRS) (e.g., a second CH1 sequence), and ii) b) the KLCP comprises a kappa light chain constant region sequence (KLCCRS), wherein: 1) the multispecific antibody molecule does not comprise a mutation in the first HCCRS (e.g., a mutation relative to a naturally existing heavy chain constant region sequence) that promotes the preferential pairing of the HCP1 and the LLCP, compared with pairing of the HCP1 and the LLCP without the mutation, or the multispecific antibody molecule does not comprise a mutation in the LLCCRS (e.g., a mutation relative to a naturally existing lambda light chain constant region sequence) that promotes the preferential pairing of the HCP1 and the LLCP, compared with pairing of the HCP1 and the LLCP without the mutation; and 2) the multispecific antibody molecule does not comprise a mutation in the second HCCRS (e.g., a mutation relative to a naturally existing heavy chain constant region sequence) that promotes the preferential pairing of the HCP2 and the KLCP, compared with pairing of the HCP2 and the KLCP without the mutation, or the multispecific antibody molecule does not comprise a mutation in the KLCCRS (e.g., a mutation relative to a naturally existing kappa light chain constant region sequence) that promotes the preferential pairing of the HCP2 and the KLCP, compared with pairing of the HCP2 and the KLCP without the mutation.

In some embodiments, the multispecific antibody molecule does not comprise a mutation in the first HCCRS (e.g., a mutation relative to a naturally existing heavy chain constant region sequence) that increases the preferential pairing of the HCP1 and the LLCP by at least 1.5, 2, 3, 4, 5, 6, 7, 8, 9, 10, 20, 30, 40, or 50 folds, compared with pairing of the HCP1 and the LLCP without the mutation, or the multispecific antibody molecule does not comprise a mutation in the LLCCRS (e.g., a mutation relative to a naturally existing lambda light chain constant region sequence) that increases the preferential pairing of the HCP1 and the LLCP by at least 1.5, 2, 3, 4, 5, 6, 7, 8, 9, 10, 20, 30, 40, or 50 folds, compared with pairing of the HCP1 and the LLCP without the mutation.

In some embodiments, the multispecific antibody molecule does not comprise a mutation in the second HCCRS (e.g., a mutation relative to a naturally existing heavy chain constant region sequence) that increases the preferential pairing of the HCP2 and the KLCP by at least 1.5, 2, 3, 4, 5, 6, 7, 8, 9, 10, 20, 30, 40, or 50 folds, compared with pairing of the HCP2 and the KLCP without the mutation, or the multispecific antibody molecule does not comprise a mutation in the KLCCRS (e.g., a mutation relative to a naturally existing kappa light chain constant region sequence) that increases the preferential pairing of the HCP2 and the KLCP by at least 1.5, 2, 3, 4, 5, 6, 7, 8, 9, 10, 20, 30, 40, or 50 folds, compared with pairing of the HCP2 and the KLCP without the mutation.

In another aspect, provided herein is a multispecific antibody molecule comprising: i) a first antigen-binding domain that binds to a first antigen, wherein the first antigen-binding domain comprises: a) a first heavy chain polypeptide (HCP1) comprising: a first heavy chain variable region sequence (HCVRS) sufficient that, when paired with i) b) allows the first antigen-binding domain to bind to the first antigen; and a first heavy chain constant region sequence (HCCRS) (e.g., a first CH1 sequence), and b) a lambda light chain polypeptide (LLCP) comprising: a lambda light chain variable region sequence (LLCVRS) sufficient that, when paired with i) a) allows the first antigen-binding domain to bind to the first antigen; and a lambda light chain constant region sequence (LLCCRS), and ii) a second antigen-binding domain that binds to a second antigen, wherein the second antigen-binding domain comprises: a) a second heavy chain polypeptide (HCP2) comprising: a second heavy chain variable region sequence (HCVRS) sufficient that, when paired with ii) b) allows the second antigen-binding domain to bind to the second antigen; and a second heavy chain constant region sequence (HCCRS) (e.g., a second CH1 sequence) and b) a kappa light chain polypeptide (KLCP) comprising: a kappa light chain variable region sequence (KLCVRS) sufficient that, when paired with ii) a) allows the second antigen-binding domain to bind to the second antigen; and a kappa light chain constant region sequence (KLCCRS), wherein: 1) the multispecific antibody molecule does not comprise a mutation in the first HCCRS (e.g., a mutation relative to a naturally existing heavy chain constant region sequence), or the multispecific antibody molecule does not comprise a mutation in the LLCCRS (e.g., a mutation relative to a naturally existing lambda light chain constant region sequence); and 2) the multispecific antibody molecule does not comprise a mutation in the second HCCRS (e.g., a mutation relative to a naturally existing heavy chain constant region sequence), or the multispecific antibody molecule does not comprise a mutation in the KLCCRS (e.g., a mutation relative to a naturally existing kappa light chain constant region sequence).

In some embodiments, the multispecific antibody molecule as provided herein comprises: i) a) the HCP1 comprises a first heavy chain constant region sequence (HCCRS) (e.g., a first CH1 sequence), i) b) the LLCP comprises a lambda light chain constant region sequence (LLCCRS), ii) a) the HCP2 comprises a second heavy chain constant region sequence (HCCRS) (e.g., a second CH1 sequence), and ii) b) the KLCP comprises a kappa light chain constant region sequence (KLCCRS), wherein: 1) the multispecific antibody molecule does not comprise a mutation in the first HCCRS (e.g., a mutation relative to a naturally existing heavy chain constant region sequence), or the multispecific antibody molecule does not comprise a mutation in the LLCCRS (e.g., a mutation relative to a naturally existing lambda light chain constant region sequence); and 2) the multispecific antibody molecule does not comprise a mutation in the second HCCRS (e.g., a mutation relative to a naturally existing heavy chain constant region sequence), or the multispecific antibody molecule does not comprise a mutation in the KLCCRS (e.g., a mutation relative to a naturally existing kappa light chain constant region sequence).

In some embodiments, the multispecific antibody molecule does not comprise a mutation in any of the following: the first HCCRS, the LLCCRS, the second HCCRS, and the KLCCRS (e.g., a mutation relative to a naturally existing heavy chain constant region sequence, a naturally existing lambda light chain constant region sequence, or a naturally existing kappa light chain constant region sequence).

In another aspect, provided herein is a multispecific antibody molecule comprising: i) a first antigen-binding domain that binds to a first antigen, wherein the first antigen-binding domain comprises: a) a first heavy chain polypeptide (HCP1) comprising: a first heavy chain variable region sequence (HCVRS) sufficient that, when paired with i) b) allows the first antigen-binding domain to bind to the first antigen; and a first heavy chain constant region sequence (HCCRS) (e.g., a first CH1 sequence), and b) a lambda light chain polypeptide (LLCP) comprising: a lambda light chain variable region sequence (LLCVRS) sufficient that, when paired with i) a) allows the first antigen-binding domain to bind to the first antigen; and a lambda light chain constant region sequence (LLCCRS), and ii) a second antigen-binding domain that binds to a second antigen, wherein the second antigen-binding domain comprises: a) a second heavy chain polypeptide (HCP2) comprising: a second heavy chain variable region sequence (HCVRS) sufficient that, when paired with ii) b) allows the second antigen-binding domain to bind to the second anti-gen; and a second heavy chain constant region sequence (HCCRS) (e.g., a second CH1 sequence) and b) a kappa light chain polypeptide (KLCP) comprising: a kappa light chain variable region sequence (KLCVRS) sufficient that, when paired with ii) a) allows the second antigen-binding domain to bind to the second antigen; and a kappa light chain constant region sequence (KLCCRS), wherein: 1) the first HCCRS comprises a naturally existing heavy chain constant region sequence, or the LLCCRS comprises a naturally existing lambda light chain constant region sequence; and 2) the second HCCRS comprises a naturally existing heavy chain constant region sequence, or the KLCCRS comprises a naturally existing kappa light chain constant region sequence.

In some embodiments, i) a) the HCP1 comprises a first heavy chain constant region sequence (HCCRS) (e.g., a first CH1 sequence), i) b) the LLCP comprises a lambda light chain constant region sequence (LLCCRS), ii) a) the HCP2 comprises a second heavy chain constant region sequence (HCCRS) (e.g., a second CH1 sequence), and ii) b) the KLCP comprises a kappa light chain constant region sequence (KLCCRS), wherein: 1) the first HCCRS comprises a naturally existing heavy chain constant region sequence, or the LLCCRS comprises a naturally existing lambda light chain constant region sequence; and 2) the second HCCRS comprises a naturally existing heavy chain constant region sequence, or the KLCCRS comprises a naturally existing kappa light chain constant region sequence.

In some embodiments, i) the first HCCRS comprises a naturally existing heavy chain constant region sequence, ii) the LLCCRS comprises a naturally existing lambda light chain constant region sequence, iii) the second HCCRS comprises a naturally existing heavy chain constant region sequence, and iv) the KLCCRS comprises a naturally existing kappa light chain constant region sequence.

In some embodiments, the HCP1 preferentially binds to the LLCP over the KLCP.

In some embodiments, the LLCP preferentially binds to the HCP1 over the HCP2.

In some embodiments, the HCP2 preferentially binds to the KLCP over the LLCP.

In some embodiments, the KLCP preferentially binds to the HCP2 over the HCP1.

In some embodiments, the HCP1 has a higher affinity, e.g., a substantially higher affinity, for the LLCP than for the KLCP (e.g., the KD for the binding between the HCP1 and the LLCP is no more than 50%, 40%, 30%, 20%, 10%, 1%, 0.1%, or 0.01% of the KD for the binding between the HCP1 and the KLCP).

In some embodiments, the LLCP has a higher affinity, e.g., a substantially higher affinity, for the HCP1 than for the HCP2 (e.g., the KD for the binding between the LLCP and the HCP1 is no more than 50%, 40%, 30%, 20%, 10%, 1%, 0.1%, or 0.01% of the KD for the binding between the LLCP and the first HCP2).

In some embodiments, the HCP2 has a higher affinity, e.g., a substantially higher affinity, for the KLCP than for the LLCP (e.g., the KD for the binding between the HCP2 and the KLCP is no more than 50%, 40%, 30%, 20%, 10%, 1%, 0.1%, or 0.01% of the KD for the binding between the HCP2 and the LLCP).

In some embodiments, the KLCP has a higher affinity, e.g., a substantially higher affinity, for the HCP2 than for the HCP1 (e.g., the KD for the binding between the KLCP and the HCP2 is no more than 50%, 40%, 30%, 20%, 10%, 1%, 0.1%, or 0.01% of the KD for the binding between the KLCP and the HCP1).

In some embodiments, the percent binding between the HCP1 and the LLCP in the presence of the KLCP is at least 75, 80, 90, 95, 98, 99, or 99.5%.

In some embodiments, the percent binding between the HCP1 and the LLCP in the presence of the HCP2 is at least 75, 80, 90, 95, 98, 99, or 99.5%.

In some embodiments, the percent binding between the HCP2 and the KLCP in the presence of the LLCP is at least 75, 80, 90, 95, 98, 99, or 99.5%.

In some embodiments, the percent binding between the HCP2 and the KLCP in the presence of the HCP1 is at least 75, 80, 90, 95, 98, 99, or 99.5%.

In some embodiments, when the HCP1, LLCP, HCP2, and KLCP are present under preselected conditions, e.g., in aqueous buffer, e.g., at pH 7, in saline, e.g., at pH 7, or under physiological conditions: i) at least 70, 75, 80, 90, 95, 98, 99, 99.5, or 99.9% of the HCP1 is complexed, or interfaced with, the LLCP; ii) at least 70, 75, 80, 90, 95, 98, 99, 99.5, or 99.9% of the LLCP is complexed, or interfaced with, the HCP1; iii) at least 70, 75, 80, 90, 95, 98, 99, 99.5, or 99.9% of the HCP2 is complexed, or interfaced with, the KLCP; or iv) at least 70, 75, 80, 90, 95, 98, 99, 99.5, or 99.9% of the KLCP is complexed, or interfaced with, the HCP2.

In some embodiments, the HCP1 is complexed, or interfaced with, the HCP2.

In some embodiments, the HCP1 has a greater affinity, e.g., a substantially greater affinity, for HCP2, than for a second molecule of HCP1.

In some embodiments, the HCP2 has a greater affinity, e.g., a substantially greater affinity, for HCP1, than for a second molecule of HCP2.

In some embodiments, the HCP1 comprises a sequence element that increases the ratio of HCP1-HCP2: HCP1-HCP1 pairings, compared to the ratio that would be seen in the absence of the sequence element, e.g., where a naturally occurring sequence replaces the sequence element.

In some embodiments, the HCP2 comprises a sequence element that increases the ratio of HCP1-HCP2: HCP2-HCP2 pairings, compared to the ratio that would be seen in the absence of the sequence element, e.g., where a naturally occurring sequence replaces the sequence element.

In some embodiments, the sequence element is not a naturally occurring constant region sequence.

In some embodiments, the sequence element is disposed in CH3.

In some embodiments, one or both of HCP1 and HCP2 were selected to minimize self-dimerization (e.g., HCP1-HCP1) as opposed to heterodimerization (e.g., HCP2-HCP2).

In some embodiments, HCP1 and HCP2 are members of a paired protuberance/cavity, e.g., knob and hole pair.

In some embodiments, HCP1-HCP2 paring is promoted by an electrostatic interaction.

In some embodiments, HCP1-HCP2 paring is promoted by strand exchange.

In some embodiments, HCP1 and HCP2 are not members of a paired protuberance/cavity, e.g., knob and hole pair.

In some embodiments, the HCP1 comprises a first heavy chain constant region sequence (HCCRS), wherein the first HCCRS does not comprise a mutation (e.g., a mutation relative to a naturally existing heavy chain constant region sequence).

In some embodiments, the HCP2 comprises a second heavy chain constant region sequence (HCCRS), wherein the second HCCRS does not comprise a mutation (e.g., a mutation relative to a naturally existing heavy chain constant region sequence).

In some embodiments, i) the HCP1 comprises a first heavy chain constant region sequence (HCCRS), wherein the first HCCRS does not comprise a mutation (e.g., a mutation relative to a naturally existing heavy chain constant region sequence); and ii) the HCP2 comprises a second heavy chain constant region sequence (HCCRS), wherein the second HCCRS does not comprise a mutation (e.g., a mutation relative to a naturally existing heavy chain constant region sequence).

In some embodiments, the HCP1 comprises a first CH2 domain sequence and a first CH3 domain sequence, wherein the first CH2 domain sequence and the first CH3 domain sequence do not comprise a mutation (e.g., a mutation relative to a naturally existing CH2 domain sequence or a naturally existing CH3 domain sequence).

In some embodiments, the HCP2 comprises a second CH2 domain sequence and a second CH3 domain sequence, wherein the second CH2 domain sequence and the second CH3 domain sequence do not comprise a mutation (e.g., a mutation relative to a naturally existing CH2 domain sequence or a naturally existing CH3 domain sequence).

In some embodiments, i) the HCP1 comprises a first CH2 domain sequence and a first CH3 domain sequence, wherein the first CH2 domain sequence and the first CH3 domain sequence do not comprise a mutation (e.g., a mutation relative to a naturally existing CH2 domain sequence or a naturally existing CH3 domain sequence); and ii) the HCP2 comprises a second CH2 domain sequence and a second CH3 domain sequence, wherein the second CH2 domain sequence and the second CH3 domain sequence do not comprise a mutation (e.g., a mutation relative to a naturally existing CH2 domain sequence or a naturally existing CH3 domain sequence).

In some embodiments, the HCP1 is derived from an antibody arising, either in vivo or in vitro, as a lambda antibody.

In some embodiments, the HCP2 is derived from an antibody arising, either in vivo or in vitro, as a kappa antibody.

In some embodiments, the HCP1 and LLCP comprise amino acid sequences selected from Table 18 (e.g., as paired in Table 18) or Table 5a (e.g., as paired in Table 5a), or functional variant or fragment thereof.

In some embodiments, the HCP2 and KLCP comprise amino acid sequences selected from Table 18 (e.g., as paired in Table 18) or Table 5a (e.g., as paired in Table 5a), or functional variant or fragment thereof.

In some embodiments, the HCP1, LLCP, HCP2, and KLCP comprise amino acid sequences selected from Table 18 (e.g., a single cell of Table 18) or Table 5a (e.g., a single row of Table 5a), or functional variant or fragment thereof.

In some embodiments, the first or second antigen is a tumor antigen, e.g., a pancreatic, lung, or colorectal tumor antigen.

In some embodiments, the first or second antigen is chosen from: PD-L1, HER3, TROP2, mesothelin, IGF-1R, or CA19-9.

In some embodiments, the first or second antigen is chosen from: PD-L1, HER3, TROP2, VEGF-A, EGFR, MUC1, DLL4, or HGF.

In some embodiments, the first or second antigen is chosen from: PD-L1, HER3, TROP2, VEGF-A, EGFR, MUC1, MAGE-A3, gpA33, NY-ESO-1, ANG2, RSPO3, HER2, CEACAM5, or CEA.

In some embodiments, the first or second antigen is an antigen of an immune effector cell, e.g., a T cell, an NK cell, or a myeloid cell.

In some embodiments, the first or second antigen is chosen from: CD3, PD-1, LAG-3, TIM-3, CTLA-4, VISTA, TIGIT, PD-L1, B7-H3, 4-1BB, or ICOS.

In some embodiments, the first antigen is a tumor antigen, e.g., mesothelin, and the second antigen is an antigen chosen from NKP30, PD-L1, CD3, NKG2D, CD47, 4-1BB, or NKP46; or the second antigen is a tumor antigen, e.g., mesothelin, and the first antigen is an antigen chosen from NKP30, PD-L1, CD3, NKG2D, CD47, 4-1BB, or NKP46.

In some embodiments, the first antigen is IGF1R and the second antigen is HER3, or the second antigen is IGF1R and the first antigen is HER3.

In some embodiments, the first antigen is mesothelin and the second antigen is PD-L1, or the second antigen is mesothelin and the first antigen is PD-L1.

In some embodiments, the first antigen is CTLA4 and the second antigen is IL12β, or the second antigen is CTLA4 and the first antigen is IL12β.

In some embodiments, the first antigen is CTLA4 and the second antigen is TRAILR2, or the second antigen is CTLA4 and the first antigen is TRAILR2.

In some embodiments, the first antigen is CTLA4 and the second antigen is CD221, or the second antigen is CTLA4 and the first antigen is CD221.

In some embodiments, the first antigen is PD1 and the second antigen is TRAILR2, or the second antigen is PD1 and the first antigen is TRAILR2.

In some embodiments, the first antigen is PD1 and the second antigen is PDL1, or the second antigen is PD1 and the first antigen is PDL1.

In some embodiments, the first antigen is PD1 and the second antigen is PDL1, or the second antigen is PD1 and the first antigen is PDL1.

In some embodiments, the multispecific antibody molecule as provided herein further comprises an IL-2 molecule or a CD40 agonist, e.g., a CD40L polypeptide or an agonistic anti-CD40 antibody molecule.

In another aspect, provided herein is a nucleic acid which encodes one, two, three, or all of HCP1, LLCP, HCP2, or KLCP as provided herein.

In another aspect, provided herein is a vector comprising the nucleic acid as provided herein.

In another aspect, provided herein is a host cell comprising the nucleic acid as provided herein or the vector as provided herein.

In another aspect, provided herein is a method of making one, two, three or all of HCP1, LLCP, HCP2, or KLCP, comprising culturing the cell as provided herein, to thereby produce one, two, three or all of HCP1, LLCP, HCP2, or KLCP.

In another aspect, provided herein is a method of making a multispecific antibody molecule comprising HCP1, LLCP, HCP2, and KLCP, e.g., a multispecific antibody molecule e as provided herein, comprising: combining HCP1, LLCP, HCP2, and KLCP under conditions suitable for association of HCP1, LLCP, HCP2, and KLCP; thereby making a multispecific antibody molecule comprising HCP1, LLCP, HCP2, and KLCP.

In some embodiments, the method produces correctly paired kappa/lambda multispecific antibody molecules in high yield.

In another aspect, provided herein is a preparation comprising the multispecific antibody molecule as provided herein.

In another aspect, provided herein is a preparation of multispecific antibody molecules, where at least 50, 60, 70, 80, 90, 95, 98, 99, or 99.9% of the multispecific antibody molecules comprise: a lambda light chain polypeptide (LLCP) complexed with, or interfaced with, a first heavy chain polypeptide (HCP1); and a kappa light chain polypeptide (KLCP) complexed with, or interfaced with, a second heavy chain polypeptide (HCP2), wherein: the HCP1 is complexed with, or interfaced with the HCP2.

In some embodiments, the multispecific antibody molecule comprises the multispecific antibody molecule as provided herein.

In some embodiments, the preparation is a pharmaceutically accepted preparation, and, e.g., comprises a pharmaceutically acceptable diluent or excipient.

In another aspect, provided herein is a pharmaceutical composition comprising the multispecific antibody molecule as provided herein and a pharmaceutically acceptable diluent or excipient.

In another aspect, provided herein is a method of providing a subject with a multispecific antibody molecule, comprising: providing the subject with a pharmaceutical preparation comprising the multispecific antibody molecule as provided herein.

In another aspect, provided herein is a method of treating a subject in need thereof, the method comprising: administering to the subject an effective amount of the multispecific antibody molecule as provided herein or the pharmaceutical composition as provided herein.

What is claimed is:

1. An antibody molecule comprising four non-contiguous polypeptides, wherein:
   (a) a first heavy chain polypeptide (HCP1) comprising a sequence having at least 95% sequence identity to the sequence of amino acids 120-449 of SEQ ID NO: 164;
   (b) a kappa light chain polypeptide (KLCP) comprising a sequence having at least 95% sequence identity to the sequence of amino acids 111-213 of SEQ ID NO: 165;
   (c) a second heavy chain polypeptide (HCP2) comprising a sequence having at least 95% sequence identity to the sequence of amino acids 121-450 of SEQ ID NO: 166; and
   (d) a lambda light chain polypeptide (LLCP) comprising a sequence having at least 95% sequence identity to the sequence of amino acids 111-216 of SEQ ID NO: 167;
   wherein the HCP1 and the HCP2 are a knob and hole pair; and wherein:
   (A) (i) the KLCP binds to the HCP1 with a higher affinity than the affinity of the LLCP to the HCP1 and the affinity of the KLCP to the HCP2; and
   (ii) the LLCP binds to the HCP2 with a higher affinity than the affinity of the KLCP to the HCP2 and the affinity of the LLCP to the HCP1; or
   (B) (i) the LLCP binds to the HCP1 with a higher affinity than the affinity of the KLCP to the HCP1 and the affinity of the LLCP to the HCP2; and
   (ii) the KLCP binds to the HCP2 with a higher affinity than the affinity of the LLCP to the HCP2 and the affinity of the KLCP to the HCP1.

2. The antibody molecule of claim 1, wherein the HCP2 further comprises a heavy chain variable region (VH) comprising the amino acid sequence of SEQ ID NO: 403.

3. The antibody molecule of claim 1, wherein the LLCP comprises a light chain variable region (VL) comprising the amino acid sequence of SEQ ID NO: 404.

4. The antibody molecule of claim 1, wherein the HCP1 comprises a sequence identical to the sequence of amino acids 120-217 of SEQ ID NO: 164 or the HCP2 comprises a sequence identical to the sequence of amino acids 121-218 of SEQ ID NO: 166.

5. The antibody molecule of claim 1, wherein the HCP1 comprises a sequence identical to the sequence of amino acids 351-409 of SEQ ID NO: 164, and the HCP2 comprises a sequence identical to the sequence of amino acids 352-410 of SEQ ID NO: 166.

6. The antibody molecule of claim 1, wherein the HCP1 comprises the sequence of amino acids 120-449 of SEQ ID NO: 164.

7. The antibody molecule of claim 1, wherein the HCP2 comprises the sequence of amino acids 121-450 of SEQ ID NO: 166.

8. The antibody molecule of claim 1, wherein the LLCP comprises the sequence of amino acids 111-216 of SEQ ID NO: 167.

9. The antibody molecule of claim 1, wherein the KLCP comprises the sequence of amino acids 111-213 of SEQ ID NO: 165.

10. The antibody of claim 1, wherein:
    (i) the HCP1 comprises the sequence of amino acids 120-449 of SEQ ID NO: 164;
    (ii) the HCP2 comprises the sequence of amino acids 121-450 of SEQ ID NO: 166;
    (iii) the LLCP comprises the sequence of amino acids 111-216 of SEQ ID NO: 167; and
    (iv) the KLCP comprises the sequence of amino acids 111-213 of SEQ ID NO: 165.

11. The antibody molecule of claim 1, wherein:
    (A) the HCP1 does not bind to the LLCP and the HCP2 does not bind to the KLCP, or
    (B) the HCP1 does not bind to the KLCP and the HCP2 does not bind to the LLCP.

12. The antibody molecule of claim 1, wherein:
    (a) the HCP1 comprises a first heavy chain constant region sequence (first HCCRS),
    (b) the KLCP comprises a kappa light chain constant region sequence (KLCCRS),
    (c) the HCP2 comprises a second heavy chain constant region sequence (second HCCRS), and
    (d) the LLCP comprises a lambda light chain constant region sequence (LLCCRS); and
    wherein:
    (i) the first HCCRS does not comprise a mutation that promotes the preferential pairing of the HCP1 and the KLCP, and the KLCCRS does not comprise a mutation that promotes the preferential pairing of the KLCP and the HCP1; and
    (ii) the second HCCRS does not comprise a mutation that increases the affinity of the HCP2 to the LLCP, and the LLCCRS does not comprise a mutation that promotes the preferential pairing of the LLCP and the HCP2.

13. The antibody molecule of claim 1, wherein:
    (a) the HCP1 comprises a first heavy chain constant region sequence (first HCCRS),
    (b) the KLCP comprises a kappa light chain constant region sequence (KLCCRS),
    (c) the HCP2 comprises a second heavy chain constant region sequence (second HCCRS), and (d) the LLCP comprises a lambda light chain constant region sequence (LLCCRS); and wherein:
  (i) the first HCCRS does not comprise a mutation that increases the affinity of the HCP1 to the LLCP, and the LLCCRS does not comprise a mutation that promotes the preferential pairing of the LLCP and the HCP1; and
  (ii) the second HCCRS does not comprise a mutation that increases the affinity of the HCP2 to the KLCP, and the KLCCRS does not comprise a mutation that promotes the preferential pairing of the KLCP and the HCP2.

* * * * *